United States Patent
Ube et al.

(10) Patent No.: US 10,561,727 B2
(45) Date of Patent: Feb. 18, 2020

(54) ANTI HUMAN GAS6 MONOCLONAL ANTIBODY

(71) Applicant: Kyowa Kirin Co., Ltd., Chiyoda-ku, Tokyo (JP)

(72) Inventors: Yuko Ube, Tokyo (JP); Tsuyoshi Yamada, Tokyo (JP); Yuji Yamazaki, Tokyo (JP); Kaname Kimura, Tokyo (JP); Akiko Hariguchi, Tokyo (JP); Shinya Ogawa, Tokyo (JP)

(73) Assignee: Kyowa Kirin Co., Ltd., Tokyo (JP)

( * ) Notice: Subject to any disclaimer, the term of this patent is extended or adjusted under 35 U.S.C. 154(b) by 30 days.

(21) Appl. No.: 15/520,623

(22) PCT Filed: Oct. 20, 2015

(86) PCT No.: PCT/JP2015/005291
§ 371 (c)(1),
(2) Date: Apr. 20, 2017

(87) PCT Pub. No.: WO2016/063522
PCT Pub. Date: Apr. 28, 2016

(65) Prior Publication Data
US 2018/0339041 A1  Nov. 29, 2018

Related U.S. Application Data

(60) Provisional application No. 62/066,687, filed on Oct. 21, 2014.

(51) Int. Cl.
*C07K 16/22* (2006.01)
*A61K 39/395* (2006.01)

(52) U.S. Cl.
CPC .... *A61K 39/3955* (2013.01); *A61K 39/39558* (2013.01)

(58) Field of Classification Search
None
See application file for complete search history.

(56) References Cited

U.S. PATENT DOCUMENTS

| 7,547,767 | B2 | 6/2009 | Yang et al. |
| 2013/0017205 | A1 | 1/2013 | Giaccia et al. |
| 2014/0227283 | A1 | 8/2014 | Robert et al. |

FOREIGN PATENT DOCUMENTS

| JP | 2013-518055 A | 5/2013 |
| JP | 2014-522639 A | 9/2014 |
| WO | WO 2004/108748 A2 | 12/2004 |
| WO | WO 2013/090776 A1 | 6/2013 |
| WO | WO 2014/035828 A2 | 3/2014 |

OTHER PUBLICATIONS

Mallbris et al. (J. Clin. Aesthet. Dermatol. 9(7): 13-15, 2016).*
Angelillo-Scherrer et al., "Role of Gas6 receptors in platelet signaling during thrombus stabilization and implications for antithrombotic therapy," The Journal of Clinical Investigation, Feb. 2005, 115(2):237-246.
Angelillo-Scherrer et al., "Deficiency or inhibition of Gas6 causes platelet dysfunction and protects mice against thrombosis," Nature Medicine, Feb. 2001, 7(2):215-221.
Cook et al., "MerTK inhibition in tumor leukocytes decreases tumor growth and metastasis," The Journal of Clinical Investigation, Aug. 2013, 123(8):3231-3242.
Fiebeler et al., "Growth Arrest Specific Protein 6/Axl Signaling in Human Inflammatory Renal Diseases," American Journal of Kidney Diseases, Feb. 2004, 43(2):286-295.
Fisher et al., "A novel site contributing to growth-arrest-specific gene 6 binding to its receptors as revealed by a human monoclonal antibody," Biochem. J., May 1, 2005, 387(3):727-735.
Gould et al., "Gas6 receptors Axl, Sky and Mer enhance platelet activation and regulate thrombotic responses," Journal of Thrombosis and Haemostasis, 2005, 3:733-741.
Lee et al., "Growth arrest-specific gene 6 (Gas6) levels are elevated in patients with chronic renal failure," Nephrol. Dial. Transplant, Aug. 20, 2012, 27:4166-4172.
Linger et al., "Taking aim at Mer and Axl receptor tyrosine kinases as novel therapeutic targets in solid tumors," Expert Opin. Ther. Targets, Oct. 2010, 14(10):1073-1090.
Manfioletti et al., "The Protein Encoded by a Growth Arrest-Specific Gene (gas6) Is a New Member of the Vitamin K-Dependent Proteins Related to Protein S, a Negative Coregulator in the Blood Coagulation Cascade," Molecular and Cellular Biology, Aug. 1993, 13(8):4976-4985.
Moody et al., "Abstract 5158: Generation of a fully human Gas6 neutralizing antibody with anti-tumor activity in vivo," Cancer Research, Apr. 15, 2013, 73(8):5158.
Nagai et al., "Growth Arrest-specific Gene 6 Is Involved in Glomerular Hypertrophy in the Early Stage of Diabetic Nephropathy," The Journal of Biological Chemistry, May 16, 2003 (online Mar. 17, 2003), 278(20):18229-18234.
Sainaghi et al., "Gas6 Induces Proliferation in Prostate Carcinoma Cell Lines Expressing the Axl Receptor," Journal of Cellular Physiology, 2005, 204:36-44.

(Continued)

Primary Examiner — Christine J Saoud
(74) Attorney, Agent, or Firm — Foley & Lardner LLP

(57) ABSTRACT

The present invention relates to an antibody specifically binding to human growth arrest specific 6 (hGas6). Specifically, the present invention relates to a monoclonal antibody or an antibody fragment thereof which binds to at least one of amino acid residues at positions 314, 315, and 316 of human Gas6, a nucleic acid comprising a nucleotide sequence encoding the antibody or the antibody fragment, a transformed cell comprising a vector comprising the nucleic acid, a method for producing the antibody or the antibody fragment, a reagent for detection or assay of Gas6, comprising the antibody or the antibody fragment, a therapeutic agent or a diagnostic agent for a Gas6-related disease, comprising the antibody or the antibody fragment as an active ingredient, and use of the antibody or the antibody fragment for the production of a therapeutic agent or a diagnostic agent for a Gas6-related disease.

8 Claims, 9 Drawing Sheets
Specification includes a Sequence Listing.

(56) References Cited

OTHER PUBLICATIONS

Sambrook et al., Molecular Cloning: A Laboratory Manual, $3^{rd}$ Edition, vol. 3, 2001, Appendix 7: Codons and Amino Acids, A7.4.

Sasaki et al., "Structural basis for Gas6-Axl signaling," The EMBO Journal, 2006, 25(1):80-87.

Schneider et al., "Genes Specifically Expressed at Growth Arrest of Mammalian Cells," Cell, Sep. 9, 1988, 54:787-793.

Stafford, D.W., "The vitamin K cycle," Journal of Thrombosis and Haemostasis, 2005, 3:1873-1878.

Tanabe et al., "Roles of γ-carboxylation and a sex hormone-binding globulin-like domain in receptor-binding and in biological activities of Gas6," FEBS Letters, 1997, 408:306-310.

Tjwa et al., "Gas6 promotes inflammation by enhancing interactions between endothelial cells, platelets, and leukocytes," Blood, Apr. 15, 2008, 111(8):4096-4105.

Yanagita et al., "Gas6 Induces Mesangial Cell Proliferation via Latent Transcription Factor STAT3," The Journal of Biological Chemistry, Nov. 9, 2001 (online Sep. 6, 2001), 276(45):42364-42369.

Yanagita et al., "Essential role of Gas6 for glomerular injury in nephrotoxic nephritis," The Journal of Clinical Investigation, Jul. 2002, 110(2):239-246.

Yanagita et al., "Gas6 Regulates Mesangial Cell Proliferation through Axl in Experimental Glomerulonephritis," American Journal of Pathology, Apr. 2001, 158(4):1423-1432.

Zhang et al., "Activation of the Axl kinase causes resistance to EGFR-targeted therapy in lung cancer," Nature Genetics, Aug. 2012, 44(8):852-860.

Supplementary European Search Report dated Apr. 17, 2018, in EP 15853067.5.

* cited by examiner

FIG.1
(A)
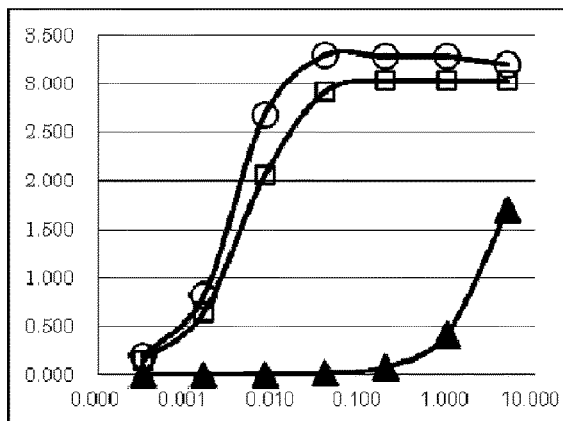
(B)
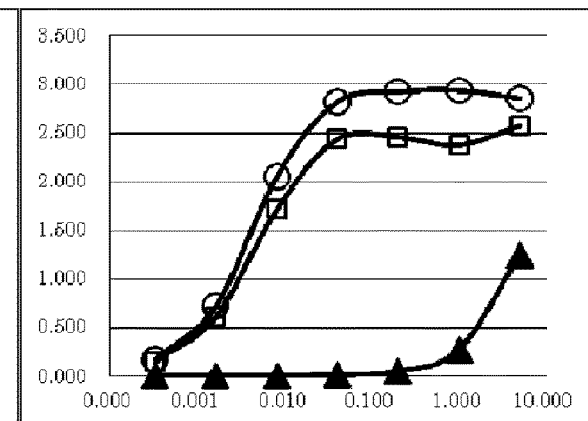
(C)
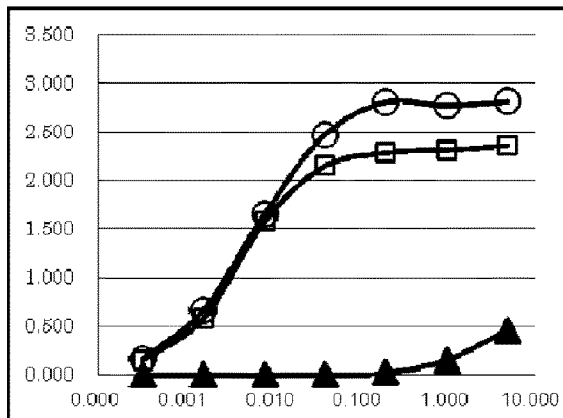
(D)
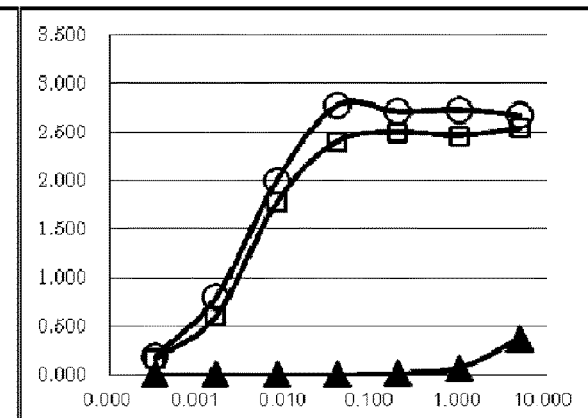
(E)
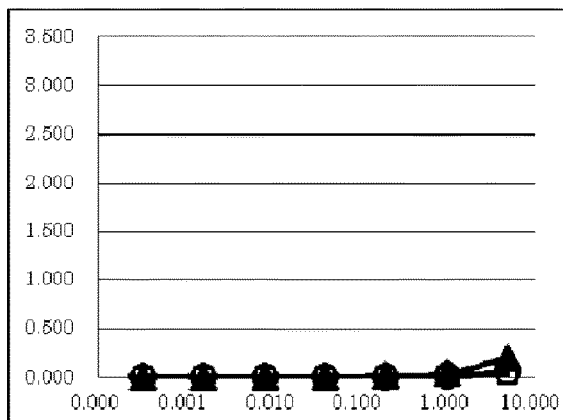
(F)
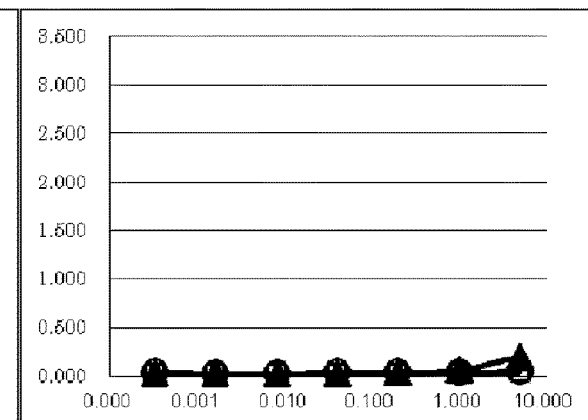

FIG.2
(A)
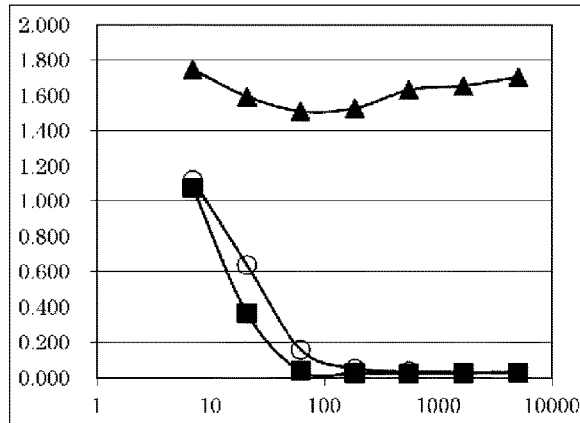
(B)
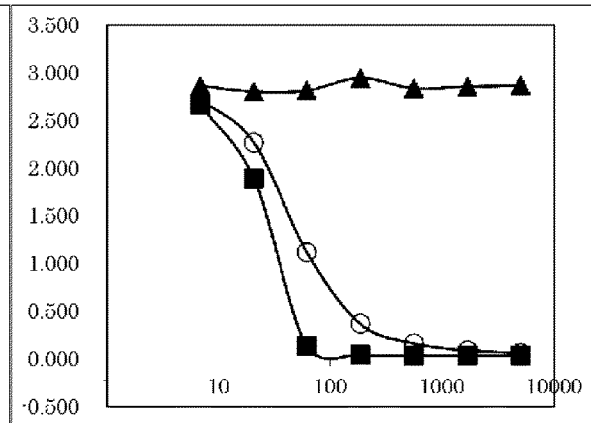
(C)
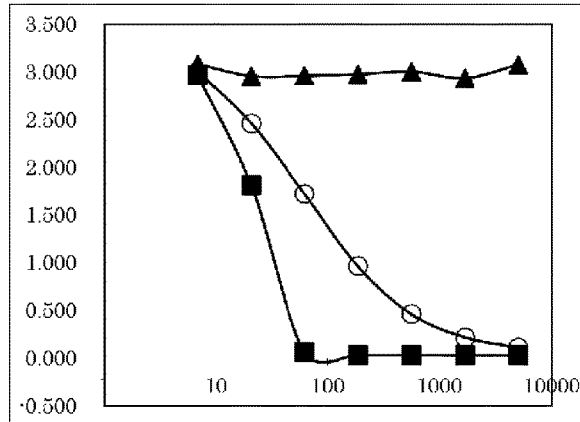
(D)
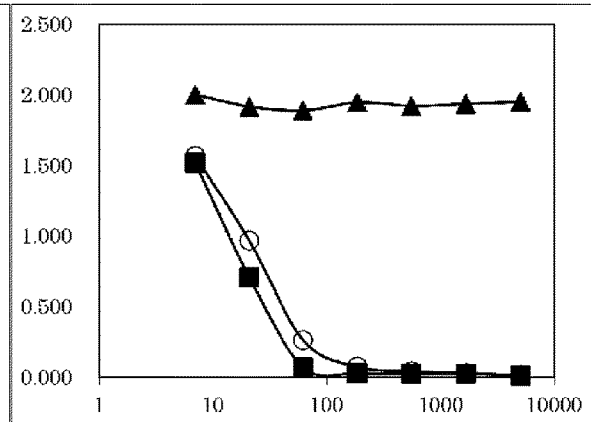

FIG.7

```
            1234567890123456789012345678901234 567890123456789 0123456
KM5320 VL   SIVMTQTPKPLLVSAGDRVTITC KASQSVSNDVA WYQQKPGQSPKVLIY YASNRYT
LV0         DVVMTQSPDSLAVSLGERVTINC             WYQQKPGQSPKLLIY
LV1a        DVVMTQSPDSLAVSLGERVTINC             WYQQKPGQSPKLLIY
LV1b        DVVMTQSPDSLAVSLGERVTINC             WYQQKPGQSPKLLIY
LV2a        DVVMTQSPDSLAVSLGERVTINC    CDR L1   WYQQKPGQSPKLLIY  CDR L2
LV2b        DVVMTQSPDSLAVSAGERVTINC             WYQQKPGQSPKLLIY
LV3         DVVMTQSPDSLAVSLGERVTINC             WYQQKPGQSPKVLIY
LV5         DIVMTQSPDSLAVSLGERVTINC             WYQQKPGQSPKVLIY
LV6         DIVMTQSPDSLAVSAGERVTINC             WYQQKPGQSPKVLIY 789012345678901234567890123456 78901234567 8901234567
KM5320 VL   GVPDRFTGSGYGTDFTFTISTVQAEDLAVYPC QQDYSSPWT  PGGGTKLEIK
LV0         GVPDRFSGSGSGTDFTLTISSLQAEDVAVYYC            PGQGTKLEIK
LV1a        GVPDRFSGSGSGTDFTLTISSLQAEDVAVYYC            PGQGTKLEIK
LV1b        GVPDRFSGSGSGTDFTLTISSVQAEDVAVYYC            PGQGTKLEIK
LV2a        GVPDRFSGSGSGTDFTLTISSVQAEDVAVYPC   CDR L3   PGQGTKLEIK
LV2b        GVPDRFSGSGSGTDFTPTISSLQAEDVAVYYC            PGQGTKLEIK
LV3         GVPDRFSGSGSGTDFTFTISSLQAEDVAVYPC            PGQGTKLEIK
LV5         GVPDRFSGSGSGTDFTFTISSVQAEDVAVYPC            PGQGTKLEIK
LV6         GVPDRFSGSGSGTDFTFTISSVQAEDVAVYPC            PGQGTKLEIK
```

FIG.8

```
            123456789012345678901234567890 12345 6789012345678 9 0123456789012345
KM5320 VH   QIQLVQSGPELKKPGETVKISCKASGYTFT  NYGMN WVKQAPGKGLKWMG  WINTETGEPTYSDDFKG
HV0         QVQLVQSGSELKKPGASVKVSCKASGYTFT        WVRQAPGQGLEWMG
HV1         QVQLVQSGSELKKPGASVKVSCKASGYTFT        WVRQAPGQGLEWMG
HV2         QVQLVQSGSELKKPGASVKVSCKASGYTFT        WVRQAPGQGLEWMG
HV3a        QVQLVQSGSELKKPGASVKVSCKASGYTFT        WVRQAPGQGLKWMG
HV3b        QIQLVQSGSELKKPGASVKISCKASGYTFT  CDR   WVRQAPGQGLEWMG   CDR H2
HV3c        QVQLVQSGPELKKPGASVKVSCKASGYTFT   H1   WVKQAPGQGLKWMG
HV4         QVQLVQSGPELKKPGASVKVSCKASGYTFT        WVRQAPGQGLKWMG
HV6         QVQLVQSGPELKKPGASVKISCKASGYTFT        WVKQAPGQGLKWMG
HV8         QIQLVQSGPELKKPGASVKISCKASGYTFT        WVKQAPGQGLKWMG 7890123456789012345678901234567 8 901234567 890123456789
KM5320 VH   RFAFSLETSATTAYLQINNLRNEDMATYFCAR  EDGYYGTLDY WGQGTSVTVSS
HV0         RFVFSLDTSVSTAYLQISSLKAEDTAVYYCAR             WGQGTTVTVSS
HV1         RFVFSLDTSVSTAYLQISSLKAEDTAVYYCAR             WGQGTTVTVSS
HV2         RFVFSLDTSVSTAYLQISSLKAEDTATYFCAR             WGQGTTVTVSS
HV3a        RFVFSLDTSVSTAYLQISSLKAEDTATYFCAR    CDR H3  WGQGTTVTVSS
HV3b        RFVFSLDTSVSTAYLQISSLKAEDTAVYYCAR             WGQGTTVTVSS
HV3c        RFVFSLDTSVSTAYLQISSLKAEDTAVYYCAR             WGQGTTVTVSS
HV4         RFVFSLDTSVSTAYLQISSLKAEDTATYFCAR             WGQGTTVTVSS
HV6         RFVFSLDTSVSTAYLQISSLKAEDTATYFCAR             WGQGTTVTVSS
HV8         RFVFSLDTSVTTAYLQISSLKAEDTATYFCAR             WGQGTTVTVSS
```

FIG.9

```
               1234567890123456789 0123 4567890 1234 567890123456789 0123456
KM5321 VL      ETTVTQSPASLSVATGEKVTIRC  ITSTDIDDDMN  WYQQKPGEPPKLLIS  EGNTLRP
LV0            ETTLTQSPSSLSASVGDRVTITC               WYQQKPGKAPKLLIS
LV1a           ETTLTQSPSSLSASVGDRVTITC               WYQQKPGKPPKLLIS
LV1b           ETTLTQSPSSLSASVGDRVTITC               WYQQKPGKAPKLLIS
LV1c           ETTLTQSPSSLSVSVGDRVTITC               WYQQKPGKAPKLLIS
LV3            ETTLTQSPSSLSASTGDRVTITC     CDR L1    WYQQKPGKAPKLLIS    CDR L2
LV4            ETTLTQSPSSLSVSTGDRVTITC               WYQQKPGKAPKLLIS
LV6            ETTLTQSPSSLSVSTGDRVTITC               WYQQKPGKPPKLLIS
LV7a           ETTLTQSPSSLSVSTGDRVTITC               WYQQKPGKPPKLLIS
LV7b           ETTVTQSPSSLSVSVGDRVTITC               WYQQKPGKAPKLLIS
LV9            ETTVTQSPSSLSVSTGDRVTITC               WYQQKPGKPPKLLIS 789012345678901234567890123456 78  901234567 8901234567
KM5321 VL      GVPSRFSSSGYGTDFVPTIENILSEDVADYYC  LQTDSVPLT   PGAGTKLELK
LV0            GVPSRFSGSGSGTDFTLTISSLQPEDFATYYC              PGQGTKVEIK
LV1a           GVPSRFSGSGSGTDFTLTISSLQPEDFATYYC              PGQGTKVEIK
LV1b           GVPSRFSGSGSGTDFTLTISSLQPEDFADYYC              PGQGTKVEIK
LV1c           GVPSRFSGSGSGTDFTLTISSLQPEDFATYYC              PGQGTKVEIK
LV3            GVPSRFSGSGSGTDFTLTISSTQPEDFADYYC    CDR L3    PGQGTKVEIK
LV4            GVPSRFSGSGSGTDFTFTISSTQPEDFATYYC              PGQGTKVEIK
LV6            GVPSRFSSSGSGTDFTLTISSTQPEDFADYYC              PGQGTKVEIK
LV7a           GVPSRFSSSGSGTDFTFTISSTQPEDFADYYC              PGQGTKVEIK
LV7b           GVPSRFSSSGSGTDFTFTISSTQPEDFADYYC              PGQGTKLEIK
LV9            GVPSRFSSSGSGTDFTFTISSTQPEDFADYYC              PGQGTKLEIK
```

FIG.10

```
              1234567890123456789012345678901  2345  6789012345678  9012345678901234567
KM5321 VH    QIQLVQSGPELKKPGETVKISCKASGYTFT    NYGMN WVKQAPGKGLKWMG  WINTNTGEPTYTEEFKG
HV0          QVHLVQSGSELKKPGASVKISCKASGYTFT          WVRQAPGQGLEWMG
HV1          QVHLVQSGSELKKPGASVKISCKASGYTFT          WVRQAPGQGLKWMG
HV2a         QVHLVQSGSELKKPGASVKISCKASGYTFT          WVKQAPGQGLKWMG
HV2b         QVHLVQSGPELKKPGASVKISCKASGYTFT          WVRQAPGQGLEWMG
HV3a         QVHLVQSGSELKKPGASVKISCKASGYTFT    CDR   WVRQAPGQGLKWMG         CDR H2
HV3b         QVHLVQSGSELKKPGASVKISCKASGYTFT    H1    WVKQAPGQGLKWMG
HV4a         QIHLVQSGPELKKPGASVKISCKASGYTFT          WVRQAPGQGLEWMG
HV4b         QVHLVQSGPELKKPGASVKISCKASGYTFT          WVKQAPGQGLKWMG
HV5          QIHLVQSGSELKKPGASVKISCKASGYTFT          WVKQAPGQGLKWMG
HV7          QIHLVQSGPELKKPGASVKISCKASGYTFT          WVRQAPGQGLKWMG 78901234567890123456789012345678  901234  567890123456
KM5321 VH    RFAFSLETSATTAYLQINDLKNEDTATYFCAR   DEGWFVY WGQGTLITVSA
HV0          RFVFSLDTSVTTSYLQISTLKAEDTAVYFCAR           WGQGTLVTVSS
HV1          RFVFSLDTSVTTSYLQISTLKAEDTAVYFCAR           WGQGTLVTVSS
HV2a         RFVFSLDTSVTTSYLQISTLKAEDTAVYFCAR           WGQGTLVTVSS
HV2b         RFVFSLDTSVTTSYLQISTLKAEDTATYFCAR           WGQGTLVTVSS
HV3a         RFVFSLDTSVTTSYLQISTLKAEDTATYFCAR   CDR H3   WGQGTLVTVSS
HV3b         RFVFSLDTSVTTSYLQISTLKAEDTATYFCAR           WGQGTLVTVSS
HV4a         RFVFSLDTSVTTAYLQISTLKAEDTAVYFCAR           WGQGTLITVSS
HV4b         RFVFSLDTSVTTSYLQISTLKAEDTATYFCAR           WGQGTLVTVSS
HV5          RFVFSLDTSVTTAYLQISTLKAEDTAVYFCAR           WGQGTLITVSS
HV7          RFVFSLDTSVTTAYLQISTLKAEDTATYFCAR           WGQGTLITVSS
```

FIG.11
(A)
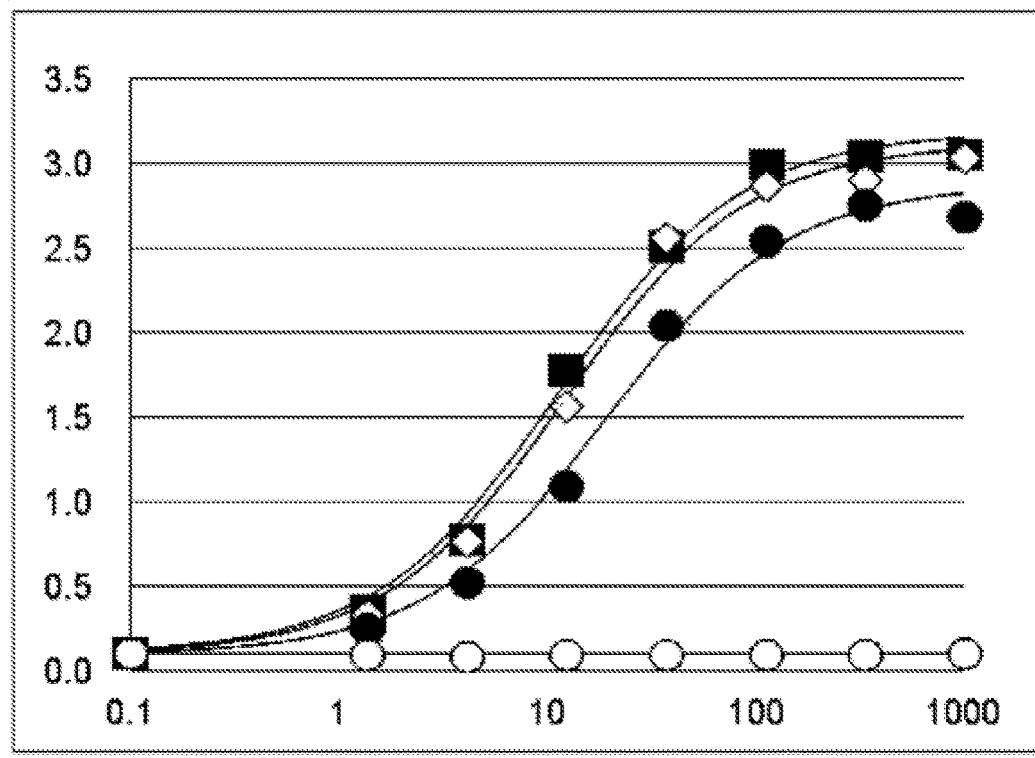
(B)
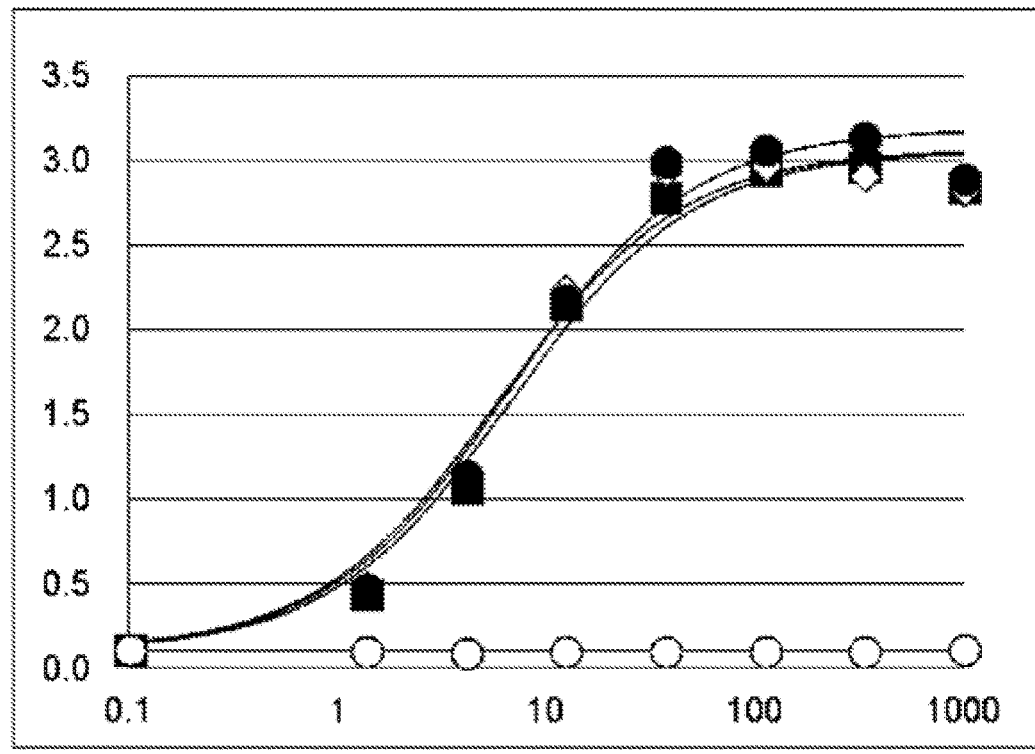

FIG.12
(A)
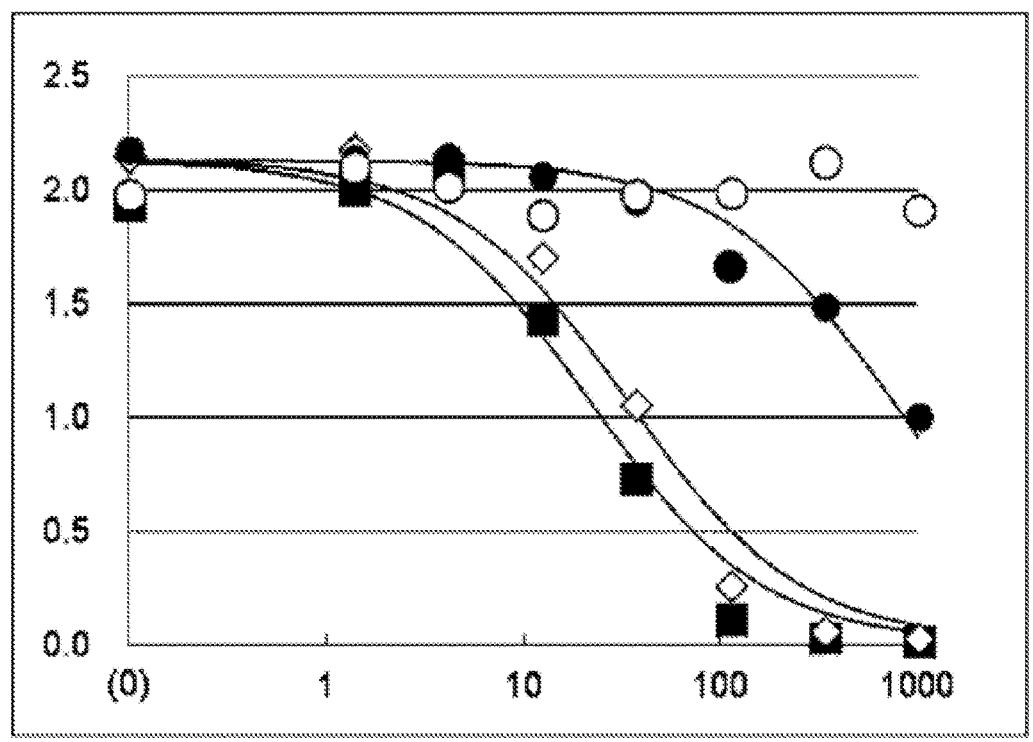
(B)
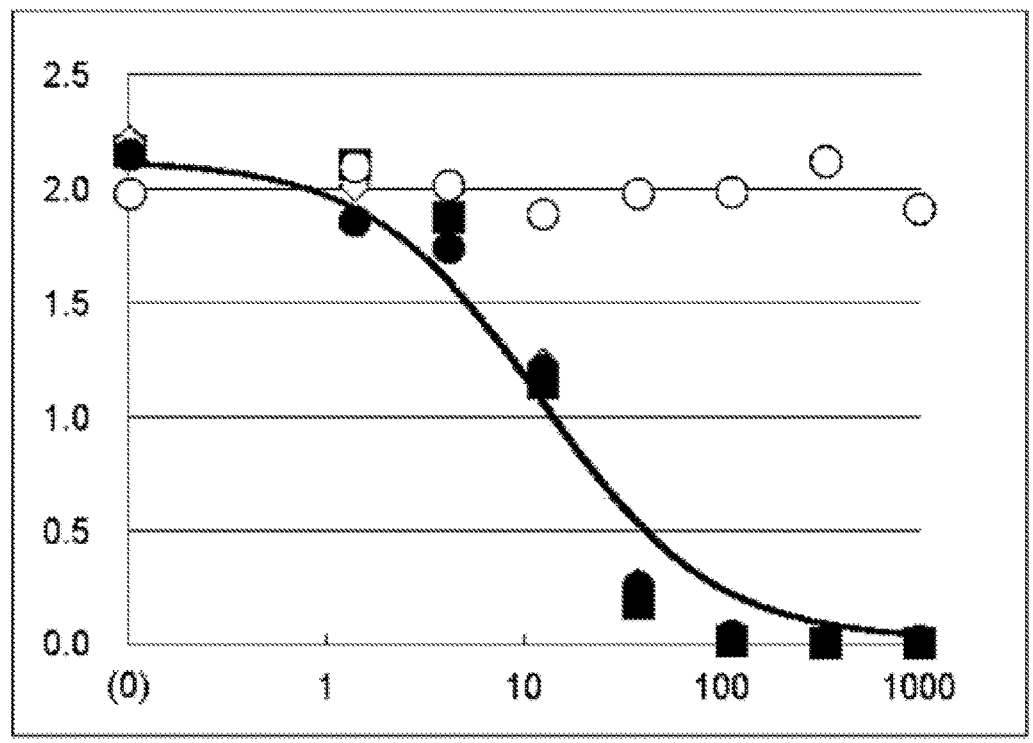

SEQUENCE LISTING

```
<160> NUMBER OF SEQ ID NOS: 214

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer 1

<400> SEQUENCE: 1
gccgaattcg ccaccatggc cccttcgctc tcgc                                  34

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      Primer 2

<400> SEQUENCE: 2
gccggatccc tacttgtcgt cgtcgtcctt gtagtcggct gcggcgggct cc              52

<210> SEQ ID NO 3
<211> LENGTH: 2037
<212> TYPE: DNA
<213> ORGANISM: Homo sapiens
<220> FEATURE:
<221> NAME/KEY: CDS
<222> LOCATION: (1)..(2034)

<400> SEQUENCE: 3 atg gcc cct tcg ctc tcg ccc ggg ccc gcc gcc ctg cgc cgc gcg ccg       48
Met Ala Pro Ser Leu Ser Pro Gly Pro Ala Ala Leu Arg Arg Ala Pro
1               5                   10                  15 cag ctg ctg ctg ctg ctg gcc gcg gag tgc gcg ctt gcc gcg ctg           96
Gln Leu Leu Leu Leu Leu Leu Ala Ala Glu Cys Ala Leu Ala Ala Leu
            20                  25                  30
```

```
ttg ccg gcg cgc gag gcc acg cag ttc ctg cgg ccc agg cag cgc cgc      144
Leu Pro Ala Arg Glu Ala Thr Gln Phe Leu Arg Pro Arg Gln Arg Arg
        35                  40                  45 gcc ttt cag gtc ttc gag gag gcc aag cag ggc cac ctg gag agg gag      192
Ala Phe Gln Val Phe Glu Glu Ala Lys Gln Gly His Leu Glu Arg Glu
    50                  55                  60 tgc gtg gag gag ctg tgc agc cgc gag gag gcg cgg gag gtg ttc gag      240
Cys Val Glu Glu Leu Cys Ser Arg Glu Glu Ala Arg Glu Val Phe Glu
65                  70                  75                  80 aac gac ccc gag acg gat tat ttt tac cca aga tac tta gac tgc atc      288
Asn Asp Pro Glu Thr Asp Tyr Phe Tyr Pro Arg Tyr Leu Asp Cys Ile
                85                  90                  95 aac aag tat ggg tct ccg tac acc aaa aac tca ggc ttc gcc acc tgc      336
Asn Lys Tyr Gly Ser Pro Tyr Thr Lys Asn Ser Gly Phe Ala Thr Cys
            100                 105                 110 gtg caa aac ctg cct gac cag tgc acg ccc aac ccc tgc gat agg aag      384
Val Gln Asn Leu Pro Asp Gln Cys Thr Pro Asn Pro Cys Asp Arg Lys
        115                 120                 125 ggg acc caa gcc tgc cag gac ctc atg ggc aac ttc ttc tgc ctg tgt      432
Gly Thr Gln Ala Cys Gln Asp Leu Met Gly Asn Phe Phe Cys Leu Cys
    130                 135                 140 aaa gct ggc tgg ggg ggc cgg ctc tgc gac aaa gat gtc aac gaa tgc      480
Lys Ala Gly Trp Gly Gly Arg Leu Cys Asp Lys Asp Val Asn Glu Cys
145                 150                 155                 160 agc cag gag aac ggg ggc tgc ctc cag atc tgc cac aac aag ccg ggt      528
Ser Gln Glu Asn Gly Gly Cys Leu Gln Ile Cys His Asn Lys Pro Gly
                165                 170                 175 agc ttc cac tgt tcc tgc cac agc ggc ttc gag ctc tcc tct gat ggc      576
Ser Phe His Cys Ser Cys His Ser Gly Phe Glu Leu Ser Ser Asp Gly
            180                 185                 190 agg acc tgc caa gac ata gac gag tgc gca gac tcg gag gcc tgc ggg      624
Arg Thr Cys Gln Asp Ile Asp Glu Cys Ala Asp Ser Glu Ala Cys Gly
        195                 200                 205 gag gcg cgc tgc aag aac ctg ccc ggc tcc tac tcc tgc ctc tgt gac      672
Glu Ala Arg Cys Lys Asn Leu Pro Gly Ser Tyr Ser Cys Leu Cys Asp
    210                 215                 220 gag ggc ttt gcg tac agc tcc cag gag aag gct tgc cga gat gtg gac      720
Glu Gly Phe Ala Tyr Ser Ser Gln Glu Lys Ala Cys Arg Asp Val Asp
225                 230                 235                 240 gag tgt ctg cag ggc cgc tgt gag cag gtc tgc gtg aac tcc cca ggg      768
Glu Cys Leu Gln Gly Arg Cys Glu Gln Val Cys Val Asn Ser Pro Gly
                245                 250                 255 agc tac acc tgc cac tgt gac ggg cgt ggg ggc ctc aag ctg tcc cag      816
Ser Tyr Thr Cys His Cys Asp Gly Arg Gly Gly Leu Lys Leu Ser Gln
            260                 265                 270 gac atg gac acc tgt gag gac atc ttg ccg tgc gtg ccc ttc agc gtg      864
Asp Met Asp Thr Cys Glu Asp Ile Leu Pro Cys Val Pro Phe Ser Val
        275                 280                 285 gcc aag agt gtg aag tcc ttg tac ctg ggc cgg atg ttc agt ggg acc      912
Ala Lys Ser Val Lys Ser Leu Tyr Leu Gly Arg Met Phe Ser Gly Thr
    290                 295                 300 ccc gtg atc cga ctg cgc ttc aag agg ctg cag ccc acc agg ctg gta      960
Pro Val Ile Arg Leu Arg Phe Lys Arg Leu Gln Pro Thr Arg Leu Val
305                 310                 315                 320 gct gag ttt gac ttc cgg acc ttt gac ccc gag ggc atc ctc ctc ttt     1008
Ala Glu Phe Asp Phe Arg Thr Phe Asp Pro Glu Gly Ile Leu Leu Phe
                325                 330                 335 gcc gga ggc cac cag gac agc acc tgg atc gtg ctg gcc ctg aga gcc     1056
Ala Gly Gly His Gln Asp Ser Thr Trp Ile Val Leu Ala Leu Arg Ala
```

-continued

```
                340                 345                 350
ggc cgg ctg gag ctg cag ctg cgc tac aac ggt gtc ggc cgt gtc acc    1104
Gly Arg Leu Glu Leu Gln Leu Arg Tyr Asn Gly Val Gly Arg Val Thr
        355                 360                 365 agc agc ggc ccg gtc atc aac cat ggc atg tgg cag aca atc tct gtt    1152
Ser Ser Gly Pro Val Ile Asn His Gly Met Trp Gln Thr Ile Ser Val
370                 375                 380 gag gag ctg gcg cgg aat ctg gtc atc aag gtc aac agg gat gct gtc    1200
Glu Glu Leu Ala Arg Asn Leu Val Ile Lys Val Asn Arg Asp Ala Val
385                 390                 395                 400 atg aaa atc gcg gtg gcc ggg gac ttg ttc caa ccg gag cga gga ctg    1248
Met Lys Ile Ala Val Ala Gly Asp Leu Phe Gln Pro Glu Arg Gly Leu
                405                 410                 415 tat cat ctg aac ctg acc gtg gga ggt att ccc ttc cat gag aag gac    1296
Tyr His Leu Asn Leu Thr Val Gly Gly Ile Pro Phe His Glu Lys Asp
            420                 425                 430 ctc gtg cag cct ata aac cct cgt ctg gat ggc tgc atg agg agc tgg    1344
Leu Val Gln Pro Ile Asn Pro Arg Leu Asp Gly Cys Met Arg Ser Trp
        435                 440                 445 aac tgg ctg aac gga gaa gac acc acc atc cag gaa acg gta aaa gtg    1392
Asn Trp Leu Asn Gly Glu Asp Thr Thr Ile Gln Glu Thr Val Lys Val
450                 455                 460 aac acg agg atg cag tgc ttc tcg gtg acg gag aga ggc tct ttc tac    1440
Asn Thr Arg Met Gln Cys Phe Ser Val Thr Glu Arg Gly Ser Phe Tyr
465                 470                 475                 480 ccc ggg agc ggc ttc gcc ttc tac agc ctg gac tac atg cgg acc cct    1488
Pro Gly Ser Gly Phe Ala Phe Tyr Ser Leu Asp Tyr Met Arg Thr Pro
                485                 490                 495 ctg gac gtc ggg act gaa tca acc tgg gaa gta gaa gtc gtg gct cac    1536
Leu Asp Val Gly Thr Glu Ser Thr Trp Glu Val Glu Val Val Ala His
            500                 505                 510 atc cgc cca gcc gca gac aca ggc gtg ctg ttt gcg ctc tgg gcc ccc    1584
Ile Arg Pro Ala Ala Asp Thr Gly Val Leu Phe Ala Leu Trp Ala Pro
        515                 520                 525 gac ctc cgt gcc gtg cct ctc tct gtg gca ctg gta gac tat cac tcc    1632
Asp Leu Arg Ala Val Pro Leu Ser Val Ala Leu Val Asp Tyr His Ser
530                 535                 540 acg aag aaa ctc aag aag cag ctg gtg gtc ctg gcc gtg gag cat acg    1680
Thr Lys Lys Leu Lys Lys Gln Leu Val Val Leu Ala Val Glu His Thr
545                 550                 555                 560 gcc ttg gcc cta atg gag atc aag gtc tgc gac ggc caa gag cac gtg    1728
Ala Leu Ala Leu Met Glu Ile Lys Val Cys Asp Gly Gln Glu His Val
                565                 570                 575 gtc acc gtc tcg ctg agg gac ggt gag gcc acc ctg gag gtg gac ggc    1776
Val Thr Val Ser Leu Arg Asp Gly Glu Ala Thr Leu Glu Val Asp Gly
            580                 585                 590 acc agg ggc cag agc gag gtg agc gcc gcg cag ctg cag gag agg ctg    1824
Thr Arg Gly Gln Ser Glu Val Ser Ala Ala Gln Leu Gln Glu Arg Leu
        595                 600                 605 gcc gtg ctc gag agg cac ctg cgg agc ccc gtg ctc acc ttt gct ggc    1872
Ala Val Leu Glu Arg His Leu Arg Ser Pro Val Leu Thr Phe Ala Gly
610                 615                 620 ggc ctg cca gat gtg ccg gtg act tca gcg cca gtc acc gcg ttc tac    1920
Gly Leu Pro Asp Val Pro Val Thr Ser Ala Pro Val Thr Ala Phe Tyr
625                 630                 635                 640 cgc ggc tgc atg aca ctg gag gtc aac cgg agg ctg ctg gac ctg gac    1968
Arg Gly Cys Met Thr Leu Glu Val Asn Arg Arg Leu Leu Asp Leu Asp
                645                 650                 655 gag gcg gcg tac aag cac agc gac atc acg gcc cac tcc tgc ccc ccc    2016
```

-continued

```
Glu Ala Ala Tyr Lys His Ser Asp Ile Thr Ala His Ser Cys Pro Pro
                660                 665                 670 gtg gag ccc gcc gca gcc tag                                          2037
Val Glu Pro Ala Ala Ala
            675

<210> SEQ ID NO 4
<211> LENGTH: 678
<212> TYPE: PRT
<213> ORGANISM: Homo sapiens

<400> SEQUENCE: 4

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
                20                  25                  30

Leu Pro Ala Arg Glu Ala Thr Gln Phe Leu Arg Pro Arg Gln Arg Arg
            35                  40                  45

Ala Phe Gln Val Phe Glu Glu Ala Lys Gln Gly His Leu Glu Arg Glu
        50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
        275                 280                 285

Ala Lys Ser Val Lys Ser Leu Tyr Leu Gly Arg Met Phe Ser Gly Thr
    290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
```

```
                340                 345                 350
Gly Arg Leu Glu Leu Gln Leu Arg Tyr Asn Gly Val Gly Arg Val Thr
            355                 360                 365
Ser Ser Gly Pro Val Ile Asn His Gly Met Trp Gln Thr Ile Ser Val
        370                 375                 380
Glu Glu Leu Ala Arg Asn Leu Val Ile Lys Val Asn Arg Asp Ala Val
385                 390                 395                 400
Met Lys Ile Ala Val Ala Gly Asp Leu Phe Gln Pro Glu Arg Gly Leu
                405                 410                 415
Tyr His Leu Asn Leu Thr Val Gly Gly Ile Pro Phe His Glu Lys Asp
            420                 425                 430
Leu Val Gln Pro Ile Asn Pro Arg Leu Asp Gly Cys Met Arg Ser Trp
        435                 440                 445
Asn Trp Leu Asn Gly Glu Asp Thr Thr Ile Gln Glu Thr Val Lys Val
    450                 455                 460
Asn Thr Arg Met Gln Cys Phe Ser Val Thr Glu Arg Gly Ser Phe Tyr
465                 470                 475                 480
Pro Gly Ser Gly Phe Ala Phe Tyr Ser Leu Asp Tyr Met Arg Thr Pro
                485                 490                 495
Leu Asp Val Gly Thr Glu Ser Thr Trp Glu Val Glu Val Val Ala His
            500                 505                 510
Ile Arg Pro Ala Ala Asp Thr Gly Val Leu Phe Ala Leu Trp Ala Pro
        515                 520                 525
Asp Leu Arg Ala Val Pro Leu Ser Val Ala Leu Val Asp Tyr His Ser
    530                 535                 540
Thr Lys Lys Leu Lys Lys Gln Leu Val Val Leu Ala Val Glu His Thr
545                 550                 555                 560
Ala Leu Ala Leu Met Glu Ile Lys Val Cys Asp Gly Gln Glu His Val
                565                 570                 575
Val Thr Val Ser Leu Arg Asp Gly Glu Ala Thr Leu Glu Val Asp Gly
            580                 585                 590
Thr Arg Gly Gln Ser Glu Val Ser Ala Ala Gln Leu Gln Glu Arg Leu
        595                 600                 605
Ala Val Leu Glu Arg His Leu Arg Ser Pro Val Leu Thr Phe Ala Gly
    610                 615                 620
Gly Leu Pro Asp Val Pro Val Thr Ser Ala Pro Val Thr Ala Phe Tyr
625                 630                 635                 640
Arg Gly Cys Met Thr Leu Glu Val Asn Arg Arg Leu Leu Asp Leu Asp
                645                 650                 655
Glu Ala Ala Tyr Lys His Ser Asp Ile Thr Ala His Ser Cys Pro Pro
            660                 665                 670
Val Glu Pro Ala Ala Ala
            675

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer 3

<400> SEQUENCE: 5
cggcctcccg ggcgctctg                                                    19
```

```
<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer 4

<400> SEQUENCE: 6
cctccgctgt ttcggacaga g                                              21

<210> SEQ ID NO 7
<211> LENGTH: 2040
<212> TYPE: DNA
<213> ORGANISM: Macaca fascicularis
<220> FEATURE:
<221> NAME/KEY: CDS
<222> LOCATION: (1)..(2037)

<400> SEQUENCE: 7
```

| atg | gcc | cct | tcg | ccc | tcg | ccc | ggg | ccc | gcc | gcc | ccg | cgc | gcc | gcg | ccg | 48 |
|---|---|---|---|---|---|---|---|---|---|---|---|---|---|---|---|---|
| Met | Ala | Pro | Ser | Pro | Ser | Pro | Gly | Pro | Ala | Ala | Pro | Arg | Ala | Ala | Pro | |
| 1 | | | | 5 | | | | | 10 | | | | | 15 | | |

| ctg | cgg | ctg | ctg | ctg | ctg | ctg | ctg | gcc | tcg | gag | tgc | gcg | ctc | gcc | gcg | 96 |
|---|---|---|---|---|---|---|---|---|---|---|---|---|---|---|---|---|
| Leu | Arg | Leu | Leu | Leu | Leu | Leu | Leu | Ala | Ser | Glu | Cys | Ala | Leu | Ala | Ala | |
| | | 20 | | | | | 25 | | | | | 30 | | | | |

| ttg | ttg | ccg | gcg | cgc | gag | gcc | acg | cag | ttc | ctg | cgg | ccc | agg | cag | cgc | 144 |
|---|---|---|---|---|---|---|---|---|---|---|---|---|---|---|---|---|
| Leu | Leu | Pro | Ala | Arg | Glu | Ala | Thr | Gln | Phe | Leu | Arg | Pro | Arg | Gln | Arg | |
| | | 35 | | | | | 40 | | | | | 45 | | | | |

| cgc | gcc | ttc | cag | gtc | ttc | gag | gag | gcc | aag | cag | ggc | cac | ctg | gag | agg | 192 |
|---|---|---|---|---|---|---|---|---|---|---|---|---|---|---|---|---|
| Arg | Ala | Phe | Gln | Val | Phe | Glu | Glu | Ala | Lys | Gln | Gly | His | Leu | Glu | Arg | |
| 50 | | | | | 55 | | | | | 60 | | | | | | |

| gag | tgc | gtg | gag | gag | ctg | tgc | agc | cgc | gag | gag | gcg | cgg | gag | gtg | ttc | 240 |
|---|---|---|---|---|---|---|---|---|---|---|---|---|---|---|---|---|
| Glu | Cys | Val | Glu | Glu | Leu | Cys | Ser | Arg | Glu | Glu | Ala | Arg | Glu | Val | Phe | |
| 65 | | | | | 70 | | | | | 75 | | | | | 80 | |

| gag | aac | gac | ccc | gag | acg | gac | tat | ttt | tac | ccg | aga | tac | tta | ggc | tgc | 288 |
|---|---|---|---|---|---|---|---|---|---|---|---|---|---|---|---|---|
| Glu | Asn | Asp | Pro | Glu | Thr | Asp | Tyr | Phe | Tyr | Pro | Arg | Tyr | Leu | Gly | Cys | |
| | | | | 85 | | | | | 90 | | | | | 95 | | |

| atc | gaa | aag | tat | ggg | tct | ccc | tac | gcc | aaa | gac | cca | ggc | ttc | gcc | acc | 336 |
|---|---|---|---|---|---|---|---|---|---|---|---|---|---|---|---|---|
| Ile | Glu | Lys | Tyr | Gly | Ser | Pro | Tyr | Ala | Lys | Asp | Pro | Gly | Phe | Ala | Thr | |
| | | | 100 | | | | | 105 | | | | | 110 | | | |

| tgc | gtg | cag | aac | ctg | cct | gac | cag | tgc | acg | ccc | aac | ccc | tgt | gat | aag | 384 |
|---|---|---|---|---|---|---|---|---|---|---|---|---|---|---|---|---|
| Cys | Val | Gln | Asn | Leu | Pro | Asp | Gln | Cys | Thr | Pro | Asn | Pro | Cys | Asp | Lys | |
| | | 115 | | | | | 120 | | | | | 125 | | | | |

| aag | ggg | acc | caa | gcc | tgc | caa | gac | ctc | atg | ggc | aac | ttc | ttc | tgc | ctg | 432 |
|---|---|---|---|---|---|---|---|---|---|---|---|---|---|---|---|---|
| Lys | Gly | Thr | Gln | Ala | Cys | Gln | Asp | Leu | Met | Gly | Asn | Phe | Phe | Cys | Leu | |
| | 130 | | | | | 135 | | | | | 140 | | | | | |

| tgt | aaa | gct | ggc | tgg | ggg | ggc | cgg | ctc | tgt | gac | aga | gat | gtc | aat | gaa | 480 |
|---|---|---|---|---|---|---|---|---|---|---|---|---|---|---|---|---|
| Cys | Lys | Ala | Gly | Trp | Gly | Gly | Arg | Leu | Cys | Asp | Arg | Asp | Val | Asn | Glu | |
| 145 | | | | 150 | | | | | 155 | | | | | 160 | | |

| tgc | agc | cag | gag | aat | ggg | ggc | tgc | ctc | cag | atc | tgc | cac | aac | aag | ccg | 528 |
|---|---|---|---|---|---|---|---|---|---|---|---|---|---|---|---|---|
| Cys | Ser | Gln | Glu | Asn | Gly | Gly | Cys | Leu | Gln | Ile | Cys | His | Asn | Lys | Pro | |
| | | | | 165 | | | | | 170 | | | | | 175 | | |

| ggc | agc | ttc | cac | tgt | gcc | tgc | cac | agc | ggc | ttc | cag | ctc | tcc | tct | gac | 576 |
|---|---|---|---|---|---|---|---|---|---|---|---|---|---|---|---|---|
| Gly | Ser | Phe | His | Cys | Ala | Cys | His | Ser | Gly | Phe | Gln | Leu | Ser | Ser | Asp | |
| | | | 180 | | | | | 185 | | | | | 190 | | | |

| ggc | agg | acc | tgc | caa | gac | ata | gac | gag | tgt | gca | gac | tcg | gag | gcc | tgc | 624 |
|---|---|---|---|---|---|---|---|---|---|---|---|---|---|---|---|---|
| Gly | Arg | Thr | Cys | Gln | Asp | Ile | Asp | Glu | Cys | Ala | Asp | Ser | Glu | Ala | Cys | |
| | | 195 | | | | | 200 | | | | | 205 | | | | |

| ggg | gag | gca | cgc | tgc | aag | aac | ctg | ccc | ggc | tcc | tac | tcc | tgc | ctc | tgt | 672 |
|---|---|---|---|---|---|---|---|---|---|---|---|---|---|---|---|---|
| Gly | Glu | Ala | Arg | Cys | Lys | Asn | Leu | Pro | Gly | Ser | Tyr | Ser | Cys | Leu | Cys | |
| | 210 | | | | | 215 | | | | | 220 | | | | | |

-continued

| | |
|---|---|
| gac aag ggc ttt gca tac agc tcc cag gag aag gcc tgc cga gat gtg<br>Asp Lys Gly Phe Ala Tyr Ser Ser Gln Glu Lys Ala Cys Arg Asp Val<br>225                            230                     235                       240 | 720 |
| gat gag tgt ctg cag ggc cgc tgt gag cag gtc tgt gtg aac tcc ccg<br>Asp Glu Cys Leu Gln Gly Arg Cys Glu Gln Val Cys Val Asn Ser Pro<br>                   245                     250                   255 | 768 |
| ggc agc tac acc tgc cac tgt gat ggg cgc ggg ggc ctc aag ctg tcc<br>Gly Ser Tyr Thr Cys His Cys Asp Gly Arg Gly Gly Leu Lys Leu Ser<br>                  260                    265                   270 | 816 |
| cag gac atg gac acc tgt gag gac atc ttg ccg tgc gtg ccc ttc agc<br>Gln Asp Met Asp Thr Cys Glu Asp Ile Leu Pro Cys Val Pro Phe Ser<br>275                            280                     285 | 864 |
| atg gcc aag agc gtg aag tcc ttg tac ctg ggc cgg atg ttc agt ggg<br>Met Ala Lys Ser Val Lys Ser Leu Tyr Leu Gly Arg Met Phe Ser Gly<br>       290                   295                     300 | 912 |
| acc ccc gtg atc cga ctg cgc ttc aag agg ctg cag ccc acc agg ctc<br>Thr Pro Val Ile Arg Leu Arg Phe Lys Arg Leu Gln Pro Thr Arg Leu<br>305                          310                     315                   320 | 960 |
| gta gct gag ttt gac ttc cgg acc ttt gac ccc gag ggc atc ctc ctc<br>Val Ala Glu Phe Asp Phe Arg Thr Phe Asp Pro Glu Gly Ile Leu Leu<br>                   325                     330                   335 | 1008 |
| ttc gct gga ggc cac cag gac agc acc tgg atc gtg ctg gcc ctg cga<br>Phe Ala Gly Gly His Gln Asp Ser Thr Trp Ile Val Leu Ala Leu Arg<br>                340                     345                     350 | 1056 |
| gcc ggc cgg ctg gag ctg cag ctg cgc tac aat ggc gtc ggc cgc gtc<br>Ala Gly Arg Leu Glu Leu Gln Leu Arg Tyr Asn Gly Val Gly Arg Val<br>              355                     360                   365 | 1104 |
| acc agc agc ggc ccg gtc atc aac cac ggc atg tgg cag acg atc tct<br>Thr Ser Ser Gly Pro Val Ile Asn His Gly Met Trp Gln Thr Ile Ser<br>370                            375                     380 | 1152 |
| gtt gag gag ctg gcg cgg aat ctg gtc atc aag gtc aac agg gac gct<br>Val Glu Glu Leu Ala Arg Asn Leu Val Ile Lys Val Asn Arg Asp Ala<br>385                          390                     395                   400 | 1200 |
| gtc atg aaa atc gcg gtg gcc ggg gac ttg ttc caa ccg gag cga gga<br>Val Met Lys Ile Ala Val Ala Gly Asp Leu Phe Gln Pro Glu Arg Gly<br>                   405                     410                   415 | 1248 |
| ctg tat cat ctg aac ctc acc gta gga ggc att ccc ttc cat gag aag<br>Leu Tyr His Leu Asn Leu Thr Val Gly Gly Ile Pro Phe His Glu Lys<br>                420                     425                     430 | 1296 |
| gac ctc gtg cag cct ata aac cct cgt ctg gat ggc tgt atg agg agc<br>Asp Leu Val Gln Pro Ile Asn Pro Arg Leu Asp Gly Cys Met Arg Ser<br>             435                     440                   445 | 1344 |
| tgg aac tgg ctg aac gga gaa gac acc acc atc caa gaa acg gtg aaa<br>Trp Asn Trp Leu Asn Gly Glu Asp Thr Thr Ile Gln Glu Thr Val Lys<br>450                            455                     460 | 1392 |
| gcg aac acg aaa atg cag tgc ttc tcg gtg aca gag aga ggc tcc ttt<br>Ala Asn Thr Lys Met Gln Cys Phe Ser Val Thr Glu Arg Gly Ser Phe<br>465                            470                     475                   480 | 1440 |
| tac ccg ggg agt ggc ttt gcc ttc tac agc ctg gac tac atg cgg acc<br>Tyr Pro Gly Ser Gly Phe Ala Phe Tyr Ser Leu Asp Tyr Met Arg Thr<br>                   485                     490                   495 | 1488 |
| cct ctg gac atc ggg aca gaa tcg acc tgg gaa ata gaa gtc gtg gct<br>Pro Leu Asp Ile Gly Thr Glu Ser Thr Trp Glu Ile Glu Val Val Ala<br>                  500                     505                   510 | 1536 |
| cac atc cgc ccg gcc gca gac aca ggg gtg ctg ttc gca ctc tgg gtc<br>His Ile Arg Pro Ala Ala Asp Thr Gly Val Leu Phe Ala Leu Trp Val<br>               515                     520                   525 | 1584 |
| ccc gac ctc cgt gcc gtg cct ctc tct gtg gcc ctg gta gac tat cac<br>Pro Asp Leu Arg Ala Val Pro Leu Ser Val Ala Leu Val Asp Tyr His<br>530                            535                     540 | 1632 |

```
tcc aca aag aag ctc aag aag cag ctg gtg gtc ctg gcc gtg gag cac       1680
Ser Thr Lys Lys Leu Lys Lys Gln Leu Val Val Leu Ala Val Glu His
545                 550                 555                 560 gtg gcc ttg gcc ctg atg gag atc aag gtc tgc gat ggt caa gag cac       1728
Val Ala Leu Ala Leu Met Glu Ile Lys Val Cys Asp Gly Gln Glu His
                565                 570                 575 atg gtc acc atc tcg ctg agg gag ggt gag gcc acc ctg gag gtg gac       1776
Met Val Thr Ile Ser Leu Arg Glu Gly Glu Ala Thr Leu Glu Val Asp
        580                 585                 590 ggc acc agg ggc cag agc gag gtg agc gcc gcg cag ctg cag gag agg       1824
Gly Thr Arg Gly Gln Ser Glu Val Ser Ala Ala Gln Leu Gln Glu Arg
    595                 600                 605 ctg gcc gtg ctc gag aag cac ctg cgg agc ccc gtg ctc acc ttt gcc       1872
Leu Ala Val Leu Glu Lys His Leu Arg Ser Pro Val Leu Thr Phe Ala
610                 615                 620 ggt ggc ctg cca gat gtg ccg gtg act tca gcg cca gtc acc gca ttc       1920
Gly Gly Leu Pro Asp Val Pro Val Thr Ser Ala Pro Val Thr Ala Phe
625                 630                 635                 640 tac cgt ggc tgc atg aca ctg gag gtc aac cgg agg ctg ctg gac ctg       1968
Tyr Arg Gly Cys Met Thr Leu Glu Val Asn Arg Arg Leu Leu Asp Leu
                645                 650                 655 gac gag gcg gca tac aag cac agt gac atc acc gcc cac tcc tgc cca       2016
Asp Glu Ala Ala Tyr Lys His Ser Asp Ile Thr Ala His Ser Cys Pro
            660                 665                 670 ccc gtg gag ccc gcc gca gcc tag                                       2040
Pro Val Glu Pro Ala Ala Ala
        675

<210> SEQ ID NO 8
<211> LENGTH: 679
<212> TYPE: PRT
<213> ORGANISM: Macaca fascicularis

<400> SEQUENCE: 8

Met Ala Pro Ser Pro Ser Pro Gly Pro Ala Ala Pro Arg Ala Ala Pro
1               5                   10                  15

Leu Arg Leu Leu Leu Leu Leu Leu Ala Ser Glu Cys Ala Leu Ala Ala
            20                  25                  30

Leu Leu Pro Ala Arg Glu Ala Thr Gln Phe Leu Arg Pro Arg Gln Arg
        35                  40                  45

Arg Ala Phe Gln Val Phe Glu Glu Ala Lys Gln Gly His Leu Glu Arg
    50                  55                  60

Glu Cys Val Glu Glu Leu Cys Ser Arg Glu Glu Ala Arg Glu Val Phe
65                  70                  75                  80

Glu Asn Asp Pro Glu Thr Asp Tyr Phe Tyr Pro Arg Tyr Leu Gly Cys
                85                  90                  95

Ile Glu Lys Tyr Gly Ser Pro Tyr Ala Lys Asp Pro Gly Phe Ala Thr
            100                 105                 110

Cys Val Gln Asn Leu Pro Asp Gln Cys Thr Pro Asn Pro Cys Asp Lys
        115                 120                 125

Lys Gly Thr Gln Ala Cys Gln Asp Leu Met Gly Asn Phe Phe Cys Leu
    130                 135                 140

Cys Lys Ala Gly Trp Gly Gly Arg Leu Cys Asp Arg Asp Val Asn Glu
145                 150                 155                 160

Cys Ser Gln Glu Asn Gly Gly Cys Leu Gln Ile Cys His Asn Lys Pro
                165                 170                 175

Gly Ser Phe His Cys Ala Cys His Ser Gly Phe Gln Leu Ser Ser Asp
```

-continued

```
            180                 185                 190
Gly Arg Thr Cys Gln Asp Ile Asp Glu Cys Ala Asp Ser Glu Ala Cys
            195                 200                 205
Gly Glu Ala Arg Cys Lys Asn Leu Pro Gly Ser Tyr Ser Cys Leu Cys
            210                 215                 220
Asp Lys Gly Phe Ala Tyr Ser Ser Gln Glu Lys Ala Cys Arg Asp Val
225                 230                 235                 240
Asp Glu Cys Leu Gln Gly Arg Cys Glu Gln Val Cys Val Asn Ser Pro
                245                 250                 255
Gly Ser Tyr Thr Cys His Cys Asp Gly Arg Gly Gly Leu Lys Leu Ser
            260                 265                 270
Gln Asp Met Asp Thr Cys Glu Asp Ile Leu Pro Cys Val Pro Phe Ser
            275                 280                 285
Met Ala Lys Ser Val Lys Ser Leu Tyr Leu Gly Arg Met Phe Ser Gly
            290                 295                 300
Thr Pro Val Ile Arg Leu Arg Phe Lys Arg Leu Gln Pro Thr Arg Leu
305                 310                 315                 320
Val Ala Glu Phe Asp Phe Arg Thr Phe Asp Pro Glu Gly Ile Leu Leu
                325                 330                 335
Phe Ala Gly Gly His Gln Asp Ser Thr Trp Ile Val Leu Ala Leu Arg
            340                 345                 350
Ala Gly Arg Leu Glu Leu Gln Leu Arg Tyr Asn Gly Val Gly Arg Val
            355                 360                 365
Thr Ser Ser Gly Pro Val Ile Asn His Gly Met Trp Gln Thr Ile Ser
            370                 375                 380
Val Glu Glu Leu Ala Arg Asn Leu Val Ile Lys Val Asn Arg Asp Ala
385                 390                 395                 400
Val Met Lys Ile Ala Val Ala Gly Asp Leu Phe Gln Pro Glu Arg Gly
                405                 410                 415
Leu Tyr His Leu Asn Leu Thr Val Gly Gly Ile Pro Phe His Glu Lys
            420                 425                 430
Asp Leu Val Gln Pro Ile Asn Pro Arg Leu Asp Gly Cys Met Arg Ser
            435                 440                 445
Trp Asn Trp Leu Asn Gly Glu Asp Thr Thr Ile Gln Glu Thr Val Lys
            450                 455                 460
Ala Asn Thr Lys Met Gln Cys Phe Ser Val Thr Glu Arg Gly Ser Phe
465                 470                 475                 480
Tyr Pro Gly Ser Gly Phe Ala Phe Tyr Ser Leu Asp Tyr Met Arg Thr
                485                 490                 495
Pro Leu Asp Ile Gly Thr Glu Ser Thr Trp Glu Ile Glu Val Val Ala
                500                 505                 510
His Ile Arg Pro Ala Ala Asp Thr Gly Val Leu Phe Ala Leu Trp Val
            515                 520                 525
Pro Asp Leu Arg Ala Val Pro Leu Ser Val Ala Leu Val Asp Tyr His
            530                 535                 540
Ser Thr Lys Lys Leu Lys Lys Gln Leu Val Val Leu Ala Val Glu His
545                 550                 555                 560
Val Ala Leu Ala Leu Met Glu Ile Lys Val Cys Asp Gly Gln Glu His
                565                 570                 575
Met Val Thr Ile Ser Leu Arg Glu Gly Glu Ala Thr Leu Glu Val Asp
            580                 585                 590
Gly Thr Arg Gly Gln Ser Glu Val Ser Ala Ala Gln Leu Gln Glu Arg
            595                 600                 605
```

-continued

```
Leu Ala Val Leu Glu Lys His Leu Arg Ser Pro Val Leu Thr Phe Ala
    610                 615                 620

Gly Gly Leu Pro Asp Val Pro Val Thr Ser Ala Pro Val Thr Ala Phe
625                 630                 635                 640

Tyr Arg Gly Cys Met Thr Leu Glu Val Asn Arg Arg Leu Leu Asp Leu
                645                 650                 655

Asp Glu Ala Ala Tyr Lys His Ser Asp Ile Thr Ala His Ser Cys Pro
            660                 665                 670

Pro Val Glu Pro Ala Ala Ala
        675

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer 5

<400> SEQUENCE: 9
cccacaagct gaattcgcca ccatggcccc ttcgc                              35

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      Primer 6

<400> SEQUENCE: 10
cgcgactagt ggatccctac ttgtcgtcgt cgtccttgta gtcggctgcg gcgggctcca   60
cgg                                                                 63

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer 7

<400> SEQUENCE: 11
ccggaattcg ccaccatgcc gccaccgccc gggc                               34

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: Synthetic
      Primer 8

<400> SEQUENCE: 12
gccggatccc tacttgtcgt cgtcgtcctt gtagtcggct gtgacgtgct ccac         54

<210> SEQ ID NO 13
<211> LENGTH: 2025
<212> TYPE: DNA
<213> ORGANISM: Rattus norvegicus
<220> FEATURE:
<221> NAME/KEY: CDS
<222> LOCATION: (1)..(2022)
```

```
<400> SEQUENCE: 13 atg ccg cca ccg ccc ggg ccc acc gcc gcc ctg ggc act gcg ctt ctg       48
Met Pro Pro Pro Gly Pro Thr Ala Ala Leu Gly Thr Ala Leu Leu
1               5                   10                  15 ctg ctc ctg ctg gcc tcc gag tct tcg cac act gtg ctg ttg cgg gcg       96
Leu Leu Leu Leu Ala Ser Glu Ser Ser His Thr Val Leu Leu Arg Ala
            20                  25                  30 cgt gag gcg gcg cag ttc ctg cgg ccc agg cag cgc gcc tac caa          144
Arg Glu Ala Ala Gln Phe Leu Arg Pro Arg Gln Arg Ala Tyr Gln
        35                  40                  45 gtc ttc gag gag gcc aag cag ggc cac ctg gaa cgg gag tgc gtg gag      192
Val Phe Glu Glu Ala Lys Gln Gly His Leu Glu Arg Glu Cys Val Glu
    50                  55                  60 gag gtg tgc agc aag gag gag gct aga gag gtg ttc gag aac gac ccc      240
Glu Val Cys Ser Lys Glu Glu Ala Arg Glu Val Phe Glu Asn Asp Pro
65              70                  75                  80 gag acg gac tat ttc tat cca aga tat caa gag tgc atg agg aaa tat      288
Glu Thr Asp Tyr Phe Tyr Pro Arg Tyr Gln Glu Cys Met Arg Lys Tyr
                85                  90                  95 ggc cgg ccc gaa gat aaa aac cca aat ttc gcc acc tgt gtt aag aac      336
Gly Arg Pro Glu Asp Lys Asn Pro Asn Phe Ala Thr Cys Val Lys Asn
            100                 105                 110 tta cct gac caa tgc acc cca aac ccc tgt gat aag aag ggc act caa      384
Leu Pro Asp Gln Cys Thr Pro Asn Pro Cys Asp Lys Lys Gly Thr Gln
        115                 120                 125 ctc tgc caa gac ctc atg ggc aac ttc ttc tgc ttg tgc aaa gat ggc      432
Leu Cys Gln Asp Leu Met Gly Asn Phe Phe Cys Leu Cys Lys Asp Gly
    130                 135                 140 tgg gga ggc cgg ctc tgt gac aaa gat gtc aac gag tgt agt cag aag      480
Trp Gly Gly Arg Leu Cys Asp Lys Asp Val Asn Glu Cys Ser Gln Lys
145                 150                 155                 160 aat ggg ggc tgc agc cag gtc tgc cat aac aaa cca gga agc ttc caa      528
Asn Gly Gly Cys Ser Gln Val Cys His Asn Lys Pro Gly Ser Phe Gln
                165                 170                 175 tgt gcc tgc cac agt ggc ttc tca ctt caa tca gac aac aag agc tgc      576
Cys Ala Cys His Ser Gly Phe Ser Leu Gln Ser Asp Asn Lys Ser Cys
            180                 185                 190 caa gat ata gat gaa tgc aca gac tca gac acc tgt ggg gat gcg cgt      624
Gln Asp Ile Asp Glu Cys Thr Asp Ser Asp Thr Cys Gly Asp Ala Arg
        195                 200                 205 tgc aag aac ctt ccg ggc tcc tac tcc tgc ctc tgc gac aag ggg tac      672
Cys Lys Asn Leu Pro Gly Ser Tyr Ser Cys Leu Cys Asp Lys Gly Tyr
    210                 215                 220 act tac agc tcc aag gag aag acc tgc caa gat gtg gat gag tgc cag      720
Thr Tyr Ser Ser Lys Glu Lys Thr Cys Gln Asp Val Asp Glu Cys Gln
225                 230                 235                 240 cag gac cgt tgt gag cag acc tgt gtc aac tcc cca ggc agc tat acc      768
Gln Asp Arg Cys Glu Gln Thr Cys Val Asn Ser Pro Gly Ser Tyr Thr
                245                 250                 255 tgc cac tgt aat ggg cgc ggg gga cta aaa ctg tcc cca gac atg gat      816
Cys His Cys Asn Gly Arg Gly Gly Leu Lys Leu Ser Pro Asp Met Asp
            260                 265                 270 acc tgt gag gac atc tta ccg tgt gtg ccc ttc agc atg gcc aag agc      864
Thr Cys Glu Asp Ile Leu Pro Cys Val Pro Phe Ser Met Ala Lys Ser
        275                 280                 285 gtc aag tcc ttg tac ctg ggc cgc atg ttc agc ggg acc ccc gtg att      912
Val Lys Ser Leu Tyr Leu Gly Arg Met Phe Ser Gly Thr Pro Val Ile
    290                 295                 300 aga cta cgc ttc aag agg ctc cag cct acc agg ctg ctg gcc gaa ttt      960
Arg Leu Arg Phe Lys Arg Leu Gln Pro Thr Arg Leu Leu Ala Glu Phe
```

```
Arg Leu Arg Phe Lys Arg Leu Gln Pro Thr Arg Leu Leu Ala Glu Phe
305                 310                 315                 320 gac ttc cgt act ttt gac cct gag gga gtc ctc ttc ttc gcc gga ggt    1008
Asp Phe Arg Thr Phe Asp Pro Glu Gly Val Leu Phe Phe Ala Gly Gly
                325                 330                 335 cgc tcg gat agc acc tgg atc gtc ctg ggc ttc agg gct ggg cga ctt    1056
Arg Ser Asp Ser Thr Trp Ile Val Leu Gly Phe Arg Ala Gly Arg Leu
                340                 345                 350 gag ttg cag cta cgg tac aat ggc gtt gga cgc atc acc agc agt ggg    1104
Glu Leu Gln Leu Arg Tyr Asn Gly Val Gly Arg Ile Thr Ser Ser Gly
                355                 360                 365 cca acc atc aac cac ggc atg tgg caa acg atc tct gtg gaa gaa ctg    1152
Pro Thr Ile Asn His Gly Met Trp Gln Thr Ile Ser Val Glu Glu Leu
            370                 375                 380 gac cgc aac ctt gtc atc aag gtc aac aaa gat gcc gtg atg aag att    1200
Asp Arg Asn Leu Val Ile Lys Val Asn Lys Asp Ala Val Met Lys Ile
385                 390                 395                 400 gcg gtg gct ggg ggc ctg ttc cag cta gag aga ggc ctg tac cac ctg    1248
Ala Val Ala Gly Gly Leu Phe Gln Leu Glu Arg Gly Leu Tyr His Leu
                405                 410                 415 aat ctc act gtg ggg ggc att ccc ttc aag gag agt gac ctc gtc cag    1296
Asn Leu Thr Val Gly Gly Ile Pro Phe Lys Glu Ser Asp Leu Val Gln
                420                 425                 430 ccg att aac cct cgc ctg gac ggg tgc atg agg agc tgg aac tgg ctg    1344
Pro Ile Asn Pro Arg Leu Asp Gly Cys Met Arg Ser Trp Asn Trp Leu
                435                 440                 445 aat ggg gaa gac agt gcc att cag gaa acg gtc aag gcc aat aca aaa    1392
Asn Gly Glu Asp Ser Ala Ile Gln Glu Thr Val Lys Ala Asn Thr Lys
450                 455                 460 atg cag tgc ttc tct gtg aca gag agg ggc tcc ttc ttc ccg ggg aat    1440
Met Gln Cys Phe Ser Val Thr Glu Arg Gly Ser Phe Phe Pro Gly Asn
465                 470                 475                 480 gga ttt gcc ttc tat agc ctc aac tac acc cgg aca tcg ctg gat gtc    1488
Gly Phe Ala Phe Tyr Ser Leu Asn Tyr Thr Arg Thr Ser Leu Asp Val
                485                 490                 495 ggc acg gaa acc acc tgg gaa gta gaa gtc gtg gct cgc att cgc cct    1536
Gly Thr Glu Thr Thr Trp Glu Val Glu Val Val Ala Arg Ile Arg Pro
                500                 505                 510 gcc act gac acg ggg gtg ctg atg gca ctg gtg ggg gac aaa gac gtc    1584
Ala Thr Asp Thr Gly Val Leu Met Ala Leu Val Gly Asp Lys Asp Val
                515                 520                 525 gtc ctc ctc tct gtg gcc ctg gtc gac tac cac tcc aca aag aag ctc    1632
Val Leu Leu Ser Val Ala Leu Val Asp Tyr His Ser Thr Lys Lys Leu
530                 535                 540 aag aag cag ctg gtg gtc ctg gca gtt gag aat gtt gcc ctg gcc ctg    1680
Lys Lys Gln Leu Val Val Leu Ala Val Glu Asn Val Ala Leu Ala Leu
545                 550                 555                 560 atg gaa atc aag gtg tgc gac agc cag gaa cac act gtc act gtc tcc    1728
Met Glu Ile Lys Val Cys Asp Ser Gln Glu His Thr Val Thr Val Ser
                565                 570                 575 ctg cgg gat ggc gag gcc acc ctg gaa gtg gat ggt acc aag ggc cag    1776
Leu Arg Asp Gly Glu Ala Thr Leu Glu Val Asp Gly Thr Lys Gly Gln
                580                 585                 590 agc gaa gtg agc acc gca cag ctg cag gag cga ctg gac ctg ctt aag    1824
Ser Glu Val Ser Thr Ala Gln Leu Gln Glu Arg Leu Asp Leu Leu Lys
                595                 600                 605 aca cgt ctg caa ggc tcc gtg ctc acc ttt gtg ggg ggc ctg cca gat    1872
Thr Arg Leu Gln Gly Ser Val Leu Thr Phe Val Gly Gly Leu Pro Asp
610                 615                 620
```

```
gta caa gtg act tcc aca ccc gtc acg gcg ttc tac cgt gga tgc atg    1920
Val Gln Val Thr Ser Thr Pro Val Thr Ala Phe Tyr Arg Gly Cys Met
625             630                 635                 640 act ctg gag gta aac ggg aag acc ctg gac ctg gat acg gcc tcc tac    1968
Thr Leu Glu Val Asn Gly Lys Thr Leu Asp Leu Asp Thr Ala Ser Tyr
                645                 650                 655 aag cac agt gac atc acc tcc cac tcc tgc ccg cct gtg gag cac gtc    2016
Lys His Ser Asp Ile Thr Ser His Ser Cys Pro Pro Val Glu His Val
            660                 665                 670 aca gcc tag                                                        2025
Thr Ala

<210> SEQ ID NO 14
<211> LENGTH: 674
<212> TYPE: PRT
<213> ORGANISM: Rattus norvegicus

<400> SEQUENCE: 14

Met Pro Pro Pro Gly Pro Thr Ala Ala Leu Gly Thr Ala Leu Leu
1               5                   10                  15

Leu Leu Leu Leu Ala Ser Glu Ser Ser His Thr Val Leu Leu Arg Ala
                20                  25                  30

Arg Glu Ala Ala Gln Phe Leu Arg Pro Arg Gln Arg Ala Tyr Gln
            35                  40                  45

Val Phe Glu Glu Ala Lys Gln Gly His Leu Glu Arg Glu Cys Val Glu
50                  55                  60

Glu Val Cys Ser Lys Glu Glu Ala Arg Glu Val Phe Glu Asn Asp Pro
65                  70                  75                  80

Glu Thr Asp Tyr Phe Tyr Pro Arg Tyr Gln Glu Cys Met Arg Lys Tyr
                85                  90                  95

Gly Arg Pro Glu Asp Lys Asn Pro Asn Phe Ala Thr Cys Val Lys Asn
            100                 105                 110

Leu Pro Asp Gln Cys Thr Pro Asn Pro Cys Asp Lys Lys Gly Thr Gln
        115                 120                 125

Leu Cys Gln Asp Leu Met Gly Asn Phe Phe Cys Leu Cys Lys Asp Gly
    130                 135                 140

Trp Gly Gly Arg Leu Cys Asp Lys Asp Val Asn Glu Cys Ser Gln Lys
145                 150                 155                 160

Asn Gly Gly Cys Ser Gln Val Cys His Asn Lys Pro Gly Ser Phe Gln
                165                 170                 175

Cys Ala Cys His Ser Gly Phe Ser Leu Gln Ser Asp Asn Lys Ser Cys
            180                 185                 190

Gln Asp Ile Asp Glu Cys Thr Asp Ser Asp Thr Cys Gly Asp Ala Arg
        195                 200                 205

Cys Lys Asn Leu Pro Gly Ser Tyr Ser Cys Leu Cys Lys Gly Tyr
    210                 215                 220

Thr Tyr Ser Ser Lys Glu Lys Thr Cys Gln Asp Val Asp Glu Cys Gln
225                 230                 235                 240

Gln Asp Arg Cys Glu Gln Thr Cys Val Asn Ser Pro Gly Ser Tyr Thr
                245                 250                 255

Cys His Cys Asn Gly Arg Gly Leu Lys Leu Ser Pro Asp Met Asp
            260                 265                 270

Thr Cys Glu Asp Ile Leu Pro Cys Val Pro Phe Ser Met Ala Lys Ser
        275                 280                 285

Val Lys Ser Leu Tyr Leu Gly Arg Met Phe Ser Gly Thr Pro Val Ile
    290                 295                 300
```

Arg Leu Arg Phe Lys Arg Leu Gln Pro Thr Arg Leu Leu Ala Glu Phe
305                 310                 315                 320

Asp Phe Arg Thr Phe Asp Pro Glu Gly Val Leu Phe Phe Ala Gly Gly
            325                 330                 335

Arg Ser Asp Ser Thr Trp Ile Val Leu Gly Phe Arg Ala Gly Arg Leu
            340                 345                 350

Glu Leu Gln Leu Arg Tyr Asn Gly Val Gly Arg Ile Thr Ser Ser Gly
            355                 360                 365

Pro Thr Ile Asn His Gly Met Trp Gln Thr Ile Ser Val Glu Glu Leu
    370                 375                 380

Asp Arg Asn Leu Val Ile Lys Val Asn Lys Asp Ala Val Met Lys Ile
385                 390                 395                 400

Ala Val Ala Gly Gly Leu Phe Gln Leu Glu Arg Gly Leu Tyr His Leu
            405                 410                 415

Asn Leu Thr Val Gly Gly Ile Pro Phe Lys Glu Ser Asp Leu Val Gln
            420                 425                 430

Pro Ile Asn Pro Arg Leu Asp Gly Cys Met Arg Ser Trp Asn Trp Leu
            435                 440                 445

Asn Gly Glu Asp Ser Ala Ile Gln Glu Thr Val Lys Ala Asn Thr Lys
450                 455                 460

Met Gln Cys Phe Ser Val Thr Glu Arg Gly Ser Phe Phe Pro Gly Asn
465                 470                 475                 480

Gly Phe Ala Phe Tyr Ser Leu Asn Tyr Thr Arg Thr Ser Leu Asp Val
            485                 490                 495

Gly Thr Glu Thr Thr Trp Glu Val Glu Val Val Ala Arg Ile Arg Pro
            500                 505                 510

Ala Thr Asp Thr Gly Val Leu Met Ala Leu Val Gly Asp Lys Asp Val
            515                 520                 525

Val Leu Leu Ser Val Ala Leu Val Asp Tyr His Ser Thr Lys Lys Leu
530                 535                 540

Lys Lys Gln Leu Val Val Leu Ala Val Glu Asn Val Ala Leu Ala Leu
545                 550                 555                 560

Met Glu Ile Lys Val Cys Asp Ser Gln Glu His Thr Val Thr Val Ser
                565                 570                 575

Leu Arg Asp Gly Glu Ala Thr Leu Glu Val Asp Gly Thr Lys Gly Gln
            580                 585                 590

Ser Glu Val Ser Thr Ala Gln Leu Gln Glu Arg Leu Asp Leu Leu Lys
            595                 600                 605

Thr Arg Leu Gln Gly Ser Val Leu Thr Phe Val Gly Gly Leu Pro Asp
    610                 615                 620

Val Gln Val Thr Ser Thr Pro Val Thr Ala Phe Tyr Arg Gly Cys Met
625                 630                 635                 640

Thr Leu Glu Val Asn Gly Lys Thr Leu Asp Leu Asp Thr Ala Ser Tyr
            645                 650                 655

Lys His Ser Asp Ile Thr Ser His Ser Cys Pro Pro Val Glu His Val
            660                 665                 670

Thr Ala

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic Primer 9

<400> SEQUENCE: 15
ggatccctac ttgtcgtcgt cgtccttgta gtcggctgtg acgtgctcca c        51

<210> SEQ ID NO 16
<211> LENGTH: 2025
<212> TYPE: DNA
<213> ORGANISM: Mus musculus
<220> FEATURE:
<221> NAME/KEY: CDS
<222> LOCATION: (1)..(2022)

<400> SEQUENCE: 16

| | | | | | | | | | | | | | | | | |
|---|---|---|---|---|---|---|---|---|---|---|---|---|---|---|---|---|
| atg | ccg | cca | ccg | ccc | ggg | ccc | gcc | gcc | gcc | ctg | ggc | act | gcg | ctt | ctg | 48 |
| Met | Pro | Pro | Pro | Pro | Gly | Pro | Ala | Ala | Ala | Leu | Gly | Thr | Ala | Leu | Leu | |
| 1 | | | | 5 | | | | | 10 | | | | | 15 | | |
| ctg | ctc | ctg | ctg | gct | tcc | gag | tct | tct | cac | act | gtg | ctg | ttg | cgg | gcg | 96 |
| Leu | Leu | Leu | Leu | Ala | Ser | Glu | Ser | Ser | His | Thr | Val | Leu | Leu | Arg | Ala | |
| | | | 20 | | | | | 25 | | | | | 30 | | | |
| cgt | gag | gcg | gcg | cag | ttt | ctg | cgg | ccc | agg | cag | cgc | cgc | gcc | tac | caa | 144 |
| Arg | Glu | Ala | Ala | Gln | Phe | Leu | Arg | Pro | Arg | Gln | Arg | Arg | Ala | Tyr | Gln | |
| | | 35 | | | | | 40 | | | | | 45 | | | | |
| gtc | ttc | gag | gag | gcc | aag | cag | ggc | cac | ctg | gaa | cgg | gag | tgc | gtg | gag | 192 |
| Val | Phe | Glu | Glu | Ala | Lys | Gln | Gly | His | Leu | Glu | Arg | Glu | Cys | Val | Glu | |
| 50 | | | | | 55 | | | | | 60 | | | | | | |
| gag | gtg | tgc | agc | aaa | gag | gag | gcc | aga | gag | gtg | ttc | gag | aac | gac | ccc | 240 |
| Glu | Val | Cys | Ser | Lys | Glu | Glu | Ala | Arg | Glu | Val | Phe | Glu | Asn | Asp | Pro | |
| 65 | | | | 70 | | | | | 75 | | | | | 80 | | |
| gag | acg | gag | tat | ttc | tat | cca | cga | tat | caa | gag | tgc | atg | aga | aaa | tat | 288 |
| Glu | Thr | Glu | Tyr | Phe | Tyr | Pro | Arg | Tyr | Gln | Glu | Cys | Met | Arg | Lys | Tyr | |
| | | | | 85 | | | | | 90 | | | | | 95 | | |
| ggc | agg | cct | gaa | gaa | aaa | aac | cca | gat | ttc | gcc | aaa | tgt | gtt | cag | aac | 336 |
| Gly | Arg | Pro | Glu | Glu | Lys | Asn | Pro | Asp | Phe | Ala | Lys | Cys | Val | Gln | Asn | |
| | | | 100 | | | | | 105 | | | | | 110 | | | |
| ttg | cct | gac | cag | tgc | acc | cca | aac | cct | tgt | gat | aag | aag | ggt | act | cat | 384 |
| Leu | Pro | Asp | Gln | Cys | Thr | Pro | Asn | Pro | Cys | Asp | Lys | Lys | Gly | Thr | His | |
| | | 115 | | | | | 120 | | | | | 125 | | | | |
| atc | tgc | caa | gac | ctc | atg | ggc | aac | ttc | ttc | tgc | gtg | tgc | aca | gat | ggc | 432 |
| Ile | Cys | Gln | Asp | Leu | Met | Gly | Asn | Phe | Phe | Cys | Val | Cys | Thr | Asp | Gly | |
| 130 | | | | | 135 | | | | | 140 | | | | | | |
| tgg | gga | ggc | cgg | ctc | tgt | gac | aaa | gat | gtc | aat | gag | tgt | gtc | cag | aag | 480 |
| Trp | Gly | Gly | Arg | Leu | Cys | Asp | Lys | Asp | Val | Asn | Glu | Cys | Val | Gln | Lys | |
| 145 | | | | 150 | | | | | 155 | | | | | 160 | | |
| aat | ggg | ggc | tgc | agc | cag | gtc | tgc | cac | aac | aaa | cca | gga | agc | ttc | caa | 528 |
| Asn | Gly | Gly | Cys | Ser | Gln | Val | Cys | His | Asn | Lys | Pro | Gly | Ser | Phe | Gln | |
| | | | 165 | | | | | 170 | | | | | 175 | | | |
| tgt | gcc | tgc | cat | agt | ggc | ttc | tcg | ctt | gca | tca | gac | ggc | cag | acc | tgc | 576 |
| Cys | Ala | Cys | His | Ser | Gly | Phe | Ser | Leu | Ala | Ser | Asp | Gly | Gln | Thr | Cys | |
| | | | 180 | | | | | 185 | | | | | 190 | | | |
| caa | gat | atc | gat | gaa | tgc | aca | gac | tca | gac | acc | tgt | ggg | gac | gcg | cga | 624 |
| Gln | Asp | Ile | Asp | Glu | Cys | Thr | Asp | Ser | Asp | Thr | Cys | Gly | Asp | Ala | Arg | |
| | | 195 | | | | | 200 | | | | | 205 | | | | |
| tgc | aag | aac | ttg | cca | ggc | tcc | tac | tct | tgc | ctc | tgc | gat | gag | gga | tat | 672 |
| Cys | Lys | Asn | Leu | Pro | Gly | Ser | Tyr | Ser | Cys | Leu | Cys | Asp | Glu | Gly | Tyr | |
| 210 | | | | | 215 | | | | | 220 | | | | | | |
| aca | tac | agc | tcc | aag | gag | aag | acc | tgc | caa | gat | gtg | gac | gag | tgc | cag | 720 |
| Thr | Tyr | Ser | Ser | Lys | Glu | Lys | Thr | Cys | Gln | Asp | Val | Asp | Glu | Cys | Gln | |
| 225 | | | | 230 | | | | | 235 | | | | | 240 | | |
| cag | gat | cgc | tgt | gag | cag | acc | tgt | gtc | aac | tcc | cca | ggc | agc | tat | acc | 768 |
| Gln | Asp | Arg | Cys | Glu | Gln | Thr | Cys | Val | Asn | Ser | Pro | Gly | Ser | Tyr | Thr | |

-continued

```
                    245                 250                 255
tgc cac tgt gat ggg cga ggg ggc cta aaa cta tcc cca gac atg gat    816
Cys His Cys Asp Gly Arg Gly Gly Leu Lys Leu Ser Pro Asp Met Asp
        260                 265                 270 act tgt gag gac atc tta cca tgt gtg ccc ttc agc atg gcc aag agc    864
Thr Cys Glu Asp Ile Leu Pro Cys Val Pro Phe Ser Met Ala Lys Ser
            275                 280                 285 gtg aag tcc ttg tac ctg ggc cgc atg ttc agc ggg acc ccc gtg att    912
Val Lys Ser Leu Tyr Leu Gly Arg Met Phe Ser Gly Thr Pro Val Ile
290                 295                 300 aga cta cgc ttc aag agg ctt cag cct acc agg ctg ctg gct gaa ttt    960
Arg Leu Arg Phe Lys Arg Leu Gln Pro Thr Arg Leu Leu Ala Glu Phe
305                 310                 315                 320 gac ttc cgc act ttt gac cct gaa gga gtc ctc ttc ttc gct gga ggc   1008
Asp Phe Arg Thr Phe Asp Pro Glu Gly Val Leu Phe Phe Ala Gly Gly
                325                 330                 335 cgt tca gac agc acc tgg att gtc ctg ggc cta aga gct ggg cgg ctt   1056
Arg Ser Asp Ser Thr Trp Ile Val Leu Gly Leu Arg Ala Gly Arg Leu
            340                 345                 350 gag ctg cag ctt cgg tac aat ggc gtt ggg cgc atc acc agc agc ggg   1104
Glu Leu Gln Leu Arg Tyr Asn Gly Val Gly Arg Ile Thr Ser Ser Gly
355                 360                 365 cca acc atc aac cac ggc atg tgg caa act atc tcc gtg gaa gag ctg   1152
Pro Thr Ile Asn His Gly Met Trp Gln Thr Ile Ser Val Glu Glu Leu
370                 375                 380 gaa cgt aac ctt gtc atc aag gtc aac aaa gat gct gta atg aag atc   1200
Glu Arg Asn Leu Val Ile Lys Val Asn Lys Asp Ala Val Met Lys Ile
385                 390                 395                 400 gcg gta gct ggg gag ctg ttt cag ctg gag agg ggc ctc tat cac ctg   1248
Ala Val Ala Gly Glu Leu Phe Gln Leu Glu Arg Gly Leu Tyr His Leu
                405                 410                 415 aat ctc acc gtg ggc ggc att ccc ttc aag gag agt gag ctc gtc cag   1296
Asn Leu Thr Val Gly Gly Ile Pro Phe Lys Glu Ser Glu Leu Val Gln
            420                 425                 430 ccg att aac cct cgc ctg gat ggg tgc atg agg agt tgg aac tgg ctg   1344
Pro Ile Asn Pro Arg Leu Asp Gly Cys Met Arg Ser Trp Asn Trp Leu
435                 440                 445 aac ggg gaa gac agc gcc atc cag gag aca gtc aag gca aac aca aaa   1392
Asn Gly Glu Asp Ser Ala Ile Gln Glu Thr Val Lys Ala Asn Thr Lys
450                 455                 460 atg cag tgc ttc tct gtg aca gaa agg ggc tcc ttc ttc ccg ggg aat   1440
Met Gln Cys Phe Ser Val Thr Glu Arg Gly Ser Phe Phe Pro Gly Asn
465                 470                 475                 480 gga ttt gct acc tac agg ctc aac tac acc cga aca tcg ctg gat gtc   1488
Gly Phe Ala Thr Tyr Arg Leu Asn Tyr Thr Arg Thr Ser Leu Asp Val
                485                 490                 495 ggc acg gaa acc acc tgg gaa gtt aaa gtt gtg gct cgg atc cgc cct   1536
Gly Thr Glu Thr Thr Trp Glu Val Lys Val Val Ala Arg Ile Arg Pro
            500                 505                 510 gcc acg gac acg ggg gtg ctg ctg gcg ctg gtg ggg gac gac gat gtc   1584
Ala Thr Asp Thr Gly Val Leu Leu Ala Leu Val Gly Asp Asp Asp Val
515                 520                 525 gtc ccc atc tct gtg gcc cta gtc gac tac cac tct aca aag aag ctc   1632
Val Pro Ile Ser Val Ala Leu Val Asp Tyr His Ser Thr Lys Lys Leu
530                 535                 540 aag aag cag ttg gtg gtc ctg gca gtt gag gat gtt gcc ctg gca ctg   1680
Lys Lys Gln Leu Val Val Leu Ala Val Glu Asp Val Ala Leu Ala Leu
545                 550                 555                 560 atg gaa atc aag gtg tgc gac agc cag gaa cac acg gtc act gtc tcc   1728
```

```
                                                                                        1776
ctg cgg gag ggt gag gcc acc cta gaa gtg gat ggc aca aag ggc cag
Leu Arg Glu Gly Glu Ala Thr Leu Glu Val Asp Gly Thr Lys Gly Gln
        580                 585                 590

1824
agt gaa gtg agc act gcc cag ctg cag gag cga ctg gac aca ctt aag
Ser Glu Val Ser Thr Ala Gln Leu Gln Glu Arg Leu Asp Thr Leu Lys
    595                 600                 605

1872
aca cat ctg caa ggc tct gtg cac acc tat gtt gga ggc ctg cca gaa
Thr His Leu Gln Gly Ser Val His Thr Tyr Val Gly Gly Leu Pro Glu
610                 615                 620

1920
gta tcg gtg att tct gca ccc gtc act gcg ttc tac cgc gga tgc atg
Val Ser Val Ile Ser Ala Pro Val Thr Ala Phe Tyr Arg Gly Cys Met
625                 630                 635                 640

1968
act ctg gag gta aac ggg aaa atc ctg gac ctg gat acg gcc tcg tac
Thr Leu Glu Val Asn Gly Lys Ile Leu Asp Leu Asp Thr Ala Ser Tyr
            645                 650                 655

2016
aag cac agt gac atc acc tcc cac tcc tgc ccg cct gtg gag cat gcc
Lys His Ser Asp Ile Thr Ser His Ser Cys Pro Pro Val Glu His Ala
        660                 665                 670

2025
acc ccc tag
Thr Pro
```

Met Glu Ile Lys Val Cys Asp Ser Gln Glu His Thr Val Thr Val Ser
                565                 570                 575

<210> SEQ ID NO 17
<211> LENGTH: 674
<212> TYPE: PRT
<213> ORGANISM: Mus musculus

<400> SEQUENCE: 17

Met Pro Pro Pro Gly Pro Ala Ala Ala Leu Gly Thr Ala Leu Leu
1               5                   10                  15

Leu Leu Leu Leu Ala Ser Glu Ser Ser His Thr Val Leu Leu Arg Ala
                20                  25                  30

Arg Glu Ala Ala Gln Phe Leu Arg Pro Arg Gln Arg Arg Ala Tyr Gln
            35                  40                  45

Val Phe Glu Glu Ala Lys Gln Gly His Leu Glu Arg Glu Cys Val Glu
    50                  55                  60

Glu Val Cys Ser Lys Glu Glu Ala Arg Glu Val Phe Glu Asn Asp Pro
65                  70                  75                  80

Glu Thr Glu Tyr Phe Tyr Pro Arg Tyr Gln Glu Cys Met Arg Lys Tyr
                85                  90                  95

Gly Arg Pro Glu Glu Lys Asn Pro Asp Phe Ala Lys Cys Val Gln Asn
            100                 105                 110

Leu Pro Asp Gln Cys Thr Pro Asn Pro Cys Asp Lys Lys Gly Thr His
    115                 120                 125

Ile Cys Gln Asp Leu Met Gly Asn Phe Phe Cys Val Cys Thr Asp Gly
130                 135                 140

Trp Gly Gly Arg Leu Cys Asp Lys Asp Val Asn Glu Cys Val Gln Lys
145                 150                 155                 160

Asn Gly Gly Cys Ser Gln Val Cys His Asn Lys Pro Gly Ser Phe Gln
                165                 170                 175

Cys Ala Cys His Ser Gly Phe Ser Leu Ala Ser Asp Gly Gln Thr Cys
            180                 185                 190

Gln Asp Ile Asp Glu Cys Thr Asp Ser Asp Thr Cys Gly Asp Ala Arg
    195                 200                 205

Cys Lys Asn Leu Pro Gly Ser Tyr Ser Cys Leu Cys Asp Glu Gly Tyr
210                 215                 220

-continued

```
Thr Tyr Ser Ser Lys Glu Lys Thr Cys Gln Asp Val Asp Glu Cys Gln
225                 230                 235                 240

Gln Asp Arg Cys Glu Gln Thr Cys Val Asn Ser Pro Gly Ser Tyr Thr
            245                 250                 255

Cys His Cys Asp Gly Arg Gly Leu Lys Leu Ser Pro Asp Met Asp
        260                 265                 270

Thr Cys Glu Asp Ile Leu Pro Cys Val Pro Phe Ser Met Ala Lys Ser
        275                 280                 285

Val Lys Ser Leu Tyr Leu Gly Arg Met Phe Ser Gly Thr Pro Val Ile
    290                 295                 300

Arg Leu Arg Phe Lys Arg Leu Gln Pro Thr Arg Leu Leu Ala Glu Phe
305                 310                 315                 320

Asp Phe Arg Thr Phe Asp Pro Glu Gly Val Leu Phe Phe Ala Gly Gly
                325                 330                 335

Arg Ser Asp Ser Thr Trp Ile Val Leu Gly Leu Arg Ala Gly Arg Leu
            340                 345                 350

Glu Leu Gln Leu Arg Tyr Asn Gly Val Gly Arg Ile Thr Ser Ser Gly
            355                 360                 365

Pro Thr Ile Asn His Gly Met Trp Gln Thr Ile Ser Val Glu Glu Leu
370                 375                 380

Glu Arg Asn Leu Val Ile Lys Val Asn Lys Asp Ala Val Met Lys Ile
385                 390                 395                 400

Ala Val Ala Gly Glu Leu Phe Gln Leu Glu Arg Gly Leu Tyr His Leu
                405                 410                 415

Asn Leu Thr Val Gly Gly Ile Pro Phe Lys Glu Ser Glu Leu Val Gln
                420                 425                 430

Pro Ile Asn Pro Arg Leu Asp Gly Cys Met Arg Ser Trp Asn Trp Leu
            435                 440                 445

Asn Gly Glu Asp Ser Ala Ile Gln Glu Thr Val Lys Ala Asn Thr Lys
450                 455                 460

Met Gln Cys Phe Ser Val Thr Glu Arg Gly Ser Phe Phe Pro Gly Asn
465                 470                 475                 480

Gly Phe Ala Thr Tyr Arg Leu Asn Tyr Thr Arg Thr Ser Leu Asp Val
                485                 490                 495

Gly Thr Glu Thr Thr Trp Glu Val Lys Val Val Ala Arg Ile Arg Pro
            500                 505                 510

Ala Thr Asp Thr Gly Val Leu Leu Ala Leu Val Gly Asp Asp Asp Val
            515                 520                 525

Val Pro Ile Ser Val Ala Leu Val Asp Tyr His Ser Thr Lys Lys Leu
            530                 535                 540

Lys Lys Gln Leu Val Val Leu Ala Val Glu Asp Val Ala Leu Ala Leu
545                 550                 555                 560

Met Glu Ile Lys Val Cys Asp Ser Gln Glu His Thr Val Thr Val Ser
                565                 570                 575

Leu Arg Glu Gly Glu Ala Thr Leu Glu Val Asp Gly Thr Lys Gly Gln
            580                 585                 590

Ser Glu Val Ser Thr Ala Gln Leu Gln Glu Arg Leu Asp Thr Leu Lys
            595                 600                 605

Thr His Leu Gln Gly Ser Val His Thr Tyr Val Gly Gly Leu Pro Glu
        610                 615                 620

Val Ser Val Ile Ser Ala Pro Val Thr Ala Phe Tyr Arg Gly Cys Met
625                 630                 635                 640
```

```
Thr Leu Glu Val Asn Gly Lys Ile Leu Asp Leu Asp Thr Ala Ser Tyr
            645                 650                 655
Lys His Ser Asp Ile Thr Ser His Ser Cys Pro Pro Val Glu His Ala
        660                 665                 670
Thr Pro
```

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic Primer 10

<400> SEQUENCE: 18
ccgaagcttg ccaccatggg caccacctgg aggagccc        38

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic Primer 11

<400> SEQUENCE: 19
ggcccgggtc agggcttttt gaccttgtgt tctggc        36

<210> SEQ ID NO 20
<211> LENGTH: 486
<212> TYPE: DNA
<213> ORGANISM: Rattus norvegicus
<220> FEATURE:
<221> NAME/KEY: CDS
<222> LOCATION: (1)..(483)

<400> SEQUENCE: 20

```
atg ggc acc acc tgg agg agc cct gga cgt ttg cgg ctt gca cta tgc        48
Met Gly Thr Thr Trp Arg Ser Pro Gly Arg Leu Arg Leu Ala Leu Cys
1               5                   10                  15 ctc gct ggc cta gcc ctc tca ctg tac gca ctg cac gtg aag gcg gcg        96
Leu Ala Gly Leu Ala Leu Ser Leu Tyr Ala Leu His Val Lys Ala Ala
            20                  25                  30 cgc gcc cgc aat gag gat tac cgc gcg ctc tgc gac gtg ggc acg gcc       144
Arg Ala Arg Asn Glu Asp Tyr Arg Ala Leu Cys Asp Val Gly Thr Ala
        35                  40                  45 atc agc tgt tcc cgc gtc ttc tcc tct cgg tgg ggc cgg ggc ttt ggg       192
Ile Ser Cys Ser Arg Val Phe Ser Ser Arg Trp Gly Arg Gly Phe Gly
    50                  55                  60 ctg gtg gag cat gtg tta gga gct gac agc atc ctc aac caa tcc aac       240
Leu Val Glu His Val Leu Gly Ala Asp Ser Ile Leu Asn Gln Ser Asn
65                  70                  75                  80 agc ata ttt ggt tgc atg ttc tac acc ata cag ctg ttg tta ggt tgc       288
Ser Ile Phe Gly Cys Met Phe Tyr Thr Ile Gln Leu Leu Leu Gly Cys
                85                  90                  95 ttg agg gga cgt tgg gcc tct atc cta ctg atc ctg agt tcc ctg gtg       336
Leu Arg Gly Arg Trp Ala Ser Ile Leu Leu Ile Leu Ser Ser Leu Val
            100                 105                 110 tct gtc gct ggt tct ctg tac ctg gcc tgg atc ctg ttc ttt gtc ctg       384
Ser Val Ala Gly Ser Leu Tyr Leu Ala Trp Ile Leu Phe Phe Val Leu
        115                 120                 125 tat gat ttc tgc att gtt tgc atc acc acc tat gcc atc aat gcg ggc       432
Tyr Asp Phe Cys Ile Val Cys Ile Thr Thr Tyr Ala Ile Asn Ala Gly
```

```
      130                 135                 140
ctg atg ttg ctt agc ttc cag aag gtg cca gaa cac aag gtc aaa aag     480
Leu Met Leu Leu Ser Phe Gln Lys Val Pro Glu His Lys Val Lys Lys
145                 150                 155                 160 ccc tga                                                             486
Pro
```

<210> SEQ ID NO 21
<211> LENGTH: 161
<212> TYPE: PRT
<213> ORGANISM: Rattus norvegicus

<400> SEQUENCE: 21

```
Met Gly Thr Thr Trp Arg Ser Pro Gly Arg Leu Arg Leu Ala Leu Cys
1               5                   10                  15

Leu Ala Gly Leu Ala Leu Ser Leu Tyr Ala Leu His Val Lys Ala Ala
            20                  25                  30

Arg Ala Arg Asn Glu Asp Tyr Arg Ala Leu Cys Asp Val Gly Thr Ala
        35                  40                  45

Ile Ser Cys Ser Arg Val Phe Ser Ser Arg Trp Gly Arg Gly Phe Gly
    50                  55                  60

Leu Val Glu His Val Leu Gly Ala Asp Ser Ile Leu Asn Gln Ser Asn
65                  70                  75                  80

Ser Ile Phe Gly Cys Met Phe Tyr Thr Ile Gln Leu Leu Gly Cys
                85                  90                  95

Leu Arg Gly Arg Trp Ala Ser Ile Leu Leu Ile Leu Ser Ser Leu Val
            100                 105                 110

Ser Val Ala Gly Ser Leu Tyr Leu Ala Trp Ile Leu Phe Phe Val Leu
        115                 120                 125

Tyr Asp Phe Cys Ile Val Cys Ile Thr Thr Tyr Ala Ile Asn Ala Gly
    130                 135                 140

Leu Met Leu Leu Ser Phe Gln Lys Val Pro Glu His Lys Val Lys Lys
145                 150                 155                 160

Pro
```

<210> SEQ ID NO 22
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer 12

<400> SEQUENCE: 22
cggtcgacgc caccatggcg gtgtctgccg ggtcc                              35

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer 13

<400> SEQUENCE: 23
ggcccgggtc agaactctga gtggacagga tc                                 32

<210> SEQ ID NO 24
<211> LENGTH: 2277
<212> TYPE: DNA

```
<213> ORGANISM: Homo sapiens
<220> FEATURE:
<221> NAME/KEY: CDS
<222> LOCATION: (1)..(2274)

<400> SEQUENCE: 24 atg gcg gtg tct gcc ggg tcc gcg cgg acc tcg ccc agc tca gat aaa         48
Met Ala Val Ser Ala Gly Ser Ala Arg Thr Ser Pro Ser Ser Asp Lys
1               5                   10                  15 gta cag aaa gac aag gct gaa ctg atc tca ggg ccc agg cag gac agc         96
Val Gln Lys Asp Lys Ala Glu Leu Ile Ser Gly Pro Arg Gln Asp Ser
                20                  25                  30 cga ata ggg aaa ctc ttg ggt ttt gag tgg aca gat ttg tcc agt tgg        144
Arg Ile Gly Lys Leu Leu Gly Phe Glu Trp Thr Asp Leu Ser Ser Trp
            35                  40                  45 cgg agg ctg gtg acc ctg ctg aat cga cca acg gac cct gca agc tta        192
Arg Arg Leu Val Thr Leu Leu Asn Arg Pro Thr Asp Pro Ala Ser Leu
        50                  55                  60 gct gtc ttt cgt ttt ctt ttt ggg ttc ttg atg gtg cta gac att ccc        240
Ala Val Phe Arg Phe Leu Phe Gly Phe Leu Met Val Leu Asp Ile Pro
65                  70                  75                  80 cag gag cgg ggg ctc agc tct ctg gac cgg aaa tac ctt gat ggg ctg        288
Gln Glu Arg Gly Leu Ser Ser Leu Asp Arg Lys Tyr Leu Asp Gly Leu
                85                  90                  95 gat gtg tgc cgc ttc ccc ttg ctg gat gcc cta cgc cca ctg cca ctt        336
Asp Val Cys Arg Phe Pro Leu Leu Asp Ala Leu Arg Pro Leu Pro Leu
                100                 105                 110 gac tgg atg tat ctt gtc tac acc atc atg ttt ctg ggg gca ctg ggc        384
Asp Trp Met Tyr Leu Val Tyr Thr Ile Met Phe Leu Gly Ala Leu Gly
            115                 120                 125 atg atg ctg ggc ctg tgc tac cgg ata agc tgt gtg tta ttc ctg ctg        432
Met Met Leu Gly Leu Cys Tyr Arg Ile Ser Cys Val Leu Phe Leu Leu
        130                 135                 140 cca tac tgg tat gtg ttt ctc ctg gac aag aca tca tgg aac aac cac        480
Pro Tyr Trp Tyr Val Phe Leu Leu Asp Lys Thr Ser Trp Asn Asn His
145                 150                 155                 160 tcc tat ctg tat ggg ttg ttg gcc ttt cag cta aca ttc atg gat gca        528
Ser Tyr Leu Tyr Gly Leu Leu Ala Phe Gln Leu Thr Phe Met Asp Ala
                165                 170                 175 aac cac tac tgg tct gtg gac ggt ctg ctg aat gcc cat agg agg aat        576
Asn His Tyr Trp Ser Val Asp Gly Leu Leu Asn Ala His Arg Arg Asn
                180                 185                 190 gcc cac gtg ccc ctt tgg aac tat gca gtg ctc cgt ggc cag atc ttc        624
Ala His Val Pro Leu Trp Asn Tyr Ala Val Leu Arg Gly Gln Ile Phe
            195                 200                 205 att gtg tac ttc att gcg ggt gtg aaa aag ctg gat gca gac tgg gtt        672
Ile Val Tyr Phe Ile Ala Gly Val Lys Lys Leu Asp Ala Asp Trp Val
        210                 215                 220 gaa ggc tat tcc atg gaa tat ttg tcc cgg cac tgg ctc ttc agt ccc        720
Glu Gly Tyr Ser Met Glu Tyr Leu Ser Arg His Trp Leu Phe Ser Pro
225                 230                 235                 240 ttc aaa ctg ctg ttg tct gag gag ctg act agc ctg ctg gtc gtg cac        768
Phe Lys Leu Leu Leu Ser Glu Glu Leu Thr Ser Leu Leu Val Val His
                245                 250                 255 tgg ggt ggg ctg ctg ctt gac ctc tca gct ggt ttc ctg ctc ttt ttt        816
Trp Gly Gly Leu Leu Leu Asp Leu Ser Ala Gly Phe Leu Leu Phe Phe
                260                 265                 270 gat gtc tca aga tcc att ggc ctg ttc ttt gtg tcc tac ttc cac tgc        864
Asp Val Ser Arg Ser Ile Gly Leu Phe Phe Val Ser Tyr Phe His Cys
            275                 280                 285
```

```
atg aat tcc cag ctt ttc agc att ggt atg ttc tcc tac gtc atg ctg      912
Met Asn Ser Gln Leu Phe Ser Ile Gly Met Phe Ser Tyr Val Met Leu
    290                 295                 300 gcc agc agc cct ctc ttc tgc tcc cct gag tgg cct cgg aag ctg gtg      960
Ala Ser Ser Pro Leu Phe Cys Ser Pro Glu Trp Pro Arg Lys Leu Val
305                 310                 315                 320 tcc tac tgc ccc cga agg ttg caa caa ctg ttg ccc ctc aag gca gcc     1008
Ser Tyr Cys Pro Arg Arg Leu Gln Gln Leu Leu Pro Leu Lys Ala Ala
                325                 330                 335 cct cag ccc agt gtt tcc tgt gtg tat aag agg agc cgg ggc aaa agt     1056
Pro Gln Pro Ser Val Ser Cys Val Tyr Lys Arg Ser Arg Gly Lys Ser
            340                 345                 350 ggc cag aag cca ggg ctg cgc cat cag ctg gga gct gcc ttc acc ctg     1104
Gly Gln Lys Pro Gly Leu Arg His Gln Leu Gly Ala Ala Phe Thr Leu
        355                 360                 365 ctc tac ctc ctg gag cag cta ttc ctg ccc tat tct cat ttt ctc acc     1152
Leu Tyr Leu Leu Glu Gln Leu Phe Leu Pro Tyr Ser His Phe Leu Thr
    370                 375                 380 cag ggc tat aac aac tgg aca aat ggg ctg tat ggc tat tcc tgg gac     1200
Gln Gly Tyr Asn Asn Trp Thr Asn Gly Leu Tyr Gly Tyr Ser Trp Asp
385                 390                 395                 400 atg atg gtg cac tcc cgc tcc cac cag cac gtg aag atc acc tac cgt     1248
Met Met Val His Ser Arg Ser His Gln His Val Lys Ile Thr Tyr Arg
                405                 410                 415 gat ggc cgc act ggc gaa ctg ggc tac ctt aac cct ggg gta ttt aca     1296
Asp Gly Arg Thr Gly Glu Leu Gly Tyr Leu Asn Pro Gly Val Phe Thr
            420                 425                 430 cag agt cgg cga tgg aag gat cat gca gac atg ctg aag caa tat gcc     1344
Gln Ser Arg Arg Trp Lys Asp His Ala Asp Met Leu Lys Gln Tyr Ala
        435                 440                 445 act tgc ctg agc cgc ctg ctt ccc aag tat aat gtc act gag ccc cag     1392
Thr Cys Leu Ser Arg Leu Leu Pro Lys Tyr Asn Val Thr Glu Pro Gln
    450                 455                 460 atc tac ttt gat att tgg gtc tcc atc aat gac cgc ttc cag cag agg     1440
Ile Tyr Phe Asp Ile Trp Val Ser Ile Asn Asp Arg Phe Gln Gln Arg
465                 470                 475                 480 att ttt gac cct cgt gtg gac atc gtg cag gcc gct tgg tca ccc ttt     1488
Ile Phe Asp Pro Arg Val Asp Ile Val Gln Ala Ala Trp Ser Pro Phe
                485                 490                 495 cag cgc aca tcc tgg gtg caa cca ctc ttg atg gac ctg tct ccc tgg     1536
Gln Arg Thr Ser Trp Val Gln Pro Leu Leu Met Asp Leu Ser Pro Trp
            500                 505                 510 agg gcc aag tta cag gaa atc aag agc agc cta gac aac cac act gag     1584
Arg Ala Lys Leu Gln Glu Ile Lys Ser Ser Leu Asp Asn His Thr Glu
        515                 520                 525 gtg gtc ttc att gca gat ttc cct gga ctg cac ttg gag aat ttt gtg     1632
Val Val Phe Ile Ala Asp Phe Pro Gly Leu His Leu Glu Asn Phe Val
    530                 535                 540 agt gaa gac ctg ggc aac act agc atc cag ctg ctg cag ggg gaa gtg     1680
Ser Glu Asp Leu Gly Asn Thr Ser Ile Gln Leu Leu Gln Gly Glu Val
545                 550                 555                 560 act gtg gag ctt gtg gca gaa cag aag aac cag act ctt cga gag gga     1728
Thr Val Glu Leu Val Ala Glu Gln Lys Asn Gln Thr Leu Arg Glu Gly
                565                 570                 575 gaa aaa atg cag ttg cct gct ggt gag tac cat aag gtg tat acg aca     1776
Glu Lys Met Gln Leu Pro Ala Gly Glu Tyr His Lys Val Tyr Thr Thr
            580                 585                 590 tca cct agc cct tct tgc tac atg tac gtc tat gtc aac act aca gag     1824
Ser Pro Ser Pro Ser Cys Tyr Met Tyr Val Tyr Val Asn Thr Thr Glu
        595                 600                 605
```

| | | | | | | | | | | | | | | | |
|---|---|---|---|---|---|---|---|---|---|---|---|---|---|---|---|
| ctt | gca | ctg | gag | caa | gac | ctg | gca | tat | ctg | caa | gaa | tta | aag | gaa aag | 1872 |
| Leu | Ala | Leu | Glu | Gln | Asp | Leu | Ala | Tyr | Leu | Gln | Glu | Leu | Lys | Glu Lys | |
| | | 610 | | | | | 615 | | | | | 620 | | | |
| gtg | gag | aat | gga | agt | gaa | aca | ggg | cct | cta | ccc | cca | gag | ctg | cag cct | 1920 |
| Val | Glu | Asn | Gly | Ser | Glu | Thr | Gly | Pro | Leu | Pro | Pro | Glu | Leu | Gln Pro | |
| 625 | | | | | 630 | | | | | 635 | | | | 640 | |
| ctg | ttg | gaa | ggg | gaa | gta | aaa | ggg | ggc | cct | gag | cca | aca | cct | ctg gtt | 1968 |
| Leu | Leu | Glu | Gly | Glu | Val | Lys | Gly | Gly | Pro | Glu | Pro | Thr | Pro | Leu Val | |
| | | | | 645 | | | | | 650 | | | | | 655 | |
| cag | acc | ttt | ctt | aga | cgc | caa | caa | agg | ctc | cag | gag | att | gaa | cgc cgg | 2016 |
| Gln | Thr | Phe | Leu | Arg | Arg | Gln | Gln | Arg | Leu | Gln | Glu | Ile | Glu | Arg Arg | |
| | | | 660 | | | | | 665 | | | | | 670 | | |
| cga | aat | act | cct | ttc | cat | gag | cga | ttc | ttc | cgc | ttc | ttg | ttg | cga aag | 2064 |
| Arg | Asn | Thr | Pro | Phe | His | Glu | Arg | Phe | Phe | Arg | Phe | Leu | Leu | Arg Lys | |
| | | 675 | | | | | 680 | | | | | 685 | | | |
| ctc | tat | gtc | ttt | cgc | cgc | agc | ttc | ctg | atg | act | tgt | atc | tca | ctt cga | 2112 |
| Leu | Tyr | Val | Phe | Arg | Arg | Ser | Phe | Leu | Met | Thr | Cys | Ile | Ser | Leu Arg | |
| | | | 690 | | | | | 695 | | | | | 700 | | |
| aat | ctg | ata | tta | ggc | cgt | cct | tcc | ctg | gag | cag | ctg | gcc | cag | gag gtg | 2160 |
| Asn | Leu | Ile | Leu | Gly | Arg | Pro | Ser | Leu | Glu | Gln | Leu | Ala | Gln | Glu Val | |
| 705 | | | | | 710 | | | | | 715 | | | | 720 | |
| act | tat | gca | aac | ttg | aga | ccc | ttt | gag | gca | gtt | gga | gaa | ctg | aat ccc | 2208 |
| Thr | Tyr | Ala | Asn | Leu | Arg | Pro | Phe | Glu | Ala | Val | Gly | Glu | Leu | Asn Pro | |
| | | | | 725 | | | | | 730 | | | | | 735 | |
| tca | aac | acg | gat | tct | tca | cat | tct | aat | cct | cct | gag | tca | aat | cct gat | 2256 |
| Ser | Asn | Thr | Asp | Ser | Ser | His | Ser | Asn | Pro | Pro | Glu | Ser | Asn | Pro Asp | |
| | | | 740 | | | | | 745 | | | | | 750 | | |
| cct | gtc | cac | tca | gag | ttc | tga | | | | | | | | | 2277 |
| Pro | Val | His | Ser | Glu | Phe | | | | | | | | | | |
| | | | 755 | | | | | | | | | | | | |

<210> SEQ ID NO 25
<211> LENGTH: 758
<212> TYPE: PRT
<213> ORGANISM: Homo sapiens

<400> SEQUENCE: 25

Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

Arg Ile Gly Lys Leu Leu Gly Phe Glu Trp Thr Asp Leu Ser Ser Trp
        35                  40                  45

Arg Arg Leu Val Thr Leu Leu Asn Arg Pro Thr Asp Pro Ala Ser Leu
    50                  55                  60

Ala Val Phe Arg Phe Leu Phe Gly Phe Leu Met Val Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Ile Ser Cys Val Leu Phe Leu Leu
130                 135                 140

Pro Tyr Trp Tyr Val Phe Leu Leu Asp Lys Thr Ser Trp Asn Asn His
145                 150                 155                 160

```
Ser Tyr Leu Tyr Gly Leu Leu Ala Phe Gln Leu Thr Phe Met Asp Ala
            165                 170                 175

Asn His Tyr Trp Ser Val Asp Gly Leu Leu Asn Ala His Arg Arg Asn
        180                 185                 190

Ala His Val Pro Leu Trp Asn Tyr Ala Val Leu Arg Gly Gln Ile Phe
        195                 200                 205

Ile Val Tyr Phe Ile Ala Gly Val Lys Lys Leu Asp Ala Asp Trp Val
    210                 215                 220

Glu Gly Tyr Ser Met Glu Tyr Leu Ser Arg His Trp Leu Phe Ser Pro
225                 230                 235                 240

Phe Lys Leu Leu Leu Ser Glu Glu Leu Thr Ser Leu Leu Val Val His
                245                 250                 255

Trp Gly Gly Leu Leu Leu Asp Leu Ser Ala Gly Phe Leu Leu Phe Phe
            260                 265                 270

Asp Val Ser Arg Ser Ile Gly Leu Phe Phe Val Ser Tyr Phe His Cys
        275                 280                 285

Met Asn Ser Gln Leu Phe Ser Ile Gly Met Phe Ser Tyr Val Met Leu
    290                 295                 300

Ala Ser Ser Pro Leu Phe Cys Ser Pro Glu Trp Pro Arg Lys Leu Val
305                 310                 315                 320

Ser Tyr Cys Pro Arg Arg Leu Gln Gln Leu Leu Pro Leu Lys Ala Ala
                325                 330                 335

Pro Gln Pro Ser Val Ser Cys Val Tyr Lys Arg Ser Arg Gly Lys Ser
            340                 345                 350

Gly Gln Lys Pro Gly Leu Arg His Gln Leu Gly Ala Ala Phe Thr Leu
        355                 360                 365

Leu Tyr Leu Leu Glu Gln Leu Phe Leu Pro Tyr Ser His Phe Leu Thr
    370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
                405                 410                 415

Asp Gly Arg Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
    435                 440                 445

Thr Cys Leu Ser Arg Leu Leu Pro Lys Tyr Asn Val Thr Glu Pro Gln
450                 455                 460

Ile Tyr Phe Asp Ile Trp Val Ser Ile Asn Asp Arg Phe Gln Gln Arg
465                 470                 475                 480

Ile Phe Asp Pro Arg Val Asp Ile Val Gln Ala Ala Trp Ser Pro Phe
                485                 490                 495

Gln Arg Thr Ser Trp Val Gln Pro Leu Leu Met Asp Leu Ser Pro Trp
            500                 505                 510

Arg Ala Lys Leu Gln Glu Ile Lys Ser Ser Leu Asp Asn His Thr Glu
    515                 520                 525

Val Val Phe Ile Ala Asp Phe Pro Gly Leu His Leu Glu Asn Phe Val
530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Arg Glu Gly
                565                 570                 575

Glu Lys Met Gln Leu Pro Ala Gly Glu Tyr His Lys Val Tyr Thr Thr
```

-continued

```
                580                 585                 590
Ser Pro Ser Pro Ser Cys Tyr Met Tyr Val Tyr Val Asn Thr Thr Glu
            595                 600                 605

Leu Ala Leu Glu Gln Asp Leu Ala Tyr Leu Gln Glu Leu Lys Glu Lys
            610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Gln Arg Leu Gln Glu Ile Glu Arg Arg
            660                 665                 670

Arg Asn Thr Pro Phe His Glu Arg Phe Phe Arg Phe Leu Leu Arg Lys
            675                 680                 685

Leu Tyr Val Phe Arg Arg Ser Phe Leu Met Thr Cys Ile Ser Leu Arg
            690                 695                 700

Asn Leu Ile Leu Gly Arg Pro Ser Leu Glu Gln Leu Ala Gln Glu Val
705                 710                 715                 720

Thr Tyr Ala Asn Leu Arg Pro Phe Glu Ala Val Gly Glu Leu Asn Pro
                725                 730                 735

Ser Asn Thr Asp Ser Ser His Ser Asn Pro Pro Glu Ser Asn Pro Asp
            740                 745                 750

Pro Val His Ser Glu Phe
            755

<210> SEQ ID NO 26
<211> LENGTH: 2685
<212> TYPE: DNA
<213> ORGANISM: Homo sapiens
<220> FEATURE:
<221> NAME/KEY: CDS
<222> LOCATION: (1)..(2682)

<400> SEQUENCE: 26 atg gcg tgg cgg tgc ccc agg atg ggc agg gtc ccg ctg gcc tgg tgc     48
Met Ala Trp Arg Cys Pro Arg Met Gly Arg Val Pro Leu Ala Trp Cys
1               5                   10                  15 ttg gcg ctg tgc ggc tgg gcg tgc atg gcc ccc agg ggc acg cag gct     96
Leu Ala Leu Cys Gly Trp Ala Cys Met Ala Pro Arg Gly Thr Gln Ala
                20                  25                  30 gaa gaa agt ccc ttc gtg ggc aac cca ggg aat atc aca ggt gcc cgg    144
Glu Glu Ser Pro Phe Val Gly Asn Pro Gly Asn Ile Thr Gly Ala Arg
            35                  40                  45 gga ctc acg ggc acc ctt cgg tgt cag ctc cag gtt cag gga gag ccc    192
Gly Leu Thr Gly Thr Leu Arg Cys Gln Leu Gln Val Gln Gly Glu Pro
        50                  55                  60 ccc gag gta cat tgg ctt cgg gat gga cag atc ctg gag ctc gcg gac    240
Pro Glu Val His Trp Leu Arg Asp Gly Gln Ile Leu Glu Leu Ala Asp
65                  70                  75                  80 agc acc cag acc cag gtg ccc ctg ggt gag gat gaa cag gat gac tgg    288
Ser Thr Gln Thr Gln Val Pro Leu Gly Glu Asp Glu Gln Asp Asp Trp
                85                  90                  95 ata gtg gtc agc cag ctc aga atc acc tcc ctg cag ctt tcc gac acg    336
Ile Val Val Ser Gln Leu Arg Ile Thr Ser Leu Gln Leu Ser Asp Thr
                100                 105                 110 gga cag tac cag tgt ttg gtg ttt cta gga cat cag acc ttc gtg tcc    384
Gly Gln Tyr Gln Cys Leu Val Phe Leu Gly His Gln Thr Phe Val Ser
            115                 120                 125 cag cct ggc tat gtt ggg ctg gag ggc ttg cct tac ttc ctg gag gag    432
```

|  |  |  |  |  |  |  |  |  |  |  |  |  |
|---|---|---|---|---|---|---|---|---|---|---|---|---|
| Gln | Pro | Gly | Tyr | Val | Gly | Leu | Glu | Gly | Leu | Pro | Tyr | Phe | Leu | Glu | Glu |
|  | 130 |  |  |  | 135 |  |  |  | 140 |  |  |  |

```
ccc gaa gac agg act gtg gcc gcc aac acc ccc ttc aac ctg agc tgc    480
Pro Glu Asp Arg Thr Val Ala Ala Asn Thr Pro Phe Asn Leu Ser Cys
145             150                 155                 160 caa gct cag gga ccc cca gag ccc gtg gac cta ctc tgg ctc cag gat    528
Gln Ala Gln Gly Pro Pro Glu Pro Val Asp Leu Leu Trp Leu Gln Asp
        165                 170                 175 gct gtc ccc ctg gcc acg gct cca ggt cac ggc ccc cag cgc agc ctg    576
Ala Val Pro Leu Ala Thr Ala Pro Gly His Gly Pro Gln Arg Ser Leu
            180                 185                 190 cat gtt cca ggg ctg aac aag aca tcc tct ttc tcc tgc gaa gcc cat    624
His Val Pro Gly Leu Asn Lys Thr Ser Ser Phe Ser Cys Glu Ala His
                195                 200                 205 aac gcc aag ggg gtc acc aca tcc cgc aca gcc acc atc aca gtg ctc    672
Asn Ala Lys Gly Val Thr Thr Ser Arg Thr Ala Thr Ile Thr Val Leu
    210                 215                 220 ccc cag cag ccc cgt aac ctc cac ctg gtc tcc cgc caa ccc acg gag    720
Pro Gln Gln Pro Arg Asn Leu His Leu Val Ser Arg Gln Pro Thr Glu
225                 230                 235                 240 ctg gag gtg gct tgg act cca ggc ctg agc ggc atc tac ccc ctg acc    768
Leu Glu Val Ala Trp Thr Pro Gly Leu Ser Gly Ile Tyr Pro Leu Thr
                245                 250                 255 cac tgc acc ctg cag gct gtg ctg tca gac gat ggg atg ggc atc cag    816
His Cys Thr Leu Gln Ala Val Leu Ser Asp Asp Gly Met Gly Ile Gln
                260                 265                 270 gcg gga gaa cca gac ccc cca gag gag ccc ctc acc tcg caa gca tcc    864
Ala Gly Glu Pro Asp Pro Pro Glu Glu Pro Leu Thr Ser Gln Ala Ser
            275                 280                 285 gtg ccc ccc cat cag ctt cgg cta ggc agc ctc cat cct cac acc cct    912
Val Pro Pro His Gln Leu Arg Leu Gly Ser Leu His Pro His Thr Pro
290                 295                 300 tat cac atc cgc gtg gca tgc acc agc agc cag ggc ccc tca tcc tgg    960
Tyr His Ile Arg Val Ala Cys Thr Ser Ser Gln Gly Pro Ser Ser Trp
305                 310                 315                 320 acc cac tgg ctt cct gtg gag acg ccg gag gga gtg ccc ctg ggc ccc   1008
Thr His Trp Leu Pro Val Glu Thr Pro Glu Gly Val Pro Leu Gly Pro
                325                 330                 335 cct gag aac att agt gct acg cgg aat ggg agc cag gcc ttc gtg cat   1056
Pro Glu Asn Ile Ser Ala Thr Arg Asn Gly Ser Gln Ala Phe Val His
                340                 345                 350 tgg caa gag ccc cgg gcg ccc ctg cag ggt acc ctg tta ggg tac cgg   1104
Trp Gln Glu Pro Arg Ala Pro Leu Gln Gly Thr Leu Leu Gly Tyr Arg
            355                 360                 365 ctg gcg tat caa ggc cag gac acc cca gag gtg cta atg gac ata ggg   1152
Leu Ala Tyr Gln Gly Gln Asp Thr Pro Glu Val Leu Met Asp Ile Gly
370                 375                 380 cta agg caa gag gtg acc ctg gag ctg cag ggg gac ggg tct gtg tcc   1200
Leu Arg Gln Glu Val Thr Leu Glu Leu Gln Gly Asp Gly Ser Val Ser
385                 390                 395                 400 aat ctg aca gtg tgt gtg gca gcc tac act gct gct ggg gat gga ccc   1248
Asn Leu Thr Val Cys Val Ala Ala Tyr Thr Ala Ala Gly Asp Gly Pro
                405                 410                 415 tgg agc ctc cca gta ccc ctg gag gcc tgg cgc cca ggg caa gca cag   1296
Trp Ser Leu Pro Val Pro Leu Glu Ala Trp Arg Pro Gly Gln Ala Gln
            420                 425                 430 cca gtc cac cag ctg gtg aag gaa cct tca act cct gcc ttc tcg tgg   1344
Pro Val His Gln Leu Val Lys Glu Pro Ser Thr Pro Ala Phe Ser Trp
435                 440                 445
```

```
                                                      -continued ccc tgg tgg tat gta ctg cta gga gca gtc gtg gcc gct gcc tgt gtc    1392
Pro Trp Trp Tyr Val Leu Leu Gly Ala Val Val Ala Ala Ala Cys Val
    450             455                 460 ctc atc ttg gct ctc ttc ctt gtc cac cgg cga aag aag gag acc cgt    1440
Leu Ile Leu Ala Leu Phe Leu Val His Arg Arg Lys Lys Glu Thr Arg
465                 470                 475                 480 tat gga gaa gtg ttt gaa cca aca gtg gaa aga ggt gaa ctg gta gtc    1488
Tyr Gly Glu Val Phe Glu Pro Thr Val Glu Arg Gly Glu Leu Val Val
                485                 490                 495 agg tac cgc gtg cgc aag tcc tac agt cgt cgg acc act gaa gct acc    1536
Arg Tyr Arg Val Arg Lys Ser Tyr Ser Arg Arg Thr Thr Glu Ala Thr
            500                 505                 510 ttg aac agc ctg ggc atc agt gaa gag ctg aag gag aag ctg cgg gat    1584
Leu Asn Ser Leu Gly Ile Ser Glu Glu Leu Lys Glu Lys Leu Arg Asp
        515                 520                 525 gtg atg gtg gac cgg cac aag gtg gcc ctg ggg aag act ctg gga gag    1632
Val Met Val Asp Arg His Lys Val Ala Leu Gly Lys Thr Leu Gly Glu
    530                 535                 540 gga gag ttt gga gct gtg atg gaa ggc cag ctc aac cag gac gac tcc    1680
Gly Glu Phe Gly Ala Val Met Glu Gly Gln Leu Asn Gln Asp Asp Ser
545                 550                 555                 560 atc ctc aag gtg gct gtg aag acg atg aag att gcc atc tgc acg agg    1728
Ile Leu Lys Val Ala Val Lys Thr Met Lys Ile Ala Ile Cys Thr Arg
                565                 570                 575 tca gag ctg gag gat ttc ctg agt gaa gcg gtc tgc atg aag gaa ttt    1776
Ser Glu Leu Glu Asp Phe Leu Ser Glu Ala Val Cys Met Lys Glu Phe
            580                 585                 590 gac cat ccc aac gtc atg agg ctc atc ggt gtc tgt ttc cag ggt tct    1824
Asp His Pro Asn Val Met Arg Leu Ile Gly Val Cys Phe Gln Gly Ser
        595                 600                 605 gaa cga gag agc ttc cca gca cct gtg gtc atc tta cct ttc atg aaa    1872
Glu Arg Glu Ser Phe Pro Ala Pro Val Val Ile Leu Pro Phe Met Lys
    610                 615                 620 cat gga gac cta cac agc ttc ctc ctc tat tcc cgg ctc ggg gac cag    1920
His Gly Asp Leu His Ser Phe Leu Leu Tyr Ser Arg Leu Gly Asp Gln
625                 630                 635                 640 cca gtg tac ctg ccc act cag atg cta gtg aag ttc atg gca gac atc    1968
Pro Val Tyr Leu Pro Thr Gln Met Leu Val Lys Phe Met Ala Asp Ile
                645                 650                 655 gcc agt ggc atg gag tat ctg agt acc aag aga ttc ata cac cgg gac    2016
Ala Ser Gly Met Glu Tyr Leu Ser Thr Lys Arg Phe Ile His Arg Asp
            660                 665                 670 ctg gcg gcc agg aac tgc atg ctg aat gag aac atg tcc gtg tgt gtg    2064
Leu Ala Ala Arg Asn Cys Met Leu Asn Glu Asn Met Ser Val Cys Val
        675                 680                 685 gcg gac ttc ggg ctc tcc aag aag atc tac aat ggg gac tac tac cgc    2112
Ala Asp Phe Gly Leu Ser Lys Lys Ile Tyr Asn Gly Asp Tyr Tyr Arg
    690                 695                 700 cag gga cgt atc gcc aag atg cca gtc aag tgg att gcc att gag agt    2160
Gln Gly Arg Ile Ala Lys Met Pro Val Lys Trp Ile Ala Ile Glu Ser
705                 710                 715                 720 cta gct gac cgt gtc tac acc agc aag agc gat gtg tgg tcc ttc ggg    2208
Leu Ala Asp Arg Val Tyr Thr Ser Lys Ser Asp Val Trp Ser Phe Gly
                725                 730                 735 gtg aca atg tgg gag att gcc aca aga ggc caa acc cca tat ccg ggc    2256
Val Thr Met Trp Glu Ile Ala Thr Arg Gly Gln Thr Pro Tyr Pro Gly
            740                 745                 750 gtg gag aac agc gag att tat gac tat ctg cgc cag gga aat cgc ctg    2304
Val Glu Asn Ser Glu Ile Tyr Asp Tyr Leu Arg Gln Gly Asn Arg Leu
        755                 760                 765
```

```
aag cag cct gcg gac tgt ctg gat gga ctg tat gcc ttg atg tcg cgg      2352
Lys Gln Pro Ala Asp Cys Leu Asp Gly Leu Tyr Ala Leu Met Ser Arg
    770             775                 780 tgc tgg gag cta aat ccc cag gac cgg cca agt ttt aca gag ctg cgg      2400
Cys Trp Glu Leu Asn Pro Gln Asp Arg Pro Ser Phe Thr Glu Leu Arg
785             790                 795                 800 gaa gat ttg gag aac aca ctg aag gcc ttg cct cct gcc cag gag cct      2448
Glu Asp Leu Glu Asn Thr Leu Lys Ala Leu Pro Pro Ala Gln Glu Pro
                805                 810                 815 gac gaa atc ctc tat gtc aac atg gat gag ggt gga ggt tat cct gaa      2496
Asp Glu Ile Leu Tyr Val Asn Met Asp Glu Gly Gly Gly Tyr Pro Glu
            820                 825                 830 ccc cct gga gct gca gga gga gct gac ccc cca acc cag cca gac cct      2544
Pro Pro Gly Ala Ala Gly Gly Ala Asp Pro Pro Thr Gln Pro Asp Pro
        835                 840                 845 aag gat tcc tgt agc tgc ctc act gcg gct gag gtc cat cct gct gga      2592
Lys Asp Ser Cys Ser Cys Leu Thr Ala Ala Glu Val His Pro Ala Gly
    850                 855                 860 cgc tat gtc ctc tgc cct tcc aca acc cct agc ccc gct cag cct gct      2640
Arg Tyr Val Leu Cys Pro Ser Thr Thr Pro Ser Pro Ala Gln Pro Ala
865             870                 875                 880 gat agg ggc tcc cca gca gcc cca ggg cag gag gat ggt gcc tga           2685
Asp Arg Gly Ser Pro Ala Ala Pro Gly Gln Glu Asp Gly Ala
                885                 890

<210> SEQ ID NO 27
<211> LENGTH: 894
<212> TYPE: PRT
<213> ORGANISM: Homo sapiens

<400> SEQUENCE: 27

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205
```

```
Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
                260                 265                 270

Ala Gly Glu Pro Asp Pro Pro Glu Glu Pro Leu Thr Ser Gln Ala Ser
            275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
                420                 425                 430

Pro Val His Gln Leu Val Lys Glu Pro Ser Thr Pro Ala Phe Ser Trp
            435                 440                 445

Pro Trp Trp Tyr Val Leu Leu Gly Ala Val Val Ala Ala Ala Cys Val
450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
            515                 520                 525

Val Met Val Asp Arg His Lys Val Ala Leu Gly Lys Thr Leu Gly Glu
530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
610                 615                 620
```

```
His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
            645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 28
<211> LENGTH: 2034
<212> TYPE: DNA
<213> ORGANISM: Artificial Sequence
<220> FEATURE:
<223> OTHER INFORMATION: Description of Artificial Sequence: Synthetic
      hAxl-hFc sequence
<220> FEATURE:
<221> NAME/KEY: CDS
<222> LOCATION: (1)..(2025)

<400> SEQUENCE: 28 aga tct acg cgt gcc acc atg gcg tgg cgg tgc ccc agg atg ggc agg     48
Arg Ser Thr Arg Ala Thr Met Ala Trp Arg Cys Pro Arg Met Gly Arg
1               5                   10                  15 gtc ccg ctg gcc tgg tgc ttg gcg ctg tgc ggc tgg gcg tgc atg gcc     96
Val Pro Leu Ala Trp Cys Leu Ala Leu Cys Gly Trp Ala Cys Met Ala
            20                  25                  30 ccc agg ggc acg cag gct gaa gaa agt ccc ttc gtg ggc aac cca ggg    144
Pro Arg Gly Thr Gln Ala Glu Glu Ser Pro Phe Val Gly Asn Pro Gly
        35                  40                  45 aat atc aca ggt gcc cgg gga ctc acg ggc acc ctt cgg tgt cag ctc    192
Asn Ile Thr Gly Ala Arg Gly Leu Thr Gly Thr Leu Arg Cys Gln Leu
```

```
            50                  55                  60
cag gtt cag gga gag ccc ccc gag gta cat tgg ctt cgg gat gga cag        240
Gln Val Gln Gly Glu Pro Pro Glu Val His Trp Leu Arg Asp Gly Gln
 65                  70                  75                  80 atc ctg gag ctc gcg gac agc acc cag acc cag gtg ccc ctg ggt gag        288
Ile Leu Glu Leu Ala Asp Ser Thr Gln Thr Gln Val Pro Leu Gly Glu
                 85                  90                  95 gat gaa cag gat gac tgg ata gtg gtc agc cag ctc aga atc acc tcc        336
Asp Glu Gln Asp Asp Trp Ile Val Val Ser Gln Leu Arg Ile Thr Ser
            100                 105                 110 ctg cag ctt tcc gac acg gga cag tac cag tgt ttg gtg ttt ctg gga        384
Leu Gln Leu Ser Asp Thr Gly Gln Tyr Gln Cys Leu Val Phe Leu Gly
        115                 120                 125 cat cag acc ttc gtg tcc cag cct ggc tat gtt ggg ctg gag ggc ttg        432
His Gln Thr Phe Val Ser Gln Pro Gly Tyr Val Gly Leu Glu Gly Leu
    130                 135                 140 cct tac ttc ctg gag gag ccc gaa gac agg act gtg gcc gcc aac acc        480
Pro Tyr Phe Leu Glu Glu Pro Glu Asp Arg Thr Val Ala Ala Asn Thr
145                 150                 155                 160 ccc ttc aac ctg agc tgc caa gct cag gga ccc cca gag ccc gtg gac        528
Pro Phe Asn Leu Ser Cys Gln Ala Gln Gly Pro Pro Glu Pro Val Asp
                165                 170                 175 cta ctc tgg ctc cag gat gct gtc ccc ctg gcc acg gct cca ggt cac        576
Leu Leu Trp Leu Gln Asp Ala Val Pro Leu Ala Thr Ala Pro Gly His
            180                 185                 190 ggc ccc cag cgc agc ctg cat gtt cca ggg ctg aac aag aca tcc tct        624
Gly Pro Gln Arg Ser Leu His Val Pro Gly Leu Asn Lys Thr Ser Ser
        195                 200                 205 ttc tcc tgc gaa gcc cat aac gcc aag ggg gtc acc aca tcc cgc aca        672
Phe Ser Cys Glu Ala His Asn Ala Lys Gly Val Thr Thr Ser Arg Thr
    210                 215                 220 gcc acc atc aca gtg ctc ccc cag cag ccc cgt aac ctc cac ctg gtc        720
Ala Thr Ile Thr Val Leu Pro Gln Gln Pro Arg Asn Leu His Leu Val
225                 230                 235                 240 tcc cgc caa ccc acg gag ctg gag gtg gct tgg act cca ggc ctg agc        768
Ser Arg Gln Pro Thr Glu Leu Glu Val Ala Trp Thr Pro Gly Leu Ser
                245                 250                 255 ggc atc tac ccc ctg acc cac tgc acc ctg cag gct gtg ctg tca gac        816
Gly Ile Tyr Pro Leu Thr His Cys Thr Leu Gln Ala Val Leu Ser Asp
            260                 265                 270 gat ggg atg ggc atc cag gcg gga gaa cca gac ccc cca gag gag ccc        864
Asp Gly Met Gly Ile Gln Ala Gly Glu Pro Asp Pro Pro Glu Glu Pro
        275                 280                 285 ctc acc tcg caa gca tcc gtg ccc ccc cat cag ctt cgg cta ggc agc        912
Leu Thr Ser Gln Ala Ser Val Pro Pro His Gln Leu Arg Leu Gly Ser
    290                 295                 300 ctc cat cct cac acc cct tat cac atc cgc gtg gca tgc acc agc agc        960
Leu His Pro His Thr Pro Tyr His Ile Arg Val Ala Cys Thr Ser Ser
305                 310                 315                 320 cag ggc ccc tca tcc tgg acc cac tgg ctt cct gtg gag acg ccg gag       1008
Gln Gly Pro Ser Ser Trp Thr His Trp Leu Pro Val Glu Thr Pro Glu
                325                 330                 335 gga gtg ccc ctg ggc ccc cct gag aac att agt gct acg cgg aat ggg       1056
Gly Val Pro Leu Gly Pro Pro Glu Asn Ile Ser Ala Thr Arg Asn Gly
            340                 345                 350 agc cag gcc ttc gtg cat tgg caa gag ccc cgg gcg ccc ctg cag ggt       1104
Ser Gln Ala Phe Val His Trp Gln Glu Pro Arg Ala Pro Leu Gln Gly
        355                 360                 365 acc ctg tta ggg tac cgg ctg gcg tat caa ggc cag gac acc cca gag       1152
Thr Leu Leu Gly Tyr Arg Leu Ala Tyr Gln Gly Gln Asp Thr Pro Glu
```

```
                Thr Leu Leu Gly Tyr Arg Leu Ala Tyr Gln Gly Gln Asp Thr Pro Glu
                    370             375             380 gtg cta atg gac ata ggg cta agg caa gag gtg acc ctg gag ctg cag        1200
Val Leu Met Asp Ile Gly Leu Arg Gln Glu Val Thr Leu Glu Leu Gln
385             390             395             400 ggg gac ggg tct gtg tcc aat ctg aca gtg tgt gtg gca gcc tac act        1248
Gly Asp Gly Ser Val Ser Asn Leu Thr Val Cys Val Ala Ala Tyr Thr
                405             410             415 gct gct ggg gat gga ccc tgg agc ctc cca gta ccc ctg gag gcc tgg        1296
Ala Ala Gly Asp Gly Pro Trp Ser Leu Pro Val Pro Leu Glu Ala Trp
            420             425             430 cgc cca ggg caa gca cag cca gtc cac cag ctg gtg gtc gac gaa ttc        1344
Arg Pro Gly Gln Ala Gln Pro Val His Gln Leu Val Val Asp Glu Phe
        435             440             445 gac aaa act cac aca tgc cca ccg tgc cca gca cct gaa ctc ctg ggg        1392
Asp Lys Thr His Thr Cys Pro Pro Cys Pro Ala Pro Glu Leu Leu Gly
    450             455             460 gga ccg tca gtc ttc ctc ttc ccc cca aaa ccc aag gac acc ctc atg        1440
Gly Pro Ser Val Phe Leu Phe Pro Pro Lys Pro Lys Asp Thr Leu Met
465             470             475             480 atc tcc cgg acc cct gag gtc aca tgc gtg gtg gtg gac gtg agc cac        1488
Ile Ser Arg Thr Pro Glu Val Thr Cys Val Val Val Asp Val Ser His
                485             490             495 gaa gac cct gag gtc aag ttc aac tgg tac gtg gac ggc gtg gag gtg        1536
Glu Asp Pro Glu Val Lys Phe Asn Trp Tyr Val Asp Gly Val Glu Val
                500             505             510 cat aat gcc aag aca aag ccg cgg gag gag cag tac aac agc acg tac        1584
His Asn Ala Lys Thr Lys Pro Arg Glu Glu Gln Tyr Asn Ser Thr Tyr
            515             520             525 cgt gtg gtc agc gtc ctc acc gtc ctg cac cag gac tgg ctg aat ggc        1632
Arg Val Val Ser Val Leu Thr Val Leu His Gln Asp Trp Leu Asn Gly
        530             535             540 aag gag tac aag tgc aag gtc tcc aac aaa gcc ctc cca gcc ccc atc        1680
Lys Glu Tyr Lys Cys Lys Val Ser Asn Lys Ala Leu Pro Ala Pro Ile
545             550             555             560 gag aaa acc atc tcc aaa gcc aaa ggg cag ccc cga gaa cca cag gtg        1728
Glu Lys Thr Ile Ser Lys Ala Lys Gly Gln Pro Arg Glu Pro Gln Val
                565             570             575 tac acc ctg ccc cca tcc cgg gat gag ctg acc aag aac cag gtc agc        1776
Tyr Thr Leu Pro Pro Ser Arg Asp Glu Leu Thr Lys Asn Gln Val Ser
                580             585             590 ctg acc tgc ctg gtc aaa ggc ttc tat ccc agc gac atc gcc gtg gag        1824
Leu Thr Cys Leu Val Lys Gly Phe Tyr Pro Ser Asp Ile Ala Val Glu
            595             600             605 tgg gag agc aat ggg cag ccg gag aac aac tac aag acc acg cct ccc        1872
Trp Glu Ser Asn Gly Gln Pro Glu Asn Asn Tyr Lys Thr Thr Pro Pro
    610             615             620 gtg ctg gac tcc gac ggc tcc ttc ttc ctc tac agc aag ctc acc gtg        1920
Val Leu Asp Ser Asp Gly Ser Phe Phe Leu Tyr Ser Lys Leu Thr Val
625             630             635             640 gac aag agc agg tgg cag cag ggg aac gtc ttc tca tgc tcc gtg atg        1968
Asp Lys Ser Arg Trp Gln Gln Gly Asn Val Phe Ser Cys Ser Val Met
                645             650             655 cat gag gct ctg cac aac cac tac acg cag aag agc ctc tcc ctg tct        2016
His Glu Ala Leu His Asn His Tyr Thr Gln Lys Ser Leu Ser Leu Ser
            660             665             670 ccg ggc aaa tgaggatcc                                                  2034
Pro Gly Lys
        675
```

<210> SEQ ID NO 29
<211> LENGTH: 675
<212> TYPE: PRT
<213> ORGANISM: Artificial Sequence
<220> FEATURE:
<223> OTHER INFORMATION: Description of Artificial Sequence: Synthetic construct

<400> SEQUENCE: 29

```
Arg Ser Thr Arg Ala Thr Met Ala Trp Arg Cys Pro Arg Met Gly Arg
1               5                   10                  15

Val Pro Leu Ala Trp Cys Leu Ala Leu Cys Gly Trp Ala Cys Met Ala
            20                  25                  30

Pro Arg Gly Thr Gln Ala Glu Glu Ser Pro Phe Val Gly Asn Pro Gly
        35                  40                  45

Asn Ile Thr Gly Ala Arg Gly Leu Thr Gly Thr Leu Arg Cys Gln Leu
    50                  55                  60

Gln Val Gln Gly Glu Pro Pro Glu Val His Trp Leu Arg Asp Gly Gln
65                  70                  75                  80

Ile Leu Glu Leu Ala Asp Ser Thr Gln Thr Gln Val Pro Leu Gly Glu
                85                  90                  95

Asp Glu Gln Asp Asp Trp Ile Val Val Ser Gln Leu Arg Ile Thr Ser
            100                 105                 110

Leu Gln Leu Ser Asp Thr Gly Gln Tyr Gln Cys Leu Val Phe Leu Gly
        115                 120                 125

His Gln Thr Phe Val Ser Gln Pro Gly Tyr Val Gly Leu Glu Gly Leu
    130                 135                 140

Pro Tyr Phe Leu Glu Glu Pro Glu Asp Arg Thr Val Ala Ala Asn Thr
145                 150                 155                 160

Pro Phe Asn Leu Ser Cys Gln Ala Gln Gly Pro Pro Glu Pro Val Asp
                165                 170                 175

Leu Leu Trp Leu Gln Asp Ala Val Pro Leu Ala Thr Ala Pro Gly His
            180                 185                 190

Gly Pro Gln Arg Ser Leu His Val Pro Gly Leu Asn Lys Thr Ser Ser
        195                 200                 205

Phe Ser Cys Glu Ala His Asn Ala Lys Gly Val Thr Thr Ser Arg Thr
    210                 215                 220

Ala Thr Ile Thr Val Leu Pro Gln Gln Pro Arg Asn Leu His Leu Val
225                 230                 235                 240

Ser Arg Gln Pro Thr Glu Leu Glu Val Ala Trp Thr Pro Gly Leu Ser
                245                 250                 255

Gly Ile Tyr Pro Leu Thr His Cys Thr Leu Gln Ala Val Leu Ser Asp
            260                 265                 270

Asp Gly Met Gly Ile Gln Ala Gly Glu Pro Asp Pro Glu Glu Pro
        275                 280                 285

Leu Thr Ser Gln Ala Ser Val Pro Pro His Gln Leu Arg Leu Gly Ser
    290                 295                 300

Leu His Pro His Thr Pro Tyr His Ile Arg Val Ala Cys Thr Ser Ser
305                 310                 315                 320

Gln Gly Pro Ser Ser Trp Thr His Trp Leu Pro Val Glu Thr Pro Glu
                325                 330                 335

Gly Val Pro Leu Gly Pro Pro Glu Asn Ile Ser Ala Thr Arg Asn Gly
            340                 345                 350

Ser Gln Ala Phe Val His Trp Gln Glu Pro Arg Ala Pro Leu Gln Gly
        355                 360                 365
```

```
Thr Leu Leu Gly Tyr Arg Leu Ala Tyr Gln Gly Gln Asp Thr Pro Glu
        370                 375                 380

Val Leu Met Asp Ile Gly Leu Arg Gln Glu Val Thr Leu Glu Leu Gln
385                 390                 395                 400

Gly Asp Gly Ser Val Ser Asn Leu Thr Val Cys Val Ala Ala Tyr Thr
                405                 410                 415

Ala Ala Gly Asp Gly Pro Trp Ser Leu Pro Val Pro Leu Glu Ala Trp
            420                 425                 430

Arg Pro Gly Gln Ala Gln Pro Val His Gln Leu Val Val Asp Glu Phe
        435                 440                 445

Asp Lys Thr His Thr Cys Pro Pro Cys Pro Ala Pro Glu Leu Leu Gly
    450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
    530                 535                 540

Lys Glu Tyr Lys Cys Lys Val Ser Asn Lys Ala Leu Pro Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Ser Arg Asp Glu Leu Thr Lys Asn Gln Val Ser
            580                 585                 590

Leu Thr Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
    610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro Gly Lys
        675

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer 14

<400> SEQUENCE: 30
gctgggcaga gccggtggc                                                    19

<210> SEQ ID NO 31
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      Primer 15

<400> SEQUENCE: 31
gtgcttagct tggatcctga gag                                                 23

<210> SEQ ID NO 32
<211> LENGTH: 2685
<212> TYPE: DNA
<213> ORGANISM: Macaca fascicularis
<220> FEATURE:
<221> NAME/KEY: CDS
<222> LOCATION: (1)..(2682)

<400> SEQUENCE: 32 atg gcg tgg cgg tgc ccc agg atg ggc agg gtc ccg ctg gcc tgg tgc           48
Met Ala Trp Arg Cys Pro Arg Met Gly Arg Val Pro Leu Ala Trp Cys
1               5                   10                  15 ttg gcg ctg tgc ggc tgg gtg tgc atg gcc ccc agg ggc aca cag gct           96
Leu Ala Leu Cys Gly Trp Val Cys Met Ala Pro Arg Gly Thr Gln Ala
                20                  25                  30 gaa gaa agt cct ttc gtg ggt aac cca ggg aat atc aca ggt gcc cgg          144
Glu Glu Ser Pro Phe Val Gly Asn Pro Gly Asn Ile Thr Gly Ala Arg
            35                  40                  45 gga ctc acg ggc acc ctt cgg tgt cag ctc cag gtt cag gga gag ccc          192
Gly Leu Thr Gly Thr Leu Arg Cys Gln Leu Gln Val Gln Gly Glu Pro
        50                  55                  60 ccc gag gta cac tgg ctt cgg gac gga cag atc ctg gag ctc gcg gac          240
Pro Glu Val His Trp Leu Arg Asp Gly Gln Ile Leu Glu Leu Ala Asp
65                  70                  75                  80 agc acc cag acc cag gtg ccc ctg ggt gaa gat gag cag gat gac tgg          288
Ser Thr Gln Thr Gln Val Pro Leu Gly Glu Asp Glu Gln Asp Asp Trp
                85                  90                  95 ata gtg gtc agc cag ctc aga atc gcc tcc cta cag ctt tcc gac gcg          336
Ile Val Val Ser Gln Leu Arg Ile Ala Ser Leu Gln Leu Ser Asp Ala
                100                 105                 110 gga cag tac cag tgt ttg gtg ttt ctg gga cat cag aac ttc gtg tcc          384
Gly Gln Tyr Gln Cys Leu Val Phe Leu Gly His Gln Asn Phe Val Ser
            115                 120                 125 cag cct ggc tac gta ggg ctg gag ggc ttg cct tac ttc ctg gag gag          432
Gln Pro Gly Tyr Val Gly Leu Glu Gly Leu Pro Tyr Phe Leu Glu Glu
        130                 135                 140 cct gag gac agg act gtg gcc gcc aac acc ccc ttc aac ctg agc tgc          480
Pro Glu Asp Arg Thr Val Ala Ala Asn Thr Pro Phe Asn Leu Ser Cys
145                 150                 155                 160 caa gcc cag gga ccc cca gag ccc gtg gac cta ctc tgg ctc cag gat          528
Gln Ala Gln Gly Pro Pro Glu Pro Val Asp Leu Leu Trp Leu Gln Asp
                165                 170                 175 gct gtc ccc ctg gcc aca gct cca ggt cat ggt ccc cag cgc aac ctg          576
Ala Val Pro Leu Ala Thr Ala Pro Gly His Gly Pro Gln Arg Asn Leu
                180                 185                 190 cat gtt cca ggg ctg aac aag aca tcc tct ttc tcc tgc gaa gcc cat          624
His Val Pro Gly Leu Asn Lys Thr Ser Ser Phe Ser Cys Glu Ala His
            195                 200                 205 aac gcc aag gga gtc acc aca tcc cgc acg gcc acc atc aca gtg ctc          672
Asn Ala Lys Gly Val Thr Thr Ser Arg Thr Ala Thr Ile Thr Val Leu
        210                 215                 220 ccc cag cag ccc cgt aac ctc cat ctg gtc tcc cgc caa ccc acg gag          720
Pro Gln Gln Pro Arg Asn Leu His Leu Val Ser Arg Gln Pro Thr Glu
225                 230                 235                 240
```

```
ctg gag gtg gct tgg act cca ggc ctg agc ggc atc tac ccc ctg acc      768
Leu Glu Val Ala Trp Thr Pro Gly Leu Ser Gly Ile Tyr Pro Leu Thr
            245                 250                 255 cac tgc acc ctg cag gct atg ctg tca gac aat gag gtg ggc atc cag      816
His Cys Thr Leu Gln Ala Met Leu Ser Asp Asn Glu Val Gly Ile Gln
        260                 265                 270 gcg gga gaa cca gac ccc cca gag gag ccc ctc acc ttg caa gca tct      864
Ala Gly Glu Pro Asp Pro Pro Glu Glu Pro Leu Thr Leu Gln Ala Ser
    275                 280                 285 gtg ccc ccc cac cag ctt cgg ctg ggc agc ctc cat cct cac acc cct      912
Val Pro Pro His Gln Leu Arg Leu Gly Ser Leu His Pro His Thr Pro
290                 295                 300 tat cac atc cgt gtg gca tgc acc agc agc cag ggc ccc tca tcc tgg      960
Tyr His Ile Arg Val Ala Cys Thr Ser Ser Gln Gly Pro Ser Ser Trp
305                 310                 315                 320 aca cac tgg ctt cct gtg gag acg ccg gag gga gtg ccc ctg ggc ccc     1008
Thr His Trp Leu Pro Val Glu Thr Pro Glu Gly Val Pro Leu Gly Pro
                325                 330                 335 cct gag aac att agt gcc acg cgg aat ggg agc cag gcc ttc gtg cat     1056
Pro Glu Asn Ile Ser Ala Thr Arg Asn Gly Ser Gln Ala Phe Val His
            340                 345                 350 tgg cag gag ccc cgg gcg ccc ctg cag ggt acc ctg tta ggg tac cgg     1104
Trp Gln Glu Pro Arg Ala Pro Leu Gln Gly Thr Leu Leu Gly Tyr Arg
        355                 360                 365 ctg gcg tat caa ggc cag gac acc cca gag gtg cta atg gac ata ggg     1152
Leu Ala Tyr Gln Gly Gln Asp Thr Pro Glu Val Leu Met Asp Ile Gly
    370                 375                 380 cta agg caa gag gtg acc ctg gag ctg cag ggg gac ggg tct gtg tcc     1200
Leu Arg Gln Glu Val Thr Leu Glu Leu Gln Gly Asp Gly Ser Val Ser
385                 390                 395                 400 aat ctg aca gtg tgt gtg gca gcc tac act gct gct ggg gat gga ccc     1248
Asn Leu Thr Val Cys Val Ala Ala Tyr Thr Ala Ala Gly Asp Gly Pro
                405                 410                 415 tgg agc ctc cca gta ccc ctg gag gcc tgg cgc cca ggg caa gca cag     1296
Trp Ser Leu Pro Val Pro Leu Glu Ala Trp Arg Pro Gly Gln Ala Gln
            420                 425                 430 cca gtc cac cag ctg gtg aag gaa act tca gct cct gcc ttc tcg tgg     1344
Pro Val His Gln Leu Val Lys Glu Thr Ser Ala Pro Ala Phe Ser Trp
        435                 440                 445 ccc tgg tgg tat ata ctg cta gga gca gtc gtg gcc gct gcc tgt gtc     1392
Pro Trp Trp Tyr Ile Leu Leu Gly Ala Val Val Ala Ala Ala Cys Val
    450                 455                 460 ctc atc ttg gct ctc ttc ctt gtc cac cgg cga aag aag gag acc cgt     1440
Leu Ile Leu Ala Leu Phe Leu Val His Arg Arg Lys Lys Glu Thr Arg
465                 470                 475                 480 tat gga gaa gtg ttc gag cca aca gtg gaa aga ggt gaa ctg gta gtc     1488
Tyr Gly Glu Val Phe Glu Pro Thr Val Glu Arg Gly Glu Leu Val Val
                485                 490                 495 agg tac cgc gtg cgc aag tcc tac agt cgc cgg acc act gaa gct acc     1536
Arg Tyr Arg Val Arg Lys Ser Tyr Ser Arg Arg Thr Thr Glu Ala Thr
            500                 505                 510 ttg aac agc ctg ggc atc agt gaa gag ctg aag gag aag ctg cgg gat     1584
Leu Asn Ser Leu Gly Ile Ser Glu Glu Leu Lys Glu Lys Leu Arg Asp
        515                 520                 525 gtg atg gtg gac cgg cac aag gtg gcc ctg ggg aag act ctg gga gaa     1632
Val Met Val Asp Arg His Lys Val Ala Leu Gly Lys Thr Leu Gly Glu
    530                 535                 540 gga gag ttt gga gcc gtg atg gaa ggc cag ctc aac cag gac gac tcc     1680
Gly Glu Phe Gly Ala Val Met Glu Gly Gln Leu Asn Gln Asp Asp Ser
545                 550                 555                 560
```

-continued

| | | | | | | | | | | | | | | | |
|---|---|---|---|---|---|---|---|---|---|---|---|---|---|---|---|
| atc | ctc | aag | gtg | gct | gtg | aag | aca | atg | aag | att | gcc | atc | tgc | aca | agg | 1728
| Ile | Leu | Lys | Val | Ala | Val | Lys | Thr | Met | Lys | Ile | Ala | Ile | Cys | Thr | Arg |
| | | | | 565 | | | | 570 | | | | | 575 | | |

```
atc ctc aag gtg gct gtg aag aca atg aag att gcc atc tgc aca agg    1728
Ile Leu Lys Val Ala Val Lys Thr Met Lys Ile Ala Ile Cys Thr Arg
            565             570                 575 tca gag ctg gag gat ttc ctg agt gaa gca gtc tgc atg aag gaa ttc    1776
Ser Glu Leu Glu Asp Phe Leu Ser Glu Ala Val Cys Met Lys Glu Phe
            580             585                 590 gac cat ccc aat gtc atg agg ctc atc ggt gtc tgt ttc cag ggt tct    1824
Asp His Pro Asn Val Met Arg Leu Ile Gly Val Cys Phe Gln Gly Ser
            595             600                 605 gaa cga gag agc ttt cca gca cct gtg gtc atc tta cct ttc atg aag    1872
Glu Arg Glu Ser Phe Pro Ala Pro Val Val Ile Leu Pro Phe Met Lys
    610             615                 620 cat gga gac cta cac agc ttc ctc ctc tat tcc cgg ctt ggg gac cag    1920
His Gly Asp Leu His Ser Phe Leu Leu Tyr Ser Arg Leu Gly Asp Gln
625             630                 635                 640 cca gtg tac ctg ccc act cag atg cta gtg aag ttc atg gcg gac atc    1968
Pro Val Tyr Leu Pro Thr Gln Met Leu Val Lys Phe Met Ala Asp Ile
            645                 650                 655 gcc agt ggc atg gaa tat ctg agt acc aag aga ttc ata cac cgg gac    2016
Ala Ser Gly Met Glu Tyr Leu Ser Thr Lys Arg Phe Ile His Arg Asp
            660                 665                 670 ctg gcg gcc agg aac tgc atg ctg aat gag aac atg tcc gtg tgt gtg    2064
Leu Ala Ala Arg Asn Cys Met Leu Asn Glu Asn Met Ser Val Cys Val
            675             680                 685 gcg gac ttc ggg ctc tcc aag aag atc tac aac ggg gac tac tac cgc    2112
Ala Asp Phe Gly Leu Ser Lys Lys Ile Tyr Asn Gly Asp Tyr Tyr Arg
    690             695             700 cag gga cgt atc gcc aag atg cca gtc aag tgg att gcc att gag agt    2160
Gln Gly Arg Ile Ala Lys Met Pro Val Lys Trp Ile Ala Ile Glu Ser
705             710             715                 720 cta gct gac cgt gtc tac acg agc aag agt gat gtg tgg tcc ttc ggg    2208
Leu Ala Asp Arg Val Tyr Thr Ser Lys Ser Asp Val Trp Ser Phe Gly
            725                 730                 735 gtg aca atg tgg gag att gcc aca aga ggc caa acc cca tat cca ggc    2256
Val Thr Met Trp Glu Ile Ala Thr Arg Gly Gln Thr Pro Tyr Pro Gly
            740             745                 750 gtg gag aac agc gag att tat gac tat ctg cgc cag gga aat cgc ctg    2304
Val Glu Asn Ser Glu Ile Tyr Asp Tyr Leu Arg Gln Gly Asn Arg Leu
    755             760                 765 aag cag cct gcg gac tgt ctg gat gga ctg tat gcc ttg atg tcg cgg    2352
Lys Gln Pro Ala Asp Cys Leu Asp Gly Leu Tyr Ala Leu Met Ser Arg
770             775                 780 tgc tgg gag cta aat ccc cag gac cgg cca agt ttt aca gag ctg cgg    2400
Cys Trp Glu Leu Asn Pro Gln Asp Arg Pro Ser Phe Thr Glu Leu Arg
785             790                 795                 800 gaa gat ttg gag aac aca ctg aag gcc ttg cct cct gcc cag gag cct    2448
Glu Asp Leu Glu Asn Thr Leu Lys Ala Leu Pro Pro Ala Gln Glu Pro
            805                 810                 815 gac gaa atc ctc tat gtc aac atg gat gaa ggt gga ggt tat cct gaa    2496
Asp Glu Ile Leu Tyr Val Asn Met Asp Glu Gly Gly Gly Tyr Pro Glu
            820                 825             830 cct ccc ggc gct gct gga gga gct gac ccc cca acc cag cta gac cct    2544
Pro Pro Gly Ala Ala Gly Gly Ala Asp Pro Pro Thr Gln Leu Asp Pro
            835             840                 845 aag gat tcc tgt agc tgc ctc act tcg gct gag gtc cat cct gct gga    2592
Lys Asp Ser Cys Ser Cys Leu Thr Ser Ala Glu Val His Pro Ala Gly
850             855                 860 cgc tat gtc ctc tgc cct tcc aca gcc cct agc ccc gct cag cct gct    2640
Arg Tyr Val Leu Cys Pro Ser Thr Ala Pro Ser Pro Ala Gln Pro Ala
```

```
                     865                 870                 875                 880
gat agg ggc tcc cca gca gcc cca ggg cag gag gat ggc gcc tga           2685
Asp Arg Gly Ser Pro Ala Ala Pro Gly Gln Glu Asp Gly Ala
                    885                 890
```

<210> SEQ ID NO 33
<211> LENGTH: 894
<212> TYPE: PRT
<213> ORGANISM: Macaca fascicularis

<400> SEQUENCE: 33

```
Met Ala Trp Arg Cys Pro Arg Met Gly Arg Val Pro Leu Ala Trp Cys
1               5                   10                  15

Leu Ala Leu Cys Gly Trp Val Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Ala Ser Leu Gln Leu Ser Asp Ala
            100                 105                 110

Gly Gln Tyr Gln Cys Leu Val Phe Leu Gly His Gln Asn Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Asn Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Met Leu Ser Asp Asn Glu Val Gly Ile Gln
            260                 265                 270

Ala Gly Glu Pro Asp Pro Pro Glu Glu Pro Leu Thr Leu Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350
```

-continued

```
Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
            420                 425                 430

Pro Val His Gln Leu Val Lys Glu Thr Ser Ala Pro Ala Phe Ser Trp
        435                 440                 445

Pro Trp Trp Tyr Ile Leu Leu Gly Ala Val Ala Ala Ala Cys Val
        450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                485                 490                 495

Arg Tyr Arg Val Arg Lys Ser Tyr Ser Arg Arg Thr Thr Glu Ala Thr
            500                 505                 510

Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
    530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765
```

```
Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Tyr Pro Glu
                820                 825                 830

Pro Pro Gly Ala Ala Gly Gly Ala Asp Pro Thr Gln Leu Asp Pro
                835                 840                 845

Lys Asp Ser Cys Ser Cys Leu Thr Ser Ala Glu Val His Pro Ala Gly
    850                 855                 860

Arg Tyr Val Leu Cys Pro Ser Thr Ala Pro Ser Pro Ala Gln Pro Ala
865                 870                 875                 880

Asp Arg Gly Ser Pro Ala Ala Pro Gly Gln Glu Asp Gly Ala
                885                 890
```

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer 16

<400> SEQUENCE: 34
tcgcgtcgaa agatctgcca ccatggcgtg gcgg        34

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer 17

<400> SEQUENCE: 35
gagttttgtc gaattccacc agctggtgga ctgg        34

<210> SEQ ID NO 36
<211> LENGTH: 2004
<212> TYPE: DNA
<213> ORGANISM: Artificial Sequence
<220> FEATURE:
<223> OTHER INFORMATION: Description of Artificial Sequence: Synthetic
      cAxl-hFc sequence
<220> FEATURE:
<221> NAME/KEY: CDS
<222> LOCATION: (1)..(2001)

<400> SEQUENCE: 36

```
atg gcg tgg cgg tgc ccc agg atg ggc agg gtc ccg ctg gcc tgg tgc        48
Met Ala Trp Arg Cys Pro Arg Met Gly Arg Val Pro Leu Ala Trp Cys
1               5                   10                  15 ttg gcg ctg tgc ggc tgg gtg tgc atg gcc ccc agg ggc aca cag gct        96
Leu Ala Leu Cys Gly Trp Val Cys Met Ala Pro Arg Gly Thr Gln Ala
            20                  25                  30 gaa gaa agt cct ttc gtg ggt aac cca ggg aat atc aca ggt gcc cgg       144
Glu Glu Ser Pro Phe Val Gly Asn Pro Gly Asn Ile Thr Gly Ala Arg
        35                  40                  45 gga ctc acg ggc acc ctt cgg tgt cag ctc cag gtt cag gga gag ccc       192
Gly Leu Thr Gly Thr Leu Arg Cys Gln Leu Gln Val Gln Gly Glu Pro
    50                  55                  60
```

| | | |
|---|---|---|
| ccc gag gta cac tgg ctt cgg gac gga cag atc ctg gag ctc gcg gac<br>Pro Glu Val His Trp Leu Arg Asp Gly Gln Ile Leu Glu Leu Ala Asp<br>65                             70                      75                     80 | 240 |
| agc acc cag acc cag gtg ccc ctg ggt gaa gat gag cag gat gac tgg<br>Ser Thr Gln Thr Gln Val Pro Leu Gly Glu Asp Glu Gln Asp Asp Trp<br>                       85                      90                      95 | 288 |
| ata gtg gtc agc cag ctc aga atc gcc tcc cta cag ctt tcc gac gcg<br>Ile Val Val Ser Gln Leu Arg Ile Ala Ser Leu Gln Leu Ser Asp Ala<br>                   100                    105                    110 | 336 |
| gga cag tac cag tgt ttg gtg ttt ctg gga cat cag aac ttc gtg tcc<br>Gly Gln Tyr Gln Cys Leu Val Phe Leu Gly His Gln Asn Phe Val Ser<br>           115                    120                    125 | 384 |
| cag cct ggc tac gta ggg ctg gag ggc ttg cct tac ttc ctg gag gag<br>Gln Pro Gly Tyr Val Gly Leu Glu Gly Leu Pro Tyr Phe Leu Glu Glu<br>       130                    135                    140 | 432 |
| cct gag gac agg act gtg gcc gcc aac acc ccc ttc aac ctg agc tgc<br>Pro Glu Asp Arg Thr Val Ala Ala Asn Thr Pro Phe Asn Leu Ser Cys<br>145                           150                    155                    160 | 480 |
| caa gcc cag gga ccc cca gag ccc gtg gac cta ctc tgg ctc cag gat<br>Gln Ala Gln Gly Pro Pro Glu Pro Val Asp Leu Leu Trp Leu Gln Asp<br>                   165                    170                    175 | 528 |
| gct gtc ccc ctg gcc aca gct cca ggt cat ggt ccc cag cgc aac ctg<br>Ala Val Pro Leu Ala Thr Ala Pro Gly His Gly Pro Gln Arg Asn Leu<br>       180                    185                    190 | 576 |
| cat gtt cca ggg ctg aac aag aca tcc tct ttc tcc tgc gaa gcc cat<br>His Val Pro Gly Leu Asn Lys Thr Ser Ser Phe Ser Cys Glu Ala His<br>           195                    200                    205 | 624 |
| aac gcc aag gga gtc acc aca tcc cgc acg gcc acc atc aca gtg ctc<br>Asn Ala Lys Gly Val Thr Thr Ser Arg Thr Ala Thr Ile Thr Val Leu<br>210                           215                    220 | 672 |
| ccc cag cag ccc cgt aac ctc cat ctg gtc tcc cgc caa ccc acg gag<br>Pro Gln Gln Pro Arg Asn Leu His Leu Val Ser Arg Gln Pro Thr Glu<br>225                           230                    235                    240 | 720 |
| ctg gag gtg gct tgg act cca ggc ctg agc ggc atc tac ccc ctg acc<br>Leu Glu Val Ala Trp Thr Pro Gly Leu Ser Gly Ile Tyr Pro Leu Thr<br>                   245                    250                    255 | 768 |
| cac tgc acc ctg cag gct atg ctg tca gac aat gag gtg ggc atc cag<br>His Cys Thr Leu Gln Ala Met Leu Ser Asp Asn Glu Val Gly Ile Gln<br>       260                    265                    270 | 816 |
| gcg gga gaa cca gac ccc cca gag gag ccc ctc acc ttg caa gca tct<br>Ala Gly Glu Pro Asp Pro Pro Glu Glu Pro Leu Thr Leu Gln Ala Ser<br>           275                    280                    285 | 864 |
| gtg ccc ccc cac cag ctt cgg ctg ggc agc ctc cat cct cac acc cct<br>Val Pro Pro His Gln Leu Arg Leu Gly Ser Leu His Pro His Thr Pro<br>       290                    295                    300 | 912 |
| tat cac atc cgt gtg gca tgc acc agc agc cag ggc ccc tca tcc tgg<br>Tyr His Ile Arg Val Ala Cys Thr Ser Ser Gln Gly Pro Ser Ser Trp<br>305                         310                    315                    320 | 960 |
| aca cac tgg ctt cct gtg gag acg ccg gag gga gtg ccc ctg ggc ccc<br>Thr His Trp Leu Pro Val Glu Thr Pro Glu Gly Val Pro Leu Gly Pro<br>                   325                    330                    335 | 1008 |
| cct gag aac att agt gcc acg cgg aat ggg agc cag gcc ttc gtg cat<br>Pro Glu Asn Ile Ser Ala Thr Arg Asn Gly Ser Gln Ala Phe Val His<br>       340                    345                    350 | 1056 |
| tgg cag gag ccc cgg gcg ccc ctg cag ggt acc ctg tta ggg tac cgg<br>Trp Gln Glu Pro Arg Ala Pro Leu Gln Gly Thr Leu Leu Gly Tyr Arg<br>           355                    360                    365 | 1104 |
| ctg gcg tat caa ggc cag gac acc cca gag gtg cta atg gac ata ggg<br>Leu Ala Tyr Gln Gly Gln Asp Thr Pro Glu Val Leu Met Asp Ile Gly | 1152 |

```
                370                 375                 380
cta agg caa gag gtg acc ctg gag ctg cag ggg gac ggg tct gtg tcc      1200
Leu Arg Gln Glu Val Thr Leu Glu Leu Gln Gly Asp Gly Ser Val Ser
385                 390                 395                 400 aat ctg aca gtg tgt gtg gca gcc tac act gct gct ggg gat gga ccc      1248
Asn Leu Thr Val Cys Val Ala Ala Tyr Thr Ala Ala Gly Asp Gly Pro
                405                 410                 415 tgg agc ctc cca gta ccc ctg gag gcc tgg cgc cca ggg caa gca cag      1296
Trp Ser Leu Pro Val Pro Leu Glu Ala Trp Arg Pro Gly Gln Ala Gln
            420                 425                 430 cca gtc cac cag ctg gtg gaa ttc gac aaa act cac aca tgc cca ccg      1344
Pro Val His Gln Leu Val Glu Phe Asp Lys Thr His Thr Cys Pro Pro
        435                 440                 445 tgc cca gca cct gaa ctc ctg ggg gga ccg tca gtc ttc ctc ttc ccc      1392
Cys Pro Ala Pro Glu Leu Leu Gly Gly Pro Ser Val Phe Leu Phe Pro
    450                 455                 460 cca aaa ccc aag gac acc ctc atg atc tcc cgg acc cct gag gtc aca      1440
Pro Lys Pro Lys Asp Thr Leu Met Ile Ser Arg Thr Pro Glu Val Thr
465                 470                 475                 480 tgc gtg gtg gtg gac gtg agc cac gaa gac cct gag gtc aag ttc aac      1488
Cys Val Val Val Asp Val Ser His Glu Asp Pro Glu Val Lys Phe Asn
                485                 490                 495 tgg tac gtg gac ggc gtg gag gtg cat aat gcc aag aca aag ccg cgg      1536
Trp Tyr Val Asp Gly Val Glu Val His Asn Ala Lys Thr Lys Pro Arg
            500                 505                 510 gag gag cag tac aac agc acg tac cgt gtg gtc agc gtc ctc acc gtc      1584
Glu Glu Gln Tyr Asn Ser Thr Tyr Arg Val Val Ser Val Leu Thr Val
        515                 520                 525 ctg cac cag gac tgg ctg aat ggc aag gag tac aag tgc aag gtc tcc      1632
Leu His Gln Asp Trp Leu Asn Gly Lys Glu Tyr Lys Cys Lys Val Ser
    530                 535                 540 aac aaa gcc ctc cca gcc ccc atc gag aaa acc atc tcc aaa gcc aaa      1680
Asn Lys Ala Leu Pro Ala Pro Ile Glu Lys Thr Ile Ser Lys Ala Lys
545                 550                 555                 560 ggg cag ccc cga gaa cca cag gtg tac acc ctg ccc cca tcc cgg gat      1728
Gly Gln Pro Arg Glu Pro Gln Val Tyr Thr Leu Pro Pro Ser Arg Asp
                565                 570                 575 gag ctg acc aag aac cag gtc agc ctg acc tgc ctg gtc aaa ggc ttc      1776
Glu Leu Thr Lys Asn Gln Val Ser Leu Thr Cys Leu Val Lys Gly Phe
            580                 585                 590 tat ccc agc gac atc gcc gtg gag tgg gag agc aat ggg cag ccg gag      1824
Tyr Pro Ser Asp Ile Ala Val Glu Trp Glu Ser Asn Gly Gln Pro Glu
        595                 600                 605 aac aac tac aag acc acg cct ccc gtg ctg gac tcc gac ggc tcc ttc      1872
Asn Asn Tyr Lys Thr Thr Pro Pro Val Leu Asp Ser Asp Gly Ser Phe
    610                 615                 620 ttc ctc tac agc aag ctc acc gtg gac aag agc agg tgg cag cag ggg      1920
Phe Leu Tyr Ser Lys Leu Thr Val Asp Lys Ser Arg Trp Gln Gln Gly
625                 630                 635                 640 aac gtc ttc tca tgc tcc gtg atg cat gag gct ctg cac aac cac tac      1968
Asn Val Phe Ser Cys Ser Val Met His Glu Ala Leu His Asn His Tyr
                645                 650                 655 acg cag aag agc ctc tcc ctg tct ccg ggt aaa tga                      2004
Thr Gln Lys Ser Leu Ser Leu Ser Pro Gly Lys
            660                 665

<210> SEQ ID NO 37
<211> LENGTH: 667
<212> TYPE: PRT
<213> ORGANISM: Artificial Sequence
```

```
<220> FEATURE:
<223> OTHER INFORMATION: Description of Artificial Sequence: Synthetic
      construct

<400> SEQUENCE: 37

Met Ala Trp Arg Cys Pro Arg Met Gly Arg Val Pro Leu Ala Trp Cys
1               5                   10                  15

Leu Ala Leu Cys Gly Trp Val Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Gln Asp Asp Trp
                85                  90                  95

Ile Val Val Ser Gln Leu Arg Ile Ala Ser Leu Gln Leu Ser Asp Ala
                100                 105                 110

Gly Gln Tyr Gln Cys Leu Val Phe Leu Gly His Gln Asn Phe Val Ser
            115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Asn Leu
                180                 185                 190

His Val Pro Gly Leu Asn Lys Thr Ser Ser Phe Ser Cys Glu Ala His
            195                 200                 205

Asn Ala Lys Gly Val Thr Thr Ser Arg Thr Ala Thr Ile Thr Val Leu
            210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Met Leu Ser Asp Asn Glu Val Gly Ile Gln
            260                 265                 270

Ala Gly Glu Pro Asp Pro Pro Glu Glu Pro Leu Thr Leu Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
```

```
            385                 390                 395                 400
        Asn Leu Thr Val Cys Val Ala Ala Tyr Thr Ala Ala Gly Asp Gly Pro
                        405                 410                 415

Trp Ser Leu Pro Val Pro Leu Glu Ala Trp Arg Pro Gly Gln Ala Gln
                    420                 425                 430

Pro Val His Gln Leu Val Glu Phe Asp Lys Thr His Thr Cys Pro Pro
                435                 440                 445

Cys Pro Ala Pro Glu Leu Leu Gly Gly Pro Ser Val Phe Leu Phe Pro
            450                 455                 460

Pro Lys Pro Lys Asp Thr Leu Met Ile Ser Arg Thr Pro Glu Val Thr
        465                 470                 475                 480

Cys Val Val Val Asp Val Ser His Glu Asp Pro Glu Val Lys Phe Asn
                        485                 490                 495

Trp Tyr Val Asp Gly Val Glu Val His Asn Ala Lys Thr Lys Pro Arg
                    500                 505                 510

Glu Glu Gln Tyr Asn Ser Thr Tyr Arg Val Val Ser Val Leu Thr Val
                515                 520                 525

Leu His Gln Asp Trp Leu Asn Gly Lys Glu Tyr Lys Cys Lys Val Ser
            530                 535                 540

Asn Lys Ala Leu Pro Ala Pro Ile Glu Lys Thr Ile Ser Lys Ala Lys
        545                 550                 555                 560

Gly Gln Pro Arg Glu Pro Gln Val Tyr Thr Leu Pro Pro Ser Arg Asp
                        565                 570                 575

Glu Leu Thr Lys Asn Gln Val Ser Leu Thr Cys Leu Val Lys Gly Phe
                    580                 585                 590

Tyr Pro Ser Asp Ile Ala Val Glu Trp Glu Ser Asn Gly Gln Pro Glu
                595                 600                 605

Asn Asn Tyr Lys Thr Thr Pro Pro Val Leu Asp Ser Asp Gly Ser Phe
            610                 615                 620

Phe Leu Tyr Ser Lys Leu Thr Val Asp Lys Ser Arg Trp Gln Gln Gly
        625                 630                 635                 640

Asn Val Phe Ser Cys Ser Val Met His Glu Ala Leu His Asn His Tyr
                        645                 650                 655

Thr Gln Lys Ser Leu Ser Leu Ser Pro Gly Lys
                    660                 665

<210> SEQ ID NO 38
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer 18

<400> SEQUENCE: 38 cgctcgag                                                                8

<210> SEQ ID NO 39
<211> LENGTH: 8
<212> TYPE: DNA
<213> ORGANISM: Artificial Sequence
<220> FEATURE:
<223> OTHER INFORMATION: Description of Artificial Sequence: Synthetic
      Primer 19

<400> SEQUENCE: 39 gagctcgc                                                                8
```

```
<210> SEQ ID NO 40
<211> LENGTH: 2667
<212> TYPE: DNA
<213> ORGANISM: Rattus norvegicus
<220> FEATURE:
<221> NAME/KEY: CDS
<222> LOCATION: (1)..(2664)

<400> SEQUENCE: 40
```

| | | | | | | | | | | | | | | | | |
|---|---|---|---|---|---|---|---|---|---|---|---|---|---|---|---|---|
| atg | ggc | agg | gtc | ccg | ctg | gcc | tgg | tgc | gtg | gcg | ctg | tgc | tgc | tgg | ggg | 48 |
| Met | Gly | Arg | Val | Pro | Leu | Ala | Trp | Cys | Val | Ala | Leu | Cys | Cys | Trp | Gly | |
| 1 | | | | 5 | | | | | 10 | | | | | 15 | | |
| tgt | gca | gcc | cct | aag | gac | aca | cag | acc | gag | gct | gac | agc | cca | ttc | gtg | 96 |
| Cys | Ala | Ala | Pro | Lys | Asp | Thr | Gln | Thr | Glu | Ala | Asp | Ser | Pro | Phe | Val | |
| | | | 20 | | | | | 25 | | | | | 30 | | | |
| ggg | aac | cca | ggg | aat | atc | acg | ggt | gcc | aga | gga | ctc | acg | ggg | acc | ctt | 144 |
| Gly | Asn | Pro | Gly | Asn | Ile | Thr | Gly | Ala | Arg | Gly | Leu | Thr | Gly | Thr | Leu | |
| | | 35 | | | | | 40 | | | | | 45 | | | | |
| cgg | tgt | gag | ctc | cag | gtt | cag | ggg | gag | ccc | cct | gag | gtg | atg | tgg | ctt | 192 |
| Arg | Cys | Glu | Leu | Gln | Val | Gln | Gly | Glu | Pro | Pro | Glu | Val | Met | Trp | Leu | |
| | 50 | | | | | 55 | | | | | 60 | | | | | |
| cga | gat | gga | cag | atc | cta | gaa | ctg | gct | gat | aac | acc | cag | acc | cag | gtg | 240 |
| Arg | Asp | Gly | Gln | Ile | Leu | Glu | Leu | Ala | Asp | Asn | Thr | Gln | Thr | Gln | Val | |
| 65 | | | | | 70 | | | | | 75 | | | | | 80 | |
| cct | ctg | ggc | gaa | gac | tgg | caa | gat | gaa | tgg | aaa | gtc | gtc | agt | cag | ctc | 288 |
| Pro | Leu | Gly | Glu | Asp | Trp | Gln | Asp | Glu | Trp | Lys | Val | Val | Ser | Gln | Leu | |
| | | | | 85 | | | | | 90 | | | | | 95 | | |
| aga | atc | tca | gcc | ctg | caa | ctt | tca | gat | gca | gga | gag | tac | cag | tgt | atg | 336 |
| Arg | Ile | Ser | Ala | Leu | Gln | Leu | Ser | Asp | Ala | Gly | Glu | Tyr | Gln | Cys | Met | |
| | | | 100 | | | | | 105 | | | | | 110 | | | |
| gtg | cac | ctg | gaa | gga | cgg | acc | ttt | gtg | tct | cag | ccg | ggc | ttt | gta | gga | 384 |
| Val | His | Leu | Glu | Gly | Arg | Thr | Phe | Val | Ser | Gln | Pro | Gly | Phe | Val | Gly | |
| | | 115 | | | | | 120 | | | | | 125 | | | | |
| ctg | gaa | ggt | ctc | ccg | tac | ttc | ctg | gag | gaa | cct | gaa | gac | aaa | gct | gtg | 432 |
| Leu | Glu | Gly | Leu | Pro | Tyr | Phe | Leu | Glu | Glu | Pro | Glu | Asp | Lys | Ala | Val | |
| | 130 | | | | | 135 | | | | | 140 | | | | | |
| cct | gcc | aac | acc | ccc | ttc | aac | cta | agc | tgc | cag | gcc | cag | gga | ccc | ccg | 480 |
| Pro | Ala | Asn | Thr | Pro | Phe | Asn | Leu | Ser | Cys | Gln | Ala | Gln | Gly | Pro | Pro | |
| 145 | | | | | 150 | | | | | 155 | | | | | 160 | |
| gaa | ccc | gtg | acc | ctg | ctc | tgg | ctt | caa | gat | gct | gtc | cct | ctg | gcc | cca | 528 |
| Glu | Pro | Val | Thr | Leu | Leu | Trp | Leu | Gln | Asp | Ala | Val | Pro | Leu | Ala | Pro | |
| | | | | 165 | | | | | 170 | | | | | 175 | | |
| gtc | gca | gga | tac | agc | ttt | cag | cac | agt | ttg | caa | gct | cca | ggc | ctg | aac | 576 |
| Val | Ala | Gly | Tyr | Ser | Phe | Gln | His | Ser | Leu | Gln | Ala | Pro | Gly | Leu | Asn | |
| | | | 180 | | | | | 185 | | | | | 190 | | | |
| aag | aca | tct | tct | ttc | tca | tgt | gaa | gcc | cac | aat | gcc | aag | gga | gtc | acc | 624 |
| Lys | Thr | Ser | Ser | Phe | Ser | Cys | Glu | Ala | His | Asn | Ala | Lys | Gly | Val | Thr | |
| | | 195 | | | | | 200 | | | | | 205 | | | | |
| acc | tcc | cgc | aca | gct | acc | atc | aca | gtg | ctc | cca | cag | aga | cct | cac | aat | 672 |
| Thr | Ser | Arg | Thr | Ala | Thr | Ile | Thr | Val | Leu | Pro | Gln | Arg | Pro | His | Asn | |
| | 210 | | | | | 215 | | | | | 220 | | | | | |
| ctc | cac | gtg | gtt | tcc | aga | cat | ccc | acg | gag | cta | gag | gta | gct | tgg | atc | 720 |
| Leu | His | Val | Val | Ser | Arg | His | Pro | Thr | Glu | Leu | Glu | Val | Ala | Trp | Ile | |
| 225 | | | | | 230 | | | | | 235 | | | | | 240 | |
| cct | acc | ctg | agt | ggc | atc | tac | ccg | ctc | acc | cac | tgc | acc | ctg | cag | gct | 768 |
| Pro | Thr | Leu | Ser | Gly | Ile | Tyr | Pro | Leu | Thr | His | Cys | Thr | Leu | Gln | Ala | |
| | | | | 245 | | | | | 250 | | | | | 255 | | |
| gtg | ctg | tca | aac | gat | ggg | gtg | ggc | gtc | tgg | ctg | gga | aag | tca | gat | cct | 816 |
| Val | Leu | Ser | Asn | Asp | Gly | Val | Gly | Val | Trp | Leu | Gly | Lys | Ser | Asp | Pro | |
| | | | 260 | | | | | 265 | | | | | 270 | | | |

```
cct gaa gaa ccc ctc acc gtg caa gta tca gtg ccc ccc cac cag ctt    864
Pro Glu Glu Pro Leu Thr Val Gln Val Ser Val Pro Pro His Gln Leu
        275                 280                 285 cgg ctg gaa aag ctc ctt cct cac acc cca tat cac atc cgg gta tcc    912
Arg Leu Glu Lys Leu Leu Pro His Thr Pro Tyr His Ile Arg Val Ser
        290                 295                 300 tgc act agc agc cag ggc ccc tca cct tgg acc cac tgg ctt cct gtg    960
Cys Thr Ser Ser Gln Gly Pro Ser Pro Trp Thr His Trp Leu Pro Val
305                 310                 315                 320 gag acc acg gag gga gtg ccc ttg ggt ccc cct gag aac gtt agc gcc   1008
Glu Thr Thr Glu Gly Val Pro Leu Gly Pro Pro Glu Asn Val Ser Ala
            325                 330                 335 atg cgg aat ggg agc cag gcc ctc gtg cgt tgg cag gag cca agg gag   1056
Met Arg Asn Gly Ser Gln Ala Leu Val Arg Trp Gln Glu Pro Arg Glu
            340                 345                 350 ccc ttg cag ggc acc ctg tta ggg tac cgg ctg gca tat cga ggc cag   1104
Pro Leu Gln Gly Thr Leu Leu Gly Tyr Arg Leu Ala Tyr Arg Gly Gln
            355                 360                 365 gac acc ccc gag gta ctt atg gat ata ggg cta act cga gag gtg acc   1152
Asp Thr Pro Glu Val Leu Met Asp Ile Gly Leu Thr Arg Glu Val Thr
370                 375                 380 ttg gaa ctt cgg ggg gac agg cct gtg gct aac ctg act gtg tct gtg   1200
Leu Glu Leu Arg Gly Asp Arg Pro Val Ala Asn Leu Thr Val Ser Val
385                 390                 395                 400 gca gcc tat acc tca gct ggg gat ggg ccc tgg agc ctt cct gtg ccc   1248
Ala Ala Tyr Thr Ser Ala Gly Asp Gly Pro Trp Ser Leu Pro Val Pro
                405                 410                 415 cta gag ccc tgg cgc cca ggg caa gga cag cca ctc cac cat ctg gtg   1296
Leu Glu Pro Trp Arg Pro Gly Gln Gly Gln Pro Leu His His Leu Val
            420                 425                 430 agt gaa ccc cca cct ccc gcc ttc tcg tgg cct tgg tgg tat gta ctg   1344
Ser Glu Pro Pro Pro Pro Ala Phe Ser Trp Pro Trp Trp Tyr Val Leu
            435                 440                 445 ctg gga gca ctt gtg gcc gcc gcc tgt gtc ctt atc ttg acc ctg ttc   1392
Leu Gly Ala Leu Val Ala Ala Ala Cys Val Leu Ile Leu Thr Leu Phe
            450                 455                 460 ctt gtc cat cgg agg aag aag gag acg aga tat ggg gag gtg ttc gag   1440
Leu Val His Arg Arg Lys Lys Glu Thr Arg Tyr Gly Glu Val Phe Glu
465                 470                 475                 480 cca act gtg gaa agg ggt gaa ctg gta gtc agg tac cgt gcc cga aag   1488
Pro Thr Val Glu Arg Gly Glu Leu Val Val Arg Tyr Arg Ala Arg Lys
                485                 490                 495 tcc tac agt cgc cgg acc acg gaa gcc acc ttg aac agt ctg ggc atc   1536
Ser Tyr Ser Arg Arg Thr Thr Glu Ala Thr Leu Asn Ser Leu Gly Ile
                500                 505                 510 agc gaa gag ctg aag gag aaa cta cga gac gtc atg gta gat cgg cat   1584
Ser Glu Glu Leu Lys Glu Lys Leu Arg Asp Val Met Val Asp Arg His
            515                 520                 525 aag gtg gcc ttg ggg aag acc ctg gga gag gga gaa ttt ggt gct gtg   1632
Lys Val Ala Leu Gly Lys Thr Leu Gly Glu Gly Glu Phe Gly Ala Val
            530                 535                 540 atg gag ggc cag ctc aac cag gat gac tcc atc ctc aag gtc gct gtg   1680
Met Glu Gly Gln Leu Asn Gln Asp Asp Ser Ile Leu Lys Val Ala Val
545                 550                 555                 560 aag acc atg aaa att gcc atc tgc aca aga tca gag ctg gag gat ttc   1728
Lys Thr Met Lys Ile Ala Ile Cys Thr Arg Ser Glu Leu Glu Asp Phe
                565                 570                 575 ctg agt gaa gct gtc tgc atg aag gaa ttt gac cac ccc aac gtc atg   1776
Leu Ser Glu Ala Val Cys Met Lys Glu Phe Asp His Pro Asn Val Met
            580                 585                 590
```

```
agg ctc att ggc gtc tgt ttc cag ggt tct gac cga gag ggt ttc cca      1824
Arg Leu Ile Gly Val Cys Phe Gln Gly Ser Asp Arg Glu Gly Phe Pro
        595                 600                 605 gaa ccg gtg gtc atc ttg cct ttc atg aaa cat gga gac ctc cac agt      1872
Glu Pro Val Val Ile Leu Pro Phe Met Lys His Gly Asp Leu His Ser
610                 615                 620 ttc ctc ctg tac tcg cgg ctc ggg gac cag cca gtg ttc ctg ccc act      1920
Phe Leu Leu Tyr Ser Arg Leu Gly Asp Gln Pro Val Phe Leu Pro Thr
625                 630                 635                 640 cag atg cta gtg aag ttt atg gcc gac att gcc agt ggc atg gag tac      1968
Gln Met Leu Val Lys Phe Met Ala Asp Ile Ala Ser Gly Met Glu Tyr
            645                 650                 655 ctc agt acc aag aga ttc ata cac cgg gac cta gct gcc agg aac tgc      2016
Leu Ser Thr Lys Arg Phe Ile His Arg Asp Leu Ala Ala Arg Asn Cys
        660                 665                 670 atg ctg aat gag aac atg tcc gtg tgc gtg gca gac ttc ggg ctc tcc      2064
Met Leu Asn Glu Asn Met Ser Val Cys Val Ala Asp Phe Gly Leu Ser
675                 680                 685 aag aag atc tac aat ggg gat tac tac cgc caa ggg cgc att gcc aag      2112
Lys Lys Ile Tyr Asn Gly Asp Tyr Tyr Arg Gln Gly Arg Ile Ala Lys
690                 695                 700 atg cca gtc aag tgg att gct atc gag agt ctg gca gat cga gtc tac      2160
Met Pro Val Lys Trp Ile Ala Ile Glu Ser Leu Ala Asp Arg Val Tyr
705                 710                 715                 720 acc agc aag agt gac gtg tgg tcc ttc ggt gtg aca atg tgg gag atc      2208
Thr Ser Lys Ser Asp Val Trp Ser Phe Gly Val Thr Met Trp Glu Ile
            725                 730                 735 gcc acc cga ggc caa act ccc tat cca ggg gtg gag aac agt gag att      2256
Ala Thr Arg Gly Gln Thr Pro Tyr Pro Gly Val Glu Asn Ser Glu Ile
        740                 745                 750 tac gac tac cta cgt caa gga aat cgc ctg aaa cag cct ctg gac tgt      2304
Tyr Asp Tyr Leu Arg Gln Gly Asn Arg Leu Lys Gln Pro Leu Asp Cys
755                 760                 765 ctg gat ggc ctc tat gcc ctg atg tcc cgg tgc tgg gag ctg aac cct      2352
Leu Asp Gly Leu Tyr Ala Leu Met Ser Arg Cys Trp Glu Leu Asn Pro
770                 775                 780 cga gac cgg cca agt ttt gca gag ctc cgg gaa gac ttg gag aac aca      2400
Arg Asp Arg Pro Ser Phe Ala Glu Leu Arg Glu Asp Leu Glu Asn Thr
785                 790                 795                 800 ttg aag gct cta ccc cct gct cag gag cct gat gaa atc ctc tat gtc      2448
Leu Lys Ala Leu Pro Pro Ala Gln Glu Pro Asp Glu Ile Leu Tyr Val
            805                 810                 815 aac atg gat gag ggc gga agt cac ctt gaa ccc cgt ggg gct gct gga      2496
Asn Met Asp Glu Gly Gly Ser His Leu Glu Pro Arg Gly Ala Ala Gly
        820                 825                 830 gga gct gac ccc cca acc caa cct gat cct aag gat tac tgt agc tgt      2544
Gly Ala Asp Pro Pro Thr Gln Pro Asp Pro Lys Asp Tyr Cys Ser Cys
835                 840                 845 ctc act gca gct gac gtc cac tca gct gga cgc tat gtc ctt tgt cct      2592
Leu Thr Ala Ala Asp Val His Ser Ala Gly Arg Tyr Val Leu Cys Pro
850                 855                 860 tct aca gcc cca gga ccc act ctg tct gct gac aga ggc tgc cca gca      2640
Ser Thr Ala Pro Gly Pro Thr Leu Ser Ala Asp Arg Gly Cys Pro Ala
865                 870                 875                 880 cct cca ggg cag gag gac gga gcc tga                                   2667
Pro Pro Gly Gln Glu Asp Gly Ala
            885
```

<210> SEQ ID NO 41

```
<211> LENGTH: 888
<212> TYPE: PRT
<213> ORGANISM: Rattus norvegicus

<400> SEQUENCE: 41

Met Gly Arg Val Pro Leu Ala Trp Cys Val Ala Leu Cys Cys Trp Gly
1               5                   10                  15

Cys Ala Ala Pro Lys Asp Thr Gln Thr Glu Ala Asp Ser Pro Phe Val
            20                  25                  30

Gly Asn Pro Gly Asn Ile Thr Gly Ala Arg Gly Leu Thr Gly Thr Leu
        35                  40                  45

Arg Cys Glu Leu Gln Val Gln Gly Glu Pro Pro Glu Val Met Trp Leu
    50                  55                  60

Arg Asp Gly Gln Ile Leu Glu Leu Ala Asp Asn Thr Gln Thr Gln Val
65                  70                  75                  80

Pro Leu Gly Glu Asp Trp Gln Asp Glu Trp Lys Val Val Ser Gln Leu
                85                  90                  95

Arg Ile Ser Ala Leu Gln Leu Ser Asp Ala Gly Glu Tyr Gln Cys Met
            100                 105                 110

Val His Leu Glu Gly Arg Thr Phe Val Ser Gln Pro Gly Phe Val Gly
        115                 120                 125

Leu Glu Gly Leu Pro Tyr Phe Leu Glu Glu Pro Glu Asp Lys Ala Val
    130                 135                 140

Pro Ala Asn Thr Pro Phe Asn Leu Ser Cys Gln Ala Gln Gly Pro Pro
145                 150                 155                 160

Glu Pro Val Thr Leu Leu Trp Leu Gln Asp Ala Val Pro Leu Ala Pro
                165                 170                 175

Val Ala Gly Tyr Ser Phe Gln His Ser Leu Gln Ala Pro Gly Leu Asn
            180                 185                 190

Lys Thr Ser Ser Phe Ser Cys Glu Ala His Asn Ala Lys Gly Val Thr
        195                 200                 205

Thr Ser Arg Thr Ala Thr Ile Thr Val Leu Pro Gln Arg Pro His Asn
    210                 215                 220

Leu His Val Val Ser Arg His Pro Thr Glu Leu Glu Val Ala Trp Ile
225                 230                 235                 240

Pro Thr Leu Ser Gly Ile Tyr Pro Leu Thr His Cys Thr Leu Gln Ala
                245                 250                 255

Val Leu Ser Asn Asp Gly Val Gly Val Trp Leu Gly Lys Ser Asp Pro
            260                 265                 270

Pro Glu Glu Pro Leu Thr Val Gln Val Ser Val Pro Pro His Gln Leu
        275                 280                 285

Arg Leu Glu Lys Leu Leu Pro His Thr Pro Tyr His Ile Arg Val Ser
    290                 295                 300

Cys Thr Ser Ser Gln Gly Pro Ser Pro Trp Thr His Trp Leu Pro Val
305                 310                 315                 320

Glu Thr Thr Glu Gly Val Pro Leu Gly Pro Glu Asn Val Ser Ala
                325                 330                 335

Met Arg Asn Gly Ser Gln Ala Leu Val Arg Trp Gln Glu Pro Arg Glu
            340                 345                 350

Pro Leu Gln Gly Thr Leu Leu Gly Tyr Arg Leu Ala Tyr Arg Gly Gln
        355                 360                 365

Asp Thr Pro Glu Val Leu Met Asp Ile Gly Leu Thr Arg Glu Val Thr
    370                 375                 380

Leu Glu Leu Arg Gly Asp Arg Pro Val Ala Asn Leu Thr Val Ser Val
```

-continued

```
            385                 390                 395                 400
Ala Ala Tyr Thr Ser Ala Gly Asp Gly Pro Trp Ser Leu Pro Val Pro
                    405                 410                 415

Leu Glu Pro Trp Arg Pro Gly Gln Gly Gln Pro Leu His His Leu Val
                    420                 425                 430

Ser Glu Pro Pro Pro Ala Phe Ser Trp Pro Trp Trp Tyr Val Leu
                    435                 440                 445

Leu Gly Ala Leu Val Ala Ala Ala Cys Val Leu Ile Leu Thr Leu Phe
                450                 455                 460

Leu Val His Arg Arg Lys Lys Glu Thr Arg Tyr Gly Glu Val Phe Glu
465                 470                 475                 480

Pro Thr Val Glu Arg Gly Glu Leu Val Val Arg Tyr Arg Ala Arg Lys
                    485                 490                 495

Ser Tyr Ser Arg Arg Thr Thr Glu Ala Thr Leu Asn Ser Leu Gly Ile
                    500                 505                 510

Ser Glu Glu Leu Lys Glu Lys Leu Arg Asp Val Met Val Asp Arg His
                    515                 520                 525

Lys Val Ala Leu Gly Lys Thr Leu Gly Glu Gly Phe Gly Ala Val
                530                 535                 540

Met Glu Gly Gln Leu Asn Gln Asp Asp Ser Ile Leu Lys Val Ala Val
545                 550                 555                 560

Lys Thr Met Lys Ile Ala Ile Cys Thr Arg Ser Glu Leu Glu Asp Phe
                    565                 570                 575

Leu Ser Glu Ala Val Cys Met Lys Glu Phe Asp His Pro Asn Val Met
                580                 585                 590

Arg Leu Ile Gly Val Cys Phe Gln Gly Ser Asp Arg Glu Gly Phe Pro
                595                 600                 605

Glu Pro Val Val Ile Leu Pro Phe Met Lys His Gly Asp Leu His Ser
                    610                 615                 620

Phe Leu Leu Tyr Ser Arg Leu Gly Asp Gln Pro Val Phe Leu Pro Thr
625                 630                 635                 640

Gln Met Leu Val Lys Phe Met Ala Asp Ile Ala Ser Gly Met Glu Tyr
                    645                 650                 655

Leu Ser Thr Lys Arg Phe Ile His Arg Asp Leu Ala Ala Arg Asn Cys
                    660                 665                 670

Met Leu Asn Glu Asn Met Ser Val Cys Val Ala Asp Phe Gly Leu Ser
                    675                 680                 685

Lys Lys Ile Tyr Asn Gly Asp Tyr Tyr Arg Gln Gly Arg Ile Ala Lys
                690                 695                 700

Met Pro Val Lys Trp Ile Ala Ile Glu Ser Leu Ala Asp Arg Val Tyr
705                 710                 715                 720

Thr Ser Lys Ser Asp Val Trp Ser Phe Gly Val Thr Met Trp Glu Ile
                    725                 730                 735

Ala Thr Arg Gly Gln Thr Pro Tyr Pro Gly Val Glu Asn Ser Glu Ile
                    740                 745                 750

Tyr Asp Tyr Leu Arg Gln Gly Asn Arg Leu Lys Gln Pro Leu Asp Cys
                    755                 760                 765

Leu Asp Gly Leu Tyr Ala Leu Met Ser Arg Cys Trp Glu Leu Asn Pro
                770                 775                 780

Arg Asp Arg Pro Ser Phe Ala Glu Leu Arg Glu Asp Leu Glu Asn Thr
785                 790                 795                 800

Leu Lys Ala Leu Pro Pro Ala Gln Glu Pro Asp Glu Ile Leu Tyr Val
                    805                 810                 815
```

```
Asn Met Asp Glu Gly Gly Ser His Leu Glu Pro Arg Gly Ala Ala Gly
            820                 825                 830

Gly Ala Asp Pro Pro Thr Gln Pro Asp Pro Lys Asp Tyr Cys Ser Cys
        835                 840                 845

Leu Thr Ala Ala Asp Val His Ser Ala Gly Arg Tyr Val Leu Cys Pro
850                 855                 860

Ser Thr Ala Pro Gly Pro Thr Leu Ser Ala Asp Arg Gly Cys Pro Ala
865                 870                 875                 880

Pro Pro Gly Gln Glu Asp Gly Ala
                885

<210> SEQ ID NO 42
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer 20

<400> SEQUENCE: 42
tcgcgtcgaa agatctgcca ccatgggcag ggtcc                              35

<210> SEQ ID NO 43
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer 21

<400> SEQUENCE: 43
gagttttgtc gaattcaggc cacgagaagg cggg                               34

<210> SEQ ID NO 44
<211> LENGTH: 2019
<212> TYPE: DNA
<213> ORGANISM: Artificial Sequence
<220> FEATURE:
<223> OTHER INFORMATION: Description of Artificial Sequence: Synthetic
      rAxl-hFc sequence
<220> FEATURE:
<221> NAME/KEY: CDS
<222> LOCATION: (1)..(2016)

<400> SEQUENCE: 44
```

| | | | | | | | | | | | | | | | | |
|---|---|---|---|---|---|---|---|---|---|---|---|---|---|---|---|---|
| atg | ggc | agg | gtc | ccg | ctg | gcc | tgg | tgc | gtg | gcg | ctg | tgc | tgc | tgg | ggg | 48 |
| Met | Gly | Arg | Val | Pro | Leu | Ala | Trp | Cys | Val | Ala | Leu | Cys | Cys | Trp | Gly |  |
| 1 |  |  |  | 5 |  |  |  |  | 10 |  |  |  |  | 15 |  |  |
| tgt | gca | gcc | cct | aag | gac | aca | cag | acc | gag | gct | gac | agc | cca | ttc | gtg | 96 |
| Cys | Ala | Ala | Pro | Lys | Asp | Thr | Gln | Thr | Glu | Ala | Asp | Ser | Pro | Phe | Val |  |
|  |  |  | 20 |  |  |  |  | 25 |  |  |  |  | 30 |  |  |  |
| ggg | aac | cca | ggg | aat | atc | acg | ggt | gcc | aga | gga | ctc | acg | ggg | acc | ctt | 144 |
| Gly | Asn | Pro | Gly | Asn | Ile | Thr | Gly | Ala | Arg | Gly | Leu | Thr | Gly | Thr | Leu |  |
|  |  | 35 |  |  |  | 40 |  |  |  |  | 45 |  |  |  |  |  |
| cgg | tgt | gag | ctc | cag | gtt | cag | ggg | gag | ccc | cct | gag | gtg | atg | tgg | ctt | 192 |
| Arg | Cys | Glu | Leu | Gln | Val | Gln | Gly | Glu | Pro | Pro | Glu | Val | Met | Trp | Leu |  |
| 50 |  |  |  |  | 55 |  |  |  |  | 60 |  |  |  |  |  |  |
| cga | gat | gga | cag | atc | cta | gaa | ctg | gct | gat | aac | acc | cag | acc | cag | gtg | 240 |
| Arg | Asp | Gly | Gln | Ile | Leu | Glu | Leu | Ala | Asp | Asn | Thr | Gln | Thr | Gln | Val |  |
| 65 |  |  |  | 70 |  |  |  |  | 75 |  |  |  |  | 80 |  |  |
| cct | ctg | ggc | gaa | gac | tgg | caa | gat | gaa | tgg | aaa | gtc | gtc | agt | cag | ctc | 288 |
| Pro | Leu | Gly | Glu | Asp | Trp | Gln | Asp | Glu | Trp | Lys | Val | Val | Ser | Gln | Leu |  |
|  |  | 85 |  |  |  | 90 |  |  |  |  | 95 |  |  |  |  |  |

| | | |
|---|---|---|
| aga atc tca gcc ctg caa ctt tca gat gca gga gag tac cag tgt atg<br>Arg Ile Ser Ala Leu Gln Leu Ser Asp Ala Gly Glu Tyr Gln Cys Met<br>100 105 110 | | 336 |
| gtg cac ctg gaa gga cgg acc ttt gtg tct cag ccg ggc ttt gta gga<br>Val His Leu Glu Gly Arg Thr Phe Val Ser Gln Pro Gly Phe Val Gly<br>115 120 125 | | 384 |
| ctg gaa ggt ctc ccg tac ttc ctg gag gaa cct gaa gac aaa gct gtg<br>Leu Glu Gly Leu Pro Tyr Phe Leu Glu Glu Pro Glu Asp Lys Ala Val<br>130 135 140 | | 432 |
| cct gcc aac acc ccc ttc aac cta agc tgc cag gcc cag gga ccc ccg<br>Pro Ala Asn Thr Pro Phe Asn Leu Ser Cys Gln Ala Gln Gly Pro Pro<br>145 150 155 160 | | 480 |
| gaa ccc gtg acc ctg ctc tgg ctt caa gat gct gtc cct ctg gcc cca<br>Glu Pro Val Thr Leu Leu Trp Leu Gln Asp Ala Val Pro Leu Ala Pro<br>165 170 175 | | 528 |
| gtc gca gga tac agc ttt cag cac agt ttg caa gct cca ggc ctg aac<br>Val Ala Gly Tyr Ser Phe Gln His Ser Leu Gln Ala Pro Gly Leu Asn<br>180 185 190 | | 576 |
| aag aca tct tct ttc tca tgt gaa gcc cac aat gcc aag gga gtc acc<br>Lys Thr Ser Ser Phe Ser Cys Glu Ala His Asn Ala Lys Gly Val Thr<br>195 200 205 | | 624 |
| acc tcc cgc aca gct acc atc aca gtg ctc cca cag aga cct cac aat<br>Thr Ser Arg Thr Ala Thr Ile Thr Val Leu Pro Gln Arg Pro His Asn<br>210 215 220 | | 672 |
| ctc cac gtg gtt tcc aga cat ccc acg gag cta gag gta gct tgg atc<br>Leu His Val Val Ser Arg His Pro Thr Glu Leu Glu Val Ala Trp Ile<br>225 230 235 240 | | 720 |
| cct acc ctg agt ggc atc tac ccg ctc acc cac tgc acc ctg cag gct<br>Pro Thr Leu Ser Gly Ile Tyr Pro Leu Thr His Cys Thr Leu Gln Ala<br>245 250 255 | | 768 |
| gtg ctg tca aac gat ggg gtg ggc gtc tgg ctg gga aag tca gat cct<br>Val Leu Ser Asn Asp Gly Val Gly Val Trp Leu Gly Lys Ser Asp Pro<br>260 265 270 | | 816 |
| cct gaa gaa ccc ctc acc gtg caa gta tca gtg ccc ccc cac cag ctt<br>Pro Glu Glu Pro Leu Thr Val Gln Val Ser Val Pro Pro His Gln Leu<br>275 280 285 | | 864 |
| cgg ctg gaa aag ctc ctt cct cac acc cca tat cac atc ggt gta tcc<br>Arg Leu Glu Lys Leu Leu Pro His Thr Pro Tyr His Ile Arg Val Ser<br>290 295 300 | | 912 |
| tgc act agc agc cag ggc ccc tca cct tgg acc cac tgg ctt cct gtg<br>Cys Thr Ser Ser Gln Gly Pro Ser Pro Trp Thr His Trp Leu Pro Val<br>305 310 315 320 | | 960 |
| gag acc acg gag gga gtg ccc ttg ggt ccc cct gag aac gtt agc gcc<br>Glu Thr Thr Glu Gly Val Pro Leu Gly Pro Pro Glu Asn Val Ser Ala<br>325 330 335 | | 1008 |
| atg cgg aat ggg agc cag gcc ctc gtg cgt tgg cag gag cca agg gag<br>Met Arg Asn Gly Ser Gln Ala Leu Val Arg Trp Gln Glu Pro Arg Glu<br>340 345 350 | | 1056 |
| ccc ttg cag ggc acc ctg tta ggg tac cgg ctg gca tat cga ggc cag<br>Pro Leu Gln Gly Thr Leu Leu Gly Tyr Arg Leu Ala Tyr Arg Gly Gln<br>355 360 365 | | 1104 |
| gac acc ccc gag gta ctt atg gat ata ggg cta act cga gag gtg acc<br>Asp Thr Pro Glu Val Leu Met Asp Ile Gly Leu Thr Arg Glu Val Thr<br>370 375 380 | | 1152 |
| ttg gaa ctt cgg ggg gac agg cct gtg gct aac ctg act gtg tct gtg<br>Leu Glu Leu Arg Gly Asp Arg Pro Val Ala Asn Leu Thr Val Ser Val<br>385 390 395 400 | | 1200 |
| gca gcc tat acc tca gct ggg gat ggg ccc tgg agc ctt cct gtg ccc<br>Ala Ala Tyr Thr Ser Ala Gly Asp Gly Pro Trp Ser Leu Pro Val Pro | | 1248 |

-continued

| | | | | | | | | | | | | |
|---|---|---|---|---|---|---|---|---|---|---|---|---|
| | | 405 | | | | 410 | | | | 415 | | |
| cta | gag | ccc | tgg | cgc | cca | ggg | caa | gga | cag | cca | ctc | cac | cat | ctg | gtg | 1296 |
| Leu | Glu | Pro | Trp | Arg | Pro | Gly | Gln | Gly | Gln | Pro | Leu | His | His | Leu | Val | |
| | | 420 | | | | 425 | | | | 430 | | |

| agt | gaa | ccc | cca | cct | ccc | gcc | ttc | tcg | tgg | cct | gaa | ttc | gac | aaa | act | 1344 |
| Ser | Glu | Pro | Pro | Pro | Pro | Ala | Phe | Ser | Trp | Pro | Glu | Phe | Asp | Lys | Thr |
| | | 435 | | | | 440 | | | | 445 | | |

| cac | aca | tgc | cca | ccg | tgc | cca | gca | cct | gaa | ctc | ctg | ggg | gga | ccg | tca | 1392 |
| His | Thr | Cys | Pro | Pro | Cys | Pro | Ala | Pro | Glu | Leu | Leu | Gly | Gly | Pro | Ser |
| 450 | | | | 455 | | | | 460 | | |

| gtc | ttc | ctc | ttc | ccc | cca | aaa | ccc | aag | gac | acc | ctc | atg | atc | tcc | cgg | 1440 |
| Val | Phe | Leu | Phe | Pro | Pro | Lys | Pro | Lys | Asp | Thr | Leu | Met | Ile | Ser | Arg |
| 465 | | | | 470 | | | | 475 | | | | 480 |

| acc | cct | gag | gtc | aca | tgc | gtg | gtg | gtg | gac | gtg | agc | cac | gaa | gac | cct | 1488 |
| Thr | Pro | Glu | Val | Thr | Cys | Val | Val | Val | Asp | Val | Ser | His | Glu | Asp | Pro |
| | | | | 485 | | | | 490 | | | | 495 |

| gag | gtc | aag | ttc | aac | tgg | tac | gtg | gac | ggc | gtg | gag | gtg | cat | aat | gcc | 1536 |
| Glu | Val | Lys | Phe | Asn | Trp | Tyr | Val | Asp | Gly | Val | Glu | Val | His | Asn | Ala |
| | | | 500 | | | | 505 | | | | 510 |

| aag | aca | aag | ccg | cgg | gag | gag | cag | tac | aac | agc | acg | tac | cgt | gtg | gtc | 1584 |
| Lys | Thr | Lys | Pro | Arg | Glu | Glu | Gln | Tyr | Asn | Ser | Thr | Tyr | Arg | Val | Val |
| | | 515 | | | | 520 | | | | 525 |

| agc | gtc | ctc | acc | gtc | ctg | cac | cag | gac | tgg | ctg | aat | ggc | aag | gag | tac | 1632 |
| Ser | Val | Leu | Thr | Val | Leu | His | Gln | Asp | Trp | Leu | Asn | Gly | Lys | Glu | Tyr |
| 530 | | | | 535 | | | | 540 |

| aag | tgc | aag | gtc | tcc | aac | aaa | gcc | ctc | cca | gcc | ccc | atc | gag | aaa | acc | 1680 |
| Lys | Cys | Lys | Val | Ser | Asn | Lys | Ala | Leu | Pro | Ala | Pro | Ile | Glu | Lys | Thr |
| 545 | | | | 550 | | | | 555 | | | | 560 |

| atc | tcc | aaa | gcc | aaa | ggg | cag | ccc | cga | gaa | cca | cag | gtg | tac | acc | ctg | 1728 |
| Ile | Ser | Lys | Ala | Lys | Gly | Gln | Pro | Arg | Glu | Pro | Gln | Val | Tyr | Thr | Leu |
| | | | | 565 | | | | 570 | | | | 575 |

| ccc | cca | tcc | cgg | gat | gag | ctg | acc | aag | aac | cag | gtc | agc | ctg | acc | tgc | 1776 |
| Pro | Pro | Ser | Arg | Asp | Glu | Leu | Thr | Lys | Asn | Gln | Val | Ser | Leu | Thr | Cys |
| | | | 580 | | | | 585 | | | | 590 |

| ctg | gtc | aaa | ggc | ttc | tat | ccc | agc | gac | atc | gcc | gtg | gag | tgg | gag | agc | 1824 |
| Leu | Val | Lys | Gly | Phe | Tyr | Pro | Ser | Asp | Ile | Ala | Val | Glu | Trp | Glu | Ser |
| | | 595 | | | | 600 | | | | 605 |

| aat | ggg | cag | ccg | gag | aac | aac | tac | aag | acc | acg | cct | ccc | gtg | ctg | gac | 1872 |
| Asn | Gly | Gln | Pro | Glu | Asn | Asn | Tyr | Lys | Thr | Thr | Pro | Pro | Val | Leu | Asp |
| 610 | | | | 615 | | | | 620 |

| tcc | gac | ggc | tcc | ttc | ttc | ctc | tac | agc | aag | ctc | acc | gtg | gac | aag | agc | 1920 |
| Ser | Asp | Gly | Ser | Phe | Phe | Leu | Tyr | Ser | Lys | Leu | Thr | Val | Asp | Lys | Ser |
| 625 | | | | 630 | | | | 635 | | | | 640 |

| agg | tgg | cag | cag | ggg | aac | gtc | ttc | tca | tgc | tcc | gtg | atg | cat | gag | gct | 1968 |
| Arg | Trp | Gln | Gln | Gly | Asn | Val | Phe | Ser | Cys | Ser | Val | Met | His | Glu | Ala |
| | | | | 645 | | | | 650 | | | | 655 |

| ctg | cac | aac | cac | tac | acg | cag | aag | agc | ctc | tcc | ctg | tct | ccg | ggc | aaa | 2016 |
| Leu | His | Asn | His | Tyr | Thr | Gln | Lys | Ser | Leu | Ser | Leu | Ser | Pro | Gly | Lys |
| | | | 660 | | | | 665 | | | | 670 |

| tga | | | | | | | | | | | | | | | | 2019 |

<210> SEQ ID NO 45
<211> LENGTH: 672
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 45

```
Met Gly Arg Val Pro Leu Ala Trp Cys Val Ala Leu Cys Cys Trp Gly
1               5                   10                  15

Cys Ala Ala Pro Lys Asp Thr Gln Thr Glu Ala Asp Ser Pro Phe Val
            20                  25                  30

Gly Asn Pro Gly Asn Ile Thr Gly Ala Arg Gly Leu Thr Gly Thr Leu
            35                  40                  45

Arg Cys Glu Leu Gln Val Gln Gly Glu Pro Pro Glu Val Met Trp Leu
        50                  55                  60

Arg Asp Gly Gln Ile Leu Glu Leu Ala Asp Asn Thr Gln Thr Gln Val
65                  70                  75                  80

Pro Leu Gly Glu Asp Trp Gln Asp Glu Trp Lys Val Val Ser Gln Leu
                85                  90                  95

Arg Ile Ser Ala Leu Gln Leu Ser Asp Ala Gly Glu Tyr Gln Cys Met
            100                 105                 110

Val His Leu Glu Gly Arg Thr Phe Val Ser Gln Pro Gly Phe Val Gly
        115                 120                 125

Leu Glu Gly Leu Pro Tyr Phe Leu Glu Glu Pro Glu Asp Lys Ala Val
        130                 135                 140

Pro Ala Asn Thr Pro Phe Asn Leu Ser Cys Gln Ala Gln Gly Pro Pro
145                 150                 155                 160

Glu Pro Val Thr Leu Leu Trp Leu Gln Asp Ala Val Pro Leu Ala Pro
                165                 170                 175

Val Ala Gly Tyr Ser Phe Gln His Ser Leu Gln Ala Pro Gly Leu Asn
            180                 185                 190

Lys Thr Ser Ser Phe Ser Cys Glu Ala His Asn Ala Lys Gly Val Thr
        195                 200                 205

Thr Ser Arg Thr Ala Thr Ile Thr Val Leu Pro Gln Arg Pro His Asn
210                 215                 220

Leu His Val Val Ser Arg His Pro Thr Glu Leu Glu Val Ala Trp Ile
225                 230                 235                 240

Pro Thr Leu Ser Gly Ile Tyr Pro Leu Thr His Cys Thr Leu Gln Ala
                245                 250                 255

Val Leu Ser Asn Asp Gly Val Gly Val Trp Leu Gly Lys Ser Asp Pro
            260                 265                 270

Pro Glu Glu Pro Leu Thr Val Gln Val Ser Val Pro Pro His Gln Leu
        275                 280                 285

Arg Leu Glu Lys Leu Leu Pro His Thr Pro Tyr His Ile Arg Val Ser
        290                 295                 300

Cys Thr Ser Ser Gln Gly Pro Ser Pro Trp Thr His Trp Leu Pro Val
305                 310                 315                 320

Glu Thr Thr Glu Gly Val Pro Leu Gly Pro Pro Glu Asn Val Ser Ala
                325                 330                 335

Met Arg Asn Gly Ser Gln Ala Leu Val Arg Trp Gln Glu Pro Arg Glu
            340                 345                 350

Pro Leu Gln Gly Thr Leu Leu Gly Tyr Arg Leu Ala Tyr Arg Gly Gln
        355                 360                 365

Asp Thr Pro Glu Val Leu Met Asp Ile Gly Leu Thr Arg Glu Val Thr
        370                 375                 380

Leu Glu Leu Arg Gly Asp Arg Pro Val Ala Asn Leu Thr Val Ser Val
385                 390                 395                 400

Ala Ala Tyr Thr Ser Ala Gly Asp Gly Pro Trp Ser Leu Pro Val Pro
            405                 410                 415

Leu Glu Pro Trp Arg Pro Gly Gln Gly Gln Pro Leu His His Leu Val
```

```
                420              425              430
Ser Glu Pro Pro Pro Ala Phe Ser Trp Pro Glu Phe Asp Lys Thr
            435              440              445
His Thr Cys Pro Pro Cys Pro Ala Pro Glu Leu Leu Gly Gly Pro Ser
        450              455              460
Val Phe Leu Phe Pro Pro Lys Pro Lys Asp Thr Leu Met Ile Ser Arg
465              470              475              480
Thr Pro Glu Val Thr Cys Val Val Val Asp Val Ser His Glu Asp Pro
                485              490              495
Glu Val Lys Phe Asn Trp Tyr Val Asp Gly Val Glu Val His Asn Ala
            500              505              510
Lys Thr Lys Pro Arg Glu Glu Gln Tyr Asn Ser Thr Tyr Arg Val Val
            515              520              525
Ser Val Leu Thr Val Leu His Gln Asp Trp Leu Asn Gly Lys Glu Tyr
            530              535              540
Lys Cys Lys Val Ser Asn Lys Ala Leu Pro Ala Pro Ile Glu Lys Thr
545              550              555              560
Ile Ser Lys Ala Lys Gly Gln Pro Arg Glu Pro Gln Val Tyr Thr Leu
            565              570              575
Pro Pro Ser Arg Asp Glu Leu Thr Lys Asn Gln Val Ser Leu Thr Cys
            580              585              590
Leu Val Lys Gly Phe Tyr Pro Ser Asp Ile Ala Val Glu Trp Glu Ser
            595              600              605
Asn Gly Gln Pro Glu Asn Asn Tyr Lys Thr Thr Pro Pro Val Leu Asp
        610              615              620
Ser Asp Gly Ser Phe Phe Leu Tyr Ser Lys Leu Thr Val Asp Lys Ser
625              630              635              640
Arg Trp Gln Gln Gly Asn Val Phe Ser Cys Ser Val Met His Glu Ala
                645              650              655
Leu His Asn His Tyr Thr Gln Lys Ser Leu Ser Leu Ser Pro Gly Lys
            660              665              670

<210> SEQ ID NO 46
<211> LENGTH: 2667
<212> TYPE: DNA
<213> ORGANISM: Mus musculus
<220> FEATURE:
<221> NAME/KEY: CDS
<222> LOCATION: (1)..(2664)

<400> SEQUENCE: 46 atg ggc agg gtc ccg ctg gcc tgg tgg ttg gcg ctg tgc tgc tgg ggg      48
Met Gly Arg Val Pro Leu Ala Trp Trp Leu Ala Leu Cys Cys Trp Gly
1               5                   10                  15 tgt gca gcc cat aag gac aca cag acc gag gct ggc agc ccg ttt gtg      96
Cys Ala Ala His Lys Asp Thr Gln Thr Glu Ala Gly Ser Pro Phe Val
            20                  25                  30 ggg aac cca ggg aat atc aca ggt gcc aga gga ctc acg ggg aca ctt     144
Gly Asn Pro Gly Asn Ile Thr Gly Ala Arg Gly Leu Thr Gly Thr Leu
        35                  40                  45 cgg tgt gag ctc cag gtt cag ggg gaa ccc cct gag gtg gtg tgg ctt     192
Arg Cys Glu Leu Gln Val Gln Gly Glu Pro Pro Glu Val Val Trp Leu
    50                  55                  60 cga gat gga cag atc cta gaa ctg gct gat aac acc cag acc cag gtg     240
Arg Asp Gly Gln Ile Leu Glu Leu Ala Asp Asn Thr Gln Thr Gln Val
65                  70                  75                  80 cct ctg ggc gaa gac tgg caa gat gaa tgg aaa gtt gtc agt cag ctc     288
```

-continued

```
                Pro Leu Gly Glu Asp Trp Gln Asp Glu Trp Lys Val Val Ser Gln Leu
                                 85                  90                  95 aga atc tca gcc ctg caa ctt tca gat gca ggg gag tac cag tgt atg        336
Arg Ile Ser Ala Leu Gln Leu Ser Asp Ala Gly Glu Tyr Gln Cys Met
            100                 105                 110 gtg cat cta gaa gga cgg acc ttt gtg tct cag ccg ggc ttt gta ggg        384
Val His Leu Glu Gly Arg Thr Phe Val Ser Gln Pro Gly Phe Val Gly
                115                 120                 125 ctg gaa ggt ctc ccg tac ttc ctg gag gag cct gag gac aaa gct gtg        432
Leu Glu Gly Leu Pro Tyr Phe Leu Glu Glu Pro Glu Asp Lys Ala Val
130                 135                 140 cct gcc aac acc cct ttc aac cta agc tgc cag gcc cag gga ccc ccg        480
Pro Ala Asn Thr Pro Phe Asn Leu Ser Cys Gln Ala Gln Gly Pro Pro
145                 150                 155                 160 gaa ccc gtg acc cta ctc tgg ctt caa gat gct gtc ccc ctg gcc cca        528
Glu Pro Val Thr Leu Leu Trp Leu Gln Asp Ala Val Pro Leu Ala Pro
                165                 170                 175 gtc aca gga cac agc tcc cag cac agt ctg caa act cca ggc ctg aac        576
Val Thr Gly His Ser Ser Gln His Ser Leu Gln Thr Pro Gly Leu Asn
                180                 185                 190 aag aca tct tct ttc tca tgt gaa gcc cac aat gcc aag gga gtc acc        624
Lys Thr Ser Ser Phe Ser Cys Glu Ala His Asn Ala Lys Gly Val Thr
                195                 200                 205 acc tcc cgc aca gcc acc atc aca gtg ctc ccc cag agg cct cac cat        672
Thr Ser Arg Thr Ala Thr Ile Thr Val Leu Pro Gln Arg Pro His His
210                 215                 220 ctc cac gtg gtt tcc aga caa cct acg gag cta gag gta gct tgg acc        720
Leu His Val Val Ser Arg Gln Pro Thr Glu Leu Glu Val Ala Trp Thr
225                 230                 235                 240 cct ggc ctg agt ggc atc tac ccg ctc acc cac tgc aac ctg cag gcc        768
Pro Gly Leu Ser Gly Ile Tyr Pro Leu Thr His Cys Asn Leu Gln Ala
                245                 250                 255 gtg ctg tca gac gat ggg gtg ggt atc tgg ctg gga aag tca gat cct        816
Val Leu Ser Asp Asp Gly Val Gly Ile Trp Leu Gly Lys Ser Asp Pro
                260                 265                 270 cct gaa gac ccc ctc acc ttg caa gta tca gtg ccc ccc cac cag ctt        864
Pro Glu Asp Pro Leu Thr Leu Gln Val Ser Val Pro Pro His Gln Leu
            275                 280                 285 cgg ctg gaa aag ctc ctt cct cac acc ccg tat cac atc cgg ata tcc        912
Arg Leu Glu Lys Leu Leu Pro His Thr Pro Tyr His Ile Arg Ile Ser
            290                 295                 300 tgc agc agc agc cag ggc ccc tca cct tgg acc cac tgg ctt cct gtg        960
Cys Ser Ser Ser Gln Gly Pro Ser Pro Trp Thr His Trp Leu Pro Val
305                 310                 315                 320 gag acc aca gag gga gtg ccc ttg ggt ccc cct gag aac gtt agc gcc       1008
Glu Thr Thr Glu Gly Val Pro Leu Gly Pro Pro Glu Asn Val Ser Ala
                325                 330                 335 atg cgg aat ggg agc cag gtc ctc gtg cgt tgg cag gag cca agg gtg       1056
Met Arg Asn Gly Ser Gln Val Leu Val Arg Trp Gln Glu Pro Arg Val
                340                 345                 350 ccc ctg caa ggc acc ctg tta ggg tac cgg ctg gca tat cga ggc cag       1104
Pro Leu Gln Gly Thr Leu Leu Gly Tyr Arg Leu Ala Tyr Arg Gly Gln
            355                 360                 365 gac acc ccc gag gta ctt atg gat ata ggg cta act cga gag gtg acc       1152
Asp Thr Pro Glu Val Leu Met Asp Ile Gly Leu Thr Arg Glu Val Thr
370                 375                 380 ttg gaa ctg cgg ggg gac agg cct gtg gct aac ctg act gtg tct gtg       1200
Leu Glu Leu Arg Gly Asp Arg Pro Val Ala Asn Leu Thr Val Ser Val
385                 390                 395                 400
```

| | | |
|---|---|---|
| aca gcc tat acc tcg gct ggg gat ggg ccc tgg agc ctt cct gtg ccc<br>Thr Ala Tyr Thr Ser Ala Gly Asp Gly Pro Trp Ser Leu Pro Val Pro<br>                   405                   410                   415 | | 1248 |
| cta gag ccc tgg cgc cca ggg caa gga cag cca ctc cac cat ctg gtg<br>Leu Glu Pro Trp Arg Pro Gly Gln Gly Gln Pro Leu His His Leu Val<br>                   420                   425                   430 | | 1296 |
| agt gaa ccc cca cct cgc gcc ttc tcg tgg cct tgg tgg tat gta ctg<br>Ser Glu Pro Pro Pro Arg Ala Phe Ser Trp Pro Trp Trp Tyr Val Leu<br>                   435                   440                   445 | | 1344 |
| ctg gga gca ctt gtg gct gcc gcc tgc gtc ctc atc ttg gcc ctg ttc<br>Leu Gly Ala Leu Val Ala Ala Ala Cys Val Leu Ile Leu Ala Leu Phe<br>     450                   455                   460 | | 1392 |
| ctt gtc cat cgg agg aag aag gag act cga tat ggg gag gtg ttt gag<br>Leu Val His Arg Arg Lys Lys Glu Thr Arg Tyr Gly Glu Val Phe Glu<br>465                   470                   475                   480 | | 1440 |
| cca acc gtg gaa aga ggt gaa ctg gta gtc agg tac cgt gtc cga aag<br>Pro Thr Val Glu Arg Gly Glu Leu Val Val Arg Tyr Arg Val Arg Lys<br>                   485                   490                   495 | | 1488 |
| tcc tac agc cgg cgg acc act gaa gcc acc ttg aac agt ctg ggc atc<br>Ser Tyr Ser Arg Arg Thr Thr Glu Ala Thr Leu Asn Ser Leu Gly Ile<br>               500                   505                   510 | | 1536 |
| agt gaa gag ctg aag gag aaa cta cga gac gtc atg gta gat cgg cat<br>Ser Glu Glu Leu Lys Glu Lys Leu Arg Asp Val Met Val Asp Arg His<br>         515                   520                   525 | | 1584 |
| aag gtg gcc ttg ggg aag acc ctg gga gaa gga gaa ttt ggc gct gtg<br>Lys Val Ala Leu Gly Lys Thr Leu Gly Glu Gly Glu Phe Gly Ala Val<br>     530                   535                   540 | | 1632 |
| atg gaa ggt cag ctc aat cag gat gac tcc atc ctc aag gtc gct gtg<br>Met Glu Gly Gln Leu Asn Gln Asp Asp Ser Ile Leu Lys Val Ala Val<br>545                   550                   555                   560 | | 1680 |
| aag acc atg aaa att gcc atc tgc aca aga tca gag ctg gag gat ttc<br>Lys Thr Met Lys Ile Ala Ile Cys Thr Arg Ser Glu Leu Glu Asp Phe<br>               565                   570                   575 | | 1728 |
| ctg agt gaa gct gtc tgc atg aag gaa ttt gac cac ccc aac gtc atg<br>Leu Ser Glu Ala Val Cys Met Lys Glu Phe Asp His Pro Asn Val Met<br>         580                   585                   590 | | 1776 |
| agg ctc att ggc gtc tgt ttt cag ggc tct gac aga gag ggt ttc cca<br>Arg Leu Ile Gly Val Cys Phe Gln Gly Ser Asp Arg Glu Gly Phe Pro<br>     595                   600                   605 | | 1824 |
| gaa cct gtg gtc atc ttg cct ttc atg aaa cac gga gac cta cac agt<br>Glu Pro Val Val Ile Leu Pro Phe Met Lys His Gly Asp Leu His Ser<br>610                   615                   620 | | 1872 |
| ttc ctc ctg tac tcc cgg ctc ggg gac cag cca gtg ttc ctg ccc act<br>Phe Leu Leu Tyr Ser Arg Leu Gly Asp Gln Pro Val Phe Leu Pro Thr<br>625                   630                   635                   640 | | 1920 |
| cag atg cta gtg aag ttc atg gcc gac att gcc agt ggt atg gag tac<br>Gln Met Leu Val Lys Phe Met Ala Asp Ile Ala Ser Gly Met Glu Tyr<br>               645                   650                   655 | | 1968 |
| ctg agt acc aag aga ttc ata cat cgg gac ctg gct gcc agg aac tgc<br>Leu Ser Thr Lys Arg Phe Ile His Arg Asp Leu Ala Ala Arg Asn Cys<br>         660                   665                   670 | | 2016 |
| atg ctg aat gag aac atg tcc gtg tgt gtg gca gac ttc ggg ctc tcc<br>Met Leu Asn Glu Asn Met Ser Val Cys Val Ala Asp Phe Gly Leu Ser<br>     675                   680                   685 | | 2064 |
| aag aag atc tac aac ggg gat tac tac cgc caa ggg cgc att gcc aag<br>Lys Lys Ile Tyr Asn Gly Asp Tyr Tyr Arg Gln Gly Arg Ile Ala Lys<br>     690                   695                   700 | | 2112 |
| atg cca gtc aag tgg att gct att gag agt ctg gca gat cgg gtc tac<br>Met Pro Val Lys Trp Ile Ala Ile Glu Ser Leu Ala Asp Arg Val Tyr<br>705                   710                   715                   720 | | 2160 |

```
acc agc aag agc gat gtg tgg tcc ttc ggt gtg aca atg tgg gag atc      2208
Thr Ser Lys Ser Asp Val Trp Ser Phe Gly Val Thr Met Trp Glu Ile
            725                 730                 735 gcc acc cga ggc caa act ccc tat cca ggg gtg gag aac agt gag att      2256
Ala Thr Arg Gly Gln Thr Pro Tyr Pro Gly Val Glu Asn Ser Glu Ile
            740                 745                 750 tac gac tac ctg cgt caa gga aat cgg ctg aaa cag cct gtg gac tgt      2304
Tyr Asp Tyr Leu Arg Gln Gly Asn Arg Leu Lys Gln Pro Val Asp Cys
            755                 760                 765 ctg gac ggc ctg tat gcc ctg atg tct cgg tgc tgg gaa ctg aac cct      2352
Leu Asp Gly Leu Tyr Ala Leu Met Ser Arg Cys Trp Glu Leu Asn Pro
            770                 775                 780 cga gac cgg cca agt ttt gcg gag ctc cgg gaa gac ttg gag aac aca      2400
Arg Asp Arg Pro Ser Phe Ala Glu Leu Arg Glu Asp Leu Glu Asn Thr
785                 790                 795                 800 ctg aag gct ctg ccc cct gct cag gag cca gat gaa atc ctc tat gtc      2448
Leu Lys Ala Leu Pro Pro Ala Gln Glu Pro Asp Glu Ile Leu Tyr Val
                805                 810                 815 aac atg gat gag ggc gga agc cac ctt gaa ccc cgt ggg gct gct gga      2496
Asn Met Asp Glu Gly Gly Ser His Leu Glu Pro Arg Gly Ala Ala Gly
            820                 825                 830 gga gct gac ccc cca acc caa cct gat cct aag gat tcc tgt agc tgt      2544
Gly Ala Asp Pro Pro Thr Gln Pro Asp Pro Lys Asp Ser Cys Ser Cys
            835                 840                 845 ctc act gca gct gac gtc cac tca gct gga cgc tat gtc ctt tgt cct      2592
Leu Thr Ala Ala Asp Val His Ser Ala Gly Arg Tyr Val Leu Cys Pro
850                 855                 860 tct aca gcc cca gga ccc act ctg tct gct gac aga ggc tgc cca gca      2640
Ser Thr Ala Pro Gly Pro Thr Leu Ser Ala Asp Arg Gly Cys Pro Ala
865                 870                 875                 880 cct cca ggg cag gag gac gga gcc tga                                  2667
Pro Pro Gly Gln Glu Asp Gly Ala
            885

<210> SEQ ID NO 47
<211> LENGTH: 888
<212> TYPE: PRT
<213> ORGANISM: Mus musculus

<400> SEQUENCE: 47

Met Gly Arg Val Pro Leu Ala Trp Trp Leu Ala Leu Cys Cys Trp Gly
1               5                   10                  15

Cys Ala Ala His Lys Asp Thr Gln Thr Glu Ala Gly Ser Pro Phe Val
            20                  25                  30

Gly Asn Pro Gly Asn Ile Thr Gly Ala Arg Gly Leu Thr Gly Thr Leu
        35                  40                  45

Arg Cys Glu Leu Gln Val Gly Glu Pro Pro Glu Val Val Trp Leu
    50                  55                  60

Arg Asp Gly Gln Ile Leu Glu Leu Ala Asp Asn Thr Gln Thr Gln Val
65                  70                  75                  80

Pro Leu Gly Glu Asp Trp Gln Asp Glu Trp Lys Val Val Ser Gln Leu
                85                  90                  95

Arg Ile Ser Ala Leu Gln Leu Ser Asp Ala Gly Glu Tyr Gln Cys Met
            100                 105                 110

Val His Leu Glu Gly Arg Thr Phe Val Ser Gln Pro Gly Phe Val Gly
        115                 120                 125

Leu Glu Gly Leu Pro Tyr Phe Leu Glu Glu Pro Glu Asp Lys Ala Val
    130                 135                 140
```

```
Pro Ala Asn Thr Pro Phe Asn Leu Ser Cys Gln Ala Gln Gly Pro Pro
145                 150                 155                 160

Glu Pro Val Thr Leu Leu Trp Leu Gln Asp Ala Val Pro Leu Ala Pro
                165                 170                 175

Val Thr Gly His Ser Ser Gln His Ser Leu Gln Thr Pro Gly Leu Asn
            180                 185                 190

Lys Thr Ser Ser Phe Ser Cys Glu Ala His Asn Ala Lys Gly Val Thr
                195                 200                 205

Thr Ser Arg Thr Ala Thr Ile Thr Val Leu Pro Gln Arg Pro His His
        210                 215                 220

Leu His Val Val Ser Arg Gln Pro Thr Glu Leu Glu Val Ala Trp Thr
225                 230                 235                 240

Pro Gly Leu Ser Gly Ile Tyr Pro Leu Thr His Cys Asn Leu Gln Ala
                245                 250                 255

Val Leu Ser Asp Asp Gly Val Gly Ile Trp Leu Gly Lys Ser Asp Pro
            260                 265                 270

Pro Glu Asp Pro Leu Thr Leu Gln Val Ser Val Pro Pro His Gln Leu
                275                 280                 285

Arg Leu Glu Lys Leu Leu Pro His Thr Pro Tyr His Ile Arg Ile Ser
        290                 295                 300

Cys Ser Ser Ser Gln Gly Pro Ser Pro Trp Thr His Trp Leu Pro Val
305                 310                 315                 320

Glu Thr Thr Glu Gly Val Pro Leu Gly Pro Pro Glu Asn Val Ser Ala
                325                 330                 335

Met Arg Asn Gly Ser Gln Val Leu Val Arg Trp Gln Glu Pro Arg Val
            340                 345                 350

Pro Leu Gln Gly Thr Leu Leu Gly Tyr Arg Leu Ala Tyr Arg Gly Gln
                355                 360                 365

Asp Thr Pro Glu Val Leu Met Asp Ile Gly Leu Thr Arg Glu Val Thr
        370                 375                 380

Leu Glu Leu Arg Gly Asp Arg Pro Val Ala Asn Leu Thr Val Ser Val
385                 390                 395                 400

Thr Ala Tyr Thr Ser Ala Gly Asp Gly Pro Trp Ser Leu Pro Val Pro
                405                 410                 415

Leu Glu Pro Trp Arg Pro Gly Gln Gly Gln Pro Leu His His Leu Val
                420                 425                 430

Ser Glu Pro Pro Pro Arg Ala Phe Ser Trp Pro Trp Trp Tyr Val Leu
        435                 440                 445

Leu Gly Ala Leu Val Ala Ala Ala Cys Val Leu Ile Leu Ala Leu Phe
450                 455                 460

Leu Val His Arg Arg Lys Lys Glu Thr Arg Tyr Gly Glu Val Phe Glu
465                 470                 475                 480

Pro Thr Val Glu Arg Gly Glu Leu Val Val Arg Tyr Arg Val Arg Lys
                485                 490                 495

Ser Tyr Ser Arg Arg Thr Thr Glu Ala Thr Leu Asn Ser Leu Gly Ile
        500                 505                 510

Ser Glu Glu Leu Lys Glu Lys Leu Arg Asp Val Met Val Asp Arg His
515                 520                 525

Lys Val Ala Leu Gly Lys Thr Leu Gly Glu Gly Glu Phe Gly Ala Val
        530                 535                 540

Met Glu Gly Gln Leu Asn Gln Asp Asp Ser Ile Leu Lys Val Ala Val
545                 550                 555                 560
```

Lys Thr Met Lys Ile Ala Ile Cys Thr Arg Ser Glu Leu Glu Asp Phe
                565                 570                 575

Leu Ser Glu Ala Val Cys Met Lys Glu Phe Asp His Pro Asn Val Met
            580                 585                 590

Arg Leu Ile Gly Val Cys Phe Gln Gly Ser Asp Arg Glu Gly Phe Pro
        595                 600                 605

Glu Pro Val Ile Leu Pro Phe Met Lys His Gly Asp Leu His Ser
    610                 615                 620

Phe Leu Leu Tyr Ser Arg Leu Gly Asp Gln Pro Val Phe Leu Pro Thr
625                 630                 635                 640

Gln Met Leu Val Lys Phe Met Ala Asp Ile Ala Ser Gly Met Glu Tyr
                645                 650                 655

Leu Ser Thr Lys Arg Phe Ile His Arg Asp Leu Ala Ala Arg Asn Cys
            660                 665                 670

Met Leu Asn Glu Asn Met Ser Val Cys Val Ala Asp Phe Gly Leu Ser
        675                 680                 685

Lys Lys Ile Tyr Asn Gly Asp Tyr Tyr Arg Gln Gly Arg Ile Ala Lys
    690                 695                 700

Met Pro Val Lys Trp Ile Ala Ile Glu Ser Leu Ala Asp Arg Val Tyr
705                 710                 715                 720

Thr Ser Lys Ser Asp Val Trp Ser Phe Gly Val Thr Met Trp Glu Ile
                725                 730                 735

Ala Thr Arg Gly Gln Thr Pro Tyr Pro Gly Val Glu Asn Ser Glu Ile
            740                 745                 750

Tyr Asp Tyr Leu Arg Gln Gly Asn Arg Leu Lys Gln Pro Val Asp Cys
        755                 760                 765

Leu Asp Gly Leu Tyr Ala Leu Met Ser Arg Cys Trp Glu Leu Asn Pro
    770                 775                 780

Arg Asp Arg Pro Ser Phe Ala Glu Leu Arg Glu Asp Leu Glu Asn Thr
785                 790                 795                 800

Leu Lys Ala Leu Pro Pro Ala Gln Glu Pro Asp Glu Ile Leu Tyr Val
                805                 810                 815

Asn Met Asp Glu Gly Gly Ser His Leu Glu Pro Arg Gly Ala Ala Gly
            820                 825                 830

Gly Ala Asp Pro Pro Thr Gln Pro Asp Pro Lys Asp Ser Cys Ser Cys
        835                 840                 845

Leu Thr Ala Ala Asp Val His Ser Ala Gly Arg Tyr Val Leu Cys Pro
    850                 855                 860

Ser Thr Ala Pro Gly Pro Thr Leu Ser Ala Asp Arg Gly Cys Pro Ala
865                 870                 875                 880

Pro Pro Gly Gln Glu Asp Gly Ala
                885

<210> SEQ ID NO 48
<211> LENGTH: 2034
<212> TYPE: DNA
<213> ORGANISM: Artificial Sequence
<220> FEATURE:
<223> OTHER INFORMATION: Description of Artificial Sequence: Synthetic
      mAxl-mFc sequence
<220> FEATURE:
<221> NAME/KEY: CDS
<222> LOCATION: (1)..(2025)

<400> SEQUENCE: 48 aga tct acg cgt gcc acc atg ggc agg gtc ccg ctg gcc tgg tgg ttg      48
Arg Ser Thr Arg Ala Thr Met Gly Arg Val Pro Leu Ala Trp Trp Leu

```
1               5                   10                  15
gcg ctg tgc tgc tgg ggg tgt gca gcc cat aag gac aca cag acc gag        96
Ala Leu Cys Cys Trp Gly Cys Ala Ala His Lys Asp Thr Gln Thr Glu
            20                  25                  30 gct ggc agc ccg ttt gtg ggg aac cca ggg aat atc aca ggt gcc aga       144
Ala Gly Ser Pro Phe Val Gly Asn Pro Gly Asn Ile Thr Gly Ala Arg
        35                  40                  45 gga ctc acg ggg aca ctt cgg tgt gag ctc cag gtt cag ggg gaa ccc       192
Gly Leu Thr Gly Thr Leu Arg Cys Glu Leu Gln Val Gln Gly Glu Pro
    50                  55                  60 cct gag gtg gtg tgg ctt cga gat gga cag atc cta gaa ctg gct gat       240
Pro Glu Val Val Trp Leu Arg Asp Gly Gln Ile Leu Glu Leu Ala Asp
65                  70                  75                  80 aac acc cag acc cag gtg cct ctg ggc gaa gac tgg caa gat gaa tgg       288
Asn Thr Gln Thr Gln Val Pro Leu Gly Glu Asp Trp Gln Asp Glu Trp
                85                  90                  95 aaa gtt gtc agt cag ctc aga atc tca gcc ctg caa ctt tca gat gca       336
Lys Val Val Ser Gln Leu Arg Ile Ser Ala Leu Gln Leu Ser Asp Ala
            100                 105                 110 ggg gag tac cag tgt atg gtg cat cta gaa gga cgg acc ttt gtg tct       384
Gly Glu Tyr Gln Cys Met Val His Leu Glu Gly Arg Thr Phe Val Ser
        115                 120                 125 cag ccg ggc ttt gta ggg ctg gaa ggt ctc ccg tac ttc ctg gag gag       432
Gln Pro Gly Phe Val Gly Leu Glu Gly Leu Pro Tyr Phe Leu Glu Glu
    130                 135                 140 cct gag gac aaa gct gtg cct gcc aac acc cct ttc aac cta agc tgc       480
Pro Glu Asp Lys Ala Val Pro Ala Asn Thr Pro Phe Asn Leu Ser Cys
145                 150                 155                 160 cag gcc cag gga ccc ccg gaa ccc gtg acc cta ctc tgg ctt caa gat       528
Gln Ala Gln Gly Pro Pro Glu Pro Val Thr Leu Leu Trp Leu Gln Asp
                165                 170                 175 gct gtc ccc ctg gcc cca gtc aca gga cac agc tcc cag cac agt ctg       576
Ala Val Pro Leu Ala Pro Val Thr Gly His Ser Ser Gln His Ser Leu
            180                 185                 190 caa act cca ggc ctg aac aag aca tct tct ttc tca tgt gaa gcc cac       624
Gln Thr Pro Gly Leu Asn Lys Thr Ser Ser Phe Ser Cys Glu Ala His
        195                 200                 205 aat gcc aag gga gtc acc acc tcc cgc aca gcc acc atc aca gtg ctc       672
Asn Ala Lys Gly Val Thr Thr Ser Arg Thr Ala Thr Ile Thr Val Leu
    210                 215                 220 ccc cag agg cct cac cat ctc cac gtg gtt tcc aga caa cct acg gag       720
Pro Gln Arg Pro His His Leu His Val Val Ser Arg Gln Pro Thr Glu
225                 230                 235                 240 cta gag gta gct tgg acc cct ggc ctg agt ggc atc tac ccg ctc acc       768
Leu Glu Val Ala Trp Thr Pro Gly Leu Ser Gly Ile Tyr Pro Leu Thr
                245                 250                 255 cac tgc aac ctg cag gcc gtg ctg tca gac gat ggg gtg ggt atc tgg       816
His Cys Asn Leu Gln Ala Val Leu Ser Asp Asp Gly Val Gly Ile Trp
            260                 265                 270 ctg gga aag tca gat cct cct gaa gac ccc ctc acc ttg caa gta tca       864
Leu Gly Lys Ser Asp Pro Pro Glu Asp Pro Leu Thr Leu Gln Val Ser
        275                 280                 285 gtg ccc ccc cac cag ctt cgg ctg gaa aag ctc ctt cct cac acc ccg       912
Val Pro Pro His Gln Leu Arg Leu Glu Lys Leu Leu Pro His Thr Pro
    290                 295                 300 tat cac atc cgg ata tcc tgc agc agc agc cag ggc ccc tca cct tgg       960
Tyr His Ile Arg Ile Ser Cys Ser Ser Ser Gln Gly Pro Ser Pro Trp
305                 310                 315                 320 acc cac tgg ctt cct gtg gag acc aca gag gga gtg ccc ttg ggt ccc      1008
```

```
Thr His Trp Leu Pro Val Glu Thr Thr Glu Gly Val Pro Leu Gly Pro
                325                 330                 335 cct gag aac gtt agc gcc atg cgg aat ggg agc cag gtc ctc gtg cgt       1056
Pro Glu Asn Val Ser Ala Met Arg Asn Gly Ser Gln Val Leu Val Arg
            340                 345                 350 tgg cag gag cca agg gtg ccc ctg caa ggc acc ctg tta ggg tac cgg       1104
Trp Gln Glu Pro Arg Val Pro Leu Gln Gly Thr Leu Leu Gly Tyr Arg
        355                 360                 365 ctg gca tat cga ggc cag gac acc ccc gag gta ctt atg gat ata ggg       1152
Leu Ala Tyr Arg Gly Gln Asp Thr Pro Glu Val Leu Met Asp Ile Gly
    370                 375                 380 cta act cga gag gtg acc ttg gaa ctg cgg ggg gac agg cct gtg gct       1200
Leu Thr Arg Glu Val Thr Leu Glu Leu Arg Gly Asp Arg Pro Val Ala
385                 390                 395                 400 aac ctg act gtg tct gtg aca gcc tat acc tcg gct ggg gat ggg ccc       1248
Asn Leu Thr Val Ser Val Thr Ala Tyr Thr Ser Ala Gly Asp Gly Pro
            405                 410                 415 tgg agc ctt cct gtg ccc cta gag ccc tgg cgc cca ggg caa gga cag       1296
Trp Ser Leu Pro Val Pro Leu Glu Pro Trp Arg Pro Gly Gln Gly Gln
        420                 425                 430 cca ctc cac cat ctg gtg agt gaa ccc cca cct cgc gcc ttc tcg tgg       1344
Pro Leu His His Leu Val Ser Glu Pro Pro Pro Arg Ala Phe Ser Trp
    435                 440                 445 cct gtc gac gaa ttc ggt tgt aag cct tgc ata tgt aca gtc cca gaa       1392
Pro Val Asp Glu Phe Gly Cys Lys Pro Cys Ile Cys Thr Val Pro Glu
450                 455                 460 gta tca tct gtc ttc atc ttc ccc cca aag ccc aag gat gtg ctc acc       1440
Val Ser Ser Val Phe Ile Phe Pro Pro Lys Pro Lys Asp Val Leu Thr
465                 470                 475                 480 att act ctg act cct aag gtc acg tgt gtt gtg gta gac atc agc aag       1488
Ile Thr Leu Thr Pro Lys Val Thr Cys Val Val Val Asp Ile Ser Lys
            485                 490                 495 gat gat ccc gag gtc cag ttc agc tgg ttt gta gat gat gtg gag gtg       1536
Asp Asp Pro Glu Val Gln Phe Ser Trp Phe Val Asp Asp Val Glu Val
        500                 505                 510 cac aca gct cag acg caa ccc cgg gag gag cag ttc aac agc act ttc       1584
His Thr Ala Gln Thr Gln Pro Arg Glu Glu Gln Phe Asn Ser Thr Phe
    515                 520                 525 cgc tca gtc agt gaa ctt ccc atc atg cac cag gac tgg ctc aat ggc       1632
Arg Ser Val Ser Glu Leu Pro Ile Met His Gln Asp Trp Leu Asn Gly
530                 535                 540 aag gag ttc aaa tgc agg gtc aac agt gca gct ttc cct gcc ccc atc       1680
Lys Glu Phe Lys Cys Arg Val Asn Ser Ala Ala Phe Pro Ala Pro Ile
545                 550                 555                 560 gag aaa acc atc tcc aaa acc aaa ggc aga ccg aag gct cca cag gtg       1728
Glu Lys Thr Ile Ser Lys Thr Lys Gly Arg Pro Lys Ala Pro Gln Val
            565                 570                 575 tac acc att cca cct ccc aag gag cag atg gcc aag gat aaa gtc agt       1776
Tyr Thr Ile Pro Pro Pro Lys Glu Gln Met Ala Lys Asp Lys Val Ser
        580                 585                 590 ctg acc tgc atg ata aca gac ttc ttc cct gaa gac att act gtg gag       1824
Leu Thr Cys Met Ile Thr Asp Phe Phe Pro Glu Asp Ile Thr Val Glu
    595                 600                 605 tgg cag tgg aat ggg cag cca gcg gag aac tac aag aac act cag ccc       1872
Trp Gln Trp Asn Gly Gln Pro Ala Glu Asn Tyr Lys Asn Thr Gln Pro
610                 615                 620 atc atg gac aca gat ggc tct tac ttc gtc tac agc aag ctc aat gtg       1920
Ile Met Asp Thr Asp Gly Ser Tyr Phe Val Tyr Ser Lys Leu Asn Val
625                 630                 635                 640
```

```
cag aag agc aac tgg gag gca gga aat act ttc acc tgc tct gtg tta   1968
Gln Lys Ser Asn Trp Glu Ala Gly Asn Thr Phe Thr Cys Ser Val Leu
                645                 650                 655 cat gag ggc ctg cac aac cac cat act gag aag agc ctc tcc cac tct   2016
His Glu Gly Leu His Asn His His Thr Glu Lys Ser Leu Ser His Ser
            660                 665                 670 cct ggt aaa tgaggatcc                                             2034
Pro Gly Lys
        675

<210> SEQ ID NO 49
<211> LENGTH: 675
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 49

Arg Ser Thr Arg Ala Thr Met Gly Arg Val Pro Leu Ala Trp Trp Leu
1               5                   10                  15

Ala Leu Cys Cys Trp Gly Cys Ala Ala His Lys Asp Thr Gln Thr Glu
            20                  25                  30

Ala Gly Ser Pro Phe Val Gly Asn Pro Gly Asn Ile Thr Gly Ala Arg
        35                  40                  45

Gly Leu Thr Gly Thr Leu Arg Cys Glu Leu Gln Val Gln Gly Glu Pro
    50                  55                  60

Pro Glu Val Val Trp Leu Arg Asp Gly Gln Ile Leu Glu Leu Ala Asp
65                  70                  75                  80

Asn Thr Gln Thr Gln Val Pro Leu Gly Glu Asp Trp Gln Asp Glu Trp
                85                  90                  95

Lys Val Val Ser Gln Leu Arg Ile Ser Ala Leu Gln Leu Ser Asp Ala
            100                 105                 110

Gly Glu Tyr Gln Cys Met Val His Leu Glu Gly Arg Thr Phe Val Ser
        115                 120                 125

Gln Pro Gly Phe Val Gly Leu Glu Gly Leu Pro Tyr Phe Leu Glu Glu
    130                 135                 140

Pro Glu Asp Lys Ala Val Pro Ala Asn Thr Pro Phe Asn Leu Ser Cys
145                 150                 155                 160

Gln Ala Gln Gly Pro Pro Glu Pro Val Thr Leu Leu Trp Leu Gln Asp
                165                 170                 175

Ala Val Pro Leu Ala Pro Val Thr Gly His Ser Ser Gln His Ser Leu
            180                 185                 190

Gln Thr Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Arg Pro His His Leu His Val Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Asn Leu Gln Ala Val Leu Ser Asp Asp Gly Val Gly Ile Trp
            260                 265                 270

Leu Gly Lys Ser Asp Pro Pro Glu Asp Pro Leu Thr Leu Gln Val Ser
        275                 280                 285

Val Pro Pro His Gln Leu Arg Leu Glu Lys Leu Leu Pro His Thr Pro
    290                 295                 300
```

Tyr His Ile Arg Ile Ser Cys Ser Ser Ser Gln Gly Pro Ser Pro Trp
305                 310                 315                 320

Thr His Trp Leu Pro Val Glu Thr Thr Glu Gly Val Pro Leu Gly Pro
            325                 330                 335

Pro Glu Asn Val Ser Ala Met Arg Asn Gly Ser Gln Val Leu Val Arg
        340                 345                 350

Trp Gln Glu Pro Arg Val Pro Leu Gln Gly Thr Leu Leu Gly Tyr Arg
    355                 360                 365

Leu Ala Tyr Arg Gly Gln Asp Thr Pro Glu Val Leu Met Asp Ile Gly
370                 375                 380

Leu Thr Arg Glu Val Thr Leu Glu Leu Arg Gly Asp Arg Pro Val Ala
385                 390                 395                 400

Asn Leu Thr Val Ser Val Thr Ala Tyr Thr Ser Ala Gly Asp Gly Pro
                405                 410                 415

Trp Ser Leu Pro Val Pro Leu Glu Pro Trp Arg Pro Gly Gln Gly Gln
            420                 425                 430

Pro Leu His His Leu Val Ser Glu Pro Pro Arg Ala Phe Ser Trp
        435                 440                 445

Pro Val Asp Glu Phe Gly Cys Lys Pro Cys Ile Cys Thr Val Pro Glu
450                 455                 460

Val Ser Ser Val Phe Ile Phe Pro Pro Lys Pro Lys Asp Val Leu Thr
465                 470                 475                 480

Ile Thr Leu Thr Pro Lys Val Thr Cys Val Val Asp Ile Ser Lys
                485                 490                 495

Asp Asp Pro Glu Val Gln Phe Ser Trp Phe Val Asp Val Glu Val
            500                 505                 510

His Thr Ala Gln Thr Gln Pro Arg Glu Glu Gln Phe Asn Ser Thr Phe
            515                 520                 525

Arg Ser Val Ser Glu Leu Pro Ile Met His Gln Asp Trp Leu Asn Gly
    530                 535                 540

Lys Glu Phe Lys Cys Arg Val Asn Ser Ala Ala Phe Pro Ala Pro Ile
545                 550                 555                 560

Glu Lys Thr Ile Ser Lys Thr Lys Gly Arg Pro Lys Ala Pro Gln Val
                565                 570                 575

Tyr Thr Ile Pro Pro Pro Lys Glu Gln Met Ala Lys Asp Lys Val Ser
            580                 585                 590

Leu Thr Cys Met Ile Thr Asp Phe Phe Pro Glu Asp Ile Thr Val Glu
        595                 600                 605

Trp Gln Trp Asn Gly Gln Pro Ala Glu Asn Tyr Lys Asn Thr Gln Pro
    610                 615                 620

Ile Met Asp Thr Asp Gly Ser Tyr Phe Val Tyr Ser Lys Leu Asn Val
625                 630                 635                 640

Gln Lys Ser Asn Trp Glu Ala Gly Asn Thr Phe Thr Cys Ser Val Leu
                645                 650                 655

His Glu Gly Leu His Asn His His Thr Glu Lys Ser Leu Ser His Ser
            660                 665                 670

Pro Gly Lys
        675

<210> SEQ ID NO 50
<211> LENGTH: 33
<212> TYPE: DNA
<213> ORGANISM: Artificial Sequence
<220> FEATURE:

```
<223> OTHER INFORMATION: Description of Artificial Sequence: Synthetic
      Primer 22

<400> SEQUENCE: 50
ctcactatag aattcgccac catggcgtgg cgg                                    33

<210> SEQ ID NO 51
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer 23

<400> SEQUENCE: 51
caataaacaa gttggatcct caggcaccat cctcctgc                               38

<210> SEQ ID NO 52
<211> LENGTH: 2673
<212> TYPE: DNA
<213> ORGANISM: Homo sapiens
<220> FEATURE:
<221> NAME/KEY: CDS
<222> LOCATION: (1)..(2670)

<400> SEQUENCE: 52
```

| | | | | | | | | | | | | | | | | |
|---|---|---|---|---|---|---|---|---|---|---|---|---|---|---|---|---|
| atg | gcg | ctg | agg | cgg | agc | atg | ggg | cgg | ccg | ggg | ctc | ccg | ccg | ctg | ccg | 48 |
| Met | Ala | Leu | Arg | Arg | Ser | Met | Gly | Arg | Pro | Gly | Leu | Pro | Pro | Leu | Pro | |
| 1 | | | | 5 | | | | | 10 | | | | | 15 | | |
| ctg | ccg | ccg | cca | ccg | cgg | ctc | ggg | ctg | ctg | ctg | gcg | gct | ctg | gct | tct | 96 |
| Leu | Pro | Pro | Pro | Pro | Arg | Leu | Gly | Leu | Leu | Leu | Ala | Ala | Leu | Ala | Ser | |
| | | 20 | | | | | 25 | | | | | 30 | | | | |
| ctg | ctg | ctc | ccg | gag | tcc | gcc | gcc | gca | ggt | ctg | aag | ctc | atg | gga | gcc | 144 |
| Leu | Leu | Leu | Pro | Glu | Ser | Ala | Ala | Ala | Gly | Leu | Lys | Leu | Met | Gly | Ala | |
| | 35 | | | | | 40 | | | | | 45 | | | | | |
| ccg | gtg | aag | ctg | aca | gtg | tct | cag | ggg | cag | ccg | gtg | aag | ctc | aac | tgc | 192 |
| Pro | Val | Lys | Leu | Thr | Val | Ser | Gln | Gly | Gln | Pro | Val | Lys | Leu | Asn | Cys | |
| 50 | | | | | 55 | | | | | 60 | | | | | | |
| agt | gtg | gag | ggg | atg | gag | gag | cct | gac | atc | cag | tgg | gtg | aag | gat | ggg | 240 |
| Ser | Val | Glu | Gly | Met | Glu | Glu | Pro | Asp | Ile | Gln | Trp | Val | Lys | Asp | Gly | |
| 65 | | | | | 70 | | | | | 75 | | | | | 80 | |
| gct | gtg | gtc | cag | aac | ttg | gac | cag | ttg | tac | atc | cca | gtc | agc | gag | cag | 288 |
| Ala | Val | Val | Gln | Asn | Leu | Asp | Gln | Leu | Tyr | Ile | Pro | Val | Ser | Glu | Gln | |
| | | | | 85 | | | | | 90 | | | | | 95 | | |
| cac | tgg | atc | ggc | ttc | ctc | agc | ctg | aag | tca | gtg | gag | cgc | tct | gac | gcc | 336 |
| His | Trp | Ile | Gly | Phe | Leu | Ser | Leu | Lys | Ser | Val | Glu | Arg | Ser | Asp | Ala | |
| | | | 100 | | | | | 105 | | | | | 110 | | | |
| ggc | cgg | tac | tgg | tgc | cag | gtg | gag | gat | ggg | ggt | gaa | acc | gag | atc | tcc | 384 |
| Gly | Arg | Tyr | Trp | Cys | Gln | Val | Glu | Asp | Gly | Gly | Glu | Thr | Glu | Ile | Ser | |
| | | 115 | | | | | 120 | | | | | 125 | | | | |
| cag | cca | gtg | tgg | ctc | acg | gta | gaa | ggt | gtg | cca | ttt | ttc | aca | gtg | gag | 432 |
| Gln | Pro | Val | Trp | Leu | Thr | Val | Glu | Gly | Val | Pro | Phe | Phe | Thr | Val | Glu | |
| | 130 | | | | | 135 | | | | | 140 | | | | | |
| cca | aaa | gat | ctg | gca | gtg | cca | ccc | aat | gcc | cct | ttc | caa | ctg | tct | tgt | 480 |
| Pro | Lys | Asp | Leu | Ala | Val | Pro | Pro | Asn | Ala | Pro | Phe | Gln | Leu | Ser | Cys | |
| 145 | | | | | 150 | | | | | 155 | | | | | 160 | |
| gag | gct | gtg | ggt | ccc | cct | gaa | cct | gtt | acc | att | gtc | tgg | tgg | aga | gga | 528 |
| Glu | Ala | Val | Gly | Pro | Pro | Glu | Pro | Val | Thr | Ile | Val | Trp | Trp | Arg | Gly | |
| | | | | 165 | | | | | 170 | | | | | 175 | | |
| act | acg | aag | atc | ggg | gga | ccc | gct | ccc | tct | cca | tct | gtt | tta | aat | gta | 576 |
| Thr | Thr | Lys | Ile | Gly | Gly | Pro | Ala | Pro | Ser | Pro | Ser | Val | Leu | Asn | Val | |
| | | | 180 | | | | | 185 | | | | | 190 | | | |

```
aca ggg gtg acc cag agc acc atg ttt tcc tgt gaa gct cac aac cta    624
Thr Gly Val Thr Gln Ser Thr Met Phe Ser Cys Glu Ala His Asn Leu
        195                 200                 205 aaa ggc ctg gcc tct tct cgc aca gcc act gtt cac ctt caa gca ctg    672
Lys Gly Leu Ala Ser Ser Arg Thr Ala Thr Val His Leu Gln Ala Leu
    210                 215                 220 cct gca gcc ccc ttc aac atc acc gtg aca aag ctt tcc agc agc aac    720
Pro Ala Ala Pro Phe Asn Ile Thr Val Thr Lys Leu Ser Ser Ser Asn
225                 230                 235                 240 gct agt gtg gcc tgg atg cca ggt gct gat ggc cga gct ctg cta cag    768
Ala Ser Val Ala Trp Met Pro Gly Ala Asp Gly Arg Ala Leu Leu Gln
                245                 250                 255 tcc tgt aca gtt cag gtg aca cag gcc cca gga ggc tgg gaa gtc ctg    816
Ser Cys Thr Val Gln Val Thr Gln Ala Pro Gly Gly Trp Glu Val Leu
            260                 265                 270 gct gtt gtg gtc cct gtg ccc ccc ttt acc tgc ctg ctc cgg gac ctg    864
Ala Val Val Val Pro Val Pro Pro Phe Thr Cys Leu Leu Arg Asp Leu
        275                 280                 285 gtg cct gcc acc aac tac agc ctc agg gtg cgc tgt gcc aat gcc ttg    912
Val Pro Ala Thr Asn Tyr Ser Leu Arg Val Arg Cys Ala Asn Ala Leu
    290                 295                 300 ggg ccc tct ccc tat gct gac tgg gtg ccc ttt cag acc aag ggt cta    960
Gly Pro Ser Pro Tyr Ala Asp Trp Val Pro Phe Gln Thr Lys Gly Leu
305                 310                 315                 320 gcc cca gcc agc gct ccc caa aac ctc cat gcc atc cgc aca gat tca   1008
Ala Pro Ala Ser Ala Pro Gln Asn Leu His Ala Ile Arg Thr Asp Ser
                325                 330                 335 ggc ctc atc ttg gag tgg gaa gaa gtg atc ccc gag gcc cct ttg gaa   1056
Gly Leu Ile Leu Glu Trp Glu Glu Val Ile Pro Glu Ala Pro Leu Glu
            340                 345                 350 ggc ccc ctg gga ccc tac aaa ctg tcc tgg gtt caa gac aat gga acc   1104
Gly Pro Leu Gly Pro Tyr Lys Leu Ser Trp Val Gln Asp Asn Gly Thr
        355                 360                 365 cag gat gag ctg aca gtg gag ggg acc agg gcc aat ttg aca ggc tgg   1152
Gln Asp Glu Leu Thr Val Glu Gly Thr Arg Ala Asn Leu Thr Gly Trp
    370                 375                 380 gat ccc caa aag gac ctg atc gta cgt gtg tgc gtc tcc aat gca gtt   1200
Asp Pro Gln Lys Asp Leu Ile Val Arg Val Cys Val Ser Asn Ala Val
385                 390                 395                 400 ggc tgt gga ccc tgg agt cag cca ctg gtg gtc tct tct cat gac cgt   1248
Gly Cys Gly Pro Trp Ser Gln Pro Leu Val Val Ser Ser His Asp Arg
                405                 410                 415 gca ggc cag cag ggc cct cct cac agc cgc aca tcc tgg gta cct gtg   1296
Ala Gly Gln Gln Gly Pro Pro His Ser Arg Thr Ser Trp Val Pro Val
            420                 425                 430 gtc ctt ggt gtg cta acg gcc ctg gtg acg gct gct gcc ctg gcc ctc   1344
Val Leu Gly Val Leu Thr Ala Leu Val Thr Ala Ala Ala Leu Ala Leu
        435                 440                 445 atc ctg ctt cga aag aga cgg aaa gag acg cgg ttt ggg caa gcc ttt   1392
Ile Leu Leu Arg Lys Arg Arg Lys Glu Thr Arg Phe Gly Gln Ala Phe
    450                 455                 460 gac agt gtc atg gcc cgg gga gag cca gcc gtt cac ttc cgg gca gcc   1440
Asp Ser Val Met Ala Arg Gly Glu Pro Ala Val His Phe Arg Ala Ala
465                 470                 475                 480 cgg tcc ttc aat cga gaa agg ccc gag cgc atc gag gcc aca ttg gac   1488
Arg Ser Phe Asn Arg Glu Arg Pro Glu Arg Ile Glu Ala Thr Leu Asp
                485                 490                 495 agc ttg ggc atc agc gat gaa cta aag gaa aaa ctg gag gat gtg ctc   1536
Ser Leu Gly Ile Ser Asp Glu Leu Lys Glu Lys Leu Glu Asp Val Leu
            500                 505                 510
```

```
atc cca gag cag cag ttc acc ctg ggc cgg atg ttg ggc aaa gga gag       1584
Ile Pro Glu Gln Gln Phe Thr Leu Gly Arg Met Leu Gly Lys Gly Glu
        515                 520                 525 ttt ggt tca gtg cgg gag gcc cag ctg aag caa gag gat ggc tcc ttt       1632
Phe Gly Ser Val Arg Glu Ala Gln Leu Lys Gln Glu Asp Gly Ser Phe
    530                 535                 540 gtg aaa gtg gct gtg aag atg ctg aaa gct gac atc att gcc tca agc       1680
Val Lys Val Ala Val Lys Met Leu Lys Ala Asp Ile Ile Ala Ser Ser
545                 550                 555                 560 gac att gaa gag ttc ctc agg gaa gca gct tgc atg aag gag ttt gac       1728
Asp Ile Glu Glu Phe Leu Arg Glu Ala Ala Cys Met Lys Glu Phe Asp
                565                 570                 575 cat cca cac gtg gcc aaa ctt gtt ggg gta agc ctc cgg agc agg gct       1776
His Pro His Val Ala Lys Leu Val Gly Val Ser Leu Arg Ser Arg Ala
            580                 585                 590 aaa ggc cgt ctc ccc atc ccc atg gtc atc ttg ccc ttc atg aag cat       1824
Lys Gly Arg Leu Pro Ile Pro Met Val Ile Leu Pro Phe Met Lys His
        595                 600                 605 ggg gac ctg cat gcc ttc ctc ctc gcc tcc cgg att ggg gag aac ccc       1872
Gly Asp Leu His Ala Phe Leu Leu Ala Ser Arg Ile Gly Glu Asn Pro
    610                 615                 620 ttt aac cta ccc ctc cag acc ctg atc cgg ttc atg gtg gac att gcc       1920
Phe Asn Leu Pro Leu Gln Thr Leu Ile Arg Phe Met Val Asp Ile Ala
625                 630                 635                 640 tgc ggc atg gag tac ctg agc tct cgg aac ttc atc cac cga gac ctg       1968
Cys Gly Met Glu Tyr Leu Ser Ser Arg Asn Phe Ile His Arg Asp Leu
                645                 650                 655 gct gct cgg aat tgc atg ctg gca gag gac atg aca gtg tgt gtg gct       2016
Ala Ala Arg Asn Cys Met Leu Ala Glu Asp Met Thr Val Cys Val Ala
            660                 665                 670 gac ttc gga ctc tcc cgg aag atc tac agt ggg gac tac tat cgt caa       2064
Asp Phe Gly Leu Ser Arg Lys Ile Tyr Ser Gly Asp Tyr Tyr Arg Gln
        675                 680                 685 ggc tgt gcc tcc aaa ctg cct gtc aag tgg ctg gcc ctg gag agc ctg       2112
Gly Cys Ala Ser Lys Leu Pro Val Lys Trp Leu Ala Leu Glu Ser Leu
    690                 695                 700 gcc gac aac ctg tat act gtg cag agt gac gtg tgg gcg ttc ggg gtg       2160
Ala Asp Asn Leu Tyr Thr Val Gln Ser Asp Val Trp Ala Phe Gly Val
705                 710                 715                 720 acc atg tgg gag atc atg aca cgt ggg cag acg cca tat gct ggc atc       2208
Thr Met Trp Glu Ile Met Thr Arg Gly Gln Thr Pro Tyr Ala Gly Ile
                725                 730                 735 gaa aac gct gag att tac aac tac ctc att ggc ggg aac cgc ctg aaa       2256
Glu Asn Ala Glu Ile Tyr Asn Tyr Leu Ile Gly Gly Asn Arg Leu Lys
            740                 745                 750 cag cct ccg gag tgt atg gag gac gtg tat gat ctc atg tac cag tgc       2304
Gln Pro Pro Glu Cys Met Glu Asp Val Tyr Asp Leu Met Tyr Gln Cys
        755                 760                 765 tgg agt gct gac ccc aag cag cgc ccg agc ttt act tgt ctg cga atg       2352
Trp Ser Ala Asp Pro Lys Gln Arg Pro Ser Phe Thr Cys Leu Arg Met
    770                 775                 780 gaa ctg gag aac atc ttg ggc cag ctg tct gtg cta tct gcc agc cag       2400
Glu Leu Glu Asn Ile Leu Gly Gln Leu Ser Val Leu Ser Ala Ser Gln
785                 790                 795                 800 gac ccc tta tac atc aac atc gag aga gct gag gag ccc act gcg gga       2448
Asp Pro Leu Tyr Ile Asn Ile Glu Arg Ala Glu Glu Pro Thr Ala Gly
                805                 810                 815 ggc agc ctg gag cta cct ggc agg gat cag ccc tac agt ggg gct ggg       2496
Gly Ser Leu Glu Leu Pro Gly Arg Asp Gln Pro Tyr Ser Gly Ala Gly
```

```
                        820                 825                 830
gat ggc agt ggc atg ggg gca gtg ggt ggc act ccc agt gac tgt cgg      2544
Asp Gly Ser Gly Met Gly Ala Val Gly Gly Thr Pro Ser Asp Cys Arg
            835                 840                 845 tac ata ctc acc ccc gga ggg ctg gct gag cag cca ggg cag gca gag      2592
Tyr Ile Leu Thr Pro Gly Gly Leu Ala Glu Gln Pro Gly Gln Ala Glu
850                 855                 860 cac cag cca gag agt ccc ctc aat gag aca cag agg ctt ttg ctg ctg      2640
His Gln Pro Glu Ser Pro Leu Asn Glu Thr Gln Arg Leu Leu Leu Leu
865                 870                 875                 880 cag caa ggg cta ctg cca cac agt agc tgt tag                          2673
Gln Gln Gly Leu Leu Pro His Ser Ser Cys
                885                 890

<210> SEQ ID NO 53
<211> LENGTH: 890
<212> TYPE: PRT
<213> ORGANISM: Homo sapiens

<400> SEQUENCE: 53

Met Ala Leu Arg Arg Ser Met Gly Arg Pro Gly Leu Pro Pro Leu Pro
1               5                   10                  15

Leu Pro Pro Pro Arg Leu Gly Leu Leu Ala Ala Leu Ala Ser
                20                  25                  30

Leu Leu Leu Pro Glu Ser Ala Ala Ala Gly Leu Lys Leu Met Gly Ala
            35                  40                  45

Pro Val Lys Leu Thr Val Ser Gln Gly Gln Pro Val Lys Leu Asn Cys
    50                  55                  60

Ser Val Glu Gly Met Glu Glu Pro Asp Ile Gln Trp Val Lys Asp Gly
65                  70                  75                  80

Ala Val Val Gln Asn Leu Asp Gln Leu Tyr Ile Pro Val Ser Glu Gln
                85                  90                  95

His Trp Ile Gly Phe Leu Ser Leu Lys Ser Val Glu Arg Ser Asp Ala
                100                 105                 110

Gly Arg Tyr Trp Cys Gln Val Glu Asp Gly Gly Glu Thr Glu Ile Ser
            115                 120                 125

Gln Pro Val Trp Leu Thr Val Glu Gly Val Pro Phe Phe Thr Val Glu
    130                 135                 140

Pro Lys Asp Leu Ala Val Pro Pro Asn Ala Pro Phe Gln Leu Ser Cys
145                 150                 155                 160

Glu Ala Val Gly Pro Pro Glu Pro Val Thr Ile Val Trp Trp Arg Gly
                165                 170                 175

Thr Thr Lys Ile Gly Gly Pro Ala Pro Ser Pro Ser Val Leu Asn Val
            180                 185                 190

Thr Gly Val Thr Gln Ser Thr Met Phe Ser Cys Glu Ala His Asn Leu
    195                 200                 205

Lys Gly Leu Ala Ser Ser Arg Thr Ala Thr Val His Leu Gln Ala Leu
210                 215                 220

Pro Ala Ala Pro Phe Asn Ile Thr Val Thr Lys Leu Ser Ser Ser Asn
225                 230                 235                 240

Ala Ser Val Ala Trp Met Pro Gly Ala Asp Gly Arg Ala Leu Leu Gln
                245                 250                 255

Ser Cys Thr Val Gln Val Thr Gln Ala Pro Gly Gly Trp Glu Val Leu
            260                 265                 270

Ala Val Val Val Pro Val Pro Pro Phe Thr Cys Leu Leu Arg Asp Leu
    275                 280                 285
```

```
Val Pro Ala Thr Asn Tyr Ser Leu Arg Val Arg Cys Ala Asn Ala Leu
    290                 295                 300

Gly Pro Ser Pro Tyr Ala Asp Trp Val Pro Phe Gln Thr Lys Gly Leu
305                 310                 315                 320

Ala Pro Ala Ser Ala Pro Gln Asn Leu His Ala Ile Arg Thr Asp Ser
                325                 330                 335

Gly Leu Ile Leu Glu Trp Glu Val Ile Pro Glu Ala Pro Leu Glu
            340                 345                 350

Gly Pro Leu Gly Pro Tyr Lys Leu Ser Trp Val Gln Asp Asn Gly Thr
        355                 360                 365

Gln Asp Glu Leu Thr Val Glu Gly Thr Arg Ala Asn Leu Thr Gly Trp
    370                 375                 380

Asp Pro Gln Lys Asp Leu Ile Val Arg Val Cys Val Ser Asn Ala Val
385                 390                 395                 400

Gly Cys Gly Pro Trp Ser Gln Pro Leu Val Val Ser Ser His Asp Arg
                405                 410                 415

Ala Gly Gln Gln Gly Pro Pro His Ser Arg Thr Ser Trp Val Pro Val
                420                 425                 430

Val Leu Gly Val Leu Thr Ala Leu Val Thr Ala Ala Leu Ala Leu
            435                 440                 445

Ile Leu Leu Arg Lys Arg Arg Lys Glu Thr Arg Phe Gly Gln Ala Phe
    450                 455                 460

Asp Ser Val Met Ala Arg Gly Glu Pro Ala Val His Phe Arg Ala Ala
465                 470                 475                 480

Arg Ser Phe Asn Arg Glu Arg Pro Glu Arg Ile Glu Ala Thr Leu Asp
                485                 490                 495

Ser Leu Gly Ile Ser Asp Glu Leu Lys Glu Lys Leu Glu Asp Val Leu
            500                 505                 510

Ile Pro Glu Gln Gln Phe Thr Leu Gly Arg Met Leu Gly Lys Gly Glu
    515                 520                 525

Phe Gly Ser Val Arg Glu Ala Gln Leu Lys Gln Glu Asp Gly Ser Phe
530                 535                 540

Val Lys Val Ala Val Lys Met Leu Lys Ala Asp Ile Ile Ala Ser Ser
545                 550                 555                 560

Asp Ile Glu Glu Phe Leu Arg Glu Ala Ala Cys Met Lys Glu Phe Asp
                565                 570                 575

His Pro His Val Ala Lys Leu Val Gly Val Ser Leu Arg Ser Arg Ala
                580                 585                 590

Lys Gly Arg Leu Pro Ile Pro Met Val Ile Leu Pro Phe Met Lys His
            595                 600                 605

Gly Asp Leu His Ala Phe Leu Leu Ala Ser Arg Ile Gly Glu Asn Pro
610                 615                 620

Phe Asn Leu Pro Leu Gln Thr Leu Ile Arg Phe Met Val Asp Ile Ala
625                 630                 635                 640

Cys Gly Met Glu Tyr Leu Ser Ser Arg Asn Phe Ile His Arg Asp Leu
                645                 650                 655

Ala Ala Arg Asn Cys Met Leu Ala Glu Asp Met Thr Val Cys Val Ala
                660                 665                 670

Asp Phe Gly Leu Ser Arg Lys Ile Tyr Ser Gly Asp Tyr Tyr Arg Gln
            675                 680                 685

Gly Cys Ala Ser Lys Leu Pro Val Lys Trp Leu Ala Leu Glu Ser Leu
    690                 695                 700
```

```
Ala Asp Asn Leu Tyr Thr Val Gln Ser Asp Val Trp Ala Phe Gly Val
705                 710                 715                 720

Thr Met Trp Glu Ile Met Thr Arg Gly Gln Thr Pro Tyr Ala Gly Ile
            725                 730                 735

Glu Asn Ala Glu Ile Tyr Asn Tyr Leu Ile Gly Gly Asn Arg Leu Lys
        740                 745                 750

Gln Pro Pro Glu Cys Met Glu Asp Val Tyr Asp Leu Met Tyr Gln Cys
    755                 760                 765

Trp Ser Ala Asp Pro Lys Gln Arg Pro Ser Phe Thr Cys Leu Arg Met
770                 775                 780

Glu Leu Glu Asn Ile Leu Gly Gln Leu Ser Val Leu Ser Ala Ser Gln
785                 790                 795                 800

Asp Pro Leu Tyr Ile Asn Ile Glu Arg Ala Glu Glu Pro Thr Ala Gly
                805                 810                 815

Gly Ser Leu Glu Leu Pro Gly Arg Asp Gln Pro Tyr Ser Gly Ala Gly
            820                 825                 830

Asp Gly Ser Gly Met Gly Ala Val Gly Gly Thr Pro Ser Asp Cys Arg
        835                 840                 845

Tyr Ile Leu Thr Pro Gly Gly Leu Ala Glu Gln Pro Gly Gln Ala Glu
    850                 855                 860

His Gln Pro Glu Ser Pro Leu Asn Glu Thr Gly Arg Leu Leu Leu Leu
865                 870                 875                 880

Gln Gln Gly Leu Leu Pro His Ser Ser Cys
                885                 890
```

<210> SEQ ID NO 54
<211> LENGTH: 35
<212> TYPE: DNA
<213> ORGANISM: Artificial Sequence
<220> FEATURE:
<223> OTHER INFORMATION: Description of Artificial Sequence: Synthetic
    Primer 24

<400> SEQUENCE: 54
ctcactatag aattcgccac catggcgctg aggcg    35

<210> SEQ ID NO 55
<211> LENGTH: 34
<212> TYPE: DNA
<213> ORGANISM: Artificial Sequence
<220> FEATURE:
<223> OTHER INFORMATION: Description of Artificial Sequence: Synthetic
    Primer 25

<400> SEQUENCE: 55
caataaacaa gttggatccc taacagctac tgtg    34

<210> SEQ ID NO 56
<211> LENGTH: 3000
<212> TYPE: DNA
<213> ORGANISM: Homo sapiens
<220> FEATURE:
<221> NAME/KEY: CDS
<222> LOCATION: (1)..(2997)

<400> SEQUENCE: 56

```
atg ggg ccg gcc ccg ctg ccg ctg ctg ctg ggc ctc ttc ctc ccc gcg    48
Met Gly Pro Ala Pro Leu Pro Leu Leu Leu Gly Leu Phe Leu Pro Ala
1               5                   10                  15 ctc tgg cgt aga gct atc act gag gca agg gaa gaa gcc aag cct tac    96
Leu Trp Arg Arg Ala Ile Thr Glu Ala Arg Glu Glu Ala Lys Pro Tyr
```

```
                    20                  25                  30
ccg cta ttc ccg gga cct ttt cca ggg agc ctg caa act gac cac aca        144
Pro Leu Phe Pro Gly Pro Phe Pro Gly Ser Leu Gln Thr Asp His Thr
         35                  40                  45 ccg ctg tta tcc ctt cct cac gcc agt ggg tac cag cct gcc ttg atg        192
Pro Leu Leu Ser Leu Pro His Ala Ser Gly Tyr Gln Pro Ala Leu Met
 50                  55                  60 ttt tca cca acc cag cct gga aga cca cat aca gga aac gta gcc att        240
Phe Ser Pro Thr Gln Pro Gly Arg Pro His Thr Gly Asn Val Ala Ile
 65                  70                  75                  80 ccc cag gtg acc tct gtc gaa tca aag ccc cta ccg cct ctt gcc ttc        288
Pro Gln Val Thr Ser Val Glu Ser Lys Pro Leu Pro Pro Leu Ala Phe
                 85                  90                  95 aaa cac aca gtt gga cac ata ata ctt tct gaa cat aaa ggt gtc aaa        336
Lys His Thr Val Gly His Ile Ile Leu Ser Glu His Lys Gly Val Lys
                100                 105                 110 ttt aat tgc tca atc agt gta cct aat ata tac cag gac acc aca att        384
Phe Asn Cys Ser Ile Ser Val Pro Asn Ile Tyr Gln Asp Thr Thr Ile
            115                 120                 125 tct tgg tgg aaa gat ggg aag gaa ttg ctt ggg gca cat cat gca att        432
Ser Trp Trp Lys Asp Gly Lys Glu Leu Leu Gly Ala His His Ala Ile
130                 135                 140 aca cag ttt tat cca gat gat gaa gtt aca gca ata atc gct tcc ttc        480
Thr Gln Phe Tyr Pro Asp Asp Glu Val Thr Ala Ile Ile Ala Ser Phe
145                 150                 155                 160 agc ata acc agt gtg cag cgt tca gac aat ggg tcg tat atc tgt aag        528
Ser Ile Thr Ser Val Gln Arg Ser Asp Asn Gly Ser Tyr Ile Cys Lys
                165                 170                 175 atg aaa ata aac aat gaa gag atc gtg tct gat ccc atc tac atc gaa        576
Met Lys Ile Asn Asn Glu Glu Ile Val Ser Asp Pro Ile Tyr Ile Glu
                180                 185                 190 gta caa gga ctt cct cac ttt act aag cag cct gag agc atg aat gtc        624
Val Gln Gly Leu Pro His Phe Thr Lys Gln Pro Glu Ser Met Asn Val
            195                 200                 205 acc aga aac aca gcc ttc aac ctc acc tgt cag gct gtg ggc cga cct        672
Thr Arg Asn Thr Ala Phe Asn Leu Thr Cys Gln Ala Val Gly Pro Pro
210                 215                 220 gag ccc gtc aac att ttc tgg gtt caa aac agt agc cgt gtt aac gaa        720
Glu Pro Val Asn Ile Phe Trp Val Gln Asn Ser Ser Arg Val Asn Glu
225                 230                 235                 240 cag cct gaa aaa tcc ccc tcc gtg cta act gtt cca ggc ctg acg gag        768
Gln Pro Glu Lys Ser Pro Ser Val Leu Thr Val Pro Gly Leu Thr Glu
                245                 250                 255 atg gcg gtc ttc agt tgt gag gcc cac aat gac aaa ggg ctg acc gtg        816
Met Ala Val Phe Ser Cys Glu Ala His Asn Asp Lys Gly Leu Thr Val
                260                 265                 270 tcc aag gga gtg cag atc aac atc aaa gca att ccc tcc cca cca act        864
Ser Lys Gly Val Gln Ile Asn Ile Lys Ala Ile Pro Ser Pro Pro Thr
            275                 280                 285 gaa gtc agc atc cgt aac agc act gca cac agc att ctg atc tcc tgg        912
Glu Val Ser Ile Arg Asn Ser Thr Ala His Ser Ile Leu Ile Ser Trp
290                 295                 300 gtt cct ggt ttt gat gga tac tcc ccg ttc agg aat tgc agc att cag        960
Val Pro Gly Phe Asp Gly Tyr Ser Pro Phe Arg Asn Cys Ser Ile Gln
305                 310                 315                 320 gtc aag gaa gct gat ccg ctg agt aat ggc tca gtc atg att ttt aac       1008
Val Lys Glu Ala Asp Pro Leu Ser Asn Gly Ser Val Met Ile Phe Asn
                325                 330                 335 acc tct gcc tta cca cat ctg tac caa atc aag cag ctg caa gcc ctg       1056
```

```
               Thr Ser Ala Leu Pro His Leu Tyr Gln Ile Lys Gln Leu Gln Ala Leu
                               340                 345                 350 gct aat tac agc att ggt gtt tcc tgc atg aat gaa ata ggc tgg tct          1104
Ala Asn Tyr Ser Ile Gly Val Ser Cys Met Asn Glu Ile Gly Trp Ser
            355                 360                 365 gca gtg agc cct tgg att cta gcc agc acg act gaa gga gcc cca tca          1152
Ala Val Ser Pro Trp Ile Leu Ala Ser Thr Thr Glu Gly Ala Pro Ser
    370                 375                 380 gta gca cct tta aat gtc act gtg ttt ctg aat gaa tct agt gat aat          1200
Val Ala Pro Leu Asn Val Thr Val Phe Leu Asn Glu Ser Ser Asp Asn
385                 390                 395                 400 gtg gac atc aga tgg atg aag cct ccg act aag cag cag gat gga gaa          1248
Val Asp Ile Arg Trp Met Lys Pro Pro Thr Lys Gln Gln Asp Gly Glu
                405                 410                 415 ctg gtg ggc tac cgg ata tcc cac gtg tgg cag agt gca ggg att tcc          1296
Leu Val Gly Tyr Arg Ile Ser His Val Trp Gln Ser Ala Gly Ile Ser
            420                 425                 430 aaa gag ctc ttg gag gaa gtt ggc cag aat ggc agc cga gct cgg atc          1344
Lys Glu Leu Leu Glu Glu Val Gly Gln Asn Gly Ser Arg Ala Arg Ile
    435                 440                 445 tct gtt caa gtc cac aat gct acg tgc aca gtg agg att gca gcc gtc          1392
Ser Val Gln Val His Asn Ala Thr Cys Thr Val Arg Ile Ala Ala Val
450                 455                 460 acc aga ggg gga gtt ggg ccc ttc agt gat cca gtg aaa ata ttt atc          1440
Thr Arg Gly Gly Val Gly Pro Phe Ser Asp Pro Val Lys Ile Phe Ile
465                 470                 475                 480 cct gca cac ggt tgg gta gat tat gcc ccc tct tca act ccg gcg cct          1488
Pro Ala His Gly Trp Val Asp Tyr Ala Pro Ser Ser Thr Pro Ala Pro
                485                 490                 495 ggc aac gca gat cct gtg ctc atc atc ttt ggc tgc ttt tgt gga ttt          1536
Gly Asn Ala Asp Pro Val Leu Ile Ile Phe Gly Cys Phe Cys Gly Phe
            500                 505                 510 att ttg att ggg ttg att tta tac atc tcc ttg gcc atc aga aaa aga          1584
Ile Leu Ile Gly Leu Ile Leu Tyr Ile Ser Leu Ala Ile Arg Lys Arg
    515                 520                 525 gtc cag gag aca aag ttt ggg aat gca ttc aca gag gag gat tct gaa          1632
Val Gln Glu Thr Lys Phe Gly Asn Ala Phe Thr Glu Glu Asp Ser Glu
530                 535                 540 tta gtg gtg aat tat ata gca aag aaa tcc ttc tgt cgg cga gcc att          1680
Leu Val Val Asn Tyr Ile Ala Lys Lys Ser Phe Cys Arg Arg Ala Ile
545                 550                 555                 560 gaa ctt acc tta cat agc ttg gga gtc agt gag gaa cta caa aat aaa          1728
Glu Leu Thr Leu His Ser Leu Gly Val Ser Glu Glu Leu Gln Asn Lys
                565                 570                 575 cta gaa gat gtt gtg att gac agg aat ctt cta att ctt gga aaa att          1776
Leu Glu Asp Val Val Ile Asp Arg Asn Leu Leu Ile Leu Gly Lys Ile
            580                 585                 590 ctg ggt gaa gga gag ttt ggg tct gta atg gaa gga aat ctt aag cag          1824
Leu Gly Glu Gly Glu Phe Gly Ser Val Met Glu Gly Asn Leu Lys Gln
    595                 600                 605 gaa gat ggg acc tct ctg aaa gtg gca gtg aag acc atg aag ttg gac          1872
Glu Asp Gly Thr Ser Leu Lys Val Ala Val Lys Thr Met Lys Leu Asp
610                 615                 620 aac tct tca cag cgg gag atc gag gag ttt ctc agt gag gca gcg tgc          1920
Asn Ser Ser Gln Arg Glu Ile Glu Glu Phe Leu Ser Glu Ala Ala Cys
625                 630                 635                 640 atg aaa gac ttc agc cac cca aat gtc att cga ctt cta ggt gtg tgt          1968
Met Lys Asp Phe Ser His Pro Asn Val Ile Arg Leu Leu Gly Val Cys
                645                 650                 655
```

```
ata gaa atg agc tct caa ggc atc cca aag ccc atg gta att tta ccc    2016
Ile Glu Met Ser Ser Gln Gly Ile Pro Lys Pro Met Val Ile Leu Pro
            660                 665                 670 ttc atg aaa tac ggg gac ctg cat act tac tta ctt tat tcc cga ttg    2064
Phe Met Lys Tyr Gly Asp Leu His Thr Tyr Leu Leu Tyr Ser Arg Leu
        675                 680                 685 gag aca gga cca aag cat att cct ctg cag aca cta ttg aag ttc atg    2112
Glu Thr Gly Pro Lys His Ile Pro Leu Gln Thr Leu Leu Lys Phe Met
    690                 695                 700 gtg gat att gcc ctg gga atg gag tat ctg agc aac agg aat ttt ctt    2160
Val Asp Ile Ala Leu Gly Met Glu Tyr Leu Ser Asn Arg Asn Phe Leu
705                 710                 715                 720 cat cga gat tta gct gct cga aac tgc atg ttg cga gat gac atg act    2208
His Arg Asp Leu Ala Ala Arg Asn Cys Met Leu Arg Asp Asp Met Thr
                725                 730                 735 gtc tgt gtt gcg gac ttc ggc ctc tct aag aag att tac agt ggc gat    2256
Val Cys Val Ala Asp Phe Gly Leu Ser Lys Lys Ile Tyr Ser Gly Asp
            740                 745                 750 tat tac cgc caa ggc cgc att gct aag atg cct gtt aaa tgg atc gcc    2304
Tyr Tyr Arg Gln Gly Arg Ile Ala Lys Met Pro Val Lys Trp Ile Ala
        755                 760                 765 ata gaa agt ctt gca gac cga gtc tac aca agt aaa agt gat gtg tgg    2352
Ile Glu Ser Leu Ala Asp Arg Val Tyr Thr Ser Lys Ser Asp Val Trp
    770                 775                 780 gca ttt ggc gtg acc atg tgg gaa ata gct acg cgg gga atg act ccc    2400
Ala Phe Gly Val Thr Met Trp Glu Ile Ala Thr Arg Gly Met Thr Pro
785                 790                 795                 800 tat cct ggg gtc cag aac cat gag atg tat gac tat ctt ctc cat ggc    2448
Tyr Pro Gly Val Gln Asn His Glu Met Tyr Asp Tyr Leu Leu His Gly
                805                 810                 815 cac agg ttg aag cag ccc gaa gac tgc ctg gat gaa ctg tat gaa ata    2496
His Arg Leu Lys Gln Pro Glu Asp Cys Leu Asp Glu Leu Tyr Glu Ile
            820                 825                 830 atg tac tct tgc tgg aga acc gat ccc tta gac cgc ccc acc ttt tca    2544
Met Tyr Ser Cys Trp Arg Thr Asp Pro Leu Asp Arg Pro Thr Phe Ser
        835                 840                 845 gta ttg agg ctg cag cta gaa aaa ctc tta gaa agt ttg cct gac gtt    2592
Val Leu Arg Leu Gln Leu Glu Lys Leu Leu Glu Ser Leu Pro Asp Val
    850                 855                 860 cgg aac caa gca gac gtt att tac gtc aat aca cag ttg ctg gag agc    2640
Arg Asn Gln Ala Asp Val Ile Tyr Val Asn Thr Gln Leu Leu Glu Ser
865                 870                 875                 880 tct gag ggc ctg gcc cag ggc tcc acc ctt gct cca ctg gac ttg aac    2688
Ser Glu Gly Leu Ala Gln Gly Ser Thr Leu Ala Pro Leu Asp Leu Asn
                885                 890                 895 atc gac cct gac tct ata att gcc tcc tgc act ccc cgc gct gcc atc    2736
Ile Asp Pro Asp Ser Ile Ile Ala Ser Cys Thr Pro Arg Ala Ala Ile
            900                 905                 910 agt gtg gtc aca gca gaa gtt cat gac agc aaa cct cat gaa gga cgg    2784
Ser Val Val Thr Ala Glu Val His Asp Ser Lys Pro His Glu Gly Arg
        915                 920                 925 tac atc ctg aat ggg ggc agt gag gaa tgg gaa gat ctg act tct gcc    2832
Tyr Ile Leu Asn Gly Gly Ser Glu Glu Trp Glu Asp Leu Thr Ser Ala
    930                 935                 940 ccc tct gct gca gtc aca gct gaa aag aac agt gtt tta ccg ggg gag    2880
Pro Ser Ala Ala Val Thr Ala Glu Lys Asn Ser Val Leu Pro Gly Glu
945                 950                 955                 960 aga ctt gtt agg aat ggg gtc tcc tgg tcc cat tcg agc atg ctg ccc    2928
Arg Leu Val Arg Asn Gly Val Ser Trp Ser His Ser Ser Met Leu Pro
                965                 970                 975
```

```
ttg gga agc tca ttg ccc gat gaa ctt ttg ttt gct gac gac tcc tca    2976
Leu Gly Ser Ser Leu Pro Asp Glu Leu Leu Phe Ala Asp Asp Ser Ser
            980                 985                 990 gaa ggc tca gaa gtc ctg atg tga                                    3000
Glu Gly Ser Glu Val Leu Met
        995
```

<210> SEQ ID NO 57
<211> LENGTH: 999
<212> TYPE: PRT
<213> ORGANISM: Homo sapiens

<400> SEQUENCE: 57

```
Met Gly Pro Ala Pro Leu Pro Leu Leu Gly Leu Phe Leu Pro Ala
1               5                   10                  15

Leu Trp Arg Arg Ala Ile Thr Glu Ala Arg Glu Ala Lys Pro Tyr
            20                  25                  30

Pro Leu Phe Pro Gly Pro Phe Pro Gly Ser Leu Gln Thr Asp His Thr
            35                  40                  45

Pro Leu Leu Ser Leu Pro His Ala Ser Gly Tyr Gln Pro Ala Leu Met
        50                  55                  60

Phe Ser Pro Thr Gln Pro Gly Arg Pro His Thr Gly Asn Val Ala Ile
65                  70                  75                  80

Pro Gln Val Thr Ser Val Glu Ser Lys Pro Leu Pro Pro Leu Ala Phe
                85                  90                  95

Lys His Thr Val Gly His Ile Ile Leu Ser Glu His Lys Gly Val Lys
                100                 105                 110

Phe Asn Cys Ser Ile Ser Val Pro Asn Ile Tyr Gln Asp Thr Thr Ile
            115                 120                 125

Ser Trp Trp Lys Asp Gly Lys Glu Leu Leu Gly Ala His His Ala Ile
            130                 135                 140

Thr Gln Phe Tyr Pro Asp Asp Glu Val Thr Ala Ile Ala Ser Phe
145                 150                 155                 160

Ser Ile Thr Ser Val Gln Arg Ser Asp Asn Gly Ser Tyr Ile Cys Lys
                165                 170                 175

Met Lys Ile Asn Asn Glu Glu Ile Val Ser Asp Pro Ile Tyr Ile Glu
            180                 185                 190

Val Gln Gly Leu Pro His Phe Thr Lys Gln Pro Glu Ser Met Asn Val
            195                 200                 205

Thr Arg Asn Thr Ala Phe Asn Leu Thr Cys Gln Ala Val Gly Pro Pro
        210                 215                 220

Glu Pro Val Asn Ile Phe Trp Val Gln Asn Ser Ser Arg Val Asn Glu
225                 230                 235                 240

Gln Pro Glu Lys Ser Pro Ser Val Leu Thr Val Pro Gly Leu Thr Glu
                245                 250                 255

Met Ala Val Phe Ser Cys Glu Ala His Asn Asp Lys Gly Leu Thr Val
            260                 265                 270

Ser Lys Gly Val Gln Ile Asn Ile Lys Ala Ile Pro Ser Pro Pro Thr
        275                 280                 285

Glu Val Ser Ile Arg Asn Ser Thr Ala His Ser Ile Leu Ile Ser Trp
    290                 295                 300

Val Pro Gly Phe Asp Gly Tyr Ser Pro Phe Arg Asn Cys Ser Ile Gln
305                 310                 315                 320

Val Lys Glu Ala Asp Pro Leu Ser Asn Gly Ser Val Met Ile Phe Asn
                325                 330                 335
```

```
Thr Ser Ala Leu Pro His Leu Tyr Gln Ile Lys Gln Leu Gln Ala Leu
            340                 345                 350

Ala Asn Tyr Ser Ile Gly Val Ser Cys Met Asn Glu Ile Gly Trp Ser
        355                 360                 365

Ala Val Ser Pro Trp Ile Leu Ala Ser Thr Thr Glu Gly Ala Pro Ser
370                 375                 380

Val Ala Pro Leu Asn Val Thr Val Phe Leu Asn Glu Ser Ser Asp Asn
385                 390                 395                 400

Val Asp Ile Arg Trp Met Lys Pro Pro Thr Lys Gln Gln Asp Gly Glu
                405                 410                 415

Leu Val Gly Tyr Arg Ile Ser His Val Trp Gln Ser Ala Gly Ile Ser
            420                 425                 430

Lys Glu Leu Leu Glu Glu Val Gly Gln Asn Gly Ser Arg Ala Arg Ile
        435                 440                 445

Ser Val Gln Val His Asn Ala Thr Cys Thr Val Arg Ile Ala Ala Val
    450                 455                 460

Thr Arg Gly Gly Val Gly Pro Phe Ser Asp Pro Val Lys Ile Phe Ile
465                 470                 475                 480

Pro Ala His Gly Trp Val Asp Tyr Ala Pro Ser Ser Thr Pro Ala Pro
                485                 490                 495

Gly Asn Ala Asp Pro Val Leu Ile Ile Phe Gly Cys Phe Cys Gly Phe
            500                 505                 510

Ile Leu Ile Gly Leu Ile Leu Tyr Ile Ser Leu Ala Ile Arg Lys Arg
        515                 520                 525

Val Gln Glu Thr Lys Phe Gly Asn Ala Phe Thr Glu Glu Asp Ser Glu
    530                 535                 540

Leu Val Val Asn Tyr Ile Ala Lys Lys Ser Phe Cys Arg Arg Ala Ile
545                 550                 555                 560

Glu Leu Thr Leu His Ser Leu Gly Val Ser Glu Glu Leu Gln Asn Lys
                565                 570                 575

Leu Glu Asp Val Val Ile Asp Arg Asn Leu Leu Ile Leu Gly Lys Ile
            580                 585                 590

Leu Gly Glu Gly Glu Phe Gly Ser Val Met Glu Gly Asn Leu Lys Gln
        595                 600                 605

Glu Asp Gly Thr Ser Leu Lys Val Ala Val Lys Thr Met Lys Leu Asp
    610                 615                 620

Asn Ser Ser Gln Arg Glu Ile Glu Glu Phe Leu Ser Glu Ala Ala Cys
625                 630                 635                 640

Met Lys Asp Phe Ser His Pro Asn Val Ile Arg Leu Leu Gly Val Cys
                645                 650                 655

Ile Glu Met Ser Ser Gln Gly Ile Pro Lys Pro Met Val Ile Leu Pro
            660                 665                 670

Phe Met Lys Tyr Gly Asp Leu His Thr Tyr Leu Leu Tyr Ser Arg Leu
        675                 680                 685

Glu Thr Gly Pro Lys His Ile Pro Leu Gln Thr Leu Leu Lys Phe Met
    690                 695                 700

Val Asp Ile Ala Leu Gly Met Glu Tyr Leu Ser Asn Arg Asn Phe Leu
705                 710                 715                 720

His Arg Asp Leu Ala Ala Arg Asn Cys Met Leu Arg Asp Asp Met Thr
                725                 730                 735

Val Cys Val Ala Asp Phe Gly Leu Ser Lys Lys Ile Tyr Ser Gly Asp
            740                 745                 750
```

-continued

```
Tyr Tyr Arg Gln Gly Arg Ile Ala Lys Met Pro Val Lys Trp Ile Ala
            755                 760                 765
Ile Glu Ser Leu Ala Asp Arg Val Tyr Thr Ser Lys Ser Asp Val Trp
        770                 775                 780
Ala Phe Gly Val Thr Met Trp Glu Ile Ala Thr Arg Gly Met Thr Pro
785                 790                 795                 800
Tyr Pro Gly Val Gln Asn His Glu Met Tyr Asp Tyr Leu Leu His Gly
                805                 810                 815
His Arg Leu Lys Gln Pro Glu Asp Cys Leu Asp Glu Leu Tyr Glu Ile
            820                 825                 830
Met Tyr Ser Cys Trp Arg Thr Asp Pro Leu Asp Arg Pro Thr Phe Ser
        835                 840                 845
Val Leu Arg Leu Gln Leu Glu Lys Leu Leu Glu Ser Leu Pro Asp Val
850                 855                 860
Arg Asn Gln Ala Asp Val Ile Tyr Val Asn Thr Gln Leu Leu Glu Ser
865                 870                 875                 880
Ser Glu Gly Leu Ala Gln Gly Ser Thr Leu Ala Pro Leu Asp Leu Asn
                885                 890                 895
Ile Asp Pro Asp Ser Ile Ile Ala Ser Cys Thr Pro Arg Ala Ala Ile
            900                 905                 910
Ser Val Val Thr Ala Glu Val His Asp Ser Lys Pro His Glu Gly Arg
        915                 920                 925
Tyr Ile Leu Asn Gly Gly Ser Glu Glu Trp Glu Asp Leu Thr Ser Ala
    930                 935                 940
Pro Ser Ala Ala Val Thr Ala Glu Lys Asn Ser Val Leu Pro Gly Glu
945                 950                 955                 960
Arg Leu Val Arg Asn Gly Val Ser Trp Ser His Ser Ser Met Leu Pro
                965                 970                 975
Leu Gly Ser Ser Leu Pro Asp Glu Leu Leu Phe Ala Asp Asp Ser Ser
            980                 985                 990
Glu Gly Ser Glu Val Leu Met
        995
```

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic Primer 26

<400> SEQUENCE: 58
ctcactatag aattcgccac catggggccg gccccgctgc       40

<210> SEQ ID NO 59
<211> LENGTH: 43
<212> TYPE: DNA
<213> ORGANISM: Artificial Sequence
<220> FEATURE:
<223> OTHER INFORMATION: Description of Artificial Sequence: Synthetic Primer 27

<400> SEQUENCE: 59
caataaacaa gttggatcct cacatcagga cttctgagcc ttc       43

<210> SEQ ID NO 60
<211> LENGTH: 1027
<212> TYPE: DNA
<213> ORGANISM: Mus musculus

<400> SEQUENCE: 60

```
aacagatcct ggcggggact taggactgac ctagaacaat cagggttccg caatccaggt    60
ccccaaaggt gggatcctca accgcaggac ggagggaata gcctttcgat tctgggtggt   120
gcattggaag ccccaggctc taaaacccc aacctactga ctggtggccg agtatgcacc   180
cgactgctag ctaggcagtg tcccaagaac cagtagccaa atgtcttggc ctcagttttc   240
ccggtgacac ctggaaagtg accctgccat tagtagaggc tcaggtcagg gccccgcctc   300
tcctgggcgg cctctgccct agcccgccct gccgctcctc ctctccgcag gctcgctccc   360
acggtccccg aggtgggcgg gtgagcccag gatgacggct gtagaacccc ggcctgactc   420
gccctcgccc ccgcgccggg cctgggcttc cctagcccag ctcgcacccg ggggccgtcg   480
gagccgccgc gcgcccagct ctacgcgcct ggcgccctcc ccacgcgggc gtccccgact   540
cccgcgcgcg ctcaggctcc cagttgggaa ccaaggaggg ggaggatggg ggggggggtg   600
tgcgccgacc cggaaacgcc atataaggag caggaaggat cccccgccgg aacagacctt   660
atttgggcag cgccttatat ggagtggccc aatatggccc tgccgcttcc ggctctggga   720
ggaggggcga gcggggttg gggcggggc aagctgggaa ctccaggcgc ctggcccggg   780
aggccactgc tgctgttcca atactaggct ttccaggagc ctgagcgctc gcgatgccgg   840
agcgggtcgc agggtggagg tgcccaccac tcttggatgg gagggcttca cgtcactccg   900
ggtcctcccg gccggtcctt ccatattagg gcttcctgct tcccatatat ggccatgtac   960
gtcacggcgg aggcgggccc gtgctgttcc agacccttga aatagaggcc gattcgggga  1020
gtcgcga                                                             1027
```

<210> SEQ ID NO 61
<211> LENGTH: 438
<212> TYPE: DNA
<213> ORGANISM: Artificial Sequence
<220> FEATURE:
<223> OTHER INFORMATION: Description of Artificial Sequence: Synthetic CNTO VH sequence
<220> FEATURE:
<221> NAME/KEY: CDS
<222> LOCATION: (1)..(438)

<400> SEQUENCE: 61

```
atg gag ttt ggg ctg acc tgg gtt ttc ctc gtt gct ctt tta aga ggt    48
Met Glu Phe Gly Leu Thr Trp Val Phe Leu Val Ala Leu Leu Arg Gly
1               5                   10                  15 gtc cag tgt cag gtg cag ctg gtg gag tct ggg gga ggc gtg gtc cag    96
Val Gln Cys Gln Val Gln Leu Val Glu Ser Gly Gly Gly Val Val Gln
            20                  25                  30 cct ggg agg tcc ctg aga ctc tcc tgt gca gcg tct gga ttc acc ttc   144
Pro Gly Arg Ser Leu Arg Leu Ser Cys Ala Ala Ser Gly Phe Thr Phe
        35                  40                  45 agt agc tat ggc atg cac tgg gtc cgc cag gct cca ggc aag ggg ctg   192
Ser Ser Tyr Gly Met His Trp Val Arg Gln Ala Pro Gly Lys Gly Leu
    50                  55                  60 gag tgg gtg gca gtt ata tgg tat gat gga agt aat aaa tac tat gca   240
Glu Trp Val Ala Val Ile Trp Tyr Asp Gly Ser Asn Lys Tyr Tyr Ala
65                  70                  75                  80 gac tcc gtg aag ggg cga ttc acc atc tcc aga gac aat tcc aag aac   288
Asp Ser Val Lys Gly Arg Phe Thr Ile Ser Arg Asp Asn Ser Lys Asn
                85                  90                  95 acg ctg tat ctg caa atg aac agc ctg aga gcc gag gac acg gct atg   336
Thr Leu Tyr Leu Gln Met Asn Ser Leu Arg Ala Glu Asp Thr Ala Met
```

```
tat ttc tgt gcg aga gaa ggg ttt tat tac gat att ttg act gct tat         384
Tyr Phe Cys Ala Arg Glu Gly Phe Tyr Tyr Asp Ile Leu Thr Ala Tyr
        115                 120                 125 tcc ctt gaa tac ttc cag cac tgg ggc cag ggc acc ctg gtc acc gtc         432
Ser Leu Glu Tyr Phe Gln His Trp Gly Gln Gly Thr Leu Val Thr Val
130                 135                 140 tcc tca                                                                 438
Ser Ser
145

<210> SEQ ID NO 62
<211> LENGTH: 146
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 62

Met Glu Phe Gly Leu Thr Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Met
            100                 105                 110

Tyr Phe Cys Ala Arg Glu Gly Phe Tyr Tyr Asp Ile Leu Thr Ala Tyr
        115                 120                 125

Ser Leu Glu Tyr Phe Gln His Trp Gly Gln Gly Thr Leu Val Thr Val
    130                 135                 140

Ser Ser
145

<210> SEQ ID NO 63
<211> LENGTH: 378
<212> TYPE: DNA
<213> ORGANISM: Artificial Sequence
<220> FEATURE:
<223> OTHER INFORMATION: Description of Artificial Sequence: Synthetic
      CNTO VL sequence
<220> FEATURE:
<221> NAME/KEY: CDS
<222> LOCATION: (1)..(378)

<400> SEQUENCE: 63 atg tcg cca tca caa ctc att ggg ttt ctg ctg ctc tgg gtt cca gcc         48
Met Ser Pro Ser Gln Leu Ile Gly Phe Leu Leu Leu Trp Val Pro Ala
1               5                   10                  15 tcc agg ggt gaa att gtg ctg act cag tct cca gac ttt cag tct gtg         96
Ser Arg Gly Glu Ile Val Leu Thr Gln Ser Pro Asp Phe Gln Ser Val
            20                  25                  30 act cca aag gag aag gtc acc atc acc tgc cgg gcc agt cag agc att         144
Thr Pro Lys Glu Lys Val Thr Ile Thr Cys Arg Ala Ser Gln Ser Ile
```

```
ggt agt agc tta cac tgg tac cag cag aaa cca gat cag tct cca aag       192
Gly Ser Ser Leu His Trp Tyr Gln Gln Lys Pro Asp Gln Ser Pro Lys
     50                  55                  60 ctc ctc atc aag tat gct tcc cag tcc ttc tca ggg gtc ccc tcg agg       240
Leu Leu Ile Lys Tyr Ala Ser Gln Ser Phe Ser Gly Val Pro Ser Arg
 65                  70                  75                  80 ttc agt ggc agt gga tct ggg aca gat ttc acc ctc acc atc aat agc       288
Phe Ser Gly Ser Gly Ser Gly Thr Asp Phe Thr Leu Thr Ile Asn Ser
                 85                  90                  95 ctg gaa gct gaa gat gct gca gcg tat tac tgt cat cag agt agt agt       336
Leu Glu Ala Glu Asp Ala Ala Ala Tyr Tyr Cys His Gln Ser Ser Ser
            100                 105                 110 tta ccg tac act ttt ggc cag ggg acc aag ctg gag atc aaa               378
Leu Pro Tyr Thr Phe Gly Gln Gly Thr Lys Leu Glu Ile Lys
        115                 120                 125

<210> SEQ ID NO 64
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 64

Met Ser Pro Ser Gln Leu Ile Gly Phe Leu Leu Leu Trp Val Pro Ala
 1               5                  10                  15

Ser Arg Gly Glu Ile Val Leu Thr Gln Ser Pro Asp Phe Gln Ser Val
             20                  25                  30

Thr Pro Lys Glu Lys Val Thr Ile Thr Cys Arg Ala Ser Gln Ser Ile
         35                  40                  45

Gly Ser Ser Leu His Trp Tyr Gln Gln Lys Pro Asp Gln Ser Pro Lys
     50                  55                  60

Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                 85                  90                  95

Leu Glu Ala Glu Asp Ala Ala Ala Tyr Tyr Cys His Gln Ser Ser Ser
            100                 105                 110

Leu Pro Tyr Thr Phe Gly Gln Gly Thr Lys Leu Glu Ile Lys
        115                 120                 125

<210> SEQ ID NO 65
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer 28

<400> SEQUENCE: 65
ccagggtcac catggagtta gtttgggcag                                       30

<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer 29
```

<400> SEQUENCE: 66

```
ctaacactca ttcctgttga agctcttgac aa                                    32
```

<210> SEQ ID NO 67
<211> LENGTH: 414
<212> TYPE: DNA
<213> ORGANISM: Artificial Sequence
<220> FEATURE:
<223> OTHER INFORMATION: Description of Artificial Sequence: Synthetic
      KM5320 VH sequence
<220> FEATURE:
<221> NAME/KEY: CDS
<222> LOCATION: (1)..(414)

<400> SEQUENCE: 67

```
atg gat tgg ctg tgg aac ttg cta ttc ctg atg gca gct gcc caa agt       48
Met Asp Trp Leu Trp Asn Leu Leu Phe Leu Met Ala Ala Ala Gln Ser
1               5                   10                  15 gcc caa gca cag atc cag ttg gtg cag tct gga cct gag ctg aag aag       96
Ala Gln Ala Gln Ile Gln Leu Val Gln Ser Gly Pro Glu Leu Lys Lys
                20                  25                  30 cct gga gag aca gtc aag atc tcc tgc aag gct tct ggg tat acc ttc     144
Pro Gly Glu Thr Val Lys Ile Ser Cys Lys Ala Ser Gly Tyr Thr Phe
            35                  40                  45 aca aac tat gga atg aac tgg gtg aag cag gct cca gga aag ggt tta     192
Thr Asn Tyr Gly Met Asn Trp Val Lys Gln Ala Pro Gly Lys Gly Leu
        50                  55                  60 aag tgg atg ggc tgg ata aac act gag act gga gag cca aca tat tct     240
Lys Trp Met Gly Trp Ile Asn Thr Glu Thr Gly Glu Pro Thr Tyr Ser
65                  70                  75                  80 gat gac ttc aag gga cgg ttt gcc ttc tct ttg gaa acc tct gcc acc     288
Asp Asp Phe Lys Gly Arg Phe Ala Phe Ser Leu Glu Thr Ser Ala Thr
                85                  90                  95 act gcc tat ttg cag atc aac aac ctc aga aat gag gac atg gct aca     336
Thr Ala Tyr Leu Gln Ile Asn Asn Leu Arg Asn Glu Asp Met Ala Thr
            100                 105                 110 tat ttc tgt gca aga gag gat ggt tac tac ggt act ttg gac tac tgg     384
Tyr Phe Cys Ala Arg Glu Asp Gly Tyr Tyr Gly Thr Leu Asp Tyr Trp
        115                 120                 125 ggt caa gga acc tca gtc acc gtc tcc tca                             414
Gly Gln Gly Thr Ser Val Thr Val Ser Ser
130                 135
```

<210> SEQ ID NO 68
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 68

```
Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Thr Phe
            35                  40                  45

Thr Asn Tyr Gly Met Asn Trp Val Lys Gln Ala Pro Gly Lys Gly Leu
        50                  55                  60

Lys Trp Met Gly Trp Ile Asn Thr Glu Thr Gly Glu Pro Thr Tyr Ser
65                  70                  75                  80
```

```
Asp Asp Phe Lys Gly Arg Phe Ala Phe Ser Leu Glu Thr Ser Ala Thr
            85                  90                  95

Thr Ala Tyr Leu Gln Ile Asn Asn Leu Arg Asn Glu Asp Met Ala Thr
        100                 105                 110

Tyr Phe Cys Ala Arg Glu Asp Gly Tyr Tyr Gly Thr Leu Asp Tyr Trp
        115                 120                 125

Gly Gln Gly Thr Ser Val Thr Val Ser Ser
        130                 135

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of KM5320 VH excluding
      signal sequence

<400> SEQUENCE: 69

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Glu Thr Gly Glu Pro Thr Tyr Ser Asp Asp Phe
    50                  55                  60

Lys Gly Arg Phe Ala Phe Ser Leu Glu Thr Ser Ala Thr Thr Ala Tyr
65                  70                  75                  80

Leu Gln Ile Asn Asn Leu Arg Asn Glu Asp Met Ala Thr Tyr Phe Cys
                85                  90                  95

Ala Arg Glu Asp Gly Tyr Tyr Gly Thr Leu Asp Tyr Trp Gly Gln Gly
            100                 105                 110

Thr Ser Val Thr Val Ser Ser
        115

<210> SEQ ID NO 70
<211> LENGTH: 381
<212> TYPE: DNA
<213> ORGANISM: Artificial Sequence
<220> FEATURE:
<223> OTHER INFORMATION: Description of Artificial Sequence: Synthetic
      KM5320 VL sequence
<220> FEATURE:
<221> NAME/KEY: CDS
<222> LOCATION: (1)..(381)

<400> SEQUENCE: 70 atg aag tca cag acc cag gtc ttc gta ttt cta ctg ctc tgt gtg tct      48
Met Lys Ser Gln Thr Gln Val Phe Val Phe Leu Leu Leu Cys Val Ser
1               5                   10                  15 ggt gct cat ggg agt att gtg atg acc cag act ccc aaa ttc ctg ctt      96
Gly Ala His Gly Ser Ile Val Met Thr Gln Thr Pro Lys Phe Leu Leu
            20                  25                  30 gta tca gca gga gac agg gtt acc ata acc tgc aag gcc agt cag agt     144
Val Ser Ala Gly Asp Arg Val Thr Ile Thr Cys Lys Ala Ser Gln Ser
        35                  40                  45 gtg agt aat gat gta gct tgg tac caa cag aag cca ggg cag tct cct     192
Val Ser Asn Asp Val Ala Trp Tyr Gln Gln Lys Pro Gly Gln Ser Pro
    50                  55                  60
```

```
aaa gtg ctg ata tac tat gca tcc aat cgc tac act gga gtc cct gat    240
Lys Val Leu Ile Tyr Tyr Ala Ser Asn Arg Tyr Thr Gly Val Pro Asp
 65                  70                  75                  80 cgc ttc act ggc agt gga tat ggg acg gat ttc act ttc acc atc agc    288
Arg Phe Thr Gly Ser Gly Tyr Gly Thr Asp Phe Thr Phe Thr Ile Ser
                 85                  90                  95 act gtg cag gct gaa gac ctg gca gtt tat ttc tgt cag cag gat tat    336
Thr Val Gln Ala Glu Asp Leu Ala Val Tyr Phe Cys Gln Gln Asp Tyr
            100                 105                 110 agc tct ccg tgg acg ttc ggt gga ggc acc aag ctg gaa atc aaa        381
Ser Ser Pro Trp Thr Phe Gly Gly Gly Thr Lys Leu Glu Ile Lys
                115                 120                 125

<210> SEQ ID NO 71
<211> LENGTH: 127
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 71

Met Lys Ser Gln Thr Gln Val Phe Val Phe Leu Leu Leu Cys Val Ser
  1               5                  10                  15

Gly Ala His Gly Ser Ile Val Met Thr Gln Thr Pro Lys Phe Leu Leu
                 20                  25                  30

Val Ser Ala Gly Asp Arg Val Thr Ile Thr Cys Lys Ala Ser Gln Ser
             35                  40                  45

Val Ser Asn Asp Val Ala Trp Tyr Gln Gln Lys Pro Gly Gln Ser Pro
         50                  55                  60

Lys Val Leu Ile Tyr Tyr Ala Ser Asn Arg Tyr Thr Gly Val Pro Asp
 65                  70                  75                  80

Arg Phe Thr Gly Ser Gly Tyr Gly Thr Asp Phe Thr Phe Thr Ile Ser
                 85                  90                  95

Thr Val Gln Ala Glu Asp Leu Ala Val Tyr Phe Cys Gln Gln Asp Tyr
            100                 105                 110

Ser Ser Pro Trp Thr Phe Gly Gly Gly Thr Lys Leu Glu Ile Lys
                115                 120                 125

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of KM5320 VL sequence excluding
      signal sequence

<400> SEQUENCE: 72

Ser Ile Val Met Thr Gln Thr Pro Lys Phe Leu Leu Val Ser Ala Gly
  1               5                  10                  15

Asp Arg Val Thr Ile Thr Cys Lys Ala Ser Gln Ser Val Ser Asn Asp
                 20                  25                  30

Val Ala Trp Tyr Gln Gln Lys Pro Gly Gln Ser Pro Lys Val Leu Ile
             35                  40                  45

Tyr Tyr Ala Ser Asn Arg Tyr Thr Gly Val Pro Asp Arg Phe Thr Gly
         50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Trp
```

<210> SEQ ID NO 73
<211> LENGTH: 405
<212> TYPE: DNA
<213> ORGANISM: Artificial Sequence
<220> FEATURE:
<223> OTHER INFORMATION: Description of Artificial Sequence: Synthetic
      KM5321 VH sequence
<220> FEATURE:
<221> NAME/KEY: CDS
<222> LOCATION: (1)..(405)

<400> SEQUENCE: 73

```
atg gat tgg ctg tgg aac ttg cta ttc ctg atg gca gct gcc caa agt      48
Met Asp Trp Leu Trp Asn Leu Leu Phe Leu Met Ala Ala Ala Gln Ser
1               5                   10                  15 atc caa gca cag atc cag ttg gtg cag tct gga cct gag ctg aag aag      96
Ile Gln Ala Gln Ile Gln Leu Val Gln Ser Gly Pro Glu Leu Lys Lys
            20                  25                  30 cct gga gag aca gtc aag atc tcc tgc agg gct tct ggg tat acc ttc     144
Pro Gly Glu Thr Val Lys Ile Ser Cys Arg Ala Ser Gly Tyr Thr Phe
        35                  40                  45 aca aac tat gga atg aac tgg gtg aag cag gct cca gga aag ggt tta     192
Thr Asn Tyr Gly Met Asn Trp Val Lys Gln Ala Pro Gly Lys Gly Leu
    50                  55                  60 aag tgg atg ggc tgg ata aac acc aac act gga gag cca act tat act     240
Lys Trp Met Gly Trp Ile Asn Thr Asn Thr Gly Glu Pro Thr Tyr Thr
65                  70                  75                  80 gaa gag ttc aag gga cgg ttt gcc ttc tct ttg gag acc tct gcc act     288
Glu Glu Phe Lys Gly Arg Phe Ala Phe Ser Leu Glu Thr Ser Ala Thr
                85                  90                  95 act gcc tat ttg cag atc aac gac ctc aaa aat gag gac acg gct aca     336
Thr Ala Tyr Leu Gln Ile Asn Asp Leu Lys Asn Glu Asp Thr Ala Thr
            100                 105                 110 tat ttc tgt gca aga gat gag gga tgg ttt gtt tac tgg ggc caa ggg     384
Tyr Phe Cys Ala Arg Asp Glu Gly Trp Phe Val Tyr Trp Gly Gln Gly
        115                 120                 125 act ctg atc act gtc tct gca                                         405
Thr Leu Ile Thr Val Ser Ala
    130                 135
```

<210> SEQ ID NO 74
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 74

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Arg Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Thr
```

```
                65                  70                  75                  80
Glu Glu Phe Lys Gly Arg Phe Ala Phe Ser Leu Glu Thr Ser Ala Thr
                        85                  90                  95

Thr Ala Tyr Leu Gln Ile Asn Asp Leu Lys Asn Glu Asp Thr Ala Thr
                100                 105                 110

Tyr Phe Cys Ala Arg Asp Glu Gly Trp Phe Val Tyr Trp Gly Gln Gly
            115                 120                 125

Thr Leu Ile Thr Val Ser Ala
        130                 135

<210> SEQ ID NO 75
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of KM5321 VH excluding
      signal sequence

<400> SEQUENCE: 75

Gln Ile Gln Leu Val Gln Ser Gly Pro Glu Leu Lys Lys Pro Gly Glu
1               5                   10                  15

Thr Val Lys Ile Ser Cys Arg Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Asn Thr Gly Glu Pro Thr Tyr Thr Glu Glu Phe
    50                  55                  60

Lys Gly Arg Phe Ala Phe Ser Leu Glu Thr Ser Ala Thr Thr Ala Tyr
65                  70                  75                  80

Leu Gln Ile Asn Asp Leu Lys Asn Glu Asp Thr Ala Thr Tyr Phe Cys
                85                  90                  95

Ala Arg Asp Glu Gly Trp Phe Val Tyr Trp Gly Gln Gly Thr Leu Ile
            100                 105                 110

Thr Val Ser Ala
        115

<210> SEQ ID NO 76
<211> LENGTH: 381
<212> TYPE: DNA
<213> ORGANISM: Artificial Sequence
<220> FEATURE:
<223> OTHER INFORMATION: Description of Artificial Sequence: Synthetic
      KM5321 VL sequence
<220> FEATURE:
<221> NAME/KEY: CDS
<222> LOCATION: (1)..(381)

<400> SEQUENCE: 76 atg ctc tca cta gct cct ctc ctc agc ctt ctt ctc ctc tgt gtc tct      48
Met Leu Ser Leu Ala Pro Leu Leu Ser Leu Leu Leu Leu Cys Val Ser
1               5                   10                  15 gat tct agg gca gaa aca act gtg acc cag tct cca gca tcc ctg tcc      96
Asp Ser Arg Ala Glu Thr Thr Val Thr Gln Ser Pro Ala Ser Leu Ser
            20                  25                  30 gtg gct aca gga gaa aaa gtc act atc aga tgc ata acc agt act gat     144
Val Ala Thr Gly Glu Lys Val Thr Ile Arg Cys Ile Thr Ser Thr Asp
        35                  40                  45 att gat gat gat atg aac tgg tac caa cag aag cca ggg gaa cct cct     192
Ile Asp Asp Asp Met Asn Trp Tyr Gln Gln Lys Pro Gly Glu Pro Pro
    50                  55                  60
```

```
aag ctc ctt att tca gaa ggc aat act ctt cgt cct gga gtc cca tcc    240
Lys Leu Leu Ile Ser Glu Gly Asn Thr Leu Arg Pro Gly Val Pro Ser
65                  70                  75                  80 cga ttc tcc agc agt ggc tat ggc aca gat ttt gtt ttt aca att gaa    288
Arg Phe Ser Ser Ser Gly Tyr Gly Thr Asp Phe Val Phe Thr Ile Glu
                85                  90                  95 aac acg ctc tca gaa gat gtt gca gat tac tac tgt ttg caa act gat    336
Asn Thr Leu Ser Glu Asp Val Ala Asp Tyr Tyr Cys Leu Gln Thr Asp
            100                 105                 110 agc gtg cct ctc acg ttc ggt gct ggg acc aag ctg gag ctg aaa        381
Ser Val Pro Leu Thr Phe Gly Ala Gly Thr Lys Leu Glu Leu Lys
        115                 120                 125
```

<210> SEQ ID NO 77
<211> LENGTH: 127
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 77

Met Leu Ser Leu Ala Pro Leu Leu Ser Leu Leu Leu Leu Cys Val Ser
1               5                   10                  15

Asp Ser Arg Ala Glu Thr Thr Val Thr Gln Ser Pro Ala Ser Leu Ser
            20                  25                  30

Val Ala Thr Gly Glu Lys Val Thr Ile Arg Cys Ile Thr Ser Thr Asp
        35                  40                  45

Ile Asp Asp Asp Met Asn Trp Tyr Gln Gln Lys Pro Gly Glu Pro Pro
    50                  55                  60

Lys Leu Leu Ile Ser Glu Gly Asn Thr Leu Arg Pro Gly Val Pro Ser
65                  70                  75                  80

Arg Phe Ser Ser Ser Gly Tyr Gly Thr Asp Phe Val Phe Thr Ile Glu
                85                  90                  95

Asn Thr Leu Ser Glu Asp Val Ala Asp Tyr Tyr Cys Leu Gln Thr Asp
            100                 105                 110

Ser Val Pro Leu Thr Phe Gly Ala Gly Thr Lys Leu Glu Leu Lys
        115                 120                 125

<210> SEQ ID NO 78
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of KM5321 VL sequence excluding
      signal sequence

<400> SEQUENCE: 78

Glu Thr Thr Val Thr Gln Ser Pro Ala Ser Leu Ser Val Ala Thr Gly
1               5                   10                  15

Glu Lys Val Thr Ile Arg Cys Ile Thr Ser Thr Asp Ile Asp Asp Asp
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Thr Leu Ser
65                  70                  75                  80

```
Glu Asp Val Ala Asp Tyr Tyr Cys Leu Gln Thr Asp Ser Val Pro Leu
            85                  90                  95

Thr Phe Gly Ala Gly Thr Lys Leu Glu Leu Lys
            100                 105

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid sequence of KM5320 VH CDR1

<400> SEQUENCE: 79

Asn Tyr Gly Met Asn
1               5

<210> SEQ ID NO 80
<211> LENGTH: 17
<212> TYPE: PRT
<213> ORGANISM: Artificial Sequence
<220> FEATURE:
<223> OTHER INFORMATION: Description of Artificial Sequence: Synthetic
      amino acid sequence of KM5320 VH CDR2

<400> SEQUENCE: 80

Trp Ile Asn Thr Glu Thr Gly Glu Pro Thr Tyr Ser Asp Asp Phe Lys
1               5                   10                  15

Gly

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      amino acid sequence of KM5320 VH CDR3

<400> SEQUENCE: 81

Glu Asp Gly Tyr Tyr Gly Thr Leu Asp Tyr
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      amino acid sequence of KM5320 VL CDR1

<400> SEQUENCE: 82

Lys Ala Ser Gln Ser Val Ser Asn Asp Val Ala
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of KM5320 VL CDR2

<400> SEQUENCE: 83

Tyr Ala Ser Asn Arg Tyr Thr
1               5
```

```
<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence of KM5320 VL CDR3

<400> SEQUENCE: 84

Gln Gln Asp Tyr Ser Ser Pro Trp Thr
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      amino acid sequence of KM5321 VH CDR1

<400> SEQUENCE: 85

Asn Tyr Gly Met Asn
1               5

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      amino acid sequence of KM5321 VH CDR2

<400> SEQUENCE: 86

Trp Ile Asn Thr Asn Thr Gly Glu Pro Thr Tyr Thr Glu Glu Phe Lys
1               5                   10                  15

Gly

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of KM5321 VH CDR3

<400> SEQUENCE: 87

Asp Glu Gly Trp Phe Val Tyr
1               5

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      amino acid sequence of KM5321 VL CDR1

<400> SEQUENCE: 88

Ile Thr Ser Thr Asp Ile Asp Asp Asp Met Asn
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      amino acid sequence of KM5321 VL CDR2
```

<400> SEQUENCE: 89

Glu Gly Asn Thr Leu Arg Pro
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      amino acid sequence of KM5321 VL CDR3

<400> SEQUENCE: 90

Leu Gln Thr Asp Ser Val Pro Leu Thr
1               5

<210> SEQ ID NO 91
<211> LENGTH: 1395
<212> TYPE: DNA
<213> ORGANISM: Artificial Sequence
<220> FEATURE:
<223> OTHER INFORMATION: Description of Artificial Sequence: Synthetic
      KM5320-rIgG1 sequence
<220> FEATURE:
<221> NAME/KEY: CDS
<222> LOCATION: (1)..(1392)

<400> SEQUENCE: 91

```
atg gat tgg ctg tgg aac ttg cta ttc ctg atg gca gct gcc caa agt      48
Met Asp Trp Leu Trp Asn Leu Leu Phe Leu Met Ala Ala Ala Gln Ser
1               5                   10                  15 gcc caa gca cag atc cag ttg gtg cag tct gga cct gag ctg aag aag      96
Ala Gln Ala Gln Ile Gln Leu Val Gln Ser Gly Pro Glu Leu Lys Lys
                20                  25                  30 cct gga gag aca gtc aag atc tcc tgc aag gct tct ggg tat acc ttc     144
Pro Gly Glu Thr Val Lys Ile Ser Cys Lys Ala Ser Gly Tyr Thr Phe
            35                  40                  45 aca aac tat gga atg aac tgg gtg aag cag gct cca gga aag ggt tta     192
Thr Asn Tyr Gly Met Asn Trp Val Lys Gln Ala Pro Gly Lys Gly Leu
        50                  55                  60 aag tgg atg ggc tgg ata aac act gag act gga gag cca aca tat tct     240
Lys Trp Met Gly Trp Ile Asn Thr Glu Thr Gly Glu Pro Thr Tyr Ser
65                  70                  75                  80 gat gac ttc aag gga cgg ttt gcc ttc tct ttg gaa acc tct gcc acc     288
Asp Asp Phe Lys Gly Arg Phe Ala Phe Ser Leu Glu Thr Ser Ala Thr
                85                  90                  95 act gcc tat ttg cag atc aac aac ctc aga aat gag gac atg gct aca     336
Thr Ala Tyr Leu Gln Ile Asn Asn Leu Arg Asn Glu Asp Met Ala Thr
            100                 105                 110 tat ttc tgt gca aga gag gat ggt tac tac ggt act ttg gac tac tgg     384
Tyr Phe Cys Ala Arg Glu Asp Gly Tyr Tyr Gly Thr Leu Asp Tyr Trp
        115                 120                 125 ggt caa gga acc tca gtc acc gtc tcc tca gct gaa aca aca gcc ccg     432
Gly Gln Gly Thr Ser Val Thr Val Ser Ser Ala Glu Thr Thr Ala Pro
    130                 135                 140 tct gtc tat cca ctg gct cct gga act gct ctc aaa agt aac tcc atg     480
Ser Val Tyr Pro Leu Ala Pro Gly Thr Ala Leu Lys Ser Asn Ser Met
145                 150                 155                 160 gtg acc ctg gga tgc ctg gtc aag ggc tat ttc cct gag cca gtc acc     528
Val Thr Leu Gly Cys Leu Val Lys Gly Tyr Phe Pro Glu Pro Val Thr
                165                 170                 175 gtg acc tgg aac tct gga gcc ctg tcc agc ggt gtg cac acc ttc cca     576
```

|  |  |  |  |  |  |  |  |  |  |  |  |  |
|---|---|---|---|---|---|---|---|---|---|---|---|---|
|  | Val | Thr | Trp | Asn | Ser | Gly | Ala | Leu | Ser | Ser | Gly | Val | His | Thr | Phe | Pro |
|  |  |  | 180 |  |  |  |  | 185 |  |  |  |  | 190 |  |  |  |

```
gct gtc ctg cag tct ggg ctc tac act ctc acc agc tca gtg act gta       624
Ala Val Leu Gln Ser Gly Leu Tyr Thr Leu Thr Ser Ser Val Thr Val
    195                 200                 205 ccc tcc agc acc tgg ccc agc cag acc gtc acc tgc aac gta gcc cac       672
Pro Ser Ser Thr Trp Pro Ser Gln Thr Val Thr Cys Asn Val Ala His
210                 215                 220 ccg gcc agc agc acc aag gtg gac aag aaa att gtg ccc aga aac tgt       720
Pro Ala Ser Ser Thr Lys Val Asp Lys Lys Ile Val Pro Arg Asn Cys
225                 230                 235                 240 gga ggt gat tgc aag cct tgt ata tgt aca ggc tca gaa gta tca tct       768
Gly Gly Asp Cys Lys Pro Cys Ile Cys Thr Gly Ser Glu Val Ser Ser
                245                 250                 255 gtc ttc atc ttc ccc cca aag ccc aaa gat gtg ctc acc atc act ctg       816
Val Phe Ile Phe Pro Pro Lys Pro Lys Asp Val Leu Thr Ile Thr Leu
            260                 265                 270 act cct aag gtc acg tgt gtt gtg gta gac att agc cag gac gat ccc       864
Thr Pro Lys Val Thr Cys Val Val Val Asp Ile Ser Gln Asp Asp Pro
        275                 280                 285 gag gtc cat ttc agc tgg ttt gta gat gac gtg gaa gtc cac aca gct       912
Glu Val His Phe Ser Trp Phe Val Asp Asp Val Glu Val His Thr Ala
290                 295                 300 cag act cga cca cca gag gag cag ttc aac agc act ttc cgc tca gtc       960
Gln Thr Arg Pro Pro Glu Glu Gln Phe Asn Ser Thr Phe Arg Ser Val
305                 310                 315                 320 agt gaa ctc ccc atc ctg cac cag gac tgg ctc aat ggc agg acg ttc      1008
Ser Glu Leu Pro Ile Leu His Gln Asp Trp Leu Asn Gly Arg Thr Phe
                325                 330                 335 aga tgc aag gtc acc agt gca gct ttc cca tcc ccc atc gag aaa acc      1056
Arg Cys Lys Val Thr Ser Ala Ala Phe Pro Ser Pro Ile Glu Lys Thr
            340                 345                 350 atc tcc aaa ccc gaa ggc aga aca caa gtt ccg cat gta tac acc atg      1104
Ile Ser Lys Pro Glu Gly Arg Thr Gln Val Pro His Val Tyr Thr Met
        355                 360                 365 tca cct acc aag gaa gag atg acc cag aat gaa gtc agt atc acc tgc      1152
Ser Pro Thr Lys Glu Glu Met Thr Gln Asn Glu Val Ser Ile Thr Cys
370                 375                 380 atg gta aaa ggc ttc tat ccc cca gac att tat gtg gag tgg cag atg      1200
Met Val Lys Gly Phe Tyr Pro Pro Asp Ile Tyr Val Glu Trp Gln Met
385                 390                 395                 400 aac ggg cag cca cag gaa aac tac aag aac act cca cct acg atg gac      1248
Asn Gly Gln Pro Gln Glu Asn Tyr Lys Asn Thr Pro Pro Thr Met Asp
                405                 410                 415 aca gat ggg agt tac ttc ctc tac agc aag ctc aat gtg aag aag gaa      1296
Thr Asp Gly Ser Tyr Phe Leu Tyr Ser Lys Leu Asn Val Lys Lys Glu
            420                 425                 430 aaa tgg cag cag gga aac acg ttc acg tgt tct gtg ctg cat gaa ggc      1344
Lys Trp Gln Gln Gly Asn Thr Phe Thr Cys Ser Val Leu His Glu Gly
        435                 440                 445 ctg cac aac cac cat act gag aag agt ctc tcc cac tct ccg ggt aaa      1392
Leu His Asn His His Thr Glu Lys Ser Leu Ser His Ser Pro Gly Lys
450                 455                 460 tga                                                                  1395
```

<210> SEQ ID NO 92
<211> LENGTH: 464
<212> TYPE: PRT
<213> ORGANISM: Artificial Sequence
<220> FEATURE:

<223> OTHER INFORMATION: Description of Artificial Sequence: Synthetic construct

<400> SEQUENCE: 92

```
Met Asp Trp Leu Trp Asn Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Glu Thr Gly Glu Pro Thr Tyr Ser
65                  70                  75                  80

Asp Asp Phe Lys Gly Arg Phe Ala Phe Ser Leu Glu Thr Ser Ala Thr
                85                  90                  95

Thr Ala Tyr Leu Gln Ile Asn Asn Leu Arg Asn Glu Asp Met Ala Thr
            100                 105                 110

Tyr Phe Cys Ala Arg Glu Asp Tyr Tyr Gly Thr Leu Asp Tyr Trp
        115                 120                 125

Gly Gln Gly Thr Ser Val Thr Val Ser Ser Ala Glu Thr Thr Ala Pro
130                 135                 140

Ser Val Tyr Pro Leu Ala Pro Gly Thr Ala Leu Lys Ser Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ala Leu Ser Ser Gly Val His Thr Phe Pro
            180                 185                 190

Ala Val Leu Gln Ser Gly Leu Tyr Thr Leu Thr Ser Ser Val Thr Val
        195                 200                 205

Pro Ser Ser Thr Trp Pro Ser Gln Thr Val Thr Cys Asn Val Ala His
210                 215                 220

Pro Ala Ser Ser Thr Lys Val Asp Lys Lys Ile Val Pro Arg Asn Cys
225                 230                 235                 240

Gly Gly Asp Cys Lys Pro Cys Ile Cys Thr Gly Ser Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Asp Ile Ser Gln Asp Asp Pro
        275                 280                 285

Glu Val His Phe Ser Trp Phe Val Asp Asp Val Glu Val His Thr Ala
290                 295                 300

Gln Thr Arg Pro Pro Glu Gln Phe Asn Ser Thr Phe Arg Ser Val
305                 310                 315                 320

Ser Glu Leu Pro Ile Leu His Gln Asp Trp Leu Asn Gly Arg Thr Phe
                325                 330                 335

Arg Cys Lys Val Thr Ser Ala Ala Phe Pro Ser Pro Ile Glu Lys Thr
            340                 345                 350

Ile Ser Lys Pro Glu Gly Arg Thr Gln Val Pro His Val Tyr Thr Met
        355                 360                 365

Ser Pro Thr Lys Glu Glu Met Thr Gln Asn Glu Val Ser Ile Thr Cys
370                 375                 380

Met Val Lys Gly Phe Tyr Pro Pro Asp Ile Tyr Val Glu Trp Gln Met
385                 390                 395                 400
```

```
Asn Gly Gln Pro Gln Glu Asn Tyr Lys Asn Thr Pro Pro Thr Met Asp
            405                 410                 415

Thr Asp Gly Ser Tyr Phe Leu Tyr Ser Lys Leu Asn Val Lys Lys Glu
            420                 425                 430

Lys Trp Gln Gln Gly Asn Thr Phe Thr Cys Ser Val Leu His Glu Gly
            435                 440                 445

Leu His Asn His His Thr Glu Lys Ser Leu Ser His Ser Pro Gly Lys
            450                 455                 460

<210> SEQ ID NO 93
<211> LENGTH: 705
<212> TYPE: DNA
<213> ORGANISM: Artificial Sequence
<220> FEATURE:
<223> OTHER INFORMATION: Description of Artificial Sequence: Synthetic
      KM5320-r_kappa sequence
<220> FEATURE:
<221> NAME/KEY: CDS
<222> LOCATION: (1)..(702)

<400> SEQUENCE: 93
```

| | | |
|---|---|---|
| atg aag tca cag acc cag gtc ttc gta ttt cta ctg ctc tgt gtg tct<br>Met Lys Ser Gln Thr Gln Val Phe Val Phe Leu Leu Leu Cys Val Ser<br>1               5                  10                  15 | 48 |
| ggt gct cat ggg agt att gtg atg acc cag act ccc aaa ttc ctg ctt<br>Gly Ala His Gly Ser Ile Val Met Thr Gln Thr Pro Lys Phe Leu Leu<br>            20                  25                  30 | 96 |
| gta tca gca gga gac agg gtt acc ata acc tgc aag gcc agt cag agt<br>Val Ser Ala Gly Asp Arg Val Thr Ile Thr Cys Lys Ala Ser Gln Ser<br>        35                  40                  45 | 144 |
| gtg agt aat gat gta gct tgg tac caa cag aag cca ggg cag tct cct<br>Val Ser Asn Asp Val Ala Trp Tyr Gln Gln Lys Pro Gly Gln Ser Pro<br>    50                  55                  60 | 192 |
| aaa gtg ctg ata tac tat gca tcc aat cgc tac act gga gtc cct gat<br>Lys Val Leu Ile Tyr Tyr Ala Ser Asn Arg Tyr Thr Gly Val Pro Asp<br>65                  70                  75                  80 | 240 |
| cgc ttc act ggc agt gga tat ggg acg gat ttc act ttc acc atc agc<br>Arg Phe Thr Gly Ser Gly Tyr Gly Thr Asp Phe Thr Phe Thr Ile Ser<br>                85                  90                  95 | 288 |
| act gtg cag gct gaa gac ctg gca gtt tat ttc tgt cag cag gat tat<br>Thr Val Gln Ala Glu Asp Leu Ala Val Tyr Phe Cys Gln Gln Asp Tyr<br>            100                 105                 110 | 336 |
| agc tct ccg tgg acg ttc ggt gga ggc acc aag ctg gaa atc aaa cgg<br>Ser Ser Pro Trp Thr Phe Gly Gly Gly Thr Lys Leu Glu Ile Lys Arg<br>        115                 120                 125 | 384 |
| gct gat gcg gca cca act gta tct atc ttc cca cca tcc acg gaa cag<br>Ala Asp Ala Ala Pro Thr Val Ser Ile Phe Pro Pro Ser Thr Glu Gln<br>    130                 135                 140 | 432 |
| tta gca act gga ggt gcc tca gtc gtg tgc ctc atg aac aac ttc tat<br>Leu Ala Thr Gly Gly Ala Ser Val Val Cys Leu Met Asn Asn Phe Tyr<br>145                 150                 155                 160 | 480 |
| ccc aga gac atc agt gtc aag tgg aag att gat ggc act gaa cga cga<br>Pro Arg Asp Ile Ser Val Lys Trp Lys Ile Asp Gly Thr Glu Arg Arg<br>                165                 170                 175 | 528 |
| gat ggt gtc ctg gac agt gtt act gat cag gac agc aaa gac agc acg<br>Asp Gly Val Leu Asp Ser Val Thr Asp Gln Asp Ser Lys Asp Ser Thr<br>            180                 185                 190 | 576 |
| tac agc atg agc agc acc ctc tcg ttg acc aag gct gac tat gaa agt<br>Tyr Ser Met Ser Ser Thr Leu Ser Leu Thr Lys Ala Asp Tyr Glu Ser<br>        195                 200                 205 | 624 |

```
cat aac ctc tat acc tgt gag gtt gtt cat aag aca tca tcc tca ccc        672
His Asn Leu Tyr Thr Cys Glu Val Val His Lys Thr Ser Ser Ser Pro
    210                 215                 220 gtc gtc aag agc ttc aac agg aat gag tgt tag                            705
Val Val Lys Ser Phe Asn Arg Asn Glu Cys
225                 230
```

<210> SEQ ID NO 94
<211> LENGTH: 234
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 94

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
                20                  25                  30

Val Ser Ala Gly Asp Arg Val Thr Ile Thr Cys Lys Ala Ser Gln Ser
            35                  40                  45

Val Ser Asn Asp Val Ala Trp Tyr Gln Gln Lys Pro Gly Gln Ser Pro
        50                  55                  60

Lys Val Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Thr Glu Gln
130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Val His Lys Thr Ser Ser Ser Pro
210                 215                 220

Val Val Lys Ser Phe Asn Arg Asn Glu Cys
225                 230
```

<210> SEQ ID NO 95
<211> LENGTH: 1386
<212> TYPE: DNA
<213> ORGANISM: Artificial Sequence
<220> FEATURE:
<223> OTHER INFORMATION: Description of Artificial Sequence: Synthetic
      KM5321-rIgG1 sequence
<220> FEATURE:
<221> NAME/KEY: CDS
<222> LOCATION: (1)..(1383)

<400> SEQUENCE: 95

```
atg gat tgg ctg tgg aac ttg cta ttc ctg atg gca gct gcc caa agt        48
```

```
Met Asp Trp Leu Trp Asn Leu Leu Phe Leu Met Ala Ala Ala Gln Ser
1               5                   10                  15 atc caa gca cag atc cag ttg gtg cag tct gga cct gag ctg aag aag        96
Ile Gln Ala Gln Ile Gln Leu Val Gln Ser Gly Pro Glu Leu Lys Lys
            20                  25                  30 cct gga gag aca gtc aag atc tcc tgc agg gct tct ggg tat acc ttc       144
Pro Gly Glu Thr Val Lys Ile Ser Cys Arg Ala Ser Gly Tyr Thr Phe
                35                  40                  45 aca aac tat gga atg aac tgg gtg aag cag gct cca gga aag ggt tta       192
Thr Asn Tyr Gly Met Asn Trp Val Lys Gln Ala Pro Gly Lys Gly Leu
        50                  55                  60 aag tgg atg ggc tgg ata aac acc aac act gga gag cca act tat act       240
Lys Trp Met Gly Trp Ile Asn Thr Asn Thr Gly Glu Pro Thr Tyr Thr
65              70                  75                  80 gaa gag ttc aag gga cgg ttt gcc ttc tct ttg gag acc tct gcc act       288
Glu Glu Phe Lys Gly Arg Phe Ala Phe Ser Leu Glu Thr Ser Ala Thr
                85                  90                  95 act gcc tat ttg cag atc aac gac ctc aaa aat gag gac acg gct aca       336
Thr Ala Tyr Leu Gln Ile Asn Asp Leu Lys Asn Glu Asp Thr Ala Thr
            100                 105                 110 tat ttc tgt gca aga gat gag gga tgg ttt gtt tac tgg ggc caa ggg       384
Tyr Phe Cys Ala Arg Asp Glu Gly Trp Phe Val Tyr Trp Gly Gln Gly
        115                 120                 125 act ctg atc act gtc tct gca gct gaa aca aca gcc ccg tct gtc tat       432
Thr Leu Ile Thr Val Ser Ala Ala Glu Thr Thr Ala Pro Ser Val Tyr
130                 135                 140 cca ctg gct cct gga act gct ctc aaa agt aac tcc atg gtg acc ctg       480
Pro Leu Ala Pro Gly Thr Ala Leu Lys Ser Asn Ser Met Val Thr Leu
145                 150                 155                 160 gga tgc ctg gtc aag ggc tat ttc cct gag cca gtc acc gtg acc tgg       528
Gly Cys Leu Val Lys Gly Tyr Phe Pro Glu Pro Val Thr Val Thr Trp
                165                 170                 175 aac tct gga gcc ctg tcc agc ggt gtg cac acc ttc cca gct gtc ctg       576
Asn Ser Gly Ala Leu Ser Ser Gly Val His Thr Phe Pro Ala Val Leu
            180                 185                 190 cag tct ggg ctc tac act ctc acc agc tca gtg act gta ccc tcc agc       624
Gln Ser Gly Leu Tyr Thr Leu Thr Ser Ser Val Thr Val Pro Ser Ser
        195                 200                 205 acc tgg ccc agc cag acc gtc acc tgc aac gta gcc cac ccg gcc agc       672
Thr Trp Pro Ser Gln Thr Val Thr Cys Asn Val Ala His Pro Ala Ser
210                 215                 220 agc acc aag gtg gac aag aaa att gtg ccc aga aac tgt gga ggt gat       720
Ser Thr Lys Val Asp Lys Lys Ile Val Pro Arg Asn Cys Gly Gly Asp
225                 230                 235                 240 tgc aag cct tgt ata tgt aca ggc tca gaa gta tca tct gtc ttc atc       768
Cys Lys Pro Cys Ile Cys Thr Gly Ser Glu Val Ser Ser Val Phe Ile
                245                 250                 255 ttc ccc cca aag ccc aaa gat gtg ctc acc atc act ctg act cct aag       816
Phe Pro Pro Lys Pro Lys Asp Val Leu Thr Ile Thr Leu Thr Pro Lys
            260                 265                 270 gtc acg tgt gtt gtg gta gac att agc cag gac gat ccc gag gtc cat       864
Val Thr Cys Val Val Val Asp Ile Ser Gln Asp Asp Pro Glu Val His
        275                 280                 285 ttc agc tgg ttt gta gat gac gtg gaa gtc cac aca gct cag act cga       912
Phe Ser Trp Phe Val Asp Asp Val Glu Val His Thr Ala Gln Thr Arg
290                 295                 300 cca cca gag gag cag ttc aac agc act ttc cgc tca gtc agt gaa ctc       960
Pro Pro Glu Glu Gln Phe Asn Ser Thr Phe Arg Ser Val Ser Glu Leu
305                 310                 315                 320
```

```
ccc atc ctg cac cag gac tgg ctc aat ggc agg acg ttc aga tgc aag    1008
Pro Ile Leu His Gln Asp Trp Leu Asn Gly Arg Thr Phe Arg Cys Lys
            325                 330                 335 gtc acc agt gca gct ttc cca tcc ccc atc gag aaa acc atc tcc aaa    1056
Val Thr Ser Ala Ala Phe Pro Ser Pro Ile Glu Lys Thr Ile Ser Lys
            340                 345                 350 ccc gaa ggc aga aca caa gtt ccg cat gta tac acc atg tca cct acc    1104
Pro Glu Gly Arg Thr Gln Val Pro His Val Tyr Thr Met Ser Pro Thr
            355                 360                 365 aag gaa gag atg acc cag aat gaa gtc agt atc acc tgc atg gta aaa    1152
Lys Glu Glu Met Thr Gln Asn Glu Val Ser Ile Thr Cys Met Val Lys
            370                 375                 380 ggc ttc tat ccc cca gac att tat gtg gag tgg cag atg aac ggg cag    1200
Gly Phe Tyr Pro Pro Asp Ile Tyr Val Glu Trp Gln Met Asn Gly Gln
385                 390                 395                 400 cca cag gaa aac tac aag aac act cca cct acg atg gac aca gat ggg    1248
Pro Gln Glu Asn Tyr Lys Asn Thr Pro Pro Thr Met Asp Thr Asp Gly
                405                 410                 415 agt tac ttc ctc tac agc aag ctc aat gtg aag aag gaa aaa tgg cag    1296
Ser Tyr Phe Leu Tyr Ser Lys Leu Asn Val Lys Lys Glu Lys Trp Gln
                420                 425                 430 cag gga aac acg ttc acg tgt tct gtg ctg cat gaa ggc ctg cac aac    1344
Gln Gly Asn Thr Phe Thr Cys Ser Val Leu His Glu Gly Leu His Asn
            435                 440                 445 cac cat act gag aag agt ctc tcc cac tct ccg ggt aaa tga              1386
His His Thr Glu Lys Ser Leu Ser His Ser Pro Gly Lys
    450                 455                 460
```

<210> SEQ ID NO 96
<211> LENGTH: 461
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 96

```
Met Asp Trp Leu Trp Asn Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Arg Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Ala Phe Ser Leu Glu Thr Ser Ala Thr
                85                  90                  95

Thr Ala Tyr Leu Gln Ile Asn Asp Leu Lys Asn Glu Asp Thr Ala Thr
            100                 105                 110

Tyr Phe Cys Ala Arg Asp Glu Gly Trp Phe Val Tyr Trp Gly Gln Gly
        115                 120                 125

Thr Leu Ile Thr Val Ser Ala Ala Glu Thr Thr Ala Pro Ser Val Tyr
    130                 135                 140

Pro Leu Ala Pro Gly Thr Ala Leu Lys Ser Asn Ser Met Val Thr Leu
145                 150                 155                 160

Gly Cys Leu Val Lys Gly Tyr Phe Pro Glu Pro Val Thr Val Thr Trp
                165                 170                 175
```

```
Asn Ser Gly Ala Leu Ser Ser Gly Val His Thr Phe Pro Ala Val Leu
            180                 185                 190

Gln Ser Gly Leu Tyr Thr Leu Thr Ser Ser Val Thr Val Pro Ser Ser
            195                 200                 205

Thr Trp Pro Ser Gln Thr Val Thr Cys Asn Val Ala His Pro Ala Ser
210                 215                 220

Ser Thr Lys Val Asp Lys Lys Ile Val Pro Arg Asn Cys Gly Gly Asp
225                 230                 235                 240

Cys Lys Pro Cys Ile Cys Thr Gly Ser Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Asp Ile Ser Gln Asp Asp Pro Glu Val His
            275                 280                 285

Phe Ser Trp Phe Val Asp Asp Val Glu Val His Thr Ala Gln Thr Arg
290                 295                 300

Pro Pro Glu Glu Gln Phe Asn Ser Thr Phe Arg Ser Val Ser Glu Leu
305                 310                 315                 320

Pro Ile Leu His Gln Asp Trp Leu Asn Gly Arg Thr Phe Arg Cys Lys
                325                 330                 335

Val Thr Ser Ala Ala Phe Pro Ser Pro Ile Glu Lys Thr Ile Ser Lys
            340                 345                 350

Pro Glu Gly Arg Thr Gln Val Pro His Val Tyr Thr Met Ser Pro Thr
            355                 360                 365

Lys Glu Glu Met Thr Gln Asn Glu Val Ser Ile Thr Cys Met Val Lys
370                 375                 380

Gly Phe Tyr Pro Pro Asp Ile Tyr Val Glu Trp Gln Met Asn Gly Gln
385                 390                 395                 400

Pro Gln Glu Asn Tyr Lys Asn Thr Pro Pro Thr Met Asp Thr Asp Gly
                405                 410                 415

Ser Tyr Phe Leu Tyr Ser Lys Leu Asn Val Lys Lys Glu Lys Trp Gln
            420                 425                 430

Gln Gly Asn Thr Phe Thr Cys Ser Val Leu His Glu Gly Leu His Asn
            435                 440                 445

His His Thr Glu Lys Ser Leu Ser His Ser Pro Gly Lys
    450                 455                 460

<210> SEQ ID NO 97
<211> LENGTH: 705
<212> TYPE: DNA
<213> ORGANISM: Artificial Sequence
<220> FEATURE:
<223> OTHER INFORMATION: Description of Artificial Sequence: Synthetic
      KM5321-r_kappa sequence
<220> FEATURE:
<221> NAME/KEY: CDS
<222> LOCATION: (1)..(702)

<400> SEQUENCE: 97 atg ctc tca cta gct cct ctc ctc agc ctt ctt ctc ctc tgt gtc tct     48
Met Leu Ser Leu Ala Pro Leu Leu Ser Leu Leu Leu Leu Cys Val Ser
1               5                   10                  15 gat tct agg gca gaa aca act gtg acc cag tct cca gca tcc ctg tcc     96
Asp Ser Arg Ala Glu Thr Thr Val Thr Gln Ser Pro Ala Ser Leu Ser
                20                  25                  30 gtg gct aca gga gaa aaa gtc act atc aga tgc ata acc agt act gat    144
Val Ala Thr Gly Glu Lys Val Thr Ile Arg Cys Ile Thr Ser Thr Asp
```

```
att gat gat gat atg aac tgg tac caa cag aag cca ggg gaa cct cct     192
Ile Asp Asp Asp Met Asn Trp Tyr Gln Gln Lys Pro Gly Glu Pro Pro
 50                  55                  60 aag ctc ctt att tca gaa ggc aat act ctt cgt cct gga gtc cca tcc     240
Lys Leu Leu Ile Ser Glu Gly Asn Thr Leu Arg Pro Gly Val Pro Ser
 65                  70                  75                  80 cga ttc tcc agc agt ggc tat ggc aca gat ttt gtt ttt aca att gaa     288
Arg Phe Ser Ser Ser Gly Tyr Gly Thr Asp Phe Val Phe Thr Ile Glu
                 85                  90                  95 aac acg ctc tca gaa gat gtt gca gat tac tac tgt ttg caa act gat     336
Asn Thr Leu Ser Glu Asp Val Ala Asp Tyr Tyr Cys Leu Gln Thr Asp
                100                 105                 110 agc gtg cct ctc acg ttc ggt gct ggg acc aag ctg gag ctg aaa cgg     384
Ser Val Pro Leu Thr Phe Gly Ala Gly Thr Lys Leu Glu Leu Lys Arg
                115                 120                 125 gct gat gcg gca cca act gta tct atc ttc cca cca tcc acg gaa cag     432
Ala Asp Ala Ala Pro Thr Val Ser Ile Phe Pro Pro Ser Thr Glu Gln
130                 135                 140 tta gca act gga ggt gcc tca gtc gtg tgc ctc atg aac aac ttc tat     480
Leu Ala Thr Gly Gly Ala Ser Val Val Cys Leu Met Asn Asn Phe Tyr
145                 150                 155                 160 ccc aga gac atc agt gtc aag tgg aag att gat ggc act gaa cga cga     528
Pro Arg Asp Ile Ser Val Lys Trp Lys Ile Asp Gly Thr Glu Arg Arg
                165                 170                 175 gat ggt gtc ctg gac agt gtt act gat cag gac agc aaa gac agc acg     576
Asp Gly Val Leu Asp Ser Val Thr Asp Gln Asp Ser Lys Asp Ser Thr
                180                 185                 190 tac agc atg agc agc acc ctc tcg ttg acc aag gct gac tat gaa agt     624
Tyr Ser Met Ser Ser Thr Leu Ser Leu Thr Lys Ala Asp Tyr Glu Ser
                195                 200                 205 cat aac ctc tat acc tgt gag gtt gtt cat aag aca tca tcc tca ccc     672
His Asn Leu Tyr Thr Cys Glu Val Val His Lys Thr Ser Ser Ser Pro
210                 215                 220 gtc gtc aag agc ttc aac agg aat gag tgt tag                         705
Val Val Lys Ser Phe Asn Arg Asn Glu Cys
225                 230
```

<210> SEQ ID NO 98
<211> LENGTH: 234
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 98

```
Met Leu Ser Leu Ala Pro Leu Leu Ser Leu Leu Leu Leu Cys Val Ser
 1               5                  10                  15

Asp Ser Arg Ala Glu Thr Thr Val Thr Gln Ser Pro Ala Ser Leu Ser
                20                  25                  30

Val Ala Thr Gly Glu Lys Val Thr Ile Arg Cys Ile Thr Ser Thr Asp
                35                  40                  45

Ile Asp Asp Asp Met Asn Trp Tyr Gln Gln Lys Pro Gly Glu Pro Pro
 50                  55                  60

Lys Leu Leu Ile Ser Glu Gly Asn Thr Leu Arg Pro Gly Val Pro Ser
 65                  70                  75                  80

Arg Phe Ser Ser Ser Gly Tyr Gly Thr Asp Phe Val Phe Thr Ile Glu
                 85                  90                  95
```

```
Asn Thr Leu Ser Glu Asp Val Ala Asp Tyr Tyr Cys Leu Gln Thr Asp
            100                 105                 110

Ser Val Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Thr Glu Gln
    130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Val His Lys Thr Ser Ser Ser Pro
    210                 215                 220

Val Val Lys Ser Phe Asn Arg Asn Glu Cys
225                 230
```

```
<210> SEQ ID NO 99
<211> LENGTH: 1896
<212> TYPE: DNA
<213> ORGANISM: Artificial Sequence
<220> FEATURE:
<223> OTHER INFORMATION: Description of Artificial Sequence: Synthetic
      hGas6-delta sequence
<220> FEATURE:
<221> NAME/KEY: CDS
<222> LOCATION: (1)..(1893)

<400> SEQUENCE: 99
```

```
atg gcc cct tcg ctc tcg ccc ggg ccc gcc gcc ctg cgc cgc gcg ccg      48
Met Ala Pro Ser Leu Ser Pro Gly Pro Ala Ala Leu Arg Arg Ala Pro
1               5                   10                  15 cag ctg ctg ctg ctg ctg ctg gcc gcg gag tgc gcg ctt gcc tac tta      96
Gln Leu Leu Leu Leu Leu Leu Ala Ala Glu Cys Ala Leu Ala Tyr Leu
                20                  25                  30 gac tgc atc aac aag tat ggg tct ccg tac acc aaa aac tca ggc ttc     144
Asp Cys Ile Asn Lys Tyr Gly Ser Pro Tyr Thr Lys Asn Ser Gly Phe
            35                  40                  45 gcc acc tgc gtg caa aac ctg cct gac cag tgc acg ccc aac ccc tgc     192
Ala Thr Cys Val Gln Asn Leu Pro Asp Gln Cys Thr Pro Asn Pro Cys
        50                  55                  60 gat agg aag ggg acc caa gcc tgc cag gac ctc atg ggc aac ttc ttc     240
Asp Arg Lys Gly Thr Gln Ala Cys Gln Asp Leu Met Gly Asn Phe Phe
65                  70                  75                  80 tgc ctg tgt aaa gct ggc tgg ggg ggc cgg ctc tgc gac aaa gat gtc     288
Cys Leu Cys Lys Ala Gly Trp Gly Gly Arg Leu Cys Asp Lys Asp Val
                85                  90                  95 aac gaa tgc agc cag gag aac ggg ggc tgc ctc cag atc tgc cac aac     336
Asn Glu Cys Ser Gln Glu Asn Gly Gly Cys Leu Gln Ile Cys His Asn
            100                 105                 110 aag ccg ggt agc ttc cac tgt tcc tgc cac agc ggc ttc gag ctc tcc     384
Lys Pro Gly Ser Phe His Cys Ser Cys His Ser Gly Phe Glu Leu Ser
        115                 120                 125 tct gat ggc agg acc tgc caa gac ata gac gag tgc gca gac tcg gag     432
Ser Asp Gly Arg Thr Cys Gln Asp Ile Asp Glu Cys Ala Asp Ser Glu
    130                 135                 140 gcc tgc ggg gag gcg cgc tgc aag aac ctg ccc ggc tcc tac tcc tgc     480
Ala Cys Gly Glu Ala Arg Cys Lys Asn Leu Pro Gly Ser Tyr Ser Cys
```

-continued

| | |
|---|---|
| ctc tgt gac gag ggc ttt gcg tac agc tcc cag gag aag gct tgc cga<br>Leu Cys Asp Glu Gly Phe Ala Tyr Ser Ser Gln Glu Lys Ala Cys Arg<br>145                                        150                                    155                                    160 | 528 |
| gat gtg gac gag tgt ctg cag ggc cgc tgt gag cag gtc tgc gtg aac<br>Asp Val Asp Glu Cys Leu Gln Gly Arg Cys Glu Gln Val Cys Val Asn<br>               180                                      185                                    190 | 576 |
| tcc cca ggg agc tac acc tgc cac tgt gac ggg cgt ggg ggc ctc aag<br>Ser Pro Gly Ser Tyr Thr Cys His Cys Asp Gly Arg Gly Gly Leu Lys<br>                     195                                      200                                  205 | 624 |
| ctg tcc cag gac atg gac acc tgt gag gac atc ttg ccg tgc gtg ccc<br>Leu Ser Gln Asp Met Asp Thr Cys Glu Asp Ile Leu Pro Cys Val Pro<br>210                                        215                                    220 | 672 |
| ttc agc gtg gcc aag agt gtg aag tcc ttg tac ctg ggc cgg atg ttc<br>Phe Ser Val Ala Lys Ser Val Lys Ser Leu Tyr Leu Gly Arg Met Phe<br>225                                        230                                    235                                    240 | 720 |
| agt ggg acc ccc gtg atc cga ctg cgc ttc aag agg ctg cag ccc acc<br>Ser Gly Thr Pro Val Ile Arg Leu Arg Phe Lys Arg Leu Gln Pro Thr<br>               245                                      250                                    255 | 768 |
| agg ctg gta gct gag ttt gac ttc cgg acc ttt gac ccc gag ggc atc<br>Arg Leu Val Ala Glu Phe Asp Phe Arg Thr Phe Asp Pro Glu Gly Ile<br>                     260                                      265                                  270 | 816 |
| ctc ctc ttt gcc gga ggc cac cag gac agc acc tgg atc gtg ctg gcc<br>Leu Leu Phe Ala Gly Gly His Gln Asp Ser Thr Trp Ile Val Leu Ala<br>               275                                      280                                    285 | 864 |
| ctg aga gcc ggc cgg ctg gag ctg cag ctg cgc tac aac ggt gtc ggc<br>Leu Arg Ala Gly Arg Leu Glu Leu Gln Leu Arg Tyr Asn Gly Val Gly<br>290                                        295                                    300 | 912 |
| cgt gtc acc agc agc ggc ccg gtc atc aac cat ggc atg tgg cag aca<br>Arg Val Thr Ser Ser Gly Pro Val Ile Asn His Gly Met Trp Gln Thr<br>305                                        310                                    315                                  320 | 960 |
| atc tct gtt gag gag ctg gcg cgg aat ctg gtc atc aag gtc aac agg<br>Ile Ser Val Glu Glu Leu Ala Arg Asn Leu Val Ile Lys Val Asn Arg<br>               325                                      330                                    335 | 1008 |
| gat gct gtc atg aaa atc gcg gtg gcc ggg gac ttg ttc caa ccg gag<br>Asp Ala Val Met Lys Ile Ala Val Ala Gly Asp Leu Phe Gln Pro Glu<br>                     340                                      345                                  350 | 1056 |
| cga gga ctg tat cat ctg aac ctg acc gtg gga ggt att ccc ttc cat<br>Arg Gly Leu Tyr His Leu Asn Leu Thr Val Gly Gly Ile Pro Phe His<br>               355                                      360                                    365 | 1104 |
| gag aag gac ctc gtg cag cct ata aac cct cgt ctg gat ggc tgc atg<br>Glu Lys Asp Leu Val Gln Pro Ile Asn Pro Arg Leu Asp Gly Cys Met<br>                     370                                      375                                  380 | 1152 |
| agg agc tgg aac tgg ctg aac gga gaa gac acc acc atc cag gaa acg<br>Arg Ser Trp Asn Trp Leu Asn Gly Glu Asp Thr Thr Ile Gln Glu Thr<br>385                                        390                                    395                                  400 | 1200 |
| gtg aaa gtg aac acg agg atg cag tgc ttc tcg gtg acg gag aga ggc<br>Val Lys Val Asn Thr Arg Met Gln Cys Phe Ser Val Thr Glu Arg Gly<br>                            405                                    410                                    415 | 1248 |
| tct ttc tac ccc ggg agc ggc ttc gcc ttc tac agc ctg gac tac atg<br>Ser Phe Tyr Pro Gly Ser Gly Phe Ala Phe Tyr Ser Leu Asp Tyr Met<br>                     420                                      425                                  430 | 1296 |
| cgg acc cct ctg gac gtc ggg act gaa tca acc tgg gaa gta gaa gtc<br>Arg Thr Pro Leu Asp Val Gly Thr Glu Ser Thr Trp Glu Val Glu Val<br>               435                                      440                                  445 | 1344 |
| gtg gct cac atc cgc cca gcc gca gac aca ggc gtg ctg ttt gcg ctc<br>Val Ala His Ile Arg Pro Ala Ala Asp Thr Gly Val Leu Phe Ala Leu<br>               450                                      455                                  460 | 1392 |
| tgg gcc ccc gac ctc cgt gcc gtg cct ctc tct gtg gca ctg gta gac | 1440 |

```
Trp Ala Pro Asp Leu Arg Ala Val Pro Leu Ser Val Ala Leu Val Asp
465                 470                 475                 480 tat cac tcc acg aag aaa ctc aag aag cag ctg gtg gtc ctg gcc gtg         1488
Tyr His Ser Thr Lys Lys Leu Lys Lys Gln Leu Val Val Leu Ala Val
                485                 490                 495 gag cat acg gcc ttg gcc cta atg gag atc aag gtc tgc gac ggc caa         1536
Glu His Thr Ala Leu Ala Leu Met Glu Ile Lys Val Cys Asp Gly Gln
            500                 505                 510 gag cac gtg gtc acc gtc tcg ctg agg gac ggt gag gcc acc ctg gag         1584
Glu His Val Val Thr Val Ser Leu Arg Asp Gly Glu Ala Thr Leu Glu
        515                 520                 525 gtg gac ggc acc agg ggc cag agc gag gtg agc gcc gcg cag ctg cag         1632
Val Asp Gly Thr Arg Gly Gln Ser Glu Val Ser Ala Ala Gln Leu Gln
    530                 535                 540 gag agg ctg gcc gtg ctc gag agg cac ctg cgg agc ccc gtg ctc acc         1680
Glu Arg Leu Ala Val Leu Glu Arg His Leu Arg Ser Pro Val Leu Thr
545                 550                 555                 560 ttt gct ggc ggc ctg cca gat gtg ccg gtg act tca gcg cca gtc acc         1728
Phe Ala Gly Gly Leu Pro Asp Val Pro Val Thr Ser Ala Pro Val Thr
                565                 570                 575 gcg ttc tac cgc ggc tgc atg aca ctg gag gtc aac cgg agg ctg ctg         1776
Ala Phe Tyr Arg Gly Cys Met Thr Leu Glu Val Asn Arg Arg Leu Leu
            580                 585                 590 gac ctg gac gag gcg gcg tac aag cac agc gac atc acg gcc cac tcc         1824
Asp Leu Asp Glu Ala Ala Tyr Lys His Ser Asp Ile Thr Ala His Ser
        595                 600                 605 tgc ccc ccc gtg gag ccc gcc gca gcc gac tac aag gac gac gac gac         1872
Cys Pro Pro Val Glu Pro Ala Ala Ala Asp Tyr Lys Asp Asp Asp Asp
    610                 615                 620 aag cac cac cac cac cac cac tag                                          1896
Lys His His His His His His
625             630

<210> SEQ ID NO 100
<211> LENGTH: 631
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 100

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Tyr Leu
            20                  25                  30

Asp Cys Ile Asn Lys Tyr Gly Ser Pro Tyr Thr Lys Asn Ser Gly Phe
        35                  40                  45

Ala Thr Cys Val Gln Asn Leu Pro Asp Gln Cys Thr Pro Asn Pro Cys
    50                  55                  60

Asp Arg Lys Gly Thr Gln Ala Cys Gln Asp Leu Met Gly Asn Phe Phe
65                  70                  75                  80

Cys Leu Cys Lys Ala Gly Trp Gly Gly Arg Leu Cys Asp Lys Asp Val
                85                  90                  95

Asn Glu Cys Ser Gln Glu Asn Gly Gly Cys Leu Gln Ile Cys His Asn
            100                 105                 110

Lys Pro Gly Ser Phe His Cys Ser Cys His Ser Gly Phe Glu Leu Ser
        115                 120                 125

Ser Asp Gly Arg Thr Cys Gln Asp Ile Asp Glu Cys Ala Asp Ser Glu
```

```
                    130                 135                 140
Ala Cys Gly Glu Ala Arg Cys Lys Asn Leu Pro Gly Ser Tyr Ser Cys
145                 150                 155                 160

Leu Cys Asp Glu Gly Phe Ala Tyr Ser Ser Gln Glu Lys Ala Cys Arg
                    165                 170                 175

Asp Val Asp Glu Cys Leu Gln Gly Arg Cys Glu Gln Val Cys Val Asn
                    180                 185                 190

Ser Pro Gly Ser Tyr Thr Cys His Cys Asp Gly Arg Gly Gly Leu Lys
                    195                 200                 205

Leu Ser Gln Asp Met Asp Thr Cys Glu Asp Ile Leu Pro Cys Val Pro
                    210                 215                 220

Phe Ser Val Ala Lys Ser Val Lys Ser Leu Tyr Leu Gly Arg Met Phe
225                 230                 235                 240

Ser Gly Thr Pro Val Ile Arg Leu Arg Phe Lys Arg Leu Gln Pro Thr
                    245                 250                 255

Arg Leu Val Ala Glu Phe Asp Phe Arg Thr Phe Asp Pro Glu Gly Ile
                    260                 265                 270

Leu Leu Phe Ala Gly Gly His Gln Asp Ser Thr Trp Ile Val Leu Ala
                    275                 280                 285

Leu Arg Ala Gly Arg Leu Glu Leu Gln Leu Arg Tyr Asn Gly Val Gly
                    290                 295                 300

Arg Val Thr Ser Ser Gly Pro Val Ile Asn His Gly Met Trp Gln Thr
305                 310                 315                 320

Ile Ser Val Glu Glu Leu Ala Arg Asn Leu Val Ile Lys Val Asn Arg
                    325                 330                 335

Asp Ala Val Met Lys Ile Ala Val Ala Gly Asp Leu Phe Gln Pro Glu
                    340                 345                 350

Arg Gly Leu Tyr His Leu Asn Leu Thr Val Gly Gly Ile Pro Phe His
                    355                 360                 365

Glu Lys Asp Leu Val Gln Pro Ile Asn Pro Arg Leu Asp Gly Cys Met
                    370                 375                 380

Arg Ser Trp Asn Trp Leu Asn Gly Glu Asp Thr Thr Ile Gln Glu Thr
385                 390                 395                 400

Val Lys Val Asn Thr Arg Met Gln Cys Phe Ser Val Thr Glu Arg Gly
                    405                 410                 415

Ser Phe Tyr Pro Gly Ser Gly Phe Ala Phe Tyr Ser Leu Asp Tyr Met
                    420                 425                 430

Arg Thr Pro Leu Asp Val Gly Thr Glu Ser Thr Trp Glu Val Glu Val
                    435                 440                 445

Val Ala His Ile Arg Pro Ala Ala Asp Thr Gly Val Leu Phe Ala Leu
                    450                 455                 460

Trp Ala Pro Asp Leu Arg Ala Val Pro Leu Ser Val Ala Leu Val Asp
465                 470                 475                 480

Tyr His Ser Thr Lys Lys Leu Lys Lys Gln Leu Val Val Leu Ala Val
                    485                 490                 495

Glu His Thr Ala Leu Ala Leu Met Glu Ile Lys Val Cys Asp Gly Gln
                    500                 505                 510

Glu His Val Val Thr Val Ser Leu Arg Asp Gly Glu Ala Thr Leu Glu
                    515                 520                 525

Val Asp Gly Thr Arg Gly Gln Ser Glu Val Ser Ala Ala Gln Leu Gln
                    530                 535                 540

Glu Arg Leu Ala Val Leu Glu Arg His Leu Arg Ser Pro Val Leu Thr
545                 550                 555                 560
```

```
Phe Ala Gly Gly Leu Pro Asp Val Pro Val Thr Ser Ala Pro Val Thr
                565                 570                 575

Ala Phe Tyr Arg Gly Cys Met Thr Leu Glu Val Asn Arg Arg Leu Leu
            580                 585                 590

Asp Leu Asp Glu Ala Ala Tyr Lys His Ser Asp Ile Thr Ala His Ser
        595                 600                 605

Cys Pro Pro Val Glu Pro Ala Ala Ala Asp Tyr Lys Asp Asp Asp Asp
    610                 615                 620

Lys His His His His His His
625                 630

<210> SEQ ID NO 101
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer 30

<400> SEQUENCE: 101
gagggcggcg gccaccaggc tggtagc                                          27

<210> SEQ ID NO 102
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer 31

<400> SEQUENCE: 102
gtggccgccg ccctcttgaa gcgcagtcg                                        29

<210> SEQ ID NO 103
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV0 sequence
<220> FEATURE:
<221> NAME/KEY: CDS
<222> LOCATION: (1)..(378)

<400> SEQUENCE: 103 atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gat gtt gtc atg act cag tca ccc gac tcc ttg gca gtt      96
Ser Ser Ser Asp Val Val Met Thr Gln Ser Pro Asp Ser Leu Ala Val
            20                  25                  30 tca ttg ggg gaa cgt gtg act att aat tgt aaa gcc tct cag tct gta     144
Ser Leu Gly Glu Arg Val Thr Ile Asn Cys Lys Ala Ser Gln Ser Val
        35                  40                  45 agc aac gat gtg gct tgg tat cag cag aag cca ggc caa tcc ccc aag     192
Ser Asn Asp Val Ala Trp Tyr Gln Gln Lys Pro Gly Gln Ser Pro Lys
    50                  55                  60 ctc ttg atc tac tac gcc tct aac cgg tat act gga gtg cct gac agg     240
Leu Leu Ile Tyr Tyr Ala Ser Asn Arg Tyr Thr Gly Val Pro Asp Arg
65                  70                  75                  80 ttt tct ggt tcc gga agc ggg act gat ttt aca ctt acc att agc agc     288
Phe Ser Gly Ser Gly Ser Gly Thr Asp Phe Thr Leu Thr Ile Ser Ser
                85                  90                  95
```

```
ttg cag gct gag gat gtg gcc gtc tat tat tgt cag cag gac tac tct      336
Leu Gln Ala Glu Asp Val Ala Val Tyr Tyr Cys Gln Gln Asp Tyr Ser
            100                 105                 110 tca cct tgg aca ttt ggc cag gga acc aag ttg gaa att aag              378
Ser Pro Trp Thr Phe Gly Gln Gly Thr Lys Leu Glu Ile Lys
        115                 120                 125

<210> SEQ ID NO 104
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 104

Met Lys Leu Pro Val Arg Leu Leu Val Leu Met Phe Trp Ile Pro Ala
1               5                   10                  15

Ser Ser Ser Asp Val Val Met Thr Gln Ser Pro Asp Ser Leu Ala Val
            20                  25                  30

Ser Leu Gly Glu Arg Val Thr Ile Asn Cys Lys Ala Ser Gln Ser Val
        35                  40                  45

Ser Asn Asp Val Ala Trp Tyr Gln Gln Lys Pro Gly Gln Ser Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Ser Gly Thr Asp Phe Thr Leu Thr Ile Ser Ser
                85                  90                  95

Leu Gln Ala Glu Asp Val Ala Val Tyr Tyr Cys Gln Gln Asp Tyr Ser
            100                 105                 110

Ser Pro Trp Thr Phe Gly Gln Gly Thr Lys Leu Glu Ile Lys
        115                 120                 125

<210> SEQ ID NO 105
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV0 excluding
      signal sequence

<400> SEQUENCE: 105

Asp Val Val Met Thr Gln Ser Pro Asp Ser Leu Ala Val Ser Leu Gly
1               5                   10                  15

Glu Arg Val Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 106
```

```
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV1a sequence
<220> FEATURE:
<221> NAME/KEY: CDS
<222> LOCATION: (1)..(378)

<400> SEQUENCE: 106
```

| atg | aag | ctg | ccc | gtt | cgc | ctg | ctt | gtg | ctg | atg | ttc | tgg | atc | ccc | gcg | 48 |
|---|---|---|---|---|---|---|---|---|---|---|---|---|---|---|---|---|
| Met | Lys | Leu | Pro | Val | Arg | Leu | Leu | Val | Leu | Met | Phe | Trp | Ile | Pro | Ala | |
| 1 | | | | 5 | | | | | 10 | | | | | 15 | | |

| tcc | tcc | tcg | gat | gtg | gtg | atg | aca | caa | tct | cca | gac | tca | ctc | gcc | gtg | 96 |
|---|---|---|---|---|---|---|---|---|---|---|---|---|---|---|---|---|
| Ser | Ser | Ser | Asp | Val | Val | Met | Thr | Gln | Ser | Pro | Asp | Ser | Leu | Ala | Val | |
| | | | 20 | | | | | 25 | | | | | 30 | | | |

| agt | ctg | ggt | gag | cga | gtc | act | atc | aac | tgc | aag | gct | agc | caa | tcc | gtg | 144 |
|---|---|---|---|---|---|---|---|---|---|---|---|---|---|---|---|---|
| Ser | Leu | Gly | Glu | Arg | Val | Thr | Ile | Asn | Cys | Lys | Ala | Ser | Gln | Ser | Val | |
| | | 35 | | | | | 40 | | | | | 45 | | | | |

| agt | aat | gat | gta | gct | tgg | tac | cag | caa | aag | ccc | gga | cag | tcc | ccc | aaa | 192 |
|---|---|---|---|---|---|---|---|---|---|---|---|---|---|---|---|---|
| Ser | Asn | Asp | Val | Ala | Trp | Tyr | Gln | Gln | Lys | Pro | Gly | Gln | Ser | Pro | Lys | |
| 50 | | | | | 55 | | | | | 60 | | | | | | |

| ctt | ctg | att | tac | tac | gct | tct | aac | cgt | tat | aca | ggc | gtg | ccc | gat | cgc | 240 |
|---|---|---|---|---|---|---|---|---|---|---|---|---|---|---|---|---|
| Leu | Leu | Ile | Tyr | Tyr | Ala | Ser | Asn | Arg | Tyr | Thr | Gly | Val | Pro | Asp | Arg | |
| 65 | | | | 70 | | | | | 75 | | | | | 80 | | |

| ttc | tct | gga | tct | ggg | agc | ggg | act | gac | ttt | acc | ctc | aca | atc | tct | agc | 288 |
|---|---|---|---|---|---|---|---|---|---|---|---|---|---|---|---|---|
| Phe | Ser | Gly | Ser | Gly | Ser | Gly | Thr | Asp | Phe | Thr | Leu | Thr | Ile | Ser | Ser | |
| | | | | 85 | | | | | 90 | | | | | 95 | | |

| ctg | caa | gcc | gag | gac | gtt | gcc | gtc | tac | ttc | tgt | cag | cag | gat | tac | agc | 336 |
|---|---|---|---|---|---|---|---|---|---|---|---|---|---|---|---|---|
| Leu | Gln | Ala | Glu | Asp | Val | Ala | Val | Tyr | Phe | Cys | Gln | Gln | Asp | Tyr | Ser | |
| | | | 100 | | | | | 105 | | | | | 110 | | | |

| agc | cca | tgg | aca | ttt | ggt | cag | ggg | aca | aag | ttg | gag | att | aaa | | | 378 |
|---|---|---|---|---|---|---|---|---|---|---|---|---|---|---|---|---|
| Ser | Pro | Trp | Thr | Phe | Gly | Gln | Gly | Thr | Lys | Leu | Glu | Ile | Lys | | | |
| | | 115 | | | | 120 | | | | | 125 | | | | | |

```
<210> SEQ ID NO 107
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 107

Met Lys Leu Pro Val Arg Leu Leu Val Leu Met Phe Trp Ile Pro Ala
1               5                   10                  15

Ser Ser Ser Asp Val Val Met Thr Gln Ser Pro Asp Ser Leu Ala Val
            20                  25                  30

Ser Leu Gly Glu Arg Val Thr Ile Asn Cys Lys Ala Ser Gln Ser Val
        35                  40                  45

Ser Asn Asp Val Ala Trp Tyr Gln Gln Lys Pro Gly Gln Ser Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Ser Gly Thr Asp Phe Thr Leu Thr Ile Ser Ser
                85                  90                  95

Leu Gln Ala Glu Asp Val Ala Val Tyr Phe Cys Gln Gln Asp Tyr Ser
            100                 105                 110

Ser Pro Trp Thr Phe Gly Gln Gly Thr Lys Leu Glu Ile Lys
        115                 120                 125
```

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV1a excluding
      signal sequence

<400> SEQUENCE: 108

```
Asp Val Val Met Thr Gln Ser Pro Asp Ser Leu Ala Val Ser Leu Gly
1               5                   10                  15

Glu Arg Val Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln Asp Tyr Ser Ser Pro Trp
                85                  90                  95

Thr Phe Gly Gln Gly Thr Lys Leu Glu Ile Lys
            100                 105
```

<210> SEQ ID NO 109
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV1b sequence
<220> FEATURE:
<221> NAME/KEY: CDS
<222> LOCATION: (1)..(378)

<400> SEQUENCE: 109

```
atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gac gtc gtg atg aca caa tct cca gac tct ctt gcc gta      96
Ser Ser Ser Asp Val Val Met Thr Gln Ser Pro Asp Ser Leu Ala Val
            20                  25                  30 tca ctg ggt gag cgc gtg aca atc aac tgc aaa gcc agt cag tcc gtg     144
Ser Leu Gly Glu Arg Val Thr Ile Asn Cys Lys Ala Ser Gln Ser Val
        35                  40                  45 tcc aat gac gtt gcc tgg tat caa cag aaa cca ggg cag tca cca aaa     192
Ser Asn Asp Val Ala Trp Tyr Gln Gln Lys Pro Gly Gln Ser Pro Lys
50                  55                  60 ctg ctc atc tat tat gcc agt aat agg tac aca ggt gtg cca gac cga     240
Leu Leu Ile Tyr Tyr Ala Ser Asn Arg Tyr Thr Gly Val Pro Asp Arg
65                  70                  75                  80 ttc agc ggc tcc ggc tct ggt acc gac ttc acc ctc aca ata tca tcc     288
Phe Ser Gly Ser Gly Ser Gly Thr Asp Phe Thr Leu Thr Ile Ser Ser
                85                  90                  95 gtt cag gcc gag gac gtt gcc gtg tat tat tgc cag cag gat tac agc     336
Val Gln Ala Glu Asp Val Ala Val Tyr Tyr Cys Gln Gln Asp Tyr Ser
            100                 105                 110 tcc ccc tgg acc ttc ggg cag ggg aca aag ctc gaa atc aaa             378
Ser Pro Trp Thr Phe Gly Gln Gly Thr Lys Leu Glu Ile Lys
        115                 120                 125
```

<210> SEQ ID NO 110
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 110

Met Lys Leu Pro Val Arg Leu Leu Val Leu Met Phe Trp Ile Pro Ala
1               5                   10                  15

Ser Ser Ser Asp Val Val Met Thr Gln Ser Pro Asp Ser Leu Ala Val
            20                  25                  30

Ser Leu Gly Glu Arg Val Thr Ile Asn Cys Lys Ala Ser Gln Ser Val
        35                  40                  45

Ser Asn Asp Val Ala Trp Tyr Gln Gln Lys Pro Gly Gln Ser Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Ser Gly Thr Asp Phe Thr Leu Thr Ile Ser Ser
                85                  90                  95

Val Gln Ala Glu Asp Val Ala Val Tyr Tyr Cys Gln Gln Asp Tyr Ser
            100                 105                 110

Ser Pro Trp Thr Phe Gly Gln Gly Thr Lys Leu Glu Ile Lys
        115                 120                 125

<210> SEQ ID NO 111
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV1b excluding
      signal sequence

<400> SEQUENCE: 111

Asp Val Val Met Thr Gln Ser Pro Asp Ser Leu Ala Val Ser Leu Gly
1               5                   10                  15

Glu Arg Val Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Leu Thr Ile Ser Ser Val Gln Ala
65                  70                  75                  80

Glu Asp Val Ala Val Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 112
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV2a sequence
<220> FEATURE:
<221> NAME/KEY: CDS
<222> LOCATION: (1)..(378)

<400> SEQUENCE: 112

```
atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gac gtg gtg atg act cag tct ccc gat tct ctc gcc gtc      96
Ser Ser Ser Asp Val Val Met Thr Gln Ser Pro Asp Ser Leu Ala Val
                20                  25                  30 tcc ctg ggg gag cgg gta act atc aat tgc aag gct agc cag tca gtc      144
Ser Leu Gly Glu Arg Val Thr Ile Asn Cys Lys Ala Ser Gln Ser Val
        35                  40                  45 agt aac gat gta gcc tgg tac cag caa aag cca ggt cag tcc cct aag      192
Ser Asn Asp Val Ala Trp Tyr Gln Gln Lys Pro Gly Gln Ser Pro Lys
    50                  55                  60 ctc ttg ata tac tac gca tct aac cgt tac acc gga gta ccc gac cgc      240
Leu Leu Ile Tyr Tyr Ala Ser Asn Arg Tyr Thr Gly Val Pro Asp Arg
65                  70                  75                  80 ttc tcc ggg agc gga agt ggc acc gac ttc acc ctg acc atc agc tct      288
Phe Ser Gly Ser Gly Ser Gly Thr Asp Phe Thr Leu Thr Ile Ser Ser
                85                  90                  95 gtg cag gca gag gac gtt gct gtc tac ttt tgc cag cag gac tac agc      336
Val Gln Ala Glu Asp Val Ala Val Tyr Phe Cys Gln Gln Asp Tyr Ser
                100                 105                 110 tct cca tgg aca ttc gga caa ggc act aaa ctc gag att aaa              378
Ser Pro Trp Thr Phe Gly Gln Gly Thr Lys Leu Glu Ile Lys
        115                 120                 125
```

<210> SEQ ID NO 113
<211> LENGTH: 126
<212> TYPE: PRT
<213> ORGANISM: Artificial Sequence
<220> FEATURE:
<223> OTHER INFORMATION: Description of Artificial Sequence: Synthetic construct

<400> SEQUENCE: 113

```
Met Lys Leu Pro Val Arg Leu Leu Val Leu Met Phe Trp Ile Pro Ala
1               5                   10                  15

Ser Ser Ser Asp Val Val Met Thr Gln Ser Pro Asp Ser Leu Ala Val
                20                  25                  30

Ser Leu Gly Glu Arg Val Thr Ile Asn Cys Lys Ala Ser Gln Ser Val
        35                  40                  45

Ser Asn Asp Val Ala Trp Tyr Gln Gln Lys Pro Gly Gln Ser Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Ser Gly Thr Asp Phe Thr Leu Thr Ile Ser Ser
                85                  90                  95

Val Gln Ala Glu Asp Val Ala Val Tyr Phe Cys Gln Gln Asp Tyr Ser
                100                 105                 110

Ser Pro Trp Thr Phe Gly Gln Gly Thr Lys Leu Glu Ile Lys
        115                 120                 125
```

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic amino acid sequence of hzKM5320 LV2a excluding signal sequence

<400> SEQUENCE: 114

| Asp | Val | Val | Met | Thr | Gln | Ser | Pro | Asp | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Glu | Arg | Val | Thr | Ile | Asn | Cys | Lys | Ala | Ser | Gln | Ser | Val | Ser | Asn | Asp |
|---|---|---|---|---|---|---|---|---|---|---|---|---|---|---|---|
| | | | 20 | | | | | 25 | | | | | 30 | | |

| Val | Ala | Trp | Tyr | Gln | Gln | Lys | Pro | Gly | Gln | Ser | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Tyr | Ala | Ser | Asn | Arg | Tyr | Thr | Gly | Val | Pro | Asp | Arg | Phe | Ser | Gly |
|---|---|---|---|---|---|---|---|---|---|---|---|---|---|---|---|
| 50 | | | | | 55 | | | | | 60 | | | | | |

| Ser | Gly | Ser | Gly | Thr | Asp | Phe | Thr | Leu | Thr | Ile | Ser | Ser | Val | Gln | Ala |
|---|---|---|---|---|---|---|---|---|---|---|---|---|---|---|---|
| 65 | | | | 70 | | | | | 75 | | | | | 80 | |

| Glu | Asp | Val | Ala | Val | Tyr | Phe | Cys | Gln | Gln | Asp | Tyr | Ser | Ser | Pro | Trp |
|---|---|---|---|---|---|---|---|---|---|---|---|---|---|---|---|
| | | | 85 | | | | | 90 | | | | | 95 | | |

| Thr | Phe | Gly | Gln | Gly | Thr | Lys | Leu | Glu | Ile | Lys |
|---|---|---|---|---|---|---|---|---|---|---|
| | | | 100 | | | | | 105 | | |

<210> SEQ ID NO 115
<211> LENGTH: 378
<212> TYPE: DNA
<213> ORGANISM: Artificial Sequence
<220> FEATURE:
<223> OTHER INFORMATION: Description of Artificial Sequence: Synthetic hzKM5320 LV2b sequence
<220> FEATURE:
<221> NAME/KEY: CDS
<222> LOCATION: (1)..(378)

<400> SEQUENCE: 115

| atg | aag | ctg | ccc | gtt | cgc | ctg | ctt | gtg | ctg | atg | ttc | tgg | atc | ccc | gcg | 48 |
|---|---|---|---|---|---|---|---|---|---|---|---|---|---|---|---|---|
| Met | Lys | Leu | Pro | Val | Arg | Leu | Leu | Val | Leu | Met | Phe | Trp | Ile | Pro | Ala | |
| 1 | | | | 5 | | | | | 10 | | | | | 15 | | |

| tcc | tcc | tcg | gat | gtg | gtc | atg | aca | cag | agc | cca | gac | agc | ctc | gct | gtg | 96 |
|---|---|---|---|---|---|---|---|---|---|---|---|---|---|---|---|---|
| Ser | Ser | Ser | Asp | Val | Val | Met | Thr | Gln | Ser | Pro | Asp | Ser | Leu | Ala | Val | |
| | | | 20 | | | | | 25 | | | | | 30 | | | |

| agc | gcc | gga | gaa | agg | gtc | acc | att | aac | tgc | aag | gcc | tct | caa | agc | gtg | 144 |
|---|---|---|---|---|---|---|---|---|---|---|---|---|---|---|---|---|
| Ser | Ala | Gly | Glu | Arg | Val | Thr | Ile | Asn | Cys | Lys | Ala | Ser | Gln | Ser | Val | |
| | | 35 | | | | | 40 | | | | | 45 | | | | |

| agt | aat | gac | gtc | gcc | tgg | tat | caa | cag | aag | cct | ggt | caa | tcc | cca | aag | 192 |
|---|---|---|---|---|---|---|---|---|---|---|---|---|---|---|---|---|
| Ser | Asn | Asp | Val | Ala | Trp | Tyr | Gln | Gln | Lys | Pro | Gly | Gln | Ser | Pro | Lys | |
| 50 | | | | | 55 | | | | | 60 | | | | | | |

| ctg | ctc | ata | tac | tat | gct | agt | aat | cgg | tac | acc | ggc | gtg | cca | gac | cgc | 240 |
|---|---|---|---|---|---|---|---|---|---|---|---|---|---|---|---|---|
| Leu | Leu | Ile | Tyr | Tyr | Ala | Ser | Asn | Arg | Tyr | Thr | Gly | Val | Pro | Asp | Arg | |
| 65 | | | | 70 | | | | | 75 | | | | | 80 | | |

| ttc | tct | ggc | tca | ggg | agt | ggg | aca | gac | ttc | acc | ttt | act | atc | agc | agt | 288 |
|---|---|---|---|---|---|---|---|---|---|---|---|---|---|---|---|---|
| Phe | Ser | Gly | Ser | Gly | Ser | Gly | Thr | Asp | Phe | Thr | Phe | Thr | Ile | Ser | Ser | |
| | | | 85 | | | | | 90 | | | | | 95 | | | |

| ctg | cag | gct | gaa | gat | gtt | gcc | gtg | tat | tac | tgc | cag | cag | gac | tat | agt | 336 |
|---|---|---|---|---|---|---|---|---|---|---|---|---|---|---|---|---|
| Leu | Gln | Ala | Glu | Asp | Val | Ala | Val | Tyr | Tyr | Cys | Gln | Gln | Asp | Tyr | Ser | |
| | | | 100 | | | | | 105 | | | | | 110 | | | |

| agc | cct | tgg | acc | ttc | gga | cag | ggt | act | aag | ctt | gaa | atc | aag | | | 378 |
|---|---|---|---|---|---|---|---|---|---|---|---|---|---|---|---|---|
| Ser | Pro | Trp | Thr | Phe | Gly | Gln | Gly | Thr | Lys | Leu | Glu | Ile | Lys | | | |
| | | 115 | | | | | 120 | | | | | 125 | | | | |

<210> SEQ ID NO 116
<211> LENGTH: 126
<212> TYPE: PRT
<213> ORGANISM: Artificial Sequence
<220> FEATURE:
<223> OTHER INFORMATION: Description of Artificial Sequence: Synthetic construct -continued

<400> SEQUENCE: 116

Met Lys Leu Pro Val Arg Leu Leu Val Leu Met Phe Trp Ile Pro Ala
1               5                   10                  15

Ser Ser Ser Asp Val Val Met Thr Gln Ser Pro Asp Ser Leu Ala Val
            20                  25                  30

Ser Ala Gly Glu Arg Val Thr Ile Asn Cys Lys Ala Ser Gln Ser Val
        35                  40                  45

Ser Asn Asp Val Ala Trp Tyr Gln Gln Lys Pro Gly Gln Ser Pro Lys
    50                  55                  60

Leu Leu Ile Tyr Tyr Ala Ser Asn Arg Tyr Thr Gly Val Pro Asp Arg
65                  70                  75                  80

Phe Ser Gly Ser Gly Ser Gly Thr Asp Phe Thr Phe Thr Ile Ser Ser
                85                  90                  95

Leu Gln Ala Glu Asp Val Ala Val Tyr Tyr Cys Gln Gln Asp Tyr Ser
            100                 105                 110

Ser Pro Trp Thr Phe Gly Gln Gly Thr Lys Leu Glu Ile Lys
        115                 120                 125

<210> SEQ ID NO 117
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV2b excluding
      signal sequence

<400> SEQUENCE: 117

Asp Val Val Met Thr Gln Ser Pro Asp Ser Leu Ala Val Ser Ala Gly
1               5                   10                  15

Glu Arg Val Thr Ile Asn Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ser Gly
    50                  55                  60

Ser Gly Ser Gly Thr Asp Phe Thr Phe Thr Ile Ser Ser Leu Gln Ala
65                  70                  75                  80

Glu Asp Val Ala Val Tyr Tyr Cys Gln Gln Asp Tyr Ser Ser Pro Trp
                85                  90                  95

Thr Phe Gly Gln Gly Thr Lys Leu Glu Ile Lys
            100                 105

<210> SEQ ID NO 118
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV3 sequence
<220> FEATURE:
<221> NAME/KEY: CDS
<222> LOCATION: (1)..(378)

<400> SEQUENCE: 118 atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gac gtg gtg atg aca cag tct ccc gac tct ttg gca gtc      96
Ser Ser Ser Asp Val Val Met Thr Gln Ser Pro Asp Ser Leu Ala Val

```
                 20                  25                  30
agc ctg ggc gag cgg gtc act atc aat tgc aaa gca tct cag agc gta       144
Ser Leu Gly Glu Arg Val Thr Ile Asn Cys Lys Ala Ser Gln Ser Val
         35                  40                  45 tca aac gac gta gct tgg tac cag cag aaa cct ggc cag agc cct aaa       192
Ser Asn Asp Val Ala Trp Tyr Gln Gln Lys Pro Gly Gln Ser Pro Lys
 50                  55                  60 gta ttg atc tac tac gca agc aac cgc tat aca ggc gtg ccc gat cgc       240
Val Leu Ile Tyr Tyr Ala Ser Asn Arg Tyr Thr Gly Val Pro Asp Arg
 65                  70                  75                  80 ttc tcc ggg tct ggc tct ggt aca gat ttt aca ttt acc att agt agc       288
Phe Ser Gly Ser Gly Ser Gly Thr Asp Phe Thr Phe Thr Ile Ser Ser
             85                   90                  95 ctc cag gcc gaa gac gtc gcc gtc tac ttc tgc cag cag gac tat agt       336
Leu Gln Ala Glu Asp Val Ala Val Tyr Phe Cys Gln Gln Asp Tyr Ser
            100                  105                  110 agc cct tgg aca ttc ggg cag gga aca aaa ctc gag atc aaa               378
Ser Pro Trp Thr Phe Gly Gln Gly Thr Lys Leu Glu Ile Lys
            115                  120                  125
```

<210> SEQ ID NO 119
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 119

```
Met Lys Leu Pro Val Arg Leu Leu Val Leu Met Phe Trp Ile Pro Ala
 1               5                  10                  15

Ser Ser Ser Asp Val Val Met Thr Gln Ser Pro Asp Ser Leu Ala Val
             20                  25                  30

Ser Leu Gly Glu Arg Val Thr Ile Asn Cys Lys Ala Ser Gln Ser Val
         35                  40                  45

Ser Asn Asp Val Ala Trp Tyr Gln Gln Lys Pro Gly Gln Ser Pro Lys
 50                  55                  60

Val Leu Ile Tyr Tyr Ala Ser Asn Arg Tyr Thr Gly Val Pro Asp Arg
 65                  70                  75                  80

Phe Ser Gly Ser Gly Ser Gly Thr Asp Phe Thr Phe Thr Ile Ser Ser
             85                   90                  95

Leu Gln Ala Glu Asp Val Ala Val Tyr Phe Cys Gln Gln Asp Tyr Ser
            100                  105                  110

Ser Pro Trp Thr Phe Gly Gln Gly Thr Lys Leu Glu Ile Lys
            115                  120                  125
```

<210> SEQ ID NO 120
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV3 excluding
      signal sequence

<400> SEQUENCE: 120

```
Asp Val Val Met Thr Gln Ser Pro Asp Ser Leu Ala Val Ser Leu Gly
 1               5                  10                  15

Glu Arg Val Thr Ile Asn Cys Lys Ala Ser Gln Ser Val Ser Asn Asp
             20                  25                  30
```

```
Val Ala Trp Tyr Gln Gln Lys Pro Gly Gln Ser Pro Lys Val Leu Ile
        35                  40                  45

Tyr Tyr Ala Ser Asn Arg Tyr Thr Gly Val Pro Asp Arg Phe Ser Gly
 50                  55                  60

Ser Gly Ser Gly Thr Asp Phe Thr Phe Thr Ile Ser Ser Leu Gln Ala
 65                  70                  75                  80

Glu Asp Val Ala Val Tyr Phe Cys Gln Gln Asp Tyr Ser Ser Pro Trp
                 85                  90                  95

Thr Phe Gly Gln Gly Thr Lys Leu Glu Ile Lys
                100                 105
```

<210> SEQ ID NO 121
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV5 sequence
<220> FEATURE:
<221> NAME/KEY: CDS
<222> LOCATION: (1)..(378)

<400> SEQUENCE: 121

```
atg aag ctg ccc gtt cgc ctg ctt gtg ctg atg ttc tgg atc ccc gcg        48
Met Lys Leu Pro Val Arg Leu Leu Val Leu Met Phe Trp Ile Pro Ala
 1               5                  10                  15 tcc tcc tcg gac atc gtg atg aca cag tcc ccc gac tcc ctg gcc gtc        96
Ser Ser Ser Asp Ile Val Met Thr Gln Ser Pro Asp Ser Leu Ala Val
                20                  25                  30 tct ctg ggt gag agg gta acc atc aac tgc aag gcc agc caa agc gtt       144
Ser Leu Gly Glu Arg Val Thr Ile Asn Cys Lys Ala Ser Gln Ser Val
        35                  40                  45 agc aac gat gtt gct tgg tat caa cag aag cct ggc caa tca ccc aag       192
Ser Asn Asp Val Ala Trp Tyr Gln Gln Lys Pro Gly Gln Ser Pro Lys
 50                  55                  60 gtt ctc att tat tat gcc tct aat aga tac act gga gtc cct gat aga       240
Val Leu Ile Tyr Tyr Ala Ser Asn Arg Tyr Thr Gly Val Pro Asp Arg
 65                  70                  75                  80 ttc agt ggc tca ggc agc ggc acc gac ttc aca ttc act atc tct agt       288
Phe Ser Gly Ser Gly Ser Gly Thr Asp Phe Thr Phe Thr Ile Ser Ser
                 85                  90                  95 gtg cag gca gag gac gtg gcc gtg tat ttc tgc cag cag gat tac agc       336
Val Gln Ala Glu Asp Val Ala Val Tyr Phe Cys Gln Gln Asp Tyr Ser
                100                 105                 110 tcc cca tgg acc ttc ggt cag gga act aaa ctt gag atc aag               378
Ser Pro Trp Thr Phe Gly Gln Gly Thr Lys Leu Glu Ile Lys
        115                 120                 125
```

<210> SEQ ID NO 122
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 122

```
Met Lys Leu Pro Val Arg Leu Leu Val Leu Met Phe Trp Ile Pro Ala
 1               5                  10                  15

Ser Ser Ser Asp Ile Val Met Thr Gln Ser Pro Asp Ser Leu Ala Val
                20                  25                  30

Ser Leu Gly Glu Arg Val Thr Ile Asn Cys Lys Ala Ser Gln Ser Val
```

```
                35                  40                  45
Ser Asn Asp Val Ala Trp Tyr Gln Gln Lys Pro Gly Gln Ser Pro Lys
 50                  55                  60

Val Leu Ile Tyr Tyr Ala Ser Asn Arg Tyr Thr Gly Val Pro Asp Arg
 65                  70                  75                  80

Phe Ser Gly Ser Gly Ser Gly Thr Asp Phe Thr Phe Thr Ile Ser Ser
                 85                  90                  95

Val Gln Ala Glu Asp Val Ala Val Tyr Phe Cys Gln Gln Asp Tyr Ser
            100                 105                 110

Ser Pro Trp Thr Phe Gly Gln Gly Thr Lys Leu Glu Ile Lys
            115                 120                 125

<210> SEQ ID NO 123
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV5 excluding
      signal sequence

<400> SEQUENCE: 123

Asp Ile Val Met Thr Gln Ser Pro Asp Ser Leu Ala Val Ser Leu Gly
 1               5                  10                  15

Glu Arg Val Thr Ile Asn Cys Lys Ala Ser Gln Ser Val Ser Asn Asp
             20                  25                  30

Val Ala Trp Tyr Gln Gln Lys Pro Gly Gln Ser Pro Lys Val Leu Ile
         35                  40                  45

Tyr Tyr Ala Ser Asn Arg Tyr Thr Gly Val Pro Asp Arg Phe Ser Gly
 50                  55                  60

Ser Gly Ser Gly Thr Asp Phe Thr Phe Thr Ile Ser Ser Val Gln Ala
 65                  70                  75                  80

Glu Asp Val Ala Val Tyr Phe Cys Gln Gln Asp Tyr Ser Ser Pro Trp
                 85                  90                  95

Thr Phe Gly Gln Gly Thr Lys Leu Glu Ile Lys
            100                 105

<210> SEQ ID NO 124
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5320 LV6 sequence
<220> FEATURE:
<221> NAME/KEY: CDS
<222> LOCATION: (1)..(378)

<400> SEQUENCE: 124 atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
 1               5                  10                  15 tcc tcc tcg gat att gtt atg aca cag tcc cct gat agt ctg gct gtc      96
Ser Ser Ser Asp Ile Val Met Thr Gln Ser Pro Asp Ser Leu Ala Val
             20                  25                  30 agc gca ggc gag cgc gta acc ata aat tgt aag gcc tcc cag agc gtc     144
Ser Ala Gly Glu Arg Val Thr Ile Asn Cys Lys Ala Ser Gln Ser Val
         35                  40                  45 tct aac gac gtc gcc tgg tac caa cag aag ccc gga cag tca cct aaa     192
Ser Asn Asp Val Ala Trp Tyr Gln Gln Lys Pro Gly Gln Ser Pro Lys
 50                  55                  60
```

```
gta ctc att tac tat gct tca aac cgt tac aca gga gtg ccc gac agg    240
Val Leu Ile Tyr Tyr Ala Ser Asn Arg Tyr Thr Gly Val Pro Asp Arg
 65                  70                  75                  80 ttc tct ggc tcc gga tca ggc acc gat ttt acc ttt act atc agc agc    288
Phe Ser Gly Ser Gly Ser Gly Thr Asp Phe Thr Phe Thr Ile Ser Ser
                 85                  90                  95 gtc cag gct gag gac gtc gcc gta tac ttc tgc cag caa gac tac tca    336
Val Gln Ala Glu Asp Val Ala Val Tyr Phe Cys Gln Gln Asp Tyr Ser
            100                 105                 110 agc cca tgg aca ttc ggg caa gga aca aag ctg gag ata aaa            378
Ser Pro Trp Thr Phe Gly Gln Gly Thr Lys Leu Glu Ile Lys
        115                 120                 125
```

<210> SEQ ID NO 125
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 125

```
Met Lys Leu Pro Val Arg Leu Leu Val Leu Met Phe Trp Ile Pro Ala
 1               5                  10                  15

Ser Ser Ser Asp Ile Val Met Thr Gln Ser Pro Asp Ser Leu Ala Val
             20                  25                  30

Ser Ala Gly Glu Arg Val Thr Ile Asn Cys Lys Ala Ser Gln Ser Val
         35                  40                  45

Ser Asn Asp Val Ala Trp Tyr Gln Gln Lys Pro Gly Gln Ser Pro Lys
 50                  55                  60

Val Leu Ile Tyr Tyr Ala Ser Asn Arg Tyr Thr Gly Val Pro Asp Arg
 65                  70                  75                  80

Phe Ser Gly Ser Gly Ser Gly Thr Asp Phe Thr Phe Thr Ile Ser Ser
                 85                  90                  95

Val Gln Ala Glu Asp Val Ala Val Tyr Phe Cys Gln Gln Asp Tyr Ser
            100                 105                 110

Ser Pro Trp Thr Phe Gly Gln Gly Thr Lys Leu Glu Ile Lys
        115                 120                 125
```

<210> SEQ ID NO 126
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 LV6 excluding
      signal sequence

<400> SEQUENCE: 126

```
Asp Ile Val Met Thr Gln Ser Pro Asp Ser Leu Ala Val Ser Ala Gly
 1               5                  10                  15

Glu Arg Val Thr Ile Asn Cys Lys Ala Ser Gln Ser Val Ser Asn Asp
             20                  25                  30

Val Ala Trp Tyr Gln Gln Lys Pro Gly Gln Ser Pro Lys Val Leu Ile
         35                  40                  45

Tyr Tyr Ala Ser Asn Arg Tyr Thr Gly Val Pro Asp Arg Phe Ser Gly
 50                  55                  60

Ser Gly Ser Gly Thr Asp Phe Thr Phe Thr Ile Ser Val Gln Ala
 65                  70                  75                  80
```

```
Glu Asp Val Ala Val Tyr Phe Cys Gln Gln Asp Tyr Ser Ser Pro Trp
                85                  90                  95

Thr Phe Gly Gln Gly Thr Lys Leu Glu Ile Lys
            100                 105
```

<210> SEQ ID NO 127
<211> LENGTH: 414
<212> TYPE: DNA
<213> ORGANISM: Artificial Sequence
<220> FEATURE:
<223> OTHER INFORMATION: Description of Artificial Sequence: Synthetic hzKM5320 HV0 sequence
<220> FEATURE:
<221> NAME/KEY: CDS
<222> LOCATION: (1)..(414)

<400> SEQUENCE: 127

```
atg aat ctg ggg ctg tcg ctg atc ttc ctg gcg ctg atc ctg aag ggc    48
Met Asn Leu Gly Leu Ser Leu Ile Phe Leu Ala Leu Ile Leu Lys Gly
1               5                   10                  15 gtg cag tgc cag gtg caa ctt gta cag tcc ggt agt gaa ctg aaa aaa    96
Val Gln Cys Gln Val Gln Leu Val Gln Ser Gly Ser Glu Leu Lys Lys
            20                  25                  30 cct ggc gct agc gtc aag gtc tcc tgc aag gca tct ggc tac acc ttc   144
Pro Gly Ala Ser Val Lys Val Ser Cys Lys Ala Ser Gly Tyr Thr Phe
        35                  40                  45 acc aac tat gga atg aac tgg gtt agg cag gca cca gga caa ggt ctg   192
Thr Asn Tyr Gly Met Asn Trp Val Arg Gln Ala Pro Gly Gln Gly Leu
    50                  55                  60 gag tgg atg gga tgg att aat aca gaa aca ggg gag cct aca tat tca   240
Glu Trp Met Gly Trp Ile Asn Thr Glu Thr Gly Glu Pro Thr Tyr Ser
65                  70                  75                  80 gac gac ttc aag ggc cgg ttc gtg ttt tcc ctg gat acc agc gtc tcc   288
Asp Asp Phe Lys Gly Arg Phe Val Phe Ser Leu Asp Thr Ser Val Ser
                85                  90                  95 aca gcc tat ttg cag atc agt agc ctg aag gct gag gac aca gcc gtt   336
Thr Ala Tyr Leu Gln Ile Ser Ser Leu Lys Ala Glu Asp Thr Ala Val
            100                 105                 110 tac tac tgt gct cgg gaa gat ggc tat tac ggg acc ctt gac tac tgg   384
Tyr Tyr Cys Ala Arg Glu Asp Gly Tyr Tyr Gly Thr Leu Asp Tyr Trp
        115                 120                 125 ggg cag ggc acc aca gtg aca gta tcc tcc                           414
Gly Gln Gly Thr Thr Val Thr Val Ser Ser
    130                 135
```

<210> SEQ ID NO 128
<211> LENGTH: 138
<212> TYPE: PRT
<213> ORGANISM: Artificial Sequence
<220> FEATURE:
<223> OTHER INFORMATION: Description of Artificial Sequence: Synthetic construct

<400> SEQUENCE: 128

```
Met Asn Leu Gly Leu Ser Leu Ile Phe Leu Ala Leu Ile Leu Lys Gly
1               5                   10                  15

Val Gln Cys Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60
```

Glu Trp Met Gly Trp Ile Asn Thr Glu Thr Gly Glu Pro Thr Tyr Ser
65                  70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Glu Asp Gly Tyr Tyr Gly Thr Leu Asp Tyr Trp
        115                 120                 125

Gly Gln Gly Thr Thr Val Thr Val Ser Ser
    130                 135

<210> SEQ ID NO 129
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV0 excluding
      signal sequence

<400> SEQUENCE: 129

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Glu Thr Gly Glu Pro Thr Tyr Ser Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Asp Gly Tyr Tyr Gly Thr Leu Asp Tyr Trp Gly Gln Gly
            100                 105                 110

Thr Thr Val Thr Val Ser Ser
        115

<210> SEQ ID NO 130
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV1 sequence
<220> FEATURE:
<221> NAME/KEY: CDS
<222> LOCATION: (1)..(414)

<400> SEQUENCE: 130 atg aat ctg ggg ctg tcg ctg atc ttc ctg gcg ctg atc ctg aag ggc    48
Met Asn Leu Gly Leu Ser Leu Ile Phe Leu Ala Leu Ile Leu Lys Gly
1               5                   10                  15 gtg cag tgc caa gtg cag ctg gtg caa agc ggc agt gaa ctg aag aag    96
Val Gln Cys Gln Val Gln Leu Val Gln Ser Gly Ser Glu Leu Lys Lys
            20                  25                  30 cct ggc gct agt gtg aag gtt tct tgc aag gct tct ggc tac acc ttt   144
Pro Gly Ala Ser Val Lys Val Ser Cys Lys Ala Ser Gly Tyr Thr Phe
        35                  40                  45 act aat tac ggc atg aac tgg gtg cgt cag gca cct ggc cag ggc ctc   192
Thr Asn Tyr Gly Met Asn Trp Val Arg Gln Ala Pro Gly Gln Gly Leu

```
aaa tgg atg ggg tgg att aac act gag acc ggt gag ccc aca tac tca      240
Lys Trp Met Gly Trp Ile Asn Thr Glu Thr Gly Glu Pro Thr Tyr Ser
 65              70                  75                  80 gat gat ttt aaa ggc cgg ttt gtc ttt tcc ctg gac aca tct gtt agc      288
Asp Asp Phe Lys Gly Arg Phe Val Phe Ser Leu Asp Thr Ser Val Ser
                85                  90                  95 acc gct tat ctg cag ata tca agt ctg aaa gcc gaa gat act gcc gtg      336
Thr Ala Tyr Leu Gln Ile Ser Ser Leu Lys Ala Glu Asp Thr Ala Val
            100                 105                 110 tat tat tgt gcc cgc gaa gat ggt tac tat gga acc ctg gac tac tgg      384
Tyr Tyr Cys Ala Arg Glu Asp Gly Tyr Tyr Gly Thr Leu Asp Tyr Trp
        115                 120                 125 ggc cag ggc act acc gtt act gtg tcc agt                              414
Gly Gln Gly Thr Thr Val Thr Val Ser Ser
    130                 135
```

<210> SEQ ID NO 131
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 131

```
Met Asn Leu Gly Leu Ser Leu Ile Phe Leu Ala Leu Ile Leu Lys Gly
 1               5                  10                  15

Val Gln Cys Gln Val Gln Leu Val Gln Ser Gly Ser Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Glu Thr Gly Glu Pro Thr Tyr Ser
 65              70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Glu Asp Gly Tyr Tyr Gly Thr Leu Asp Tyr Trp
        115                 120                 125

Gly Gln Gly Thr Thr Val Thr Val Ser Ser
    130                 135
```

<210> SEQ ID NO 132
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV1 excluding
      signal sequence

<400> SEQUENCE: 132

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
```

```
                        35                  40                  45
Gly Trp Ile Asn Thr Glu Thr Gly Glu Pro Thr Tyr Ser Asp Asp Phe
             50                  55                  60

Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Glu Asp Gly Tyr Tyr Gly Thr Leu Asp Tyr Trp Gly Gln Gly
             100                 105                 110

Thr Thr Val Thr Val Ser Ser
        115

<210> SEQ ID NO 133
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV2 sequence
<220> FEATURE:
<221> NAME/KEY: CDS
<222> LOCATION: (1)..(414)

<400> SEQUENCE: 133 atg aat ctg ggg ctg tcg ctg atc ttc ctg gcg ctg atc ctg aag ggc     48
Met Asn Leu Gly Leu Ser Leu Ile Phe Leu Ala Leu Ile Leu Lys Gly
 1               5                  10                  15 gtg cag tgc caa gtt cag ctt gtg cag agt gga agc gaa ctc aag aaa     96
Val Gln Cys Gln Val Gln Leu Val Gln Ser Gly Ser Glu Leu Lys Lys
             20                  25                  30 ccc ggt gcc tct gta aaa gtc tca tgt aaa gct tca ggc tac aca ttt    144
Pro Gly Ala Ser Val Lys Val Ser Cys Lys Ala Ser Gly Tyr Thr Phe
         35                  40                  45 aca aat tat ggt atg aat tgg gtc cga cag gct ccc ggt caa gga ctc    192
Thr Asn Tyr Gly Met Asn Trp Val Arg Gln Ala Pro Gly Gln Gly Leu
     50                  55                  60 gaa tgg atg ggc tgg ata aat act gag aca ggg gag ccc act tac tct    240
Glu Trp Met Gly Trp Ile Asn Thr Glu Thr Gly Glu Pro Thr Tyr Ser
 65                  70                  75                  80 gac gat ttc aag ggc aga ttc gtg ttc agc ttg gac aca tca gtg tca    288
Asp Asp Phe Lys Gly Arg Phe Val Phe Ser Leu Asp Thr Ser Val Ser
                 85                  90                  95 acc gct tat ttg cag att tcc agc ctg aaa gct gag gat act gct act    336
Thr Ala Tyr Leu Gln Ile Ser Ser Leu Lys Ala Glu Asp Thr Ala Thr
            100                 105                 110 tat ttc tgt gcc cgc gag gat ggg tac tat gga act ctg gac tac tgg    384
Tyr Phe Cys Ala Arg Glu Asp Gly Tyr Tyr Gly Thr Leu Asp Tyr Trp
        115                 120                 125 gga cag ggc aca act gtc act gtt agc agt                            414
Gly Gln Gly Thr Thr Val Thr Val Ser Ser
    130                 135

<210> SEQ ID NO 134
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 134

Met Asn Leu Gly Leu Ser Leu Ile Phe Leu Ala Leu Ile Leu Lys Gly
```

```
              1               5                  10                 15
Val Gln Cys Gln Val Gln Leu Val Gln Ser Gly Ser Glu Leu Lys Lys
              20                 25                 30

Pro Gly Ala Ser Val Lys Val Ser Cys Lys Ala Ser Gly Tyr Thr Phe
              35                 40                 45

Thr Asn Tyr Gly Met Asn Trp Val Arg Gln Ala Pro Gly Gln Gly Leu
              50                 55                 60

Glu Trp Met Gly Trp Ile Asn Thr Glu Thr Gly Glu Pro Thr Tyr Ser
 65                 70                 75                 80

Asp Asp Phe Lys Gly Arg Phe Val Phe Ser Leu Asp Thr Ser Val Ser
                    85                 90                 95

Thr Ala Tyr Leu Gln Ile Ser Ser Leu Lys Ala Glu Asp Thr Ala Thr
                 100                105                110

Tyr Phe Cys Ala Arg Glu Asp Gly Tyr Tyr Gly Thr Leu Asp Tyr Trp
             115                120                125

Gly Gln Gly Thr Thr Val Thr Val Ser Ser
         130                135
```

<210> SEQ ID NO 135
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV2 excluding
      signal sequence

<400> SEQUENCE: 135

```
Gln Val Gln Leu Val Gln Ser Gly Ser Glu Leu Lys Lys Pro Gly Ala
1               5                  10                 15

Ser Val Lys Val Ser Cys Lys Ala Ser Gly Tyr Thr Phe Thr Asn Tyr
             20                 25                 30

Gly Met Asn Trp Val Arg Gln Ala Pro Gly Gln Gly Leu Glu Trp Met
         35                 40                 45

Gly Trp Ile Asn Thr Glu Thr Gly Glu Pro Thr Tyr Ser Asp Asp Phe
     50                 55                 60

Lys Gly Arg Phe Val Phe Ser Leu Asp Thr Ser Val Ser Thr Ala Tyr
 65                 70                 75                 80

Leu Gln Ile Ser Ser Leu Lys Ala Glu Asp Thr Ala Thr Tyr Phe Cys
                 85                 90                 95

Ala Arg Glu Asp Gly Tyr Tyr Gly Thr Leu Asp Tyr Trp Gly Gln Gly
             100                105                110

Thr Thr Val Thr Val Ser Ser
         115
```

<210> SEQ ID NO 136
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV3a sequence
<220> FEATURE:
<221> NAME/KEY: CDS
<222> LOCATION: (1)..(414)

<400> SEQUENCE: 136

```
atg aat ctg ggg ctg tcg ctg atc ttc ctg gcg ctg atc ctg aag ggc     48
Met Asn Leu Gly Leu Ser Leu Ile Phe Leu Ala Leu Ile Leu Lys Gly
1               5                  10                 15
```

```
gtg cag tgc cag gtg cag ctt gtg cag tct gga tct gaa ctt aaa aag    96
Val Gln Cys Gln Val Gln Leu Val Gln Ser Gly Ser Glu Leu Lys Lys
             20                  25                  30 cct ggc gct tca gtc aag gtt tct tgt aag gca agc gga tac acc ttt   144
Pro Gly Ala Ser Val Lys Val Ser Cys Lys Ala Ser Gly Tyr Thr Phe
         35                  40                  45 act aat tat ggt atg aat tgg gta cgc caa gcc cca ggc caa ggt ctc   192
Thr Asn Tyr Gly Met Asn Trp Val Arg Gln Ala Pro Gly Gln Gly Leu
 50                  55                  60 aag tgg atg ggt tgg att aac acc gag acc gga gag cct acc tat tcc   240
Lys Trp Met Gly Trp Ile Asn Thr Glu Thr Gly Glu Pro Thr Tyr Ser
65                  70                  75                  80 gac gat ttc aag ggc cgc ttc gtg ttc tca ttg gac act agc gtg agt   288
Asp Asp Phe Lys Gly Arg Phe Val Phe Ser Leu Asp Thr Ser Val Ser
                 85                  90                  95 acc gcc tac ctc cag atc tcc agt ttg aaa gca gag gac aca gcc acc   336
Thr Ala Tyr Leu Gln Ile Ser Ser Leu Lys Ala Glu Asp Thr Ala Thr
            100                 105                 110 tac ttc tgt gcc agg gag gac gga tac tac gga acc ctg gac tac tgg   384
Tyr Phe Cys Ala Arg Glu Asp Gly Tyr Tyr Gly Thr Leu Asp Tyr Trp
        115                 120                 125 ggg cag ggc aca acc gtg aca gtg tcc tct                           414
Gly Gln Gly Thr Thr Val Thr Val Ser Ser
130                 135
```

<210> SEQ ID NO 137
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 137

```
Met Asn Leu Gly Leu Ser Leu Ile Phe Leu Ala Leu Ile Leu Lys Gly
 1               5                  10                  15

Val Gln Cys Gln Val Gln Leu Val Gln Ser Gly Ser Glu Leu Lys Lys
             20                  25                  30

Pro Gly Ala Ser Val Lys Val Ser Cys Lys Ala Ser Gly Tyr Thr Phe
         35                  40                  45

Thr Asn Tyr Gly Met Asn Trp Val Arg Gln Ala Pro Gly Gln Gly Leu
 50                  55                  60

Lys Trp Met Gly Trp Ile Asn Thr Glu Thr Gly Glu Pro Thr Tyr Ser
65                  70                  75                  80

Asp Asp Phe Lys Gly Arg Phe Val Phe Ser Leu Asp Thr Ser Val Ser
                 85                  90                  95

Thr Ala Tyr Leu Gln Ile Ser Ser Leu Lys Ala Glu Asp Thr Ala Thr
            100                 105                 110

Tyr Phe Cys Ala Arg Glu Asp Gly Tyr Tyr Gly Thr Leu Asp Tyr Trp
        115                 120                 125

Gly Gln Gly Thr Thr Val Thr Val Ser Ser
130                 135
```

<210> SEQ ID NO 138
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV3a excluding signal sequence

<400> SEQUENCE: 138

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Glu Thr Gly Glu Pro Thr Tyr Ser Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Ala Arg Glu Asp Gly Tyr Tyr Gly Thr Leu Asp Tyr Trp Gly Gln Gly
            100                 105                 110

Thr Thr Val Thr Val Ser Ser
        115

<210> SEQ ID NO 139
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV3b sequence
<220> FEATURE:
<221> NAME/KEY: CDS
<222> LOCATION: (1)..(414)

<400> SEQUENCE: 139

```
atg aat ctg ggg ctg tcg ctg atc ttc ctg gcg ctg atc ctg aag ggc     48
Met Asn Leu Gly Leu Ser Leu Ile Phe Leu Ala Leu Ile Leu Lys Gly
1               5                   10                  15 gtg cag tgc cag ata cag ctg gtg cag tcc ggc agc gaa ctg aaa aag     96
Val Gln Cys Gln Ile Gln Leu Val Gln Ser Gly Ser Glu Leu Lys Lys
            20                  25                  30 cct ggg gcc tct gtc aaa atc tct tgc aag gct agt ggg tac aca ttt    144
Pro Gly Ala Ser Val Lys Ile Ser Cys Lys Ala Ser Gly Tyr Thr Phe
        35                  40                  45 aca aac tac ggt atg aat tgg gtg cgg caa gcc cca ggt cag ggc ctg    192
Thr Asn Tyr Gly Met Asn Trp Val Arg Gln Ala Pro Gly Gln Gly Leu
    50                  55                  60 gaa tgg atg ggt tgg att aat aca gag act ggg gag cca act tac agc    240
Glu Trp Met Gly Trp Ile Asn Thr Glu Thr Gly Glu Pro Thr Tyr Ser
65                  70                  75                  80 gat gat ttc aaa ggt cgc ttc gtc ttc agc ctc gac act tct gtc tct    288
Asp Asp Phe Lys Gly Arg Phe Val Phe Ser Leu Asp Thr Ser Val Ser
                85                  90                  95 acc gct tac ttg cag atc agc agc ctg aag gca gaa gac acc gca gtc    336
Thr Ala Tyr Leu Gln Ile Ser Ser Leu Lys Ala Glu Asp Thr Ala Val
            100                 105                 110 tat ttc tgt gcc agg gaa gat ggc tac tac ggc act ctg gat tat tgg    384
Tyr Phe Cys Ala Arg Glu Asp Gly Tyr Tyr Gly Thr Leu Asp Tyr Trp
        115                 120                 125 ggt cag ggt act acc gtg act gtc agc agt                            414
Gly Gln Gly Thr Thr Val Thr Val Ser Ser
    130                 135
```

```
<210> SEQ ID NO 140
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 140

Met Asn Leu Gly Leu Ser Leu Ile Phe Leu Ala Leu Ile Leu Lys Gly
1               5                   10                  15

Val Gln Cys Gln Ile Gln Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Glu Thr Gly Glu Pro Thr Tyr Ser
65                  70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Phe Cys Ala Arg Glu Asp Gly Tyr Tyr Gly Thr Leu Asp Tyr Trp
        115                 120                 125

Gly Gln Gly Thr Thr Val Thr Val Ser Ser
    130                 135

<210> SEQ ID NO 141
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV3b excluding
      signal sequence

<400> SEQUENCE: 141

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Glu Thr Gly Glu Pro Thr Tyr Ser Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Glu Asp Gly Tyr Tyr Gly Thr Leu Asp Tyr Trp Gly Gln Gly
            100                 105                 110

Thr Thr Val Thr Val Ser Ser
        115

<210> SEQ ID NO 142
<211> LENGTH: 414
<212> TYPE: DNA
<213> ORGANISM: Artificial Sequence
<220> FEATURE:
```

<223> OTHER INFORMATION: Description of Artificial Sequence: Synthetic
      hzKM5320 HV3c sequence
<220> FEATURE:
<221> NAME/KEY: CDS
<222> LOCATION: (1)..(414)

<400> SEQUENCE: 142

```
atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                   10                  15 gtg cag tgc cag gtt cag ctg gtg cag agc ggg ccc gag ctg aaa aag      96
Val Gln Cys Gln Val Gln Leu Val Gln Ser Gly Pro Glu Leu Lys Lys
            20                  25                  30 cct ggc gct agt gta aag gtt tca tgt aag gct agc ggc tat acc ttt     144
Pro Gly Ala Ser Val Lys Val Ser Cys Lys Ala Ser Gly Tyr Thr Phe
        35                  40                  45 act aac tat ggt atg aac tgg gtc aaa caa gcc cct gga caa ggt ttg     192
Thr Asn Tyr Gly Met Asn Trp Val Lys Gln Ala Pro Gly Gln Gly Leu
    50                  55                  60 aaa tgg atg ggg tgg atc aat aca gaa acc ggt gag cca aca tat tct     240
Lys Trp Met Gly Trp Ile Asn Thr Glu Thr Gly Glu Pro Thr Tyr Ser
65                  70                  75                  80 gac gac ttc aaa ggc cgc ttc gtc ttc tct ctg gat aca tcc gtg agc     288
Asp Asp Phe Lys Gly Arg Phe Val Phe Ser Leu Asp Thr Ser Val Ser
                85                  90                  95 act gcc tac ctg cag atc agc agc ctc aag gct gaa gac aca gca gtg     336
Thr Ala Tyr Leu Gln Ile Ser Ser Leu Lys Ala Glu Asp Thr Ala Val
            100                 105                 110 tat tat tgc gct agg gag gac gga tac tat ggc act ctg gat tac tgg     384
Tyr Tyr Cys Ala Arg Glu Asp Gly Tyr Tyr Gly Thr Leu Asp Tyr Trp
        115                 120                 125 ggt cag ggc acc acc gtg act gtt tct agc                             414
Gly Gln Gly Thr Thr Val Thr Val Ser Ser
    130                 135
```

<210> SEQ ID NO 143
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 143

Met Asn Leu Gly Leu Ser Leu Ile Phe Leu Ala Leu Ile Leu Lys Gly
1               5                   10                  15

Val Gln Cys Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Glu Thr Gly Glu Pro Thr Tyr Ser
65                  70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Val
            100                 105                 110

Tyr Tyr Cys Ala Arg Glu Asp Gly Tyr Tyr Gly Thr Leu Asp Tyr Trp
        115                 120                 125

```
<210> SEQ ID NO 144
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV3c excluding
      signal sequence

<400> SEQUENCE: 144
```

Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Glu Thr Gly Glu Pro Thr Tyr Ser Asp Asp Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Glu Asp Gly Tyr Tyr Gly Thr Leu Asp Tyr Trp Gly Gln Gly
            100                 105                 110

Thr Thr Val Thr Val Ser Ser
        115

```
<210> SEQ ID NO 145
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV4 sequence
<220> FEATURE:
<221> NAME/KEY: CDS
<222> LOCATION: (1)..(414)

<400> SEQUENCE: 145
```

| atg aat ctg ggg ctg tcg ctg atc ttc ctg gcg ctg atc ctg aag ggc | 48 |
| Met Asn Leu Gly Leu Ser Leu Ile Phe Leu Ala Leu Ile Leu Lys Gly | |
| 1               5                   10                  15 | |

| gtg cag tgc cag gtt cag ttg gtt cag tct ggc ccc gaa ctg aaa aag | 96 |
| Val Gln Cys Gln Val Gln Leu Val Gln Ser Gly Pro Glu Leu Lys Lys | |
|             20                  25                  30 | |

| ccc ggg gca agc gtg aag gtc tct tgt aag gca agc ggc tat aca ttt | 144 |
| Pro Gly Ala Ser Val Lys Val Ser Cys Lys Ala Ser Gly Tyr Thr Phe | |
|         35                  40                  45 | |

| aca aac tac ggc atg aac tgg gtg cga cag gct cct ggc cag ggg ctt | 192 |
| Thr Asn Tyr Gly Met Asn Trp Val Arg Gln Ala Pro Gly Gln Gly Leu | |
|     50                  55                  60 | |

| aag tgg atg gga tgg atc aac aca gag aca ggt gaa cca aca tat agc | 240 |
| Lys Trp Met Gly Trp Ile Asn Thr Glu Thr Gly Glu Pro Thr Tyr Ser | |
| 65                  70                  75                  80 | |

| gac gac ttc aag ggc aga ttt gtc ttt tcc ttg gac act tct gtc tcc | 288 |
| Asp Asp Phe Lys Gly Arg Phe Val Phe Ser Leu Asp Thr Ser Val Ser | |
|                 85                  90                  95 | |

| acc gcc tac ctg cag att tct agc ctg aag gca gag gac aca gcc aca | 336 |
| Thr Ala Tyr Leu Gln Ile Ser Ser Leu Lys Ala Glu Asp Thr Ala Thr | |

```
                    100                 105                 110
tac ttt tgc gcc cgc gaa gac ggc tac tac ggg aca ctg gac tac tgg       384
Tyr Phe Cys Ala Arg Glu Asp Gly Tyr Tyr Gly Thr Leu Asp Tyr Trp
        115                 120                 125 gga caa ggt acc acc gtg aca gtt tct agc                               414
Gly Gln Gly Thr Thr Val Thr Val Ser Ser
        130                 135
```

<210> SEQ ID NO 146
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 146

```
Met Asn Leu Gly Leu Ser Leu Ile Phe Leu Ala Leu Ile Leu Lys Gly
1               5                   10                  15

Val Gln Cys Gln Val Gln Leu Val Gln Ser Gly Pro Glu Leu Lys Lys
            20                  25                  30

Pro Gly Ala Ser Val Lys Val Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Glu Thr Gly Glu Pro Thr Tyr Ser
65                  70                  75                  80

Asp Asp Phe Lys Gly Arg Phe Val Phe Ser Leu Asp Thr Ser Val Ser
                85                  90                  95

Thr Ala Tyr Leu Gln Ile Ser Ser Leu Lys Ala Glu Asp Thr Ala Thr
            100                 105                 110

Tyr Phe Cys Ala Arg Glu Asp Gly Tyr Tyr Gly Thr Leu Asp Tyr Trp
        115                 120                 125

Gly Gln Gly Thr Thr Val Thr Val Ser Ser
    130                 135
```

<210> SEQ ID NO 147
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV4 excluding
      signal sequence

<400> SEQUENCE: 147

```
Gln Val Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Glu Thr Gly Glu Pro Thr Tyr Ser Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Ala Arg Glu Asp Gly Tyr Tyr Gly Thr Leu Asp Tyr Trp Gly Gln Gly
```

```
                  100                 105                 110
Thr Thr Val Thr Val Ser Ser
        115

<210> SEQ ID NO 148
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV6 sequence
<220> FEATURE:
<221> NAME/KEY: CDS
<222> LOCATION: (1)..(414)

<400> SEQUENCE: 148 atg aat ctg ggg ctg tcg ctg atc ttc ctg gcg ctg atc ctg aag ggc        48
Met Asn Leu Gly Leu Ser Leu Ile Phe Leu Ala Leu Ile Leu Lys Gly
1               5                  10                  15 gtg cag tgc cag gtg cag ctg gtg cag tca gga ccc gag ctg aag aag        96
Val Gln Cys Gln Val Gln Leu Val Gln Ser Gly Pro Glu Leu Lys Lys
            20                  25                  30 cca gga gca tca gta aag att tct tgt aaa gct tca ggc tac aca ttt       144
Pro Gly Ala Ser Val Lys Ile Ser Cys Lys Ala Ser Gly Tyr Thr Phe
        35                  40                  45 act aat tat ggg atg aat tgg gtt aaa cag gct ccc ggt cag ggt ctg       192
Thr Asn Tyr Gly Met Asn Trp Val Lys Gln Ala Pro Gly Gln Gly Leu
    50                  55                  60 aag tgg atg gga tgg att aat acc gaa act gga gag cca acc tac tct       240
Lys Trp Met Gly Trp Ile Asn Thr Glu Thr Gly Glu Pro Thr Tyr Ser
65                  70                  75                  80 gat gac ttc aaa ggg cgc ttc gtg ttc agc ctg gat act tct gtt tct       288
Asp Asp Phe Lys Gly Arg Phe Val Phe Ser Leu Asp Thr Ser Val Ser
                85                  90                  95 act gcc tat ctg cag atc tcc tcc ctc aag gcc gag gac acc gct act       336
Thr Ala Tyr Leu Gln Ile Ser Ser Leu Lys Ala Glu Asp Thr Ala Thr
            100                 105                 110 tac ttc tgc gcc cga gaa gac gga tat tac ggc acc ctg gat tac tgg       384
Tyr Phe Cys Ala Arg Glu Asp Gly Tyr Tyr Gly Thr Leu Asp Tyr Trp
        115                 120                 125 ggc caa ggc aca aca gtc acc gta tca tct                               414
Gly Gln Gly Thr Thr Val Thr Val Ser Ser
    130                 135

<210> SEQ ID NO 149
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 149

Met Asn Leu Gly Leu Ser Leu Ile Phe Leu Ala Leu Ile Leu Lys Gly
1               5                  10                  15

Val Gln Cys Gln Val Gln Leu Val Gln Ser Gly Pro Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Glu Thr Gly Glu Pro Thr Tyr Ser
```

```
                65                  70                  75                  80
Asp Asp Phe Lys Gly Arg Phe Val Phe Ser Leu Asp Thr Ser Val Ser
                    85                  90                  95

Thr Ala Tyr Leu Gln Ile Ser Ser Leu Lys Ala Glu Asp Thr Ala Thr
                100                 105                 110

Tyr Phe Cys Ala Arg Glu Asp Gly Tyr Tyr Gly Thr Leu Asp Tyr Trp
                115                 120                 125

Gly Gln Gly Thr Thr Val Thr Val Ser Ser
            130                 135

<210> SEQ ID NO 150
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV6 excluding
      signal sequence

<400> SEQUENCE: 150

Gln Val Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Glu Thr Gly Glu Pro Thr Tyr Ser Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Thr Tyr Phe Cys
                85                  90                  95

Ala Arg Glu Asp Gly Tyr Tyr Gly Thr Leu Asp Tyr Trp Gly Gln Gly
            100                 105                 110

Thr Thr Val Thr Val Ser Ser
        115

<210> SEQ ID NO 151
<211> LENGTH: 414
<212> TYPE: DNA
<213> ORGANISM: Artificial Sequence
<220> FEATURE:
<223> OTHER INFORMATION: Description of Artificial Sequence: Synthetic
      hzKM5320 HV8 sequence
<220> FEATURE:
<221> NAME/KEY: CDS
<222> LOCATION: (1)..(414)

<400> SEQUENCE: 151 atg aat ctg ggg ctg tcg ctg atc ttc ctg gcg ctg atc ctg aag ggc       48
Met Asn Leu Gly Leu Ser Leu Ile Phe Leu Ala Leu Ile Leu Lys Gly
1               5                   10                  15 gtg cag tgc cag att cag ctt gtg cag tcc ggt cca gaa ctg aag aag       96
Val Gln Cys Gln Ile Gln Leu Val Gln Ser Gly Pro Glu Leu Lys Lys
            20                  25                  30 cca gga gca agc gta aag atc tct tgt aag gca tct ggt tac acc ttc      144
Pro Gly Ala Ser Val Lys Ile Ser Cys Lys Ala Ser Gly Tyr Thr Phe
        35                  40                  45 aca aac tac ggc atg aat tgg gta aag caa gca ccc ggt cag ggg ctg      192
Thr Asn Tyr Gly Met Asn Trp Val Lys Gln Ala Pro Gly Gln Gly Leu
    50                  55                  60
```

```
aag tgg atg ggt tgg att aat act gaa acc gga gag cct aca tat tct    240
Lys Trp Met Gly Trp Ile Asn Thr Glu Thr Gly Glu Pro Thr Tyr Ser
 65              70                  75                  80 gac gac ttc aaa gga cgg ttc gtc ttc tca ctg gat aca agt gta aca    288
Asp Asp Phe Lys Gly Arg Phe Val Phe Ser Leu Asp Thr Ser Val Thr
                 85                  90                  95 acc gcc tac ctg cag att tcc tct ttg aag gca gaa gac aca gcc acc    336
Thr Ala Tyr Leu Gln Ile Ser Ser Leu Lys Ala Glu Asp Thr Ala Thr
                100                 105                 110 tac ttc tgc gct cga gaa gat ggt tac tat gga acc ctg gat tac tgg    384
Tyr Phe Cys Ala Arg Glu Asp Gly Tyr Tyr Gly Thr Leu Asp Tyr Trp
            115                 120                 125 gga cag ggt acc aca gtc act gtg tct tcc                            414
Gly Gln Gly Thr Thr Val Thr Val Ser Ser
        130                 135
```

<210> SEQ ID NO 152
<211> LENGTH: 138
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 152

```
Met Asn Leu Gly Leu Ser Leu Ile Phe Leu Ala Leu Ile Leu Lys Gly
 1               5                   10                  15

Val Gln Cys Gln Ile Gln Leu Val Gln Ser Gly Pro Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Glu Thr Gly Glu Pro Thr Tyr Ser
 65              70                  75                  80

Asp Asp Phe Lys Gly Arg Phe Val Phe Ser Leu Asp Thr Ser Val Thr
                 85                  90                  95

Thr Ala Tyr Leu Gln Ile Ser Ser Leu Lys Ala Glu Asp Thr Ala Thr
                100                 105                 110

Tyr Phe Cys Ala Arg Glu Asp Gly Tyr Tyr Gly Thr Leu Asp Tyr Trp
            115                 120                 125

Gly Gln Gly Thr Thr Val Thr Val Ser Ser
        130                 135
```

<210> SEQ ID NO 153
<211> LENGTH: 119
<212> TYPE: PRT
<213> ORGANISM: Artificial Sequence
<220> FEATURE:
<223> OTHER INFORMATION: Description of Artificial Sequence: Synthetic
      amino acid sequence of hzKM5320 HV8 excluding
      signal sequence

<400> SEQUENCE: 153

```
Gln Ile Gln Leu Val Gln Ser Gly Pro Glu Leu Lys Lys Pro Gly Ala
 1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45
```

```
Gly Trp Ile Asn Thr Glu Thr Gly Glu Pro Thr Tyr Ser Asp Asp Phe
        50                  55                  60

Lys Gly Arg Phe Val Phe Ser Leu Asp Thr Ser Val Thr Ala Tyr
 65                  70                  75                  80

Leu Gln Ile Ser Ser Leu Lys Ala Glu Asp Thr Ala Thr Tyr Phe Cys
                    85                  90                  95

Ala Arg Glu Asp Gly Tyr Tyr Gly Thr Leu Asp Tyr Trp Gly Gln Gly
                100                 105                 110

Thr Thr Val Thr Val Ser Ser
            115

<210> SEQ ID NO 154
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5321 LV0 sequence
<220> FEATURE:
<221> NAME/KEY: CDS
<222> LOCATION: (1)..(378)

<400> SEQUENCE: 154 atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
 1               5                  10                  15 tcc tcc tcg gag act act ctg act cag tcc ccc tcc ctg tcc gct          96
Ser Ser Ser Glu Thr Thr Leu Thr Gln Ser Pro Ser Ser Leu Ser Ala
                20                  25                  30 tcc gtg ggg gat cgc gtg acc atc acc tgt atc act tcc act gac atc     144
Ser Val Gly Asp Arg Val Thr Ile Thr Cys Ile Thr Ser Thr Asp Ile
            35                  40                  45 gac gat gac atg aac tgg tac cag cag aag cct ggg aag gct ccc aag     192
Asp Asp Asp Met Asn Trp Tyr Gln Gln Lys Pro Gly Lys Ala Pro Lys
        50                  55                  60 ctg ctg atc tcc gag ggg aac act ctg cgc cct ggc gtt cct tcc cgc     240
Leu Leu Ile Ser Glu Gly Asn Thr Leu Arg Pro Gly Val Pro Ser Arg
 65                  70                 75                  80 ttc tcc ggc tct ggc tct ggg act gac ttc act ctg act atc tcc tcc    288
Phe Ser Gly Ser Gly Ser Gly Thr Asp Phe Thr Leu Thr Ile Ser Ser
                    85                  90                  95 ctg cag ccc gag gac ttc gcc acc tac tac tgc ctg cag act gat tcc    336
Leu Gln Pro Glu Asp Phe Ala Thr Tyr Tyr Cys Leu Gln Thr Asp Ser
                100                 105                 110 gtg ccc ctg act ttc ggg cag ggg act aaa gtg gag atc aag            378
Val Pro Leu Thr Phe Gly Gln Gly Thr Lys Val Glu Ile Lys
            115                 120                 125

<210> SEQ ID NO 155
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 155

Met Lys Leu Pro Val Arg Leu Leu Val Leu Met Phe Trp Ile Pro Ala
 1               5                  10                  15

Ser Ser Ser Glu Thr Thr Leu Thr Gln Ser Pro Ser Ser Leu Ser Ala
                20                  25                  30
```

```
Ser Val Gly Asp Arg Val Thr Ile Thr Cys Ile Ser Thr Asp Ile
            35                  40                  45

Asp Asp Asp Met Asn Trp Tyr Gln Gln Lys Pro Gly Lys Ala Pro Lys
 50                  55                  60

Leu Leu Ile Ser Glu Gly Asn Thr Leu Arg Pro Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Leu Gln Thr Asp Ser
                100                 105                 110

Val Pro Leu Thr Phe Gly Gln Gly Thr Lys Val Glu Ile Lys
            115                 120                 125

<210> SEQ ID NO 156
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV0 excluding
      signal sequence

<400> SEQUENCE: 156

Glu Thr Thr Leu Thr Gln Ser Pro Ser Ser Leu Ser Ala Ser Val Gly
 1               5                  10                  15

Asp Arg Val Thr Ile Thr Cys Ile Thr Ser Thr Asp Ile Asp Asp Asp
                 20                  25                  30

Met Asn Trp Tyr Gln Gln Lys Pro Gly Lys Ala Pro Lys Leu Leu Ile
             35                  40                  45

Ser Glu Gly Asn Thr Leu Arg Pro Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Thr Asp Ser Val Pro Leu
                 85                  90                  95

Thr Phe Gly Gln Gly Thr Lys Val Glu Ile Lys
            100                 105

<210> SEQ ID NO 157
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5321 LV1a sequence
<220> FEATURE:
<221> NAME/KEY: CDS
<222> LOCATION: (1)..(378)

<400> SEQUENCE: 157 atg aag ctg ccc gtt cgc ctg ctt gtg ctg atg ttc tgg atc ccc gcg     48
Met Lys Leu Pro Val Arg Leu Leu Val Leu Met Phe Trp Ile Pro Ala
 1               5                  10                  15 tcc tcc tcg gag act act ctg act cag tcc ccc tcc tcc ctg tcc gct     96
Ser Ser Ser Glu Thr Thr Leu Thr Gln Ser Pro Ser Ser Leu Ser Ala
             20                  25                  30 tcc gtg ggg gat cgc gtg act atc acc tgt atc act tcc act gac atc    144
Ser Val Gly Asp Arg Val Thr Ile Thr Cys Ile Thr Ser Thr Asp Ile
         35                  40                  45 gac gat gac atg aac tgg tac cag cag aag cct ggg aag cct ccc aag    192
Asp Asp Asp Met Asn Trp Tyr Gln Gln Lys Pro Gly Lys Pro Pro Lys
 50                  55                  60
```

```
                50                  55                  60
ctg ctg atc tcc gag ggg aac act ctg cgc cct ggt gtt cct tcc cgc       240
Leu Leu Ile Ser Glu Gly Asn Thr Leu Arg Pro Gly Val Pro Ser Arg
 65                  70                  75                  80 ttc tcc ggc tct ggc tct ggg act gac ttc act ctg act atc tcc tcc       288
Phe Ser Gly Ser Gly Ser Gly Thr Asp Phe Thr Leu Thr Ile Ser Ser
                 85                  90                  95 ctg cag ccc gag gac ttc gcc acc tac tac tgc ctg cag act gat tcc       336
Leu Gln Pro Glu Asp Phe Ala Thr Tyr Tyr Cys Leu Gln Thr Asp Ser
            100                 105                 110 gtg ccc ctg act ttc ggg cag ggg act aaa gtg gag atc aag               378
Val Pro Leu Thr Phe Gly Gln Gly Thr Lys Val Glu Ile Lys
        115                 120                 125

<210> SEQ ID NO 158
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 158

Met Lys Leu Pro Val Arg Leu Leu Val Leu Met Phe Trp Ile Pro Ala
  1               5                  10                  15

Ser Ser Ser Glu Thr Thr Leu Thr Gln Ser Pro Ser Ser Leu Ser Ala
                 20                  25                  30

Ser Val Gly Asp Arg Val Thr Ile Thr Cys Ile Thr Ser Thr Asp Ile
             35                  40                  45

Asp Asp Asp Met Asn Trp Tyr Gln Gln Lys Pro Gly Lys Pro Pro Lys
         50                  55                  60

Leu Leu Ile Ser Glu Gly Asn Thr Leu Arg Pro Gly Val Pro Ser Arg
 65                  70                  75                  80

Phe Ser Gly Ser Gly Ser Gly Thr Asp Phe Thr Leu Thr Ile Ser Ser
                 85                  90                  95

Leu Gln Pro Glu Asp Phe Ala Thr Tyr Tyr Cys Leu Gln Thr Asp Ser
            100                 105                 110

Val Pro Leu Thr Phe Gly Gln Gly Thr Lys Val Glu Ile Lys
        115                 120                 125

<210> SEQ ID NO 159
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV1a excluding
      signal sequence

<400> SEQUENCE: 159

Glu Thr Thr Leu Thr Gln Ser Pro Ser Ser Leu Ser Ala Ser Val Gly
  1               5                  10                  15

Asp Arg Val Thr Ile Thr Cys Ile Thr Ser Thr Asp Ile Asp Asp Asp
                 20                  25                  30

Met Asn Trp Tyr Gln Gln Lys Pro Gly Lys Pro Pro Lys Leu Leu Ile
             35                  40                  45

Ser Glu Gly Asn Thr Leu Arg Pro Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80
```

```
Glu Asp Phe Ala Thr Tyr Tyr Cys Leu Gln Thr Asp Ser Val Pro Leu
                85                  90                  95

Thr Phe Gly Gln Gly Thr Lys Val Glu Ile Lys
            100                 105
```

<210> SEQ ID NO 160
<211> LENGTH: 378
<212> TYPE: DNA
<213> ORGANISM: Artificial Sequence
<220> FEATURE:
<223> OTHER INFORMATION: Description of Artificial Sequence: Synthetic hzKM5321 LV1b sequence
<220> FEATURE:
<221> NAME/KEY: CDS
<222> LOCATION: (1)..(378)

<400> SEQUENCE: 160

```
atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gag act act ctg act cag tcc ccc tcc tcc ctg tcc gct      96
Ser Ser Ser Glu Thr Thr Leu Thr Gln Ser Pro Ser Ser Leu Ser Ala
            20                  25                  30 tcc gtg ggg gat cgc gtg acc atc acc tgt atc act tcc act gac atc     144
Ser Val Gly Asp Arg Val Thr Ile Thr Cys Ile Thr Ser Thr Asp Ile
        35                  40                  45 gac gat gac atg aac tgg tac cag cag aag cct ggg aag gct ccc aag     192
Asp Asp Asp Met Asn Trp Tyr Gln Gln Lys Pro Gly Lys Ala Pro Lys
    50                  55                  60 ctg ctg atc tcc gag ggg aac act ctg cgc cct ggc gtt cct tcc cgc     240
Leu Leu Ile Ser Glu Gly Asn Thr Leu Arg Pro Gly Val Pro Ser Arg
65                  70                  75                  80 ttc tcc ggc tct ggc tct ggg act gac ttc act ctg act atc tcc tcc     288
Phe Ser Gly Ser Gly Ser Gly Thr Asp Phe Thr Leu Thr Ile Ser Ser
                85                  90                  95 ctg cag ccc gag gac ttc gcc gac tac tac tgc ctg cag act gat tcc     336
Leu Gln Pro Glu Asp Phe Ala Asp Tyr Tyr Cys Leu Gln Thr Asp Ser
            100                 105                 110 gtg ccc ctg act ttc ggg cag ggg act aaa gtg gag atc aag             378
Val Pro Leu Thr Phe Gly Gln Gly Thr Lys Val Glu Ile Lys
        115                 120                 125
```

<210> SEQ ID NO 161
<211> LENGTH: 126
<212> TYPE: PRT
<213> ORGANISM: Artificial Sequence
<220> FEATURE:
<223> OTHER INFORMATION: Description of Artificial Sequence: Synthetic construct

<400> SEQUENCE: 161

```
Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Ala
            20                  25                  30

Ser Val Gly Asp Arg Val Thr Ile Thr Cys Ile Thr Ser Thr Asp Ile
        35                  40                  45

Asp Asp Asp Met Asn Trp Tyr Gln Gln Lys Pro Gly Lys Ala Pro Lys
    50                  55                  60

Leu Leu Ile Ser Glu Gly Asn Thr Leu Arg Pro Gly Val Pro Ser Arg
65                  70                  75                  80
```

```
Phe Ser Gly Ser Gly Ser Gly Thr Asp Phe Thr Leu Thr Ile Ser Ser
                85                  90                  95

Leu Gln Pro Glu Asp Phe Ala Asp Tyr Tyr Cys Leu Gln Thr Asp Ser
            100                 105                 110

Val Pro Leu Thr Phe Gly Gln Gly Thr Lys Val Glu Ile Lys
        115                 120                 125

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV1b excluding
      signal sequence

<400> SEQUENCE: 162

Glu Thr Thr Leu Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Asp Tyr Tyr Cys Leu Gln Thr Asp Ser Val Pro Leu
                85                  90                  95

Thr Phe Gly Gln Gly Thr Lys Val Glu Ile Lys
            100                 105

<210> SEQ ID NO 163
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5321 LV1c sequence
<220> FEATURE:
<221> NAME/KEY: CDS
<222> LOCATION: (1)..(378)

<400> SEQUENCE: 163 atg aag ctg ccc gtt cgc ctg ctt gtg ctg atg ttc tgg atc ccc gcg     48
Met Lys Leu Pro Val Arg Leu Leu Val Leu Met Phe Trp Ile Pro Ala
1               5                   10                  15 tcc tcc tcg gag act act ctg act cag tcc ccc tcc tcc ctg tcc gtg     96
Ser Ser Ser Glu Thr Thr Leu Thr Gln Ser Pro Ser Ser Leu Ser Val
            20                  25                  30 tcc gtg ggg gat cgc gtg acc atc acc tgt atc act tcc act gac atc    144
Ser Val Gly Asp Arg Val Thr Ile Thr Cys Ile Thr Ser Thr Asp Ile
        35                  40                  45 gac gat gac atg aac tgg tac cag cag aag cct ggg aag gct ccc aag    192
Asp Asp Asp Met Asn Trp Tyr Gln Gln Lys Pro Gly Lys Ala Pro Lys
    50                  55                  60 ctg ctg atc tcc gag ggg aac act ctg cgc cct ggc gtt cct tcc cgc    240
Leu Leu Ile Ser Glu Gly Asn Thr Leu Arg Pro Gly Val Pro Ser Arg
65                  70                  75                  80 ttc tcc ggc tct ggc tct ggg act gac ttc act ctg act atc tcc tcc    288
Phe Ser Gly Ser Gly Ser Gly Thr Asp Phe Thr Leu Thr Ile Ser Ser
                85                  90                  95
```

```
ctg cag ccc gag gac ttc gcc acc tac tac tgc ctg cag act gat tcc    336
Leu Gln Pro Glu Asp Phe Ala Thr Tyr Tyr Cys Leu Gln Thr Asp Ser
            100                 105                 110 gtg ccc ctg act ttc ggg cag ggg act aaa gtg gag atc aag            378
Val Pro Leu Thr Phe Gly Gln Gly Thr Lys Val Glu Ile Lys
        115                 120                 125

<210> SEQ ID NO 164
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 164

Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Val
            20                  25                  30

Ser Val Gly Asp Arg Val Thr Ile Thr Cys Ile Thr Ser Thr Asp Ile
        35                  40                  45

Asp Asp Asp Met Asn Trp Tyr Gln Gln Lys Pro Gly Lys Ala Pro Lys
    50                  55                  60

Leu Leu Ile Ser Glu Gly Asn Thr Leu Arg Pro Gly Val Pro Ser Arg
65                  70                  75                  80

Phe Ser Gly Ser Gly Ser Gly Thr Asp Phe Thr Leu Thr Ile Ser Ser
                85                  90                  95

Leu Gln Pro Glu Asp Phe Ala Thr Tyr Tyr Cys Leu Gln Thr Asp Ser
            100                 105                 110

Val Pro Leu Thr Phe Gly Gln Gly Thr Lys Val Glu Ile Lys
        115                 120                 125

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV1c excluding
      signal sequence

<400> SEQUENCE: 165

Glu Thr Thr Leu Thr Gln Ser Pro Ser Ser Leu Ser Val Ser Val Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Thr Asp Ser Val Pro Leu
                85                  90                  95

Thr Phe Gly Gln Gly Thr Lys Val Glu Ile Lys
            100                 105

<210> SEQ ID NO 166
```

<211> LENGTH: 378
<212> TYPE: DNA
<213> ORGANISM: Artificial Sequence
<220> FEATURE:
<223> OTHER INFORMATION: Description of Artificial Sequence: Synthetic hzKM5321 LV3 sequence
<220> FEATURE:
<221> NAME/KEY: CDS
<222> LOCATION: (1)..(378)

<400> SEQUENCE: 166

```
atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
1               5                   10                  15 tcc tcc tcg gag act act ctg act cag tcc ccc tcc tcc ctg tcc gcc      96
Ser Ser Ser Glu Thr Thr Leu Thr Gln Ser Pro Ser Ser Leu Ser Ala
                20                  25                  30 tcc act ggg gat cgc gtg acc atc acc tgt atc act tcc act gac atc     144
Ser Thr Gly Asp Arg Val Thr Ile Thr Cys Ile Thr Ser Thr Asp Ile
            35                  40                  45 gac gat gac atg aac tgg tac cag cag aag cct ggg aag gct ccc aag     192
Asp Asp Asp Met Asn Trp Tyr Gln Gln Lys Pro Gly Lys Ala Pro Lys
        50                  55                  60 ctg ctg atc tcc gag ggg aac act ctg cgc cct ggc gtt cct tcc cgc     240
Leu Leu Ile Ser Glu Gly Asn Thr Leu Arg Pro Gly Val Pro Ser Arg
65                  70                  75                  80 ttc tcc ggc tct ggc tct ggg act gac ttc act ctg act atc tcc tcc     288
Phe Ser Gly Ser Gly Ser Gly Thr Asp Phe Thr Leu Thr Ile Ser Ser
                85                  90                  95 act cag ccc gag gac ttc gcc gac tac tac tgc ctg cag act gat tcc     336
Thr Gln Pro Glu Asp Phe Ala Asp Tyr Tyr Cys Leu Gln Thr Asp Ser
                100                 105                 110 gtg ccc ctg act ttc ggg cag ggg act aaa gtg gag atc aag             378
Val Pro Leu Thr Phe Gly Gln Gly Thr Lys Val Glu Ile Lys
            115                 120                 125
```

<210> SEQ ID NO 167
<211> LENGTH: 126
<212> TYPE: PRT
<213> ORGANISM: Artificial Sequence
<220> FEATURE:
<223> OTHER INFORMATION: Description of Artificial Sequence: Synthetic construct

<400> SEQUENCE: 167

```
Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Ala
                20                  25                  30

Ser Thr Gly Asp Arg Val Thr Ile Thr Cys Ile Thr Ser Thr Asp Ile
            35                  40                  45

Asp Asp Asp Met Asn Trp Tyr Gln Gln Lys Pro Gly Lys Ala Pro Lys
        50                  55                  60

Leu Leu Ile Ser Glu Gly Asn Thr Leu Arg Pro Gly Val Pro Ser Arg
65                  70                  75                  80

Phe Ser Gly Ser Gly Ser Gly Thr Asp Phe Thr Leu Thr Ile Ser Ser
                85                  90                  95

Thr Gln Pro Glu Asp Phe Ala Asp Tyr Tyr Cys Leu Gln Thr Asp Ser
                100                 105                 110

Val Pro Leu Thr Phe Gly Gln Gly Thr Lys Val Glu Ile Lys
            115                 120                 125
```

<210> SEQ ID NO 168
<211> LENGTH: 107
<212> TYPE: PRT
<213> ORGANISM: Artificial Sequence
<220> FEATURE:
<223> OTHER INFORMATION: Description of Artificial Sequence: Synthetic amino acid sequence of hzKM5321 LV3 excluding signal sequence

<400> SEQUENCE: 168

```
Glu Thr Thr Leu Thr Gln Ser Pro Ser Ser Leu Ser Ala Ser Thr Gly
1               5                  10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Thr Gln Pro
65                  70                  75                  80

Glu Asp Phe Ala Asp Tyr Tyr Cys Leu Gln Thr Asp Ser Val Pro Leu
                85                  90                  95

Thr Phe Gly Gln Gly Thr Lys Val Glu Ile Lys
            100                 105
```

<210> SEQ ID NO 169
<211> LENGTH: 378
<212> TYPE: DNA
<213> ORGANISM: Artificial Sequence
<220> FEATURE:
<223> OTHER INFORMATION: Description of Artificial Sequence: Synthetic hzKM5321 LV4 sequence
<220> FEATURE:
<221> NAME/KEY: CDS
<222> LOCATION: (1)..(378)

<400> SEQUENCE: 169

```
atg aag ctg ccc gtt cgc ctg ctt gtg ctg atg ttc tgg atc ccc gcg        48
Met Lys Leu Pro Val Arg Leu Leu Val Leu Met Phe Trp Ile Pro Ala
1               5                  10                  15 tcc tcc tcg gag act act ctg act cag tcc ccc tcc tcc ctg tcc gtg        96
Ser Ser Ser Glu Thr Thr Leu Thr Gln Ser Pro Ser Ser Leu Ser Val
            20                  25                  30 tcc act ggg gat cgc gtg act atc acc tgt atc act tcc act gac atc       144
Ser Thr Gly Asp Arg Val Thr Ile Thr Cys Ile Thr Ser Thr Asp Ile
        35                  40                  45 gac gat gac atg aac tgg tac cag cag aag cct ggg aag gct ccc aag       192
Asp Asp Asp Met Asn Trp Tyr Gln Gln Lys Pro Gly Lys Ala Pro Lys
    50                  55                  60 ctg ctg atc tcc gag ggg aac act ctg cgc cct ggc gtt cct tcc cgc       240
Leu Leu Ile Ser Glu Gly Asn Thr Leu Arg Pro Gly Val Pro Ser Arg
65                  70                  75                  80 ttc tcc ggc tct ggc tct ggg act gac ttc acc ttc act atc tcc tcc       288
Phe Ser Gly Ser Gly Ser Gly Thr Asp Phe Thr Phe Thr Ile Ser Ser
                85                  90                  95 act cag ccc gag gac ttc gcc acc tac tac tgc ctg cag act gat tcc       336
Thr Gln Pro Glu Asp Phe Ala Thr Tyr Tyr Cys Leu Gln Thr Asp Ser
            100                 105                 110 gtg ccc ctg act ttc ggg cag ggg act aaa gtg gag atc aag                378
Val Pro Leu Thr Phe Gly Gln Gly Thr Lys Val Glu Ile Lys
        115                 120                 125
```

<210> SEQ ID NO 170
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 170

Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Val
            20                  25                  30

Ser Thr Gly Asp Arg Val Thr Ile Thr Cys Ile Thr Ser Thr Asp Ile
        35                  40                  45

Asp Asp Asp Met Asn Trp Tyr Gln Gln Lys Pro Gly Lys Ala Pro Lys
    50                  55                  60

Leu Leu Ile Ser Glu Gly Asn Thr Leu Arg Pro Gly Val Pro Ser Arg
65                  70                  75                  80

Phe Ser Gly Ser Gly Ser Gly Thr Asp Phe Thr Phe Thr Ile Ser Ser
                85                  90                  95

Thr Gln Pro Glu Asp Phe Ala Thr Tyr Tyr Cys Leu Gln Thr Asp Ser
            100                 105                 110

Val Pro Leu Thr Phe Gly Gln Gly Thr Lys Val Glu Ile Lys
        115                 120                 125

<210> SEQ ID NO 171
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV4 excluding
      signal sequence

<400> SEQUENCE: 171

Glu Thr Thr Leu Thr Gln Ser Pro Ser Ser Leu Ser Val Ser Thr Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Ala Pro Lys Leu Leu Ile
        35                  40                  45

Ser Glu Gly Asn Thr Leu Arg Pro Gly Val Pro Ser Arg Phe Ser Gly
    50                  55                  60

Ser Gly Ser Gly Thr Asp Phe Thr Phe Thr Ile Ser Ser Thr Gln Pro
65                  70                  75                  80

Glu Asp Phe Ala Thr Tyr Tyr Cys Leu Gln Thr Asp Ser Val Pro Leu
                85                  90                  95

Thr Phe Gly Gln Gly Thr Lys Val Glu Ile Lys
            100                 105

<210> SEQ ID NO 172
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5321 LV6 sequence
<220> FEATURE:
<221> NAME/KEY: CDS
<222> LOCATION: (1)..(378)

<400> SEQUENCE: 172

```
atg aag ctg ccc gtt cgc ctg ctt gtg ctg atg ttc tgg atc ccc gcg    48
Met Lys Leu Pro Val Arg Leu Leu Val Leu Met Phe Trp Ile Pro Ala
1               5                   10                  15 tcc tcc tcg gag act act ctg act cag tcc ccc tcc tcc ctg tcc gtg    96
Ser Ser Ser Glu Thr Thr Leu Thr Gln Ser Pro Ser Ser Leu Ser Val
                20                  25                  30 tcc act ggg gat cgc gtg acc atc acc tgt atc act tcc act gac atc   144
Ser Thr Gly Asp Arg Val Thr Ile Thr Cys Ile Thr Ser Thr Asp Ile
            35                  40                  45 gac gat gac atg aac tgg tac cag cag aag cct ggg aag cct ccc aag   192
Asp Asp Asp Met Asn Trp Tyr Gln Gln Lys Pro Gly Lys Pro Pro Lys
        50                  55                  60 ctg ctg atc tcc gag ggg aac act ctg cgc cct ggc gtt cct tcc cgc   240
Leu Leu Ile Ser Glu Gly Asn Thr Leu Arg Pro Gly Val Pro Ser Arg
65                  70                  75                  80 ttc tcc tct tcc ggc tcc ggg act gac ttc act ctg act atc tcc tcc   288
Phe Ser Ser Ser Gly Ser Gly Thr Asp Phe Thr Leu Thr Ile Ser Ser
                85                  90                  95 act cag ccc gag gac ttc gcc gac tac tac tgc ctg cag act gat tcc   336
Thr Gln Pro Glu Asp Phe Ala Asp Tyr Tyr Cys Leu Gln Thr Asp Ser
                100                 105                 110 gtg ccc ctg act ttc ggg cag ggg act aaa gtg gag atc aag           378
Val Pro Leu Thr Phe Gly Gln Gly Thr Lys Val Glu Ile Lys
            115                 120                 125
```

<210> SEQ ID NO 173
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 173

```
Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Val
                20                  25                  30

Ser Thr Gly Asp Arg Val Thr Ile Thr Cys Ile Thr Ser Thr Asp Ile
            35                  40                  45

Asp Asp Asp Met Asn Trp Tyr Gln Gln Lys Pro Gly Lys Pro Pro Lys
        50                  55                  60

Leu Leu Ile Ser Glu Gly Asn Thr Leu Arg Pro Gly Val Pro Ser Arg
65                  70                  75                  80

Phe Ser Ser Ser Gly Ser Gly Thr Asp Phe Thr Leu Thr Ile Ser Ser
                85                  90                  95

Thr Gln Pro Glu Asp Phe Ala Asp Tyr Tyr Cys Leu Gln Thr Asp Ser
                100                 105                 110

Val Pro Leu Thr Phe Gly Gln Gly Thr Lys Val Glu Ile Lys
            115                 120                 125
```

<210> SEQ ID NO 174
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV6 excluding
      signal sequence

<400> SEQUENCE: 174

| Glu | Thr | Thr | Leu | Thr | Gln | Ser | Pro | Ser | Ser | Leu | Ser | Val | Ser | Thr | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Ile | Thr | Ser | Thr | Asp | Ile | Asp | Asp | Asp |
| | | | 20 | | | | | 25 | | | | | 30 | | |

| Met | Asn | Trp | Tyr | Gln | Gln | Lys | Pro | Gly | Lys | Pro | Pro | Lys | Leu | Leu | Ile |
| | | | 35 | | | | | 40 | | | | | 45 | | |

| Ser | Glu | Gly | Asn | Thr | Leu | Arg | Pro | Gly | Val | Pro | Ser | Arg | Phe | Ser | Ser |
| | 50 | | | | | 55 | | | | | 60 | | | | |

| Ser | Gly | Ser | Gly | Thr | Asp | Phe | Thr | Leu | Thr | Ile | Ser | Ser | Thr | Gln | Pro |
| 65 | | | | | 70 | | | | | 75 | | | | | 80 |

| Glu | Asp | Phe | Ala | Asp | Tyr | Tyr | Cys | Leu | Gln | Thr | Asp | Ser | Val | Pro | Leu |
| | | | | 85 | | | | | 90 | | | | | 95 | |

| Thr | Phe | Gly | Gln | Gly | Thr | Lys | Val | Glu | Ile | Lys |
|---|---|---|---|---|---|---|---|---|---|---|
| | | | 100 | | | | | 105 | | |

<210> SEQ ID NO 175
<211> LENGTH: 378
<212> TYPE: DNA
<213> ORGANISM: Artificial Sequence
<220> FEATURE:
<223> OTHER INFORMATION: Description of Artificial Sequence: Synthetic hzKM5321 LV7a sequence
<220> FEATURE:
<221> NAME/KEY: CDS
<222> LOCATION: (1)..(378)

<400> SEQUENCE: 175

| atg | aag | ctg | ccc | gtt | cgc | ctg | ctt | gtg | ctg | atg | ttc | tgg | atc | ccc | gcg | 48 |
|---|---|---|---|---|---|---|---|---|---|---|---|---|---|---|---|---|
| Met | Lys | Leu | Pro | Val | Arg | Leu | Leu | Val | Leu | Met | Phe | Trp | Ile | Pro | Ala | |
| 1 | | | | 5 | | | | | 10 | | | | | 15 | | |

| tcc | tcc | tcg | gag | act | act | ctg | act | cag | tcc | ccc | tcc | ctg | tcc | gtg | | 96 |
| Ser | Ser | Ser | Glu | Thr | Thr | Leu | Thr | Gln | Ser | Pro | Ser | Leu | Ser | Val | | |
| | | | 20 | | | | | 25 | | | | | 30 | | | |

| tcc | act | ggg | gat | cgc | gtg | act | atc | acc | tgt | atc | act | tcc | act | gac | atc | 144 |
| Ser | Thr | Gly | Asp | Arg | Val | Thr | Ile | Thr | Cys | Ile | Thr | Ser | Thr | Asp | Ile | |
| | | 35 | | | | | 40 | | | | | 45 | | | | |

| gac | gat | gac | atg | aac | tgg | tac | cag | cag | aag | cct | ggg | aag | cct | ccc | aag | 192 |
| Asp | Asp | Asp | Met | Asn | Trp | Tyr | Gln | Gln | Lys | Pro | Gly | Lys | Pro | Pro | Lys | |
| | 50 | | | | | 55 | | | | | 60 | | | | | |

| ctg | ctg | atc | tcc | gag | ggg | aac | act | ctg | cgc | cct | ggc | gtt | cct | tcc | cgc | 240 |
| Leu | Leu | Ile | Ser | Glu | Gly | Asn | Thr | Leu | Arg | Pro | Gly | Val | Pro | Ser | Arg | |
| 65 | | | | | 70 | | | | | 75 | | | | | 80 | |

| ttc | tcc | tct | tcc | ggc | tcc | ggg | act | gac | ttc | acc | ttc | act | atc | tcc | tcc | 288 |
| Phe | Ser | Ser | Ser | Gly | Ser | Gly | Thr | Asp | Phe | Thr | Phe | Thr | Ile | Ser | Ser | |
| | | | | 85 | | | | | 90 | | | | | 95 | | |

| act | cag | ccc | gag | gac | ttc | gcc | gac | tac | tac | tgc | ctg | cag | act | gat | tcc | 336 |
| Thr | Gln | Pro | Glu | Asp | Phe | Ala | Asp | Tyr | Tyr | Cys | Leu | Gln | Thr | Asp | Ser | |
| | | | 100 | | | | | 105 | | | | | 110 | | | |

| gtg | ccc | ctg | act | ttc | ggg | cag | ggg | act | aaa | gtg | gag | atc | aag | | | 378 |
| Val | Pro | Leu | Thr | Phe | Gly | Gln | Gly | Thr | Lys | Val | Glu | Ile | Lys | | | |
| | | 115 | | | | | 120 | | | | | 125 | | | | |

<210> SEQ ID NO 176
<211> LENGTH: 126
<212> TYPE: PRT
<213> ORGANISM: Artificial Sequence
<220> FEATURE:
<223> OTHER INFORMATION: Description of Artificial Sequence: Synthetic construct

<400> SEQUENCE: 176

Met Lys Leu Pro Val Arg Leu Leu Val Leu Met Phe Trp Ile Pro Ala
1               5                   10                  15

Ser Ser Ser Glu Thr Thr Leu Thr Gln Ser Pro Ser Ser Leu Ser Val
            20                  25                  30

Ser Thr Gly Asp Arg Val Thr Ile Thr Cys Ile Thr Ser Thr Asp Ile
        35                  40                  45

Asp Asp Asp Met Asn Trp Tyr Gln Gln Lys Pro Gly Lys Pro Pro Lys
    50                  55                  60

Leu Leu Ile Ser Glu Gly Asn Thr Leu Arg Pro Gly Val Pro Ser Arg
65                  70                  75                  80

Phe Ser Ser Ser Gly Ser Gly Thr Asp Phe Thr Phe Thr Ile Ser Ser
                85                  90                  95

Thr Gln Pro Glu Asp Phe Ala Asp Tyr Tyr Cys Leu Gln Thr Asp Ser
            100                 105                 110

Val Pro Leu Thr Phe Gly Gln Gly Thr Lys Val Glu Ile Lys
        115                 120                 125

<210> SEQ ID NO 177
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV7a excluding
      signal sequence

<400> SEQUENCE: 177

Glu Thr Thr Leu Thr Gln Ser Pro Ser Ser Leu Ser Val Ser Thr Gly
1               5                   10                  15

Asp Arg Val Thr Ile Thr Cys Ile Thr Ser Thr Asp Ile Asp Asp Asp
            20                  25                  30

Met Asn Trp Tyr Gln Gln Lys Pro Gly Lys Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Ser Gly Thr Asp Phe Thr Phe Thr Ile Ser Ser Thr Gln Pro
65                  70                  75                  80

Glu Asp Phe Ala Asp Tyr Tyr Cys Leu Gln Thr Asp Ser Val Pro Leu
                85                  90                  95

Thr Phe Gly Gln Gly Thr Lys Val Glu Ile Lys
            100                 105

<210> SEQ ID NO 178
<211> LENGTH: 378
<212> TYPE: DNA
<213> ORGANISM: Artificial Sequence
<220> FEATURE:
<223> OTHER INFORMATION: Description of Artificial Sequence: Synthetic
      hzKM5321 LV7b sequence
<220> FEATURE:
<221> NAME/KEY: CDS
<222> LOCATION: (1)..(378)

<400> SEQUENCE: 178 atg aag ctg ccc gtt cgc ctg ctt gtg ctg atg ttc tgg atc ccc gcg    48
Met Lys Leu Pro Val Arg Leu Leu Val Leu Met Phe Trp Ile Pro Ala
1               5                   10                  15 tcc tcg tcg gag act act gtg act cag tcc ccc tcc tcc ctg tcc gtg    96
Ser Ser Ser Glu Thr Thr Val Thr Gln Ser Pro Ser Ser Leu Ser Val

```
                     20                  25                  30 tcc gtg ggg gat cgc gtg act atc acc tgt atc act tcc act gac atc      144
Ser Val Gly Asp Arg Val Thr Ile Thr Cys Ile Thr Ser Thr Asp Ile
         35                  40                  45 gac gat gac atg aac tgg tac cag cag aag cct ggg aag gct ccc aag      192
Asp Asp Asp Met Asn Trp Tyr Gln Gln Lys Pro Gly Lys Ala Pro Lys
 50                  55                  60 ctg ctg atc tcc gag ggg aac act ctg cgc cct ggc gtt cct tcc cgc      240
Leu Leu Ile Ser Glu Gly Asn Thr Leu Arg Pro Gly Val Pro Ser Arg
65                  70                  75                  80 ttc tcc tct tcc ggc tcc ggg act gac ttc acc ttc act atc tcc tcc      288
Phe Ser Ser Ser Gly Ser Gly Thr Asp Phe Thr Phe Thr Ile Ser Ser
                 85                  90                  95 act cag ccc gag gac ttc gcc gac tac tac tgc ctg cag act gat tcc      336
Thr Gln Pro Glu Asp Phe Ala Asp Tyr Tyr Cys Leu Gln Thr Asp Ser
            100                 105                 110 gtg ccc ctg act ttc ggg cag ggg act aag ctg gag atc aag              378
Val Pro Leu Thr Phe Gly Gln Gly Thr Lys Leu Glu Ile Lys
        115                 120                 125

<210> SEQ ID NO 179
<211> LENGTH: 126
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 179

Met Lys Leu Pro Val Arg Leu Leu Val Leu Met Phe Trp Ile Pro Ala
1               5                   10                  15

Ser Ser Ser Glu Thr Thr Val Thr Gln Ser Pro Ser Ser Leu Ser Val
            20                  25                  30

Ser Val Gly Asp Arg Val Thr Ile Thr Cys Ile Thr Ser Thr Asp Ile
        35                  40                  45

Asp Asp Asp Met Asn Trp Tyr Gln Gln Lys Pro Gly Lys Ala Pro Lys
    50                  55                  60

Leu Leu Ile Ser Glu Gly Asn Thr Leu Arg Pro Gly Val Pro Ser Arg
65                  70                  75                  80

Phe Ser Ser Ser Gly Ser Gly Thr Asp Phe Thr Phe Thr Ile Ser Ser
                85                  90                  95

Thr Gln Pro Glu Asp Phe Ala Asp Tyr Tyr Cys Leu Gln Thr Asp Ser
            100                 105                 110

Val Pro Leu Thr Phe Gly Gln Gly Thr Lys Leu Glu Ile Lys
        115                 120                 125

<210> SEQ ID NO 180
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV7b excluding
      signal sequence

<400> SEQUENCE: 180

Glu Thr Thr Val Thr Gln Ser Pro Ser Ser Leu Ser Val Ser Val Gly
1               5                   10                  15

Asp Arg Val Thr Ile Thr Cys Ile Thr Ser Thr Asp Ile Asp Asp Asp
            20                  25                  30
```

```
Met Asn Trp Tyr Gln Gln Lys Pro Gly Lys Ala Pro Lys Leu Leu Ile
         35                  40                  45

Ser Glu Gly Asn Thr Leu Arg Pro Gly Val Pro Ser Arg Phe Ser Ser
 50                  55                  60

Ser Gly Ser Gly Thr Asp Phe Thr Phe Thr Ile Ser Ser Thr Gln Pro
 65                  70                  75                  80

Glu Asp Phe Ala Asp Tyr Tyr Cys Leu Gln Thr Asp Ser Val Pro Leu
                 85                  90                  95

Thr Phe Gly Gln Gly Thr Lys Leu Glu Ile Lys
                100                 105
```

<210> SEQ ID NO 181
<211> LENGTH: 378
<212> TYPE: DNA
<213> ORGANISM: Artificial Sequence
<220> FEATURE:
<223> OTHER INFORMATION: Description of Artificial Sequence: Synthetic hzKM5321 LV9 sequence
<220> FEATURE:
<221> NAME/KEY: CDS
<222> LOCATION: (1)..(378)

<400> SEQUENCE: 181

```
atg aag ctg ccc gtt cgc ctg ctt gtg ctg atg ttc tgg atc ccc gcg      48
Met Lys Leu Pro Val Arg Leu Leu Val Leu Met Phe Trp Ile Pro Ala
 1               5                  10                  15 tcc tcc tcg gag act act gtg act cag tcc ccc tcc ctg tcc gtg          96
Ser Ser Ser Glu Thr Thr Val Thr Gln Ser Pro Ser Ser Leu Ser Val
                 20                  25                  30 tcc act ggg gat cgc gtg act atc acc tgt atc act tcc act gac atc     144
Ser Thr Gly Asp Arg Val Thr Ile Thr Cys Ile Thr Ser Thr Asp Ile
             35                  40                  45 gac gat gac atg aac tgg tac cag cag aag cct ggg aag cct ccc aag     192
Asp Asp Asp Met Asn Trp Tyr Gln Gln Lys Pro Gly Lys Pro Pro Lys
 50                  55                  60 ctg ctg atc tcc gag ggg aac act ctg cgc cct ggc gtt cct tcc cgc     240
Leu Leu Ile Ser Glu Gly Asn Thr Leu Arg Pro Gly Val Pro Ser Arg
 65                  70                  75                  80 ttc tcc tct tcc ggc tcc ggg act gac ttc acc ttc act atc tcc tcc     288
Phe Ser Ser Ser Gly Ser Gly Thr Asp Phe Thr Phe Thr Ile Ser Ser
                 85                  90                  95 act cag ccc gag gac ttc gcc gac tac tac tgc ctg cag act gat tcc     336
Thr Gln Pro Glu Asp Phe Ala Asp Tyr Tyr Cys Leu Gln Thr Asp Ser
                100                 105                 110 gtg ccc ctg act ttc ggg cag ggg act aag ctg gag atc aag             378
Val Pro Leu Thr Phe Gly Gln Gly Thr Lys Leu Glu Ile Lys
            115                 120                 125
```

<210> SEQ ID NO 182
<211> LENGTH: 126
<212> TYPE: PRT
<213> ORGANISM: Artificial Sequence
<220> FEATURE:
<223> OTHER INFORMATION: Description of Artificial Sequence: Synthetic construct

<400> SEQUENCE: 182

```
Met Lys Leu Pro Val Arg Leu Leu Val Leu Met Phe Trp Ile Pro Ala
 1               5                  10                  15

Ser Ser Ser Glu Thr Thr Val Thr Gln Ser Pro Ser Ser Leu Ser Val
                 20                  25                  30

Ser Thr Gly Asp Arg Val Thr Ile Thr Cys Ile Thr Ser Thr Asp Ile
```

```
                35                  40                  45
Asp Asp Asp Met Asn Trp Tyr Gln Gln Lys Pro Gly Lys Pro Pro Lys
         50                  55                  60

Leu Leu Ile Ser Glu Gly Asn Thr Leu Arg Pro Gly Val Pro Ser Arg
 65                  70                  75                  80

Phe Ser Ser Ser Gly Ser Gly Thr Asp Phe Thr Phe Thr Ile Ser Ser
                 85                  90                  95

Thr Gln Pro Glu Asp Phe Ala Asp Tyr Tyr Cys Leu Gln Thr Asp Ser
            100                 105                 110

Val Pro Leu Thr Phe Gly Gln Gly Thr Lys Leu Glu Ile Lys
        115                 120                 125

<210> SEQ ID NO 183
<211> LENGTH: 107
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 LV9 excluding
      signal sequence

<400> SEQUENCE: 183

Glu Thr Thr Val Thr Gln Ser Pro Ser Ser Leu Ser Val Ser Thr Gly
 1               5                  10                  15

Asp Arg Val Thr Ile Thr Cys Ile Thr Ser Thr Asp Ile Asp Asp Asp
             20                  25                  30

Met Asn Trp Tyr Gln Gln Lys Pro Gly Lys Pro Pro Lys Leu Leu Ile
         35                  40                  45

Ser Glu Gly Asn Thr Leu Arg Pro Gly Val Pro Ser Arg Phe Ser Ser
 50                  55                  60

Ser Gly Ser Gly Thr Asp Phe Thr Phe Thr Ile Ser Ser Thr Gln Pro
 65                  70                  75                  80

Glu Asp Phe Ala Asp Tyr Tyr Cys Leu Gln Thr Asp Ser Val Pro Leu
                 85                  90                  95

Thr Phe Gly Gln Gly Thr Lys Leu Glu Ile Lys
            100                 105

<210> SEQ ID NO 184
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV0 sequence
<220> FEATURE:
<221> NAME/KEY: CDS
<222> LOCATION: (1)..(405)

<400> SEQUENCE: 184 atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
 1               5                  10                  15 gtg cag tgc cag gtg cat ctc gtg cag tct ggc tcc gag ctg aag aag      96
Val Gln Cys Gln Val His Leu Val Gln Ser Gly Ser Glu Leu Lys Lys
             20                  25                  30 cct ggc gct tct gtg aag atc tcc tgc aag gct tct ggc tac acc ttc     144
Pro Gly Ala Ser Val Lys Ile Ser Cys Lys Ala Ser Gly Tyr Thr Phe
         35                  40                  45 acc aac tac ggc atg aac tgg gtg aga cag gct cct ggc cag ggc ctg     192
Thr Asn Tyr Gly Met Asn Trp Val Arg Gln Ala Pro Gly Gln Gly Leu
 50                  55                  60
```

```
gaa tgg atg ggc tgg atc aac acc aac act ggc gag cct acc tac acc        240
Glu Trp Met Gly Trp Ile Asn Thr Asn Thr Gly Glu Pro Thr Tyr Thr
 65                  70                  75                  80 gag gag ttc aag ggc aga ttc gtg ttc tcc ctg gac acc tct gtg acc        288
Glu Glu Phe Lys Gly Arg Phe Val Phe Ser Leu Asp Thr Ser Val Thr
                 85                  90                  95 acc tcc tac ctg cag atc tcc acc ctg aag gct gag gat acc gct gtg        336
Thr Ser Tyr Leu Gln Ile Ser Thr Leu Lys Ala Glu Asp Thr Ala Val
            100                 105                 110 tac ttc tgc gct cga gat gag ggc tgg ttt gtg tac tgg ggc cag ggc        384
Tyr Phe Cys Ala Arg Asp Glu Gly Trp Phe Val Tyr Trp Gly Gln Gly
        115                 120                 125 acc ctc gtg acc gtg tcc tcc                                            405
Thr Leu Val Thr Val Ser Ser
    130                 135

<210> SEQ ID NO 185
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 185

Met Asn Leu Gly Leu Ser Leu Ile Phe Leu Ala Leu Ile Leu Lys Gly
 1               5                  10                  15

Val Gln Cys Gln Val His Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Asn Thr Gly Glu Pro Thr Tyr Thr
 65                  70                  75                  80

Glu Glu Phe Lys Gly Arg Phe Val Phe Ser Leu Asp Thr Ser Val Thr
                 85                  90                  95

Thr Ser Tyr Leu Gln Ile Ser Thr Leu Lys Ala Glu Asp Thr Ala Val
            100                 105                 110

Tyr Phe Cys Ala Arg Asp Glu Gly Trp Phe Val Tyr Trp Gly Gln Gly
        115                 120                 125

Thr Leu Val Thr Val Ser Ser
    130                 135

<210> SEQ ID NO 186
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV0 excluding
      signal sequence

<400> SEQUENCE: 186

Gln Val His Leu Val Gln Ser Gly Ser Glu Leu Lys Lys Pro Gly Ala
 1               5                  10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45
```

```
Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ser Tyr
65                  70                  75                  80

Leu Gln Ile Ser Thr Leu Lys Ala Glu Asp Thr Ala Val Tyr Phe Cys
                85                  90                  95

Ala Arg Asp Glu Gly Trp Phe Val Tyr Trp Gly Gln Gly Thr Leu Val
            100                 105                 110

Thr Val Ser Ser
        115

<210> SEQ ID NO 187
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV1 sequence
<220> FEATURE:
<221> NAME/KEY: CDS
<222> LOCATION: (1)..(405)

<400> SEQUENCE: 187 atg aat ctg ggg ctg tcg ctg atc ttc ctg gcg ctg atc ctg aag ggc     48
Met Asn Leu Gly Leu Ser Leu Ile Phe Leu Ala Leu Ile Leu Lys Gly
1               5                   10                  15 gtg cag tgc cag gtg cat ctc gtg cag tct ggc tcc gag ctg aag aag     96
Val Gln Cys Gln Val His Leu Val Gln Ser Gly Ser Glu Leu Lys Lys
            20                  25                  30 cct ggc gct tct gtg aag atc tcc tgc aag gct tct ggc tac acc ttc    144
Pro Gly Ala Ser Val Lys Ile Ser Cys Lys Ala Ser Gly Tyr Thr Phe
        35                  40                  45 acc aac tac ggc atg aac tgg gtg aga cag gct cct ggc cag ggc ctg    192
Thr Asn Tyr Gly Met Asn Trp Val Arg Gln Ala Pro Gly Gln Gly Leu
    50                  55                  60 aag tgg atg ggc tgg atc aac acc aac act ggc gag cct acc tac acc    240
Lys Trp Met Gly Trp Ile Asn Thr Asn Thr Gly Glu Pro Thr Tyr Thr
65                  70                  75                  80 gag gag ttc aag ggc aga ttc gtg ttc tcc ctg gac acc tct gtg acc    288
Glu Glu Phe Lys Gly Arg Phe Val Phe Ser Leu Asp Thr Ser Val Thr
                85                  90                  95 acc tcc tac ctg cag atc tcc acc ctg aag gct gag gat acc gct gtg    336
Thr Ser Tyr Leu Gln Ile Ser Thr Leu Lys Ala Glu Asp Thr Ala Val
            100                 105                 110 tac ttc tgc gct cga gat gag ggc tgg ttt gtg tac tgg ggc cag ggc    384
Tyr Phe Cys Ala Arg Asp Glu Gly Trp Phe Val Tyr Trp Gly Gln Gly
        115                 120                 125 act ctc gtg acc gtg tcc tcc                                        405
Thr Leu Val Thr Val Ser Ser
    130                 135

<210> SEQ ID NO 188
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 188

Met Asn Leu Gly Leu Ser Leu Ile Phe Leu Ala Leu Ile Leu Lys Gly
1               5                   10                  15
```

```
Val Gln Cys Gln Val His Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ser Tyr Leu Gln Ile Ser Thr Leu Lys Ala Glu Asp Thr Ala Val
            100                 105                 110

Tyr Phe Cys Ala Arg Asp Glu Gly Trp Phe Val Tyr Trp Gly Gln Gly
        115                 120                 125

Thr Leu Val Thr Val Ser Ser
    130                 135
```

<210> SEQ ID NO 189
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV1 excluding
      signal sequence

<400> SEQUENCE: 189

```
Gln Val His Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ser Tyr
65                  70                  75                  80

Leu Gln Ile Ser Thr Leu Lys Ala Glu Asp Thr Ala Val Tyr Phe Cys
                85                  90                  95

Ala Arg Asp Glu Gly Trp Phe Val Tyr Trp Gly Gln Gly Thr Leu Val
            100                 105                 110

Thr Val Ser Ser
        115
```

<210> SEQ ID NO 190
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV2a sequence
<220> FEATURE:
<221> NAME/KEY: CDS
<222> LOCATION: (1)..(405)

<400> SEQUENCE: 190

```
atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                   10                  15
```

| | | | | | | | | | | | | | | | |
|---|---|---|---|---|---|---|---|---|---|---|---|---|---|---|---|
| gtg | cag | tgc | cag | gtg | cat | ctc | gtg | cag | tct | ggc | tcc | gag | ctg | aag | aag | 96 |
| Val | Gln | Cys | Gln | Val | His | Leu | Val | Gln | Ser | Gly | Ser | Glu | Leu | Lys | Lys |
| | | | 20 | | | | | 25 | | | | | 30 | | |

| cct | ggc | gct | tct | gtg | aag | atc | tcc | tgc | aag | gct | tct | ggc | tac | acc | ttc | 144 |
| Pro | Gly | Ala | Ser | Val | Lys | Ile | Ser | Cys | Lys | Ala | Ser | Gly | Tyr | Thr | Phe |
| | 35 | | | | | 40 | | | | | 45 | | | | |

| acc | aac | tac | ggc | atg | aac | tgg | gtg | aag | cag | gct | cct | ggc | cag | ggc | ctg | 192 |
| Thr | Asn | Tyr | Gly | Met | Asn | Trp | Val | Lys | Gln | Ala | Pro | Gly | Gln | Gly | Leu |
| 50 | | | | | 55 | | | | | 60 | | | | | |

| aag | tgg | atg | ggc | tgg | atc | aac | acc | aac | act | ggc | gag | cct | acc | tac | acc | 240 |
| Lys | Trp | Met | Gly | Trp | Ile | Asn | Thr | Asn | Thr | Gly | Glu | Pro | Thr | Tyr | Thr |
| 65 | | | | 70 | | | | | 75 | | | | | 80 | |

| gag | gag | ttc | aag | ggc | aga | ttc | gtg | ttc | tcc | ctg | gac | acc | tct | gtg | acc | 288 |
| Glu | Glu | Phe | Lys | Gly | Arg | Phe | Val | Phe | Ser | Leu | Asp | Thr | Ser | Val | Thr |
| | | | | 85 | | | | | 90 | | | | | 95 | |

| acc | tcc | tac | ctg | cag | atc | tcc | acc | ctg | aag | gct | gag | gat | acc | gct | gtg | 336 |
| Thr | Ser | Tyr | Leu | Gln | Ile | Ser | Thr | Leu | Lys | Ala | Glu | Asp | Thr | Ala | Val |
| | | | 100 | | | | | 105 | | | | | 110 | | |

| tac | ttc | tgc | gct | cga | gat | gag | ggc | tgg | ttt | gtg | tac | tgg | ggc | cag | ggc | 384 |
| Tyr | Phe | Cys | Ala | Arg | Asp | Glu | Gly | Trp | Phe | Val | Tyr | Trp | Gly | Gln | Gly |
| | | 115 | | | | | 120 | | | | | 125 | | | |

| act | ctc | gtg | acc | gtg | tcc | tcc | | | | | | | | | | 405 |
| Thr | Leu | Val | Thr | Val | Ser | Ser |
| | 130 | | | | | 135 |

<210> SEQ ID NO 191
<211> LENGTH: 135
<212> TYPE: PRT
<213> ORGANISM: Artificial Sequence
<220> FEATURE:
<223> OTHER INFORMATION: Description of Artificial Sequence: Synthetic
construct

<400> SEQUENCE: 191

Met Asn Leu Gly Leu Ser Leu Ile Phe Leu Ala Leu Ile Leu Lys Gly
1               5                   10                  15

Val Gln Cys Gln Val His Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ser Tyr Leu Gln Ile Ser Thr Leu Lys Ala Glu Asp Thr Ala Val
            100                 105                 110

Tyr Phe Cys Ala Arg Asp Glu Gly Trp Phe Val Tyr Trp Gly Gln Gly
        115                 120                 125

Thr Leu Val Thr Val Ser Ser
    130                 135

<210> SEQ ID NO 192
<211> LENGTH: 116
<212> TYPE: PRT
<213> ORGANISM: Artificial Sequence
<220> FEATURE:
<223> OTHER INFORMATION: Description of Artificial Sequence: Synthetic
amino acid sequence of hzKM5321 HV2a excluding
signal sequence

<400> SEQUENCE: 192

```
Gln Val His Leu Val Gln Ser Gly Ser Glu Leu Lys Lys Pro Gly Ala
 1               5                  10                  15
Ser Val Lys Ile Ser Cys Lys Ala Ser Gly Tyr Thr Phe Thr Asn Tyr
             20                  25                  30
Gly Met Asn Trp Val Lys Gln Ala Pro Gly Gln Gly Leu Lys Trp Met
         35                  40                  45
Gly Trp Ile Asn Thr Asn Thr Gly Glu Pro Thr Tyr Thr Glu Glu Phe
     50                  55                  60
Lys Gly Arg Phe Val Phe Ser Leu Asp Thr Ser Val Thr Thr Ser Tyr
 65                  70                  75                  80
Leu Gln Ile Ser Thr Leu Lys Ala Glu Asp Thr Ala Val Tyr Phe Cys
                 85                  90                  95
Ala Arg Asp Glu Gly Trp Phe Val Tyr Trp Gly Gln Gly Thr Leu Val
            100                 105                 110
Thr Val Ser Ser
        115
```

<210> SEQ ID NO 193
<211> LENGTH: 405
<212> TYPE: DNA
<213> ORGANISM: Artificial Sequence
<220> FEATURE:
<223> OTHER INFORMATION: Description of Artificial Sequence: Synthetic hzKM5321 HV2b sequence
<220> FEATURE:
<221> NAME/KEY: CDS
<222> LOCATION: (1)..(405)

<400> SEQUENCE: 193

```
atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
 1               5                  10                  15 gtg cag tgc cag gtg cat ctc gtg cag tct ggc cct gag ctg aag aag      96
Val Gln Cys Gln Val His Leu Val Gln Ser Gly Pro Glu Leu Lys Lys
             20                  25                  30 cct ggc gct tct gtg aag atc tcc tgc aag gct tct ggc tac acc ttc     144
Pro Gly Ala Ser Val Lys Ile Ser Cys Lys Ala Ser Gly Tyr Thr Phe
         35                  40                  45 acc aac tac ggc atg aac tgg gtg aga cag gct cct ggc cag ggc ctg     192
Thr Asn Tyr Gly Met Asn Trp Val Arg Gln Ala Pro Gly Gln Gly Leu
     50                  55                  60 gaa tgg atg ggc tgg atc aac acc aac act ggc gag cct acc tac acc     240
Glu Trp Met Gly Trp Ile Asn Thr Asn Thr Gly Glu Pro Thr Tyr Thr
 65                  70                  75                  80 gag gag ttc aag ggc aga ttc gtg ttc tcc ctg gac acc tct gtg acc     288
Glu Glu Phe Lys Gly Arg Phe Val Phe Ser Leu Asp Thr Ser Val Thr
                 85                  90                  95 acc tcc tac ctg cag atc tcc acc ctg aag gct gag gat acc gct acc     336
Thr Ser Tyr Leu Gln Ile Ser Thr Leu Lys Ala Glu Asp Thr Ala Thr
            100                 105                 110 tac ttc tgc gct cga gat gag ggc tgg ttt gtg tac tgg ggc cag ggc     384
Tyr Phe Cys Ala Arg Asp Glu Gly Trp Phe Val Tyr Trp Gly Gln Gly
        115                 120                 125 acc ctc gtg acc gtg tcc tcc                                          405
Thr Leu Val Thr Val Ser Ser
        130                 135
```

<210> SEQ ID NO 194

<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 194

Met Asn Leu Gly Leu Ser Leu Ile Phe Leu Ala Leu Ile Leu Lys Gly
1               5                   10                  15

Val Gln Cys Gln Val His Leu Val Gln Ser Gly Pro Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ser Tyr Leu Gln Ile Ser Thr Leu Lys Ala Glu Asp Thr Ala Thr
            100                 105                 110

Tyr Phe Cys Ala Arg Asp Glu Gly Trp Phe Val Tyr Trp Gly Gln Gly
        115                 120                 125

Thr Leu Val Thr Val Ser Ser
        130                 135

<210> SEQ ID NO 195
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV2b excluding
      signal sequence

<400> SEQUENCE: 195

Gln Val His Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ser Tyr
65                  70                  75                  80

Leu Gln Ile Ser Thr Leu Lys Ala Glu Asp Thr Ala Thr Tyr Phe Cys
                85                  90                  95

Ala Arg Asp Glu Gly Trp Phe Val Tyr Trp Gly Gln Gly Thr Leu Val
            100                 105                 110

Thr Val Ser Ser
        115

<210> SEQ ID NO 196
<211> LENGTH: 405
<212> TYPE: DNA
<213> ORGANISM: Artificial Sequence
<220> FEATURE:
<223> OTHER INFORMATION: Description of Artificial Sequence: Synthetic hzKM5321 HV3a sequence
<220> FEATURE:
<221> NAME/KEY: CDS
<222> LOCATION: (1)..(405)

<400> SEQUENCE: 196

| | | | | | | | | | | | | | | | | |
|---|---|---|---|---|---|---|---|---|---|---|---|---|---|---|---|---|
| atg | aat | ctg | ggg | ctg | tcg | ctg | atc | ttc | ctg | gcg | ctg | atc | ctg | aag | ggc | 48 |
| Met | Asn | Leu | Gly | Leu | Ser | Leu | Ile | Phe | Leu | Ala | Leu | Ile | Leu | Lys | Gly | |
| 1 | | | | 5 | | | | | 10 | | | | | 15 | | |
| gtg | cag | tgc | cag | gtg | cat | ctc | gtg | cag | tct | ggc | cct | gag | ctg | aag | aag | 96 |
| Val | Gln | Cys | Gln | Val | His | Leu | Val | Gln | Ser | Gly | Pro | Glu | Leu | Lys | Lys | |
| | | | 20 | | | | | 25 | | | | | 30 | | | |
| cct | ggc | gct | tct | gtg | aag | atc | tcc | tgc | aag | gct | tct | ggc | tac | acc | ttc | 144 |
| Pro | Gly | Ala | Ser | Val | Lys | Ile | Ser | Cys | Lys | Ala | Ser | Gly | Tyr | Thr | Phe | |
| | | 35 | | | | | 40 | | | | | 45 | | | | |
| acc | aac | tac | ggc | atg | aac | tgg | gtg | aga | cag | gct | cct | ggc | cag | ggc | ctg | 192 |
| Thr | Asn | Tyr | Gly | Met | Asn | Trp | Val | Arg | Gln | Ala | Pro | Gly | Gln | Gly | Leu | |
| | 50 | | | | | 55 | | | | | 60 | | | | | |
| aag | tgg | atg | ggc | tgg | atc | aac | acc | aac | act | ggc | gag | cct | acc | tac | acc | 240 |
| Lys | Trp | Met | Gly | Trp | Ile | Asn | Thr | Asn | Thr | Gly | Glu | Pro | Thr | Tyr | Thr | |
| 65 | | | | | 70 | | | | | 75 | | | | | 80 | |
| gag | gag | ttc | aag | ggc | aga | ttc | gtg | ttc | tcc | ctg | gac | acc | tct | gtg | acc | 288 |
| Glu | Glu | Phe | Lys | Gly | Arg | Phe | Val | Phe | Ser | Leu | Asp | Thr | Ser | Val | Thr | |
| | | | | 85 | | | | | 90 | | | | | 95 | | |
| acc | tcc | tac | ctg | cag | atc | tcc | acc | ctg | aag | gct | gag | gat | acc | gct | acc | 336 |
| Thr | Ser | Tyr | Leu | Gln | Ile | Ser | Thr | Leu | Lys | Ala | Glu | Asp | Thr | Ala | Thr | |
| | | | 100 | | | | | 105 | | | | | 110 | | | |
| tac | ttc | tgc | gct | cga | gat | gag | ggc | tgg | ttt | gtg | tac | tgg | ggc | cag | ggc | 384 |
| Tyr | Phe | Cys | Ala | Arg | Asp | Glu | Gly | Trp | Phe | Val | Tyr | Trp | Gly | Gln | Gly | |
| | | 115 | | | | | 120 | | | | | 125 | | | | |
| act | ctc | gtg | acc | gtg | tcc | tcc | | | | | | | | | | 405 |
| Thr | Leu | Val | Thr | Val | Ser | Ser | | | | | | | | | | |
| | 130 | | | | | 135 | | | | | | | | | | |

<210> SEQ ID NO 197
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 197

Met Asn Leu Gly Leu Ser Leu Ile Phe Leu Ala Leu Ile Leu Lys Gly
1               5                   10                  15

Val Gln Cys Gln Val His Leu Val Gln Ser Gly Pro Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ser Tyr Leu Gln Ile Ser Thr Leu Lys Ala Glu Asp Thr Ala Thr
            100                 105                 110

Tyr Phe Cys Ala Arg Asp Glu Gly Trp Phe Val Tyr Trp Gly Gln Gly
        115                 120                 125

Thr Leu Val Thr Val Ser Ser

<210> SEQ ID NO 198
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV3a excluding
      signal sequence

<400> SEQUENCE: 198

Gln Val His Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Arg Gln Ala Pro Gly Gln Gly Leu Lys Trp Met
            35                  40                  45

Gly Trp Ile Asn Thr Asn Thr Gly Glu Pro Thr Tyr Thr Glu Glu Phe
        50                  55                  60

Lys Gly Arg Phe Val Phe Ser Leu Asp Thr Ser Val Thr Thr Ser Tyr
65                  70                  75                  80

Leu Gln Ile Ser Thr Leu Lys Ala Glu Asp Thr Ala Thr Tyr Phe Cys
                85                  90                  95

Ala Arg Asp Glu Gly Trp Phe Val Tyr Trp Gly Gln Gly Thr Leu Val
            100                 105                 110

Thr Val Ser Ser
        115

<210> SEQ ID NO 199
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV3b sequence
<220> FEATURE:
<221> NAME/KEY: CDS
<222> LOCATION: (1)..(405)

<400> SEQUENCE: 199 atg aat ctg ggg ctg tcg ctg atc ttc ctg gcg ctg atc ctg aag ggc     48
Met Asn Leu Gly Leu Ser Leu Ile Phe Leu Ala Leu Ile Leu Lys Gly
1               5                   10                  15 gtg cag tgc cag gtg cat ctc gtg cag tct ggc tcc gag ctg aag aag     96
Val Gln Cys Gln Val His Leu Val Gln Ser Gly Ser Glu Leu Lys Lys
                20                  25                  30 cct ggc gct tct gtg aag atc tcc tgc aag gct tct ggc tac acc ttc    144
Pro Gly Ala Ser Val Lys Ile Ser Cys Lys Ala Ser Gly Tyr Thr Phe
            35                  40                  45 acc aac tac ggc atg aac tgg gtg aag cag gct cct ggc cag ggc ctg    192
Thr Asn Tyr Gly Met Asn Trp Val Lys Gln Ala Pro Gly Gln Gly Leu
        50                  55                  60 aag tgg atg ggc tgg atc aac acc aac act ggc gag cct acc tac acc    240
Lys Trp Met Gly Trp Ile Asn Thr Asn Thr Gly Glu Pro Thr Tyr Thr
65                  70                  75                  80 gag gag ttc aag ggc aga ttc gtg ttc tcc ctg gac acc tct gtg acc    288
Glu Glu Phe Lys Gly Arg Phe Val Phe Ser Leu Asp Thr Ser Val Thr
                85                  90                  95 acc tcc tac ctg cag atc tcc acc ctg aag gct gag gat acc gct acc    336
Thr Ser Tyr Leu Gln Ile Ser Thr Leu Lys Ala Glu Asp Thr Ala Thr
            100                 105                 110

```
tac ttc tgc gct cga gat gag ggc tgg ttt gtg tac tgg ggc cag ggc      384
Tyr Phe Cys Ala Arg Asp Glu Gly Trp Phe Val Tyr Trp Gly Gln Gly
        115                 120                 125 act ctc gtg acc gtg tcc tcc                                          405
Thr Leu Val Thr Val Ser Ser
    130                 135

<210> SEQ ID NO 200
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 200

Met Asn Leu Gly Leu Ser Leu Ile Phe Leu Ala Leu Ile Leu Lys Gly
1               5                   10                  15

Val Gln Cys Gln Val His Leu Val Gln Ser Gly Ser Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Lys Gln Ala Pro Gly Gln Gly Leu
    50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ser Tyr Leu Gln Ile Ser Thr Leu Lys Ala Glu Asp Thr Ala Thr
            100                 105                 110

Tyr Phe Cys Ala Arg Asp Glu Gly Trp Phe Val Tyr Trp Gly Gln Gly
        115                 120                 125

Thr Leu Val Thr Val Ser Ser
    130                 135

<210> SEQ ID NO 201
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV3b excluding
      signal sequence

<400> SEQUENCE: 201

Gln Val His Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ser Tyr
65                  70                  75                  80

Leu Gln Ile Ser Thr Leu Lys Ala Glu Asp Thr Ala Thr Tyr Phe Cys
                85                  90                  95

Ala Arg Asp Glu Gly Trp Phe Val Tyr Trp Gly Gln Gly Thr Leu Val
            100                 105                 110
```

<210> SEQ ID NO 202
<211> LENGTH: 405
<212> TYPE: DNA
<213> ORGANISM: Artificial Sequence
<220> FEATURE:
<223> OTHER INFORMATION: Description of Artificial Sequence: Synthetic hzKM5321 HV4a sequence
<220> FEATURE:
<221> NAME/KEY: CDS
<222> LOCATION: (1)..(405)

<400> SEQUENCE: 202

```
atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                   10                  15 gtg cag tgc cag atc cac ctc gtg cag tct ggc cct gag ctg aag aag      96
Val Gln Cys Gln Ile His Leu Val Gln Ser Gly Pro Glu Leu Lys Lys
            20                  25                  30 cct ggc gct tct gtg aag atc tcc tgc aag gct tct ggc tac acc ttc     144
Pro Gly Ala Ser Val Lys Ile Ser Cys Lys Ala Ser Gly Tyr Thr Phe
        35                  40                  45 acc aac tac ggc atg aac tgg gtg aga cag gct cct ggc cag ggc ctg     192
Thr Asn Tyr Gly Met Asn Trp Val Arg Gln Ala Pro Gly Gln Gly Leu
    50                  55                  60 gaa tgg atg ggc tgg atc aac acc aac acc ggc gag cct acc tac acc     240
Glu Trp Met Gly Trp Ile Asn Thr Asn Thr Gly Glu Pro Thr Tyr Thr
65                  70                  75                  80 gag gag ttc aag ggc aga ttc gtg ttc tcc ctg gac acc tcc gtg acc     288
Glu Glu Phe Lys Gly Arg Phe Val Phe Ser Leu Asp Thr Ser Val Thr
                85                  90                  95 acc gct tac ctg cag atc tcc acc ctg aag gct gag gat acc gct gtg     336
Thr Ala Tyr Leu Gln Ile Ser Thr Leu Lys Ala Glu Asp Thr Ala Val
            100                 105                 110 tac ttc tgc gct cga gat gag ggc tgg ttt gtg tac tgg ggc cag ggc     384
Tyr Phe Cys Ala Arg Asp Glu Gly Trp Phe Val Tyr Trp Gly Gln Gly
        115                 120                 125 acc ctg atc acc gtg tcc tcc                                          405
Thr Leu Ile Thr Val Ser Ser
    130                 135
```

<210> SEQ ID NO 203
<211> LENGTH: 135
<212> TYPE: PRT
<213> ORGANISM: Artificial Sequence
<220> FEATURE:
<223> OTHER INFORMATION: Description of Artificial Sequence: Synthetic construct

<400> SEQUENCE: 203

```
Met Asn Leu Gly Leu Ser Leu Ile Phe Leu Ala Leu Ile Leu Lys Gly
1               5                   10                  15

Val Gln Cys Gln Ile His Leu Val Gln Ser Gly Pro Glu Leu Lys Lys
            20                  25                  30

Pro Gly Ala Ser Val Lys Ile Ser Cys Lys Ala Ser Gly Tyr Thr Phe
        35                  40                  45

Thr Asn Tyr Gly Met Asn Trp Val Arg Gln Ala Pro Gly Gln Gly Leu
    50                  55                  60

Glu Trp Met Gly Trp Ile Asn Thr Asn Thr Gly Glu Pro Thr Tyr Thr
65                  70                  75                  80
```

```
Glu Glu Phe Lys Gly Arg Phe Val Phe Ser Leu Asp Thr Ser Val Thr
                85                  90                  95

Thr Ala Tyr Leu Gln Ile Ser Thr Leu Lys Ala Glu Asp Thr Ala Val
            100                 105                 110

Tyr Phe Cys Ala Arg Asp Glu Gly Trp Phe Val Tyr Trp Gly Gln Gly
        115                 120                 125

Thr Leu Ile Thr Val Ser Ser
    130                 135

<210> SEQ ID NO 204
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV4a excluding
      signal sequence

<400> SEQUENCE: 204

Gln Ile His Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ala Tyr
65                  70                  75                  80

Leu Gln Ile Ser Thr Leu Lys Ala Glu Asp Thr Ala Val Tyr Phe Cys
                85                  90                  95

Ala Arg Asp Glu Gly Trp Phe Val Tyr Trp Gly Gln Gly Thr Leu Ile
            100                 105                 110

Thr Val Ser Ser
        115

<210> SEQ ID NO 205
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV4b sequence
<220> FEATURE:
<221> NAME/KEY: CDS
<222> LOCATION: (1)..(405)

<400> SEQUENCE: 205 atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                   10                  15 gtg cag tgc cag gtg cat ctc gtg cag tct ggc cct gag ctg aag aag      96
Val Gln Cys Gln Val His Leu Val Gln Ser Gly Pro Glu Leu Lys Lys
            20                  25                  30 cct ggc gct tct gtg aag atc tcc tgc aag gct tct ggc tac acc ttc     144
Pro Gly Ala Ser Val Lys Ile Ser Cys Lys Ala Ser Gly Tyr Thr Phe
        35                  40                  45 acc aac tac ggc atg aac tgg gtg aag cag gct cct ggc cag ggc ctg     192
Thr Asn Tyr Gly Met Asn Trp Val Lys Gln Ala Pro Gly Gln Gly Leu
    50                  55                  60
```

```
aag tgg atg ggc tgg atc aac acc aac act ggc gag cct acc tac acc   240
Lys Trp Met Gly Trp Ile Asn Thr Asn Thr Gly Glu Pro Thr Tyr Thr
 65              70                  75                  80 gag gag ttc aag ggc aga ttc gtg ttc tcc ctg gac acc tct gtg acc   288
Glu Glu Phe Lys Gly Arg Phe Val Phe Ser Leu Asp Thr Ser Val Thr
             85                  90                  95 acc tcc tac ctg cag atc tcc acc ctg aag gct gag gat acc gct acc   336
Thr Ser Tyr Leu Gln Ile Ser Thr Leu Lys Ala Glu Asp Thr Ala Thr
             100                 105                 110 tac ttc tgc gct cga gat gag ggc tgg ttt gtg tac tgg ggc cag ggc   384
Tyr Phe Cys Ala Arg Asp Glu Gly Trp Phe Val Tyr Trp Gly Gln Gly
         115                 120                 125 act ctc gtg acc gtg tcc tcc                                       405
Thr Leu Val Thr Val Ser Ser
     130             135

<210> SEQ ID NO 206
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 206

Met Asn Leu Gly Leu Ser Leu Ile Phe Leu Ala Leu Ile Leu Lys Gly
 1               5                   10                  15

Val Gln Cys Gln Val His Leu Val Gln Ser Gly Pro Glu Leu Lys Lys
             20                  25                  30

Pro Gly Ala Ser Val Lys Ile Ser Cys Lys Ala Ser Gly Tyr Thr Phe
         35                  40                  45

Thr Asn Tyr Gly Met Asn Trp Val Lys Gln Ala Pro Gly Gln Gly Leu
     50                  55                  60

Lys Trp Met Gly Trp Ile Asn Thr Asn Thr Gly Glu Pro Thr Tyr Thr
 65              70                  75                  80

Glu Glu Phe Lys Gly Arg Phe Val Phe Ser Leu Asp Thr Ser Val Thr
             85                  90                  95

Thr Ser Tyr Leu Gln Ile Ser Thr Leu Lys Ala Glu Asp Thr Ala Thr
             100                 105                 110

Tyr Phe Cys Ala Arg Asp Glu Gly Trp Phe Val Tyr Trp Gly Gln Gly
         115                 120                 125

Thr Leu Val Thr Val Ser Ser
     130             135

<210> SEQ ID NO 207
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV4b excluding
      signal sequence

<400> SEQUENCE: 207

Gln Val His Leu Val Gln Ser Gly Pro Glu Leu Lys Lys Pro Gly Ala
 1               5                   10                  15

Ser Val Lys Ile Ser Cys Lys Ala Ser Gly Tyr Thr Phe Thr Asn Tyr
             20                  25                  30

Gly Met Asn Trp Val Lys Gln Ala Pro Gly Gln Gly Leu Lys Trp Met
         35                  40                  45
```

```
Gly Trp Ile Asn Thr Asn Thr Gly Glu Pro Thr Tyr Thr Glu Phe
 50              55                  60

Lys Gly Arg Phe Val Phe Ser Leu Asp Thr Ser Val Thr Thr Ser Tyr
 65              70                  75                  80

Leu Gln Ile Ser Thr Leu Lys Ala Glu Asp Thr Ala Thr Tyr Phe Cys
             85                  90                  95

Ala Arg Asp Glu Gly Trp Phe Val Tyr Trp Gly Gln Gly Thr Leu Val
             100                 105                 110

Thr Val Ser Ser
         115
```

<210> SEQ ID NO 208
<211> LENGTH: 405
<212> TYPE: DNA
<213> ORGANISM: Artificial Sequence
<220> FEATURE:
<223> OTHER INFORMATION: Description of Artificial Sequence: Synthetic hzKM5321 HV5 sequence
<220> FEATURE:
<221> NAME/KEY: CDS
<222> LOCATION: (1)..(405)

<400> SEQUENCE: 208

```
atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                  10                  15 gtg cag tgc cag atc cac ctc gtg cag tct ggc tcc gag ctg aag aag      96
Val Gln Cys Gln Ile His Leu Val Gln Ser Gly Ser Glu Leu Lys Lys
             20                  25                  30 cct ggc gct tct gtg aag atc tcc tgc aag gct tct ggc tac acc ttc     144
Pro Gly Ala Ser Val Lys Ile Ser Cys Lys Ala Ser Gly Tyr Thr Phe
         35                  40                  45 acc aac tac ggc atg aac tgg gtg aag cag gct cct ggc cag ggc ctg     192
Thr Asn Tyr Gly Met Asn Trp Val Lys Gln Ala Pro Gly Gln Gly Leu
     50                  55                  60 aag tgg atg ggc tgg atc aac acc aac acc ggc gag cct acc tac acc     240
Lys Trp Met Gly Trp Ile Asn Thr Asn Thr Gly Glu Pro Thr Tyr Thr
 65                  70                  75                  80 gag gag ttc aag ggc aga ttc gtg ttc tct ctg gac acc tcc gtg acc     288
Glu Glu Phe Lys Gly Arg Phe Val Phe Ser Leu Asp Thr Ser Val Thr
                 85                  90                  95 acc gct tac ctg cag atc tcc acc ctg aag gct gag gat acc gct gtg     336
Thr Ala Tyr Leu Gln Ile Ser Thr Leu Lys Ala Glu Asp Thr Ala Val
             100                 105                 110 tac ttc tgc gct cga gat gag ggc tgg ttt gtg tac tgg ggc cag ggc     384
Tyr Phe Cys Ala Arg Asp Glu Gly Trp Phe Val Tyr Trp Gly Gln Gly
         115                 120                 125 acc ctg atc acc gtg tcc tcc                                         405
Thr Leu Ile Thr Val Ser Ser
     130                 135
```

<210> SEQ ID NO 209
<211> LENGTH: 135
<212> TYPE: PRT
<213> ORGANISM: Artificial Sequence
<220> FEATURE:
<223> OTHER INFORMATION: Description of Artificial Sequence: Synthetic construct

<400> SEQUENCE: 209

```
Met Asn Leu Gly Leu Ser Leu Ile Phe Leu Ala Leu Ile Leu Lys Gly
1               5                  10                  15
```

Val Gln Cys Gln Ile His Leu Val Gln Ser Gly Ser Glu Leu Lys Lys
                20                  25                  30

Pro Gly Ala Ser Val Lys Ile Ser Cys Lys Ala Ser Gly Tyr Thr Phe
            35                  40                  45

Thr Asn Tyr Gly Met Asn Trp Val Lys Gln Ala Pro Gly Gln Gly Leu
        50                  55                  60

Lys Trp Met Gly Trp Ile Asn Thr Asn Thr Gly Glu Pro Thr Tyr Thr
65                  70                  75                  80

Glu Glu Phe Lys Gly Arg Phe Val Phe Ser Leu Asp Thr Ser Val Thr
                85                  90                  95

Thr Ala Tyr Leu Gln Ile Ser Thr Leu Lys Ala Glu Asp Thr Ala Val
            100                 105                 110

Tyr Phe Cys Ala Arg Asp Glu Gly Trp Phe Val Tyr Trp Gly Gln Gly
        115                 120                 125

Thr Leu Ile Thr Val Ser Ser
        130                 135

<210> SEQ ID NO 210
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV5 excluding
      signal sequence

<400> SEQUENCE: 210

Gln Ile His Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Asn Thr Gly Glu Pro Thr Tyr Thr Glu Glu Phe
    50                  55                  60

Lys Gly Arg Phe Val Phe Ser Leu Asp Thr Ser Val Thr Thr Ala Tyr
65                  70                  75                  80

Leu Gln Ile Ser Thr Leu Lys Ala Glu Asp Thr Ala Val Tyr Phe Cys
                85                  90                  95

Ala Arg Asp Glu Gly Trp Phe Val Tyr Trp Gly Gln Gly Thr Leu Ile
            100                 105                 110

Thr Val Ser Ser
        115

<210> SEQ ID NO 211
<211> LENGTH: 405
<212> TYPE: DNA
<213> ORGANISM: Artificial Sequence
<220> FEATURE:
<223> OTHER INFORMATION: Description of Artificial Sequence: Synthetic
      hzKM5321 HV7 sequence
<220> FEATURE:
<221> NAME/KEY: CDS
<222> LOCATION: (1)..(405)

<400> SEQUENCE: 211 atg aat ctg ggg ctg tcg ctg atc ttc ctg gcg ctg atc ctg aag ggc      48
Met Asn Leu Gly Leu Ser Leu Ile Phe Leu Ala Leu Ile Leu Lys Gly
1               5                   10                  15 gtg cag tgc cag atc cac ctc gtg cag tct ggc cct gag ctg aag aag      96

```
Val Gln Cys Gln Ile His Leu Val Gln Ser Gly Pro Glu Leu Lys Lys
         20                  25                  30 cct ggc gct tct gtg aag atc tcc tgc aag gct tct ggc tac acc ttc      144
Pro Gly Ala Ser Val Lys Ile Ser Cys Lys Ala Ser Gly Tyr Thr Phe
             35                  40                  45 acc aac tac ggc atg aac tgg gtg aag cag gct cct ggc cag ggc ctg      192
Thr Asn Tyr Gly Met Asn Trp Val Lys Gln Ala Pro Gly Gln Gly Leu
     50                  55                  60 aag tgg atg ggc tgg atc aac acc aac acc ggc gag cct acc tac acc      240
Lys Trp Met Gly Trp Ile Asn Thr Asn Thr Gly Glu Pro Thr Tyr Thr
 65                  70                  75                  80 gag gag ttc aag ggc aga ttc gtg ttc tct ctg gac acc tcc gtg acc      288
Glu Glu Phe Lys Gly Arg Phe Val Phe Ser Leu Asp Thr Ser Val Thr
                 85                  90                  95 acc gct tac ctg cag atc tcc acc ctg aag gct gag gat acc gct acc      336
Thr Ala Tyr Leu Gln Ile Ser Thr Leu Lys Ala Glu Asp Thr Ala Thr
                100                 105                 110 tac ttc tgc gct cga gat gag ggc tgg ttt gtg tac tgg ggc cag ggc      384
Tyr Phe Cys Ala Arg Asp Glu Gly Trp Phe Val Tyr Trp Gly Gln Gly
            115                 120                 125 acc ctg atc acc gtg tcc tcc                                          405
Thr Leu Ile Thr Val Ser Ser
        130                 135

<210> SEQ ID NO 212
<211> LENGTH: 135
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 212

Met Asn Leu Gly Leu Ser Leu Ile Phe Leu Ala Leu Ile Leu Lys Gly
 1               5                  10                  15

Val Gln Cys Gln Ile His Leu Val Gln Ser Gly Pro Glu Leu Lys Lys
             20                  25                  30

Pro Gly Ala Ser Val Lys Ile Ser Cys Lys Ala Ser Gly Tyr Thr Phe
         35                  40                  45

Thr Asn Tyr Gly Met Asn Trp Val Lys Gln Ala Pro Gly Gln Gly Leu
     50                  55                  60

Lys Trp Met Gly Trp Ile Asn Thr Asn Thr Gly Glu Pro Thr Tyr Thr
 65                  70                  75                  80

Glu Glu Phe Lys Gly Arg Phe Val Phe Ser Leu Asp Thr Ser Val Thr
                 85                  90                  95

Thr Ala Tyr Leu Gln Ile Ser Thr Leu Lys Ala Glu Asp Thr Ala Thr
                100                 105                 110

Tyr Phe Cys Ala Arg Asp Glu Gly Trp Phe Val Tyr Trp Gly Gln Gly
            115                 120                 125

Thr Leu Ile Thr Val Ser Ser
        130                 135

<210> SEQ ID NO 213
<211> LENGTH: 116
<212> TYPE: PRT
<213> ORGANISM: Artificial Sequence
<220> FEATURE:
<223> OTHER INFORMATION: Description of Artificial Sequence: Synthetic
      amino acid sequence of hzKM5321 HV7 excluding
      signal sequence
```

```
<400> SEQUENCE: 213

Gln Ile His Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Asn Thr Gly Glu Pro Thr Tyr Thr Glu Glu Phe
        50                  55                  60

Lys Gly Arg Phe Val Phe Ser Leu Asp Thr Ser Val Thr Thr Ala Tyr
65                      70                  75                  80

Leu Gln Ile Ser Thr Leu Lys Ala Glu Asp Thr Ala Thr Tyr Phe Cys
                85                  90                  95

Ala Arg Asp Glu Gly Trp Phe Val Tyr Trp Gly Gln Gly Thr Leu Ile
            100                 105                 110

Thr Val Ser Ser
            115

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gly Gly Gly Gly Ser
1               5
```

ANTI HUMAN GAS6 MONOCLONAL ANTIBODY

CROSS-REFERENCE TO RELATED APPLICATIONS

This application is a National Stage application of PCT/JP2015/005291, filed Oct. 20, 2015, which claims priority from U.S. Provisional Application No. 62/066,687, filed Oct. 21, 2014.

TECHNICAL FIELD

Sequence Listing

The instant application contains a Sequence Listing which has been submitted electronically in ASCII format and is hereby incorporated by reference in its entirety. Said ASCII copy, created on May 15, 2017, is named 116129-0101_SL.txt and is 531,607 bytes in size.

RELATED APPLICATION

The present specification encompasses the contents described in the specification of U.S. Provisional Application No. 62/066,687 (filed on Oct. 21, 2014) on which the priority of the present application is based. The present invention relates to an antibody specifically binding to human growth arrest specific 6 (hGas6). Specifically, the present invention relates to a monoclonal antibody or an antibody fragment thereof which binds to at least one of amino acid residues at positions 314, 315, and 316 of human Gas6, a nucleic acid comprising a nucleotide sequence encoding the antibody or the antibody fragment, a transformed cell comprising the nucleic acid, a method for producing the antibody or the antibody fragment, a reagent for detection or assay of Gas6, comprising the antibody or the antibody fragment, a therapeutic agent or a diagnostic agent for a Gas6-related disease, comprising the antibody or the antibody fragment as an active ingredient, and use of the antibody or the antibody fragment for the production of a therapeutic agent or a diagnostic agent for a Gas6-related disease.

Background Art

Growth arrest specific 6 (Gas6) (AXL tyrosine kinase receptor ligand; also called AXLLG) gene was cloned in 1998 as a gene overexpressed in serum-starved cells (Non Patent Literature 1). Its protein Gas6 is constituted by 678 amino acids and consists of three domains: a γ-carboxy glutamic acid (Gla) domain, an epidermal growth factor (EGF)-like domain, and a sex hormone binding globulin (SHBG)-like domain containing two laminin G-type (LG) domains from the N terminus toward the C terminus (Non Patent Literature 2).

Gas6 has high amino acid sequence homology (44%) to protein S and is classified into the vitamin K-dependent Gla protein family, as with protein S. Gla is a glutamic acid residue carboxylated at its γ-carbon by γ-glutamyl carboxylase (GGCX) (Non Patent Literature 3). The binding activity of non-γ-carboxylated Gas6 against a receptor is reduced to approximately 1/10 as compared with γ-carboxylated Gas6 (Non Patent Literature 4), and its physiological activity is also reduced. The C-terminal SHBG domain is known as a domain binding to the receptor Axl (Non Patent Literature 5).

Other vitamin K-dependent proteins such as prothrombin or factor X are synthesized mainly in the liver, whereas Gas6 mRNA is hardly detected in the liver (Non Patent Literature 2). In humans, its mRNA expression has been observed in the lung, the intestine, the bone marrow, and the endothelium. In mice, the mRNA expression has been confirmed in the heart, the stomach, and the kidney. At the protein level, Gas6 has been confirmed to be present at 13 to 23 ng/mL in human plasma without apparent variations depending on age or sex. In addition, it has been reported that the pregnancy and childbirth of Gas6-knockout (KO) mice are normal, and their born children are free from problems associated with body weight, size, or reproductive capacity (Non Patent Literature 6).

Three receptors of Gas6 are known: Axl (Axl receptor tyrosine kinase), Sky (Rse, Tyro3 (Tyro3 protein tyrosine kinase)), and Mer TK (Mer tyrosine kinase protooncogene). All of these three receptors are single-pass transmembrane tyrosine kinases, and their extracellular domains are each constituted by two immunoglobulin-like domains followed by two fibronectin-III-like domains (Non Patent Literature 7). Gas6 has very high affinity for these three receptors. Although reported dissociation constants (Kd values) differ among literatures, $5\times10^{-11}$ M for Axl, $3\times10^{-11}$ M for Sky, and $3\times10^{-10}$ M for Mer have been reported as the highest affinity (Non Patent Literature 8).

The expression level of Gas6 or Axl is known to be increased in kidney diseases (Non Patent Literatures 9 and 10). In a test using NTN models (progressive glomerulonephritis models), the remarkable suppression of pathological conditions has been confirmed in Gas6 KO mice as compared with wild-type mice. It has also been confirmed that the pathological conditions suppressed in Gas6 KO mice are aggravated again by the administration of Gas6 (Non Patent Literature 11). It has been further confirmed that Gas6 and Axl are overexpressed by the initiation of pathological conditions in the kidneys of Thy1 nephritis rats that exhibit mesangioproliferative glomerulonephritis-like pathological conditions. In an experiment conducted by the administration of Axl Fc to Thy1 nephritis rats, the drastic amelioration of pathological conditions has been confirmed (Non Patent Literature 12). In models having a chronic disease type I diabetic nephropathy (STZ), it has also been confirmed that pathological conditions are suppressed in Gas6 KO mice (Non Patent Literature 13). For example, inhibition of PDGF expression and mesangial cell growth (Non Patent Literature 14), anti-inflammatory effects (Non Patent Literature 15), and antiplatelet effects (Non Patent Literatures 16 and 17) have been reported as mechanisms of action under which the aggravation of kidney diseases is suppressed by the neutralization of Gas6.

In recent years, many reports have described the association of Gas6 and a Gas6 receptor with the pathological conditions of cancer (Non Patent Literatures 18, 19, 20, and 21).

WG1 (Patent Literature 1) and CNTO300 (Non Patent Literature 22) have heretofore been known as anti-human Gas6 monoclonal antibodies. WG1 and CNTO300 reportedly have the activity of inhibiting the binding of Gas6 to its receptor Axl in vitro. Any other Gas6 neutralizing antibody has not yet been known.

CITATION LIST

Patent Literature

Patent Literature 1: U.S. Pat. No. 7,547,767

Non Patent Literature

Non Patent Literature 1: Cell 54, 787-793 (1988)
Non Patent Literature 2: Mol Cell Biol 13, 4976-4985 (1993)
Non Patent Literature 3: Journal of Thrombosis and Haemostasis 3, 1873-1878 (2005)
Non Patent Literature 4: FEBS Lett 408, 306-310 (1997)
Non Patent Literature 5: EMBO J 25, 80-87 (2006)
Non Patent Literature 6: Nat Med 7, 215-221 (2001)
Non Patent Literature 7: J Thromb Haemost 3, 733-741 (2005)
Non Patent Literature 8: Biochem J 387, 727-735 (2005)
Non Patent Literature 9: Am J Kidney Dis 43, 286-295 (2004)
Non Patent Literature 10: Transplant 27: 4166-4172 (2012)
Non Patent Literature 11: J Clin Invest 110, 239-246, doi: 10.1172/jci14861 (2002)
Non Patent Literature 12: Am J Pathol 158, 1423-1432 (2001)
Non Patent Literature 13: The Journal of biological chemistry 278, 20, 18229-18234 (2003)
Non Patent Literature 14: The Journal of biological chemistry 276, 45, 42364-42369 (2001)
Non Patent Literature 15: Blood 111, 8, 4096-4105 (2008)
Non Patent Literature 16: The Journal of Clinical Investigation 115, 237-246 (2005)
Non Patent Literature 17: Nature Medicine 7, 2, 215-221 (2001)
Non Patent Literature 18: The Journal of Clinical Investigation 123, 8, 3231-3242 (2013)
Non Patent Literature 19: Expert Opin Ther Targets. 14, 19, 1073-1090 (2010)
Non Patent Literature 20: Nature genetics 44, 8, 852-860 (2012)
Non Patent Literature 21: JOURNAL OF CELLULAR PHYSIOLOGY 204, 36-44 (2005)
Non Patent Literature 22: Biochem. J., 727-735 387 (2005)

SUMMARY OF INVENTION

Technical Problem

An object of the present invention is to provide a novel anti-human Gas6 monoclonal antibody specifically binding to a particular site of human Gas6 and having high neutralizing activity, and a therapeutic agent and a diagnostic agent for a Gas6-related disease, comprising the antibody.

Solution to Problem

As means for solving the problem, the present invention provides an anti-human Gas6 monoclonal antibody binding to at least one of amino acid residues at positions 314, 315, and 316 of human Gas6.

Specifically, the present invention relates to the following (1) to (19):

(1) A monoclonal antibody or an antibody fragment thereof which binds to at least one of amino acid residues at positions 314, 315, and 316 of human Gas6.

(2) The monoclonal antibody or the antibody fragment thereof according to (1), wherein the monoclonal antibody is a monoclonal antibody binding to amino acid residues at positions 314, 315, and 316 of human Gas6.

(3) The monoclonal antibody or the antibody fragment thereof according to (1) or (2), wherein the monoclonal antibody is any one antibody selected from the following antibodies (a) to (e):

(a) an antibody in which the amino acid sequences CDR1 to CDR3 of VH are the amino acid sequences shown in SEQ ID NOs: 79, 80, and 81, respectively, and the amino acid sequences of CDR1 to CDR3 of VL are the amino acid sequences shown in SEQ ID NOs: 82, 83, and 84, respectively;

(b) an antibody in which the amino acid sequences of CDR1 to CDR3 of VH are the amino acid sequences shown in SEQ ID NOs: 85, 86, and 87, respectively, and the amino acid sequences of CDR1 to CDR3 of VL are the amino acid sequences shown in SEQ ID NOs: 88, 89, and 90, respectively;

(c) an antibody which competes with the antibody (a) or (b) for binding to human Gas6;

(d) an antibody which binds to an epitope comprising an epitope to which the antibody (a) or (b) binds, i.e., an antibody which competes with the antibody (a) or (b) for binding to an epitope comprising an epitope to which the antibody (a) or (b) binds; and (e) an antibody which binds to the same epitope as an epitope to which the antibody (a) or (b) binds, i.e., an antibody which competes with the antibody (a) or (b) for binding to an epitope to which the antibody (a) or (b) binds.

(4) The monoclonal antibody or the antibody fragment thereof according to any one of (1) to (3), wherein the monoclonal antibody is any one antibody selected from the following antibodies (a) to (e):

(a) an antibody in which the amino acid sequence of VH is the amino acid sequence shown in SEQ ID NO: 69, and the amino acid sequence of VL is the amino acid sequence shown in SEQ ID NO: 72;

(b) an antibody in which the amino acid sequence of VH is the amino acid sequence shown in SEQ ID NO: 75, and the amino acid sequence of VL is the amino acid sequence shown in SEQ ID NO: 78;

(c) an antibody in which the amino acid sequence of VH is the amino acid sequence shown in SEQ ID NO: 135, and the amino acid sequence of VL is the amino acid sequence shown in SEQ ID NO: 123;

(d) an antibody in which the amino acid sequence of VH is the amino acid sequence shown in SEQ ID NO: 195, and the amino acid sequence of VL is the amino acid sequence shown in SEQ ID NO: 174; and (e) an antibody in which the amino acid sequence of VH is the amino acid sequence shown in SEQ ID NO: 186, and the amino acid sequence of VL is the amino acid sequence shown in SEQ ID NO: 180.

(5) The monoclonal antibody or the antibody fragment thereof according to any one of (1) to (4), wherein the monoclonal antibody is a recombinant antibody.

(6) The monoclonal antibody or the antibody fragment thereof according to (5), wherein the recombinant antibody is a recombinant antibody selected from a human chimeric antibody, a humanized antibody, and a human antibody.

(7) The antibody fragment according to any one of (1) to (6), wherein the antibody fragment is selected from Fab, Fab', F(ab')$_2$, single chain Fv (scFv), diabody, disulfide-stabilized Fv (dsFv), and a peptide comprising CDRs
(8) A nucleic acid having a nucleotide sequence encoding the antibody or the antibody fragment thereof according to any one of (1) to (7).
(9) A transformed cell comprising the nucleic acid according to (8).
(10) A method for producing the antibody or the antibody fragment thereof according to any one of (1) to (7), comprising culturing the cell according to (9) in a medium and collecting the antibody or the antibody fragment thereof from the culture medium.
(11) A reagent for detection or assay of Gas6, comprising the antibody or the antibody fragment thereof according to any one of (1) to (7) (if desired, together with a pharmacologically acceptable carrier).
(12) A therapeutic agent for a Gas6-related disease, comprising the antibody or the antibody fragment thereof according to any one of (1) to (7) as an active ingredient (if desired, together with a pharmacologically acceptable carrier).
(13) The therapeutic agent according to (12), wherein the Gas6-related disease is a kidney or cancer disease.
(14) The therapeutic agent according to (13), wherein the kidney disease is progressive glomerulonephritis, mesangioproliferative glomerulonephritis, diabetic nephropathy, or IgA nephropathy.
(15) The therapeutic agent according to (13), wherein the cancer disease is lung cancer, breast cancer, ovary cancer, prostate cancer, pancreatic cancer, kidney cancer, or glioblastoma.
(16) A diagnostic agent for a Gas6-related disease, comprising the antibody or the antibody fragment thereof according to any one of (1) to (7) as an active ingredient (if desired, together with a pharmacologically acceptable carrier).
(17) A method for diagnosing a Gas6-related disease, comprising detecting or assaying Gas6 using the antibody or the antibody fragment thereof according to any one of (1) to (7).
(18) Use of the antibody or the antibody fragment thereof according to any one of (1) to (7) for a production of a therapeutic agent for a Gas6-related disease.
(19) Use of the antibody or the antibody fragment thereof according to any one of (1) to (7) for a production of a diagnostic agent for a Gas6-related disease.

Advantageous Effects of Invention

The monoclonal antibody of the present invention specifically binds to a particular site of human Gas6 and inhibits the binding of Gas6 to a Gas6 receptor to suppress the activation of signal transduction in Gas6 receptor-expressing cells or to suppress increase in the growth of Gas6 receptor-expressing cells. Hence, the monoclonal antibody of the present invention can be used as a therapeutic agent and a diagnostic agent for Gas6-related diseases.

BRIEF DESCRIPTION OF DRAWINGS

FIG. 1 shows results of measuring the binding activity of obtained anti-Gas6 monoclonal antibodies against various antigens by ELISA. ELISA was carried out at N=2, and an average value thereof is shown in the graphs. In each graph, absorbance is shown in the vertical axis, and antibody concentration (μg/mL) is shown in the horizontal axis. The antigens used were (A) human Gas6-F, (B) cynomolgus monkey Gas6-F, (C) rat Gas6-F, (D) mouse Gas6-F, (E) BAP-F, and (F) protein S. o depicts the results about a KM5320-mKG1 antibody. □ depicts the results about a KM5321-mKG1 antibody. ▲ depicts the results about a CNTO antibody.
FIG. 2 shows results of evaluating the inhibitory activity of the anti-Gas6 monoclonal antibodies against the binding between each Gas6 and Axl ((A) human, (B) rat, (C) mouse, and (D) cynomolgus monkey). The experiment was carried out at N=2, and an average value thereof is shown in the graphs. In each graph, absorbance is shown in the vertical axis, and antibody concentration (ng/mL) is shown in the horizontal axis. o depicts the results about the KM5320-mKG1 antibody. ■ depicts the results about the KM5321-mKG1 antibody. ▲ depicts the results about a CNTO antibody.

FIG. 7 shows the amino acid sequences of the light chain variable region of a KM5320 antibody (SEQ ID NO: 72) and the light chain variable regions (LV0 (SEQ ID NO: 105), LV1a (SEQ ID NO: 108), LV1b (SEQ ID NO: 111), LV2a (SEQ ID NO: 114), LV2b (SEQ ID NO: 117), LV3 (SEQ ID NO: 120), LV5 (SEQ ID NO: 123), and LV6 (SEQ ID NO: 126)) of KM5320 humanized antibodies (hereinafter, referred to as hzKM5320 antibodies) without signal sequences. The boxed regions in these sequences show the amino acid sequences of CDRs.

FIG. 8 shows the amino acid sequences of the heavy chain variable region of the KM5320 antibody (SEQ ID NO: 69) and the heavy chain variable regions (HV0 (SEQ ID NO: 129), HV1 (SEQ ID NO: 132), HV2 (SEQ ID NO: 135), HV3a (SEQ ID NO: 138), HV3b (SEQ ID NO: 141), HV3c (SEQ ID NO: 144), HV4 (SEQ ID NO: 147), HV6 (SEQ ID NO: 150), and HV8 (SEQ ID NO: 153)) of the hzKM5320 antibodies without signal sequences. The boxed regions in these sequences show the amino acid sequences of CDRs.

FIG. 9 shows the amino acid sequences of the light chain variable region of a KM5321 antibody (SEQ ID NO: 78) and the light chain variable regions (LV0 (SEQ ID NO: 156), LV1a (SEQ ID NO: 159), LV1b (SEQ ID NO: 162), LV1c (SEQ ID NO: 165), LV3 (SEQ ID NO: 168), LV4 (SEQ ID NO: 171), LV6 (SEQ ID NO: 174), LV7a (SEQ ID NO: 177), LV7b (SEQ ID NO: 180), and LV9 (SEQ ID NO: 183)) of KM5321 humanized antibodies (hereinafter, referred to as hzKM5321 antibodies) without signal sequences. The boxed regions in these sequences show the amino acid sequences of CDRs.

FIG. 10 shows the amino acid sequences of the heavy chain variable region of the KM5321 antibody (SEQ ID NO: 75) and the heavy chain variable regions (HV0 (SEQ ID NO: 186), HV1 (SEQ ID NO: 189), HV2a (SEQ ID NO: 192), HV2b (SEQ ID NO: 195), HV3a (SEQ ID NO: 198), HV3b (SEQ ID NO: 201), HV4a (SEQ ID NO: 204), HV4b (SEQ ID NO: 207), HV5 (SEQ ID NO: 210), and HV7 (SEQ ID NO: 213)) of the hzKM5321 antibodies without signal sequences. The boxed regions in these sequences show the amino acid sequences of CDRs.

FIG. 11 shows the binding activity of (A) a KM5320 chimeric antibody and a hzKM5320 antibody and (B) a KM5321 chimeric antibody and a hzKM5321 antibody against human Gas6 protein. The experiment was carried out at N=2, and an average value thereof is shown in the graphs. In each graph, absorbance is shown in the vertical axis, and antibody concentration (ng/mL) is shown in the horizontal axis. In FIG. 11(A), ■ depicts the results about the KM5320 chimeric antibody. ◇ depicts the results about hzKM5320 LV5HV2. ● depicts the results about hzKM5320 LV1bHV0. ○ depicts the results about a negative control anti-DNP antibody. In FIG. 11(B), ■ depicts the results about the KM5321 chimeric antibody. ◇ depicts the results about hzKM5321 LV6HV2b. ● depicts the results about hzKM5321 LV7bHV0. ○ depicts the results about a negative control anti-DNP antibody.

FIG. 12 shows the inhibitory activity of (A) the KM5320 chimeric antibody and the hzKM5320 antibody and (B) the KM5321 chimeric antibody and the hzKM5321 antibody against the binding between human Gas6 protein and Axl. The experiment was carried out at N=2, and an average value thereof is shown in the graphs. In each graph, absorbance is shown in the vertical axis, and antibody concentration (ng/mL) is shown in the horizontal axis. In FIG. 12(A), ■ depicts the results about the KM5320 chimeric antibody. ◇ depicts the results about hzKM5320 LV5HV2. ● depicts the results about hzKM5320 LV1bHV0. a depicts the results about a negative control anti-DNP antibody. In FIG. 12(B), ■ depicts the results about the KM5321 chimeric antibody. ◇ depicts the results about hzKM5321 LV6HV2b. ● depicts the results about hzKM5321 LV7bHV0. ○ depicts the results about a negative control anti-DNP antibody.

DESCRIPTION OF EMBODIMENTS

Figure 3:
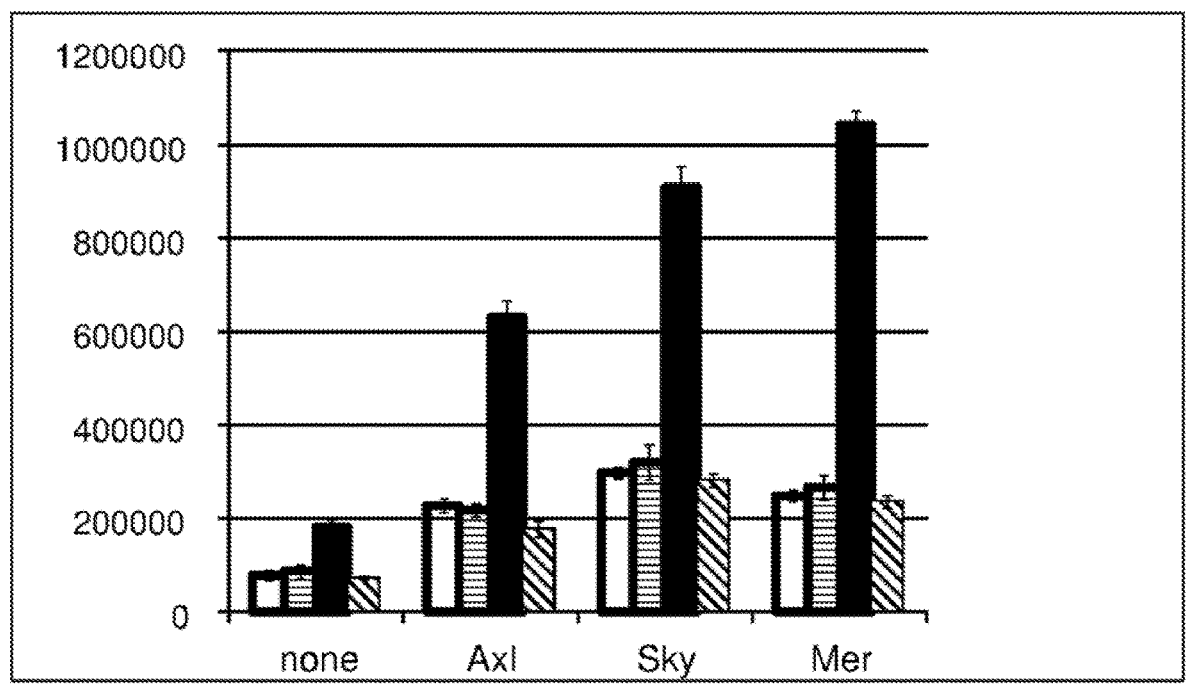
FIG. 3 shows results of evaluating the effects of the anti-Gas6 monoclonal antibodies on intracellular signal transduction by reporter assay. The experiment was carried out at N=3, and an average value thereof is shown in the graph. A value of standard deviation (SD) was used in the error bar. The vertical axis of the graph shows luminescence intensity, and the horizontal axis shows Gas6 receptors which were forcedly expressed on cells. The open bar depicts the results about the KM5320-mKG1 antibody. The bar with horizontal lines depicts the results about the KM5321-mKG1 antibody. The filled bar depicts the results about an isotype control. The bar with oblique lines depicts the results about a medium alone.

The present invention relates to a monoclonal antibody or an antibody fragment thereof which binds to at least one of amino acid residues at positions 314, 315, and 316 in the amino acid sequence of human Gas6. Specifically, the present invention relates to a monoclonal antibody or an antibody fragment thereof which binds to at least one of amino acid residues at positions 314, 315, and 316 present in the SHBG domain in the amino acid sequence of human Gas6, and a monoclonal antibody or an antibody fragment thereof which binds to at least one of amino acid residues at positions 314, 315, and 316 of human Gas6 comprising the amino acid sequence shown in SEQ ID NO: 4. Examples of the antibody of the present invention include an antibody binding to amino acid residue at position 314 of human Gas6 comprising the amino acid sequence shown in SEQ ID NO: 4, an antibody binding to amino acid residue at position 315 thereof, an antibody binding to amino acid residue at position 316 thereof, an antibody binding to amino acid residues at positions 314 and 315 thereof, an antibody binding to amino acid residues at positions 314 and 316 thereof, an antibody binding to amino acid residues at positions 315 and 316 thereof, and an antibody binding to amino acid residues at positions 314, 315, and 316 thereof.

Specific examples of the antibody of the present invention include any one antibody selected from the following antibodies (a) to (e):
(a) an antibody in which the amino acid sequences of complementarity determining region (hereinafter, abbreviated to CDR) 1 to CDR3 of heavy chain variable region (hereinafter, abbreviated to VH) are the amino acid sequences shown in SEQ ID NOs: 79, 80, and 81, respectively, and the amino acid sequences of CDR1 to CDR3 of light chain variable region (hereinafter, abbreviated to VL) are the amino acid sequences shown in SEQ ID NOs: 82, 83, and 84, respectively;
(b) an antibody in which the amino acid sequences of CDR1 to CDR3 of VH are the amino acid sequences shown in SEQ ID NOs: 85, 86, and 87, respectively, and the amino acid sequences of CDR1 to CDR3 of VL are the amino acid sequences shown in SEQ ID NOs: 88, 89, and 90, respectively;
(c) an antibody which competes with the antibody (a) or (b) for binding to human Gas6;
(d) an antibody which binds to an epitope comprising an epitope to which the antibody (a) or (b) binds; and
(e) an antibody which binds to the same epitope as an epitope to which the antibody (a) or (b) binds.

In one embodiment of the present invention, examples of the antibody (a) in which the amino acid sequences of CDR1 to CDR3 of VH are the amino acid sequences shown in SEQ ID NOs: 79, 80, and 81, respectively, and the amino acid sequences of CDR1 to CDR3 of VL are the amino acid sequences shown in SEQ ID NOs: 82, 83, and 84, respectively, include a mouse anti-human Gas6 monoclonal antibody KM5320-mKG1, an anti-human Gas6 mouse-rat chimeric KM5320-rKG1, and an anti-human Gas6 humanized antibody hzKM5320.

In one embodiment of the present invention, examples of the antibody (b) in which the amino acid sequences of CDR1 to CDR3 of VH are the amino acid sequences shown in SEQ ID NOs: 85, 86, and 87, respectively, and the amino acid sequences of CDR1 to CDR3 of VL are the amino acid sequences shown in SEQ ID NOs: 88, 89, and 90, respectively, include a mouse anti-human Gas6 monoclonal antibody KM5321-mKG1, an anti-human Gas6 mouse-rat chimeric antibody KM5321-rKG1, and an anti-human Gas6 humanized antibody hzKM5321.

When the antibody (a) or (b) is defined as a first antibody and an epitope to which the first antibody binds is defined as a first epitope, the antibody (d) of the present invention refers to a second antibody binding to a second epitope comprising the first epitope.

Specific examples of the antibody of the present invention also include any one antibody selected from the following antibodies (a) to (e):
(a) an antibody in which the amino acid sequence of VH is the amino acid sequence shown in SEQ ID NO: 69, and the amino acid sequence of VL is the amino acid sequence shown in SEQ ID NO: 72;
(b) an antibody in which the amino acid sequence of VH is the amino acid sequence shown in SEQ ID NO: 75, and the amino acid sequence of VL is the amino acid sequence shown in SEQ ID NO: 78;
(c) an antibody in which the amino acid sequence of VH is the amino acid sequence shown in SEQ ID NO: 135, and the amino acid sequence of VL is the amino acid sequence shown in SEQ ID NO: 123;
(d) an antibody in which the amino acid sequence of VH is the amino acid sequence shown in SEQ ID NO: 195, and the amino acid sequence of VL is the amino acid sequence shown in SEQ ID NO: 174; and
(e) an antibody in which the amino acid sequence of VH is the amino acid sequence shown in SEQ ID NO: 186, and the amino acid sequence of VL is the amino acid sequence shown in SEQ ID NO: 180.

In one embodiment, examples of the antibody (a) include KM5320-mKG1 and KM5320-rKG1. In one embodiment, examples of the antibody (b) include KM5321-mKG1 and KM5321-rKG1. In one embodiment, examples of the antibody (c) include an anti-human Gas6 humanized antibody hzKM5320 LV5HV2. In one embodiment, examples of the antibody (d) include an anti-human Gas6 humanized antibody hzKM5321 LV6HV2b. In one embodiment, examples of the antibody (e) include an anti-human Gas6 humanized antibody hzKM5321 LV7bHV0.

In the present invention, growth arrest-specific 6 (Gas6) is also referred to as AXL receptor kinase ligand (AXLLG) or AXL stimulatory factor (AXSF).

In the present invention, examples of human Gas6 include a polypeptide comprising the amino acid sequence shown in SEQ ID NO: 4 or the amino acid sequence of NCBI Accession No. NP_000811, a polypeptide that consists of an amino acid sequence in which one or more amino acids are deleted, substituted, or added in the amino acid sequence shown in SEQ ID NO: 4 or the amino acid sequence of NCBI Accession No. NP_000811, and has the functions of human Gas6, and a polypeptide that consists of an amino acid sequence having 60% or higher, preferably 80% or higher, more preferably 90% or higher, most preferably 95% or higher homology to the amino acid sequence shown in SEQ ID NO: 4 or the amino acid sequence of NCBI Accession No. NP_000811, and has the functions of human Gas6.

A polypeptide having the amino acid sequence in which one or more amino acids are deleted, substituted, or added in the amino acid sequence shown in SEQ ID NO: 4 or the amino acid sequence shown in NCBI Accession No. NP_000811 can be obtained by introducing a site-directed mutation to DNA encoding, for example, a polypeptide comprising the amino acid sequence of SEQ ID NO: 4 by use of site-directed mutagenesis [Molecular Cloning, A Laboratory Manual, Second Edition, Cold Spring Harbor Laboratory Press (1989); Current Protocols in Molecular Biology, John Wiley & Sons (1987-1997); Nucleic acids Research, 10, 6487 (1982); Proc. Natl. Acad. Sci. USA, 79, 6409 (1982); Gene, 34, 315 (1985); Nucleic Acids Research, 13, 4431 (1985); and Proc. Natl. Acad. Sci. USA, 82, 488 (1985)], etc.

The number of amino acids to be deleted, substituted, or added is not particularly limited and is preferably 1 to several dozen, for example, 1 to 20, more preferably 1 to several, for example, 1 to 5 amino acids.

Examples of the gene encoding human Gas6 include the nucleotide sequence shown in SEQ ID NO: 3 and the nucleotide sequence of NCBI Accession No. NM_000820. The gene encoding human Gas6 of the present invention also includes a gene comprising DNA that consists of a nucleotide sequence in which one or more nucleotides are deleted, substituted, or added in the nucleotide sequence shown in SEQ ID NO: 3 or the nucleotide sequence of NM_000820, and encodes a polypeptide having the functions of human Gas6, a gene comprising DNA that consists of a nucleotide sequence having at least 60% or higher homology, preferably 80% or higher homology, more preferably 95% or higher homology, to the nucleotide sequence shown in SEQ ID NO: 3 or the nucleotide sequence of NM_000820, and encodes a polypeptide having the functions of human Gas6, or a gene that consists of DNA hybridizing under stringent conditions to DNA comprising the nucleotide sequence shown in SEQ ID NO: 3 or the nucleotide sequence of NM_000820, and encodes a polypeptide having the functions of human Gas6.

The DNA hybridizing under stringent conditions refers to hybridizable DNA obtained by colony hybridization, plaque hybridization, Southern blot hybridization, or a DNA microarray method using DNA comprising the nucleotide sequence shown in SEQ ID NO: 3 or the nucleotide sequence of NM_000820 as a probe. Specific examples thereof can include DNA derived from a hybridized colony or plaque, or DNA that can be identified by hybridization at 65° C. in the presence of 0.7 to 1.0 mol/L sodium chloride using a filter or a glass slide on which a PCR product or oligo DNA having the sequence is immobilized [Molecular Cloning, A Laboratory Manual, Second Edition, Cold Spring Harbor Laboratory Press (1989); Current Protocols in Molecular Biology, John Wiley & Sons (1987-1997); and DNA Cloning 1: Core Techniques, A Practical Approach, Second Edition, Oxford University, (1995)], followed by the washing of the filter or the glass slide under a condition of 65° C. using a 0.1× to 2×SSC solution (the composition of a 1×SSC solution consists of 150 mmol/L sodium chloride and 15 mmol/L sodium citrate). Examples of the hybridizable DNA can include DNA having at least 60% or higher homology, preferably 80% or higher homology, more preferably 95% or higher homology, to the nucleotide sequence shown in SEQ ID NO: 3 or the nucleotide sequence of NM_000820.

Genetic polymorphisms are often found in the nucleotide sequences of genes encoding eukaryotic proteins. The gene encoding human Gas6 of the present invention also includes a gene having a small-scale mutation in its nucleotide sequence used in present invention resulting from such a polymorphism.

In the present invention, the numerical value of homology may be a numerical value calculated using a homology search program generally known to those skilled in the art, unless otherwise specified. Examples of the numerical value of nucleotide sequence homology include a numerical value calculated using the default parameters of BLAST [J. Mol. Biol., 215, 403 (1990)]. Examples of the numerical value of amino acid sequence homology include a numerical value calculated using the default parameters of BLAST2 [Nucleic Acids Res., 25, 3389 (1997); Genome Res., 7, 649 (1997); and ncbi.nlm.nih.gov/Education/BLASTinfo/information3.htmL].

The default parameters involve G (cost to open gap) of 5 for the nucleotide sequence and 11 for the amino acid sequence, -E (cost to extend gap) of 2 for the nucleotide sequence and 1 for the amino acid sequence, -q (penalty for nucleotide mismatch) of -3, -r (reward for nucleotide match) of 1, -e (expect value) of 10, -W (wordsize) of 11 residues for the nucleotide sequence and 3 residues for the amino acid sequence, -y [dropoff (X) for blast extensions in bits] of 20 for blastn and 7 for programs other than blastn, -X (X dropoff value for gapped alignment in bits) of 15, and -Z (final X dropoff value for gapped alignment in bits) of 50 for blastn and 25 for programs other than blastn (http://www.ncbi.nlm.nih.gov/blast/htmL/blastcgihelp.htmL).

A polypeptide comprising a partial sequence of the amino acid sequence shown in SEQ ID NO: 4 or the amino acid sequence of NCBI Accession No. NP_000811 can be prepared by a method generally known to those skilled in the art. Specifically, the polypeptide can be prepared by partially deleting DNA encoding the amino acid sequence of SEQ ID NO: 4 and culturing a transformant harboring an expression vector containing the resulting DNA fragment. The polypeptide having an amino acid sequence in which one or more amino acids are deleted, substituted, or added in the amino acid sequence shown in SEQ ID NO: 4 or the amino acid sequence of NCBI Accession No. NP_000811 can also be obtained in the same way as above. The polypeptide consisting of the amino acid sequence shown in SEQ ID NO: 4 or the amino acid sequence of NCBI Accession No. NP_000811, or the polypeptide having an amino acid sequence in which one or more amino acids are deleted, substituted, or added in the amino acid sequence shown in SEQ ID NO: 4 or the amino acid sequence of NCBI Accession No. NP_000811 can also be produced by a chemical synthesis method such as a fluorenylmethyloxycarbonyl (Fmoc) method or a t-butyloxycarbonyl (tBoc) method.

Examples of the monoclonal antibody according to the present invention can include an antibody produced by a hybridoma or a recombinant antibody produced by a transformant obtained by transformation with an expression vector containing the antibody gene.

The monoclonal antibody is an antibody secreted by a single clone of antibody-producing cells. The monoclonal antibody recognizes only one epitope (also called antigen determinant), and the amino acid sequence (primary sequence) constituting the monoclonal antibody is uniform.

Examples of the epitope include a single amino acid sequence that is recognized and bound by the monoclonal antibody, a conformation consisting of the amino acid sequence, an amino acid sequence modified by posttranslational modification, and a conformation consisting of the modified amino acid sequence.

Examples of the amino acid sequence modified by posttranslational modification include an amino acid sequence having an O-linked sugar chain composed of a sugar chain attached to Tyr and Ser having an OH substituent, a N-linked sugar chain composed of a sugar chain attached to Gln and Asn having a $NH_2$ substituent, and a sulfate group containing a sulfate molecule attached to Tyr having an OH group.

Examples of the amino acid residue or the epitope on human Gas6 to which the antibody of the present invention binds include an epitope at a Gas6 receptor binding site, an epitope present in the SHBG domain of human Gas6, an epitope comprising at least one amino acid residue selected from amino acid residues at positions 314, 315, and 316 present in the SHBG domain in the amino acid sequence of human Gas6, and an epitope consisting of amino acid residues at positions 314, 315, and 316 present in the SHBG domain in the amino acid sequence of human Gas6.

The binding of the antibody of the present invention to human Gas6 can be confirmed by, for example, radioimmunoassay using a solid-phase sandwich method or the like, an immunological detection method known in the art for human Gas6 using enzyme-linked immunosorbent assay (ELISA) or the like, or a surface plasmon resonance method using a Biacore system (manufactured by GE Healthcare Japan Corp.) or the like. Alternatively, the binding can also be confirmed by the combination of, for example, immunological detection methods known in the art [Monoclonal Antibodies-Principles and practice, Third edition, Academic Press (1996); Antibodies-A Laboratory Manual, Cold Spring Harbor Laboratory (1988); and Tan-Clone-Kotai-Jikken-Manual (Experimental Manual for Monoclonal Antibody in English), Kodansha Scientific Ltd. (1987)].

The amino acid residue or the epitope on human Gas6 to which the antibody of the present invention binds can be determined by the binding experiment of the antibody using, for example, a deletion variant lacking a portion of the domains of human Gas6, a variant of human Gas6 with its domain replaced with a domain derived from another protein, or a partial peptide fragment of human Gas6. Alternatively, the amino acid residue or the epitope on human Gas6 to which the antibody of the present invention binds can also be determined by adding the antibody of the present invention to a peptide fragment of human Gas6 digested with a proteolytic enzyme, followed by epitope mapping using known mass spectrometry.

Specific examples of the antibody of the present invention include an antibody having binding activity and neutralizing activity against human Gas6 as a result of binding to at least one of amino acid residues at positions 314, 315, and 316 in the amino acid sequence of human Gas6.

As for the functions of human Gas6, Gas6 is known to bind to a Gas6 receptor to activate the receptor, consequently causing the activation of intracellular signal transduction and increase in cell growth.

In the present invention, specific examples of the Gas6 receptor include Axl, Sky, and Mer TK.

In the present invention, the neutralizing activity refers to the activity of inhibiting the functions of human Gas6, i.e., inhibiting the Gas6 receptor activation mentioned above and various reactions associated with the activation. Specific examples thereof include the activity of inhibiting the activity of the Gas6 receptor, the activity of suppressing the activation of signal transduction in Gas6 receptor-expressing cells by the addition of Gas6, and the activity of suppressing increase in the growth of Gas6 receptor-expressing cells by the addition of Gas6 as a result of inhibiting the binding between Gas6 and the Gas6 receptor.

The specific binding of the antibody of the present invention to Gas6 and its activity inhibiting the binding between Gas6 and the Gas6 receptor can be confirmed by an immunological detection method known in the art such as ELISA, a surface plasmon resonance method using a Biacore® system (manufactured by GE Healthcare Japan Corp.) or the like, or combination thereof.

The activity of the antibody of the present invention of suppressing the activation of signal transduction in Gas6 receptor-expressing cells by Gas6 binding can be confirmed by detecting the expression level of a particular gene product by use of reporter assay known in the art, or detecting the phosphorylation level of a particular signal transduction substance by use of Western blot, a flow cytometer, or the like. Alternatively, the activity can also be confirmed, for example, by comprehensively detecting the activated states or expression levels of genes using a microarray.

The activity of the antibody of the present invention of suppressing increase in the growth of Gas6 receptor-expressing cells by Gas6 can be confirmed by use of cell growth assay known in the art. Specific examples of the cell growth assay known in the art include a method for measuring the survival activity of the cells using a tetrazolium salt such as MTT or WST-1, or a method for measuring intracellular DNA synthesis using a radioisotope such as [$^3$H]-thymidine.

In the present invention, the high binding activity or high neutralizing activity of the monoclonal antibody of the present invention refers to stronger binding activity or neutralizing activity than that of an anti-human Gas6 antibody known in the art or a commercially available anti-human Gas6 antibody against hGas6. Specifically, the anti-hGas6 monoclonal antibody of the present invention has high binding activity and high neutralizing activity against hGas6 as compared with an anti-hGas6 monoclonal antibody WG1 (U.S. Pat. No. 7,547,767).

Antibody molecules are also called immunoglobulins (hereinafter, also referred to as Igs). Human antibodies are classified into isotypes of IgA1, IgA2, IgD, IgE, IgG1, IgG2, IgG3, IgG4, and IgM according to difference in molecular structure. IgG1, IgG2, IgG3, and IgG4, which have relatively high amino acid sequence homology, are also collectively called IgG.

Each antibody molecule is constituted by polypeptides called heavy chains (hereinafter, referred to as H chains) and light chains (hereinafter, referred to as L chains). The H chain is constituted by an H chain variable region (also referred to as VH) and an H chain constant region (also referred to as CH) from the N terminus toward the C terminus. The L chain is constituted by an L chain variable region (also referred to as VL) and an L chain constant region (also referred to as CL) from the N terminus toward the C terminus. CH is known as α, δ, ε, γ, and μchains depending on subclass. CH is further constituted by a CH1 domain, a hinge domain, a CH2 domain, and a CH3 domain from the N terminus to the C terminus. The domain refers to a functional structural unit constituting each polypeptide of the antibody molecule. The CH2 and CH3 domains together are referred to as a Fc region or simply Fc. CL is known as Cλ and Cκ chains.

In the present invention, the CH1 domain, the hinge domain, the CH2 domain, the CH3 domain, and the Fc region can be specified by the positions of amino acid residues counted from the N terminus according to the EU index [Kabat et al., Sequences of Proteins of Immunological Interest, US Dept. Health and Human Services (1991)]. Specifically, CH1 is specified by an amino acid sequence from positions 118 to 215 of the EU index. The hinge is specified by an amino acid sequence from positions 216 to 230 of the EU index. CH2 is specified by an amino acid sequence from positions 231 to 340 of the EU index. CH3 is specified by an amino acid sequence from positions 341 to 447 of the EU index.

The antibody of the present invention also includes, particularly, recombinant antibodies such as a genetically engineered mouse antibody, rat antibody, human chimeric antibody (hereinafter, also simply referred to as a chimeric antibody), humanized antibody [also called human complementarity determining region (CDR)-grafted antibody], and human antibody.

The chimeric antibody means an antibody consisting of VH and VL of an antibody of an animal other than humans (nonhuman animal) and CH and CL of a human antibody. Any nonhuman animal, such as a mouse, a rat, a hamster, or a rabbit, can be used as long as hybridomas can be prepared.

The hybridomas refer to cells that produce monoclonal antibodies having the desired antigen specificity and are obtained by the cell fusion between B cells obtained by the immunization of the nonhuman animal with the antigen, and myeloma cells derived from a mouse or the like. Thus, variable regions constituting an antibody produced by each hybridoma consist of the amino acid sequences of the nonhuman animal antibody.

The human chimeric antibody can be produced by obtaining cDNAs encoding VH and VL of a monoclonal antibody from a nonhuman animal cell-derived hybridoma producing the monoclonal antibody, and respectively inserting the cDNAs to expression vectors for animal cells having DNAs encoding CH and CL of a human antibody to construct human chimeric antibody expression vectors, and transfecting animal cells with the expression vectors, followed by expression.

The humanized antibody refers to an antibody comprising the amino acid sequences of CDRs of VH and VL of nonhuman animal antibody grafted in the corresponding CDRs of VH and VL of human antibody. Regions other than CDRs in VH and VL are referred to as framework regions (hereinafter, abbreviated to FRs).

The humanized antibody can be produced by constructing cDNA encoding the amino acid sequence of VH consisting of the amino acid sequences of CDRs of VH of nonhuman animal antibody and the amino acid sequences of FRs of VH of an arbitrary human antibody, and cDNA encoding the amino acid sequence of VL consisting of the amino acid sequences of CDRs of VL nonhuman animal antibody and the amino acid sequences of FRs of VL of the arbitrary human antibody, respectively inserting the cDNAs to expression vectors for animal cells having DNAs encoding CH and CL of human antibody to construct humanized antibody expression vectors, and transfecting animal cells with the expression vectors, followed by expression.

Specific examples of the humanized antibody of the present invention include: a KM5320 humanized antibody comprising VH of antibody comprising CDR1 to CDR3 comprising the amino acid sequences shown in SEQ ID NOs: 79 to 81, respectively, and VL of antibody comprising CDR1 to CDR3 comprising the amino acid sequences shown in SEQ ID NOs: 82 to 84, respectively; and a KM5321 humanized antibody comprising VH of antibody comprising CDR1 to CDR3 comprising the amino acid sequences shown in SEQ ID NOs: 85 to 87, respectively, and VL of antibody comprising CDR1 to CDR3 comprising the amino acid sequences shown in SEQ ID NOs: 88 to 90, respectively.

Specific examples of the humanized antibody of the present invention include a KM5320 humanized antibody comprising at least one of the following VL (a) and VH (b), and a KM5321 humanized antibody comprising at least one of the following VL (c) and VH (d):

(a) VL of antibody comprising the amino acid sequence shown in SEQ ID NO: 105 or an amino acid sequence substituting at least one amino acid residue selected from Val at position 2, Leu at position 15, Leu at position 46, Leu at position 73, Leu at position 78, and Tyr at position 87 by another amino acid residue in the amino acid sequence shown in SEQ ID NO: 105;

(b) VH of antibody comprising the amino acid sequence shown in SEQ ID NO: 129 or an amino acid sequence substituting at least one amino acid residue selected from Val at position 2, Ser at position 9, Val at position 20, Arg at position 38, Glu at position 46, Ser at position 77, Val at position 93, and Tyr at position 95 by another amino acid residue in the amino acid sequence shown in SEQ ID NO: 129;

(c) VL of antibody comprising the amino acid sequence shown in SEQ ID NO: 156 or an amino acid sequence substituting at least one amino acid residue selected from Leu at position 4, Ala at position 13, Val at position 15, Ala at position 43, Gly at position 64, Leu at position 73, Leu at position 78, Thr at position 85, and Val at position 104 by another amino acid residue in the amino acid sequence shown in SEQ ID NO: 156; and (d) VH of antibody comprising the amino acid sequence shown in SEQ ID NO: 186 or an amino acid sequence substituting at least one amino acid residue selected from Val at position 2, Ser at position 9, Arg at position 38, Glu at position 46, Ser at position 79, Val at position 93, and Val at position 112 by another amino acid residue in the amino acid sequence shown in SEQ ID NO: 186.

The VL contained in the KM5320 humanized antibody of the present invention is preferably any of the following VLs (1) to (7):

(1) VL of antibody comprising an amino acid sequence substituting Val at position 2, Leu at position 15, Leu at position 46, Leu at position 73, Leu at position 78, and Tyr at position 87 by other amino acid residues in the amino acid sequence shown in SEQ ID NO: 105;

(2) VL of antibody comprising an amino acid sequence substituting Val at position 2, Leu at position 46, Leu at position 73, Leu at position 78, and Tyr at position 87 by other amino acid residues in the amino acid sequence shown in SEQ ID NO: 105;

(3) VL of antibody comprising an amino acid sequence substituting Leu at position 46, Leu at position 73, and Tyr at position 87 by other amino acid residues in the amino acid sequence shown in SEQ ID NO: 105;

(4) VL of antibody comprising an amino acid sequence substituting Leu at position 15 and Leu at position 73 by other amino acid residues in the amino acid sequence shown in SEQ ID NO: 105;

(5) VL of antibody comprising an amino acid sequence substituting Leu at position 78 and Tyr at position 87 by other amino acid residues in the amino acid sequence shown in SEQ ID NO: 105;

(6) VL of antibody comprising an amino acid sequence substituting Leu at position 78 by another amino acid residue in the amino acid sequence shown in SEQ ID NO: 105; and (7) VL of antibody comprising an amino acid sequence substituting Tyr at position 87 by another amino acid residue in the amino acid sequence shown in SEQ ID NO: 105.

Examples of the amino acid sequence of the VL include an amino acid sequence containing at least one modification selected form modifications that substitute Val at position 2 by Ile, Leu at position 15 by Ala, Leu at position 46 by Val, Leu at position 73 by Phe, Leu at position 78 by Val, and Tyr at position 87 by Phe, in the amino acid sequence shown in SEQ ID NO: 105.

Specific examples of the amino acid sequence of VL containing 6 modifications include an amino acid sequence substituting Val at position 2 by Ile, Leu at position 15 by Ala, Leu at position 46 by Val, Leu at position 73 by Phe, Leu at position 78 by Val, and Tyr at position 87 by Phe in the amino acid sequence shown in SEQ ID NO: 105.

Specific examples of the amino acid sequence of VL containing 5 modifications include the following amino acid sequences (1) to (4):

(1) an amino acid sequence substituting Val at position 2 by Ile, Leu at position 46 by Val, Leu at position 73 by Phe, Leu at position 78 by Val, and Tyr at position 87 by Phe in the amino acid sequence shown in SEQ ID NO: 105;

(2) an amino acid sequence substituting Val at position 2 by Ile, Leu at position 15 by Ala, Leu at position 46 by Val, Leu at position 73 by Phe, and Tyr at position 87 by Phe in the amino acid sequence shown in SEQ ID NO: 105;

(3) an amino acid sequence substituting Val at position 2 by Ile, Leu at position 15 by Ala, Leu at position 73 by Phe, Leu at position 78 by Val, and Tyr at position 87 by Phe in the amino acid sequence shown in SEQ ID NO: 105; and (4) an amino acid sequence substituting Leu at position 15 by Ala, Leu at position 46 by Val, Leu at position 73 by Phe, Leu at position 78 by Val, and Tyr at position 87 by Phe in the amino acid sequence shown in SEQ ID NO: 105.

Specific examples of the amino acid sequence of VL containing 4 modifications include the following amino acid sequences (1) to (4):

(1) an amino acid sequence substituting Leu at position 46 by Val, Leu at position 73 by Phe, Leu at position 78 by Val, and Tyr at position 87 by Phe in the amino acid sequence shown in SEQ ID NO: 105;

(2) an amino acid sequence substituting Val at position 2 by Ile, Leu at position 73 by Phe, Leu at position 78 by Val, and Tyr at position 87 by Phe in the amino acid sequence shown in SEQ ID NO: 105;

(3) an amino acid sequence substituting Val at position 2 by Ile, Leu at position 46 by Val, Leu at position 73 by Phe, and Leu at position 78 by Val in the amino acid sequence shown in SEQ ID NO: 105; and (4) an amino acid sequence substituting Val at position 2 by Ile, Leu at position 15 by Ala, Leu at position 73 by Phe, and Tyr at position 87 by Phe in the amino acid sequence shown in SEQ ID NO: 105s.

Specific examples of the amino acid sequence of VL containing 3 modifications include the following amino acid sequences (1) to (4):

(1) an amino acid sequence substituting Leu at position 46 by Val, Leu at position 73 by Phe, and Tyr at position 87 by Phe in the amino acid sequence shown in SEQ ID NO: 105;

(2) an amino acid sequence substituting Leu at position 15 by Ala, Leu at position 46 by Val, and Tyr at position 87 by Phe in the amino acid sequence shown in SEQ ID NO: 105;

(3) an amino acid sequence substituting Leu at position 15 by Ala, Leu at position 46 by Val, and Leu at position 78 by Val in the amino acid sequence shown in SEQ ID NO: 105; and (4) an amino acid sequence substituting Leu at position 46 by Val, Leu at position 73 by Phe, and Leu at position 78 by Val in the amino acid sequence shown in SEQ ID NO: 105.

Specific examples of the amino acid sequence of VL containing 2 modifications include the following amino acid sequences (1) to (4):
(1) an amino acid sequence derived from the amino acid sequence shown in SEQ ID NO: 105 by the substitution of Leu at position 78 by Val and Tyr at position 87 by Phe;
(2) an amino acid sequence substituting Leu at position 15 by Ala and Leu at position 73 by Phe in the amino acid sequence shown in SEQ ID NO: 105;
(3) an amino acid sequence by the substituting Leu at position 46 by Val and Leu at position 78 by Val in the amino acid sequence shown in SEQ ID NO: 105; and
(4) an amino acid sequence substituting Val at position 2 by Ile and Leu at position 15 by Ala in the amino acid sequence shown in SEQ ID NO: 105.

Specific examples of the amino acid sequence of VL containing 1 modification include the following amino acid sequences (1) to (4):
(1) an amino acid sequence substituting of Val at position 2 by Ile in the amino acid sequence shown in SEQ ID NO: 105;
(2) an amino acid sequence substituting Leu at position 46 by Val in the amino acid sequence shown in SEQ ID NO: 105;
(3) an amino acid sequence substituting Leu at position 78 by Val in the amino acid sequence shown in SEQ ID NO: 105; and
(4) an amino acid sequence substituting Tyr at position 87 by Phe in the amino acid sequence shown in SEQ ID NO: 105.

The VH contained in the KM5320 humanized antibody of the present invention is preferably any of the following VHs (1) to (8):
(1) VH comprising an amino acid sequence substituting Val at position 2, Ser at position 9, Val at position 20, Arg at position 38, Glu at position 46, Ser at position 77, Val at position 93, and Tyr at position 95 by other amino acid residues in the amino acid sequence shown in SEQ ID NO: 129;
(2) VH comprising an amino acid sequence substituting Ser at position 9, Val at position 20, Arg at position 38, Glu at position 46, Val at position 93, and Tyr at position 95 by other amino acid residues in the amino acid sequence shown in SEQ ID NO: 129;
(3) VH comprising an amino acid sequence substituting Ser at position 9, Glu at position 46, Val at position 93, and Tyr at position 95 by other amino acid residues in the amino acid sequence shown in SEQ ID NO: 129;
(4) VH comprising an amino acid sequence substituting Glu at position 46, Val at position 93, and Tyr at position 95 by other amino acid residues in the amino acid sequence shown in SEQ ID NO: 129;
(5) VH comprising an amino acid sequence substituting Val at position 2, Val at position 20, and Tyr at position 95 by other amino acid residues in the amino acid sequence shown in SEQ ID NO: 129;
(6) VH comprising an amino acid sequence substituting Ser at position 9, Arg at position 38, and Glu at position 46, by other amino acid residues in the amino acid sequence shown in SEQ ID NO: 129;
(7) VH comprising an amino acid sequence substituting Val at position 93 and Tyr at position 95 by other amino acid residues in the amino acid sequence shown in SEQ ID NO: 129; and
(8) VH comprising an amino acid sequence substituting Glu at position 46 by another amino acid residue in the amino acid sequence shown in SEQ ID NO: 129.

Examples of the amino acid sequence of the VH include an amino acid sequence containing at least one modification selected from alterations that substitute Val at position 2 by Ile, Ser at position 9 by Pro, Val at position 20 by Ile, Arg at position 38 by Lys, Glu at position 46 by Lys, Ser at position 77 by Thr, Val at position 93 by Thr, and Tyr at position 95 by Phe, in the amino acid sequence shown in SEQ ID NO: 129.

Specific examples of the amino acid sequence of VH containing 8 modifications include an amino acid sequence substituting Val at position 2 by Ile, Ser at position 9 by Pro, Val at position 20 by Ile, Arg at position 38 by Lys, Glu at position 46 by Lys, Ser at position 77 by Thr, Val at position 93 by Thr, and Tyr at position 95 by Phe in the amino acid sequence shown in SEQ ID NO: 129.

Specific examples of the amino acid sequence of VH containing 6 modifications include the following amino acid sequences (1) to (4):
(1) an amino acid sequence substituting Val at position 20 by Ile, Arg at position 38 by Lys, Glu at position 46 by Lys, Ser at position 77 by Thr, Val at position 93 by Thr, and Tyr at position 95 by Phe in the amino acid sequence shown in SEQ ID NO: 129;
(2) an amino acid sequence substituting Val at position 2 by Ile, Ser at position 9 by Pro, Val at position 20 by Ile, Arg at position 38 by Lys, Ser at position 77 by Thr, and Val at position 93 by Thr in the amino acid sequence shown in SEQ ID NO: 129;
(3) an amino acid sequence substituting Ser at position 9 by Pro, Val at position 20 by Ile, Arg at position 38 by Lys, Glu at position 46 by Lys, Val at position 93 by Thr, and Tyr at position 95 by Phe in the amino acid sequence shown in SEQ ID NO: 129; and
(4) an amino acid sequence substituting Ser at position 9 by Pro, Arg at position 38 by Lys, Glu at position 46 by Lys, Ser at position 77 by Thr, Val at position 93 by Thr, and Tyr at position 95 by Phe in the amino acid sequence shown in SEQ ID NO: 129.

Specific examples of the amino acid sequence of VH containing 4 modifications include the following amino acid sequences (1) to (4):
(1) an amino acid sequence substituting Ser at position 9 by Pro, Val at position 20 by Ile, Glu at position 46 by Lys, and Val at position 93 by Thr in the amino acid sequence shown in SEQ ID NO: 129;
(2) an amino acid sequence substituting Ser at position 9 by Pro, Glu at position 46 by Lys, Val at position 93 by Thr, and Tyr at position 95 by Phe in the amino acid sequence shown in SEQ ID NO: 129;
(3) an amino acid sequence substituting Val at position 20 by Ile, Glu at position 46 by Lys, Val at position 93 by Thr, and Tyr at position 95 by Phe in the amino acid sequence shown in SEQ ID NO: 129; and
(4) an amino acid sequence substituting Arg at position 38 by Lys, Glu at position 46 by Lys, Val at position 93 by Thr, and Tyr at position 95 by Phe in the amino acid sequence shown in SEQ ID NO: 129.

Specific examples of the amino acid sequence of VH containing 3 modifications include one amino acid sequence selected from the following amino acid sequences (1) to (4):
(1) an amino acid sequence substituting Val at position 2 by Ile, Val at position 20 by Ile, and Tyr at position 95 by Phe in the amino acid sequence shown in SEQ ID NO: 129;

(2) an amino acid sequence substituting Ser at position 9 by Pro, Arg at position 38 by Lys, and Glu at position 46 by Lys in the amino acid sequence shown in SEQ ID NO: 129;
(3) an amino acid sequence substituting Glu at position 46 by Lys, Val at position 93 by Thr, and Tyr at position 95 by Phe in the amino acid sequence shown in SEQ ID NO: 129; and
(4) an amino acid sequence substituting Ser at position 9 by Pro, Arg at position 38 by Lys, and Tyr at position 95 by Phe in the amino acid sequence shown in SEQ ID NO: 129.

Specific examples of the amino acid sequence of VH containing 2 modifications include the following amino acid sequences (1) to (4):
(1) an amino acid sequence substituting Ser at position 9 by Pro and Arg at position 38 by Lys in the amino acid sequence shown in SEQ ID NO: 129;
(2) an amino acid sequence substituting Val at position 20 by Ile and Ser at position 77 by Thr in the amino acid sequence shown in SEQ ID NO: 129;
(3) an amino acid sequence substituting Glu at position 46 by Lys and Tyr at position 95 by Phe in the amino acid sequence shown in SEQ ID NO: 129; and
(4) an amino acid sequence substituting Val at position 93 by Thr and Tyr at position 95 by Phe in the amino acid sequence shown in SEQ ID NO: 129.

Specific examples of the amino acid sequence of VH containing 1 modification include the following amino acid sequences (1) to (4):
(1) an amino acid sequence derived from by the substitution of Val at position 20 by Ile in the amino acid sequence shown in SEQ ID NO: 129;
(2) an amino acid sequence substituting Arg at position 38 by Lys in the the amino acid sequence shown in SEQ ID NO: 129;
(3) an amino acid sequence substituting Glu at position 46 by Lys in the amino acid sequence shown in SEQ ID NO: 129; and
(4) an amino acid sequence substituting Tyr at position 95 by Phe in the amino acid sequence shown in SEQ ID NO: 129.

Specific examples of the KM5320 humanized antibody of the present invention include the following humanized antibodies (1) to (3):
(1) a humanized antibody comprising VH of antibody comprising the amino acid sequence shown in SEQ ID NO: 135 and/or VL of antibody comprising the amino acid sequence shown in SEQ ID NO: 123;
(2) a humanized antibody comprising VH of antibody comprising any amino acid sequence shown in FIG. 8 and/or VL of antibody comprising the amino acid sequence shown in SEQ ID NO: 123; and
(3) a humanized antibody comprising VH of antibody comprising the amino acid sequence shown in SEQ ID NO: 135 and/or VL of antibody comprising any amino acid sequence shown in FIG. 7.

The VL contained in the KM5321 humanized antibody of the present invention is preferably any of the following VLs (1) to (7):
(1) VL of antibody comprising an amino acid sequence substituting Leu at position 4, Ala at position 13, Val at position 15, Ala at position 43, Gly at position 64, Leu at position 73, Leu at position 78, Thr at position 85, and Val at position 104 by other amino acid residues in the amino acid sequence shown in SEQ ID NO: 156;
(2) VL of antibody comprising an amino acid sequence substituting Ala at position 13, Val at position 15, Gly at position 64, Leu at position 73, Leu at position 78, Thr at position 85, and Val at position 104 by other amino acid residues in the amino acid sequence shown in SEQ ID NO: 156;
(3) VL of antibody comprising an amino acid sequence substituting Ala at position 13, Val at position 15, Ala at position 43, Leu at position 73, Leu at position 78, and Thr at position 85, by other amino acid residues in the amino acid sequence shown in SEQ ID NO: 156;
(4) VL of antibody comprising an amino acid sequence substituting Ala at position 13, Val at position 15, Leu at position 73, and Leu at position 78 by other amino acid residues in the amino acid sequence shown in SEQ ID NO: 156;
(5) VL of antibody comprising an amino acid sequence substituting Val at position 15, Leu at position 78, and Thr at position 85 by other amino acid residues in the amino acid sequence shown in SEQ ID NO: 156;
(6) VL of antibody comprising an amino acid sequence substituting Ala at position 13 and Ala at position 43 by other amino acid residues in the amino acid sequence shown in SEQ ID NO: 156; and
(7) VL of antibody comprising an amino acid sequence substituting Ala at position 43 by another amino acid residue in the amino acid sequence shown in SEQ ID NO: 156.

Examples of the amino acid sequence of the VL include an amino acid sequence containing at least one alteration selected from alterations that substitute Leu at position 4 by Val, Ala at position 13 by Val, Val at position 15 by Thr, Ala at position 43 by Pro, Gly at position 64 by Ser, Leu at position 73 by Phe, Leu at position 78 by Thr, Thr at position 85 by Asp, and Val at position 104 by Leu, in the amino acid sequence shown in SEQ ID NO: 156.

Specific examples of the amino acid sequence of VL containing 9 modifications include an amino acid sequence substituting Leu at position 4 by Val, Ala at position 13 by Val, Val at position 15 by Thr, Ala at position 43 by Pro, Gly at position 64 by Ser, Leu at position 73 by Phe, Leu at position 78 by Thr, Thr at position 85 by Asp, and Val at position 104 by Leu in the amino acid sequence shown in SEQ ID NO: 156.

Specific examples of the amino acid sequence of VL containing 7 modifications include the following amino acid sequences (1) to (4):
(1) an amino acid sequence substituting Leu at position 4 by Val, Ala at position 13 by Val, Gly at position 64 by Ser, Leu at position 73 by Phe, Leu at position 78 by Thr, Thr at position 85 by Asp, and Val at position 104 by Leu in the amino acid sequence shown in SEQ ID NO: 156;
(2) an amino acid sequence substituting Ala at position 13 by Val, Val at position 15 by Thr, Ala at position 43 by Pro, Gly at position 64 by Ser, Leu at position 73 by Phe, Leu at position 78 by Thr, and Thr at position 85 by Asp in the amino acid sequence shown in SEQ ID NO: 156;
(3) an amino acid sequence substituting Leu at position 4 by Val, Val at position 15 by Thr, Ala at position 43 by Pro, Gly at position 64 by Ser, Leu at position 78 by Thr, Thr at position 85 by Asp, and Val at position 104 by Leu in the amino acid sequence shown in SEQ ID NO: 156; and
(4) an amino acid sequence substituting Leu at position 4 by Val, Val at position 15 by Thr, Ala at position 43 by Pro, Gly at position 64 by Ser, Leu at position 73 by Phe, Leu at position 78 by Thr, and Thr at position 85 by Asp in the amino acid sequence shown in SEQ ID NO: 156.

Specific examples of the amino acid sequence of VL containing 6 modifications include the following amino acid sequences (1) to (4):
(1) an amino acid sequence substituting Leu at position 4 by Val, Val at position 15 by Thr, Ala at position 43 by Pro, Gly at position 64 by Ser, Thr at position 85 by Asp, and Val at position 104 by Leu in the amino acid sequence shown in SEQ ID NO: 156;
(2) an amino acid sequence substituting Ala at position 13 by Val, Val at position 15 by Thr, Ala at position 43 by Pro, Gly at position 64 by Ser, Leu at position 78 by Thr, and Thr at position 85 by Asp in the amino acid sequence shown in SEQ ID NO: 156;
(3) an amino acid sequence substituting Val at position 15 by Thr, Ala at position 43 by Pro, Gly at position 64 by Ser, Leu at position 73 by Phe, Leu at position 78 by Thr, and Thr at position 85 by Asp in the amino acid sequence shown in SEQ ID NO: 156; and
(4) an amino acid sequence substituting Ala at position 13 by Val, Ala at position 43 by Pro, Gly at position 64 by Ser, Leu at position 73 by Phe, Leu at position 78 by Thr, and Thr at position 85 by Asp in the amino acid sequence shown in SEQ ID NO: 156.

Specific examples of the amino acid sequence of VL containing 4 modifications include the following amino acid sequences (1) to (4):
(1) an amino acid sequence substituting Leu at position 4 by Val, Ala at position 13 by Val, Val at position 15 by Thr, and Ala at position 43 by Pro in the amino acid sequence shown in SEQ ID NO: 156;
(2) an amino acid sequence substituting Ala at position 13 by Val, Val at position 15 by Thr, Ala at position 43 by Pro, and Thr at position 85 by Asp in the amino acid sequence shown in SEQ ID NO: 156;
(3) an amino acid sequence substituting Ala at position 13 by Val, Val at position 15 by Thr, Leu at position 73 by Phe, and Leu at position 78 by Thr in the amino acid sequence shown in SEQ ID NO: 156; and
(4) an amino acid sequence substituting Ala at position 13 by Val, Val at position 15 by Thr, Leu at position 73 by Phe, and Thr at position 85 by Asp in the amino acid sequence shown in SEQ ID NO: 156.

Specific examples of the amino acid sequence of VL containing 3 modifications include the following amino acid sequences (1) to (4):
(1) an amino acid sequence substituting Ala at position 13 by Val, Val at position 15 by Thr, and Leu at position 73 by Phe in the amino acid sequence shown in SEQ ID NO: 156;
(2) an amino acid sequence substituting Ala at position 13 by Val, Leu at position 73 by Phe, and Thr at position 85 by Asp in the amino acid sequence shown in SEQ ID NO: 156;
(3) an amino acid sequence substituting Val at position 15 by Thr, Leu at position 78 by Thr, and Thr at position 85 by Asp in the amino acid sequence shown in SEQ ID NO: 156; and
(4) an amino acid sequence substituting Ala at position 43 by Pro, Leu at position 73 by Phe, and Leu at position 78 by Thr in the amino acid sequence shown in SEQ ID NO: 156.

Specific examples of the amino acid sequence of VL containing 2 modifications include the following amino acid sequences (1) to (4):
(1) an amino acid sequence substituting Ala at position 13 by Val and Val at position 15 by Thr in the amino acid sequence shown in SEQ ID NO: 156;
(2) an amino acid sequence substituting Ala at position 13 by Val and Ala at position 43 by Pro in the amino acid sequence shown in SEQ ID NO: 156;
(3) an amino acid sequence substituting Val at position 15 by Thr and Thr at position 85 by Asp in the amino acid sequence shown in SEQ ID NO: 156; and
(4) an amino acid sequence substituting Ala at position 43 by Pro and Gly at position 64 by Ser in the amino acid sequence shown in SEQ ID NO: 156.

Specific examples of the amino acid sequence of VL containing 1 modification include the following amino acid sequences (1) to (4):
(1) an amino acid sequence substituting Ala at position 13 by Val in the amino acid sequence shown in SEQ ID NO: 156;
(2) an amino acid sequence substituting Ala at position 43 by Pro in the amino acid sequence shown in SEQ ID NO: 156;
(3) an amino acid sequence substituting Leu at position 73 by Phe in the amino acid sequence shown in SEQ ID NO: 156; and
(4) an amino acid sequence substituting Thr at position 85 by Asp in the amino acid sequence shown in SEQ ID NO: 156.

The VH contained in the KM5321 humanized antibody of the present invention is preferably any of the following VHs (1) to (8):
(1) VH comprising an amino acid sequence substituting Val at position 2, Ser at position 9, Arg at position 38, Glu at position 46, Ser at position 79, Val at position 93, and Val at position 112 by other amino acid residues in the amino acid sequence shown in SEQ ID NO: 186;
(2) VH comprising an amino acid sequence substituting Val at position 2, Arg at position 38, Glu at position 46, Ser at position 79, and Val at position 112 by other amino acid residues in the amino acid sequence shown in SEQ ID NO: 186;
(3) VH comprising an amino acid sequence substituting Val at position 2, Ser at position 9, Ser at position 79, and Val at position 112 by other amino acid residues in the amino acid sequence shown in SEQ ID NO: 186;
(4) VH comprising an amino acid sequence substituting Ser at position 9, Glu at position 46, and Val at position 93 by other amino acid residues in the amino acid sequence shown in SEQ ID NO: 186;
(5) VH comprising an amino acid sequence substituting Arg at position 38, Glu at position 46, and Val at position 93 by other amino acid residues in the amino acid sequence shown in SEQ ID NO: 186;
(6) VH comprising an amino acid sequence substituting Arg at position 38 and Glu at position 46 by other amino acid residues in the amino acid sequence shown in SEQ ID NO: 186;
(7) VH comprising an amino acid sequence substituting Ser at position 9 and Val at position 93 by other amino acid residues in the amino acid sequence shown in SEQ ID NO: 186; and
(8) VH comprising an amino acid sequence substituting Glu at position 46 by another amino acid residue in the amino acid sequence shown in SEQ ID NO: 186.

Examples of the amino acid sequence of the VH include an amino acid sequence containing at least one modification selected from modifications that substitute Val at position 2 by Ile, Ser at position 9 by Pro, Arg at position 38 by Lys, Glu at position 46 by Lys, Ser at position 79 by Ala, Val at position 93 by Thr, and Val at position 112 by Ile, in the amino acid sequence shown in SEQ ID NO: 186.

Specific examples of the amino acid sequence of VH containing 7 modifications include an amino acid sequence substituting Val at position 2 by Ile, Ser at position 9 by Pro, Arg at position 38 by Lys, Glu at position 46 by Lys, Ser at position 79 by Ala, Val at position 93 by Thr, and Val at position 112 by Ile in the amino acid sequence shown in SEQ ID NO: 186.

Specific examples of the amino acid sequence of VH containing 5 modifications include the following amino acid sequences (1) to (4):
(1) an amino acid sequence substituting Val at position 2 by Ile, Ser at position 9 by Pro, Arg at position 38 by Lys, Glu at position 46 by Lys, and Val at position 112 by Ile in the amino acid sequence shown in SEQ ID NO: 186;
(2) an amino acid sequence substituting Val at position 2 by Ile, Arg at position 38 by Lys, Glu at position 46 by Lys, Ser at position 79 by Ala, and Val at position 112 by Ile in the amino acid sequence shown in SEQ ID NO: 186;
(3) an amino acid sequence substituting Val at position 2 by Ile, Arg at position 38 by Lys, Glu at position 46 by Lys, Ser at position 79 by Ala, and Val at position 93 by Thr in the amino acid sequence shown in SEQ ID NO: 186; and
(4) an amino acid sequence substituting Ser at position 9 by Pro, Arg at position 38 by Lys, Glu at position 46 by Lys, Val at position 93 by Thr, and Val at position 112 by Ile in the amino acid sequence shown in SEQ ID NO: 186.

Specific examples of the amino acid sequence of VH containing 4 modifications include the following amino acid sequences (1) to (4):
(1) an amino acid sequence substituting Val at position 2 by Ile, Ser at position 9 by Pro, Ser at position 79 by Ala, and Val at position 112 by Ile in the amino acid sequence shown in SEQ ID NO: 186;
(2) an amino acid sequence substituting Ser at position 9 by Pro, Arg at position 38 by Lys, Glu at position 46 by Lys, and Ser at position 79 by Ala in the amino acid sequence shown in SEQ ID NO: 186;
(3) an amino acid sequence substituting Ser at position 9 by Pro, Arg at position 38 by Lys, Glu at position 46 by Lys, and Val at position 93 by Thr in the amino acid sequence shown in SEQ ID NO: 186; and
(4) an amino acid sequence substituting Ser at position 9 by Pro, Glu at position 46 by Lys, Ser at position 79 by Ala, and Val at position 112 by Ile in the amino acid sequence shown in SEQ ID NO: 186.

Specific examples of the amino acid sequence of VH containing 3 modifications include the following amino acid sequences (1) to (4):
(1) an amino acid sequence substituting Ser at position 9 by Pro, Glu at position 46 by Lys, and Val at position 93 by Thr in the amino acid sequence shown in SEQ ID NO: 186;
(2) an amino acid sequence substituting Val at position 2 by Ile, Arg at position 38 by Lys, and Glu at position 46 by Lys in the amino acid sequence shown in SEQ ID NO: 186;
(3) an amino acid sequence substituting Arg at position 38 by Lys, Glu at position 46 by Lys, and Ser at position 79 by Ala in the amino acid sequence shown in SEQ ID NO: 186; and
(4) an amino acid sequence substituting Arg at position 38 by Lys, Glu at position 46 by Lys, and Val at position 93 by Thr in the amino acid sequence shown in SEQ ID NO: 186.

Specific examples of the amino acid sequence of VH containing 2 modifications include the following amino acid sequences (1) to (4):
(1) an amino acid sequence substituting Arg at position 38 by Lys and Glu at position 46 by Lys in the amino acid sequence shown in SEQ ID NO: 186;
(2) an amino acid sequence substituting Ser at position 9 by Pro and Val at position 93 by Thr in the amino acid sequence shown in SEQ ID NO: 186;
(3) an amino acid sequence substituting Ser at position 9 by Pro and Arg at position 38 by Lys in the amino acid sequence shown in SEQ ID NO: 186; and
(4) an amino acid sequence substituting Ser at position 79 by Ala and Val at position 93 by Thr in the amino acid sequence shown in SEQ ID NO: 186.

Specific examples of the amino acid sequence of VH containing 1 modification include the following amino acid sequences (1) to (4):
(1) an amino acid sequence substituting Ser at position 9 by Pro in the amino acid sequence shown in SEQ ID NO: 186;
(2) an amino acid sequence substituting Arg at position 38 by Lys in the amino acid sequence shown in SEQ ID NO: 186;
(3) an amino acid sequence substituting Glu at position 46 by Lys in the amino acid sequence shown in SEQ ID NO: 186; and
(4) an amino acid sequence substituting Val at position 93 by Thr in the amino acid sequence shown in SEQ ID NO: 186.

Specific examples of the KM5321 humanized antibody of the present invention include the following humanized antibodies (1) to (6):
(1) a humanized antibody comprising antibody VH comprising the amino acid sequence shown in SEQ ID NO: 195 and/or antibody VL comprising the amino acid sequence shown in SEQ ID NO: 174;
(2) a humanized antibody comprising antibody VH comprising any amino acid sequence shown in FIG. 10 and/or antibody VL comprising the amino acid sequence shown in SEQ ID NO: 174;
(3) a humanized antibody comprising antibody VH comprising the amino acid sequence shown in SEQ ID NO: 195 and/or antibody VL comprising any amino acid sequence shown in FIG. 9;
(4) a humanized antibody comprising antibody VH comprising the amino acid sequence shown in SEQ ID NO: 186 and/or antibody VL comprising the amino acid sequence shown in SEQ ID NO: 180;
(5) a humanized antibody comprising antibody VH comprising any amino acid sequence shown in FIG. 10 and/or antibody VL comprising the amino acid sequence shown in SEQ ID NO: 180; and
(6) a humanized antibody comprising antibody VH comprising the amino acid sequence shown in SEQ ID NO: 186 and/or antibody VL comprising any amino acid sequence shown in FIG. 9.

The human antibody originally refers to a naturally occurring antibody in a human body and also includes, for example, antibodies obtained from a human antibody phage library and a human antibody-producing transgenic animal prepared with recent advancement in genetic engineering, cellular engineering, or developmental engineering technique.

The human antibody can be obtained by immunizing a mouse carrying human immunoglobulin genes (Tomizuka K. et al., Proc Natl Acad Sci USA. 97, 722-7, 2000.) with the desired antigen. Alternatively, the human antibody can be obtained, without immunization, by selecting the human antibody having the desired binding activity by use of a phage display library containing antibody genes amplified from human-derived B cells (Winter G. et al., Annu Rev Immunol. 12: 433-55. 1994). In addition, the human antibody can be obtained by immortalizing human B cells using EB virus and thereby preparing cells producing the human antibody having the desired binding activity (Rosen A. et al., Nature 267, 52-54. 1977).

In order to obtain an antibody present in a human body, for example, lymphocytes isolated from human peripheral blood can be immortalized by infection with EB virus or the like and then cloned to obtain lymphocytes producing the antibody. The lymphocytes are cultured, and the antibody can be purified from the cultures.

The human antibody phage library is a library of phages caused to express antibody fragments such as Fab or scFv on the surface by inserting antibody genes prepared from human B cells to phage genes. From the library, a phage expressing an antibody fragment having the desired antigen binding activity can be recovered with binding activity against an antigen-immobilized substrate as an index. The antibody fragment may be further converted, by a genetic engineering approach, to a human antibody molecule consisting of two complete H chains and two complete L chains.

The human antibody-producing transgenic animal refers to a host animal having a human antibody gene integrated in its chromosomes. Specifically, the human antibody-producing transgenic animal can be prepared by transfecting mouse ES cells with the human antibody gene and transplanting the ES cells into the early embryo of a different mouse, followed by development. The human antibody can be prepared from the human antibody-producing transgenic animal by a method which involves obtaining a human antibody-producing hybridoma by an ordinary hybridoma preparation method practiced in nonhuman mammals, and culturing the hybridoma so that the human antibody is produced and accumulated in the cultures.

The amino acid sequences of VH and VL of the antibody of the present invention may be the amino acid sequences of VH and VL of a human antibody, the amino acid sequences of VH and VL of a nonhuman animal antibody, or the amino acid sequences of VH and VL of a humanized antibody containing CDRs of nonhuman animal antibody grafted in frameworks of an arbitrary human antibody. Specific examples thereof include the amino acid sequences of VH and VL of a nonhuman animal antibody produced by a hybridoma, the amino acid sequences of VH and VL of a humanized antibody, and the amino acid sequences of VH and VL of a human antibody.

The amino acid sequence of CL in the antibody of the present invention may be the amino acid sequence of a human antibody or the amino acid sequence of a nonhuman animal antibody and is preferably Cκ or Cλ in the amino acid sequence of a human antibody.

Any CH can be used in the antibody of the present invention as long as the CH belongs to an immunoglobulin. Preferably, any of γ1 (IgG1), γ2 (IgG2), γ3 (IgG3), and γ4 (IgG4), which are subclasses belonging to the IgG classes, can be used.

The antibody of the present invention also encompasses, for example, a Fc fusion protein comprising Fc bound with an antibody fragment, a Fc fusion protein comprising Fc bound with a naturally occurring ligand or receptor (also called immunoadhesin), and a Fc fusion protein comprising a plurality of Fc regions fused with each other. For example, a Fc region containing an amino acid residue modified in order to stabilize the antibody and control half-life in blood can also be used in the antibody of the present invention.

The antibody of the present invention or the antibody fragment thereof encompasses even an antibody containing any posttranslationally modified amino acid residue. Examples of the posttranslational modification include the deletion of the C-terminal lysine residue of an H chain [lysine clipping], and the conversion of a N-terminal glutamine residue of a polypeptide to pyroglutamine (pyroGlu) [Beck et al., Analytical Chemistry, 85, 715-736 (2013)].

In the present invention, examples of the antibody fragment include Fab, Fab', F(ab')$_2$, scFv, diabody, dsFv, and peptide comprising a plurality of CDRs.

The Fab is an antibody fragment having a molecular weight of approximately 50,000 and having antigen binding activity, in which approximately N-terminal half of an H chain and the whole L chain are joined through a disulfide bond (S—S bond) in a fragment obtained by the treatment of an IgG antibody with a proteolytic enzyme papain (which cleaves the H chain at amino acid residue 224).

The F(ab')$_2$ is an antibody fragment having a molecular weight of approximately 100,000 and having antigen binding activity, in which the F(ab')$_2$ is slightly larger than Fabs joined through a S—S bond in the hinge region in a fragment obtained by the treatment of IgG with a proteolytic enzyme pepsin (which cleaves the H chain at amino acid residue 234).

The Fab' is an antibody fragment having a molecular weight of approximately 50,000 and having antigen binding activity, which is obtained by the cleavage of the S—S bond in the hinge region of the F(ab')$_2$.

The scFv is an antibody fragment having antigen binding activity, which is a VH-P-VL or VL-P-VH polypeptide comprising one VH and one VL linked using an appropriate peptide linker (P) such as a linker peptide in which any number of linkers (G4S (SEQ ID NO: 214)) each consisting of four Gly and one Ser residues are connected.

The diabody is an antibody fragment comprising a dimer formed by scFvs having the same or different antigen binding specificity, and is an antibody fragment having divalent antigen binding activity against the same antigen or antigen binding activity specific for different antigens.

The dsFv refers to a fragment in which polypeptides obtained by substituting one amino acid residue each of VH and VL by cysteine residues are joined via a S—S bond between the cysteine residues.

The peptide comprising CDRs is configured to comprise at least one or more CDR regions of VH or VL. In the peptide comprising a plurality of CDRs, the CDRs can be joined either directly or via an appropriate peptide linker. DNAs encoding CDRs of VH and VL of the engineered antibody of the present invention are constructed. The DNAs are inserted to expression vectors for prokaryotes or expression vectors for eukaryotes. A prokaryote or a eukaryote can be transfected with the expression vectors, followed by expression to produce the peptide comprising CDRs. Alternatively, the peptide comprising CDRs can also be produced by a chemical synthesis method such as a Fmoc method or a tBoc method.

The monoclonal antibody of the present invention encompasses an antibody derivative obtained through the chemical or genetic engineering conjugation of, for example, a radioisotope, a low-molecular agent, a high-molecular agent, a protein, or an antibody drug to the monoclonal antibody of the present invention or the antibody fragment thereof which binds to human Gas6.

The antibody derivative can be produced by conjugating, for example, a radioisotope, a low-molecular agent, a high-molecular agent, an immunostimulant, a protein, an antibody drug, or a nucleic acid drug, by a chemical approach [Kotai-Kogaku-Nyumon (Antibody Engineering Manual in English), Chijinshokan Co., Ltd. (1994)], to the N or C terminus of the H or L chain of the monoclonal antibody of the present invention or the antibody fragment thereof which binds to human Gas6, or an appropriate substituent, side chain, sugar chain, or the like in the antibody molecule.

Alternatively, the antibody derivative can be produced by a genetic engineering approach which involves linking DNA encoding the monoclonal antibody of the present invention or the antibody fragment thereof which binds to human Gas6 to DNA encoding the protein or the antibody drug to be conjugated, inserting the resulting DNA construct to expression vectors, and transfecting appropriate host cells with the expression vectors, followed by expression.

Examples of the radioisotope include 11In, $^{131}$I, $^{125}$I, $^{90}$Y, $^{64}$Cu, $^{99}$Tc, $^{77}$Lu, and $^{211}$At. The radioisotope can be conjugated directly to the antibody by a chloramine T method or the like. Alternatively, a substance chelating the radioisotope may be conjugated to the antibody. Examples of the chelating agent include 1-isothiocyanatobenzyl-3-methyldiethylenetriamine pentaacetic acid (MX-DTPA).

Examples of the low-molecular agent include: anticancer agents such as alkylating agents, nitrosourea agents, antimetabolites, antibiotics, vegetable alkaloids, topoisomerase inhibitors, hormone therapeutics, hormone antagonists, aromatase inhibitors, P glycoprotein inhibitors, platinum complex derivatives, M phase inhibitors, and kinase inhibitors [Clinical Oncology, Japanese Journal of Cancer & Chemotherapy Publishers (1996)]; and anti-inflammatory agents including steroids such as hydrocortisone and prednisone, non-steroidal agents such as aspirin and indomethacin, immunomodulators such as gold thiomalate and penicillamine, immunosuppressants such as cyclophosphamide and azathioprine, and antihistaminic agents such as chlorpheniramine maleate and clemastine [Ensho-To-Koensho-Ryoho (Inflammation and Anti-inflammatory Therapy in English), Ishiyaku Pub, Inc. (1982)].

Examples of the anticancer agent include amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (adriamycin), epirubicin, gemcitabine (Gemzar), daunorubicin, procarbazine, mitomycin, cytarabine, etoposide, methotrexate, 5-fluorouracil, fluorouracil, vinblastine, vincristine, bleomycin, daunomycin, peplomycin, estramustine, paclitaxel (Taxol), docetaxel (Taxotere), aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaliplatin, gefitinib (Iressa), imatinib (STI571), erlotinib, FMS-like tyrosine kinase 3 (Flt3) inhibitors, vascular endothelial growth factor receptor (VEGFR) inhibitors, fibroblast growth factor receptor (FGFR) inhibitors, epidermal growth factor receptor (EGFR) inhibitors such as Iressa and Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, gold thiomalate, D-penicillamine, bucillamine, azathioprine, mizoribine, cyclosporine, rapamycin, hydrocortisone, bexarotene (Targretin), tamoxifen, dexamethasone, progestins, estrogens, anastrozole (Arimidex), Leuplin, aspirin, indomethacin, celecoxib, penicillamine, gold thiomalate, chlorpheniramine maleate, chlorpheniramine, clemastine, tretinoin, bexarotene, arsenic, bortezomib, allopurinol, calicheamicin, ibritumomab tiuxetan, Targretin, ozogamicin, clarithromycin, leucovorin, ketoconazole, aminoglutethimide, suramin, maytansinoid, and derivatives thereof.

Examples of the method for conjugating the low-molecular agent to the antibody include a method of bonding the amino group of the agent to the amino group of the antibody via glutaraldehyde, and a method of bonding the amino group of the agent to the carboxyl group of the antibody via water-soluble carbodiimide.

Examples of the high-molecular agent include polyethylene glycol (hereinafter, abbreviated to PEG), albumin, dextran, polyoxyethylene, styrene-maleic acid copolymers, polyvinylpyrrolidone, pyran copolymers, and hydroxypropylmethacrylamide. The conjugation of such a high-molecular compound to the antibody or the antibody fragment thereof is expected to produce effects such as (1) improvement in stability against various chemical, physical, or biological factors, (2) remarkable prolongation of half-life in blood, and (3) disappearance of immunogenicity or suppression of antibody production [Bioconjugate Drugs, The Second series of pharmaceutical research and development, Hirokawa Shoten Co., Ltd. (1993)]. Examples of the method for conjugating PEG to the antibody include a method of reacting the antibody with a PEGylation reagent [Bioconjugate Drugs, The Second series of pharmaceutical research and development, Hirokawa Shoten Co., Ltd. (1993)]. Examples of the PEGylation reagent include a modifying agent for the ε-amino group of lysine (Japanese Patent Laid-Open No. 61-178926), a modifying agent for the carboxyl groups of aspartic acid and glutamic acid (Japanese Patent Laid-Open No. 56-23587), and a modifying agent for the guanidino group of arginine (Japanese Patent Laid-Open No. 2-117920).

The immunostimulant may be a natural product known as an immunoadjuvant. Specific examples thereof include agents enhancing the immunity, such as $\beta(1\rightarrow 3)$glucanes (lentinan and sizofiran) and α-galactosylceramide (KRN7000).

Examples of the protein include cytokines and growth factors that activate immunocompetent cells such as NK cells, macrophages, or neutrophils, and toxin proteins.

Examples of the cytokine and the growth factor include interferon (hereinafter, abbreviated to IFN)-α, IFN-β, IFN-γ, interleukin (hereinafter, abbreviated to IL)-2, IL-12, IL-15, IL-18, IL-21, IL-23, granulocyte colony-stimulating factor (G-CSF), granulocyte/macrophage colony-stimulating factor (GM-CSF), and macrophage colony-stimulating factor (M-CSF). Examples of the toxin protein include ricin, diphtheria toxin, and ONTAK. The toxin protein also includes protein toxins containing a protein mutation in order to adjust toxicity.

Examples of the antibody drug include antibodies against antigens inducing apoptosis by antibody binding, antigens involved in the pathomorphogenesis of tumor, antigens regulating immune functions, or antigens involved in the vascularization of a lesion site.

Examples of the antigen inducing apoptosis by antibody binding include cluster of differentiation (hereinafter, abbreviated to CD) 19, CD20, CD21, CD22, CD23, CD24, CD37, CD53, CD72, CD73, CD74, CDw75, CDw76, CD77, CDw78, CD79a, CD79b, CD80 (B7.1), CD81, CD82, CD83, CDw84, CD85, CD86 (B7.2), human leukocyte antigen (HLA)-class II, and epidermal growth factor receptor (EGFR).

Examples of the antigen involved in the pathomorphogenesis of tumor or the antigen of an antibody regulating immune functions include CD4, CD40, CD40 ligands, B7 family molecules (CD80, CD86, CD274, B7-DC, B7-H2, B7-H3, and B7-H4), ligands of B7 family molecules (CD28, CTLA-4, ICOS, PD-1, and BTLA), OX-40, OX-40 ligands, CD137, tumor necrosis factor (TNF) receptor family molecules (DR4, DR5, TNFR1, and TNFR2), TNF-related apoptosis-inducing ligand receptor (TRAIL) family molecules, receptor family of TRAIL family molecules (TRAIL-R1, TRAIL-R2, TRAIL-R3, and TRAIL-R4), receptor activator of nuclear factor kappa B ligand (RANK), RANK ligands, CD25, folate receptors, cytokines [IL-1α, IL-1β, IL-4, IL-5, IL-6, IL-10, IL-13, transforming growth factor (TGF) β, TNFα, etc.], receptors of these cytokines, chemokines (SLC, ELC, 1-309, TARC, MDC, CTACK, etc.), and receptors of these chemokines.

Examples of the antigen of an antibody inhibiting the vascularization of a lesion site include vascular endothelial growth factor (VEGF), angiopoietin, fibroblast growth factor (FGF), EGF, hepatocyte growth factor (HGF), platelet-derived growth factor (PDGF), insulin-like growth factor (IGF), erythropoietin (EPO), TGFβ, IL-8, ephrin, SDF-1, and their receptors.

A fusion antibody with the protein or the antibody drug can be produced by linking cDNA encoding the protein or the antibody contained in the antibody drug to cDNA encoding the monoclonal antibody or the antibody fragment to construct DNA encoding the fusion antibody, inserting the DNA to expression vectors for prokaryotes or eukaryotes, and transfecting a prokaryote or a eukaryote with the expression vectors, followed by expression.

Examples of the nucleic acid drug include drugs comprising a nucleic acid, such as small interference ribonucleic acid (siRNA) or microRNA, which acts on an organism by controlling gene functions. For example, a conjugate with a nucleic acid drug inhibiting a master transcriptional factor RORγt of Th17 cells is possible.

In the case of using the derivative of the antibody of the present invention in a detection method, an assay method, or a diagnosis method, or in the case of using the derivative of the antibody of the present invention as a reagent for detection, a reagent for assay, or a diagnostic agent, examples of an agent to be bound with the antibody include labels for use in ordinary immunological detection or assay methods. Examples of the label include: enzymes such as alkaline phosphatase, peroxidase, and luciferase; luminescent materials such as acridinium ester and lophine; and fluorescent materials such as fluorescein isothiocyanate (FITC) and tetramethylrhodamine isothiocyanate (RITC).

The present invention also relates to a therapeutic agent for a human Gas6-related disease, comprising the monoclonal antibody or the antibody fragment thereof which binds to human Gas6 as an active ingredient. The present invention also relates to a method for treating a human Gas6-related disease, comprising administering the monoclonal antibody or the antibody fragment thereof which binds to human Gas6.

The human Gas6-related disease can be any disease as long as human Gas6 or a human Gas6 receptor is involved in the disease. Examples thereof include kidney diseases and cancer diseases. Examples of the kidney disease include glomerulonephritis, IgA nephropathy, and diabetic nephropathy. Examples of the glomerulonephritis include progressive glomerulonephritis and mesangioproliferative glomerulonephritis. Specific examples of the cancer disease include lung cancer, breast cancer, ovary cancer, prostate cancer, pancreatic cancer, kidney cancer, and glioblastoma. Other examples of the disease include thromboembolism, ischemic diseases, venous thromboembolism, arterial thrombosis, venous thrombosis, pulmonary embolism, restenosis, diabetic vascular disorder, and allograft atherosclerosis.

The therapeutic agent comprising the antibody of the present invention or the antibody fragment thereof may be a therapeutic agent containing only the antibody or the antibody fragment thereof as an active ingredient and is usually desirably provided as a pharmaceutical preparation produced by an arbitrary method known in the technical field of pharmaceutics, which involves mixing the active ingredient with one or more pharmacologically acceptable carriers.

An administration route which is most effective for treatment is desirably used. Examples thereof include oral administration and parenteral administration such as intraoral administration, intra-tracheal administration, intrarectal administration, subcutaneous administration, intramuscular administration, and intravenous administration and preferably include intravenous administration. Examples of the dosage form include aerosols, capsules, tablets, powders, granules, syrups, emulsions, suppositories, injections, ointments, and tapes.

The dose or the number of doses differs depending on intended therapeutic effects, an administration method, the length of treatment, age, and body weight, etc. and is usually 10 μg/kg to 10 mg/kg per day in adult.

The present invention relates to a reagent for detection or assay of Gas6, comprising the monoclonal antibody or the antibody fragment thereof which binds to human Gas6, and a method for detecting or assaying Gas6 using the monoclonal antibody or the antibody fragment thereof which binds to human Gas6. In the present invention, examples of the method for detecting or assaying human Gas6 include arbitrary methods known in the art. Examples thereof include immunological detection or assay methods.

The immunological detection or assay method is a method which involves using a labeled antigen or antibody to detect or measure the amount of the antibody or the amount of the antigen. Examples of the immunological detection or assay method include radioimmunoassay (RIA), enzyme immunoassay (EIA or ELISA), fluorescent immunoassay (FIA), luminescent immunoassay, Western blot, and physicochemical approaches.

The present invention relates to a diagnostic agent for a Gas6-related disease, comprising the monoclonal antibody or the antibody fragment thereof which binds to human Gas6 as an active ingredient, and a method for diagnosing a Gas6-related disease, comprising detecting or assaying Gas6 using the monoclonal antibody or the antibody fragment thereof which binds to human Gas6. The human Gas6-related disease can be diagnosed by detecting or assaying cells expressing human Gas6 according to the aforementioned method using the monoclonal antibody of the present invention or the antibody fragment thereof.

In the present invention, a biological sample to be subjected to the detection or assay of human Gas6 is not particularly limited and is, for example, tissues, cells, blood, plasma, serum, pancreatic juice, urine, feces, tissue fluids, or culture solutions, as long as the biological sample is likely to contain human Gas6 or cells expressing human Gas6.

The diagnostic agent comprising the monoclonal antibody of the present invention or the antibody fragment thereof may comprise a reagent for antigen-antibody reaction and a reagent for detection of the reaction, according to an intended diagnosis method.

Examples of the reagent for antigen-antibody reaction include buffers and salts. Examples of the reagent for detection include reagents for use in ordinary immunological detection or assay methods, such as a labeled secondary antibody recognizing the monoclonal antibody or the antibody fragment thereof, and a substrate appropriate for the label.

The present invention also relates to use of the anti-human Gas6 monoclonal antibody or the antibody fragment thereof for the production of a therapeutic agent or a diagnostic agent for a Gas6-related disease.

Hereinafter, a method for producing the antibody of the present invention, a method for treating a disease, and a method for diagnosing a disease will be specifically described.

1. Method for Producing Antibody (1) Preparation of Antigen Human Gas6 serving as an antigen is obtained by purification from human Gas6-expressing cells prepared by transfecting, for example, E. coli, yeast, insect cells, or animal cells with an expression vector containing cDNA encoding the full-length human Gas6 or a partial length thereof. Alternatively, human Gas6 can also be obtained by purifying human Gas6 from various human cell lines, human cells, human tissues, etc., expressing a large amount of human Gas6. A synthetic peptide having a partial sequence of human Gas6 can be prepared by a chemical synthesis method such as a Fmoc method or a tBoc method and used as an antigen. A tag known in the art such as FLAG or His may be added to the C or N terminus of the human Gas6 or the synthetic peptide having a partial sequence of human Gas6.

The human Gas6 used in the present invention can be produced according to a method described in, for example, Molecular Cloning, A Laboratory Manual, Second Edition, Cold Spring Harbor Laboratory Press (1989) or Current Protocols In Molecular Biology, John Wiley & Sons (1987-1997), for example, the following method which involves allowing host cells to express DNA encoding the human Gas6.

First, full-length cDNA containing a portion encoding human Gas6 is inserted to downstream of a promoter in an appropriate expression vector to prepare a recombinant vector. A DNA fragment of appropriate length containing the portion encoding the polypeptide may be prepared on the basis of the full-length cDNA and used instead of the full-length cDNA. Next, host cells compatible with the expression vector can be transfected with the obtained recombinant vector to obtain transformants producing the polypeptide.

Any expression vector can be used as long as the expression vector is capable of replicating autonomously or being chromosomally integrated in the host cells used and contains an appropriate promoter at a position that can transcribe DNA encoding the polypeptide.

Any host cell such as a microbe belonging to the genus Escherichia (e.g., E. coli), yeast, insect cells, or animal cells can be used as long as the host cell can express the gene of interest.

In the case of using a prokaryote such as E. coli as the host cells, the recombinant vector is preferably a vector that is capable of replicating autonomously in the prokaryote and also contains a promoter, a ribosomal binding sequence, DNA containing a portion encoding human Gas6, and a transcription termination sequence. Although the recombinant vector is not necessarily required to have the transcription termination sequence, it is preferred to place the transcription termination sequence immediately downstream of a structural gene. The recombinant vector may further contain a gene controlling the promoter.

A plasmid having an appropriately adjusted distance (e.g., 6 to 18 bases) between a Shine-Dalgarno sequence (also called SD sequence) as a ribosomal binding sequence and a start codon is preferably used as the recombinant vector.

For the nucleotide sequence of DNA encoding the human Gas6, a base can be substituted so as to give a codon optimal for expression in a host. This can improve the rate of production of the human Gas6 of interest.

Any expression vector can be used as long as the expression vector can exert its functions in the host cells used. Examples thereof include pBTrp2, pBTac1, and pBTac2 (all manufactured by Roche Diagnostics K.K.), pKK233-2 (manufactured by Pharmacia Corp.), pSE280 (manufactured by Invitrogen Corp.), pGEMEX-1 (manufactured by Promega Corp.), pQE-8 (manufactured by Qiagen N.V.), pKYP10 (Japanese Patent Laid-Open No. 58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (manufactured by Stratagene Corp.), pTrs30 [prepared from E. coli JM109/pTrS30 (FERM BP-5407)], pTrs32 [prepared from E. coli JM109/pTrS32 (FERM BP-5408)], pGHA2 [prepared from E. coli IGHA2 (FERM BP-400); Japanese Patent Laid-Open No. 60-221091], pGKA2 [prepared from E. coli IGKA2 (FERM BP-6798); Japanese Patent Laid-Open No. 60-221091], pTerm2 (U.S. Pat. Nos. 4,686,191, 4,939,094, and 5,160,735), pSupex, pUB110, pTP5, pC194, pEG400 [J. Bacteriol., 172, 2392 (1990)], pGEX (manufactured by Pharmacia Corp.), pET system (manufactured by Novagen/Merck KGaA), and pME18SFL3.

Any promoter can be used as long as the promoter can exert its functions in the host cells used. Examples thereof can include E. coli- or phage-derived promoters such as trp promoter (Ptrp), lac promoter, PL promoter, PR promoter, and T7 promoter. Alternatively, for example, an artificially designed and engineered promoter such as a tandem promoter (two Ptrp promoters connected in series), tac promoter, lacT7 promoter, or let I promoter can also be used.

Examples of the host cells include E. coli XL1-Blue, E. coli XL2-Blue, E. coli DH1, E. coli MC1000, E. coli KY3276, E. coli W1485, E. coli JM109, E. coli HB101, E. coli No. 49, E. coli W3110, E. coli NY49, and E. coli DH5a.

Any method that can transfer DNA to the host cells used can be used as a method for transfecting the host cells with the recombinant vector. Examples thereof include a method using calcium ions [Proc. Natl. Acad. Sci. USA, 69, 2110 (1972); Gene, 17, 107 (1982); and Molecular & General Genetics, 168, 111 (1979)].

In the case of using animal cells as the host, any expression vector can be used as long as the expression vector can exert its functions in the animal cells. Examples thereof include pcDNAI, pCDM8 (manufactured by Funakoshi Co., Ltd.), pAGE107 [Japanese Patent Laid-Open No. 3-22979; and Cytotechnology, 3, 133 (1990)], pAS3-3 (Japanese Patent Laid-Open No. 2-227075), pCDM8 [Nature, 329, 840 (1987)], pcDNAI/Amp (manufactured by Invitrogen Corp.), pcDNA3.1 (manufactured by Invitrogen Corp.), pREP4 (manufactured by Invitrogen Corp.), pAGE103 [J. Biochemistry, 101, 1307 (1987)], pAGE210, pME18SFL3, pKANTEX93 (WO97/10354), N5KG1val (U.S. Pat. No. 6,001,358), INPEP4 (manufactured by Biogen-IDEC Inc.), and transposon vector (WO2010/143698).

Any promoter can be used as long as the promoter can exert its functions in the animal cells. Examples thereof include cytomegalovirus (CMV) immediate early (IE) gene promoter, SV40 early promoter, retrovirus promoter, metallothionein promoter, heat shock promoter, SRα promoter, and Moloney mouse leukemia virus promoter or enhancer. Also, human CMV IE gene enhancer may be used with the promoter.

Examples of the host cells include human leukemia Namalwa cells, monkey COS cells, Chinese hamster ovary (CHO) cells (Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); and Molecular Cell Genetics, Appendix I, II (pp. 883-900)), CHO cells deficient in dihydrofolate reductase gene (hereinafter, abbreviated to dhfr) (Proc. Natl. Acad. Sci. USA, 77, 4216 (1980)), CHO-K1 (ATCC CCL-61), DUkXB11 (ATCC CCL-9096), Pro-5 (ATCC CCL-1781), CHO-S(Life Technologies Corp., Cat #11619), Pro-3, rat myeloma cells YB2/3HL.P2.G11.16Ag.20 (or also referred to as YB2/0), mouse myeloma cells NS0, mouse myeloma cells SP2/0-Ag14, and Syrian hamster cells BHK or HBT5637 (Japanese Patent Laid-Open No. 63-000299).

Any method of transferring DNA to the animal cells can be used as a method for transfecting the host cells with the recombinant vector. Examples thereof include electroporation [Cytotechnology, 3, 133 (1990)], a calcium phosphate method (Japanese Patent Laid-Open No. 2-227075), and lipofection [Proc. Natl. Acad. Sci. USA, 84, 7413 (1987)].

The thus-obtained transformants (derived from a microbe, animal cells, etc.) harboring the recombinant vector having an insert of the DNA encoding human Gas6 are cultured in a medium so that the human Gas6 is produced and accumulated in the culture solution. The human Gas6 can be produced by collection from the culture solution. The method for culturing the transformants in the medium can be performed according to an ordinary method for use in the culture of the host.

The human Gas6 expressed in eukaryote-derived cells can be obtained in a sugar- or sugar chain-added form.

In order to prepare a Gas6 protein comprising the Gla domain of Gas6 bound with a γ-carboxyglutamic acid residue (Gla), cells harboring vitamin K epoxide reductase (VKOR) or γ-glutamyl carboxylase (GGCX) which is an enzyme involved in the γ-carboxylation of a glutamic acid residue may be used. Preferably, cells harboring both of vitamin K epoxide reductase complex subunit 1 (VKORC1) and GGCX are used for promoting the induction of reduced vitamin K.

Each of VKOR, VKORC1, and GGCX may be any enzyme that can efficiently introduce a Gla residue to Gas6. An enzyme of any species such as a human, a rat, or a mouse may be used, and these enzymes can be selected, for use, according to the host cells used. Preferably, γ-carboxylated Gas6 can be prepared using cells transfected with human or rat VKORC1 and GGCX genes.

When a microbe transformed with a recombinant vector containing an inducible promoter is cultured, an inducer may be added to the medium, if necessary. For example, in the case of culturing a microbe transformed with a recombinant vector containing lac promoter, isopropyl-β-D-thiogalactopyranoside or the like may be added to the medium. In the case of culturing a microbe transformed with a recombinant vector containing trp promoter, indoleacrylic acid or the like may be added to the medium.

Examples of the medium for the culture of the transformants obtained with animal cells as the host include RPMI1640 medium [The Journal of the American Medical Association, 199, 519 (1967)], Eagle's MEM medium [Science, 122, 501 (1952)], Dulbecco's modified MEM medium [Virology, 8, 396 (1959)], 199 medium [Proc. Soc. Exp. Biol. Med., 73, 1 (1950)], and Iscove's Modified Dulbecco's Medium (IMDM) medium generally used, and these media supplemented with fetal bovine serum (FBS) or the like. The culture is usually performed for 1 to 7 days under conditions such as pH 6 to 8, 30 to 40° C., and in the presence of 5% $CO_2$. During the culture, an antibiotic such as kanamycin or penicillin may be added, if necessary, into the medium.

Direct expression as well as a method such as secretory production or fusion protein expression [Molecular Cloning, A Laboratory Manual, Second Edition, Cold Spring Harbor Laboratory Press (1989)] can be used as a method for expressing the gene encoding human Gas6.

The method for producing human Gas6 is a method of intracellularly producing human Gas6 by the host cells, a method of extracellularly secreting human Gas6 by the host cells, or a method of producing human Gas6 on the outer membranes of the host cells. An appropriate method can be selected according to the host cells used or by changing the structure of human Gas6 to be produced.

In the case of intracellularly producing human Gas6 by the host cells or producing human Gas6 on the outer membranes of the host cells, the human Gas6 can be aggressively secreted to the outside of the host cells by use of the method of Paulson et al. [J. Biol. Chem., 264, 17619 (1989)], the method of Lowe et al. [Proc. Natl. Acad. Sci., USA, 86, 8227 (1989); and Genes Develop., 4, 1288 (1990)], or a method described in, for example, Japanese Patent Laid-Open No. 05-336963 or WO94/23021.

The amount of the human Gas6 produced may be elevated by use of a gene amplification system using dihydrofolate reductase gene or the like (Japanese Patent Laid-Open No. 2-227075).

The obtained human Gas6 can be isolated and purified, for example, as follows.

For human Gas6 intracellularly expressed in a dissolved state, the cells after the completion of culture are recovered by centrifugation and suspended in an aqueous buffer solution, and the cells are then homogenized using, for example, an ultrasonic homogenizer, a French press, a Manton-Gaulin homogenizer, or Dyno-Mill to obtain cell-free extracts. From a supernatant obtained by the centrifugation of the cell-free extracts, a purified preparation can be obtained by use of ordinary protein isolation and purification methods, i.e., approaches such as a solvent extraction method, a salting-out method using ammonium sulfate or the like, a desalting method, a precipitation method with an organic solvent, anion-exchange chromatography using a resin such as diethylaminoethyl (DEAE)-Sepharose or DIAION HPA-75 (manufactured by Mitsubishi Chemical Corp.), cation-exchange chromatography using a resin such as S-Sepharose FF (manufactured by Pharmacia Corp.), hydrophobic chromatography using a resin such as butyl Sepharose or phenyl Sepharose, a gel filtration method using a molecular sieve, affinity chromatography, and electrophoresis such as chromatofocusing or isoelectric focusing, each alone or in combination.

For human Gas6 intracellularly expressed in an insoluble form, the cells are recovered, then homogenized, and centrifuged in the same way as above to recover the human Gas6 in an insoluble form as a precipitated fraction. The recovered human Gas6 in an insoluble form is lysed with a protein denaturant. The lysate is diluted or dialyzed to restore the normal conformation of the human Gas6. Then, a purified preparation of the polypeptide can be obtained by the same isolation and purification method as above.

For extracellularly secreted human Gas6 or derivative (e.g., glycosylated form) thereof, the human Gas6 or the derivative (e.g., glycosylated form) thereof can be recovered into a culture supernatant. The cultures are treated by the same approach as above, such as centrifugation, to obtain a soluble fraction. From the soluble fraction, a purified preparation can be obtained by the same isolation and purification method as above.

The human Gas6 used in the present invention can also be produced by a chemical synthesis method such as a Fmoc method or a tBoc method. Alternatively, the human Gas6 can also be chemically synthesized using a peptide synthesizer manufactured by, for example, Advanced ChemTech, Inc., PerkinElmer, Inc., Pharmacia Corp., Protein Technology Instruments Inc., Synthecell/Vega Biomolecules Corp, PerSeptive Biosystems, Inc., or Shimadzu Corp.

(2) Immunization of Animal and Preparation of Antibody-Producing Cell for Fusion 3- to 20-week-old animals such as mice, rats, or hamsters are immunized with the antigen obtained in the paragraph (1), and antibody-producing cells are collected from the spleens, lymph nodes, or peripheral blood of the animal. Alternatively, mouse Gas6-knockout mice can also be used as the animals to be immunized.

The immunization is performed by subcutaneously, intravenously, or intraperitoneally administering the antigen, for example, with an appropriate adjuvant such as a complete Freund's adjuvant, or aluminum hydroxide gel and *Bordetella pertussis* vaccine, to the animals. When the antigen is a partial peptide, its conjugate with a carrier protein such as BSA (bovine serum albumin) or KLH (keyhole limpet hemocyanin) is prepared and used as an immunogen.

The administration of the antigen is performed 5 to 10 times at 1- to 2-week intervals after priming. 3 to 7 days after each administration, blood is collected from the fundus venous plexus, and an antibody titer in the serum is measured by use of enzyme immunoassay [Antibodies—A Laboratory Manual, Cold Spring Harbor Laboratory (1988)] or the like. An animal that exhibits an adequate antibody titer in the serum for the antigen used in the immunization is used as a source of antibody-producing cells for fusion.

3 to 7 days after the final administration of the antigen, a tissue, such as the spleen, which contains antibody-producing cells is harvested from the immunized animal to collect the antibody-producing cells. In the case of using spleen cells, the spleen is chopped, loosened, and then centrifuged for the further removal of erythrocytes to obtain antibody-producing cells for fusion.

(3) Preparation of Myeloma Cell

An established cell line obtained from a mouse is used as myeloma cells. Examples of the myeloma cells used include 8-azaguanine-resistant mouse (BALB/c-derived) myeloma cell lines P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], and P3-X63-Ag8 (X63) [Nature, 256, 495 (1975)].

The myeloma cells are subcultured in a normal medium [RPMI1640 medium supplemented with glutamine, 2-mercaptoethanol, gentamicin, FBS, and 8-azaguanine] and subcultured in a normal medium 3 to 4 days before cell fusion to secure $2 \times 10^7$ cells on the fusion day.

(4) Cell Fusion and Preparation of Monoclonal Antibody-Producing Hybridoma

The antibody-producing cells for fusion obtained in the paragraph (2) and the myeloma cells obtained in the paragraph (3) are thoroughly washed with minimum essential medium (MEM) medium or PBS (1.83 g of disodium phosphate, 0.21 g of monopotassium phosphate, 7.65 g of common salt, and 1 l of distilled water, pH 7.2) and mixed such that the number of cells is antibody-producing cells for fusion:myeloma cells=5 to 10:1. After centrifugation, the supernatant is removed. The precipitated cell group is well loosened, and a mixed solution of polyethylene glycol-1000 (PEG-1000), MEM medium, and dimethyl sulfoxide is then added thereto at 37° C. with stirring. 1 to 2 mL of MEM medium is further added thereto several times at 1- to 2-minute intervals. Then, the whole amount is adjusted to 50 mL by the addition of MEM medium. After centrifugation, the supernatant is removed. The precipitated cell group is mildly loosened, and the cells are then mildly suspended in HAT medium [normal medium supplemented with hypoxanthine, thymidine, and aminopterin]. This suspension is cultured at 37° C. for 7 to 14 days in a 5% $CO_2$ incubator.

After the culture, a portion of the culture supernatant is sampled, and a cell group that reacts with an antigen comprising human Gas6 and does not react with an antigen free from human Gas6 is selected by a hybridoma selection method such as binding assay mentioned later. In addition, a hybridoma cell group producing an anti-human Gas6 antibody that inhibits the binding between human Gas6 and a Gas6 receptor such as Axl is selected by, for example, competition assay mentioned later. Next, the selected hybridomas are cloned by a limiting dilution method, and a hybridoma that stably exhibits a strong antibody titer is selected as a monoclonal antibody-producing hybridoma.

(5) Preparation of Purified Monoclonal Antibody

The monoclonal antibody-producing hybridoma obtained in the paragraph (4) is intraperitoneally injected to an 8- to 10-week-old mouse treated with pristane [0.5 mL of 2,6,10,14-tetramethylpentadecane (pristane) is intraperitoneally administered to the mouse, which is then raised for 2 weeks] or a nude mouse. The hybridoma forms ascites cancer in 10 to 21 days. The ascetic fluid is collected from this mouse and centrifuged for the removal of solid matter, followed by salting-out with 40 to 50% ammonium sulfate. An IgG or IgM fraction is collected by purification using a caprylic acid precipitation method, a DEAE-Sepharose column, a protein A column, or a gel filtration column and used as a purified monoclonal antibody.

Alternatively, the monoclonal antibody-producing hybridoma obtained in the paragraph (4) is cultured in, for example, RPMI1640 medium supplemented with 10% FBS, then centrifuged for the removal of a supernatant, suspended in Hybridoma SFM medium, and cultured for 3 to 7 days. The obtained cell suspension is centrifuged. From the obtained supernatant, an IgG fraction can be collected by purification using a protein A column or a protein G column to obtain a purified monoclonal antibody. The Hybridoma SFM medium may be supplemented with 5% Daigo's GF21.

The subclass of the antibody is determined by enzyme immunoassay using a subclass typing kit. The amount of the protein is determined by a Lowry method or calculation from absorbance at 280 nm.

(6) Selection of Monoclonal Antibody

The monoclonal antibody is selected by, for example, binding assay or competition assay based on enzyme immunoassay given below. The monoclonal antibody can also be selected by, for example, kinetics analysis using Biacore®, in addition to these methods. Alternatively, the monoclonal antibody may be selected by identifying a target antigen of the antibody according to a method known in the art [The Prostate, 67, 1163 (2007)].

(6-a) Binding Assay

For example, a recombinant protein obtained by transfecting *E. coli*, yeast, insect cells, animal cells, or the like with an expression vector comprising cDNA encoding human Gas6 as described in the paragraph (1), or a purified polypeptide or a partial peptide obtained from human tissues is used as an antigen. When the antigen is a recombinant protein, a tag such as FLAG or His may be added thereto. When the antigen is a partial peptide, its conjugate with a carrier protein such as BSA or KLH is prepared and used.

The antigen is dispensed to wells of a plate such as a 96-well plate and immobilized thereon. Then, a test substance such as serum, the culture supernatant of the hybridoma, or the purified monoclonal antibody is dispensed thereto as a primary antibody and reacted. The plate is thoroughly washed with PBS, PBS-Tween, or the like, and an anti-immunoglobulin antibody labeled with biotin, an enzyme, a chemiluminescent material, a radioactive compound, or the like is then dispensed thereto as a secondary antibody and reacted. The plate is thoroughly washed with PBS-Tween, and reaction appropriate for the labeling material on the secondary antibody is then performed to select a monoclonal antibody specifically reacting with the immunogen.

An antibody binding to an epitope comprising an epitope to which the human Gas6-binding monoclonal antibody of the present invention binds can be obtained by identifying an epitope for the antibody obtained in the aforementioned binding assay system by a method known in the art, and preparing a synthetic peptide or the like containing the identified epitope, followed by immunization.

An antibody binding to the same epitope as an epitope to which the human Gas6-binding monoclonal antibody of the present invention binds can be obtained by identifying an epitope for the antibody obtained in the aforementioned binding assay system, and preparing a partial synthetic peptide of the identified epitope, a synthetic peptide mimicking the conformation of the epitope, or the like, followed by immunization.

(6-b) Competition Assay

A fusion protein of a human Axl extracellular domain and a human IgG1 heavy chain constant region (hAxl-hFc) is prepared according to the method described in the paragraph (1). The hAxl-hFc may have an appropriate restriction enzyme recognition sequence between the human Axl extracellular domain and the IgG1 heavy chain constant region. The obtained hAxl-hFc is dispensed to wells of a 96-well plate and immobilized thereon. Next, a mixed solution of a test substance such as the hybridoma culture supernatant or the purified monoclonal antibody and the tagged hGas6 obtained in the paragraph (1) is dispensed to the wells and reacted. The plate is thoroughly washed with PBS, PBS-Tween, or the like, and an antibody, against the tag, labeled with biotin, an enzyme, a chemiluminescent material, a radioactive compound, or the like is then dispensed thereto as an antibody for detection and reacted. The plate is thoroughly washed with PBS-Tween, and reaction appropriate for the labeling material on the antibody for detection is then performed to select a monoclonal antibody inhibiting the binding between hGas6 and hAxl-hFc.

(6-c) Kinetics Analysis Using Biacore®

The kinetics of the binding between an antigen and a test substance is measured using Biacore® T100, and the results are analyzed using analytical software attached to the instrument. An anti-mouse IgG antibody is immobilized on a sensor chip CM5 by an amine coupling method. Then, a test substance such as the hybridoma culture supernatant or the purified monoclonal antibody is injected thereto so that an appropriate amount of the test substance is bound thereto. Plural concentrations of an antigen with known concentrations are further injected thereto, and association and dissociation are measured. The obtained data is subjected to kinetics analysis on a 1:1 binding model using software attached to the instrument to obtain various parameters. Alternatively, human Gas6, a partial peptide thereof, or a conjugate of the partial peptide with a carrier protein is immobilized onto a sensor chip, for example, by an amine coupling method. Then, plural concentrations of the purified monoclonal antibody with known concentrations are injected thereto, and association and dissociation are measured. The obtained data is subjected to kinetics analysis on a bivalent binding model using software attached to the instrument to obtain various parameters.

2. Preparation of Recombinant Antibody

Hereinafter, methods for preparing a human chimeric antibody and a humanized antibody will be shown as examples of preparation of a recombinant antibody.

(1) Construction of Vector for Recombinant Antibody Expression

The vector for recombinant antibody expression is an expression vector for animal cells having an insert of DNAs encoding human antibody CH and CL and can be constructed by cloning the DNAs encoding human antibody CH and CL into an expression vector for animal cells.

CH and CL of an arbitrary human antibody can be used as the human antibody C regions. For example, CH of γ1 subclass and CL of κ class from a human antibody are used. cDNA is used as the DNAs encoding human antibody CH and CL, and chromosomal DNA composed of exons and introns can also be used. Any expression vector for animal cells can be used as long as the genes encoding human antibody C regions can be inserted to the expression vector and expressed. Examples of the expression vector used include pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], and pSE1UK1Sed1-3 [Cytotechnol., 13, 79 (1993)]. For example, SV40 early promoter [J. Biochem., 101, 1307 (1987)], Moloney mouse leukemia virus LTR [Biochem. Biophys. Res. Commun., 149, 960 (1987)], or immunoglobulin H chain promoter [Cell, 41, 479 (1985)] and enhancer [Cell, 33, 717 (1983)] are used as a promoter and an enhancer in the expression vector for animal cells.

A vector for recombinant antibody expression of type in which genes encoding antibody H and L chains reside on the same vector (tandem type) [J. Immunol. Methods, 167, 271(1994)] is used as the vector for recombinant antibody expression from the viewpoint of the easy construction of a recombinant antibody expression vector, the easy transfection of animal cells, and the balanced expression levels between the antibody H and L chains in the animal cells. Vectors for recombinant antibody expression of type in which genes encoding antibody H and L chains reside on separate vectors can also be used. pKANTEX93 (WO97/10354), pEE18 [Hybridoma, 17, 559 (1998)], or the like is used as the tandem vector for recombinant antibody expression.

(2) Obtainment of cDNAs Encoding V Regions of Nonhuman Animal-Derived Antibody and Analysis of Amino Acid Sequence The obtainment of cDNAs encoding nonhuman antibody VH and VL and amino acid sequence analysis can be performed as follows.

mRNA is extracted from nonhuman antibody-producing hybridoma cells, and cDNA is synthesized. The synthesized cDNA is cloned into vectors such as phages or plasmids to prepare a cDNA library. From the library, each recombinant phage or recombinant plasmid having cDNA encoding VH or VL is isolated using DNA encoding a mouse antibody C or V region moiety as a probe. Each whole nucleotide sequence encoding the mouse antibody VH or VL of interest on the recombinant phage or the recombinant plasmid is determined, and the respective whole amino acid sequences of VH and VL are predicted from the nucleotide sequence.

For example, a mouse, a rat, a hamster, or a rabbit is used as a nonhuman animal for preparing the nonhuman antibody-producing hybridoma cells, and any animal can also be used as long as hybridoma cells can be prepared from the animal.

For example, a guanidine thiocyanate-cesium trifluoroacetate method [Methods in Enzymol., 154, 3 (1987)] or a kit such as RNeasy kit (manufactured by Qiagen N.V.) can be used in the preparation of total RNA from the hybridoma cells.

For example, an oligo (dT)-immobilized cellulose column method [Molecular Cloning, A Laboratory Manual, Second Edition, Cold Spring Harbor Laboratory Press (1989)] or a kit such as Oligo-dT30<Super> mRNA Purification® Kit (manufactured by Takara Bio Inc.) is used in the preparation of mRNA from the total RNA. Alternatively, the mRNA can also be prepared from the hybridoma cells using a kit such as Fast Track mRNA Isolation® Kit (manufactured by Invitrogen Corp.) or QuickPrep mRNA Purification® Kit (manufactured by Pharmacia Corp.).

For example, a method known in the art [Molecular Cloning, A Laboratory Manual, Second Edition, Cold Spring Harbor Laboratory Press (1989); and Current Protocols in Molecular Biology, Supplement 1, John Wiley & Sons (1987-1997)] or a kit such as SuperScript Plasmid System for cDNA Synthesis and Plasmid Cloning (manufactured by Invitrogen Corp.) or ZAP-cDNA Synthesis® Kit (manufactured by Stratagene Corp.) is used in the synthesis of cDNA and the preparation of the cDNA library.

For the preparation of the cDNA library, any vector can be used in the insertion of the cDNA synthesized with the mRNA extracted from the hybridoma cells as a template as long as the cDNA can be inserted to the vector. Examples of the vector used include ZAP Express [Strategies, 5, 58 (1992)], pBluescript II SK(+) [Nucleic Acids Research, 17, 9494 (1989)], XZAP II (manufactured by Stratagene Corp.), λgt10, λgt11 [DNA Cloning: A Practical Approach, I, 49 (1985)], Lambda BlueMid (manufactured by Clontech Laboratories, Inc.), λExCell, pT7T3-18U (manufactured by Pharmacia Corp.), pCD2 [Mol. Cell. Biol., 3, 280 (1983)], and pUC18 [Gene, 33, 103 (1985)].

Any *E. coli* can be used in the transfer of the cDNA library constructed using phage or plasmid vectors as long as the *E. coli* can harbor, express, and maintain the cDNA library. Examples of the *E. coli* used include XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], and JM105 [Gene, 38, 275 (1985)].

For example, colony hybridization or plaque hybridization [Molecular Cloning, A Laboratory Manual, Second Edition, Cold Spring Harbor Laboratory Press (1989)] using an isotopically or fluorescently labeled probe is used in the selection of a cDNA clone encoding nonhuman antibody VH or VL from the cDNA library.

Alternatively, the cDNA encoding VH or VL can also be prepared by polymerase chain reaction [hereinafter, abbreviated to PCR; Molecular Cloning, A Laboratory Manual, Second Edition, Cold Spring Harbor Laboratory Press (1989); and Current Protocols in Molecular Biology, Supplement 1, John Wiley & Sons (1987-1997)] using prepared primers and the cDNA synthesized from mRNA or the cDNA library as a template.

The selected cDNA is cleaved with appropriate restriction enzymes or the like, then cloned into a plasmid such as pBluescript SK(−) (manufactured by Stratagene Corp.), and sequenced by, for example, a nucleotide sequence analysis method usually used. For example, reaction by a dideoxy method [Proc. Natl. Acad. Sci. USA, 74, 5463 (1977)] followed by analysis using an automatic nucleotide sequence analysis apparatus such as ABI PRISM3700 (manufactured by PE Biosystems) or A.L.F. DNA sequencer (manufactured by Pharmacia Corp.) is used in the nucleotide sequence analysis method.

The respective whole amino acid sequences of VH and VL are predicted from the determined nucleotide sequence and compared with the whole amino acid sequences of known antibody VH and VL [Sequences of Proteins of Immunological Interest, US Dept. Health and Human Services (1991)] to confirm that each obtained cDNA encodes the complete amino acid sequence of antibody VH or VL containing a secretory signal sequence. For the complete amino acid sequence of antibody VH or VL containing a secretory signal sequence, the length of the secretory signal sequence and a N-terminal amino acid sequence can be predicted by comparison with the whole amino acid sequences of known antibody VH and VL [Sequences of Proteins of Immunological Interest, US Dept. Health and Human Services (1991)], and subgroups to which these regions belong can be further determined. The amino acid sequence of CDR of each VH or VL can also be found by comparison with the amino acid sequences of known antibody VH and VL [Sequences of Proteins of Immunological Interest, US Dept. Health and Human Services (1991)].

Homology search such as a BLAST method [J. Mol. Biol., 215, 403 (1990)] can be conducted in, for example, an arbitrary database such as SWISS-PROT or PIR-Protein, using the obtained complete amino acid sequences of VH and VL to confirm whether the complete amino acid sequences of VH and VL are novel.

(3) Construction of Human Chimeric Antibody Expression Vector cDNAs encoding nonhuman antibody VH and VL can be respectively cloned upstream of the genes encoding human antibody CH and CL in the vector for recombinant antibody expression obtained in the paragraph (1) to construct a human chimeric antibody expression vector.

In order to link the 3' end of the cDNA encoding nonhuman antibody VH or VL to the 5' end of the gene encoding human antibody CH or CL, VH and VL cDNAs designed such that the nucleotide sequence of the linking portion encodes an appropriate amino acid and is an appropriate restriction enzyme recognition sequence are prepared. The prepared VH and VL cDNAs are respectively cloned upstream of the genes encoding human antibody CH and CL in the vector for recombinant antibody expression obtained in the paragraph (1) such that these genes are expressed in an appropriate form to construct a human chimeric antibody expression vector.

Alternatively, each cDNA encoding nonhuman antibody VH or VL can also be amplified by PCR using synthetic DNA having appropriate restriction enzyme recognition sequences at both ends and cloned into the vector for recombinant antibody expression obtained in the paragraph (1).

(4) Construction of cDNAs Encoding Humanized Antibody V Regions

The cDNA encoding humanized antibody VH or VL can be constructed as follows.

The amino acid sequences of human antibody VH or VL FRs are each selected for the grafting of the amino acid sequences of CDRs of VH or VL of nonhuman antibody. Any amino acid sequence of FR to be selected can be used as long as the amino acid sequence is derived from the human antibody. For example, the amino acid sequences of human antibody FRs registered in a database such as Protein Data Bank, or the common amino acid sequence of each human antibody FR subgroup [Sequences of Proteins of Immunological Interest, US Dept. Health and Human Services (1991)] is used. In order to suppress reduction in the binding activity of the antibody, the amino acid sequences of FRs are selected to have as high homology as possible (at least 60% or higher) to the amino acid sequences of VH or VL FRs of the original antibody.

Next, the amino acid sequences of CDRs of VH or VL of the original antibody are grafted to the selected amino acid sequences of FRs of VH or VL of human antibody to design the amino acid sequence of VH or VL of a humanized antibody. The designed amino acid sequence is converted to a DNA sequence in consideration of codon usage found in the nucleotide sequences of antibody genes [Sequences of Proteins of Immunological Interest, US Dept. Health and Human Services (1991)] to design each DNA sequence encoding the amino acid sequence of humanized antibody VH or VL.

On the basis of the designed DNA sequence, several synthetic DNA strands each having a length of approximately 100 bases are synthesized and used in PCR reaction. In this case, preferably, 6 synthetic DNA strands each for VH and VL are designed from the viewpoint of the reaction efficiency of the PCR reaction and the length of synthesizable DNA. Appropriate restriction enzyme recognition sequences can be further introduced to the 5' or 3' ends of the synthetic DNAs positioned at both ends and thereby facilitate cloning the cDNA encoding humanized antibody VH or VL into the vector for recombinant antibody expression obtained in the paragraph (1).

After the PCR reaction, the amplification products are each cloned into plasmids such as pBluescript SK(−) (manufactured by Stratagene Corp.) and sequenced in the same way as the method described in the paragraph (2) to obtain plasmids having a DNA sequence encoding the amino acid sequence of VH or VL of the desired humanized antibody.

Alternatively, on the basis of the designed DNA sequence, one long DNA strand each for full-length VH and full-length VL can also be synthesized and used instead of the PCR amplification products. Appropriate restriction enzyme recognition sequences can be further introduced to both ends of the synthesized long DNA strand and thereby facilitate cloning the cDNA encoding humanized antibody VH or VL into the vector for recombinant antibody expression obtained in the paragraph (1).

(5) Alteration of Amino Acid Sequence of V Region of Humanized Antibody

A humanized antibody obtained by merely grafting CDRs of VH and VL of a nonhuman antibody to FRs of VH and VL of human antibody has lower antigen binding activity than that of the original nonhuman antibody [BIO/TECHNOLOGY, 9, 266 (1991)]. The reduced antigen binding activity of the humanized antibody can be elevated by identifying an amino acid residue involved directly in binding to the antigen, an amino acid residue interacting with an amino acid residue of CDR, and an amino acid residue involved indirectly in binding to the antigen through the maintenance of antibody conformation, in the amino acid sequences of human antibody VH and VL FRs, and replacing these amino acid residues with the amino acid residues of the original nonhuman antibody.

In order to identify the amino acid residue of FR involved in antigen binding activity, the antibody conformation can be constructed and analyzed by use of, for example, X-ray crystal analysis [J. Mol. Biol., 112, 535 (1977)] or computer modeling [Protein Engineering, 7, 1501 (1994)]. Also, several altered forms can be prepared for each antibody and repetitively studied for their correlation with antigen binding activity to obtain a humanized antibody having necessary antigen binding activity through trial and error.

The amino acid residues of human antibody VH and VL FRs can be altered through the PCR reaction described in the paragraph (4) using synthetic DNA for alteration. The amplification products after the PCR reaction are sequenced by the method described in the paragraph (2) to confirm that the alteration of interest is contained therein.

(6) Construction of Humanized Antibody Expression Vector cDNAs encoding VH and VL of the constructed recombinant antibody can be respectively cloned upstream of the genes encoding human antibody CH or CL in the vector for recombinant antibody expression obtained in the paragraph (1) to construct a humanized antibody expression vector.

For example, appropriate restriction enzyme recognition sequences are introduced to the 5' or 3' ends of the synthesized DNAs positioned at both ends among the synthesized DNAs used for the construction of VH or VL of the humanized antibody obtained in the paragraphs (4) and (5). The resulting VH and VL DNAs are respectively cloned upstream of the genes encoding human antibody CH and CL in the vector for humanized antibody expression obtained in the paragraph (1) such that these genes are expressed in an appropriate form.

(7) Transient Expression of Recombinant Antibody

Recombinant antibodies are transiently expressed using the recombinant antibody expression vectors obtained in the paragraphs (3) and (6) or altered expression vectors thereof. Many types of prepared human chimeric antibodies and humanized antibodies can be efficiently evaluated for their antigen binding activity.

Any host cell can be used for the transfer of each expression vector as long as the host cell can express the recombinant antibody. For example, COS-7 cells [American Type Culture Collection (ATCC) No: CRL1651] are used [Methods in Nucleic Acids Res., CRC press, 283 (1991)].

For example, a DEAE-dextran method [Methods in Nucleic Acids Res., CRC press (1991)] or a lipofection method [Proc. Natl. Acad. Sci. USA, 84, 7413 (1987)] is used in the transfection of the COS-7 cells with the expression vector.

After the transfection with the expression vector, the expression level and antigen binding activity of the recombinant antibody in a culture supernatant are measured by use of, for example, enzyme-linked immunosorbent assay [Monoclonal Antibodies-Principles and practice, Third edition, Academic Press (1996); Antibodies—A Laboratory Manual, Cold Spring Harbor Laboratory (1988); and Tan-Clone-Kotai-Jikken-Manual (Experimental Manual for Monoclonal Antibody in English), Kodansha Scientific Ltd. (1987)].

(8) Obtainment of Transformant Stably Expressing Recombinant Antibody and Preparation of Recombinant Antibody Appropriate host cells can be transfected with the recombinant antibody expression vector obtained in the paragraph (3) or (6) to obtain transformants stably expressing the recombinant antibody.

For example, electroporation [Japanese Patent Laid-Open No. 2-257891; and Cytotechnology, 3, 133 (1990)] is used in the transfection of the host cells with the expression vector.

Any host cell can be used for the transfer of the recombinant antibody expression vector as long as the host cell can express the recombinant antibody. Examples of the host cells used include CHO-K1 (ATCC CCL-61), DUKXB11 (ATCC CCL-9096), Pro-5 (ATCC CCL-1781), CHO-S (Life Technologies Corp., Cat #11619), rat myeloma cells YB2/3HL.P2.G11.16Ag.20 (ATCC No: CRL1662; also referred to as YB2/0), mouse myeloma cells NS0, mouse myeloma cells SP2/0-Ag14 (ATCC No: CRL1581), mouse P3X63-Ag8.653 cells (ATCC No: CRL1580), and CHO cells deficient in dihydrofolate reductase (hereinafter, abbreviated to dhfr) gene [Proc. Natl. Acad. Sci. USA, 77, 4216 (1980)].

Other examples of the host cells that can be used include host cells having the reduced activity of or lacking the activity of a protein such as an enzyme involved in the intracellular synthesis of sugar nucleotide GDP-fucose, a protein such as an enzyme involved in sugar chain modification that bonds position 1 of fucose through an α-bond to position 6 of N-acetylglucosamine at the reducing end of a N-glycoside-linked complex sugar chain, or a protein involved in the intracellular transport of sugar nucleotide GDP-fucose to the Golgi body, for example, CHO cells deficient in α1,6-fucosyltransferase gene (WO2005/035586 and WO02/31140), and Lec13 that has acquired lectin resistance [Somatic Cell and Molecular genetics, 12, 55 (1986)].

After the transfection with the expression vector, the transformants stably expressing the recombinant antibody are selected by culture in a medium for animal cell culture containing an agent such as G418 sulfate (hereinafter, referred to as G418) (Japanese Patent Laid-Open No. 2-257891).

For example, RPMI1640 medium (manufactured by Invitrogen Corp.), GIT medium (manufactured by Nihon Pharmaceutical Co., Ltd.), EX-CELL301 medium (manufactured by JRH Biosciences Inc.), IMDM medium (manufactured by Invitrogen Corp.), Hybridoma-SFM medium (manufactured by Invitrogen Corp.), or any of these media supplemented with various additives such as FBS is used as the medium for animal cell culture. The obtained transformants are cultured in the medium so that the recombinant antibody is expressed and accumulated in the culture supernatant. The expression level and antigen binding activity of the recombinant antibody in the culture supernatant can be measured by ELISA or the like. Also, the expression level of the recombinant antibody produced by the transformants can be improved by use of a dhfr gene amplification system (Japanese Patent Laid-Open No. 2-257891) or the like.

The recombinant antibody is purified from the transformant culture supernatant using a protein A column [Monoclonal Antibodies—Principles and practice, Third edition, Academic Press (1996); and Antibodies—A Laboratory Manual, Cold Spring Harbor Laboratory (1988)]. Alternatively, methods for use in protein purification, such as gel filtration, ion-exchange chromatography, and ultrafiltration, may be combined.

The molecular weight of the H chain, L chain, or whole antibody molecule of the purified recombinant antibody can be measured by use of, for example, polyacrylamide gel electrophoresis [Nature, 227, 680 (1970)] or Western blotting [Monoclonal Antibodies—Principles and practice, Third edition, Academic Press (1996); and Antibodies—A Laboratory Manual, Cold Spring Harbor Laboratory (1988)].

3. Activity Evaluation of Purified Monoclonal Antibody or Antibody Fragment Thereof The activity evaluation of the purified monoclonal antibody of the present invention or the antibody fragment thereof can be conducted as follows.

The binding activity against human Gas6 is measured by use of the binding assay described in the paragraph 1-(6a) and a surface plasmon resonance method using the Biacore® system or the like described in the paragraph 1-(6c). Alternatively, the binding activity can be measured by use of a fluorescent antibody method [Cancer Immunol. Immunother., 36, 373 (1993)] or the like.

The inhibitory activity against the binding between human Gas6 and a Gas6 receptor can be measured by, for example, the competition assay described in the paragraph 1-(6b).

4. Method for Treating Disease Using Anti-Human Gas6 Monoclonal Antibody of Present Invention or Antibody Fragment Thereof The monoclonal antibody of the present invention or the antibody fragment thereof can be used in the treatment of any human Gas6-related disease as long as the disease involves human Gas6-dependent cell growth, a Gas6-related lesion, etc.

The therapeutic agent comprising the monoclonal antibody of the present invention or the antibody fragment thereof may be a therapeutic agent containing only the antibody or the antibody fragment thereof as an active ingredient and is usually provided as a pharmaceutical preparation produced by an arbitrary method known in the technical field of pharmaceutics, which involves mixing the active ingredient with one or more pharmacologically acceptable carriers.

Examples of the administration route include oral administration and parenteral administration such as intraoral administration, intra-tracheal administration, intrarectal administration, subcutaneous administration, intramuscular administration, and intravenous administration. Examples of the dosage form include aerosols, capsules, tablets, powders, granules, syrups, emulsions, suppositories, injections, ointments, and tapes.

Preparations appropriate for oral administration are, for example, emulsions, syrups, capsules, tablets, powders, or granules.

Liquid preparations such as the emulsions or the syrups are produced using additives such as water, sugars (e.g., sucrose, sorbitol, and fructose), glycols (e.g., polyethylene glycol and propylene glycol), oils (sesame oil, olive oil, and soybean oil), antiseptics (e.g., p-hydroxybenzoic acid esters), and flavors (e.g., strawberry flavor and peppermint flavor).

The capsules, the tablets, the powders, or the granules, etc., are produced using additives such as excipients (e.g., lactose, glucose, sucrose, and mannitol), disintegrants (e.g., starch and sodium alginate), lubricants (e.g., magnesium stearate and talc), binders (e.g., polyvinyl alcohol, hydroxypropylcellulose, and gelatin), surfactants (e.g., fatty acid ester), and plasticizers (e.g., glycerin).

Preparations appropriate for parenteral administration are, for example, injections, suppositories, or aerosols.

The injections are produced using, for example, a carrier consisting of a salt solution, a glucose solution, or a mixture thereof.

The suppositories are produced using a carrier such as cacao butter, or hydrogenated fatty or carboxylic acid.

The aerosols are produced using, for example, a carrier that does not stimulate the oral and airway mucosae of a recipient, and facilitates absorbing the monoclonal antibody of the present invention or the antibody fragment thereof by dispersing the antibody or the antibody fragment as fine powders. For example, lactose or glycerin is used as the carrier. Alternatively, the preparations can also be produced as aerosols or dry powders.

These parenteral preparations can also be further supplemented with the components listed as additives for the preparations appropriate for oral administration.

5. Method for Diagnosing Disease Using Anti-Human Gas6 Monoclonal Antibody of Present Invention or Antibody Fragment Thereof The human Gas6-related disease can be diagnosed by detecting or assaying human Gas6 or cells expressing human Gas6 using the monoclonal antibody of the present invention or the antibody fragment thereof.

A kidney or cancer disease as the human Gas6-related disease can be diagnosed, for example, by detecting or assaying human Gas6 present in the body of a patient by an immunological approach. Also, the diagnosis can be conducted by detecting human Gas6 expressed on cells in the body of a patient by use of an immunological approach such as flow cytometry.

The immunological approach is a method which involves using a labeled antigen or antibody to detect or measure the amount of the antibody or the amount of the antigen. Examples of the immunological approach used include radioimmunoassay, enzyme immunoassay, fluorescent immunoassay, luminescent immunoassay, Western blot, and physicochemical approaches.

The radioimmunoassay involves, for example, reacting the antibody of the present invention or the antibody fragment thereof with the antigen or cells expressing the antigen, and further reacting therewith a radiolabeled anti-immunoglobulin antibody or binding fragment, followed by measurement using a scintillation counter or the like.

The enzyme immunoassay involves, for example, reacting the antibody of the present invention or the antibody fragment thereof with the antigen or cells expressing the antigen, and further reacting therewith a labeled anti-immunoglobulin antibody or binding fragment, followed by the measurement of a color-forming dye using an absorptiometer. For example, sandwich ELISA is used. An enzyme label known in the art [Enzyme Immunoassay, Igaku Shoin Ltd. (1987)] can be used as the label for the enzyme immunoassay.

For example, an alkaline phosphatase label, a peroxidase label, a luciferase label, or a biotin label is used. The sandwich ELISA is a method which involves binding an antibody to a solid phase, then entrapping the antigen to be detected or assayed, and reacting a secondary antibody with the entrapped antigen. In this ELISA, two types of antibodies or antibody fragments that recognize the antigen to be detected or assayed and differ in antigen recognition site are prepared. One of these antibodies or antibody fragments is adsorbed as a primary antibody onto a plate (e.g., a 96-well plate) in advance. Next, the other antibody or antibody fragment is labeled as a secondary antibody with, for example, a fluorescent material such as FITC, an enzyme such as peroxidase, or biotin. For example, cells separated from a living body or a homogenate thereof, tissues separated from a living body or a homogenate thereof, a cell culture supernatant, serum, pleural effusion, ascitic fluid, or ocular fluid is reacted with the antibody-adsorbed plate. Then, the labeled monoclonal antibody or antibody fragment is reacted therewith, followed by detection reaction appropriate for the labeling material. The antigen concentration in the test sample is calculated from a calibration curve prepared from serial dilutions of an antigen having a known concentration. Polyclonal antibodies or monoclonal antibodies may be used as the antibodies for the sandwich ELISA. Antibody fragments such as Fab, Fab', or F(ab')$_2$ may be used. The combination of the two types of antibodies for use in the sandwich ELISA may be the combination of monoclonal antibodies or antibody fragments recognizing different epitopes, or may be the combination of a polyclonal antibody and a monoclonal antibody or an antibody fragment.

The fluorescent immunoassay is performed by a method described in, for example, the literature [Monoclonal Antibodies-Principles and practice, Third edition, Academic Press (1996); and Tan-Clone-Kotai-Jikken-Manual (Experimental Manual for Monoclonal Antibody in English), Kodansha Scientific Ltd. (1987)]. A fluorescent label known in the art [Zusetsu-Keiko-Kotai-Ho (Illustrated Fluorescent Antibody Method in English), Soft Science, Inc. (1983)] can be used as the label for the fluorescent immunoassay. For example, FITC or RITC is used.

The luminescent immunoassay is measured by a method described in, for example, the literature [Bioluminescence and Chemiluminescence, Journal of clinical laboratory medicine 42, Hirokawa Shoten Co., Ltd. (1998)]. Examples of the label for use in the luminescent immunoassay include luminescent labels known in the art. For example, acridinium ester or lophine is used.

The Western blot involves, for example, fractionating the antigen or cells expressing the antigen with SDS (sodium dodecyl sulfate)-PAGE (polyacrylamide gel) [Antibodies—A Laboratory Manual Cold Spring Harbor Laboratory (1988)], then blotting the gel to a polyvinylidene fluoride (PVDF) membrane or a nitrocellulose membrane, reacting an antibody or an antibody fragment recognizing the antigen with the membrane, and further reacting therewith an anti-mouse IgG antibody or binding fragment labeled with a fluorescent material such as FITC, an enzyme such as peroxidase, or biotin, followed by the visualization of the label for measurement.

One example is given below. Cells or tissues expressing a polypeptide having the amino acid sequence of SEQ ID NO: 4 are lysed, and 0.1 to 30 g/lane of proteins is electrophoresed by SDS-PAGE under reductive conditions. The electrophoresed proteins are transferred to a PVDF membrane, which is then reacted with PBS containing 1 to 10% BSA (hereinafter, referred to as BSA-PBS) at room temperature for 30 minutes for blocking operation. Here, the monoclonal antibody of the present invention is reacted with the membrane, which is then washed with PBS containing 0.05 to 0.1% Tween-20 (hereinafter, referred to as Tween- PBS). Peroxidase-labeled goat anti-mouse IgG is reacted therewith at room temperature for 2 hours. The membrane is washed with Tween-PBS, and a band bound with the monoclonal antibody is detected using ECL Western Blotting Detection Reagents (manufactured by Amersham plc) or the like to detect the polypeptide having the amino acid sequence of SEQ ID NO: 4. An antibody that can bind to a polypeptide carrying no natural conformation is used as the antibody for the detection by Western blotting.

The physicochemical approach is performed, for example, by forming an aggregate through the binding of the antigen human Gas6 to the monoclonal antibody of the present invention or the antibody fragment thereof, and detecting this aggregate. In addition, for example, a capillary method, a single immunodiffusion method, turbidimetric immunoassay, or latex turbidimetric immunoassay [Kanai's Manual of Clinical Laboratory Medicine, Kanehara & Co., Ltd. (1998)] can also be used as the physicochemical approach. In the latex turbidimetric immunoassay, when a carrier, such as polystyrene latex having a particle size on the order of 0.1 to 1 μm, sensitized with an antibody or an antigen, is used to cause antigen-antibody reaction with the corresponding antigen or antibody, scattered light in the reaction solution is increased while transmitted light is decreased. This change is detected as absorbance or integrating sphere turbidity to measure the antigen concentration or the like in the test sample.

An immunological detection method known in the art can be used in the detection or assay of the cells expressing human Gas6. Among others, for example, an immunoprecipitation method, an immunocytochemical staining method, an immunohistochemical staining method, or a fluorescent antibody staining method is preferably used.

The immunoprecipitation method involves, for example, reacting the cells expressing human Gas6 with the monoclonal antibody of the present invention or the antibody fragment thereof, and then adding thereto a carrier having the ability to specifically bind to an immunoglobulin, such as protein G-Sepharose, to precipitate an antigen-antibody complex. Alternatively, the immunoprecipitation method can also be performed by a method as described below. The monoclonal antibody of the present invention or the antibody fragment thereof mentioned above is immobilized on a 96-well plate for ELISA, which is then blocked with BSA-PBS. When the antibody is, for example, in an unpurified state such as a hybridoma culture supernatant, for example, an anti-mouse immunoglobulin, an anti-rat immunoglobulin, protein-A, or protein-G is immobilized on the 96-well plate for ELISA in advance, which is then blocked with BSA-PBS. Then, the hybridoma culture supernatant is dispensed to the wells and bound therewith. Next, BSA-PBS is discarded, and the plate is thoroughly washed with PBS and then reacted with a lysate of cells or tissues expressing human Gas6. After thorough washing, immunoprecipitates are extracted from the plate with a sample buffer for SDS-PAGE, followed by detection by the Western blotting described above.

The immunocytochemical staining method or the immunohistochemical staining method is a method which involves, for example, treating cells or tissues expressing the antigen with a surfactant, methanol, or the like in order to improve antibody penetrability in some cases, then reacting the cells or the tissues with the monoclonal antibody of the present invention, further reacting therewith an anti-immunoglobulin antibody or binding fragment thereof labeled with, for example, a fluorescent material such as FITC, an enzyme such as peroxidase, or biotin, and then visualizing the label, followed by observation under a microscope. Also, the detection can be performed by a fluorescent antibody staining method which involves reacting a fluorescently labeled antibody with the cells, followed by analysis using a flow cytometer [Monoclonal Antibodies-Principles and practice, Third edition, Academic Press (1996); and Tan-Clone-Kotai-Jikken-Manual (Experimental Manual for Monoclonal Antibody in English), Kodansha Scientific Ltd. (1987)]. Particularly, the monoclonal antibody of the present invention or the antibody fragment thereof which binds to human Gas6 can be used in the detection of cells expressing human Gas6 carrying a natural conformation by the fluorescent antibody staining method.

In the case of using, for example, FMAT8100HTS system (manufactured by Applied Biosystems, Inc.) in the fluorescent antibody staining method, the amount of the antigen or the amount of the antibody can be measured without separating a formed antibody-antigen complex from a free antibody or antigen that is not involved in the formation of the antibody-antigen complex.

Hereinafter, the present invention will be specifically described with reference to Examples. However, the present invention is not intended to be limited by Examples described below.

EXAMPLES

[Example 1] Obtainment of Gas6-Knockout (Hereinafter, Abbreviated to KO) Mouse

Sperms of Gas6 hetero KO mice were purchased from Taconic Biosciences, Inc. The purchased sperms of Gas6 hetero KO mice had 129/SvEv-C57BL/6 background. At CLEA Japan, Inc., the Gas6 hetero KO mouse sperms were fertilized in vitro with the ova of C57BL/6NJcl mice, and the fertilized eggs were then transplanted to recipient mice to obtain children. The obtained children were genotyped by a method known in the art to confirm that the Gas6 gene was knocked out. In this way, Gas6 homo KO mice were obtained.

[Example 2] Preparation of Various Gas6 Recombinants

For use in immunization and screening, C-terminally FLAG-tagged human, cynomolgus monkey, rat, and mouse Gas6 recombinant proteins were prepared by methods described below. Hereinafter, these recombinant proteins are referred to as hGas6-F, cGas6-F, rGas6-F, and mGas6-F, respectively.

(1) Construction of hGas6-F Expression Vector

An expression vector for animal cells having an insert of a hGas6-F gene sequence was prepared from a plasmid (manufactured by Invitrogen Corp.) having an insert of the gene sequence of human Gas6 (SEQ ID NO: 3, GenBank Accession No: NM_000820) as follows.

A DNA fragment containing the hGas6-F gene was amplified by polymerase chain reaction (PCR) using the plasmid as a template and primers 1 and 2 (SEQ ID NOs: 1 and 2). The PCR reaction was performed by incubation at 94° C. for 2 minutes using 20 μL of a prepared reaction solution containing the template plasmid, 10 pmol each of the two types of primers, and KOD FX (manufactured by Toyobo Co., Ltd.), followed by 30 cycles each involving 94° C. for 15 seconds, 58° C. for 30 seconds, and 68° C. for 2.5 minutes. The obtained PCR product was subjected to agarose gel electrophoresis, and approximately 2 kbp of an amplified DNA fragment (DNA fragment containing the hGas6-F gene) was recovered using QIAquick Gel Extraction Kit (manufactured by Qiagen N.V.). The obtained amplified DNA fragment was inserted in a pCR4-Blunt-TOPO vector using ZERO BLUNT TOPO PCR CLONING KIT (manufactured by Invitrogen Corp.) to obtain a reaction solution containing a plasmid pCR4-hGas6-F. An E. coli DH5a strain (manufactured by Toyobo Co., Ltd.) was transformed with the reaction solution by an ordinary method, and the plasmid pCR4-hGas6-F was extracted from the obtained transformants. The obtained pCR4-hGas6-F was selected as a clone having the inserted gene sequence without a mutation caused by PCR, and used in the subsequent experiments.

Next, pCR4-hGas6-F was enzymatically treated with restriction enzymes EcoRI and BamHI. The reaction solution was subjected to agarose gel electrophoresis, and approximately 2 kbp of a DNA fragment (hereinafter, referred to as hGas6-F-EcoRI-BamHI) was then recovered using QIAquick Gel Extraction Kit. Similarly, a vector pKANTEX93 for expression in animal cells (WO97/10354) was enzymatically treated with EcoRI and BamHI. The reaction solution was subjected to agarose gel electrophoresis, and approximately 9.3 kbp of a DNA fragment (hereinafter, referred to as pKANTEX93-EcoRI-BamHI) was then recovered using QIAquick Gel Extraction Kit. The two types of DNA fragments thus obtained were ligated using Ligation High ver. 2 (manufactured by Toyobo Co., Ltd.), and an E. coli DH5a strain (Toyobo Co., Ltd.) was transformed with the reaction solution. From the obtained transformant, pKANTEX-hGas6-F was obtained as a hGas6-F expression vector for animal cells.

(2) Construction of cGas6-F Expression Vector

An expression vector for animal cells having an insert of cGas6-F gene was constructed by a method given below. First, the cynomolgus monkey Gas6 gene was cloned. A DNA fragment containing the cynomolgus monkey Gas6 gene was amplified by PCR. The PCR was performed by incubation at 94° C. for 2 minutes using 20 µL of a prepared reaction solution containing cynomolgus monkey lung-derived cDNA (manufactured by CytoMol) as a template, 10 pmol each of primers 3 and 4 (SEQ ID NOs: 5 and 6), KOD-plus- (manufactured by Toyobo Co., Ltd.), and 2% DMSO, followed by 35 cycles each involving 94° C. for 15 seconds, 65° C. for 30 seconds, and 68° C. for 2.5 minutes. The subsequent procedures were performed in the same way as in the paragraph (1) to obtain a plasmid pCR4-cGas6 having an insert of the amplified DNA fragment (DNA fragment containing the cGas6 gene) in a pCR4-Blunt-TOPO vector. The obtained plasmid was sequenced by an ordinary method. The obtained nucleotide sequence encoding cynomolgus monkey Gas6 is shown in SEQ ID NO: 7, and the amino acid sequence of cynomolgus monkey Gas6 predicted from the nucleotide sequence is shown in SEQ ID NO: 8.

Subsequently, the DNA fragment containing the cGas6-F gene was amplified by PCR and inserted to a vector pKANTEX93 for expression in animal cells. The PCR was performed by incubation at 94° C. for 5 minutes using 20 µL of a prepared reaction solution containing pCR4-Gas6 as a template, 10 pmol each of primers 5 and 6 (SEQ ID NOs: 9 and 10), and PrimeSTAR HS DNA Polymerase (manufactured by Takara Bio Inc.), followed by 35 cycles each involving 98° C. for 10 seconds and 68° C. for 2 minutes and 20 seconds.

DNA fragments (cGas6-F-EcoRI-BamHI and pKANTEX93-EcoRI-BamHI) were recovered from the obtained PCR product and pKANTEX93 by digestion with restriction enzymes in the same way as in the paragraph (1). The two types of DNA fragments thus obtained were ligated using In-Fusion HD Cloning Kit (manufactured by Clontech Laboratories, Inc.), and pKANTEX-cGas6-F was obtained as a vector for cGas6-F expression in animal cells in the same way as in the paragraph (1). The obtained vector was selected as a clone having the inserted gene without a mutation caused by PCR, and used in the subsequent experiments.

(3) Construction of rGas6-F Expression Vector

An expression vector for animal cells having an insert of rGas6-F gene was prepared by a method given below.

A DNA fragment containing the rGas6-F gene was amplified by PCR. The PCR was performed by incubation at 94° C. for 2 minutes using 20 µL of a prepared reaction solution containing rat heart- or liver-derived cDNA (manufactured by Takara Bio Inc.) as a template, 10 pmol each of primers 7 and 8 (SEQ ID NOs: 11 and 12), and KOD FX (manufactured by Toyobo Co., Ltd.), followed by 30 cycles each involving 94° C. for 15 seconds, 58° C. for 30 seconds, and 68° C. for 2.5 minutes.

The DNA fragment (DNA fragment containing the rGas6-F gene) amplified by PCR was inserted to a pCR4-Blunt-TOPO vector in the same way as in the paragraph (1) to obtain a plasmid pCR4-rGas6-F. The nucleotide sequence of the rat Gas6 gene carried by the obtained plasmid was consistent with the nucleotide sequence of the rat Gas6 gene shown in GenBank Accession No: NM_057100 (SEQ ID NO: 13) to confirm that any gene mutation caused by PCR did not occur.

On the basis of the obtained pCR4-rGas6-F, the rGas6-F gene was inserted to pKANTEX93 in the same way as in the paragraph (1) to obtain pKANTEX-rGas6-F as a rGas6-F expression vector for animal cells.

(4) Construction of mGas6-F Expression Vector

An expression vector for animal cells having an insert of mGas6-F gene was prepared by a method described below.

A DNA fragment containing the mGas6-F gene was amplified by PCR. The PCR was performed by incubation at 94° C. for 2 minutes using 20 µL of a prepared reaction solution containing mouse kidney- or lung-derived cDNA (manufactured by Ambion/Thermo Fisher Scientific Inc.) as a template, 10 pmol each of primers 7 and 9 (SEQ ID NOs: 11 and 15), and KOD FX (manufactured by Toyobo Co., Ltd.), followed by 30 cycles each involving 94° C. for 15 seconds, 58° C. for 30 seconds, and 68° C. for 2.5 minutes. The DNA fragment (DNA fragment containing the mGas6-F gene) amplified by PCR was inserted to a pCR4-Blunt-TOPO vector in the same way as in the paragraph (1) to obtain a plasmid pCR4-mGas6-F. The nucleotide sequence of the mouse Gas6 gene carried by the obtained plasmid was consistent with the nucleotide sequence of the mouse Gas6 gene shown in GenBank Accession No: NM_019521 (SEQ ID NO: 16) to confirm that any gene mutation caused by PCR did not occur. On the basis of the obtained pCR4-mGas6-F, the mGas6-F gene was inserted to pKANTEX93 in the same way as in the paragraph (1) to obtain pKANTEX-mGas6-F as a mGas6-F expression vector for animal cells.

(5) Establishment of Stably hGas6-F-Expressing Cell Line

In order to establish a cell line stably expressing hGas6-F, the hGas6-F expression vector pKANTEX-hGas6-F prepared in the paragraph (1) was transfected into CHO cells deficient in dhfr [Proc. Natl. Acad. Sci. USA, 77, 4216 (1980)] by use of electroporation [Cytotechnology, 3, 133 (199)] as follows.

The cells were usually cultured for subculture using a basal medium [IMDM (manufactured by Invitrogen Corp.) containing 10% dialyzed FBS (manufactured by Gibco/Thermo Fisher Scientific Inc.), 1× HT solution (manufactured by Invitrogen Corp.), and 50 µg/mL gentamicin (manufactured by Nacalai Tesque, Inc.)]. The cells thus transfected were screened using a basal medium containing 50 nM, 200 nM, or 500 nM methotrexate hydrate (manufactured by Sigma-Aldrich Co. LLC) (hereinafter, abbreviated to MTX) (MTX medium). All of the cells were statically cultured under conditions involving 37° C. and 5% $CO_2$.

10 µg of a plasmid solution containing pKANTEX-hGas6-F [solution containing pKANTEX-hGas6-F obtained in the paragraph (1), dissolved in sterile water] was added to a cuvette for electroporation (manufactured by Bio-Rad Laboratories, Inc.). $8 \times 10^6$ cells/mL of a cell suspension prepared with K-PBS [mixed solvent of 137 mmol/L KCl, 2.7 mmol/L NaCl, 8.1 mmol/L $Na_2HPO_4$, 1.5 mmol/L $KH_2PO_4$, and 4.0 mmol/L $MgCl_2$] was added to the cuvette and mixed, followed by transfection under conditions involving a pulse voltage of 350 V and an electrical capacitance of 250 µF using Gene Pulser (Bio-Rad Laboratories, Inc.).

The cell suspension thus transfected was suspended in 50 mL of a basal medium free from the HT solution and inoculated at 100 µL/well to five 96-well plates. The medium was replaced with 50 nM MTX medium 14 days after the start of culture and with 200 nM MTX medium 22 days after the start of culture to select MTX-resistant cell lines. The expression level of hGas6-F in the culture supernatants of cell lines whose colonies were able to be confirmed on culture day 35 was measured using human Gas6 ELISA kit (manufactured by R&D Systems, Inc.). Lines having a high expression level of hGas6-F were expanded to 24-well plates, and the medium was replaced with 500 nM MTX medium 42 days after the start of culture. The expression level of hGas6-F in the culture supernatants of cell lines resistant to 500 nM MTX was measured in the same way as above, and a line having the highest expression level of hGas6-F was selected as a stably hGas6-F-expressing cell line.

(6) Preparation of Stably cGas6-F-, rGas6-F-, and mGas6-F-Expressing Cell Lines pKANTEX-cGas6-F, pKANTEX-rGas6-F, and pKANTEX-mGas6 prepared in the paragraphs (2) to (4) were each transfected into host cells in the same way as in the paragraph (5) to establish stably cGas6-F-, rGas6-F-, and mGas6-F-expressing cell lines.

These vectors were each linearized by enzymatic treatment with a restriction enzyme Mull. Each vector thus linearized was purified by phenol/chloroform extraction and ethanol precipitation, dissolved in sterile water, and subjected to the experiment.

The expression level of cGas6-F in a culture supernatant was measured using human Gas6 ELISA kit (manufactured by R&D Systems, Inc.). The expression levels of rGas6-F and mGas6-F were measured using mouse Gas6 ELISA kit (manufactured by R&D Systems, Inc.).

(7) Construction of Tandem Vector for Rat VKOR and Human GGCX Expression

For obtaining active Gas6 protein, it is required that carbon-γ of a glutamic acid residue contained in the Gla domain of Gas6 should be carboxylated by a γ-carboxylation-related enzyme GGCX. Reduced vitamin K is essential for the activation of GGCX, and the reduced vitamin K is formed by the reduction of vitamin K epoxide by VKOR (vitamin K epoxide reductase complex subunit 1) [Journal of Thrombosis and Haemostasis 3, 1873-1878 (2005)]. Accordingly, in order to obtain active Gas6, a human GGCX (hereinafter, abbreviated to hGGCX) and rat VKOR (hereinafter, abbreviated to rVKOR) expression vector was prepared.

First, rVKOR gene was inserted to a pCR4-Blunt-TOPO vector in the same way as in the paragraph (1) to obtain a plasmid pCR4-rVKOR. For PCR, a reaction solution containing rat liver-derived cDNA (manufactured by Takara Bio Inc.) as a template, 10 pmol each of primers 10 and 11 (SEQ ID NOs: 18 and 19), and KOD-plus- (manufactured by Toyobo Co., Ltd.) was prepared and subjected to the experiment. The rVKOR gene sequence carried by the obtained plasmid was consistent with the nucleotide sequence of the rat VKOR gene shown in GenBank Accession No. NM_203335 (SEQ ID NO: 20) to confirm that any gene mutation caused by PCR did not occur.

pCR4-rVKOR enzymatically treated with restriction enzymes HindIII and SmaI was inserted to a pAGE249 expression vector (J. Biol. Chem., 278, 3466-3473, 2003) treated with the same restriction enzymes as above, in the same way as in the paragraph (1) to obtain pAGE-rVKOR. pAGE-rVKOR was enzymatically treated with a restriction enzyme ClaI and annealed with two 5'-terminally phosphorylated synthetic oligo DNAs (primers 18 and 19) (SEQ ID NOs: 38 and 39). A vector pAGE-rVKOR(XhoI) having an insert of an XhoI restriction site in pAGE-rVKOR was obtained in the same way as in the paragraph (1).

hGGCX gene was inserted to a pCR4-Blunt-TOPO vector in the same way as in the paragraph (1) to obtain a plasmid pCR4-hGGCX. For PCR, a reaction solution containing human liver-derived cDNA (manufactured by Ambion/Thermo Fisher Scientific Inc.) as a template, 10 pmol each of primers 12 and 13 (SEQ ID NOs: 22 and 23), and KOD-plus- (manufactured by Toyobo Co., Ltd.) was prepared and subjected to the experiment. The hGGCX gene sequence carried by the obtained plasmid was a sequence substituting cytosine at position 145 by adenine in the hGGCX gene sequence shown in GenBank Accession No. NM 000821 (SEQ ID NO: 24). However, the amino acid sequences of hGGCX encoded by these nucleotide sequences were identical. Therefore, the obtained plasmid was used in the subsequent experiment.

pCR4-hGGCX enzymatically digested with restriction enzymes SalI and SmaI was inserted to a pAGE249 expression vector treated with the same restriction enzymes as above, in the same way as in the paragraph (1) to obtain pAGE-hGGCX.

pAGE-rVKOR(XhoI) and pAGE-hGGCX were each enzymatically treated with XhoI, and the hGGCX fragment containing a pAGE249-derived promoter region was inserted to pAGE-rVKOR(XhoI) in the same way as in the paragraph (1) to obtain pAGE-VKOR-hGGCX.

(8) Transfection of Various Stably Gas6-F-Expressing Cell Lines with pAGE-VKOR-hGGCX In order to prepare a line stably expressing each active Gas6-F, the various stably Gas6-F-expressing cell lines prepared in the paragraphs (5) and (6) were transfected with the γ-carboxylation-related enzyme expression vector pAGE-VKOR-hGGCX prepared in the paragraph (7), in the same way as in the paragraph (5).

Each cell suspension thus transfected was suspended in 10 mL of 500 nM MTX medium and inoculated to a 125-cm² flask. The medium was replaced with MTX-hygromycin medium [500 mM MTX medium containing 500 μg/mL hygromycin (manufactured by Wako Pure Chemical Industries Ltd.)] on the next day, and the cells were expanded and cultured in a 175-cm² flask approximately 1 month after the start of culture. The obtained cell line is referred to as each stably active Gas6-F-expressing cell line.

(9) Purification of Each Gas6-F

Each stably active Gas6-F-expressing cell line established in the paragraph (8) was suspended in MTX-hygromycin medium and cultured in a flask for adherent cells for 3 days. Next, the medium was replaced with a serum-free medium [EX-CELL 302 medium (manufactured by Sigma-Aldrich Co. LLC) supplemented with 6 mM L-glutamine (manufactured by Invitrogen Corp.), 100 ng/mL vitamin K3 (manufactured by Nacalai Tesque, Inc.), 500 nM MTX, 500 g/mL hygromycin, 100 nM 3,3',5-triiodo-L-thyronine sodium salt (manufactured by Sigma-Aldrich Co. LLC), and 50 μg/mL gentamicin], and the cells were cultured for 5 days, followed by the recovery of the medium. The recovered medium was centrifuged, and the obtained culture supernatant was sterilely filtered through a 0.22-μm filter (manufactured by Thermo Fisher Scientific Inc.).

Each Gas6-F was purified using the recovered culture supernatant. An open column packed with ANTI-FLAG M2 Affinity Gel (manufactured by Sigma-Aldrich Co. LLC) was used in the purification. The culture supernatant was added to the column, and the column was then washed with an equilibration buffer solution [50 mM Tris (manufactured by Nacalai Tesque, Inc.), 150 mM NaCl (manufactured by Nacalai Tesque, Inc.), and 0.5% polyoxyethylene sorbitan monolaurate (manufactured by Nacalai Tesque, Inc.) (pH 8.2)]. Subsequently, the column was washed with an equilibration buffer solution free from polyoxyethylene sorbitan monolaurate, followed by the elution of each Gas6-F using an elution buffer solution [0.1 M glycine (manufactured by Nacalai Tesque, Inc.) (pH 3.5) or 3 M magnesium chloride (manufactured by Nacalai Tesque, Inc.)]. The buffer solution in each Gas6-F solution thus obtained was replaced with a buffer solution for Gas6 (20 mM Tris and 150 mM NaCl, pH 8.2) using NAP (manufactured by GE Healthcare Japan Corp.), sterilely filtered through a 0.22-μm filter, and then used in the test.

The absorptivity of each protein was calculated by dividing molar absorptivity by its molecular weight (Protein Science, 4, 2411-2423 (1995)). The absorptivity of hGas6-F and cGas6-F was 0.95. The absorptivity of rGas6-F and mGas6-F was 0.89. The protein concentration in the protein solution was measured using Nanodrop (manufactured by Thermo Fisher Scientific Inc.).

[Example 3] Preparation of Complex of Axl Extracellular Domain and IgG1 Heavy Chain Constant Region (1) Construction of expression vector for complex of human Axl extracellular domain and human IgG1 heavy chain constant region (hereinafter, referred to as hAxl-hFc) A vector for expression in animal cells having an insert of a hAxl-hFc gene sequence was prepared by a method given below.

A gene sequence containing hAxl-hFc gene (SEQ ID NO: 28) was totally synthesized to obtain pMD19-hAxl-hFc (Takara Bio Inc.). The nucleotide sequence shown in SEQ ID NO: 28 consists of BglII and MluI restriction enzyme recognition sequences, a nucleotide sequence encoding the extracellular domain of human Axl (nucleotide sequence from positions 1 to 1314 in the nucleotide sequence shown in SEQ ID NO: 26 encoding full-length human Axl), BamHI, SalI, and EcoRI restriction enzyme recognition sequences, and a nucleotide sequence encoding a human IgG1 heavy chain constant region, from the 5' end toward the 3' end.

pMD19-hAxl-hFc and an expression vector pKTABEX-Tc26.2 for animal cells (WO2013/005649) were each enzymatically treated with restriction enzymes BglII and BamHI. The reaction solutions were subjected to agarose gel electrophoresis, and approximately 2 kbp of a DNA fragment (hereinafter, referred to as hAxl-hFc-BglII-BamHI) and approximately 9.6 kbp of a DNA fragment (hereinafter, referred to as pKTABEX-BglII-BamHI), respectively, were obtained using QIAquick Gel Extraction Kit.

These two types of DNA fragments were ligated using Ligation High ver. 2 (manufactured by Toyobo Co., Ltd.). A hAxl-hFc recombinant expression vector pKTABEX-hAxl-hFc was obtained in the same way as in Example 2(1).

(2) Construction of Expression Vector for Complex of Monkey Axl Extracellular Domain and Human IgG1 Heavy Chain Constant Region (Hereinafter, Referred to as cAxl-hFc)

An expression vector necessary for the preparation of cAxl-hFc was constructed. First, cynomolgus monkey Axl gene was inserted to a pCR4-Blunt-TOPO vector in the same way as in Example 2(1) to obtain a plasmid. PCR was performed by incubation at 94° C. for 2 minutes using 20 μL of a prepared reaction solution containing cynomolgus monkey kidney-derived cDNA (manufactured by CytoMol) as a template, 10 pmol each of primers 14 and 15 (SEQ ID NOs: 30 and 31), KOD-FX (manufactured by Toyobo Co., Ltd.), and 2% DMSO, followed by 30 cycles each involving 94° C. for 15 seconds, 60° C. for 30 seconds, and 68° C. for 3.5 minutes. The nucleotide sequence of the cynomolgus monkey Axl gene carried by the obtained plasmid is shown in SEQ ID NO: 32. The amino acid sequence of cynomolgus monkey Axl predicted from the nucleotide sequence is shown in SEQ ID NO: 33.

Subsequently, a DNA fragment containing a nucleotide sequence encoding a cynomolgus monkey Axl extracellular domain was amplified by PCR using the obtained plasmid as a template. The PCR was performed by incubation at 94° C. for 5 minutes using 20 μL of a prepared reaction solution containing the template plasmid, 10 pmol each of primers 16 and 17 (SEQ ID NOs: 34 and 35), and PrimeSTAR HS DNA Polymerase (manufactured by Takara Bio Inc.), followed by 30 cycles each involving 94° C. for 15 seconds, 55° C. for 10 seconds, and 68° C. for 1 minute and 40 seconds. The PCR product was subjected to agarose gel electrophoresis, and approximately 1.3 kbp of a DNA fragment (hereinafter, referred to as cAxl-BglII-EcoRI) was obtained using QIAquick Gel Extraction Kit (manufactured by Qiagen N.V.)

pKTABEX-hAxl-hFc prepared in the paragraph (1) was enzymatically treated with restriction enzymes BglII and EcoRI. The reaction solution was subjected to agarose gel electrophoresis, and approximately 9.6 kbp of a DNA fragment (hereinafter, referred to as pKTABEX-hFc-BglII-EcoRI) was then obtained using QIAquick Gel Extraction Kit.

Finally, cAxl-BglII-EcoRI was inserted to pKTABEX-hFc-BglII-EcoRI using In-Fusion HD Cloning Kit (manufactured by Clontech Laboratories, Inc.) to obtain a cAxl-hFc recombinant expression vector pKTABEX-cAxl-hFc. The nucleotide sequence of the cAxl-hFc gene carried by pKTABEX-cAxl-hFc is shown in SEQ ID NO: 36, the amino acid sequence of cAxl-hFc predicted from the nucleotide sequence is shown in SEQ ID NO: 37.

(3) Construction of Expression Vector for Complex of Rat Axl Extracellular Domain and Human IgG1 Heavy Chain Constant Region (Hereinafter, Referred to as rAxl-hFc)

An expression vector necessary for the preparation of rAxl-hFc was constructed by a method given below. At GenScript Japan Inc., a nucleotide sequence encoding the extracellular domain of rat Axl was totally synthesized and inserted to a pUC57 plasmid to obtain pUC57-rAxl. Nucleotides 1 to 1329 in the nucleotide sequence of the rat Axl gene shown in SEQ ID NO: 40 (GenBank Accession No. NM_0317941) were used in the nucleotide sequence encoding the extracellular domain of rat Axl.

Subsequently, on the basis of pUC57-rAxl, a rAxl-hFc recombinant expression vector pKTABEX-rAxl-hFc was obtained in the same way as in the paragraph (2). PCR was performed by incubation at 94° C. for 5 minutes using 20 µL of a prepared reaction solution containing pUC57-rAxl as a template, 10 pmol each of primers 20 and 21 (SEQ ID NOs: 42 and 43), and PrimeSTAR HS DNA Polymerase (manufactured by Takara Bio Inc.), followed by 30 cycles each involving 94° C. for 15 seconds, 55° C. for 10 seconds, and 68° C. for 1 minute and 40 seconds. The nucleotide sequence encoding rAxl-hFc is shown in SEQ ID NO: 40, and the amino acid sequence of rAxl-hFc predicted from the nucleotide sequence is shown in SEQ ID NO: 41.

(4) Construction of Expression Vector for Complex of Mouse Axl Extracellular Domain and Mouse IgG1 Heavy Chain Constant Region (Hereinafter, Referred to as mAxl-mFc)

An expression vector necessary for the preparation of mAxl-mFc was constructed by a method described below. At Takara Bio Inc., a nucleotide sequence containing mAxl-mFc gene shown in SEQ ID NO: 48 was totally synthesized and inserted to a pMD19 plasmid to obtain pMD19-mAxl-mFc. The mAxl-mFc gene consists of BglII and MluI recognition sequences, a nucleotide sequence encoding the extracellular domain of mouse Axl (nucleotide sequence from positions 1 to 1329 in the nucleotide sequence of the mouse Axl gene shown in SEQ ID NO: 46), BamHI, SalI, and EcoRI recognition sequences, and a nucleotide sequence encoding a mouse IgG1 heavy chain constant region, from the 5' end toward the 3' end. pMD19-mAxl-mFc was enzymatically treated with restriction enzymes BglII and BamHI and inserted to pKTABEX-Tc26.2 in the same way as in the paragraph (1) to obtain a mAxl-mFc recombinant expression vector pKTABEX-mAxl-mFc.

(5) Preparation of Stably hAxl-hFc- and mAxl-mFc-Expressing Cell Lines

In order to prepare lines stably expressing hAxl-hFc and mAxl-mFc, host cells were transfected with each expression vector. CHO-K1 (Riken, Japan) was used as the host cells for hAxl-hFc and mAxl-mFc expression. The cells were usually cultured for subculture using EX-CELL 325 PF (manufactured by Nichirei Biosciences Inc.) containing 4 mM L-glutamine (manufactured by Invitrogen Corp.) and 50 µg/mL gentamicin (manufactured by Nacalai Tesque, Inc.) (basal medium). Transfected lines were screened using a basal medium containing 3 µg/mL Cycloheximide Ready Made Solution (manufactured by Sigma-Aldrich Co. LLC) (CHX medium). All of the cells were shake-cultured under conditions involving 37° C. and 5% $CO_2$.

The cells were transfected in the same way as in Example 2(5).

A solution containing 10 µg of pKTABEX-hAxl-hFc obtained in the paragraph (1) and 20 µg of a transposase expression vector (WO2010/143698) (hereinafter, referred to as TPEX_pMug) was added to a cuvette for electroporation (Gene Pulser cuvette, manufactured by Bio-Rad Laboratories, Inc.). 400 µL of $4\times10^6$ cells/mL of a CHO-K1 cell suspension prepared with PBS was added to the cuvette. The cell suspension in the cuvette was mixed, followed by transfection under conditions involving a pulse voltage of 300 V and an electrical capacitance of 500 µF using Gene Pulser (Bio-Rad Laboratories, Inc.).

The cells thus transfected in the cuvette were suspended in 20 mL of a basal medium and inoculated at 200 µL/well to one 96-well plate. The medium was replaced with CHX medium 4 days after the start of culture, and the transfected lines were screened. Cell lines whose medium was discolored yellow on culture day 29 were each expanded to 24 wells and further cultured for 3 days. The expression level of hAxl-hFc in the supernatants was measured by a method described below.

In order to measure the expression level of hAxl-hFc, ELISA was conducted as follows. Goat anti-human IgG (H&L) (manufactured by American Qualex International, Inc.) diluted 750-fold with PBS was dispensed as a primary antibody at 50 µL/well to a 96-well plate (manufactured by Nalge Nunc International), and the plate was left standing overnight at 4° C. for immobilization. The plate was washed five times with PBS containing 0.05 to 0.1% Tween-20 (hereinafter, referred to as Tween 20-PBS) (manufactured by Wako Pure Chemical Industries Ltd.) PBS containing 1% BSA (hereinafter, referred to as 1% BSA-PBS) (manufactured by Nacalai Tesque, Inc.) was dispensed at 100 µL/well to the ELISA plate, and the plate was left standing at room temperature for 2 hours for blocking. The plate was washed five times with Tween 20-PBS (manufactured by Wako Pure Chemical Industries Ltd.). The culture supernatant diluted with 1% BSA-PBS was dispensed thereto as a specimen at 50 µL/well, and the plate was left standing for 1 hour. The standard used was a human IgG1 antibody known in the art. The plate was washed five times with Tween 20-PBS (manufactured by Wako Pure Chemical Industries Ltd.). Then, Goat anti-human IgG (H&L)-HRP (manufactured by American Qualex International, Inc.) diluted 2000-fold with 1% BSA-PBS was dispensed thereto as a secondary antibody at 50 µL/well, and the plate was left standing for 1 hour. The plate was washed with Tween 20-PBS. Then, ABTS (2,2-azino-bis(3-ethylbenzothiazoline)-6-sulfonic acid) (manufactured by Thermo Fisher Scientific Inc.) was dispensed thereto at 50 µL/well for color development. A 5% SDS solution was dispensed thereto at 50 µL/well to terminate the color development. The absorbance at a sample wavelength of 415 nm and a reference wavelength of 490 nm (415 nm-490 nm) was measured using a plate reader.

Lines having a high hAxl-hFc expression level were serially expanded from 6-well plates to 125-mL Erlenmeyer flasks, and the hAxl-hFc expression level was measured again. As a result, a cell line having the highest expression level was selected as a stably hAxl-hFc-expressing cell line.

Similarly, a stably mAxl-mFc-expressing cell line was obtained using pKTABEX-mAxl-mFc obtained in the paragraph (4). The expression level of mAxl-mFc was measured by ELISA in the same way as above. The primary antibody used was Polyclonal Rabbit Anti-mouse Immunoglobulins (manufactured by Dako Denmark A/S) diluted 100-fold with PBS, and the secondary antibody used was Polyclonal Rabbit Anti-mouse Immunoglobulins HRP (manufactured by Dako Denmark A/S) diluted 400-fold with 1% BSA-PBS. The standard used was a mouse IgG1 antibody known in the art.

(6) Preparation of Transiently cAxl-hFc- and rAxl-hFc-Expressing Cell Lines

In order to prepare lines transiently expressing cAxl-hFc and rAxl-hFc, host cells were transfected with each expression vector.

CHO-S(manufactured by Life Technologies Corp.) was used as the host cells for cAxl-hFc and rAxl-hFc expression. The cells were subcultured using Free Style CHO (manufactured by Invitrogen Corp.) containing 4 mM L-glutamine (manufactured by Invitrogen Corp.) and shake-cultured under conditions involving 37° C. and 5% $CO_2$.

1.25 mg of pKTABEX-cAxl-hFc prepared in the paragraph (2) was dissolved in 20 mL of Opti-Pro SFM (manufactured by Invitrogen Corp.), and 1.25 mL of FreeStyle MAX Reagent (manufactured by Invitrogen Corp.) was dissolved in 20 mL of Opti-Pro SFM. These solutions were left at room temperature for 5 minutes. These two solutions were mixed and left at room temperature for 15 minutes. The mixed solution was added dropwise to the CHO-S culture medium to obtain a transiently cAxl-hFc-expressing cell line. Similarly, a transiently rAxl-hFc-expressing cell line was obtained using pKTABEX-rAxl-hFc prepared in the paragraph (3).

(7) Purification of Each Axl-hFc and mAxl-mFc

The stably hAxl-hFc- and mAxl-mFc-expressing cell lines obtained in the paragraph (5) were each suspended in a medium for protein expression known in the art and cultured for 7 days in an Erlenmeyer flask, followed by the recovery of the culture supernatant. The recovered culture supernatant was centrifuged, and the obtained culture supernatant was filtered through a 0.22-µm filter to prepare a culture supernatant containing hAxl-hFc. A culture supernatant containing mAxl-mFc was prepared by the same approach as above.

The transiently cAxl-hFc- and rAxl-hFc-expressing cell lines obtained in the paragraph (6) were each suspended in Free Style CHO (manufactured by Invitrogen Corp.) supplemented with 4 mM L-glutamine (manufactured by Invitrogen Corp.), and cultured for 5 days in an Erlenmeyer flask, followed by the recovery of the culture supernatant. The recovered culture supernatant was centrifuged, and the obtained culture supernatant was filtered through a 0.22-µm filter to prepare a culture supernatant containing cAxl-hFc. A culture supernatant containing rAxl-hFc was prepared by the same approach as above.

Each Axl-Fc was purified from the prepared culture supernatant by an ordinary method. The resin used was HiTrap MabSelect SuRe (manufactured by GE Healthcare Japan Corp.). The obtained purified protein solution was sterilely filtered through a 0.22-µm and then used in the test. The absorptivity of each protein was calculated by use of the method described in Example 2(9). The absorptivity of hAxl-hFc, mAxl-mFc, cAxl-hFc, and rAxl-hFc was 1.38, 1.54, 1.42, and 1.8, respectively.

[Example 4] Preparation of Conventional Anti-Human Gas6 Monoclonal Antibody

(1) Preparation of CNTO Antibody Expression Vector

On the basis of nucleotide sequences encoding VH and VL (SEQ ID NOs: 25 and 27 described in the patent specification of U.S. Pat. No. 7,547,767) of an anti-Gas6 monoclonal antibody WG1 described in the patent specification of U.S. Pat. No. 7,547,767, an expression vector for this antibody (hereinafter, referred to as a CNTO antibody) was prepared by a method described below. At Integrated Device Technology, Inc. (IDT), the nucleotide sequences encoding VH and VL of the CNTO antibody were totally synthesized and inserted to an appropriate plasmid. The nucleotide sequences encoding VH and VL of the CNTO antibody are shown in SEQ ID NOs: 61 and 63, respectively. The amino acid sequences of VH and VL of the CNTO antibody are shown in SEQ ID NOs: 62 and 64, respectively. Since U.S. Pat. No. 7,547,767 describes N at position 305 in the nucleotide sequence of WG1 VH shown in SEQ ID NO: 25, thymidine was used as the nucleotide 305 in light of the Kabat human antibody sequence information (Sequences of Proteins of Immunological Interest, US Dept Health and Human Services (1991)) and a nucleotide sequence of positions 304 and 306 that formed a codon with the nucleotide 305. The gene sequence of the CNTO antibody was inserted to an appropriate position of a vector pKANTEX93 (WO97/10354) for expression by a method known in the art to construct pKANTEX-CNTO as a CNTO antibody expression vector.

(2) Preparation of Stably CNTO Antibody-Expressing Cell Line

CHO cells deficient in dhfr were transfected with pKANTEX-CNTO prepared in the paragraph (1), in the same way as in Example 2(5) to prepare a stably CNTO antibody-expressing cell line.

(3) Purification of CNTO Antibody

The stably CNTO antibody-expressing cell line obtained in the paragraph (2) was suspended in 500 nM MTX medium and cultured for 3 days in a flask for adherent cells. Next, the medium was replaced with EX-CELL 302 (containing 6 mM L-glutamine, 100 nM 3,3',5-triiodo-L-thyronine sodium salt, and 50 µg/mL gentamicin), and the cells were cultured for 5 days, followed by the recovery of the culture supernatant. The recovered culture supernatant was centrifuged, and the supernatant was filtered through a 0.22-µm filter to prepare a culture supernatant containing the CNTO antibody.

The CNTO antibody was purified from the prepared culture supernatant by an ordinary method. The resin used was MabSelect SuRe (manufactured by GE Healthcare Japan Corp.). The obtained CNTO antibody was sterilely filtered through a 0.22-µm filter and then used in the test. The absorptivity of the CNTO antibody was 1.43.

[Example 5] Preparation of Anti-Human Gas6 Monoclonal Antibody

(1) Immunization with Animal and Preparation of Antibody-Producing Cell

The KO mice obtained in Example 1 were immunized with hGas6-F or rGas6-F prepared in Example 2(9). Aluminum hydroxide (Antibodies A Laboratory Manual, Cold Spring Harbor Laboratory, p. 99, 1988) and a pertussis vaccine (manufactured by Nacalai Tesque, Inc.) were used as an adjuvant in the mouse immunization.

Specifically, 80 µL of aluminum hydroxide and 5 µL of a pertussis vaccine were used per mouse to prepare a suspension with hGas6-F or rGas6-F. The suspension was intraperitoneally administered to the KO mice such that 30 µg of hGas6-F or rGas6-F was administered per mouse.

The adjuvant was used only in priming, and the immunization was performed a total of four times including final boosting. The mice were divided into a group for which only hGas6-F was used in immunization and a group to which rGas6-F and hGas6-F were alternately administered, and each group involving 4 mice was immunized. 4 days after the final immunization, the spleen was harvested from each mouse. The harvested spleen was chopped in MEM medium (manufactured by Invitrogen Corp.), and a spleen cell fraction was then recovered by centrifugation (1200 rpm, 5 min). Since the obtained spleen cell fraction contained erythrocytes, RED Blood Cell Lysing Buffer (manufactured by Sigma-Aldrich Co. LLC) was added thereto and reacted at 37° C. to remove the erythrocytes. The obtained spleen cells were washed twice with MEM medium and then subjected to cell fusion.

(2) Preparation of Mouse Myeloma Cell

An 8-azaguanine-resistant mouse myeloma cell line P3X63Ag8U.1 (P3-U1; purchased from ATCC) was cultured in RPMI1640 (manufactured by Wako Pure Chemical Industries Ltd.) containing 10% FCS (manufactured by Moregate Biotech) and used as a parent line for cell fusion.

(3) Preparation of Hybridoma

The mouse spleen cells obtained in the paragraph (1) and the myeloma cells obtained in the paragraph (2) were mixed at a ratio of 8:1 and centrifuged (1200 rpm, 5 min) 0.5 mL of polyethylene glycol-1000 (manufactured by Roche Diagnostics K.K.) was gradually added to the obtained precipitated fraction (cell group) with gentle shaking. Next, 1 mL of MEM was added to the cell suspension five times at 1-minute intervals in a water bath of 37° C. Finally, 45 mL of MEM was added thereto. Then, the cells were centrifuged (900 rpm, 5 min). The obtained precipitated fraction (cell group) was suspended in HAT medium (RPMI1640 medium supplemented with 10% fetal bovine serum and further supplemented with HAT Media Supplement (manufactured by Invitrogen Corp.)) to adjust the number of spleen cells to $1.5 \times 10^7$ cells/plate. The cell suspension was inoculated at 200 μL/well to a 96-well plate and cultured under conditions involving 37° C. and 5% $CO_2$. The medium was replaced with HAT medium on the day before the cells in the wells reached the number of cells suitable for screening.

(4) Screening of Hybridoma

The hybridomas prepared in the paragraph (3) were screened by competitive ELISA described below to select hybridomas producing an antibody inhibiting the binding of human Gas6 and rat Gas6 to Axl.

First, a 2 μg/mL hAxl-hFc solution (solution obtained by diluting the hAxl-hFc solution obtained in Example 3(7) with PBS (manufactured by Nacalai Tesque, Inc.)) was dispensed at 50 μL/well to a 96-well plate for ELISA (manufactured by Nalge Nunc International), and the plate was left standing overnight at 4° C. for adsorption. The plate was washed five times with Tween 20-PBS. Then, 1% BSA-PBS (manufactured by Nacalai Tesque, Inc.) was added thereto at 300 μL/well, and the plate was left standing at room temperature for 1 hour for blocking and washed five times with Tween 20-PBS (manufactured by Wako Pure Chemical Industries Ltd.).

Next, a reaction solution prepared by a method given below was dispensed at 50 μL/well to the plate, and the plate was left standing at room temperature for 1 hour and then washed five times with Tween 20-PBS. The reaction solution was prepared by mixing equal amounts of a 100 ng/mL hGas6-F solution (solution obtained by diluting the hGas6-F solution obtained in Example 2(9) with 1% BSA-PBS) and the hybridoma culture supernatant or a medium for hybridomas (negative control) and leaving the mixture standing at 4° C. for 30 minutes.

Next, Monoclonal ANTI-FLAG M2-Peroxidase (HRP) antibody produced in mouse (Sigma-Aldrich Co. LLC) diluted 2000-fold with 1% BSA-PBS was dispensed thereto as an antibody for detection at 50 μL/well, and the plate was left standing at room temperature for 1 hour. This plate was washed five times with Tween 20-PBS, and TMB (manufactured by Sigma-Aldrich Co. LLC) was added thereto at 50 μL/well and reacted. At an appropriate point in time, the reaction was terminated by the addition of 1 N hydrochloric acid (manufactured by Wako Pure Chemical Industries Ltd.) at 50 μL/well. The absorbance at a sample wavelength of 450 nm and a reference wavelength of 570 nm (450 nm-570 nm) was measured as to the solution of each well using a plate reader.

In this assay system, the absorbance from a well supplemented with the hybridoma culture supernatant is lower than that of wells supplemented with the negative control when the culture supernatant contained an antibody inhibiting the binding between hGas6 and hAxl. Accordingly, wells having lower absorbance than that of the wells supplemented with the negative control were selected to select hybridomas corresponding to the culture supernatants added to the wells.

Hybridomas producing an antibody inhibiting the binding between rGas6 and rAxl were selected in the same way as above. The samples used were rGas6-F and rAxl-hFc obtained in Examples 2(9) and 3(7).

(5) ELISA for Gas6 Binding Activity Measurement Using Immobilized Antigen

The antibody in the culture supernatant of each hybridoma selected in the paragraph (4) was confirmed by antigen binding ELISA described below to bind to hGas6-F and rGas6-F, but to bind to neither human protein S having high homology to hGas6, nor FLAG-tag (BAP-F).

hGas6-F and rGas6-F purified in Example 2(9), human protein S (derived from human serum; manufactured by Enzyme Research Laboratories Inc.) having high homology to hGas6, or Carboxy-terminal FLAG-BAP Fusion Protein (hereinafter, referred to as BAP-F) (manufactured by Sigma-Aldrich Co. LLC) was used as an antigen to be adsorbed onto a plate for ELISA.

First, a 2 μg/mL solution of the antigen (prepared from each antigen with PBS (manufactured by Nacalai Tesque, Inc.)) was dispensed at 50 μL/well to a 96-well plate for ELISA (manufactured by Nalge Nunc International), and the plate was left standing overnight at 4° C. for adsorption. The plate was washed five times with Tween 20-PBS. Then, 1% BSA-PBS (manufactured by Nacalai Tesque, Inc.) was added thereto at 300 μL/well, and the plate was left standing at room temperature for 1 hour for blocking and washed five times with Tween 20-PBS (manufactured by Wako Pure Chemical Industries Ltd.). Next, the hybridoma culture supernatant was dispensed thereto as a test substance at 50 μL/well, and the plate was left standing at room temperature for 1 hour and then washed five times with Tween 20-PBS. Next, polyclonal goat anti-mouse immunoglobulins/HRP (Dako Denmark A/S, P0447) diluted 2000-fold with 1% BSA-PBS was dispensed thereto at 50 μL/well, and the plate was left standing at room temperature for 1 hour. The plate was washed five times with Tween 20-PBS, and TMB (manufactured by Sigma-Aldrich Co. LLC) was added thereto at 50 μL/well and reacted. At an appropriate point in time, the reaction was terminated by the addition of 1 N hydrochloric acid (manufactured by Wako Pure Chemical Industries Ltd.) at 50 μL/well. The absorbance at a sample wavelength of 450 nm and a reference wavelength of 570 nm (450 nm-570 nm) was measured using a plate reader (Spectra Max, manufactured by Molecular Devices, LLC).

(6) Cloning of Hybridoma

Each hybridoma selected in the paragraphs (4) and (5) was limiting-diluted using a medium for cloning (S-Clone Cloning Medium (manufactured by EIDIA Co., Ltd.) supplemented with 10% fetal bovine serum, 1% HT Supplement (manufactured by Invitrogen Corp.), and 0.2% Gentamicin Sulfate Solution (manufactured by Nacalai Tesque, Inc.)), inoculated to a 96-well plate, and cloned. The cloning was performed only once. Two hybridomas producing an antibody that bound to human Gas6 and rat Gas6 and further had the activity of inhibiting the binding of human Gas6 and rat Gas6 to Axl were isolated by these operations.

(7) Antibody Obtainment from Hybridoma

Each hybridoma isolated in the paragraph (6) was inoculated at a cell density of $1 \times 10^7$ cells/100 mL to a floating flask. The medium used was Hybridoma SFM medium (manufactured by Invitrogen Corp.) containing 5% Fetal Bovine Serum-Ultra Low IgG (manufactured by Invitrogen Corp.). The cells were statically cultured at 37° C. for 7 days, and the medium containing the cells was then recovered. The recovered medium was centrifuged, and the obtained culture supernatant was filtered through a 0.22-µm filter.

Hybridoma-derived anti-human Gas6 mouse monoclonal antibodies, KM5320 antibody (hereinafter, also referred to as a KM5320-mKG1 antibody) and KM5321 antibody (hereinafter, also referred to as a KM5321-mKG1 antibody), were purified from the culture supernatants filtered through a filter by an ordinary method. The resin used was Protein G Sepharose 4 Fast Flow (manufactured by GE Healthcare Japan Corp.). The obtained antibody solutions were each sterilized using a 0.22-µm filter and then used in the experiment. As a result of calculating absorptivity by the method described in Example 2(9), the absorptivity of the KM5320-mKG1 antibody and the KM5321-mKG1 antibody was 1.54 and 1.45, respectively.

[Example 6] Gas6 Binding Activity Evaluation Using Floating Antigen

The binding activity of the obtained antibodies against each Gas6 having a more natural state was confirmed by use of competitive ELISA described below.

First, 2 µg/mL anti-FLAG antibody [Monoclonal ANTI-FLAG M2 antibody produced in mouse (manufactured by Sigma-Aldrich Co. LLC) diluted with PBS (manufactured by Nacalai Tesque, Inc.)] was dispensed at 50 µL/well to a 96-well plate for ELISA (manufactured by Nalge Nunc International), and the plate was left standing overnight at 4° C. for adsorption. After removal of the immobilization solution, 1% BSA-PBS (manufactured by Nacalai Tesque, Inc.) was added thereto at 300 µL/well, and the plate was left standing at room temperature for 1 hour for blocking and washed five times with Tween 20-PBS (manufactured by Wako Pure Chemical Industries Ltd.).

Next, a 1 µg/mL solution of each Gas6-F or BAP-F [each Gas6-F solution obtained in Example 2(9) or BAP-F (manufactured by Sigma-Aldrich Co. LLC) diluted with 1% BSA-PBS] was dispensed thereto at 50 µL/well, and the plate was left standing at room temperature for 1 hour and then washed five times with Tween 20-PBS. Subsequently, the KM5320-mKG, KM5321-mKG, and CNTO antibodies were each biotinylated using Biotin Labeling Kit-NH2 (manufactured by Dojindo Laboratories) and adjusted to an appropriate concentration with 1% BSA-PBS. Each antibody solution was dispensed thereto at 50 µL/well, and the plate was left standing at room temperature for 1 hour. This plate was washed five times with Tween 20-PBS. Then, Streptavidin HRP Conjugate (manufactured by R&D Systems, Inc.) diluted 200-fold with 1% BSA-PBS was dispensed thereto at 50 µL/well, and the plate was left standing at room temperature for 1 hour. This plate was washed five times with Tween 20-PBS, and TMB (manufactured by Sigma-Aldrich Co. LLC) was added thereto at 50 µL/well and reacted. At an appropriate point in time, the reaction was terminated by the addition of 1 N hydrochloric acid (manufactured by Wako Pure Chemical Industries Ltd.) at 50 µL/well. The absorbance at a sample wavelength of 450 nm and a reference wavelength of 570 nm (450 nm-570 nm) was measured using a plate reader.

The binding activity of the obtained antibodies against human protein S was measured in the same way as in Example 5(5). The biotinylated KM5320-mKG, KM5321-mKG, and CNTO antibodies prepared above as test substances were diluted to an appropriate concentration with 1% BSA-PBS and used as samples. The secondary detection reagent used was Streptavidin HRP Conjugate (manufactured by R&D Systems, Inc.) diluted 200-fold with 1% BSA-PBS.

The results are shown in FIG. 1. The KM5320-mKG1 antibody and the KM5321-mKG1 antibody bound to human Gas6-F, monkey Gas6-F, rat Gas6-F, and mouse Gas6-F, but bound to neither human protein S nor BAP-F. These results demonstrated that the KM5320-mKG1 antibody and the KM5321-mKG1 antibody are antibodies specifically binding to human Gas6, monkey Gas6, rat Gas6, and mouse Gas6.

The binding activity of the KM5320-mKG1 antibody and the KM5321-mKG1 antibody against human Gas6-F was detected at an antibody concentration of 0.0003 µg/mL and reached the largest activity at 0.04 µg/mL. On the other hand, the binding activity of the CNTO antibody against human Gas6-F was detected at an antibody concentration of 0.04 µg/mL and exhibited, even at 5 µg/mL, only activity smaller than half the largest activity of the KM5320-mKG1 antibody and the KM5321-mKG1 (FIG. 1-A). These results demonstrated that the KM5320-mKG1 antibody and the KM5321-mKG1 antibody bind to each Gas6 more strongly than the CNTO antibody.

[Example 7] Evaluation of Inhibitory Activity of Anti-Gas6 Monoclonal Antibody Against Binding Between Gas6 and Axl The inhibitory activity of the KM5320-mKG1 antibody, the KM5321-mKG1 antibody, and the CNTO antibody against the binding between each Gas6 and Axl was measured in the same way as in Example 5(4). The reaction solution used was a mixture of equal amounts of a 100 ng/mL solution of each Gas6-F (solution obtained by diluting each Gas6-F solution obtained in Example 2(9) with 1% BSA-PBS) and each antibody solution having twice the final concentration (solution obtained by diluting the antibody solution obtained in Examples 4(3) and 5(7) with 1% BSA-PBS).

The results are shown in FIG. 2. The KM5320-mKG1 antibody and the KM5321-mKG1 antibody inhibited the binding of human Gas6, monkey Gas6, rat Gas6, and mouse Gas6 to Axl of the respective species. The KM5320-mKG1 antibody almost completely inhibited the binding between human Gas6 and human Axl when approximately 200 ng/mL of the antibody was added to 50 ng/mL of human Gas6. The human Gas6 has a molecular weight of approximately 70 kDa, and the antibody has a molecular weight of approximately 140 to 150 kDa. Hence, these results demonstrated that the KM5320-mKG1 antibody completely inhibits the binding between human Gas6 and human Axl when the antibody and Gas6 are at a molar concentration ratio of 2:1. Likewise, the KM5321-mKG1 antibody almost completely inhibited the binding between human Gas6 and human Axl when approximately 60 ng/mL of the antibody was added to 50 ng/mL of human Gas6. These results demonstrated that the KM5321-mKG1 antibody completely inhibits the binding between human Gas6 and human Axl when the antibody and Gas6 are at a molar concentration ratio of 1:2. Since one molecule of the antibody binds to two molecules of the antigen at maximum, the KM5321-mKG1 antibody was shown to have very strong binding activity.

On the other hand. the CNTO antibody did not inhibit the binding between each Gas6 and Axl at any of the studied antibody concentrations.

These results demonstrated that the KM5320-mKG1 antibody and the KM5321-mKG1 antibody have stronger neutralizing activity than that of the CNTO antibody.

[Example 8] Effect of Obtained Antibody on Gas6-Dependent Intracellular Signal

In addition to Axl, Sky and Mer are known as receptors of Gas6. Upon binding of Gas6 to the receptor expressed on cells, a signaling pathway mediated by the receptor is activated in the cells. In order to confirm the effects of the obtained antibodies on this intracellular signal transduction, reporter assay was carried out using a cell line forced to express the Gas6 receptor.

The cell line forced to express the Gas6 receptor was transfected with a vector containing a recognition sequence of Egr1 (early growth response 1), a transcriptional factor involved in the downstream signal transduction of the Gas6 receptor. Luciferase gene was also inserted to downstream of the Egr1 recognition sequence in the vector. In this assay system, the binding of Gas6 to the Gas6 receptor on the cell line activates the intracellular signaling pathway to increase the expression of Egr1. The Egr1 binds to the Egr1 recognition sequence to increase the expression of the luciferase gene. Thus, the luminescence intensity of the biosynthesized luciferase can be detected to confirm the activated state of the intracellular signaling pathway by the addition of Gas6.

(1) Construction of Gas6 Receptor Expression Vector

First, a Human Axl Expression Vector was Constructed.

The vector was prepared by a method described below using a plasmid having an insert of the human Axl gene sequence shown in SEQ ID NO: 26 (manufactured by GeneCopoeia, Inc.) (GenBank Accession No. NM_021913) as a template. PCR was performed by incubation at 94° C. for 5 minutes using 20 µL of a prepared reaction solution containing the template plasmid, 10 pmol each of primers 22 and 23 (SEQ ID NOs: 50 and 51), and PrimeSTAR HS DNA Polymerase (manufactured by Takara Bio Inc.), followed by 30 cycles each involving 98° C. for 10 seconds, 55° C. for 5 seconds, and 72° C. for 3 minutes and 30 seconds. The obtained PCR product was subjected to agarose gel electrophoresis, and approximately 2.7 kbp of an amplified DNA fragment (DNA fragment containing the nucleotide sequence of the hAxl gene) was recovered using QIAquick Gel Extraction Kit (manufactured by Qiagen N.V.) An appropriate expression vector for animal cells known in the art was enzymatically digested with EcoRI and BamHI and subjected to agarose gel electrophoresis, and the DNA fragment of interest was then recovered using QIAquick Gel Extraction Kit. The two types of DNA fragments thus obtained were ligated using In-Fusion HD Cloning Kit (manufactured by Clontech Laboratories, Inc.) to obtain a hAxl recombinant expression vector. As a result of analyzing the human Axl gene sequence contained in the obtained expression vector, cytosine at position 1546 of the human Axl gene shown in SEQ ID NO: 26 was substituted by thymidine. However, amino acid sequences predicted from these nucleotide sequences were identical (GenBank Accession No. NP_068713), and there exists the same genetic polymorphism thereas in the nucleotide sequences. Therefore, this sequence was used in the subsequent experiment.

Human Sky gene was inserted to an appropriate expression vector for animal cells known in the art in the same way as above to prepare a human Sky recombinant expression vector. The PCR template used was a plasmid (manufactured by Invitrogen Corp.) having an insert of the human Sky gene sequence shown in SEQ ID NO: 52 (GenBank Accession No. NM_006293)). PCR was performed by incubation at 98° C. for 10 minutes using 20 µL of a prepared reaction solution containing the template plasmid, 10 pmol each of primers 24 and 25 (SEQ ID NOs: 54 and 55), and PrimeSTAR Max DNA Polymerase (manufactured by Takara Bio Inc.), followed by 30 cycles each involving 98° C. for 10 seconds, 55° C. for 5 seconds, and 72° C. for 1 minute and 30 seconds. As a result of analyzing the nucleotide sequence of the human Sky gene contained in the obtained expression vector, thymidine at position 2168 of the nucleotide sequence of the human Sky gene shown in SEQ ID NO: 52 was substituted by cytosine. However, amino acid sequences predicted from these nucleotide sequences were identical (GenBank Accession No. NP_06284), and there exists the same genetic polymorphism thereas in the nucleotide sequences. Therefore, this sequence was used.

Human Mer gene was inserted to an appropriate expression vector for animal cells known in the art in the same way as above to prepare a human Mer recombinant expression vector. The PCR template plasmid used was a plasmid (manufactured by GeneCopoeia, Inc.) having an insert of the human Mer gene sequence shown in SEQ ID NO: 56 (GenBank Accession No. NM_006343)). PCR was performed by incubation at 98° C. for 10 minutes using 20 µL of a prepared reaction solution containing the template plasmid, 10 pmol each of primers 26 and 27 (SEQ ID NOs: 58 and 59), and PrimeSTAR Max DNA Polymerase (manufactured by Takara Bio Inc.), followed by 30 cycles each involving 98° C. for 10 seconds, 55° C. for 5 seconds, and 72° C. for 5 seconds.

(2) Transfection of Host Cell with Gas6 Receptor Expression Vector and Luciferase Reporter Vector HEK293F cells (Invitrogen Corp.) were transfected as host cells with each of the 3 types of Gas6 receptor expression vectors prepared in the paragraph (1) and a reporter vector by a method described below. The cell culture medium used was FreeStyle 293 Expression Medium (manufactured by Invitrogen Corp.), and the cells were shake-cultured under conditions involving 37° C. and 5% $CO_2$. The reporter vector used was pGL3-mEgr1 prepared by inserting a mouse Egr1 recognition sequence (SEQ ID NO: 60) to a luciferase reporter vector pGL3 vector (manufactured by Promega Corp.) (Nature 444, 770-774, 2006; and PNAS 85 (21), 7857-61, 1988).

Each Gas6 receptor expression vector and pGL3-mEgr1 were dissolved in Opti-Pro SFM (manufactured by Invitrogen Corp.), and 293fectin Transfection Reagent (manufactured by Invitrogen Corp.) was dissolved in Opti-Pro SFM. These solutions were left at room temperature for 5 minutes. These two solutions were mixed, left at room temperature for 20 minutes, and then added dropwise to the HEK293F cell culture solution, followed by shake-culture for 5 hours. The cell lines thus obtained are respectively referred to as a reporter cell line of human Axl-mEgr1 transcriptional factor promoter, a reporter cell line of human Sky-mEgr1 transcriptional factor promoter, and a reporter cell line of human Mer-mEgr1 transcriptional factor promoter.

(3) Reporter Assay

The three reporter cell lines of Gas6 receptor (Axl, Sky, or Mer)-mEgr1 transcriptional factor promoter prepared in the paragraph (2) were each inoculated at 80 μL/well (1.6× $10^4$ cells/well) to a 96-well black plate. Next, a medium containing 80 μg/mL (10 times the final concentration) of KM5320-mKG1 or KM5321-mKG1 [antibody solution obtained in Example 5(7), diluted with FreeStyle 293 Expression Medium (manufactured by Invitrogen Corp.)] was added thereto at 10 μL/well, and the cells were statically cultured for 1 hour. A medium containing 80 μg/mL of an IgG1 isotype control (purified mouse monoclonal IgG1, manufactured by R&D Systems, Inc.) adjusted in the same way as above was added thereto as an isotype control at 10 μL/well.

Subsequently, a medium containing 20 μg/mL (10 times the final concentration) of hGas6-F [hGas6-F solution prepared in Example 2(9), diluted with FreeStyle 293 Expression Medium] was added thereto at 10 μL/well, and the cells were statically cultured. Wells supplemented with the cell lines and a medium alone were also prepared as negative controls. 12 to 14 hours later, a chemiluminescent reagent (Steady Glo Luciferase assay system, manufactured by Promega Corp.) was added thereto at 100 μL/well. The luminescence intensity of each well was measured using a luminometer (manufactured by Veritas Corp.).

The results are shown in FIG. 3. In all of the cell lines forced to express the Gas6 receptor, the luminescence intensity was increased by approximately 3 times by the addition of hGas6-F and the isotype control as compared with the addition of a medium alone. On the other hand, the same level of luminescence intensity was exhibited by the addition of hGas6-F and KM5320-mKG1 or KM5321-mKG1 as compared with the addition of a medium alone.

As mentioned above, in this assay system, the luminescence intensity of detected luciferase is increased with the activation of the intracellular signaling pathway. These results demonstrated that the addition of human Gas6 to the cell line forced to express each Gas6 receptor activates the intracellular signaling pathway, and both of KM5320-mKG1 and KM5321-mKG1 inhibit this activation.

As a result of conducting calculation in the same way as in Example 7, both of the KM5320-mKG1 antibody and the KM5321-mKG1 antibody completely inhibited the activation of the intracellular signaling pathway by Gas6 when the antibody and Gas6 were at a molar concentration ratio of 2:1. This indicated that the KM5320-mKG1 antibody and the KM5321-mKG1 antibody have very strong neutralizing activity.

[Example 9] Effect of Anti-Human Gas6 Monoclonal Antibody of Present Invention on Phosphorylation Signal in Human Renal Mesangial Cell The effects of the obtained antibodies on intracellular signals generated by the binding between Gas6 and a Gas6 receptor were confirmed under conditions closer to a living body than those of Example 8. It is known that a Gas6 receptor is activated by the binding of Gas6 so that Akt is phosphorylated in cells expressing the receptor. Therefore, the phosphorylation level of Akt by the addition of Gas6 was detected by a method described below using human renal mesangial cells (manufactured by ScienCell Research Laboratories, Inc.; hereinafter, simply referred to as human mesangial cells) naturally expressing each Gas6 receptor.

The expression of each Gas6 receptor (Axl, Sky, and Mer) on the human mesangial cells was confirmed by FACS analysis according to a method known in the art. For the FACS analysis, Anti-Axl antibody (manufactured by Abcam plc, MM0098-2N33), Human Dtk MAb (manufactured by R&D Systems, Inc., Clone 96201), Human Mer MAb (manufactured by R&D Systems, Inc., Clone 125518) were used in the detection of these Gas6 receptors, respectively. The secondary antibody used was Alexa Fluor 488 goat anti-mouse IgG (H+L) Antibody (manufactured by Invitrogen Corp.).

The human mesangial cells were suspended in Mesangial Cell Medium (manufactured by ScienCell Research Laboratories, Inc.; hereinafter, abbreviated to MCM) supplemented with 2% FBS and 1% mesangial cell growth supplement (attached to MCM), inoculated at $0.5 \times 10^4$ cells/well to a 12-well plate, and statically cultured under conditions involving 37° C. and 5% $CO_2$. 2 days later, the medium was replaced with additive-free MCM, and the cells were statically cultured. 1 day later, the wells were washed once with MCM, and 400 μL/well of fresh MCM was added thereto.

Next, each antibody sample prepared in Example 4(3), hAXL-hFc, and an isotype control antibody, diluted to 10 times the final concentration with MCM, were each added thereto at 50 μL/well, and the cells were statically cultured for 1 hour. The isotype control antibody (negative control) used was an IgG1 isotype control (purified mouse monoclonal IgG1, manufactured by R&D Systems, Inc.). Subsequently, hGas6-F diluted to 10 times the final concentration (0.1 μg/mL) with MCM, or MCM alone was added thereto at 50 μL/well, and the cells were statically cultured for 10 minutes. The medium was removed on ice, and the plate was washed with PBS containing Protease inhibitor cocktail (manufactured by Sigma-Aldrich Co. LLC). Then, Lane Marker Non-Reducing Sample Buffer (manufactured by Thermo Fisher Scientific Inc.) diluted 5-fold with PBS containing Protease inhibitor cocktail and 2-mercaptoethanol (manufactured by Nacalai Tesque, Inc.) was added thereto at 120 μL/well.

The sample in each well was recovered and heated at 95° C. for 10 minutes. The sample thus heated was applied to e-PAGEL (5 to 20%, manufactured by ATTO Corp.), and proteins were then fractionated by SDS acrylamide gel electrophoresis. The proteins thus fractionated were transferred to a PVDF membrane by semi-dry blotting and subjected to Western blotting. The primary antibody used was anti-Akt antibody (manufactured by Cell Signaling Technology, Inc., #4691) diluted 1000-fold or anti-Phospho-Akt (Ser273) antibody (manufactured by Cell Signaling Technology, Inc., #4060) diluted 2000-fold. The secondary antibody used was anti-rabbit IgG antibody-HRP (manufactured by Dako Denmark A/S, P0448). 1×TBST (manufactured by Santa Cruz Biotechnology, Inc.) containing 5% ECL Blocking Agent (manufactured by GE Healthcare Japan Corp.) was used in the dilution of these antibodies. The chromogenic substrate used was ECL Select Western Blotting Detection Reagent (manufactured by GE Healthcare Japan Corp.). The chemiluminescence was detected using ImageQuant LAS500 (manufactured by GE Healthcare Japan Corp.).

Figure 4:
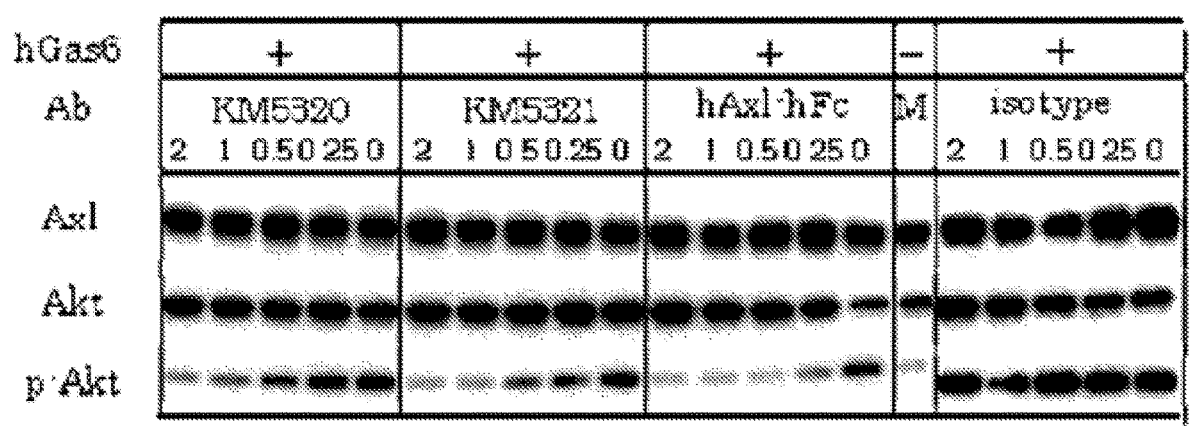
FIG. 4 shows results of evaluating the effects of the anti-Gas6 monoclonal antibodies on increase in the phosphorylation level of Akt by human Gas6 by Western blotting. As for the item indicated by hGas6 in the drawing, + denotes that 0.1 □g/mL hGas6 was added, and – denotes that hGas6 was not added. The item indicated by Ab in the drawing shows a test substance added to wells. KM5320 represents the KM5320-mKG1 antibody. KM5321 represents the KM5321-mKG1 antibody. isotype represents an IgG1 isotype control (negative control). Axl-hFc represents a fusion protein of the extracellular domain of the Axl receptor and the Fc region of a human IgG1 antibody (positive control). The numerical values described below each test substance name represent concentrations (μg/mL). Axl, Akt, and p-Akt in the drawing represent the Axl receptor, Akt protein, and phosphorylated Akt protein, respectively.

The results are shown in FIG. 4. The addition of hGas6 to the mesangial cells increased the phosphorylation level of Akt. On the other hand, all of hAXL-hFc, the KM5320-mKG1 antibody, and the KM5321-mKG1 antibody suppressed, in a concentration-dependent manner, the increase in the phosphorylation level of Akt by hGas6. By contrast, the isotype control did not suppress the increase in the phosphorylation level of Akt by hGas6.

These results demonstrated that the KM5320-mKG1 antibody and the KM5321-mKG1 antibody also inhibit the activation of the intracellular signaling pathway by the addition of hGas6 to the human mesangial cells originally expressing the Gas6 receptors.

[Example 10] Competitive Inhibition Experiment of Anti-Human Gas6 Monoclonal Antibody of Present Invention and Anti-Human Gas6 Monoclonal Antibody CNTO Antibody Whether or not the obtained antibodies would compete with the CNTO antibody for binding to human Gas6 was confirmed by competitive ELISA.

The competitive ELISA was conducted by a method described below. Monoclonal ANTI-FLAG M2 antibody produced in mouse (manufactured by Sigma-Aldrich Co. LLC) adjusted to 2 µg/mL with PBS (manufactured by Nacalai Tesque, Inc.) was dispensed at 50 µL/well to a 96-well plate for ELISA (manufactured by Nalge Nunc International), and the plate was left standing overnight at 4° C. for adsorption. After removal of the immobilization solution, 1% BSA-PBS (manufactured by Nacalai Tesque, Inc.) was added thereto at 300 µL/well, and the plate was left standing at room temperature for 1 hour for blocking and washed five times with Tween 20-PBS (manufactured by Wako Pure Chemical Industries Ltd.). Next, hGas6-F adjusted to a concentration of 1 µg/mL with 1% BSA-PBS was dispensed thereto at 50 µL/well, and the plate was left standing at room temperature for 1 hour.

Next, the CNTO antibody prepared in Example 4(3) was biotinylated using Biotin Labeling Kit-NH2 (manufactured by Dojindo Laboratories) and diluted to twice the final concentration (2 µg/mL) with 1% BSA-PBS to prepare a biotinylated CNTO antibody solution. The unlabeled KM5320-mKG1 antibody and KM5321-mKG1 antibody prepared in Example 5(7) and the unlabeled CNT0300 prepared in Example 4(3) were each diluted as a test substance to twice the final concentration with 1% BSA-PBS, mixed with the biotinylated CNTO antibody solution in equal amounts, and left standing at room temperature for 1 hour. The plate was washed five times with Tween 20-PBS. Then, the mixed samples were each dispensed thereto at 50 µL/well, and the plate was left standing at room temperature for 1 hour.

The plate was washed five times with Tween 20-PBS. Then, Streptavidin HRP Conjugate (manufactured by R&D Systems, Inc.) diluted 200-fold with 1% BSA-PBS was dispensed thereto at 50 µL/well, and the plate was left standing at room temperature for 1 hour. The plate was washed five times with Tween 20-PBS, and TMB (manufactured by Sigma-Aldrich Co. LLC) was added thereto at 50 µL/well to develop color. When appropriate color was obtained, 1 N hydrochloric acid (manufactured by Wako Pure Chemical Industries Ltd.) was added thereto at 50 µL/well. The absorbance at a sample wavelength of 450 nm and a reference wavelength of 570 nm (450 nm-570 nm) was measured using a plate reader.

Figure 5:
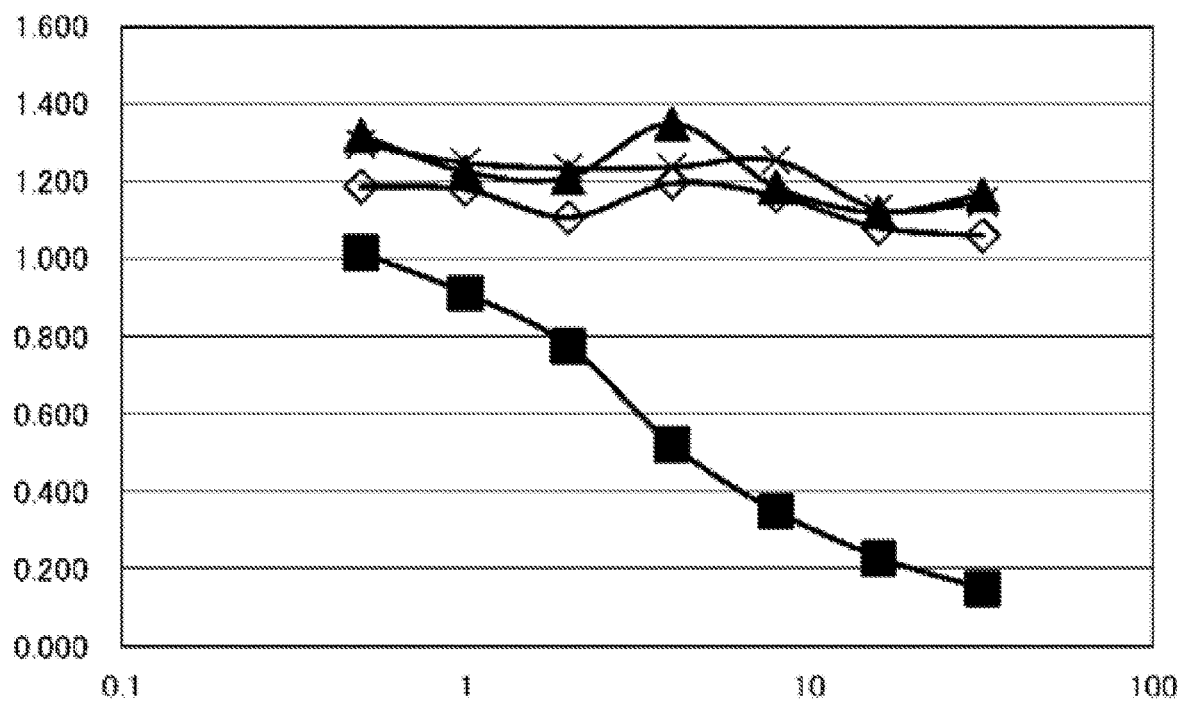
FIG. 5 shows results of evaluating whether or not the KM5320 antibody or the KM5321 antibody, the anti-Gas6 monoclonal antibody of the present invention, competes with the CNTO antibody for binding to hGas6. The experiment was carried out at N=2, and an average value thereof is shown in the graph. Absorbance is shown in the vertical axis of the graph, and antibody concentration (μg/mL) is shown in the horizontal axis. ◊ depicts the results about 1% BSA-PBS (buffer solution) alone. ■ depicts the results about the CNTO antibody. ▲ depicts the results about the KM5320-mKG1 antibody. x depicts the results about the KM5321-mKG1 antibody.

The results are shown in FIG. 5. In the case of using the CNTO antibody as a test substance, the absorbance was reduced as compared with the negative control. On the other hand, in the case of using the KM5320-mKG1 antibody or the KM5321-mKG1 antibody as a test substance, the same level of absorbance as in the negative control was obtained.

When the unlabeled anyi-Gas6 monoclonal antibody serving as a test substance competes with the biotinylated CNTO antibody for binding to human Gas6, the detected absorbance is reduced as compared with the negative control. Thus, the KM5320-mKG1 antibody and the KM5321-mKG1 antibody were shown to bind to hGas6 without competing with the CNTO antibody.

[Example 11] Isolation of Gene Sequences Encoding VH and VL of Anti-Human Gas6 Monoclonal Antibody (1) Preparation of Total RNA from Anti-Human Gas6 Monoclonal Antibody-Producing Hybridoma Cell Total RNA was prepared from $5 \times 10^6$ cells of each hybridoma producing the KM5320-mKG1 antibody or the KM5321-mKG1 antibody using RNeasy Mini kit (manufactured by Qiagen N.V.) and QIA shredder (manufactured by Qiagen N.V.).

(2) Gene Cloning of VH and VL of Anti-Human Gas6 Monoclonal Antibody

From 1 µg of the total RNA obtained in the paragraph (1), cDNA was prepared using SMARTer RACE cDNA Amplification Kit (manufactured by Clontech Laboratories, Inc.). 25 µL of a reaction solution containing the obtained cDNA as a template, universal primer A mix (containing a forward primer) attached to the kit, a reverse primer (primer 28 (SEQ ID NO: 65)) encoding a mouse IgG1 heavy chain constant region, and PrimeSTAR Max DNA Polymerase (manufactured by Takara Bio Inc.) was prepared and used in PCR. The PCR was performed by incubation at 98° C. for 10 seconds, followed by 30 cycles each involving 98° C. for 10 seconds, 55° C. for 5 seconds, and 72° C. for 5 seconds to amplify a DNA fragment containing the VH gene of each antibody.

PCR was similarly performed using universal primer A and a mouse Ig (κ)-specific primer (primer 29 (SEQ ID NO: 66)) to amplify a DNA fragment containing the VL gene of each antibody. Each PCR product was subjected to agarose gel electrophoresis, and the amplified DNA fragment was recovered using QIAquick Gel Extraction Kit (manufactured by Qiagen N.V.). The obtained amplified DNA fragment was inserted to a pCR4-Blunt-TOPO vector using ZERO BLUNT TOPO PCR CLONING KIT (manufactured by Invitrogen Corp.), and a plasmid was obtained in the same way as in Example 2(1). The nucleotide sequence of the obtained plasmid was analyzed to confirm that full-length VH cDNA and VL cDNA containing an ATG sequence presumed to be a start codon at the 5' end of the cDNA were obtained.

(3) Analysis of Gene Sequences of Anti-Human Gas6 Monoclonal Antibody V Regions

The whole nucleotide sequence encoding VH of the KM5320-mKG1 antibody, obtained in the paragraph (2), is shown in SEQ ID NO: 67. The whole amino acid sequence of VH containing a signal sequence, predicted from the sequence, is shown in SEQ ID NO: 68. The amino acid sequence shown in SEQ ID NO: 68 except for the signal sequence is shown in SEQ ID NO: 69. The whole nucleotide sequence encoding VL of the KM5320-mKG1 antibody is shown in SEQ ID NO: 70. The whole amino acid sequence of VL containing a signal sequence, predicted from the sequence, is shown in SEQ ID NO: 71. The amino acid sequence shown in SEQ ID NO: 71 except for the signal sequence is shown in SEQ ID NO: 72.

The whole nucleotide sequence encoding VH of the KM5321-mKG1 antibody is shown in SEQ ID NO: 73. The whole amino acid sequence of VH containing a signal sequence, predicted from the sequence is shown in SEQ ID NO: 74. The amino acid sequence shown in SEQ ID NO: 74 except for the signal sequence is shown in SEQ ID NO: 75. The whole nucleotide sequence encoding VL of the KM5321-mKG1 antibody is shown in SEQ ID NO: 76. The whole amino acid sequence of VL containing a signal sequence, predicted from the sequence, is shown in SEQ ID NO: 77. The amino acid sequence shown in SEQ ID NO: 77 except for the signal sequence is shown in SEQ ID NO: 78.

From comparison with the known mouse antibody sequence data [SEQUENCES of Proteins of Immunological Interest, US Dept. Health and Human Services (1991)], the isolated cDNAs were confirmed to be full-length cDNAs respectively encoding the KM5320-mKG1 antibody and the KM5321-mKG1 antibody containing a secretory signal sequence.

The CDRs of VH and VL of each monoclonal antibody were identified by comparison with the amino acid sequences of known antibodies. The amino acid sequences of CDR1, CDR2, and CDR3 of VH of the KM5320-mKG1 antibody are shown in SEQ ID NOs: 79, 80, and 81, respectively. The amino acid sequences of CDR1, CDR2, and CDR3 of VL thereof are shown in SEQ ID NOs: 82, 83, and 84, respectively. The amino acid sequences of CDR1, CDR2, and CDR3 of VH of the KM5321-mKG1 antibody are shown in SEQ ID NOs: 85, 86, and 87, respectively. The amino acid sequences of CDR1, CDR2, and CDR3 of VL thereof are shown in SEQ ID NOs: 88, 89, and 90, respectively.

[Example 12] Preparation of Anti-Human Gas6 Mouse-Rat Chimeric Antibody

Mouse-rat IgG1 chimeric antibodies (hereinafter, simply referred to as rat chimeric antibodies) were prepared from the anti-Gas6 mouse monoclonal antibodies KM5320-mKG1 antibody and KM5321-mKG1 antibody by a method described below. Hereinafter, the rat chimeric antibodies are referred to as a KM5320-rKG1 antibody and a KM5321-rKG1 antibody, respectively.

(1) Construction of Rat Chimeric Antibody Expression Vector

A nucleotide sequence encoding the full-length heavy chain (SEQ ID NO: 91) of the KM5320-rKG1 antibody and a nucleotide sequence encoding the full-length light chain (SEQ ID NO: 93) thereof were tandemly inserted to an appropriate position of an appropriate expression vector for animal cells known in the art by use of an ordinary method. The nucleotide sequence shown in SEQ ID NO: 91 encoding the full-length heavy chain of the KM5320-rKG1 antibody consists of the whole nucleotide sequence of the VH gene of the KM5320 antibody (SEQ ID NO: 67) and a gene sequence containing a gene of a rat IgG1 heavy chain constant region. The nucleotide sequence shown in SEQ ID NO: 93 encoding the full-length light chain of the KM5320-rKG1 antibody consists of the whole nucleotide sequence of the VL gene of the KM5320 antibody (SEQ ID NO: 70) and a gene sequence containing a gene of a rat Ig (K) constant region.

Similarly, a nucleotide sequence encoding the full-length heavy chain (SEQ ID NO: 95) of the KM5321-rKG1 antibody and a nucleotide sequence encoding the full-length light chain (SEQ ID NO: 97) thereof were tandemly inserted to an appropriate position of an appropriate expression vector for animal cells known in the art by use of an ordinary method. The nucleotide sequence shown in SEQ ID NO: 95 encoding the full-length heavy chain of the KM5321-rKG1 antibody consists of the whole nucleotide sequence of the VH gene of the KM5321 antibody (SEQ ID NO: 73) and a gene sequence containing a gene of a rat IgG1 heavy chain constant region. The nucleotide sequence shown in SEQ ID NO: 97 encoding the full-length light chain of the KM5321-rKG1 antibody consists of the whole nucleotide sequence of the VL gene of the KM5321 antibody (SEQ ID NO: 76) and a gene sequence containing a gene of a rat Ig (K) constant region.

(2) Preparation of Stably Rat Chimeric Antibody-Expressing Cell Line

CHO-K1 cells (European Collection of Cell Cultures: ECACC) were transfected with each expression vector prepared in the paragraph (1) according to Example 2(5) and an ordinary method to prepare stably rat chimeric antibody-expressing cell lines.

(3) Purification of Rat Chimeric Antibody

Each stably rat chimeric antibody-expressing cell line prepared in the paragraph (2) was cultured for several days in a medium for protein expression known in the art, and the culture supernatant was recovered. KM5320-rKG1 and KM5321-rKG1 were purified from the recovered culture supernatants according to Example 3(7) and a method known in the art. As a result of measuring the absorbance of the antibodies according to the method described in Example 2(9), the absorptivity of the KM5320-rKG1 antibody was 1.54, and the absorptivity of the KM5321-rKG1 antibody was 1.45.

The obtained rat chimeric antibodies were confirmed in the same way as in Examples 6 and 7 to have binding activity against hGas6 and activity of inhibiting the binding between hGas6 and hAxl-Fc, which were equivalent to those of their respective parent antibodies.

[Example 13] Epitope Analysis of Anti-Human Gas6 Monoclonal Antibody

In order to analyze epitopes for the obtained antibodies, a human Gas6 domain deletion variant and a variant protein substituting a portion of amino acids by alanine in the protein were prepared, and change in the binding activity of the obtained antibodies was confirmed.

(1) Preparation of Human Gas6 Variant (Domain Deletion Variant) Expression Vector In order to obtain a C-terminally FLAG- and His-tagged Gas6 variant lacking the Gla domain of hGas6 (hereinafter, referred to as hGas6-FH), an expression vector for the protein was prepared by a method described below.

At GenScript Japan, Inc., the nucleotide sequence shown in SEQ ID NO: 99 (hGas6-delta) was totally synthesized and integrated to an appropriate plasmid. The nucleotide sequence shown in SEQ ID NO: 99 consists of an EcoRI recognition sequence, the nucleotide sequence of the hGas6-FH gene, and a BamHI recognition sequence from the 5' end toward the 3' end. The nucleotide sequence of the hGas6-FH gene is a nucleotide sequence that lacks a nucleotide sequence from positions 91 to 273 in the nucleotide sequence of the hGas6 gene shown in SEQ ID NO: 3, and has 3'-terminally bound nucleotide sequences encoding FLAG and His tags known in the art.

The obtained plasmid and a vector INPEP4 for expression in animal cells (manufactured by Biogen-IDEC) were each enzymatically treated with EcoRI and BamHI, and a hGas6-FH expression vector INPEP-hGas6-FH was obtained in the same way as in Example 2(1).

(2) Preparation of Human Gas6 Variant (Alanine Substitution Variant) Expression Vector An expression vector was prepared for a variant in which all of amino acids corresponding to leucine at position 314, glutamine at position 315, and proline at position 316 of the whole amino acid sequence of human Gas6 shown in SEQ ID NO: 4 in the amino acid sequence of hGas6-FH described in the paragraph (1) were substituted by alanine (hereinafter, referred to as hGas6-FH-L314A, Q315A, P316A or simply an alanine substitution variant).

The vector for the expression of the alanine variant was prepared by the site-directed mutagenesis of INPEP-hGas6-FH prepared in the paragraph (1) by a method described below. 25 μL of a reaction solution containing INPEP-hGas6-FH as a template, 10 pmol each of primers 30 and 31 (SEQ ID NOs: 101 and 102), and PrimeSTAR Max DNA Polymerase (manufactured by Takara Bio Inc.) was prepared and used in PCR. The PCR was performed by incubation at 98° C. for 10 seconds, followed by 30 cycles each involving 98° C. for 10 seconds, 55° C. for 5 seconds, and 72° C. for 5 seconds to amplify a DNA fragment containing a nucleotide sequence encoding each variant. DpnI was added to the PCR product, followed by restriction enzyme treatment at 37° C. for 1 hour to digest the template vector containing no mutation. The PCR product thus digested with DpnI was transfected into E. coli DH5a, and a plasmid having the gene containing the desired mutation was obtained from the obtained transformants.

(3) Preparation of Transiently Human Gas6 Variant-Expressing Cell Line

Expi293 cells (manufactured by Invitrogen Corp.) were used in the preparation of human Gas6 variant (hGas6-F and alanine substitution variant)-expressing cell lines. The cell culture medium used was Expi293(TM) Expression Medium (manufactured by Invitrogen Corp.), and the cells were shake-cultured under conditions involving 37° C. and 5% $CO_2$. The Expi293 cells were transfected with each human Gas6 variant expression vector prepared in the paragraphs (1) and (2) to obtain transiently human Gas6 variant-expressing cell lines. For the transfection of the cells with the expression vector, ExpiFectamine 293 Transfection Kit (manufactured by Invitrogen Corp.) was used according to the attached manual.

(4) Purification of Each Human Gas6 Variant from Culture Supernatant Containing the Human Gas6 Variant Each transiently human Gas6 variant-expressing cell line obtained in the paragraph (3) was cultured for 4 days according to the attached manual of ExpiFectamine 293 Transfection Kit (manufactured by Invitrogen Corp.), and the medium was recovered. The recovered medium was centrifuged, and the obtained culture supernatant was filtered through a 0.22-μm filter to prepare a culture supernatant containing each human Gas6 variant.

The culture supernatant was purified in the same way as in Example 2(9) using ANTI-FLAG M2 Affinity Gel (manufactured by Sigma-Aldrich Co. LLC). The elution buffer solution used was 3 M magnesium chloride (manufactured by Nacalai Tesque, Inc.). The buffer solution in the obtained human Gas6 variant solution was replaced with PBS (manufactured by Nacalai Tesque, Inc.), and the resulting solution was sterilely filtered through a 0.22 μm filter and then used in the test.

(5) Evaluation of Binding Activity of Obtained Antibody Against Various Human Gas6 Variants In order to determine epitopes on Gas6 to which the obtained antibodies bound, their binding activity against various human Gas6 variants purified in the paragraph (4) was evaluated according to the method described in Example 6. The experiment was conducted at N=2, and each antibody was assessed as not binding when an average value of the obtained absorbance was 0.1 or less, and as binding when the average value was 2 or more.

The antigen samples used were hGas6-F prepared in Example 2(9) and various human Gas6 variants prepared in the paragraph (3). The antibody samples used were the KM5320-rKG1 and KM5321-rKG1 antibodies prepared in Example 12(3), which were biotinylated using Biotin Labeling Kit—NH2 (manufactured by Dojindo Laboratories) and diluted to 1 μg/mL with 1% BSA-PBS. The positive control used was anti-human Gas6 (manufactured by R&D Systems, Inc., DY885) diluted to 0.2 ng/mL with 1% BSA-PBS.

The results are shown in Table 1. The results were indicated by ◯ when the antibody bound to each antigen, and by X when the antibody did not bind to each antigen.

TABLE 1

Binding of anti-human Gas6 antibody to human Gas6 variant

| Antigen | Antibody | | |
|---|---|---|---|
| | KM5320-rKG1 | KM5321-rKG1 | Anti-human Gas6(R&D, DY885) |
| hGas6-F | ◯ | ◯ | ◯ |
| hGas6-FH | ◯ | ◯ | ◯ |
| hGas6-FH-L314A, Q315A, P316A | X | X | ◯ |

The KM5320-rKG1 and KM5321-rKG1 antibodies bound to hGas6-F and hGas6-FH with the same level of strength. On the other hand, these antibodies did not bind to hGas6-FH-L314A, Q315A, P316A. These results demonstrated that the KM5320-rKG1 and KM5321-rKG1 antibodies bind to at least any one of leucine at position 314, glutamine at position 315, and proline at position 316 in the whole amino acid sequence of human Gas6 shown in SEQ ID NO: 4.

[Example 14] Evaluation of Cell Proliferation Inhibitory Activity of Anti-Human Gas6 Monoclonal Antibody Against Cancer Cell Line In order to confirm the effects of the anti-human Gas6 monoclonal antibodies on Gas6-dependent cancer cell growth, cell growth assay was conducted using 3 types of human cancer cell lines.

The growth assay was conducted using pancreatic cancer cell line Panc-1 cells (American Type Culture Collection), malignant melanoma cell line A375 cells (Dainippon Pharmaceutical Co., Ltd.), and stomach cancer cell line MKN7 cells (Riken Cell Bank). The presence or absence of the expression of a Gas6 receptor on the cells of each line was determined in the same way as in Example 9 using a flow cytometer to confirm that Axl and Mer, Axl and Sky, and Axl and Sky were expressed on the cell lines, respectively.

The Panc-1 cells or the A375 cells were suspended in a DMEM (manufactured by Life Technologies Corp.) medium supplemented with 10% FBS (manufactured by Life Technologies Corp.). The MKN7 cells were suspended in a RPMI 1640 (manufactured by Life Technologies Corp.) medium supplemented with 10% FBS. These cell suspensions were inoculated at $2.0 \times 10^4$, $1.0 \times 10^4$, and $0.6 \times 10^4$ cells/well, respectively, to 96-well plates and statically cultured under conditions involving 37° C. and 5% $CO_2$. 1 day later, the medium was replaced with a FBS-free medium, and the cells were statically cultured. 1 day later, the medium was discarded, and each test substance adjusted to a final concentration given below with a FBS-free medium was added thereto at 200 l/well, followed by static culture. The test substances used were hGas6-F (final concentration: 1 μg/ml) and hAxl-hFc, the KM5320-rKG1 antibody, the KM5321-rKG1 antibody, and an anti-dinitrophenylhydrazine (DNP) antibody prepared by a method known in the art (Motoki K et al., Clin. Cancer Res. 11, 3126-3135, 2005) (final concentration: 20 μg/ml) The negative control used was PBS diluted 20-fold with the medium. 3 days later, the medium was discarded, and CellTiter-Glo Reagent dissolved in CellTiter-Glo Buffer attached to CellTiter-Glo Substrate (manufactured by Promega Corp.) was added thereto at 50 l/well. The plate was stirred for 1 minute in a shaker and left standing at room temperature for 10 minutes, followed by the detection of luminescence.

Figure 6:
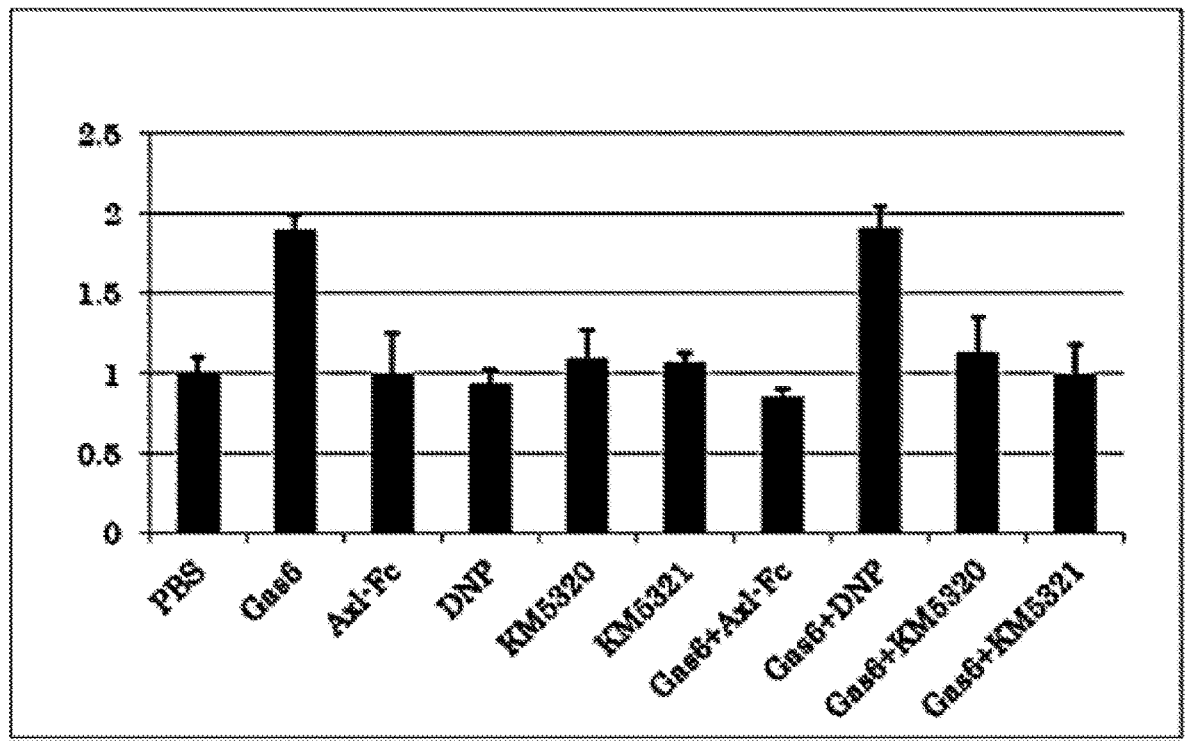
FIG. 6 shows results of evaluating the cell proliferation inhibitory activity of anti-Gas6 monoclonal antibodies against cancer cells. Fluorescence intensity is shown in the vertical axis of the graph, and the name of a sample added to wells is shown in the horizontal axis. In the drawing, Gas6 represents hGas6-F. Axl-Fc represents a fusion protein of the extracellular domain of the Axl receptor and the human Fc of an IgG1 antibody (positive control). KM5320 represents a KM5320-rKG1 antibody. KM5321 represents a KM5321-rKG1 antibody. DNP represents an anti-DNP antibody (negative control).

The results obtained about the Panc-1 cells are shown in FIG. 6. The addition of hGas6 to the Panc-1 cells increased the number of cells by approximately twice as compared with the addition of PBS. By contrast, KM5320-rKG1 and KM5321-rKG1 reduced the increase in cell growth by hGas6 to the same level as PBS. The anti-DNP antibody had no influence on the increase in cell growth by hGas6. The same results as in the Panc-1 cells were also obtained about the other 2 cell lines. These results demonstrated that KM5320-rKG1 and KM5321-rKG1 also inhibit hGas6-dependent cell growth in the cancer cell lines expressing the Gas6 receptors.

[Example 15] Design of Light Chain and Heavy Chain Variable Regions of KM5320 and KM5321 Humanized Antibodies (1) Design of Amino Acid Sequences of VL and VH of KM5320 Humanized Antibody Various amino acid sequences of VL and VH of a KM5320 humanized antibody were designed by a method described below. In the description below, KM5320 humanized antibodies having various amino acid sequences of VL and VH are collectively referred to as a hzKM5320 antibody.

First, in order to select amino acids of known human antibody FRs suitable for the grafting of the amino acid sequences of CDRs of the KM5320 antibody, the BLASTP database provided by The National Center for Biotechnology Information was searched for the amino acid sequences of human antibody frameworks (hereinafter, abbreviated to FRs) having high homology to the amino acid sequences of VL and VH FRs of the KM5320 antibody.

As a result, the amino acid sequences of FRs in the amino acid sequences shown in GenBank Accession No. AAW69164.1 (anti-tetanus toxoid immunoglobulin light chain variable region) and DDBJ Accession No. BAC01510.1 (immunoglobulin heavy chain VHDJ region) (hereinafter, referred to as AAW69164.1 and BAC01510.1, respectively) respectively had the highest homology to the amino acid sequences of FRs of VL and VH of the KM5320 antibody.

Accordingly, the amino acid sequences of CDR1, CDR2, and CDR3 of VL of KM5320 shown in SEQ ID NOs: 82, 83, and 84, respectively, were grafted to appropriate positions in the amino acid sequences of AAW69164.1 FRs to design hzKM5320 LV0 (SEQ ID NO: 105). The amino acid sequences of CDR1, CDR2, and CDR3 of VH of KM5320 shown in SEQ ID NOs: 79, 80, and 81, respectively, were grafted to appropriate positions in the amino acid sequences of BAC01510.1 FRs to design hzKM5320 HV0 (SEQ ID NO: 129).

hzKM5320 LV0 and hzKM5320 HV0 thus designed are amino acid sequences obtained by grafting only the amino acid sequences of mouse monoclonal antibody KM5320-derived CDRs to the amino acid sequences of the selected human antibody FRs.

However, in the case of generally preparing humanized antibodies, a humanized antibody obtained by merely grafting the amino acid sequences of CDRs of a rodent-derived antibody to the amino acid sequences of FRs of human antibody often exhibits reduced binding activity. In order to circumvent such reduction in binding activity, an amino acid residue considered to influence the binding activity of the antibody among the amino acid residues of FRs differing between the human and rodent antibodies is modified, in addition to the grafting of the amino acid sequences of CDRs.

Accordingly, in this Example as well, FR amino acid residues considered to influence the binding activity of the antibody were identified and modified as follows.

First, an antibody having the designed hzKM5320 LV0 and hzKM5320 HV0 in VL and VH, respectively, is referred to as a hzKM5320 LV0HV0 antibody or simply hzKM5320 LV0HV0. Other hzKM5320 antibodies are also designated in the same way as above. The three-dimensional structures of the variable regions of the hzKM5320 LV0HV0 antibody were constructed by use of a computer modeling approach. Discovery Studio (Accelrys) was used in the preparation of three-dimensional structure covertical axis and the display of the three-dimensional structures. Also, a computer model having the three-dimensional structures of the variable regions of the KM5320 antibody was similarly constructed.

In the amino acid sequences of FRs of VL and VH of the hzKM5320 LV0HV0 antibody, amino acid residues different from those of the KM5320 antibody were substituted by the counterpart amino acid residues of the KM5320 antibody to prepare amino acid sequences. Similarly, a three-dimensional structure model was constructed.

The three-dimensional structures of variable regions were compared among the prepared KM5320 antibody, hzKM5320 LV0HV0 antibody, and modified forms to identify amino acid residues presumed to influence the binding activity of the antibody.

As a result, among the amino acid residues of FRs of variable region of the hzKM5320 LV0HV0 antibody, Val at position 2, Leu at position 15, Leu at position 46, Leu at position 73, Leu at position 78, and Tyr at position 87 in the amino acid sequence of VL shown in SEQ ID NO: 105, and Val at position 2, Ser at position 9, Val at position 20, Arg at position 38, Glu at position 46, Ser at position 77, Val at position 93, and Tyr at position 95 in the amino acid sequence of VH shown in SEQ ID NO: 129 were selected as amino acid residues considered to change the three-dimensional structure of the antigen binding site and to influence the binding activity of the antibody.

At least one or more of these selected amino acid residues were substituted by the counterpart amino acid residues of the KM5320 antibody to design VL and VH of humanized antibody having various modifications.

Specifically, at least one of amino acid modifications that substituted Val at position 2 by Ile, Leu at position 15 by Ala, Leu at position 46 by Val, Leu at position 73 by Phe, Leu at position 78 by Val, and Tyr at position 87 by Phe, in the amino acid sequence shown in SEQ ID NO: 105, was introduced to VL.

In this way, hzKM5320 LV0 (SEQ ID NO: 105), LV1a (SEQ ID NO: 108), LV1b (SEQ ID NO: 111), LV2a (SEQ ID NO: 114), LV2b (SEQ ID NO: 117), LV3 (SEQ ID NO: 120), LV5 (SEQ ID NO: 123), and LV6 (SEQ ID NO: 126) were designed as VLs of hzKM5320 antibody, and their respective amino acid sequences are shown in FIG. 7.

At least one of amino acid modifications that substituted Val at position 2 by Ile, Ser at position 9 by Pro, Val at position 20 by Ile, Arg at position 38 by Lys, Glu at position 46 by Lys, Ser at position 77 by Thr, Val at position 93 by Thr, and Tyr at position 95 by Phe, in the amino acid sequence shown in SEQ ID NO: 129, was introduced to VH.

In this way, hzKM5320 HV0 (SEQ ID NO: 129), HV1 (SEQ ID NO: 132), HV2 (SEQ ID NO: 135), HV3a (SEQ ID NO: 138), HV3b (SEQ ID NO: 141), HV3c (SEQ ID NO: 144), HV4 (SEQ ID NO: 147), HV6 (SEQ ID NO: 150), and HV8 (SEQ ID NO: 153) were designed as VHs of hzKM5320 antibody, and their respective amino acid sequences are shown in FIG. 8.

(2) Design of Amino Acid Sequences of VL and VH of KM5321 Humanized Antibody

Various amino acid sequences of VL and VH of a KM5321 humanized antibody were designed in the same way as in Example 15(1). In the description below, KM5321 humanized antibodies having various amino acid sequences of VL and VH are collectively referred to as a hzKM5321 antibody.

The amino acid sequences of CDR1, CDR2, and CDR3 of VL (SEQ ID NOs: 88, 89, and 90, respectively) of the KM5321 antibody were grafted to appropriate positions in the amino acid sequences of FRs of VL of the human antibody shown in GenBank Accession No. AAW67414.1 (rotavirus-specific intestinal-homing antibody light chain variable region) to design hzKM5321 LV0 (SEQ ID NO: 156).

The amino acid sequences of CDR1, CDR2, and CDR3 of VH (SEQ ID NOs: 85, 86, and 87, respectively) of the KM5321 antibody were grafted to appropriate positions in the amino acid sequences of FRs of VH of the human antibody shown in EMBL Accession No. CAJ13496.1 (immunoglobulin heavy chain variable region) to design hzKM5321 HV0 (SEQ ID NO: 186).

Amino acid residues of FRs of VL and VH considered to influence the binding activity of the hzKM5321 antibody were also selected by the same approach as in the hzKM5320 antibody. At least one or more of the selected amino acid residues were substituted by the counterpart amino acid residues of the KM5321 antibody to design VL and VH of humanized antibody having various modifications.

Specifically, at least one of amino acid modifications that substituted Leu at position 4 by Val, Ala at position 13 by Val, Val at position 15 by Thr, Ala at position 43 by Pro, Gly at position 64 by Ser, Leu at position 73 by Phe, Leu at position 78 by Thr, Thr at position 85 by Asp, and Val at position 104 by Leu, in the amino acid sequence shown in SEQ ID NO: 156, was introduced to VL.

In this way, hzKM5321 LV0 (SEQ ID NO: 156), LV1a (SEQ ID NO: 159), LV1b (SEQ ID NO: 162), LV1c (SEQ ID NO: 165), LV3 (SEQ ID NO: 168), LV4 (SEQ ID NO: 171), LV6 (SEQ ID NO: 174), LV7a (SEQ ID NO: 177), LV7b (SEQ ID NO: 180), and LV9 (SEQ ID NO: 183) were designed as VLs of hzKM5321 antibody, and their respective amino acid sequences are shown in FIG. 9.

At least one of amino acid modifications that substituted Val at position 2 by Ile, Ser at position 9 by Pro, Arg at position 38 by Lys, Glu at position 46 by Lys, Ser at position 79 by Ala, Val at position 93 by Thr, and Val at position 112 by Ile, in the amino acid sequence shown in SEQ ID NO: 186, was introduced to VH.

In this way, hzKM5321 HV0 (SEQ ID NO: 186), HV1 (SEQ ID NO: 189), HV2a (SEQ ID NO: 192), HV2b (SEQ ID NO: 195), HV3a (SEQ ID NO: 198), HV3b (SEQ ID NO: 201), HV4a (SEQ ID NO: 204), HV4b (SEQ ID NO: 207), HV5 (SEQ ID NO: 210), and HV7 (SEQ ID NO: 213) were designed as VHs of hzKM5321 antibody, and their respective amino acid sequences are shown in FIG. 10.

In the description below, an antibody having hzKM5321 LV0 and hzKM5321 HV0 in VL and VH, respectively, is referred to as a hzKM5321 LV0HV0 antibody or simply hzKM5321 LV0HV0. Other hzKM5321 antibodies are also designated in the same way as above.

(3) Design of Variable Region Genes of Humanized Antibody

Nucleotide sequences encoding the amino acid sequences of the variable regions of the humanized antibodies (hzKM5320 and hzKM5321 antibodies) were designed using codons highly frequently used in animal cells. Humanized antibody expression vectors were constructed using these nucleotide sequences, and the humanized antibodies were expressed.

[Example 16] Construction of hzKM5320 and hzKM5321 Antibody Expression Vectors

Expression vectors for the hzKM5320 and hzKM5321 antibodies shown in Table 2 were constructed by a method described below.

TABLE 2

| Prepared hzKM5320 antibody and hzKM5321 antibody | |
|---|---|
| hzKMS320 antibody | hzKM5321 antibody |
| hzKM5320 LV0HV0 | hzKM5321 LV0HV0 |
| hzKM5320 LV1aHV0 | hzKM5321 LV1aHV0 |
| hzKM5320 LV1bHV0 | hzKM5321 LV1bHV0 |
| hzKM5320 LV2aHV0 | hzKM5321 LV1cHV0 |
| hzKM5320 LV2bHV0 | hzKM5321 LV3HV0 |
| hzKMS320 LV3HV0 | hzKM5321 LV4HV0 |
| hzKM5320 LV5HV0 | hzKM5321 LV6HV0 |
| hzKM5320 LV6HV0 | hzKM5321 LV7aHV0 |
| hzKMS320 LV0HV8 | hzKM5321 LV7bHV0 |
| hzKM5320 LV1aHV8 | hzKM5321 LV9HV0 |
| hzKMS320 LV1bHV8 | hzKM5321 LV0HV7 |
| hzKM5320 LV2aHV8 | hzKM5321 LV1aHV7 |
| hzKM5320 LV2bHV8 | hzKM5321 LV1bHV7 |
| hzKM5320 LV3HV8 | hzKM5321 LV1cHV7 |
| hzKM5320 LV5HV8 | hzKM5321 LV3HV7 |
| hzKM5320 LV6HV8 | hzKM5321 LV4HV7 |
| hzKM5320 LV5HV1 | hzKM5321 LV6HV7 |
| hzKM5320 LV5HV2 | hzKM5321 LV7aHV7 |
| hzKM5320 LV5HV3a | hzKM5321 LV7bHV7 |
| hzKM5320 LV5HV3b | hzKM5321 LV9HV7 |
| hzKMS320 LV5HV3c | hzKM5321 LV6HV1 |
| hzKM5320 LV5HV4 | hzKM5321 LV6HV2a |
| hzKM5320 LV5HV6 | hzKM5321 LV6HV2b |
| | hzKM5321 LV6HV3a |
| | hzKM5321 LV6HV3b |
| | hzKM5321 LV6HV4a |
| | hzKM5321 LV6HV4b |
| | hzKM5321 LV6HV5 |

First, necessary gene fragments were synthesized at Fasmac Co., Ltd. for nucleotide sequences encoding the amino acid sequences of the signal sequence-containing variable regions of each humanized antibody described in Table 3.

TABLE 3

| Name of variable region of antibody | Amino acid sequence of variable region containing signal sequence | Nucleotide sequence encoding amino acid sequence of variable region containing signal sequence |
|---|---|---|
| hzKM5320 LV0 | SEQ ID NO: 104 | SEQ ID NO: 103 |
| hzKM5320 LV1a | SEQ ID NO: 107 | SEQ ID NO: 106 |
| hzKM5320 LV1b | SEQ ID NO: 110 | SEQ ID NO: 109 |
| hzKM5320 LV2a | SEQ ID NO: 113 | SEQ ID NO: 112 |
| hzKM5320 LV2b | SEQ ID NO: 116 | SEQ ID NO: 115 |
| hzKM5320 LV3 | SEQ ID NO: 119 | SEQ ID NO: 118 |
| hzKM5320 LV5 | SEQ ID NO: 122 | SEQ ID NO: 121 |
| hzKM5320 LV6 | SEQ ID NO: 125 | SEQ ID NO: 124 |
| hzKM5320 HV0 | SEQ ID NO: 128 | SEQ ID NO: 127 |
| hzKM5320 HV1 | SEQ ID NO: 131 | SEQ ID NO: 130 |
| hzKM5320 HV2 | SEQ ID NO: 134 | SEQ ID NO: 133 |
| hzKM5320 HV3a | SEQ ID NO: 137 | SEQ ID NO: 136 |
| hzKM5320 HV3b | SEQ ID NO: 140 | SEQ ID NO: 139 |
| hzKM5320 HV3c | SEQ ID NO: 143 | SEQ ID NO: 142 |
| hzKM5320 HV4 | SEQ ID NO: 146 | SEQ ID NO: 145 |
| hzKM5320 HV6 | SEQ ID NO: 149 | SEQ ID NO: 148 |
| hzKM5320 HV8 | SEQ ID NO: 152 | SEQ ID NO: 151 |
| hzKM5321 LV0 | SEQ ID NO: 155 | SEQ ID NO: 154 |
| hzKM5321 LV1a | SEQ ID NO: 158 | SEQ ID NO: 157 |
| hzKM5321 LV1b | SEQ ID NO: 161 | SEQ ID NO: 160 |
| hzKM5321 LV1c | SEQ ID NO: 164 | SEQ ID NO: 163 |
| hzKM5321 LV3 | SEQ ID NO: 167 | SEQ ID NO: 166 |
| hzKM5321 LV4 | SEQ ID NO: 170 | SEQ ID NO: 169 |
| hzKM5321 LV6 | SEQ ID NO: 173 | SEQ ID NO: 172 |
| hzKM5321 LV7a | SEQ ID NO: 176 | SEQ ID NO: 175 |
| hzKM5321 LV7b | SEQ ID NO: 179 | SEQ ID NO: 178 |
| hzKM5321 LV9 | SEQ ID NO: 182 | SEQ ID NO: 181 |
| hzKM5321 HV0 | SEQ ID NO: 185 | SEQ ID NO: 184 |
| hzKM5321 HV1 | SEQ ID NO: 188 | SEQ ID NO: 187 |
| hzKM5321 HV2a | SEQ ID NO: 191 | SEQ ID NO: 190 |
| hzKM5321 HV2b | SEQ ID NO: 194 | SEQ ID NO: 193 |
| hzKM5321 HV3a | SEQ ID NO: 197 | SEQ ID NO: 196 |
| hzKM5321 HV3b | SEQ ID NO: 200 | SEQ ID NO: 199 |
| hzKM5321 HV4a | SEQ ID NO: 203 | SEQ ID NO: 202 |
| hzKM5321 HV4b | SEQ ID NO: 206 | SEQ ID NO: 205 |
| hzKM5321 HV5 | SEQ ID NO: 209 | SEQ ID NO: 208 |
| hzKM5321 HV7 | SEQ ID NO: 212 | SEQ ID NO: 211 |

The synthesized gene fragments and a human K chain constant region expression vector (treated with EcoNI/BsiWI) and a human heavy chain constant region expression vector (treated with FspAI/NheI) containing an appropriate antibody secretion signal were used in subcloning into the vectors using In-Fusion HD Cloning Kit (Clontech Laboratories, Inc.). E. coli DH5α competent cells (Takara Bio Inc.) were transformed therewith, and the obtained plasmid was sequenced. A colony of E. coli producing the plasmid having an insert of the correct nucleotide sequence was selected, and the plasmid was prepared using NucleoBond Xtra Midi EF kit (Takara Bio Inc.).

In order to express anti-human Gas6 humanized antibodies containing a variant human IgG4 constant region containing EU index S228P, L235E, and R409K amino acid residue substitutions, the human heavy chain constant region expression vector used was a vector obtained by removing nucleotide sequences encoding light chain and heavy chain constant regions in a N5KG1 vector (U.S. Pat. No. 6,001,358) using restriction enzymes Bgl2 and BamHI, and substituting this portion by a nucleotide sequence encoding the variant human IgG4 constant region.

[Example 17] Transient Expression and Purification of hzKM5320 and hzKM5321 Antibodies The prepared humanized antibodies were transiently expressed using Expi293F Expression System Kit (manufactured by Life Technologies Corp.). The plasmid transfection method followed the attached manual. Light chain and heavy chain expression vectors were mixed at a ratio of 1:2 and used in the transfer.

The cells after the plasmid transfection were cultured for 3 days in 120 mL of a culture medium under conditions involving 37° C., 5% $CO_2$, and 125 rpm. Then, the cell culture medium was centrifuged and filtered through a 0.2-μm filter (Thermo Fisher Scientific Inc.) to recover a culture supernatant.

Purified antibodies were obtained from the culture supernatants by affinity purification using MabSelect SuRe (manufactured by GE Healthcare Japan Corp.). Specifically, a resin filled in a column was equilibrated with PBS, and each culture supernatant was then added to the column. The column was washed twice with PBS and washed once with wash buffer 1 (PBS with 1 M NaCl) and once with wash buffer 2 (20 mM citric acid and 50 mM NaCl, pH 5.0), followed by the elution of the antibody using an elution buffer (20 mM citric acid and 50 mM NaCl, pH 3.4). The obtained antibody solution was neutralized by the addition of a neutralization buffer (1 M phosphoric acid-NaOH, pH 7.0) in an amount of ⅒, and the solvent in the antibody solution was replaced with a preservation buffer (10 mM citric acid and 150 mM NaCl, pH 6.0) using NAP25 (manufactured by GE Healthcare Japan Corp.). The antibody solution thus buffer-replaced was concentrated by ultrafiltration using Amicon Ultra-4 Centrifugal Filter Units (manufactured by Merck Millipore). The absorbance $A_{280}$ was measured using Nanodrop (Thermo Fisher Scientific Inc.) to measure and adjust the concentration of the antibody solution.

[Example 18] Evaluation of Binding Activity of hzKM5320 and hzKM5321 Antibodies Against Human Gas6 Protein Using Biacore®

Human chimeric antibodies comprising the amino acid sequences of variable regions of KM5320 and KM5321 joined to a variant human IgG4 constant region containing EU index S228P, L235E, and R409K amino acid residue substitutions (hereinafter, referred to as a KM5320 chimeric antibody and a KM5321 chimeric antibody, respectively) were prepared according to the method described in Example 16. For the purpose of comparing the binding activity of these chimeric antibodies with the binding activity of the hzKM5320 and hzKM5321 antibodies obtained in Example 17 against human Gas6, a binding activity test was carried out by the surface plasmon resonance method (SPR method) using the human Gas6 prepared in Example 2. The measurement instrument used was Biacore® T100 (manufactured by GE Healthcare Japan Corp.).

An anti-human IgG antibody was immobilized on a CM5 sensor chip (manufactured by GE Healthcare Japan Corp.) using Human Antibody Capture Kit (manufactured by GE Healthcare Japan Corp.) according to the attached manual. Each test antibody adjusted to 1 μg/mL was added for 10 seconds at a flow rate of 10 μL/min to flow cells. Subsequently, 5 serial dilutions from 10 μg/mL of a human Gas6 protein solution diluted 3-fold (HBS-EP+ containing 0.1% BSA was used in the dilution) were added thereto as an analyte at a flow rate of 30 μL/min to measure association reaction between each antibody and the analyte for 2 minutes and dissociation reaction for 10 minutes. The measurement was performed by the signal cycle kinetics method. The obtained sensorgram was analyzed using Bia Evaluation Software (manufactured by GE Healthcare Japan Corp.), and the kinetic constant of each antibody was calculated.

The preliminary test of this measurement revealed that while the binding activity of a large number of antibodies was measured over a long time, even the same antibody exhibited a lower ka value measured in the last half than that measured in the first half. This phenomenon seemed to occur because the human Gas6 protein used as an analyte was gradually adsorbed to a vial during the measurement to decrease the substantial concentration. In order to exclude the influence of the adsorption of the analyte to the vial on measurement results, in this assay, the vial was left standing for a sufficient length of time after addition of the human Gas6 protein solution to the vial, and the measurement of the binding activity of each antibody was started when the adsorption of the human Gas6 protein to the vial reached a plateau.

The calculated smallest values of association rate constants (ka), dissociation rate constants (kd), and largest values of dissociation constants [kd/ka=KD] of the KM5320 chimeric antibody and the hzKM5320 antibody for human Gas6 are described in Table 4. The binding activity of the KM5321 chimeric antibody and the hzKM5321 antibody was also measured in the same way as above, and the obtained results are described in Table 6.

The binding activity test was conducted again by the SPR method only on the KM5320 chimeric antibody, the hzKM5320 LV5HV2 antibody, and the hzKM5320 LV1bHV0 antibody to calculate ka, kd, and KD. The results are described in Table 5. In this retest, unlike the test mentioned above, the number of antibodies to be measured and variations in the concentration of the analyte were decreased, and the assay was conducted for a short time (within several hours), instead of sufficiently leaving standing the analyte added to the vial. The analyte used was 3 serial dilutions from 10 μg/mL of a Gas6 protein solution diluted 3-fold (HBS-EP+ containing 0.1% BSA was used in the dilution). This minimizes the adsorption of the analyte to the vial and permits more accurate calculation of ka and KD values than that in the test mentioned above.

The binding activity of the KM5321 chimeric antibody, the hzKM5321 LV6HV2b antibody, and the hzKM5321 LV7bHV0 antibody was also measured again in the same way as above, and the obtained results are described in Table 7.

As seen from Table 4, the ka values of the KM5320 chimeric antibody and various hzKM5320 antibodies were equivalent. The kd value of the hzKM5320 LV0HV0 antibody was increased by approximately 6 times as compared with the KM5320 chimeric antibody, and the KD value was accordingly increased by 10 or more times. However, the increase in KD value with respect to the KM5320 chimeric antibody was reduced to approximately 2-fold increase in more than half of the other hzKM5320 antibodies.

As seen from Table 6, the ka values of the KM5321 chimeric antibody and various hzKM5321 antibodies were equivalent. The kd and KD values of the hzKM5321 LV0HV0 antibody were increased by approximately 3 times as compared with the KM5321 chimeric antibody. However, the increase in KD value with respect to the KM5321 chimeric antibody was reduced to approximately 2-fold increase in more than 1/3 of the other hzKM5321 antibodies.

These results demonstrated that the binding activity against the Gas6 protein is drastically reduced in the hzKM5320 LV0HV0 antibody and the hzKM5321 LV0HV0 antibody, which are obtained by merely grafting CDRs of the KM5320 or KM5321 antibody to FRs of human antibody, as compared with the KM5320 and KM5321 chimeric antibodies. However, this reduction in the binding activity of the antibodies is suppressed by substituting some amino acid residues of FRs of the hzKM5320 LV0HV0 and hzKM5321 LV0HV0 antibodies by the counterpart amino acid residues of FRs of the KM5320 antibody or the KM5321 antibody. As a result, a plurality of humanized antibodies retaining approximately 50% of the binding activity of the KM5320 or KM5321 chimeric antibody were successfully prepared.

As seen from Table 5, the KD value of the KM5320 chimeric antibody was 0.73 nM whereas the KD value of the hzKM5320 LV5HV2 antibody was 1.29 nM. From these results, as in the results of Table 4, the hzKM5320 LV5HV2 antibody was able to be confirmed to retain 50% or more of the binding activity of the KM5320 chimeric antibody. As seen from Table 7, the KD value of the KM5321 chimeric antibody was 0.2 nM whereas the KD values of the hzKM5321 LV6HV2b antibody and the hzKM5321 LV7bHV0 antibody were 0.48 nM and 0.40 nM, respectively. These humanized antibodies were able to be confirmed again to retain approximately 50% of the binding activity of the KM5321 chimeric antibody.

TABLE 4

Binding activity of KM5320 chimeric antibody and hzKM5320 antibody against human Gas6 - (1)

| mAb | ka (1/Ms) | kd (1/s) | SE(kd) | KD (M) |
| --- | --- | --- | --- | --- |
| A-01. KM5320 chimera | >8.37E+4 | 1.56E-4 | 1.18E-6 | <1.87E-9 |
| A-02. hzKM5320 LV0HV0 | >6.68E+4 | 9.24E-4 | 2.59E-6 | <13.84E-9 |
| A-03. hzKM5320 LV1aHV0 | >6.57E+4 | 8.29E-4 | 2.22E-6 | <12.63E-9 |
| A-04. hzKM5320 LV1bHV0 | >7.20E+4 | 11.53E-4 | 3.49E-6 | <16.01E-9 |
| A-05. hzKM5320 LV2aHV0 | >6.91E+4 | 10.50E-4 | 3.33E-6 | <15.18E-9 |
| A-06. hzKM5320 LV2bHV0 | >7.26E+4 | 10.45E-4 | 3.03E-6 | <14.40E-9 |
| A-07. hzKM5320 LV3HV0 | >7.19E+4 | 2.09E-4 | 1.48E-6 | <2.91E-9 |
| A-08. hzKM5320 LV5HV0 | >6.67E+4 | 1.90E-4 | 1.58E-6 | <2.85E-9 |
| A-09. hzKM5320 LV6HV0 | >6.72E+4 | 2.16E-4 | 1.80E-6 | <3.22E-9 |
| A-10. hzKM5320 LV0HV8 | >7.29E+4 | 7.14E-4 | 3.00E-6 | <9.79E-9 |
| A-11. hzKM5320 LV1aHV8 | >7.20E+4 | 6.94E-4 | 2.65E-6 | <9.64E-9 |
| A-12. hzKM5320 LV1bHV8 | >7.79E+4 | 8.56E-4 | 3.19E-6 | <10.98E-9 |
| A-13. hzKM5320 LV2aHV8 | >7.86E+4 | 8.00E-4 | 3.03E-6 | <10.17E-9 |
| A-14. hzKM5320 LV2bHV8 | >8.10E+4 | 7.91E-4 | 3.70E-6 | <9.77E-9 |
| A-15. hzKM5320 LV3HV8 | >7.56E+4 | 1.74E-4 | 1.66E-6 | <2.30E-9 |
| A-16. hzKM5320 LV5HV8 | >7.36E+4 | 1.55E-4 | 2.08E-6 | <2.11E-9 |
| A-17. hzKM5320 LV6HV8 | >7.25E+4 | 1.58E-4 | 2.21E-6 | <2.18E-9 |
| A-01. KM5320 chimera | >8.37E+4 | 1.56E-4 | 1.18E-6 | <1.87E-9 |

TABLE 4-continued

Binding activity of KM5320 chimeric antibody and hzKM5320 antibody against human Gas6 - (1)

| mAb | ka (1/Ms) | kd (1/s) | SE(kd) | KD (M) |
| --- | --- | --- | --- | --- |
| A-08. hzKM5320 LV5HV0 | >6.67E+4 | 1.90E−4 | 1.58E−6 | <2.85E−9 |
| A-19. hzKM5320 LV5HV1 | >7.41E+4 | 1.84E−4 | 2.17E−6 | <2.48E−9 |
| A-20. hzKM5320 LV5HV2 | >7.43E+4 | 1.58E−4 | 2.39E−6 | <2.13E−9 |
| A-21. hzKM5320 LV5HV3a | >7.71E+4 | 1.77E−4 | 2.06E−6 | <2.30E−9 |
| A-22. hzKM5320 LV5HV3b | >7.63E+4 | 1.53E−4 | 2.18E−6 | <2.01E−9 |
| A-23. hzKM5320 LV5HV3c | >7.79E+4 | 1.40E−4 | 2.20E−6 | <1.79E−9 |
| A-24. hzKM5320 LV5HV4 | >7.92E+4 | 1.73E−4 | 2.26E−6 | <2.19E−9 |
| A-25. hzKM5320 LV5HV6 | >8.17E+4 | 1.47E−4 | 2.57E−6 | <1.80E−9 |
| A-16. hzKM5320 LV5HV8 | >7.36E+4 | 1.55E−4 | 2.08E−6 | <2.11E−9 |

TABLE 5

Binding activity of KM5320 chimeric antibody and hzKM5320 antibody against human Gas6 - (2)

| mAb | ka (1/Ms) | SE(ka) | kd (1/s) | SE(kd) | KD (M) |
| --- | --- | --- | --- | --- | --- |
| A-01. KM5320 chimera | 1.86E+5 | 168 | 1.35E−4 | 6.95E−7 | 0.73E−9 |
| A-20. hzKM5320 LV5HV2 | 1.52E+5 | 197 | 1.97E−4 | 9.63E−7 | 1.29E−9 |
| A-04. hzKM5320 LV1bHV0 | 0.90E+5 | 507 | 14.89E−4 | 41.57E−7 | 16.51E−9 |

TABLE 6

Binding activity of KM5321 chimeric antibody and hzKM5321 antibody against human Gas6 - (1)

| mAb | ka (1/Ms) | kd (1/s) | SE(kd) | KD (M) |
| --- | --- | --- | --- | --- |
| B-01. KM5321 chimera | >1.21E+5 | 1.41E−4 | 1.29E−6 | <1.16E−9 |
| B-02. LV0HV0 | >1.31E+5 | 4.68E−4 | 2.08E−6 | <3.57E−9 |
| B-03. LV1aHV0 | >1.26E+5 | 4.92E−4 | 2.22E−6 | <3.92E−9 |
| B-04. LV1bHV0 | >1.27E+5 | 5.43E−4 | 2.66E−6 | <4.26E−9 |
| B-05. LV1cHV0 | >1.26E+5 | 5.11E−4 | 2.96E−6 | <4.05E−9 |
| B-06. LV3HV0 | >1.53E+5 | 2.85E−4 | 4.89E−6 | <1.86E−9 |
| B-07. LV4HV0 | >1.26E+5 | 5.51E−4 | 3.34E−6 | <4.38E−9 |
| B-08. LV6HV0 | >1.34E+5 | 1.59E−4 | 3.02E−6 | <1.19E−9 |
| B-09. LV7aHV0 | >1.33E+5 | 1.88E−4 | 3.13E−6 | <1.41E−9 |
| B-10. LV7bHV0 | >1.29E+5 | 2.42E−4 | 1.93E−6 | <1.88E−9 |
| B-11. LV9HV0 | >1.26E+5 | 2.47E−4 | 2.27E−6 | <1.96E−9 |
| B-12. LV0HV7 | >1.00E+5 | 6.72E−4 | 1.65E−6 | <6.74E−9 |
| B-13. LV1aHV7 | >1.00E+5 | 6.84E−4 | 1.94E−6 | <6.83E−9 |
| B-19. LV7aHV7 | >1.03E+5 | 2.99E−4 | 1.64E−6 | <2.91E−9 |
| B-20. LV7bHV7 | >1.07E+5 | 3.29E−4 | 1.61E−6 | <3.07E−9 |
| B-21. LV9HV7 | >1.06E+5 | 3.52E−4 | 1.76E−6 | <3.33E−9 |
| B-01. KM5321 chimera | >1.10E+5 | 1.37E−4 | 1.77E−6 | <1.25E−9 |
| B-08. LV6HV0 | >1.03E+5 | 2.38E−4 | 2.32E−6 | <2.32E−9 |
| B-22. LV6HV1 | >1.02E+5 | 2.39E−4 | 2.06E−6 | <2.35E−9 |
| B-23. LV6HV2a | >1.02E+5 | 2.12E−4 | 1.99E−6 | <2.07E−9 |
| B-24. LV6HV2b | >1.03E+5 | 2.39E−4 | 1.97E−6 | <2.33E−9 |
| B-25. LV6HV3a | >1.05E+5 | 2.26E−4 | 1.94E−6 | <2.15E−9 |
| B-26. LV6HV3b | >1.06E+5 | 2.00E−4 | 1.93E−6 | <1.88E−9 |
| B-27. LV6HV4a | >1.06E+5 | 3.41E−4 | 2.41E−6 | <3.20E−9 |
| B-28. LV6HV4b | >1.06E+5 | 2.04E−4 | 2.03E−6 | <1.92E−9 |
| B-29. LV6HV5 | >1.06E+5 | 2.77E−4 | 2.47E−6 | <2.61E−9 |
| B-18. LV6HV7 | >1.07E+5 | 2.78E−4 | 2.44E−6 | <2.59E−9 |
| B-14. LV1bHV7 | >1.00E+5 | 7.51E−4 | 1.92E−6 | <7.49E−9 |
| B-15. LV1cHV7 | >1.01E+5 | 7.50E−4 | 2.09E−6 | <7.45E−9 |
| B-16. LV3HV7 | >1.01E+5 | 7.12E−4 | 1.95E−6 | <7.03E−9 |
| B-17. LV4HV7 | >1.00E+5 | 8.59E−4 | 2.45E−6 | <8.59E−9 |
| B-18. LV6HV7 | >1.00E+5 | 2.81E−4 | 1.57E−6 | <2.81E−9 |

TABLE 7

Binding activity of KM5321 chimeric antibody and hzKM5321 antibody against human Gas6 - (2)

| mAb | ka (1/Ms) | SE(ka) | kd (1/s) | SE(kd) | KD (M) |
| --- | --- | --- | --- | --- | --- |
| B-01. KM5321 chimera | 3.80E+5 | 515 | 7.66E−5 | 9.92E−7 | 2.02E−10 |
| B-24. LV6HV2b | 3.19E+5 | 397 | 15.43E−5 | 9.37E−7 | 4.84E−10 |
| B-10. LV7bHV0 | 3.53E+5 | 607 | 14.23E−5 | 12.80E−7 | 4.03E−10 |

[Example 19] Evaluation of Binding Activity of hzKM5320 and hzKM5321 Antibodies Against Human Gas6 Protein by ELISA The binding activity of the hzKM5320 antibody and the hzKM5321 antibody against the human Gas6 protein was measured by ELISA according to the method described in Example 6. Since the chimeric and humanized antibodies had human-derived constant regions, the secondary antibody used was a solution containing Goat anti Human IgG (H&L) Ads to Ms, Rb, Bv, Ho Horseradish Peroxidase (manufactured by American Qualex International, Inc., A110PD) diluted 3000-fold with 1% BSA-PBS. In order to reduce the backgrounds of measurement values, the diluted secondary antibody solution was mixed with 50 μg/mL of an anti-DNP mouse IgG1 antibody and incubated at room temperature for 1 hour for use. The obtained results are shown in FIG. 11. For the graphs of FIG. 11, curve fitting was conducted using a logistic curve from the absorbance at each concentration per antibody, and the $EC_{50}$ values of binding of the KM5320 and KM5321 chimeric antibodies and the hzKM5320 and hzKM5321 antibodies, and SE values thereof were calculated using R statistical language (Ver. 3.02). The results are shown in Table 8. The hzKM5320 LV5HV2 antibody exhibited the same level of binding activity as in the KM5320 chimeric antibody. Also, the hzKM5321 LV6HV2b and LV7bHV0 antibodies also exhibited the same level of binding activity as in the KM5321 chimeric antibody.

TABLE 8

Binding activity of KM5320 and KM5321 chimeric antibodies and hzKM5320 and hzKM5321 antibodies against human Gas6 protein (ELISA)

| Antibody | $EC_{50}$ [ng/mL] | S.E. ($EC_{50}$) |
|---|---|---|
| KM5320 chimera | 11.32 | 1.235 |
| hzKM5320 LV5HV2 | 12.19 | 1.546 |
| hzKM5320 LV1bHV0 | 19.05 | 2.407 |
| KM5321 chimera | 6.78 | 1.221 |
| hzKM5321 LV6HV2b | 5.95 | 1.342 |
| hzKM5321 LV7bHV0 | 6.69 | 1.386 |
| DNP | — | — |

[Example 20] Evaluation of Inhibitory Activity of hzKM5320 and hzKM5321 Antibodies Against Binding Between Human Gas6 Protein and Axl The inhibitory activity of the hzKM5320 and hzKM5321 antibodies against the binding between the human Gas6 protein and Axl was measured in the same way as in Example 7. The obtained results are shown in FIG. 12. For the graphs of FIG. 12, curve fitting was conducted using a logistic curve from the ELISA absorbance at each concentration per antibody, and the $IC_{50}$ values of binding inhibition of the KM5320 and KM5321 chimeric antibodies and the hzKM5320 and hzKM5321 antibodies, and SE values thereof were calculated using R statistical language (Ver. 3.02). The results are shown in Table 9. The hzKM5320 LV5HV2 antibody was shown to maintain approximately 70% of the binding inhibitory activity of the KM5320 chimeric antibody. The hzKM5321 LV6HV2b antibody and the hzKM5321 LV7bHV0 antibody were shown to maintain the same level of binding inhibitory activity as in the KM5321 chimeric antibody.

TABLE 9

Inhibitory activity of KM5320 and KM5321 chimeric antibodies and hzKM5320 and hzKM5321 antibodies against binding between human Gas6 protein and Axl (ELISA)

| Antibody | $IC_{50}$ [ng/mL] | S.E. ($IC_{50}$) |
|---|---|---|
| KM5320 chimera | 21.80 | 4.485 |
| kzKM5320 LV5HV2 | 33.62 | 6.328 |
| hzKM5320 LV1bHV0 | 742.27 | 96.190 |
| KM5321 chimera | 12.32 | 3.354 |
| hzKM5321 LV6HV2b | 12.65 | 2.651 |
| hzKM5321 LV7bHV0 | 11.78 | 2.351 |
| DNP | — | — |

INDUSTRIAL APPLICABILITY

The monoclonal antibody of the present invention is useful in the treatment and diagnosis of Gas6-related diseases such as kidney or cancer diseases.

All publications, patents, and patent applications cited herein are incorporated herein by reference in their entirety.

Free Text for Sequence Listing

SEQ ID NO: 1—Description of an artificial sequence: Primer 1

SEQ ID NO: 2—Description of an artificial sequence: Primer 2

SEQ ID NO: 5—Description of an artificial sequence: Primer 3

SEQ ID NO: 6—Description of an artificial sequence: Primer 4

SEQ ID NO: 9—Description of an artificial sequence: Primer 5

SEQ ID NO: 10—Description of an artificial sequence: Primer 6

SEQ ID NO: 11—Description of an artificial sequence: Primer 7

SEQ ID NO: 12—Description of an artificial sequence: Primer 8

SEQ ID NO: 15—Description of an artificial sequence: Primer 9

SEQ ID NO: 18—Description of an artificial sequence: Primer 10

SEQ ID NO: 19—Description of an artificial sequence: Primer 11

SEQ ID NO: 22—Description of an artificial sequence: Primer 12

SEQ ID NO: 23—Description of an artificial sequence: Primer 13

SEQ ID NO: 28—Description of an artificial sequence: hAxl-hFc

SEQ ID NO: 29—Synthetic construct

SEQ ID NO: 30—Description of an artificial sequence: Primer 14

SEQ ID NO: 31—Description of an artificial sequence: Primer 15

SEQ ID NO: 34—Description of an artificial sequence: Primer 16

SEQ ID NO: 35—Description of an artificial sequence: Primer 17

SEQ ID NO: 36—Description of an artificial sequence: cAxl-hFc

SEQ ID NO: 37—Synthetic construct

SEQ ID NO: 38—Description of an artificial sequence: Primer 18

SEQ ID NO: 39—Description of an artificial sequence: Primer 19

SEQ ID NO: 42—Description of an artificial sequence: Primer 20

SEQ ID NO: 43—Description of an artificial sequence: Primer 21

SEQ ID NO: 44—Description of an artificial sequence: rAxl-hFc
SEQ ID NO: 45—Synthetic construct
SEQ ID NO: 48—Description of an artificial sequence: mAxl-mFc
SEQ ID NO: 49—Synthetic construct
SEQ ID NO: 50—Description of an artificial sequence: Primer 22
SEQ ID NO: 51—Description of an artificial sequence: Primer 23
SEQ ID NO: 54—Description of an artificial sequence: Primer 24
SEQ ID NO: 55—Description of an artificial sequence: Primer 25
SEQ ID NO: 58—Description of an artificial sequence: Primer 26
SEQ ID NO: 59—Description of an artificial sequence: Primer 27
SEQ ID NO: 61—Description of an artificial sequence: CNTO VH
SEQ ID NO: 62—Synthetic construct
SEQ ID NO: 63—Description of an artificial sequence: CNTO VL
SEQ ID NO: 64—Synthetic construct
SEQ ID NO: 65—Description of an artificial sequence: Primer 28
SEQ ID NO: 66—Description of an artificial sequence: Primer 29
SEQ ID NO: 67—Description of an artificial sequence: KM5320 VH
SEQ ID NO: 68—Synthetic construct
SEQ ID NO: 69—Description of an artificial sequence: Amino acid sequence of KM5320 VH except for a signal sequence
SEQ ID NO: 70—Description of an artificial sequence: KM5320 VL
SEQ ID NO: 71—Synthetic construct
SEQ ID NO: 72—Description of an artificial sequence: Amino acid sequence of KM5320 VL except for a signal sequence
SEQ ID NO: 73—Description of an artificial sequence: KM5321 VH
SEQ ID NO: 74—Synthetic construct
SEQ ID NO: 75—Description of an artificial sequence: Amino acid sequence of KM5321 VH except for a signal sequence
SEQ ID NO: 76—Description of an artificial sequence: KM5321 VL
SEQ ID NO: 77—Synthetic construct
SEQ ID NO: 78—Description of an artificial sequence: Amino acid sequence of KM5321 VL except for a signal sequence
SEQ ID NO: 79—Description of an artificial sequence: Amino acid sequence of KM5320 VH CDR1
SEQ ID NO: 80—Description of an artificial sequence: Amino acid sequence of KM5320 VH CDR2
SEQ ID NO: 81—Description of an artificial sequence: Amino acid sequence of KM5320 VH CDR3
SEQ ID NO: 82—Description of an artificial sequence: Amino acid sequence of KM5320 VL CDR1
SEQ ID NO: 83—Description of an artificial sequence: Amino acid sequence of KM5320 VL CDR2
SEQ ID NO: 84—Description of an artificial sequence: Amino acid sequence of KM5320 VL CDR3
SEQ ID NO: 85—Description of an artificial sequence: Amino acid sequence of KM5321 VH CDR1
SEQ ID NO: 86—Description of an artificial sequence: Amino acid sequence of KM5321 VH CDR2
SEQ ID NO: 87—Description of an artificial sequence: Amino acid sequence of KM5321 VH CDR3
SEQ ID NO: 88—Description of an artificial sequence: Amino acid sequence of KM5321 VL CDR1
SEQ ID NO: 89—Description of an artificial sequence: Amino acid sequence of KM5321 VL CDR2
SEQ ID NO: 90—Description of an artificial sequence: Amino acid sequence of KM5321 VL CDR3
SEQ ID NO: 91—Description of an artificial sequence: KM5320-rIgG1
SEQ ID NO: 92—Synthetic construct
SEQ ID NO: 93—Description of an artificial sequence: KM5320-r_kappa
SEQ ID NO: 94—Synthetic construct
SEQ ID NO: 95—Description of an artificial sequence: KM5321-rIgG1
SEQ ID NO: 96—Synthetic construct
SEQ ID NO: 97—Description of an artificial sequence: KM5321-r_kappa
SEQ ID NO: 98—Synthetic construct
SEQ ID NO: 99—Description of an artificial sequence: hGas6-delta
SEQ ID NO: 100—Synthetic construct
SEQ ID NO: 101—Description of an artificial sequence: Primer 30
SEQ ID NO: 102—Description of an artificial sequence: Primer 31
SEQ ID NO: 103—Description of an artificial sequence: hzKM5320 LV0 sequence
SEQ ID NO: 104—Synthetic construct
SEQ ID NO: 105—Description of an artificial sequence: Amino acid sequence of hzKM5320 LV0 except for a signal sequence
SEQ ID NO: 106—Description of an artificial sequence: hzKM5320 LV1a sequence
SEQ ID NO: 107—Synthetic construct
SEQ ID NO: 108—Description of an artificial sequence: Amino acid sequence of hzKM5320 LV1a except for a signal sequence
SEQ ID NO: 109—Description of an artificial sequence: hzKM5320 LV1b sequence
SEQ ID NO: 110—Synthetic construct
SEQ ID NO: 111—Description of an artificial sequence: Amino acid sequence of hzKM5320 LV1b except for a signal sequence
SEQ ID NO: 112—Description of an artificial sequence: hzKM5320 LV2a sequence
SEQ ID NO: 113—Synthetic construct
SEQ ID NO: 114—Description of an artificial sequence: Amino acid sequence of hzKM5320 LV2a except for a signal sequence
SEQ ID NO: 115—Description of an artificial sequence: hzKM5320 LV2b sequence
SEQ ID NO: 116—Synthetic construct
SEQ ID NO: 117—Description of an artificial sequence: Amino acid sequence of hzKM5320 LV2b except for a signal sequence
SEQ ID NO: 118—Description of an artificial sequence: hzKM5320 LV3 sequence
SEQ ID NO: 119—Synthetic construct
SEQ ID NO: 120—Description of an artificial sequence: Amino acid sequence of hzKM5320 LV3 except for a signal sequence
SEQ ID NO: 121—Description of an artificial sequence: hzKM5320 LV5 sequence SEQ ID NO: 122—Synthetic construct
SEQ ID NO: 123—Description of an artificial sequence: Amino acid sequence of hzKM5320 LV5 except for a signal sequence
SEQ ID NO: 124—Description of an artificial sequence: hzKM5320 LV6 sequence
SEQ ID NO: 125—Synthetic construct
SEQ ID NO: 126—Description of an artificial sequence: Amino acid sequence of hzKM5320 LV6 except for a signal sequence
SEQ ID NO: 127—Description of an artificial sequence: hzKM5320 HV0 sequence
SEQ ID NO: 128—Synthetic construct
SEQ ID NO: 129—Description of an artificial sequence: Amino acid sequence of hzKM5320 HV0 except for a signal sequence
SEQ ID NO: 130—Description of an artificial sequence: hzKM5320 HV1 sequence
SEQ ID NO: 131—Synthetic construct
SEQ ID NO: 132—Description of an artificial sequence: Amino acid sequence of hzKM5320 HV1 except for a signal sequence
SEQ ID NO: 133—Description of an artificial sequence: hzKM5320 HV2 sequence
SEQ ID NO: 134—Synthetic construct
SEQ ID NO: 135—Description of an artificial sequence: Amino acid sequence of hzKM5320 HV2 except for a signal sequence
SEQ ID NO: 136—Description of an artificial sequence: hzKM5320 HV3a sequence
SEQ ID NO: 137—Synthetic construct
SEQ ID NO: 138—Description of an artificial sequence: Amino acid sequence of hzKM5320 HV3a except for a signal sequence
SEQ ID NO: 139—Description of an artificial sequence: hzKM5320 HV3b sequence
SEQ ID NO: 140—Synthetic construct
SEQ ID NO: 141—Description of an artificial sequence: Amino acid sequence of hzKM5320 HV3b except for a signal sequence
SEQ ID NO: 142—Description of an artificial sequence: hzKM5320 HV3c sequence
SEQ ID NO: 143—Synthetic construct
SEQ ID NO: 144—Description of an artificial sequence: Amino acid sequence of hzKM5320 HV3c except for a signal sequence
SEQ ID NO: 145—Description of an artificial sequence: hzKM5320 HV4 sequence
SEQ ID NO: 146—Synthetic construct
SEQ ID NO: 147—Description of an artificial sequence: Amino acid sequence of hzKM5320 HV4 except for a signal sequence
SEQ ID NO: 148—Description of an artificial sequence: hzKM5320 HV6 sequence
SEQ ID NO: 149—Synthetic construct
SEQ ID NO: 150—Description of an artificial sequence: Amino acid sequence of hzKM5320 HV6 except for a signal sequence
SEQ ID NO: 151—Description of an artificial sequence: hzKM5320 HV8 sequence
SEQ ID NO: 152—Synthetic construct
SEQ ID NO: 153—Description of an artificial sequence: Amino acid sequence of hzKM5320 HV8 except for a signal sequence
SEQ ID NO: 154—Description of an artificial sequence: hzKM5321 LV0 sequence
SEQ ID NO: 155—Synthetic construct
SEQ ID NO: 156—Description of an artificial sequence: Amino acid sequence of hzKM5321 LV0 except for a signal sequence
SEQ ID NO: 157—Description of an artificial sequence: hzKM5321 LV1a sequence
SEQ ID NO: 158—Synthetic construct
SEQ ID NO: 159—Description of an artificial sequence: Amino acid sequence of hzKM5321 LV1a except for a signal sequence
SEQ ID NO: 160—Description of an artificial sequence: hzKM5321 LV1b sequence
SEQ ID NO: 161—Synthetic construct
SEQ ID NO: 162—Description of an artificial sequence: Amino acid sequence of hzKM5321 LV1b except for a signal sequence
SEQ ID NO: 163—Description of an artificial sequence: hzKM5321 LV1c sequence
SEQ ID NO: 164—Synthetic construct
SEQ ID NO: 165—Description of an artificial sequence: Amino acid sequence of hzKM5321 LV1c except for a signal sequence
SEQ ID NO: 166—Description of an artificial sequence: hzKM5321 LV3 sequence
SEQ ID NO: 167—Synthetic construct
SEQ ID NO: 168—Description of an artificial sequence: Amino acid sequence of hzKM5321 LV3 except for a signal sequence
SEQ ID NO: 169—Description of an artificial sequence: hzKM5321 LV4 sequence
SEQ ID NO: 170—Synthetic construct
SEQ ID NO: 171—Description of an artificial sequence: Amino acid sequence of hzKM5321 LV4 except for a signal sequence
SEQ ID NO: 172—Description of an artificial sequence: hzKM5321 LV6 sequence
SEQ ID NO: 173—Synthetic construct
SEQ ID NO: 174—Description of an artificial sequence: Amino acid sequence of hzKM5321 LV6 except for a signal sequence
SEQ ID NO: 175—Description of an artificial sequence: hzKM5321 LV7a sequence
SEQ ID NO: 176—Synthetic construct
SEQ ID NO: 177—Description of an artificial sequence: Amino acid sequence of hzKM5321 LV7a except for a signal sequence
SEQ ID NO: 178—Description of an artificial sequence: hzKM5321 LV7b sequence
SEQ ID NO: 179—Synthetic construct
SEQ ID NO: 180—Description of an artificial sequence: Amino acid sequence of hzKM5321 LV7b except for a signal sequence
SEQ ID NO: 181—Description of an artificial sequence: hzKM5321 LV9 sequence
SEQ ID NO: 182—Synthetic construct
SEQ ID NO: 183—Description of an artificial sequence: Amino acid sequence of hzKM5321 LV9 except for a signal sequence
SEQ ID NO: 184—Description of an artificial sequence: hzKM5321 HV0 sequence
SEQ ID NO: 185—Synthetic construct
SEQ ID NO: 186—Description of an artificial sequence: Amino acid sequence of hzKM5321 HV0 except for a signal sequence
SEQ ID NO: 187—Description of an artificial sequence: hzKM5321 HV1 sequence
SEQ ID NO: 188—Synthetic construct SEQ ID NO: 189—Description of an artificial sequence: Amino acid sequence of hzKM5321 HV1 except for a signal sequence
SEQ ID NO: 190—Description of an artificial sequence: hzKM5321 HV2a sequence
SEQ ID NO: 191—Synthetic construct
SEQ ID NO: 192—Description of an artificial sequence: Amino acid sequence of hzKM5321 HV2a except for a signal sequence
SEQ ID NO: 193—Description of an artificial sequence: hzKM5321 HV2b sequence
SEQ ID NO: 194—Synthetic construct
SEQ ID NO: 195—Description of an artificial sequence: Amino acid sequence of hzKM5321 HV2b except for a signal sequence
SEQ ID NO: 196—Description of an artificial sequence: hzKM5321 HV3a sequence
SEQ ID NO: 197—Synthetic construct
SEQ ID NO: 198—Description of an artificial sequence: Amino acid sequence of hzKM5321 HV3a except for a signal sequence
SEQ ID NO: 199—Description of an artificial sequence: hzKM5321 HV3b sequence
SEQ ID NO: 200—Synthetic construct
SEQ ID NO: 201—Description of an artificial sequence: Amino acid sequence of hzKM5321 HV3b except for a signal sequence
SEQ ID NO: 202—Description of an artificial sequence: hzKM5321 HV4a sequence
SEQ ID NO: 203—Synthetic construct
SEQ ID NO: 204—Description of an artificial sequence: Amino acid sequence of hzKM5321 HV4a except for a signal sequence
SEQ ID NO: 205—Description of an artificial sequence: hzKM5321 HV4b sequence
SEQ ID NO: 206—Synthetic construct
SEQ ID NO: 207—Description of an artificial sequence: Amino acid sequence of hzKM5321 HV4b except for a signal sequence
SEQ ID NO: 208—Description of an artificial sequence: hzKM5321 HV5 sequence
SEQ ID NO: 209—Synthetic construct
SEQ ID NO: 210—Description of an artificial sequence: Amino acid sequence of hzKM5321 HV5 except for a signal sequence
SEQ ID NO: 211—Description of an artificial sequence: hzKM5321 HV7 sequence
SEQ ID NO: 212—Synthetic construct
SEQ ID NO: 213—Description of an artificial sequence: Amino acid sequence of hzKM5321 HV7 except for a signal sequence

The invention claimed is:

1. A monoclonal antibody or an antibody fragment thereof which binds to at least one of amino acid residues at positions 314, 315, and 316 in the amino acid sequence of human Gas6 shown in SEQ ID NO: 4, wherein the monoclonal antibody is an antibody in which the amino acid sequences of heavy chain (hereinafter, abbreviated to H chain) variable region (hereinafter, abbreviated to VH) complementarity determining region (hereinafter, abbreviated to CDR) 1 to CDR3 are the amino acid sequences shown in SEQ ID NOs: 79, 80, and 81, respectively, and the amino acid sequences of light chain (hereinafter, abbreviated to L chain) variable region (hereinafter, abbreviated to VL) CDR1 to CDR3 are the amino acid sequences shown in SEQ ID NOs: 82, 83, and 84, respectively.

2. The monoclonal antibody or the antibody fragment thereof according to claim 1, wherein the monoclonal antibody is any one antibody selected from the following antibodies (a) and (b):

(a) an antibody in which the amino acid sequence of VH is the amino acid sequence shown in SEQ ID NO: 69, and the amino acid sequence of VL is the amino acid sequence shown in SEQ ID NO: 72;

(b) an antibody in which the amino acid sequence of VH is the amino acid sequence shown in SEQ ID NO: 135, and the amino acid sequence of VL is the amino acid sequence shown in SEQ ID NO: 123.

3. The monoclonal antibody or the antibody fragment thereof according to claim 1, wherein the monoclonal antibody is a recombinant antibody.

4. The monoclonal antibody or the antibody fragment thereof according to claim 3, wherein the recombinant antibody is a recombinant antibody selected from a human chimeric antibody, and a humanized antibody.

5. The monoclonal antibody or the antibody fragment according to claim 1, wherein the monoclonal antibody or the antibody fragment is selected from Fab, Fab', F(ab')$_2$, single chain Fv (scFv), diabody, and disulfide-stabilized Fv (dsFv).

6. A reagent for detection or assay of Gas6, comprising the antibody or the antibody fragment thereof according to claim 1 and an agent to label the antibody.

7. A therapeutic agent comprising the antibody or the antibody fragment thereof according to claim 1 as an active ingredient and one or more pharmaceutically acceptable carriers.

8. A diagnostic agent comprising the antibody or the antibody fragment thereof according to claim 1 as an active ingredient and a reagent for detecting antigen-antibody reaction.

* * * * *

UNITED STATES PATENT AND TRADEMARK OFFICE
CERTIFICATE OF CORRECTION

PATENT NO. : 10,561,727 B2
APPLICATION NO. : 15/520623
DATED : February 18, 2020
INVENTOR(S) : Ube et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Twenty-fourth Day of November, 2020

Andrei Iancu
*Director of the United States Patent and Trademark Office*